(12) United States Patent
Konradi et al.

(10) Patent No.: US 8,283,358 B2
(45) Date of Patent: Oct. 9, 2012

(54) N-SULFONAMIDO POLYCYCLIC PYRAZOLYL COMPOUNDS

(75) Inventors: Andrei W. Konradi, Burlingame, CA (US); Xiaocong Michael Ye, Palo Alto, CA (US); Simeon Bowers, Oakland, CA (US); Albert W. Garofalo, South San Francisco, CA (US); Danielle L. Aubele, Burlingame, CA (US); Darren Dressen, Fremont, CA (US); Raymond Ng, San Ramon, CA (US); Gary Probst, San Francisco, CA (US); Christopher M. Semko, Fremont, CA (US); Minghua Sun, Burlingame, CA (US); Anh P. Truong, Burlingame, CA (US); Michael S. Dappen, Emerald Hills, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 468 days.

(21) Appl. No.: 12/554,134

(22) Filed: Sep. 4, 2009

(65) Prior Publication Data

US 2010/0081680 A1    Apr. 1, 2010

Related U.S. Application Data

(60) Provisional application No. 61/226,532, filed on Jul. 17, 2009, provisional application No. 61/173,278, filed on Apr. 28, 2009, provisional application No. 61/099,241, filed on Sep. 23, 2008, provisional application No. 61/094,799, filed on Sep. 5, 2008.

(51) Int. Cl.
*A61K 31/439* (2006.01)
*C07D 471/18* (2006.01)
(52) U.S. Cl. .................................. 514/286; 546/63
(58) Field of Classification Search .................. 514/286; 546/63
See application file for complete search history.

(56) References Cited

FOREIGN PATENT DOCUMENTS
EP    0330788    9/1989
WO    2005/113542    12/2005
(Continued)

OTHER PUBLICATIONS

International Search Report for PCT/US2009/055987 mailed Apr. 8, 2010.

(Continued)

*Primary Examiner* — Charanjit Aulakh
(74) *Attorney, Agent, or Firm* — McDonnell Boehnen Hulbert & Berghoff LLP

(57) ABSTRACT

The current invention provides compounds having a structure according to Formulae 1, 2, 3, and 4:

Formula 1

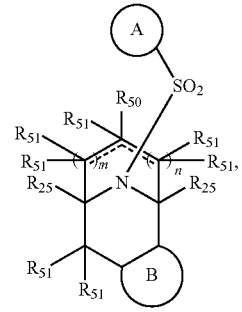

Formula 2

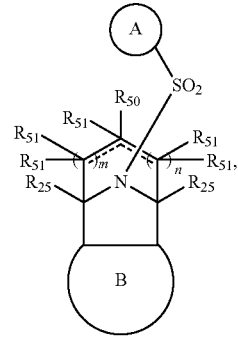

Formula 3

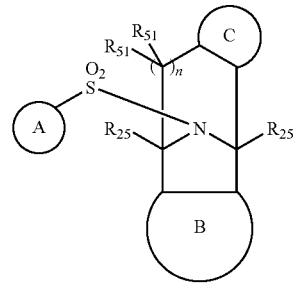

Formula 4
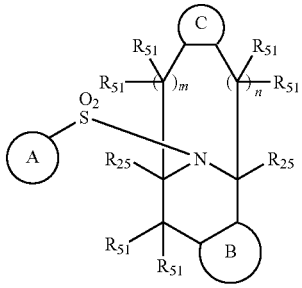

wherein the A-ring, B-ring, C-ring, m, n, $R_{25}$, $R_{50}$, and $R_{51}$ are as described in the specification. The invention also provides pharmaceutical compositions comprising compounds of Formulae 1, 2, 3, and 4, as well as methods of treating cognitive disorders, such as Alzheimer's disease. The invention further provides intermediates useful in preparing the compounds of Formulae 1, 2, 3, and 4.

24 Claims, No Drawings

FOREIGN PATENT DOCUMENTS

| | | |
|---|---|---|
| WO | 2007/022502 | 2/2007 |
| WO | 2008/022502 | 2/2007 |
| WO | 2007/143523 | 12/2007 |
| WO | 2008/147800 | 12/2008 |
| WO | 2010/028213 | 3/2010 |

OTHER PUBLICATIONS

Mitsuhashi et al., "Reactions of 7-Oxa-Aza-norbornenes and—dienes with 1,3—Dipolar Compounds," Seikei Daigaku Dogakubu Kogaku Hokoku, 44:2983-2992 (Jun. 2, 1987) XP002575111 (English Abstract).

Durand et al., "Preparation of 4-Arylcyclopentenes by Sequential Diallylation of Arylaldehydes and Ring-Closing Metathesis," Synth. Commun., 35(13):1825 (2005).

Mach, R.H. et al., "18F-Labeled Benzamides for Studying the Dopamine D2 Receptor with Positron Emission Tomography," J. Med. Chem., 36(23):3707 (1993).

Castellano, S. et al., "Small-Molecule Inhibitors of Protein Geranylgeranyltransferase Type I," J. Am. Chem. Soc., 129(18):5843-5845 (2007).

N-SULFONAMIDO POLYCYCLIC PYRAZOLYL COMPOUNDS

BACKGROUND OF THE INVENTION

1. Field of the Invention

The invention relates to N-sulfonamido polycyclic pyrazolyl compounds having a pendant or fused aryl or heteroaryl ring on the polycyclic ring, which inhibit gamma secretase and β-amyloid peptide release and/or its synthesis. Therefore, the N-sulfonamido polycyclic pyrazolyl compounds of the present invention are useful in the prevention of cognitive disorders in patients susceptible to cognitive disorders and/or in the treatment of patients with cognitive disorders in order to inhibit further deterioration in their condition.

2. State of the Art

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39-43 amino acids designated the β-amyloid peptide (βAP) or sometimes Aβ, AβP or β/A4. β-Amyloid peptide was first purified and a partial amino acid sequence was provided by Glenner et al., Biochem. Biophys. Res. Commun., 120:885-890 (1984). The isolation procedure and the sequence data for the first 28 amino acids are described in U.S. Pat. No. 4,666, 829.

Molecular biological and protein chemical analyses have shown that the β-amyloid peptide is a small fragment of a much larger precursor protein termed the amyloid precursor protein (APP), that is normally produced by cells in many tissues of various animals, including humans. Knowledge of the structure of the gene encoding APP has demonstrated that β-amyloid peptide arises as a peptide fragment that is cleaved from APP by protease enzyme(s). Sequential processing of the precursor protein by the enzymes referred to generically as beta- and gamma-secretases, gives rise to the β-amyloid peptide fragment. Both enzymes have now been molecularly cloned, and characterized to differing levels.

Several lines of evidence indicate that progressive cerebral deposition of β-amyloid peptide plays a seminal role in the pathogenesis of AD and can precede cognitive symptoms by years or decades. See, e.g., Selkoe, Neuron, 6:487-498 (1991). The most important line of evidence is the discovery that missense DNA mutations at amino acid 717 of the 770-amino acid isoform of APP can be found in affected members but not unaffected members of several families with a genetically determined (familial) form of AD (Goate et al., Nature, 349:704-706 (1990); Chartier Harlan et al., Nature, 353:844-846 (1989); and Murrell et al., Science, 254:97-99 (1991).) Another such mutation, known as the Swedish variant, is comprised of a double mutation changing lysine$^{595}$-methionine$^{596}$ to asparagine$^{595}$-leucine$^{596}$ (with reference to the 695 isoform was found in a Swedish family) was reported in 1992 (Mullan et al., Nature Genet., 1:345-347 (1992). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP metabolism, and subsequent deposition of its β-amyloid peptide fragment, can cause AD.

Despite the progress which has been made in understanding the underlying mechanisms of AD and other β-amyloid peptide related diseases, there remains a need to develop methods and compositions for treatment of the disease(s). Ideally, the treatment methods would advantageously be based on drugs, which are capable of inhibiting β-amyloid peptide release and/or its synthesis in vivo.

One approach toward inhibiting amyloid peptide synthesis in vivo is by inhibiting gamma secretase, the enzyme responsible for the carboxy-terminal cleavage resulting in production of fβ-amyloid peptide fragments of 40 or 42 residues in length. The immediate substrates for gamma secretase are β-cleaved, as well as α-cleaved carboxy-terminal fragments (CTF) of APP. The gamma-secretase cleavage site on β- and α-CTF fragments occurs in the predicted transmembrane domain of APP. Inhibitors of gamma-secretase have been demonstrated to effect amyloid pathology in transgenic mouse models (Dovey, H. F., V. John, J. P. Anderson, L. Z. Chen, P. de Saint Andrieu, L. Y. Fang, S. B. Freedman, B. Folmer, E. Goldbach, E. J. Holsztynska et al. (2001). "Functional gamma-secretase inhibitors reduce beta-amyloid peptide levels in brain." J Neurochem 76(1): 173-81.)

Gamma secretase is recognized to be a multi-subunit complex comprised of the presenilins (PS1 or PS2), Nicastrin, Aph-1, and Pen 2 (De Strooper, B. (2003). "Aph-1, Pen-2, and Nicastrin with Presenilin generate an active gamma-Secretase complex." Neuron 38(1): 9-12; Edbauer, D., E. Winkler, J. T. Regula, B. Pesold, H. Steiner and C. Haass (2003). "Reconstitution of gamma-secretase activity." Nat Cell Biol 5(5): 486-8; Kimberly, W. T., M. J. LaVoie, B. L. Ostaszewski, W. Ye, M. S. Wolfe and D. J. Selkoe (2003). "Gamma-secretase is a membrane protein complex comprised of presenilin, nicastrin, Aph-1, and Pen-2." Proc Natl Acad Sci USA 100(11): 6382-7). Much evidence indicates that PS comprises the catalytic moiety of the complex, while the other identified subunits are necessary for proper maturation and sub-cellular localization of the active enzyme complex (reviewed in De Strooper, B. (2003). "Aph-1, Pen-2, and Nicastrin with Presenilin generate an active gamma-Secretase complex." Neuron 38(1): 9-12.) Consistent with this hypothesis: PS knock-out mice exhibit significant reductions in β-amyloid production (De Strooper, B., P. Saftig, K. Craessaerts, H. Vanderstichele, G. Guhde, W. Annaert, K. Von Figura and F. Van Leuven (1998). "Deficiency of presenilin-1 inhibits the normal cleavage of amyloid precursor protein." Nature 391(6665): 387-90; Haass, C. and D. J. Selkoe (1998). "Alzheimer's disease. A technical KO of amyloid-beta peptide." Nature 391(6665): 339-40; Herreman, A., L. Serneels, W. Annaert, D. Collen, L. Schoonjans and B. De Strooper (2000). "Total inactivation of gamma-secretase activity in presenilin-deficient embryonic stem cells." Nat Cell Biol 2(7): 461-2); point mutations of putative active site aspartate residues in PS trans-membrane domains inhibit (β-amyloid production in cells in a dominant negative fashion (Wolfe, M. S, W. Xia, B. L. Ostaszewski, T. S. Diehl, W. T. Kimberly and D. J. Selkoe (1999). "Two transmembrane aspartates in presenilin-1 required for presenilin endoproteolysis and gamma-secretase activity." Nature 398(6727): 513-7; Kimberly, W. T., W. Xia, T. Rahmati, M. S. Wolfe and D. J. Selkoe (2000). "The transmembrane aspartates in presenilin 1 and 2 are obligatory for gamma-secretase activity and amyloid beta-protein generation." J Biol Chem 275(5): 3173-8); active site directed substrate-based transition state isosteres designed to inhibit gamma secretase directly conjugate to PS (Esler, W. P., W. T. Kimberly, B. L. Ostaszewski, T. S. Diehl, C. L. Moore, J. Y. Tsai, T. Rahmati, W. Xia, D. J. Selkoe and M. S. Wolfe (2000). "Transition-state analogue inhibitors of gamma-secretase bind directly to presenilin-1." Nat Cell Biol 2(7): 428-34; Li, Y. M., M. Xu, M. T. Lai, Q. Huang, J. L. Castro, J. DiMuzio-Mower, T. Harrison, C. Lellis, A. Nadin, J. G. Neduvelil et al. (2000). "Photoactivated gamma-secretase inhibitors directed to the active site covalently label presenilin 1." Nature 405(6787): 689-94); finally, allosteric gamma secretase inhibitors have likewise been demonstrated to bind directly to PS (Seiffert, D., J. D. Bradley, C. M. Rominger, D. H. Rominger, F. Yang, J. E. Meredith, Jr., Q. Wang, A. H. Roach, L. A. Thompson, S. M. Spitz et al. (2000). "Presenilin-1 and -2 are molecular targets for gamma-secretase inhibitors." J Biol Chem 275(44): 34086-91.)

Current evidence indicates that in addition to APP processing leading to (β-amyloid synthesis, gamma-secretase also mediates the intra-membrane cleavage of other type I trans-membrane proteins (reviewed in Fortini, M. E. (2002). "Gamma-secretase-mediated proteolysis in cell-surface-receptor signaling." Nat Rev Mol Cell Biol 3(9): 673-84, see also Struhl, G. and A. Adachi (2000). "Requirements for presenilin-dependent cleavage of notch and other transmembrane proteins." Mol Cell 6(3): 625-36). Noteworthy among the known substrates of gamma-secretase is mammalian Notch 1. The Notch 1 protein is important for cell fate determination during development, and tissue homeostasis in the adult. Upon ligand engagement via the Notch ecto-domain, Notch undergoes sequential extra-cellular and intra-membrane processing analogous to APP. The intra-membrane processing of Notch mediated by gamma secretase leads to release of the Notch intracellular domain (NICD). The NICD fragment mediates Notch signaling via translocation to the nucleus, where it regulates expression of genes mediating cellular differentiation in many tissues during development, as well as in the adult.

Disruption of Notch signaling via genetic knock-out (KO) results in embryonic lethal phenotype in mice (Swiatek, P. J., C. E. Lindsell, F. F. del Amo, G. Weinmaster and T. Gridley (1994). "Notch1 is essential for postimplantation development in mice." Genes Dev 8(6): 707-19; Conlon, R. A., A. G. Reaume and J. Rossant (1995). "Notch1 is required for the coordinate segmentation of somites." Development 121(5): 1533-45.) The Notch KO phenotype is very similar to the phenotype observed PS1 KO mice, and precisely reproduced by PS1/PS2 double KO mice (De Strooper et al. (1998). "Deficiency of presenilin-1 inhibits the normal cleavage of amyloid precursor protein." Nature 391(6665): 387-90; Donoviel, D. B., A. K. Hadjantonakis, M. Ikeda, H. Zheng, P. S. Hyslop and A. Bernstein (1999). "Mice lacking both presenilin genes exhibit early embryonic patterning defects." Genes Dev 13(21): 2801-10; Herreman, A., L. Serneels, W. Annaert, D. Collen, L. Schoonjans and B. De Strooper (2000). "Total inactivation of gamma-secretase activity in presenilin-deficient embryonic stem cells." Nat Cell Biol 2(7): 461-2.) This convergence of phenotypes observed in knock-out mice of either the substrate (Notch) or the enzyme (PS) suggests that inhibitors of gamma secretase that also inhibit Notch function may be limited as therapeutic agents owing to the importance of Notch function in adult tissues (Fortini, M. E. (2002). "Gamma-secretase-mediated proteolysis in cell-surface-receptor signaling." Nat Rev Mol Cell Biol 3(9): 673-84.) As APP knock-out mice develop normally and without an overt phenotype Zheng, H., M. Jiang, M. E. Trumbauer, R. Hopkins, D. J. Sirinathsinghji, K. A. Stevens, M. W. Conner, H. H. Slunt, S. S. Sisodia, H. Y. Chen et al. (1996). "Mice deficient for the amyloid precursor protein gene." Ann N Y Acad Sci 777: 421-6; Zheng, H., M. Jiang, M. E. Trumbauer, D. J. Sirinathsinghji, R. Hopkins, D. W. Smith, R. P. Heavens, G. R. Dawson, S. Boyce, M. W. Conner et al. (1995). "beta-Amyloid precursor protein-deficient mice show reactive gliosis and decreased locomotor activity." Cell 81(4): 525-31, the cumulative evidence, therefore, suggests that preferred gamma secretase inhibitors would have selectivity for inhibiting gamma secretase processing of APP over gamma secretase processing of Notch.

SUMMARY OF THE INVENTION

Provided herein are compounds of Formulas 1, 2, 3, and 4, which have the following formulas:

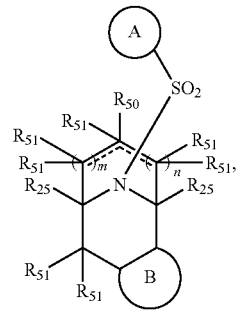

Formula 1

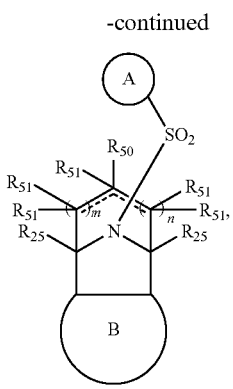

Formula 2

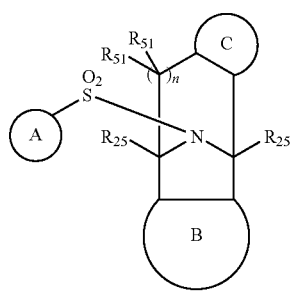

Formula 3

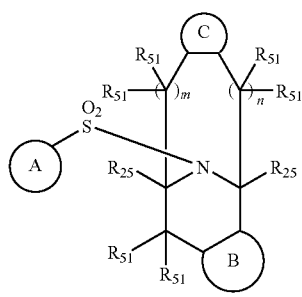

Formula 4 or stereoisomers, enantiomers, pharmaceutically acceptable salts, or solvates thereof, wherein in Formulae 1 and 2, m and n are independently selected from 0, 1 and 2, with the proviso that (m+n) is 1 or 2; in Formula 3 n is 0 or 1; in Formula 4, m and n are independently 0 or 1, provided that m+n=0 or 1;

wherein the C-ring is aryl (e.g., phenyl) substituted with $R_{30}$, $R_{35}$, $R_{40}$, and $R_{45}$, heteroaryl, heterocycloalkyl or cycloalkyl, wherein the heteroaryl, heterocycloalkyl and cycloalkyl groups are optionally substituted e.g., with halogen, $C_1$-$C_6$ alkyl, $C_1$-$C_6$ haloalkyl, $C_1$-$C_6$ haloalkoxy, $C_2$-$C_8$ alkenyl, $C_2$-$C_8$ alkynyl, $C_2$-$C_8$ haloalkenyl, $C_2$-$C_8$ haloalkynyl, —C(O)OR$_{11}$, CN, hydroxyl, $C_1$-$C_6$ alkoxy, —$C_1$-$C_6$ alkyl-OH, —$C_1$-$C_6$ alkyl-$C_1$-$C_6$alkoxy, aryloxy (e.g., phenyloxy), —S(O$_2$)R$_{10}$, —NR$_{11}$R$_{11}$, —C(O)NR$_{11}$R$_{11}$, —SO$_2$NR$_{11}$R$_{11}$, —NR$_{11}$C(O)R$_{10}$, —NR$_{11}$SO$_2$R$_{10}$, —O—C(O)NR$_{11}$R$_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, wherein the phenyl portions of the above are optionally substituted e.g., with one or more groups that are independently $C_1$-$C_6$ alkyl, $C_1$-$C_6$ alkoxy, $C_1$-$C_4$ haloalkyl (e.g. CF$_3$), $C_1$-$C_4$ haloalkoxy (e.g. OCF$_3$), hydroxyl, CN, NO$_2$ or halogen;

$R_{30}$, $R_{35}$, $R_{40}$, and $R_{45}$ are independently H, halogen, $C_1$-$C_6$ alkyl, $C_2$-$C_8$ alkenyl, $C_2$-$C_8$ alkynyl, $C_2$-$C_8$ haloalkenyl, $C_2$-$C_8$ haloalkynyl, —C(O)OR$_{11}$, —SO$_2$NR$_{11}$R$_{11}$, arylalkyl, cycloalkyl, $C_1$-$C_6$ haloalkyl, $C_1$-$C_6$ haloalkoxy, CN, NO$_2$, hydroxyl, $C_1$-$C_6$ alkoxy, —$C_1$-$C_6$ alkyl-OH, —$C_1$-$C_6$ alkyl-$C_1$-$C_6$ alkoxy, aryloxy, —S(O$_2$)R$_{10}$, —NR$_{11}$R$_{11}$, —C(O)NR$_{11}$R$_{11}$, —NR$_{11}$C(O)R$_{10}$, —NR$_{11}$SO$_2$R$_{10}$, —O—C(O)NR$_{11}$R$_{11}$, $C_2$-$C_6$ alkanoyl, heteroarylalkyl, heteroaryl, wherein each heteroaryl group is optionally substituted with a $C_1$-$C_6$ alkyl group, heterocycloalkyl $C_1$-$C_6$ alkyl, heterocycloalkyl (e.g., pyrrolidinyl, imidazolidinyl, piperidinyl, morpholinyl), wherein each heterocycloalkyl group is optionally substituted e.g., with one or two groups that are independently $C_1$-$C_6$ alkyl, $C_1$-$C_6$ alkoxy or halogen, aryl (e.g., phenyl or naphthyl), aryloxy (e.g., phenyloxy or naphthyloxy) or arylalkyl (e.g., phenyl $C_1$-$C_6$ alkyl), where the aryl portions of the above are optionally substituted e.g., with one or more groups that are independently $C_1$-$C_6$ alkyl, $C_1$-$C_6$ alkoxy, $C_1$-$C_4$ haloalky (e.g. CF$_3$), $C_1$-$C_4$ haloalkoxy (e.g. OCF$_3$), hydroxyl, CN, NO$_2$ or halogen; and wherein when the C-ring is aryl or heteroaryl, two adjacent substituents of the C-ring, together with the carbons to which they are attached, optionally form a heterocycloalkyl (e.g., —OCH$_2$O—, —OC(O)O— or —OCH$_2$CH$_2$O—) or a heteroaryl ring, each of which is optionally substituted e.g., with one or more groups that are independently alkyl, alkoxy, halogen or $C_2$-$C_4$ alkanoyl wherein the alkanoyl group is optionally further substituted with up to 3 halogen atoms; or two adjacent carbons of the C-ring optionally form a benzo ring which is optionally substituted e.g., with 1 to 4 groups that are independently halogen, hydroxyl, alkyl, alkoxy, haloalkyl, haloalkoxy, CN or NO$_2$;

dashed bonds may be a single or double bond;

the A-ring is aryl, cycloalkyl, heteroaryl or heterocycloalkyl, where each ring is optionally substituted e.g., at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, aryloxy, —S(O)$_{0-2}$—($C_1$-$C_6$ alkyl), —NR$_{11}$R$_{11}$, —C(O)NR$_{11}$R$_{11}$, —NR$_{11}$C(O)R$_{10}$, —NR$_{11}$SO$_2$R$_{10}$, —O—C(O)NR$_{11}$R$_{11}$, NO$_2$, CN, $C_2$-$C_6$ alkanoyl, $C_0$-$C_3$alkylCO$_2$R$_{11}$, heteroaryl, heterocycloalkyl, aryl, arylalkyl, —OCH$_2$O—, —OCH$_2$CH$_2$O— or —SO$_2$NR$_{11}$R$_{11}$;

the B-ring is a heteroaryl ring (e.g., imidazolyl or pyrazolyl) or a heterocycloalkyl ring (e.g. dihydropyrazolyl, pyrazolonyl or pyrazolidinonyl) each of which is optionally substituted at a substitutable position e.g., with one or more R$_{20}$ groups, which are independently selected from —NR$_{11}$—$C_2$-$C_6$ alkanoyl, $C_1$-$C_6$ alkyl, $C_3$-$C_8$ cycloalkyl, $C_2$-$C_6$ alkenyl, $C_2$-$C_6$ alkynyl, $C_1$-$C_6$ alkoxy, amino, $C_1$-$C_6$ alkylamino, $C_1$-$C_6$ dialkylamino, —S(O)$_{0-2}$R$_{10}$, hydroxy, hydroxyalkyl, halo, $C_1$-$C_4$ haloalkyl, $C_1$-$C_4$ haloalkoxy, —NR$_{11}$C(O)R$_{10}$, —NR$_{11}$SO$_2$R$_{10}$, —C(O)R$_{10}$, —C(O)OR$_{11}$, —C(O)alkylOC(O)R$_{10}$, —C(O)NR$_{11}$R$_{11}$, —NR$_{11}$C(O)R$_{10}$, —NR$_{11}$SO$_2$R$_{10}$, oxo, CN or $C_0$-$C_1$alkylaryl (where the aryl group is, e.g., phenyl or naphthyl, where phenyl is preferred), where the aryl is optionally substituted e.g., with 1, 2, 3, 4 or 5 groups that are independently selected from halogen, $C_1$-$C_6$ alkyl, —CO$_2$R$_{11}$, $C_1$-$C_6$ alkoxy, haloalkyl, haloalkoxy, hydroxyl, CN, NO$_2$, aryloxy, —S(O)$_{0-2}$—($C_1$-$C_6$ alkyl), —NR$_{11}$R$_{11}$, $C_2$-$C_6$ alkanoyl, pyridyl, phenyl, and —SO$_2$NR$_{11}$R$_{11}$;

$R_{50}$ is oxo, =N—NHR$_{12}$ or =N—O—R$_{13}$ (provided that $R_{51}$ is absent, and $R_{50}$ is not attached to a carbon-carbon double bond) or $R_{50}$ is halogen, $C_1$-$C_6$ alkyl, $C_2$-$C_8$ alkenyl, $C_2$-$C_8$ alkynyl, hydroxy, hydroxy $C_1$-$C_6$ alkyl, $C_1$-$C_6$ alkoxy, $C_1$-$C_6$ haloalkoxy, $C_1$-$C_6$ haloalkyl, halo $C_2$-$C_8$ alkenyl, $C_2$-$C_6$ alkanoyl, halo $C_2$-$C_8$ alkynyl, —C(O)OR$_{11}$, —($C_1$-$C_4$ alkyl)-C(O)OR$_{11}$, —CONR$_{11}$R$_{11}$, —OC(O)NR$_{11}$R$_{11}$, —NR$_{11}$C(O)OR$_{10}$, —NR$_{11}$S(O)$_2$R$_{10}$, —OS(O)$_2$R$_{10}$, —S(O)$_2$R$_{10}$, NR$_{11}$C(O)R$_{10}$, CN, —NR$_{11}$R$_{11}$, —SO$_2$NR$_{11}$R$_{11}$, heteroaryl, for instance, pyrazolyl, thiadiazolyl, triazolyl, isoxazolyl, isothiazolyl, imidazolyl, thiazolyl, oxadiazolyl, and pyridyl, heterocycloalkyl, for instance, tetrahydrofuranyl, pyrrolidinyl, piperidinyl, morpholinyl, and imidazolidinyl, $C_3$-$C_6$ cycloalkyl, aryl, for instance, phenyl and naphthyl; wherein the aforementioned heteroaryl, heterocycloalkyl, cycloalkyl and aryl groups are optionally substituted with 1 or more groups that are independently halogen, $C_1$-$C_6$ alkyl, $C_2$-$C_6$ alkenyl, $C_2$-$C_6$ alkynyl, hydroxy, hydroxy$C_1$-$C_6$ alkyl, $C_1$-$C_6$ alkoxy, $C_1$-$C_6$ haloalkoxy, $C_1$-$C_6$ haloalkyl, halo $C_2$-$C_6$ alkenyl, halo $C_2$-$C_6$ alkynyl, —C(O)$OR_{11}$, —($C_1$-$C_4$ alkyl)-C(O)$OR_{11}$, —$CONR_{11}R_{11}$, —OC(O)$NR_{11}R_{11}$, —$NR_{11}$C(O)$OR_{10}$, —$NR_{11}$S(O)$_2R_{10}$, —OS(O)$_2$$R_{10}$, —S(O)$_2R_{10}$, —$NR_{11}$C(O)$R_{10}$, CN, =N—$NHR_{12}$, —$NR_{11}R_{11}$, —SO$_2NR_{11}R_{11}$, heteroaryl that is selected from pyrazolyl, thiadiazolyl, triazolyl isoxazolyl, isothiazolyl, imidazolyl, thiazolyl, oxadiazolyl, oxazolyl, tetrazolyl, and pyridyl, heterocycloalkyl that is selected from tetrahydrofuranyl, pyrrolidinyl, piperidinyl, morpholinyl, and imidazolidinyl, $C_3$-$C_6$ cycloalkyl, aryl that is selected from phenyl, benzo[d][1,3]dioxolyl, and naphthyl or =N—O—$R_{13}$; wherein the aforementioned heteroaryl, heterocycloalkyl, cycloalkyl and aryl substituents are optionally substituted with 1 or more groups that are independently halogen, $C_1$-$C_6$ alkyl, $C_1$-$C_6$ alkoxy, hydroxy, $C_1$-$C_6$ hydroxyalkyl, $C_1$-$C_6$ haloalkoxy or $C_1$-$C_6$ haloalkyl;

each $R_{51}$ is independently absent, H, $C_1$-$C_4$ alkyl, halogen (e.g., F or Cl), OH, $C_1$-$C_4$ alkoxy, CN, amino, mono alkylamino, dialkylamino, $C_1$-$C_4$ haloalkoxy (e.g., OCF$_3$) or $C_1$-$C_4$ haloalkyl (e.g., CF$_3$); or when there are two $R_{51}$ groups on a carbon atom, the two $R_{51}$ groups and the carbon to which they are attached may form a 3- to 6-membered cycloalkyl or heterocycloalkyl ring; or when there are two $R_{51}$ groups on a carbon, the two $R_{51}$ groups may form an oxo group; or when there are two $R_{51}$ groups on a carbon, the two $R_{51}$ groups may form an alkene group; or when there are two $R_5$, groups on a carbon, the two $R_{51}$ groups may form an oxime or a $C_1$-$C_4$ alkylated oxime (e.g., O-methyl oxime);

a non-bridgehead carbon (and any substituent or substituents thereon) in the [3.3.1], [3.2.1] or [2.2.1] ring systems may be replaced with an $NR_{15}$ group;

$R_{10}$ and $R_{11}$ at each occurrence are independently $C_3$-$C_6$ cycloalkyl, heteroaryl, heterocycloalkyl, aryl, $C_2$-$C_6$ alkanoyl or $C_1$-$C_6$ alkyl optionally substituted e.g., with —C(O)$OR_{11}$ or alkoxy, where the alkoxy group is optionally further substituted with —C(O)$OR_{11}$, and where the heteroaryl and aryl groups are optionally substituted e.g., with 1 to 3 groups that are independently halogen, hydroxyl, alkyl, alkoxy, haloalkyl, haloalkoxy, CN or NO$_2$; or if two $R_{11}$ groups are on a nitrogen, then the two $R_{11}$ groups together with the nitrogen to which they are attached, may form a 3-8 membered ring optionally including an additional heteroatom such as e.g., NH, $NR_{12}$, $NR_{13}$, O or S, and additionally $R_{11}$ may be H;

$R_{12}$ is H, $C_1$-$C_6$ alkyl, aryl or —SO$_2$-aryl, where each aryl is optionally substituted e.g., with 1 to 5 groups that are independently halogen, hydroxyl, alkyl, alkoxy, haloalkyl, haloalkoxy, CN or NO$_2$;

$R_{13}$ is H, aryl or $C_1$-$C_6$ alkyl optionally substituted e.g., with aryl (such as phenyl or naphthyl, more preferably, phenyl), hydroxyl, $C_1$-$C_6$ alkoxy or halogen, where each aryl group is optionally substituted e.g., with 1 to 5 groups that are independently halogen, hydroxyl, alkyl, alkoxy, haloalkyl, haloalkoxy, CN or NO$_2$;

$R_{15}$ is H, phenyl, pyridyl, pyrimidinyl, oxazolyl, thiazolyl, imidazolyl, thienyl, furanyl, pyrrolyl, piperidinyl, piperazinyl, pyrrolidinyl, imidazolidinyl, indolyl, quinolinyl, —SO$_2R_{10}$, —C(O)$R_{10}$, C(O)$OR_{11}$ or $C_1$-$C_6$ alkyl optionally substituted e.g., with phenyl, hydroxyl or halogen, where the above cyclic groups are optionally substituted e.g., with 1 to 5 groups that are independently halogen, hydroxyl, $C_1$-$C_6$ alkyl, $C_1$-$C_6$ alkoxy, $C_1$-$C_6$ haloalkyl (e.g., CF$_3$ or CH$_2$CF$_3$), $C_1$-$C_4$ haloalkoxy (e.g., OCF$_3$ or OCH$_2$CF$_3$), CN, amino, NH($C_1$-$C_6$ alkyl), N($C_1$-$C_6$ alkyl) ($C_1$-$C_6$ alkyl) or NO$_2$; and each $R_{25}$ is independently H, $C_1$-$C_6$ alkyl, $C_1$-$C_6$ haloalkyl, —C(O)$OR_{11}$, —($C_1$-$C_6$ alkyl)-C(O)$OR_{11}$, $C_1$-$C_6$ alkoxy $C_1$-$C_6$ alkyl, —$CONR_{11}R_{11}$, CN or hydroxy $C_1$-$C_6$ alkyl. One bridgehead carbon and the corresponding $R_{25}$ group in Formulas 1, 2, 3, 4 and/or 5 is optionally replaced with an N; and in an [3.3.1] core, a non-bridgehead carbon may be replaced with a Z group, where Z is N.

The compounds of Formulas 1, 2, 3, and 4 inhibit β-amyloid peptide release and/or its synthesis and, therefore, are useful in the prevention of neurodegenerative diseases, such as Alzheimers Disease (AD), e.g., in patients susceptible to AD and/or in the treatment of patients with AD in order to inhibit further deterioration in their condition. The invention also encompasses pharmaceutical compositions containing a compound of the invention and methods employing such compounds or compositions in the treatment of cognitive diseases, including Alzheimers disease.

The compounds of Formulas 1, 2, 3, and 4, also provide methods of treating a patient who has AD, methods of preventing a patient from getting Alzheimers disease, methods of helping to prevent or delay the onset of Alzheimers disease, for treating patients with mild cognitive impairment (MCI) and preventing or delaying the onset of Alzheimers disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, age related macular degeneration or diffuse Lewy body type of Alzheimers disease and who is in need of such treatment which comprises administration of a therapeutically effective amount of a compound of the invention.

In another aspect, provided herein are methods of preparing the compounds of the invention, as well as intermediates useful in preparing the compounds of the invention.

DETAILED DESCRIPTION OF THE INVENTION

In one aspect, provided herein are compounds of Formula 1a, i.e., compounds of Formula 1 having the formula:

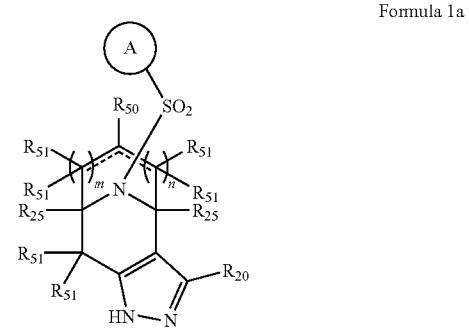

Formula 1a or stereoisomers, enantiomers or pharmaceutically acceptable salts thereof, wherein $R_{25}$, $R_{50}$, $R_{51}$, m, n, the dashed bonds and the A-ring is as defined above, and wherein $R_{20}$ is H, $C_1$-$C_6$ alkyl, $C_1$-$C_6$ alkoxy, amino, $C_1$-$C_6$ alkylamino, $C_1$-$C_6$ dialkylamino, halo, $CF_3$ or $-NR_{11}C(O)R_{10}$.

In another aspect, provided herein are compounds of Formulas 1b, 1c, 1d, 1e, 1f or 1g, i.e., compounds of Formula 1 that have the following formulas:

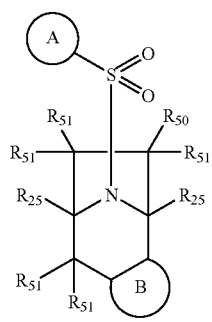

Formula Ib

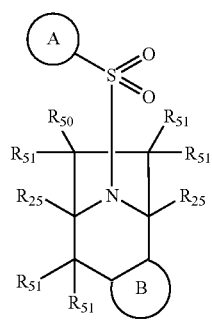

Formula Ic

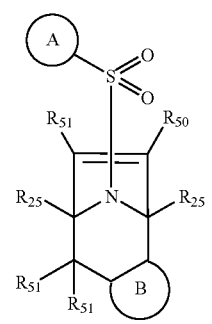

Formula Id

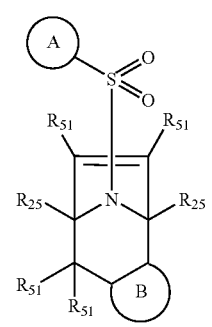

Formula Ie

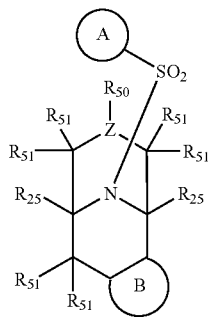

Formula If

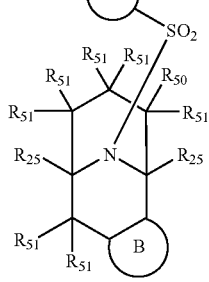

Formula Ig

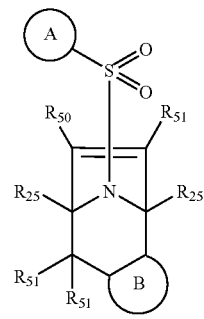

Formula Ih

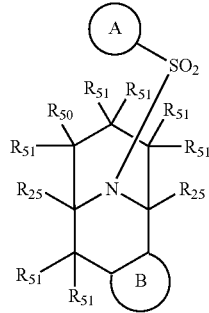

Formula Ii and enantiomers and/or pharmaceutically acceptable salts thereof, wherein the A-ring, B-ring, $R_{25}$, $R_{50}$ and $R_{51}$ are as defined above and where Z is N or CH.

In a first aspect, in the compounds of Formulas 1b, 1c, 1d, 1e, 1f, 1g, 1h, and 1i, the B-ring is pyrazolyl, dihydropyrazolyl, pyrazolonyl or pyrazolidinonyl, each of which is optionally substituted with $NR_{11}$—$C_2$-$C_6$ alkanoyl, $C_1$-$C_6$ alkyl, $C_3$-$C_6$ cycloalkyl, $C_2$-$C_4$ alkenyl, $C_2$-$C_4$ alkynyl, $C_1$-$C_4$ alkoxy, amino, $C_1$-$C_4$ alkylamino, $C_1$-$C_4$ dialkylamino, hydroxy, hydroxyalkyl, halo, $C_1$-$C_4$ haloalkyl, $C_1$-$C_4$ haloalkoxy, $-NR_{11}C(O)R_{10}$, $-NR_{11}SO_2R_{10}$ or CN.

In an embodiment of this aspect, in the above Formulae, $R_{50}$ is oxo, =N—$NHR_{12}$ or =N—O—$R_{13}$ (except in Formulas 2d, 2e, and 2o or $R_{50}$ is halogen, $C_1$-$C_6$ alkyl, $C_2$-$C_6$ alkenyl, $C_2$-$C_6$ alkynyl, hydroxy, hydroxy $C_1$-$C_6$ alkyl, $C_1$-$C_6$ alkoxy, $C_1$-$C_6$ haloalkoxy, $C_1$-$C_6$ haloalkyl, halo $C_2$-$C_6$ alkenyl, halo $C_2$-$C_6$ alkynyl, —C(O)OR$_{11}$, —($C_1$-$C_4$ alkyl)-C(O)OR$_{11}$, —CONR$_{11}$R$_{11}$, —OC(O)NR$_{11}$R$_{11}$, —NR$_{11}$C(O)OR$_{10}$, —NR$_{11}$S(O)$_2$R$_{10}$, —OS(O)$_2$R$_{10}$, —S(O)$_2$R$_{10}$, —NR$_{11}$C(O)R$_{10}$, CN, —NR$_{11}$R$_{11}$, —SO$_2$NR$_{11}$R$_{11}$, heteroaryl that is selected from pyrazolyl, thiadiazolyl, triazolyl isoxazolyl, isothiazolyl, imidazolyl, thiazolyl, oxadiazolyl, and pyridyl, heterocycloalkyl that is selected from tetrahydrofuranyl, pyrrolidinyl, piperidinyl, morpholinyl, and imidazolidinyl, $C_3$-$C_6$ cycloalkyl, aryl that is selected from phenyl and naphthyl; wherein the aforementioned heteroaryl, heterocycloalkyl, cycloalkyl and aryl groups are optionally substituted with 1 or more groups that are independently halogen, $C_1$-$C_6$ alkyl, $C_2$-$C_6$ alkenyl, $C_2$-$C_6$ alkynyl, hydroxy, hydroxy$C_1$-$C_6$ alkyl, $C_1$-$C_6$ alkoxy, $C_1$-$C_6$ haloalkoxy, $C_1$-$C_6$haloalkyl, halo $C_2$-$C_6$ alkenyl, halo $C_2$-$C_6$ alkynyl, —C(O)OR$_{11}$, —($C_1$-$C_4$ alkyl)-C(O)OR$_{11}$, —CONR$_{11}$R$_{11}$, —OC(O)NR$_{11}$R$_{11}$, —NR$_{11}$C(O)OR$_{10}$, —NR$_{11}$S(O)$_2$R$_{10}$, —OS(O)$_2$R$_{10}$, —S(O)$_2$R$_{10}$, —NR$_{11}$C(O)R$_{10}$, CN, =N—NHR$_{12}$, —NR$_{11}$R$_{11}$, —SO$_2$NR$_{11}$R$_{11}$, heteroaryl that is selected from pyrazolyl, thiadiazolyl, triazolyl isoxazolyl, isothiazolyl, imidazolyl, thiazolyl, oxadiazolyl, oxazolyl, tetrazolyl, and pyridyl, heterocycloalkyl that is selected from tetrahydrofuranyl, pyrrolidinyl, piperidinyl, morpholinyl, and imidazolidinyl, $C_3$-$C_6$ cycloalkyl, aryl that is selected from phenyl, benzo[d][1,3]dioxolyl, and naphthyl or =N—O—R$_{13}$; wherein the aforementioned heteroaryl, heterocycloalkyl, cycloalkyl and aryl substituents are optionally substituted with 1 or more groups that are independently halogen, $C_1$-$C_6$ alkyl, $C_1$-$C_6$ alkoxy, hydroxy, $C_1$-$C_6$ hydroxyalkyl, $C_1$-$C_6$ haloalkoxy or $C_1$-$C_6$ haloalkyl;

provided that in Formulas 1d and 1h, R$_{50}$ is not oxo, =N—O—R$_{13}$ or =N—NHR$_{12}$;

each R$_{51}$ is independently absent, H, $C_1$-$C_4$ alkyl, halogen (e.g., F, Cl or Br), CN, amino, mono alkylamino, dialkylamino, OH, $C_1$-$C_4$ haloalkoxy (e.g., OCF$_3$) or $C_1$-$C_4$ haloalkyl (e.g., CF$_3$); or when there are two R$_5$, groups on a carbon atom, the two R$_{51}$ groups and the carbon to which they are attached may form a 3- to 6-membered cycloalkyl or heterocycloalkyl ring; or when there are two R$_{51}$ groups on a carbon, the two R$_{51}$ groups may form an oxo group; or when there are two R$_{51}$ groups on a carbon, the two R$_{51}$ groups may form an alkene group; or when there are two R$_{51}$ groups on a carbon, the two R$_{51}$ groups may form an oxime or a $C_1$-$C_4$ alkylated oxime (e.g., O-methyl oxime);

R$_{10}$ and R$_{11}$ at each occurrence are independently $C_1$-$C_6$ alkyl, heteroaryl that is selected from pyrazolyl, thiadiazolyl, triazolyl, isoxazolyl, isothiazolyl, imidazolyl, thiazolyl, oxadiazolyl, and pyridyl or aryl that is selected from phenyl and naphthyl, where the heteroaryl and aryl groups are optionally substituted with 1 to 3 groups that are independently halogen, hydroxyl, alkyl, alkoxy, haloalkyl, haloalkoxy, CN or NO$_2$; or if two R$_{11}$ groups are on a nitrogen, then the two R$_{11}$ groups together with the nitrogen to which they are attached, may form a 3-8 membered ring optionally including an additional heteroatom such as NH, NR$_{12}$, NR$_{13}$, O or S; and additionally R$_{11}$ may be H;

R$_{12}$ is H, $C_1$-$C_6$ alkyl, aryl or —SO$_2$-aryl (e.g., phenyl or naphthyl, where phenyl is preferred), where each aryl group is optionally substituted with 1 to 5 groups that are independently halogen, hydroxyl, alkyl, alkoxy, haloalkyl, haloalkoxy, CN or NO$_2$;

R$_{13}$ is H, aryl or $C_1$-$C_6$ alkyl optionally substituted with aryl (such as phenyl or naphthyl, more preferably, phenyl), hydroxyl or halogen, where each aryl group is optionally substituted with 1 to 5 groups that are independently halogen, hydroxyl, alkyl, alkoxy, haloalkyl, haloalkoxy, CN or NO$_2$. In a further embodiment of this aspect, R$_{50}$ is oxo, =N—NHR$_{12}$ or =N—O—R$_{13}$, (provided that R$_{51}$ is absent, and R$_{50}$ is not attached to a carbon-carbon double bond) or R$_{50}$ is $C_2$-$C_8$ alkenyl, $C_2$-$C_8$ alkynyl, halo $C_2$-$C_8$ alkenyl, halo $C_2$-$C_8$ alkynyl, $C_2$-$C_6$ alkanoyl, —C(O)OR$_{11}$, —OS(O)$_2$R$_{10}$, —S(O)$_2$R$_{10}$, —NR$_{11}$R$_{11}$, —SO$_2$NR$_{11}$R$_{11}$, heteroaryl, heterocycloalkyl, cycloalkyl or aryl, wherein the heteroaryl, heterocycloalkyl, cycloalkyl and aryl groups are optionally substituted e.g., with 1 or more groups that are independently halogen, $C_1$-$C_6$ alkyl, $C_2$-$C_6$ alkenyl, $C_2$-$C_6$ alkynyl, hydroxy, hydroxy$C_1$-$C_6$ alkyl, $C_1$-$C_6$ alkoxy, $C_1$-$C_6$ haloalkoxy, $C_1$-$C_6$haloalkyl, halo $C_2$-$C_6$ alkenyl, halo $C_2$-$C_6$ alkynyl, —C(O)OR$_{11}$, —($C_1$-$C_4$ alkyl)-C(O)OR$_{11}$, —CONR$_{11}$R$_{11}$, —OC(O)NR$_{11}$R$_{11}$, —NR$_{11}$C(O)OR$_{10}$, —NR$_{11}$S(O)$_2$R$_{10}$, —OS(O)$_2$R$_{10}$, —S(O)$_2$R$_{10}$, —NR$_{11}$C(O)R$_{10}$, CN, =N—NHR$_{12}$, —NR$_{11}$R$_{11}$, —SO$_2$NR$_{11}$R$_{11}$, heteroaryl that is selected from pyrazolyl, thiadiazolyl, triazolyl isoxazolyl, isothiazolyl, imidazolyl, thiazolyl, oxadiazolyl, oxazolyl, tetrazolyl, and pyridyl, heterocycloalkyl that is selected from tetrahydrofuranyl, pyrrolidinyl, piperidinyl, morpholinyl, and imidazolidinyl, $C_3$-$C_6$ cycloalkyl, aryl that is selected from phenyl, benzo[d][1,3]dioxolyl, and naphthyl or =N—O—R$_{13}$; wherein the aforementioned heteroaryl, heterocycloalkyl, cycloalkyl and aryl substituents are optionally substituted with 1 or more groups that are independently halogen, $C_1$-$C_6$ alkyl, $C_1$-$C_6$ alkoxy, hydroxy, $C_1$-$C_6$ hydroxyalkyl, $C_1$-$C_6$ haloalkoxy or $C_1$-$C_6$ haloalkyl. In a further embodiment, R$_{50}$ is $C_2$-$C_6$ alkenyl, $C_2$-$C_6$ alkynyl, halo $C_2$-$C_6$ alkenyl, halo $C_2$-$C_6$ alkynyl, $C_2$-$C_6$ alkanoyl, OS(O)$_2$R$_{10}$, —S(O)$_2$R$_{10}$, —NR$_{11}$R$_{11}$, C(O)OR$_{11}$—SO$_2$NR$_{11}$R$_{11}$, heteroaryl that is selected from pyrazolyl, thiadiazolyl (e.g., 1,2,4-thiadiazolyl or 1,3,4-thiadiazolyl), triazolyl (e.g., 1,2,3-triazolyl or 1,2,4-triazolyl), isoxazolyl, isothiazolyl, imidazolyl, thiazolyl, oxadiazolyl (e.g., 1,2,4-oxadiazolyl or 1,3,4-oxadiazolyl), oxazolyl, tetrazolyl, and pyridyl, heterocycloalkyl that is selected from tetrahydrofuranyl, pyrrolidinyl, piperidinyl, morpholinyl, and imidazolidinyl, $C_3$-$C_6$ cycloalkyl, aryl that is selected from phenyl, benzo[d][1,3]dioxolyl, and naphthyl or =N—O—R$_{13}$; wherein the aforementioned heteroaryl, heterocycloalkyl, cycloalkyl and aryl substituents are optionally substituted with 1 or more groups that are independently halogen, $C_1$-$C_6$ alkyl, $C_1$-$C_6$ alkoxy, hydroxy, $C_1$-$C_6$ hydroxyalkyl, $C_1$-$C_6$ haloalkoxy or $C_1$-$C_6$ haloalkyl;

In an aspect, provided herein are compounds of Formula 1b, 1c, 1d, 1e, 1f, 1g, 1 h, and 1i, wherein the B-ring is pyrazolyl, dihydropyrazolyl, pyrazolonyl or pyrazolidinonyl, each of which is as defined in the first aspect, and R$_{50}$ is halogen, $C_1$-$C_6$ alkyl, $C_2$-$C_6$ alkenyl, $C_2$-$C_6$ alkynyl, hydroxy $C_1$-$C_6$ alkyl, $C_1$-$C_6$ alkoxy, halo $C_2$-$C_6$ alkenyl, halo $C_2$-$C_6$ alkynyl, $C_1$-$C_6$ haloalkoxy or $C_1$-$C_6$ haloalkyl. In one embodiment, $R_{50}$ is halogen, $C_1$-$C_4$ alkyl, hydroxy, hydroxy $C_1$-$C_4$ alkyl, $C_1$-$C_4$ alkoxy, halo $C_2$-$C_4$ alkenyl, halo $C_2$-$C_4$ alkynyl, $C_1$-$C_4$ haloalkoxy or $C_1$-$C_4$ haloalkyl. In another embodiment, $R_{50}$ is $C_1$-$C_4$ alkyl, $C_1$-$C_4$ haloalkyl, hydroxy $C_1$-$C_4$ alkyl or $C_1$-$C_4$ alkoxy. In still another embodiment, $R_{50}$ is $C_1$-$C_4$ alkyl. In yet another embodiment, $R_{50}$ is $C_1$-$C_4$ haloalkyl (e.g., $CF_3$ or $CH_2CF_3$), hydroxy $C_1$-$C_4$ alkyl or $C_1$-$C_4$ alkoxy (e.g., methoxy or ethoxy). In another embodiment, $R_{50}$ is $C_2$-$C_4$ alkenyl, $C_2$-$C_4$ alkynyl, halo $C_2$-$C_5$ alkenyl, halo $C_2$-$C_4$ alkynyl. In still another embodiment, $R_{50}$ is halogen, hydroxy or hydroxy $C_1$-$C_4$ alkyl. In yet still another embodiment, $R_{50}$ is halogen. In yet still another embodiment, $R_{50}$ is hydroxy or hydroxy $C_1$-$C_4$ alkyl.

In another aspect, provided herein are compounds of Formula 1b, 1c, 1d, 1e, 1f, 1g, 1h, and 1i, wherein the B-ring is pyrazolyl, dihydropyrazolyl, pyrazolonyl or pyrazolidinonyl, each of which is as defined above and wherein $R_{50}$ is —C(O)OR$_{11}$, —($C_1$-$C_4$ alkyl)-C(O)OR$_{11}$, —CONR$_{11}$R$_{11}$, —OC(O)NR$_{11}$R$_{11}$, —NR$_{11}$C(O)OR$_{11}$, —NR$_{11}$S(O)$_2$R$_{10}$, —OS(O)$_2$R$_{10}$, —S(O)$_2$R$_{10}$, —NR$_{11}$C(O)R$_{10}$, CN, =N—NHR$_{12}$, =N—O—R$_{13}$, NR$_{11}$R$_{11}$ or —SO$_2$NR$_{11}$R$_{11}$;

$R_{10}$ and $R_{11}$ at each occurrence are independently $C_1$-$C_6$ alkyl, heteroaryl that is selected from pyrazolyl, thiadiazolyl, triazolyl, isoxazolyl, isothiazolyl, imidazolyl, thiazolyl, oxadiazolyl, and pyridyl or aryl that is selected from phenyl and naphthyl, where the heteroaryl and aryl groups are optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or NO$_2$; and additionally $R_{11}$ may be H; or if two $R_{11}$ groups are on a nitrogen, then the two $R_{11}$ groups together with the nitrogen to which they are attached, may form a 3-8 membered ring optionally including an additional heteroatom such as NH, NR$_{12}$, NR$_{13}$, O or S;

$R_{12}$ is H, $C_1$-$C_6$ alkyl, aryl or SO$_2$-aryl (e.g., phenyl or naphthyl, where phenyl is preferred), where each aryl group is optionally substituted with 1 to 5 groups that are independently halogen, hydroxyl, alkyl, alkoxy, haloalkyl, haloalkoxy, CN or NO$_2$;

$R_{13}$ is H, aryl or $C_1$-$C_6$ alkyl optionally substituted with aryl (such as phenyl or naphthyl, more preferably, phenyl), hydroxyl or halogen, where each aryl group is optionally substituted with 1 to 5 groups that are independently halogen, hydroxyl, alkyl, alkoxy, haloalkyl, haloalkoxy, CN or NO$_2$.

In an embodiment of this aspect, $R_{10}$ is $C_1$-$C_4$ alkyl and $R_{11}$ is independently hydrogen or $C_1$-$C_4$ alkyl.

In still another embodiment of this aspect, $R_{11}$ is H.

In still another embodiment of this aspect, one of $R_{10}$ and $R_{11}$ is CH$_3$.

In another embodiment of this aspect, $R_{10}$ and $R_{11}$ together with the nitrogen to which they are attached may form a 3-8 membered ring, which optionally includes an additional heteroatom that is NH, NR$_{12}$, NR$_{13}$, O or S.

In still another embodiment of this aspect, $R_{10}$ and $R_{11}$ at each occurrence are independently phenyl optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or NO$_2$; and additionally $R_{11}$ may be H.

In another embodiment of this aspect, $R_{10}$ and $R_{11}$ at each occurrence are independently pyrazolyl, isoxazolyl, isothiazolyl, imidazolyl or thiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or NO$_2$; and additionally $R_{11}$ may be H.

In another embodiment of this aspect, $R_{10}$ and $R_{11}$ at each occurrence are independently thiadiazolyl, triazolyl or oxadiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or NO$_2$; and additionally $R_{11}$ may be H.

In yet still another embodiment of this aspect, $R_{13}$ is H, $C_1$-$C_4$ alkyl or benzyl, where then phenyl portion is optionally substituted with halogen, hydroxyl, $C_1$-$C_4$ alkyl, $C_1$-$C_4$ alkoxy, $CF_3$ or $OCF_3$. In another embodiment, $R_{13}$ is $C_1$-$C_4$ alkyl or benzyl.

In another aspect, provided herein are compounds of Formula 1b, 1c, 1d, 1e, 1f, 1g, 1h, and 1i, wherein the B-ring is pyrazolyl, dihydropyrazolyl, pyrazolonyl or pyrazolidinonyl, each of which is as defined above, and wherein $R_{50}$ is —C(O)OR$_{11}$, —CONR$_{11}$R$_{11}$, —OC(O)NR$_{11}$R$_{11}$, —NR$_{11}$C(O)OR$_{10}$, —NR$_{11}$S(O)$_2$R$_{10}$, —OS(O)$_2$R$_{10}$, —S(O)$_2$R$_{10}$, —NR$_{11}$C(O)R$_{10}$, NR$_{11}$R$_{11}$ or —SO$_2$NR$_{11}$R$_{11}$, wherein $R_{10}$ and $R_{11}$ at each occurrence are independently $C_1$-$C_6$ alkyl, heteroaryl that is selected from pyrazolyl, thiadiazolyl, triazolyl, isoxazolyl, isothiazolyl, imidazolyl, thiazolyl, oxadiazolyl, and pyridyl or aryl that is selected from phenyl and naphthyl, where the heteroaryl and aryl groups are optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or NO$_2$; or if two $R_{11}$ groups are on a nitrogen, then the two $R_{11}$ groups together with the nitrogen to which they are attached, may form a 3-8 membered ring optionally including an additional heteroatom such as NH, NR$_{12}$, NR$_{13}$, O or S, and additionally $R_{11}$ may be H;

$R_{12}$ is H, $C_1$-$C_6$ alkyl, aryl or SO$_2$-aryl (e.g., phenyl or naphthyl, where phenyl is preferred), where each aryl group is optionally substituted with 1 to 5 groups that are independently halogen, hydroxyl, alkyl, alkoxy, haloalkyl, haloalkoxy, CN or NO$_2$;

$R_{13}$ is H, aryl or $C_1$-$C_6$ alkyl optionally substituted with aryl (such as phenyl or naphthyl, more preferably, phenyl), hydroxyl or halogen, where each aryl group is optionally substituted with 1 to 5 groups that are independently halogen, hydroxyl, alkyl, alkoxy, haloalkyl, haloalkoxy, CN or NO$_2$.

In an embodiment of this aspect, $R_{10}$ is $C_1$-$C_4$ alkyl and $R_{11}$ is independently hydrogen or $C_1$-$C_4$ alkyl.

In still another embodiment of this aspect, $R_{11}$ is H.

In still another embodiment of this aspect, one of $R_{10}$ and $R_{11}$ is CH$_3$.

In another embodiment of this aspect, the two $R_{11}$ groups together with the nitrogen to which they are attached form a 3-8 membered ring, which optionally includes an additional heteroatom that is NH, NR$_{12}$, NR$_{13}$, O or S.

In another embodiment of this aspect, $R_{10}$ and $R_{11}$ at each occurrence are independently phenyl optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or NO$_2$; and additionally $R_{11}$ may be H.

In another embodiment of this aspect, $R_{10}$ and $R_{11}$ at each occurrence are independently pyrazolyl, isoxazolyl, isothiazolyl, imidazolyl or thiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or NO$_2$; and additionally $R_{11}$ may be H.

In another embodiment of this aspect, $R_{10}$ and $R_{11}$ at each occurrence are independently H, thiadiazolyl, triazolyl or oxadiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or NO$_2$; and additionally $R_{11}$ may be H.

In yet still another embodiment of this aspect, $R_{13}$ is H, $C_1$-$C_4$ alkyl or benzyl, where then phenyl portion is optionally substituted with halogen, hydroxyl, $C_1$-$C_4$ alkyl, $C_1$-$C_4$ alkoxy, $CF_3$ or $OCF_3$. In another embodiment, $R_{13}$ is $C_1$-$C_4$ alkyl or benzyl.

In another aspect, provided herein are compounds of Formula 1b, 1c, 1d, 1e, 1f, 1g, 1 h, and 1i, wherein the B-ring is pyrazolyl, dihydropyrazolyl, pyrazolonyl or pyrazolidinonyl, each of which is as defined above, and wherein $R_{50}$ is heteroaryl that is selected from pyrazolyl, thiadiazolyl, triazolyl, isoxazolyl, isothiazolyl, imidazolyl, thiazolyl, oxadiazolyl, and pyridyl, heterocycloalkyl that is selected from tetrahydrofuranyl, pyrrolidinyl, piperidinyl, morpholinyl, and imidazolidinyl, each of which is optionally substituted with 1 or more groups that are independently halogen, $C_1$-$C_6$ alkyl, $C_1$-$C_6$ alkoxy, hydroxy, $C_1$-$C_6$ hydroxyalkyl, $C_1$-$C_6$ haloalkoxy or $C_1$-$C_6$ haloalkyl.

In an embodiment of this aspect, $R_{50}$ is pyrazolyl or imidazolyl, each of which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., $OCF_3$) or $C_1$-$C_4$ haloalkyl (e.g., $CF_3$). In a further embodiment of this aspect, $R_{50}$ is unsubstituted.

In an embodiment of this aspect, $R_{50}$ is thiazolyl or oxadiazolyl each of which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., $OCF_3$) or $C_1$-$C_4$ haloalkyl (e.g., $CF_3$). In a further embodiment of this aspect, $R_{50}$ is unsubstituted.

In an embodiment of this aspect, $R_{50}$ is pyridyl, which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., $OCF_3$) or $C_1$-$C_4$ haloalkyl (e.g., $CF_3$). In a further embodiment of this aspect, $R_{50}$ is unsubstituted.

In an embodiment of this aspect, $R_{50}$ is thiadiazolyl, which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., $OCF_3$) or $C_1$-$C_4$ haloalkyl (e.g., $CF_3$). In a further embodiment of this aspect, $R_{50}$ is unsubstituted.

In an embodiment of this aspect, $R_{50}$ is triazolyl, which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., $OCF_3$) or $C_1$-$C_4$ haloalkyl (e.g., $CF_3$). In a further embodiment of this aspect, $R_{50}$ is unsubstituted.

In an embodiment of this aspect, $R_{50}$ is isoxazolyl, which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., $OCF_3$) or $C_1$-$C_4$ haloalkyl (e.g., $CF_3$). In a further embodiment of this aspect, $R_{40}$ is unsubstituted.

In an embodiment of this aspect, $R_{50}$ is isothiazolyl, which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., $OCF_3$) or $C_1$-$C_4$ haloalkyl (e.g., $CF_3$). In a further embodiment of this aspect, $R_{50}$ is unsubstituted.

In an embodiment of this aspect, $R_{50}$ is selected from tetrahydrofuranyl, pyrrolidinyl, and imidazolidinyl, each of which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., $OCF_3$) or $C_1$-$C_4$ haloalkyl (e.g., $CF_3$). In a further embodiment of this aspect, $R_{50}$ is unsubstituted.

In an embodiment of this aspect, $R_{50}$ is piperidinyl or morpholinyl, each of which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., $OCF_3$) or $C_1$-$C_4$ haloalkyl (e.g., $CF_3$). In a further embodiment of this aspect, $R_{50}$ is unsubstituted.

In a further embodiment of this aspect, $R_{50}$ is unsubstituted.

In a still further embodiment of this aspect, $R_{50}$ is substituted with one group that is halogen, $C_1$-$C_2$ alkyl, $C_1$-$C_2$ alkoxy, hydroxy, $C_1$-$C_2$ hydroxyalkyl, $C_1$-$C_2$ haloalkoxy (e.g., $OCF_3$) or $C_1$-$C_2$ haloalkyl (e.g., $CF_3$).

In another aspect, provided herein are compounds of Formula 1b, 1c, 1d, 1e, 1f, 1g, 1 h, and 1i, wherein the B-ring is pyrazolyl, dihydropyrazolyl, pyrazolonyl or pyrazolidinonyl, each of which is as defined above, and wherein $R_{50}$ is $C_3$-$C_6$ cycloalkyl, which is optionally substituted with 1 or more groups that are independently halogen, $C_1$-$C_6$ alkyl, $C_1$-$C_6$ alkoxy, hydroxy, $C_1$-$C_6$ hydroxyalkyl, $C_1$-$C_6$ haloalkoxy or $C_1$-$C_6$ haloalkyl.

In an embodiment of this aspect, $R_{50}$ is unsubstituted $C_3$-$C_6$ cycloalkyl. In a further embodiment, $R_{50}$ is cyclopropyl.

In another embodiment of this aspect, $R_{50}$ is $C_3$-$C_6$ cycloalkyl substituted with one or two groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., $OCF_3$) or $C_1$-$C_4$ haloalkyl (e.g., $CF_3$).

In still another embodiment, $R_{50}$ is cyclopropyl, cyclopentyl or cyclohexyl, each of which is optionally substituted with halogen, $C_1$-$C_2$ alkyl, $C_1$-$C_2$ alkoxy (e.g., methoxy), hydroxy, $C_1$-$C_2$ hydroxyalkyl, $C_1$-$C_2$ haloalkoxy (e.g., $OCF_3$) or $C_1$-$C_2$ haloalkyl (e.g., $CF_3$).

In still another embodiment, $R_{50}$ is cyclopropyl, substituted with one group that is halogen, $C_1$-$C_2$ alkyl, $C_1$-$C_2$ alkoxy (e.g., methoxy), hydroxy or $C_1$-$C_2$ hydroxyalkyl.

In another aspect, provided herein are compounds of Formula 1b, 1c, 1d, 1e, 1f, 1g, 1 h, and 1i, wherein the B-ring is pyrazolyl, dihydropyrazolyl, pyrazolonyl or pyrazolidinonyl, each of which is as defined above, and wherein $R_{50}$ is aryl that is selected from phenyl, benzo[d][1,3]dioxolyl, and naphthyl, each of which is optionally substituted with one or more groups that are independently halogen, $C_1$-$C_6$ alkyl, $C_1$-$C_6$ alkoxy, hydroxy, $C_1$-$C_6$ hydroxyalkyl, $C_1$-$C_6$ haloalkoxy or $C_1$-$C_6$ haloalkyl.

In an embodiment of this aspect, $R_{50}$ is phenyl, which is optionally substituted with one or more groups that are independently halogen (e.g., F), $C_1$-$C_4$ alkyl, $C_1$-$C_4$ alkoxy, hydroxy, $C_1$-$C_4$ hydroxyalkyl, $C_1$-$C_4$ haloalkoxy (e.g., $OCF_3$) or $C_1$-$C_4$ haloalkyl (e.g., $CF_3$).

In another embodiment of this aspect, $R_{50}$ is unsubstituted phenyl.

In still yet another embodiment of this aspect, $R_{50}$ is phenyl, which is substituted with at least one group that is halogen (e.g., F), $C_1$-$C_2$ alkyl, $C_1$-$C_2$ alkoxy, hydroxy, $C_1$-$C_2$ hydroxyalkyl, $C_1$-$C_2$ haloalkoxy (e.g., $OCF_3$), $C_1$-$C_2$ haloalkyl (e.g., $CF_3$) or —CN. In a further embodiment, the phenyl group is substituted with two independently selected groups.

In still yet another embodiment of this aspect, $R_{50}$ is phenyl, which is substituted with at least one group that is halogen (e.g., F), $C_1$-$C_2$ alkyl, $C_1$-$C_2$ alkoxy, hydroxy, $C_1$-$C_2$ hydroxyalkyl, $C_1$-$C_2$ haloalkoxy (e.g., $OCF_3$), $C_1$-$C_2$ haloalkyl (e.g., $CF_3$) or —CN. In a further embodiment, the phenyl group is substituted with two groups. In a still further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In still yet another embodiment of this aspect, $R_{50}$ is phenyl, which is substituted with one group that is halogen (e.g., F), $C_1$-$C_2$ alkyl, $C_1$-$C_2$ alkoxy, hydroxy, $C_1$-$C_2$ hydroxyalkyl, $C_1$-$C_2$ haloalkoxy (e.g., $OCF_3$) or $C_1$-$C_2$ haloalkyl (e.g., $CF_3$).

In an embodiment of this aspect, $R_{50}$ is benzo[d][1,3]dioxolyl, which is optionally substituted with one or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., $OCF_3$) or $C_1$-$C_4$ haloalkyl (e.g., $CF_3$). In a further embodiment, the methylene group of the benzo[d][1,3]dioxolyl group is substituted with one or two $C_1$-$C_4$ alkyl groups (such as, e.g., one or two methyl groups).

In another embodiment of this aspect, $R_{50}$ is benzo[d][1,3]dioxolyl, which is unsubstituted.

In still yet another embodiment of this aspect, $R_{50}$ is benzo[d][1,3]dioxolyl, which is substituted with at least one group that is halogen, $C_1$-$C_2$ alkyl, $C_1$-$C_2$ alkoxy, hydroxy, $C_1$-$C_2$ hydroxyalkyl, $C_1$-$C_2$ haloalkoxy (e.g., $OCF_3$), $C_1$-$C_2$ haloalkyl (e.g., $CF_3$) or —CN.

In still yet another embodiment of this aspect, $R_{50}$ is benzo[d][1,3]dioxolyl, which is substituted with one group that is halogen, $C_1$-$C_2$ alkyl, $C_1$-$C_2$ alkoxy, hydroxy, $C_1$-$C_2$ hydroxyalkyl, $OCF_3$ or $CF_3$.

In another aspect, provided herein are compounds of Formula 1b, 1c, 1d, 1e, 1f, 1g, 1 h, and 1i, wherein the B-ring is pyrazolyl, dihydropyrazolyl, pyrazolonyl or pyrazolidinonyl, each of which is as defined above, and wherein $R_{50}$ is $C_1$-$C_4$ alkyl and $R_{51}$H or $C_1$-$C_4$ alkyl. In a further embodiment, $R_{50}$ and $R_{51}$ are both methyl.

In one aspect of Formula 1f, Z is N. In a further embodiment of this aspect, $R_{50}$ is —C(O)$OR_{11}$, $C_2$-$C_6$ alkanoyl, —$SO_2R_{10}$ or —$CONR_{11}R_{11}$; wherein $R_{10}$ is $C_1$-$C_4$ alkyl or $C_3$-$C_6$ cycloalkyl; $R_{11}$ is H or $C_1$-$C_6$ alkyl; and $R_{13}$ is H or $C_1$-$C_4$ alkyl optionally substituted with $C_1$-$C_4$ alkoxy. In an embodiment of this aspect, $R_{50}$ is —C(O)$OR_{11}$ and $R_{13}$ is $C_1$-$C_1$-$C_4$ alkyl or $C_1$-$C_4$ alkyl substituted with $C_1$-$C_4$ alkoxy. In another embodiment of this aspect, $R_{50}$ is $C_2$-$C_4$ alkanoyl. In an embodiment of this aspect, $R_{50}$ is —$SO_2R_{10}$ and $R_{10}$ is $C_1$-$C_3$ alkyl or cyclopropyl. In a further embodiment of this aspect, $R_{50}$ is —$CONR_{11}R_{11}$ and each $R_{11}$ is H or $C_1$-$C_4$ alkyl.

In a further embodiment of this aspect, all $R_{51}$ groups are H and the B-ring is pyrazolyl, dihydropyrazolyl, pyrazolonyl or pyrazolidinonyl, each of which is as defined above.

In one aspect of Formula 1e (when Z is CH) and in an aspect of Formula 1a, wherein $R_{50}$ is $NR_{11}R_{11}$, or $SO_2NR_{11}R_{11}$, or $S(O)_2R_{10}$, or oxadiazolyl, optionally substituted with $C_1$-$C_4$ alkyl, or $C_3$-$C_6$ cycloalkyl optionally substituted with $C_1$-$C_4$ alkyl or $C_1$-$C_4$ alkoxy, or phenyl optionally substituted with one or more groups that are independently $C_1$-$C_4$ alkyl, $C_1$-$C_4$ alkoxy, halogen, —$OCH_2O$—, —$OCH_2CH_2O$—, oxazolidinone (e.g., oxazolidin-2-one), imidazolyl, thiazolyl, —$NR_{11}$-cyclohexyl, where the cyclohexyl is optionally substituted with $NR_{11}R_{11}$, $C_1$-$C_4$ alkyl or $C_1$-$C_4$ alkoxy; pyrazolyl, tetrazolyl, pyrrolidinonyl, —$NR_{11}R_{11}$, morpholinyl (e.g., morpholin-2-onyl),

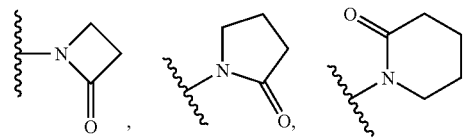

or $C_2$-$C_6$ alkanoyl; or pyrazolyl optionally substituted with $C_1$-$C_4$ alkyl; or thiazolyl optionally substituted with $C_1$-$C_4$ alkyl, $C_1$-$C_4$ haloalkyl (e.g., $CF_3$ or $CHF_2$); or oxazolyl optionally substituted with $C_1$-$C_4$ alkyl; or benzimidazolyl optionally substituted with $C_1$-$C_4$ alkyl, $C_1$-$C_4$ alkoxy or halogen; or $C_2$-$C_6$ alkenyl optionally substituted with a halogen (e.g., Cl) or $C_1$-$C_4$ haloalkyl (e.g., $CF_3$); or triazolyl optionally substituted with one or two groups that are independently $C_1$-$C_4$ alkyl; or $C_2$-$C_6$ alkynyl optionally substituted with a halogen (e.g., Cl) or $C_1$-$C_4$ alkoxy; or thiadiazolyl optionally substituted with $C_1$-$C_4$ alkyl, $C_1$-$C_4$ haloalkyl (e.g., $CF_3$ or $CHF_2$); or pyridyl optionally substituted with one or more groups that are independently $C_1$-$C_4$ alkyl, halogen or $C_1$-$C_4$ alkoxy; or wherein $R_{11}$ is H, $C_1$-$C_6$ alkyl or $C_2$-$C_6$ alkanoyl, where the alkyl portions of $R_{11}$ are optionally substituted with one or two groups that are independently —$CO_2$—($C_1$-$C_6$ alkyl), $C_1$-$C_6$ alkyl-O—($C_1$-$C_6$ alkyl), $C_1$-$C_6$ alkyl-O—($C_1$-$C_4$ alkyl)-$CO_2$—($C_1$-$C_6$ alkyl), $C_1$-$C_6$ alkyl-O—($C_1$-$C_4$ alkyl)-$CO_2$H.

In an embodiment of this aspect, $R_{50}$ is $C_1$-$C_4$ haloalkyl (e.g., $CF_3$ or $CHF_2$), CN, $C_1$-$C_4$ alkoxy $C_1$-$C_6$ alkyl or $NR_{11}R_{11}$; where each $R_{11}$ is independently H or $C_1$-$C_4$ alkyl. In a further embodiment, $R_{50}$ is CN. In a still further embodiment, $R_{50}$ is methoxymethyl, methoxyethy, ethoxymethyl or ethoxyethyl.

In an embodiment of this aspect, $R_{50}$ is oxadiazolyl, substituted with a $C_1$-$C_2$ alkyl.

In an embodiment of this aspect, $R_{50}$ is phenyl optionally substituted with one or more groups that are independently $C_1$-$C_4$ alkyl, $C_1$-$C_4$ alkoxy, halogen, —$OCH_2O$—; —$OCH_2CH_2O$—, oxazolidinone (e.g., oxazolidin-2-one), imidazolyl, thiazolyl, —$NR_{11}$-cyclohexyl, where the cyclohexyl is optionally substituted with $NR_{11}R_{11}$, $C_1$-$C_4$ alkyl or $C_1$-$C_4$ alkoxy; pyrazolyl, tetrazolyl, pyrrolidinonyl, —$NR_{11}R_{11}$, morpholinyl (e.g., morpholin-2-only),

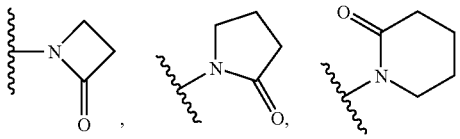

or $C_2$-$C_6$ alkanoyl. In a further embodiment, $R_{50}$ is unsubstituted phenyl. In another embodiment, $R_{50}$ is phenyl substituted with one or more groups that are independently $C_1$-$C_4$ alkyl, $C_1$-$C_4$ alkoxy or halogen (e.g., F, Cl or Br). In a further embodiment, $R_{50}$ is phenyl substituted with one group that is $C_1$-$C_4$ alkyl, $C_1$-$C_4$ alkoxy or halogen (e.g., F, Cl or Br). In another embodiment, $R_{50}$ is phenyl substituted with one group that is selected from oxazolidinonyl, imidazolyl, thiazolyl, pyrazolyl, tetrazolyl, morpholinyl and pyrrolidinonyl. In another embodiment, $R_{50}$ is phenyl substituted with —$NR_{11}R_{11}$. In a further embodiment, the —$NR_{11}R_{11}$ group is —$NHC(O)CH_3$, —NH—($C_1$-$C_4$ alkyl)-$CO_2$—($C_1$-$C_4$ alkyl), —NH—($C_1$-$C_4$ alkyl)-O—($C_1$-$C_4$ alkyl)-$CO_2$—($C_1$-$C_4$ alkyl) or —NH—($C_1$-$C_4$ alkyl)-O—($C_1$-$C_4$ alkyl)-$CO_2$H. In another embodiment, $R_{50}$ is phenyl substituted with one group that is

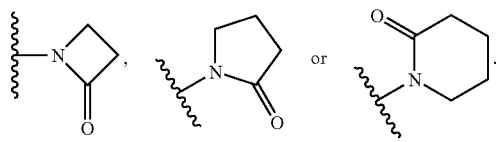

In another embodiment, $R_{50}$ is phenyl substituted with $C_2$-$C_4$ alkanoyl. In a further embodiment, the phenyl is substituted at the four-position.

In an embodiment of this aspect, $R_{50}$ is pyrazolyl optionally substituted with $C_1$-$C_4$ alkyl; thiazolyl optionally substituted with $C_1$-$C_4$ alkyl (e.g., methyl), $C_1$-$C_4$ haloalkyl (e.g., $CF_3$ or $CHF_2$); oxazolyl optionally substituted with $C_1$-$C_4$ alkyl (e.g., methyl); triazolyl optionally substituted with one or two groups that are independently $C_1$-$C_4$ alkyl; or benzimidazolyl optionally substituted with $C_1$-$C_4$ alkyl (e.g., methyl), $C_1$-$C_4$ alkoxy or halogen.

In an embodiment of this aspect, $R_{50}$ is $C_2$-$C_6$ alkenyl optionally substituted with a halogen (e.g., Cl) or $C_1$-$C_4$ haloalkyl (e.g., $CF_3$).

In an embodiment of this aspect, $R_{50}$ is $C_2$-$C_6$ alkynyl optionally substituted with a halogen (e.g., Cl) or $C_1$-$C_4$ alkoxy.

In an embodiment of this aspect, $R_{50}$ is pyridyl optionally substituted with one or more groups that are independently $C_1$-$C_4$ alkyl, halogen or $C_1$-$C_4$ alkoxy.

In an aspect of Formula 1f, all $R_{51}$ groups are H and the B-ring is unsubstituted pyrazolyl. In an embodiment of this aspect, Z is CH and $R_{50}$ is $CHF_2$, CN, —$CH_2$—O—($C_1$-$C_4$ alkyl), oxadiazolyl optionally substituted with methyl, cyclopropyl, phenyl optionally substituted with one group that is halogen, $C_1$-$C_4$ alkyl, oxazolidinonyl, imidazolyl, thiazolyl, pyrazolyl, —$NR_{11}R_{11}$ or $C_1$-$C_4$ alkoxy, oxazolyl optionally substituted with $C_1$-$C_4$ alkyl, isoxazolyl optionally substituted with $C_1$-$C_4$ alkyl, thiazolyl optionally substituted with $CF_3$, $C_2$-$C_4$ alkenyl optionally substituted with a halogen or a $CF_3$ group, $C_2$-$C_4$ alkynyl, thiadiazolyl, triazolyl optionally substituted with $C_1$-$C_4$ alkyl or pyridyl optionally substituted with $C_1$-$C_4$ alkyl or $C_1$-$C_4$ alkoxy.

In one aspect of Formulas 1g and 1i, $R_{50}$ is phenyl optionally substituted with one or more groups that are independently phenyl, optionally substituted with one group that is halogen, $C_1$-$C_4$ alkyl, oxazolidinonyl, imidazolyl, thiazolyl, pyrazolyl, —$NR_{11}R_{11}$ or $C_1$-$C_4$ alkoxy. In an embodiment of this aspect, $R_{50}$ is unsubstituted phenyl.

In one aspect, the compounds of 1b, 1c, 1d, 1e, 1f, 1g, 1 h and 1i are of the following formulas, respectively:

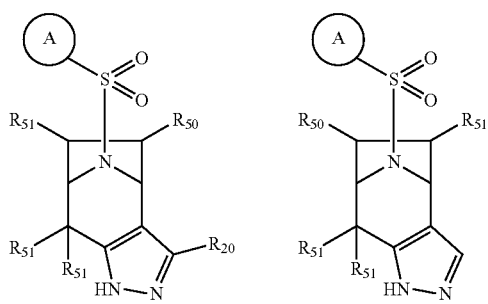

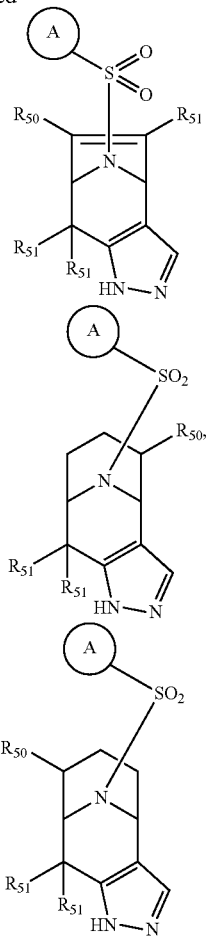

wherein $R_{51}$ and $R_{50}$ are as previously defined in any of the above aspects and/or embodiments.

In a still further embodiment, $R_{13}$ is $C_1$-$C_4$ alkyl substituted with phenyl, hydroxyl, $C_1$-$C_6$ alkoxy or halogen, where the phenyl is optionally substituted e.g., with 1 to 5 groups that are independently halogen, hydroxyl, $C_1$-$C_4$ alkyl, $C_1$-$C_4$ alkoxy, $C_1$-$C_4$ haloalkyl (e.g., $CF_3$), $C_1$-$C_4$ haloalkoxy (e.g., $OCF_3$), CN or $NO_2$. In a yet still further embodiment, $R_{13}$ is $C_1$-$C_4$ alkyl substituted with an unsubstituted phenyl. In a still further embodiment, $R_{13}$ is $C_1$-$C_4$ alkyl substituted with phenyl, which is substituted with at least one group that is independently halogen, hydroxyl, $C_1$-$C_4$ alkyl, $C_1$-$C_4$ alkoxy, $CF_3$, $OCF_3$, CN or $NO_2$.

In one aspect, the compounds of Formula 1 are the compounds of Formula 1b.

In one aspect, the compounds of Formula 1 are the compounds of Formula 1c.

In one aspect, the compounds of Formula 1 are the compounds of Formula 1d.

In one aspect, the compounds of Formula 1 are the compounds of Formula 1e.

In one aspect, the compounds of Formula 1 are the compounds of Formula 1f.

In one aspect, the compounds of Formula 1 are the compounds of Formula 1g.

In one aspect, the compounds of Formula 1 are the compounds of Formula 1h.

In one aspect, the compounds of Formula 1 are the compounds of Formula 1i.

In one aspect, provided herein are compounds of Formulas 2a, 2b, 2c, 2d, 2e or 2f, i.e., compounds of Formula 2 that have the following formulas:

Formula 2a

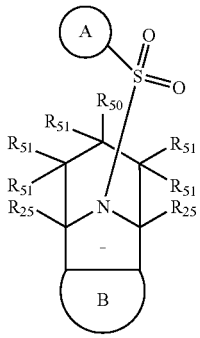

Formula 2b

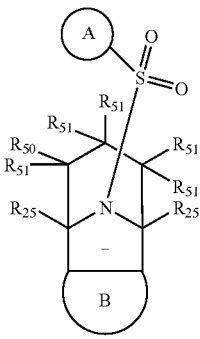

Formula 2c

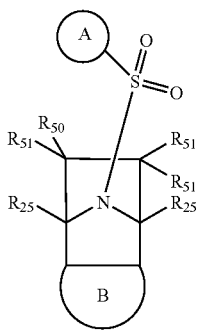

Formula 2d

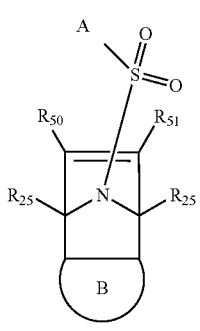

Formula 2e

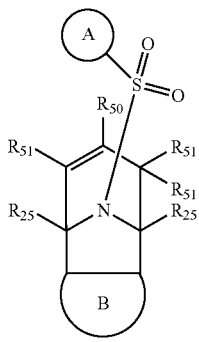

Formula 2f

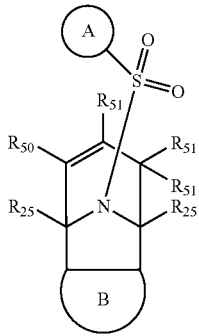

including enantiomers, pharmaceutically acceptable salts, and solvates thereof, wherein, B-ring is pyrazolyl, dihydropyrazolyl, pyrazolonyl or pyrazolidinonyl, each of which is optionally substituted with —$NR_{11}$—$C_2$-$C_6$ alkanoyl, $C_1$-$C_6$ alkyl, $C_3$-$C_6$ cycloalkyl, $C_2$-$C_4$ alkenyl, $C_2$-$C_4$ alkynyl, $C_1$-$C_4$ alkoxy, amino, $C_1$-$C_4$ alkylamino, $C_1$-$C_4$ dialkylamino, hydroxy, hydroxyalkyl, halo, $C_1$-$C_4$ haloalkyl, $C_1$-$C_4$ haloalkoxy, —$NR_{11}C(O)R_{10}$, —$NR_{11}SO_2R_{10}$ or CN;

$R_{50}$ is oxo, =N—$NHR_{12}$ or =N—O—$R_{13}$ (except in Formulas 2d, 2e, and 2f) or $R_{50}$ is halogen, $C_1$-$C_6$ alkyl, $C_2$-$C_6$ alkenyl, $C_2$-$C_6$ alkynyl, hydroxy, hydroxy $C_1$-$C_6$ alkyl, $C_1$-$C_6$ alkoxy, $C_1$-$C_6$ haloalkoxy, $C_1$-$C_6$ haloalkyl, halo $C_2$-$C_6$ alkenyl, halo $C_2$-$C_6$ alkynyl, —$C(O)OR_{11}$, —$(C_1$-$C_4$ alkyl)-C(O)$OR_{11}$, —$CONR_{11}R_{11}$, —$OC(O)NR_{11}R_{11}$, —$NR_{11}C(O)OR_{10}$, —$NR_{11}S(O)_2R_{10}$, —$OS(O)_2R_{10}$, —$S(O)_2R_{10}$, —$NR_{11}C(O)R_{10}$, CN, —$NR_{11}R_{11}$, —$SO_2NR_{11}R_{11}$, heteroaryl that is selected from pyrazolyl, thiadiazolyl, triazolyl, isoxazolyl, isothiazolyl, imidazolyl, thiazolyl, oxadiazolyl, and pyridyl, heterocycloalkyl that is selected from tetrahydrofuranyl, pyrrolidinyl, piperidinyl, morpholinyl, and imidazolidinyl, $C_3$-$C_6$ cycloalkyl, aryl that is selected from phenyl and naphthyl; wherein the aforementioned heteroaryl, heterocycloalkyl, cycloalkyl and aryl groups are optionally substituted with 1 or more groups that are independently halogen, $C_1$-$C_6$ alkyl, $C_2$-$C_6$ alkenyl, $C_2$-$C_6$ alkynyl, hydroxy, hydroxy$C_1$-$C_6$ alkyl, $C_1$-$C_6$ alkoxy, $C_1$-$C_6$ haloalkoxy, $C_1$-$C_6$haloalkyl, halo $C_2$-$C_6$ alkenyl, halo $C_2$-$C_6$ alkynyl, —$C(O)OR_{11}$, —$(C_1$-$C_4$ alkyl)-$C(O)OR_{11}$, —$CONR_{11}R_{11}$, —$OC(O)NR_{11}R_{11}$, —$NR_{11}C(O)OR_{10}$, —$NR_{11}S(O)_2R_{10}$, —$OS(O)_2R_{10}$, —$S(O)_2R_{10}$, —$NR_{11}C(O)R_{10}$, CN, =N—$NHR_{12}$, —$NR_{11}R_{11}$, —$SO_2NR_{11}R_{11}$, heteroaryl that is selected from pyrazolyl, thiadiazolyl, triazolyl isoxazolyl, isothiazolyl, imidazolyl, thiazolyl, oxadiazolyl, oxazolyl, tetrazolyl, and pyridyl, heterocycloalkyl that is selected from tetrahydrofuranyl, pyrrolidinyl, piperidinyl, morpholinyl, and imidazolidinyl, $C_3$-$C_6$ cycloalkyl, aryl that is selected from phenyl, benzo[d][1,3]dioxolyl, and naphthyl or =N—O—$R_{13}$; wherein the aforementioned heteroaryl, heterocycloalkyl, cycloalkyl and aryl substituents are optionally substituted with 1 or more groups that are independently halogen, $C_1$-$C_6$ alkyl, $C_1$-$C_6$ alkoxy, hydroxy, $C_1$-$C_6$ hydroxyalkyl, $C_1$-$C_6$ haloalkoxy or $C_1$-$C_6$ haloalkyl;

each $R_{51}$ is independently absent, H, $C_1$-$C_4$ alkyl, halogen (e.g., F, Cl or Br), CN, amino, mono alkylamino, dialkylamino, OH, $C_1$-$C_4$ haloalkoxy (e.g., $OCF_3$) or $C_1$-$C_4$ haloalkyl (e.g., $CF_3$); or when there are two $R_{51}$ groups on a carbon atom, the two $R_{51}$ groups and the carbon to which they are attached may form a 3- to 6-membered cycloalkyl or heterocycloalkyl ring; or when there are two $R_{51}$ groups on a carbon, the two $R_{51}$ groups may form an oxo group; or when there are two $R_{51}$ groups on a carbon, the two $R_{51}$ groups may form an alkene group; or when there are two $R_{51}$ groups on a carbon, the two $R_{51}$ groups may form an oxime or a $C_1$-$C_4$ alkylated oxime (e.g., O-methyl oxime);

a non-bridgehead carbon (and any substituent or substituents thereon) in the [3.3.1], [3.2.1] or [2.2.1] ring systems may be replaced with an $NR_{15}$ group; provided that in Formulas 2d, 2e, and 2f, $R_{50}$ is not oxo, =N—O—$R_{13}$ or =N—$NHR_{12}$;

$R_{10}$ and $R_{11}$ at each occurrence are independently $C_1$-$C_6$ alkyl, heteroaryl that is selected from pyrazolyl, thiadiazolyl, triazolyl, isoxazolyl, isothiazolyl, imidazolyl, thiazolyl, oxadiazolyl, and pyridyl or aryl that is selected from phenyl and naphthyl, where the heteroaryl and aryl groups are optionally substituted with 1 to 3 groups that are independently halogen, hydroxyl, alkyl, alkoxy, haloalkyl, haloalkoxy, CN or $NO_2$; or if two $R_{11}$ groups are on a nitrogen, then the two $R_{11}$ groups together with the nitrogen to which they are attached, may form a 3-8 membered ring optionally including an additional heteroatom such as NH, $NR_{12}$, $NR_{13}$, O or S, and additionally $R_{11}$ may be H;

$R_{12}$ is H, $C_1$-$C_6$ alkyl, aryl or —$SO_2$-aryl (e.g., phenyl or naphthyl, where phenyl is preferred), where each aryl group is optionally substituted with 1 to 5 groups that are independently halogen, hydroxyl, alkyl, alkoxy, haloalkyl, haloalkoxy, CN or $NO_2$; $R_{13}$ is H, aryl or $C_1$-$C_6$ alkyl optionally substituted with aryl (such as phenyl or naphthyl, more preferably, phenyl), hydroxyl or halogen, where each aryl group is optionally substituted with 1 to 5 groups that are independently halogen, hydroxyl, alkyl, alkoxy, haloalkyl, haloalkoxy, CN or $NO_2$. In a further embodiment, $R_{50}$ is $C_2$-$C_6$ alkenyl, $C_2$-$C_6$ alkynyl, halo $C_2$-$C_6$ alkenyl, halo $C_2$-$C_6$ alkynyl, $C_2$-$C_6$ alkanoyl, $OS(O)_2R_{10}$, —$S(O)_2R_{10}$, —$NR_{11}R_{11}$, $C(O)OR_{11}C(O)OR_{11}$—$SO_2NR_{11}R_{11}$, heteroaryl that is selected from pyrazolyl, thiadiazolyl (e.g., 1,2,4-thiadiazolyl or 1,3,4-thiadiazolyl), triazolyl (e.g., 1,2,3-triazolyl or 1,2,4-triazolyl), isoxazolyl, isothiazolyl, imidazolyl, thiazolyl, oxadiazolyl (e.g., 1,2,4-oxadiazolyl or 1,3,4-oxadiazolyl), oxazolyl, tetrazolyl, and pyridyl, heterocycloalkyl that is selected from tetrahydrofuranyl, pyrrolidinyl, piperidinyl, morpholinyl, and imidazolidinyl, $C_3$-$C_6$ cycloalkyl, aryl that is selected from phenyl, benzo[d][1,3]dioxolyl, and naphthyl or =N—O—$R_{13}$; wherein the aforementioned heteroaryl, heterocycloalkyl, cycloalkyl and aryl groups are optionally substituted with 1 or more groups that are independently halogen, $C_1$-$C_6$ alkyl, $C_2$-$C_6$ alkenyl, $C_2$-$C_6$ alkynyl, hydroxy, hydroxy$C_1$-$C_6$ alkyl, $C_1$-$C_6$ alkoxy, $C_1$-$C_6$ haloalkoxy, $C_1$-$C_6$haloalkyl, halo $C_2$-$C_6$ alkenyl, halo $C_2$-$C_6$ alkynyl, —$C(O)OR_{11}$, —($C_1$-$C_4$ alkyl)-$C(O)OR_{11}$, —$CONR_{11}R_{11}$, —$OC(O)NR_{11}R_{11}$, —$NR_{11}C(O)OR_{10}$, —$NR_{11}S(O)_2R_{10}$, —$OS(O)_2R_{10}$, —$S(O)_2R_{10}$, —$NR_{11}C(O)R_{10}$, CN, =N—$NHR_{12}$, —$NR_{11}R_{11}$, —$SO_2NR_{11}R_{11}$, heteroaryl that is selected from pyrazolyl, thiadiazolyl, triazolyl, isoxazolyl, isothiazolyl, imidazolyl, thiazolyl, oxadiazolyl, oxazolyl, tetrazolyl, and pyridyl, heterocycloalkyl that is selected from tetrahydrofuranyl, pyrrolidinyl, piperidinyl, morpholinyl, and imidazolidinyl, $C_3$-$C_6$ cycloalkyl, aryl that is selected from phenyl, benzo[d][1,3]dioxolyl, and naphthyl or =N—O—$R_{13}$; wherein the aforementioned heteroaryl, heterocycloalkyl, cycloalkyl and aryl substituents are optionally substituted with 1 or more groups that are independently halogen, $C_1$-$C_6$ alkyl, $C_1$-$C_6$ alkoxy, hydroxy, $C_1$-$C_6$ hydroxyalkyl, $C_1$-$C_6$ haloalkoxy or $C_1$-$C_6$ haloalkyl.

In an aspect, provided herein are compounds of Formula 2a, 2b, 2c, 2d, 2e or 2f, wherein $R_{50}$ is halogen, $C_1$-$C_6$ alkyl, $C_2$-$C_6$ alkenyl, $C_2$-$C_6$ alkynyl, hydroxy $C_1$-$C_6$ alkyl, $C_1$-$C_6$ alkoxy, $C_1$-$C_6$ haloalkoxy or $C_1$-$C_6$ haloalkyl. In one embodiment, $R_{50}$ is halogen, $C_1$-$C_4$ alkyl, hydroxy, hydroxy $C_1$-$C_4$ alkyl, $C_1$-$C_4$ alkoxy, $C_1$-$C_4$ haloalkoxy or $C_1$-$C_4$ haloalkyl. In another embodiment, $R_{50}$ is $C_1$-$C_4$ alkyl, $C_1$-$C_4$ haloalkyl, hydroxy $C_1$-$C_4$ alkyl or $C_1$-$C_4$ alkoxy. In still another embodiment, $R_{50}$ is $C_1$-$C_4$ alkyl. In yet another embodiment, $R_{50}$ is $C_1$-$C_4$ haloalkyl (e.g., $CF_3$ or $CH_2CF_3$), hydroxy $C_1$-$C_4$ alkyl or $C_1$-$C_4$ alkoxy (e.g., methoxy or ethoxy). In another embodiment, $R_{50}$ is $C_2$-$C_4$ alkenyl or $C_2$-$C_4$ alkynyl. In still another embodiment, $R_{50}$ is halogen, hydroxy or hydroxy $C_1$-$C_4$ alkyl. In yet still another embodiment, $R_{50}$ is halogen. In yet still another embodiment, $R_{50}$ is hydroxy or hydroxy $C_1$-$C_4$ alkyl.

In an aspect, provided herein are compounds of Formula 2a, 2b, 2c, 2d, 2e or 2f, wherein $R_{50}$ is $NR_{11}R_{11}$, or $SO_2NR_{11}R_{11}$, or $S(O)_2R_{10}$, or
oxadiazolyl, optionally substituted with $C_1$-$C_4$ alkyl, or
$C_3$-$C_6$ cycloalkyl optionally substituted with $C_1$-$C_4$ alkyl or $C_1$-$C_4$ alkoxy, or
phenyl optionally substituted with one or more groups that are independently $C_1$-$C_4$ alkyl, $C_1$-$C_4$ alkoxy, halogen, —$OCH_2O$—, —$OCH_2CH_2O$—, oxazolidinone (e.g., oxazolidin-2-one), imidazolyl, thiazolyl, —$NR_{11}$-cyclohexyl, where the cyclohexyl is optionally substituted with $NR_{11}R_{11}$, $C_1$-$C_4$ alkyl or $C_1$-$C_4$ alkoxy; pyrazolyl, tetrazolyl, pyrrolidinonyl, —$NR_{11}R_{11}$, morpholinyl (e.g., morpholin-2-onyl),

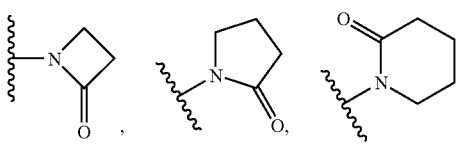

or $C_2$-$C_6$ alkanoyl; or
pyrazolyl optionally substituted with $C_1$-$C_4$ alkyl; or thiazolyl optionally substituted with $C_1$-$C_4$ alkyl, $C_1$-$C_4$ haloalkyl (e.g., $CF_3$ or $CHF_2$); or
oxazolyl optionally substituted with $C_1$-$C_4$ alkyl; or
benzimidazolyl optionally substituted with $C_1$-$C_4$ alkyl, $C_1$-$C_4$ alkoxy or halogen; or
$C_2$-$C_6$ alkenyl optionally substituted with a halogen (e.g., Cl) or $C_1$-$C_4$ haloalkyl (e.g., $CF_3$); or
triazolyl optionally substituted with one or two groups that are independently $C_1$-$C_4$ alkyl; or
$C_2$-$C_6$ alkynyl optionally substituted with a halogen (e.g., Cl) or $C_1$-$C_4$ alkoxy; or
thiadiazolyl optionally substituted with $C_1$-$C_4$ alkyl, $C_1$-$C_4$ haloalkyl (e.g., $CF_3$ or $CHF_2$); or
pyridyl optionally substituted with one or more groups that are independently $C_1$-$C_4$ alkyl, halogen or $C_1$-$C_4$ alkoxy; or
wherein $R_{11}$ is H, $C_1$-$C_6$ alkyl or $C_2$-$C_6$ alkanoyl, where the alkyl portions of $R_{11}$ are optionally substituted with one or two groups that are independently —$CO_2$—($C_1$-$C_6$ alkyl), $C_1$-$C_6$ alkyl-O—($C_1$-$C_6$ alkyl), $C_1$-$C_6$ alkyl-O—($C_1$-$C_4$ alkyl)-$CO_2$—($C_1$-$C_6$ alkyl), $C_1$-$C_6$ alkyl-O—($C_1$-$C_4$ alkyl)-$CO_2H$.

In an embodiment of this aspect, $R_{50}$ is $C_1$-$C_4$ haloalkyl (e.g., $CF_3$ or $CHF_2$), CN, $C_1$-$C_4$ alkoxy $C_1$-$C_6$ alkyl or $NR_{11}R_{11}$; where each $R_{11}$ is independently H or $C_1$-$C_4$ alkyl. In a further embodiment, $R_{50}$ is CN. In a still further embodiment, $R_{50}$ is methoxymethyl, methoxyethy, ethoxymethyl or ethoxyethyl.

In an embodiment of this aspect, $R_{50}$ is oxadiazolyl, substituted with a $C_1$-$C_2$ alkyl.

In an embodiment of this aspect, $R_{50}$ is phenyl optionally substituted with one or more groups that are independently $C_1$-$C_4$ alkyl, $C_1$-$C_4$ alkoxy, halogen, —$OCH_2O$—, —$OCH_2CH_2O$—, oxazolidinone (e.g., oxazolidin-2-one), imidazolyl, thiazolyl, —$NR_{11}$-cyclohexyl, where the cyclohexyl is optionally substituted with $NR_{11}R_{11}$, $C_1$-$C_4$ alkyl or $C_1$-$C_4$ alkoxy; pyrazolyl, tetrazolyl, pyrrolidinonyl, —$NR_{11}R_{11}$, morpholinyl (e.g., morpholin-2-onyl),

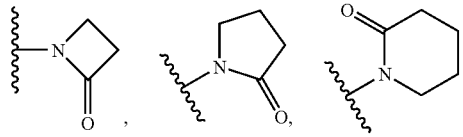

or $C_2$-$C_6$ alkanoyl. In a further embodiment, $R_{50}$ is unsubstituted phenyl. In another embodiment, $R_{50}$ is phenyl substituted with one or more groups that are independently $C_1$-$C_4$ alkyl, $C_1$-$C_4$ alkoxy or halogen (e.g., F, Cl or Br). In a further embodiment, $R_{50}$ is phenyl substituted with one group that is $C_1$-$C_4$ alkyl, $C_1$-$C_4$ alkoxy or halogen (e.g., F, Cl or Br). In another embodiment, $R_{50}$ is phenyl substituted with one group that is selected from oxazolidinonyl, imidazolyl, thiazolyl, pyrazolyl, tetrazolyl, morpholinyl and pyrrolidinonyl. In another embodiment, $R_{50}$ is phenyl substituted with —$NR_{11}R_{11}$. In a further embodiment, the —$NR_{11}R_{11}$ group is —$NHC(O)CH_3$, —NH—($C_1$-$C_4$ alkyl)-$CO_2$—($C_1$-$C_4$ alkyl), —NH—($C_1$-$C_4$ alkyl)-O—($C_1$-$C_4$ alkyl)-$CO_2$—($C_1$-$C_4$ alkyl) or —NH—($C_1$-$C_4$ alkyl)-O—($C_1$-$C_4$ alkyl)-$CO_2H$. In another embodiment, $R_{50}$ is phenyl substituted with one group that is

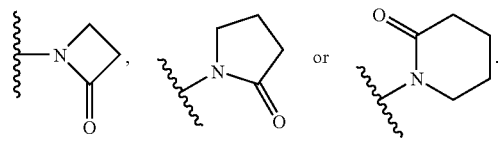

In another embodiment, $R_{50}$ is phenyl substituted with $C_2$-$C_4$ alkanoyl. In a further embodiment, the phenyl is substituted at the four-position.

In an embodiment of this aspect, $R_{50}$ is pyrazolyl optionally substituted with $C_1$-$C_4$ alkyl; thiazolyl optionally substituted with $C_1$-$C_4$ alkyl (e.g., methyl), $C_1$-$C_4$ haloalkyl (e.g., $CF_3$ or $CHF_2$); oxazolyl optionally substituted with $C_1$-$C_4$ alkyl (e.g., methyl); triazolyl optionally substituted with one or two groups that are independently $C_1$-$C_4$ alkyl; or benzimidazolyl optionally substituted with $C_1$-$C_4$ alkyl (e.g., methyl), $C_1$-$C_4$ alkoxy or halogen.

In an embodiment of this aspect, $R_{50}$ is $C_2$-$C_6$ alkenyl optionally substituted with a halogen (e.g., Cl) or $C_1$-$C_4$ haloalkyl (e.g., $CF_3$).

In an embodiment of this aspect, $R_{50}$ is $C_2$-$C_6$ alkynyl optionally substituted with a halogen (e.g., Cl) or $C_1$-$C_4$ alkoxy.

In an embodiment of this aspect, $R_{50}$ is pyridyl optionally substituted with one or more groups that are independently $C_1$-$C_4$ alkyl, halogen or $C_1$-$C_4$ alkoxy.

In another aspect, provided herein are compounds of Formula 2a, 2b, 2c, 2d, 2e or 2f, wherein $R_{50}$ is —$C(O)OR_{11}OR_{11}$, —($C_1$-$C_4$ alkyl)-$C(O)OR_{11}$, —$CONR_{11}R_{11}$, —$OC(O)NR_{11}R_{11}$, —$NR_{11}C(O)OR_{10}$, —$NR_{11}S(O)_2R_{10}$, —$OS(O)_2R_{10}$, —$S(O)_2R_{10}$, —$NR_{11}C(O)R_{10}$, CN, =N—$NHR_{12}$, —$NR_{11}R_{11}$, —$SO_2NR_{11}R_{11}$, or =N—O—$R_{13}$;

$R_{10}$ and $R_{11}$ at each occurrence are independently $C_1$-$C_6$ alkyl, heteroaryl that is selected from pyrazolyl, thiadiazolyl, triazolyl, isoxazolyl, isothiazolyl, imidazolyl, thiazolyl, oxadiazolyl, and pyridyl or aryl that is selected from phenyl and naphthyl, where the heteroaryl and aryl groups are optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$; and additionally $R_{11}$ may be H; or if two $R_{11}$ groups are on a nitrogen, then the two $R_{11}$ groups together with the nitrogen to which they are attached, may form a 3-8 membered ring optionally including an additional heteroatom such as NH, $NR_{12}$, $NR_{13}$, O or S;

$R_{12}$ is H, $C_1$-$C_6$ alkyl, aryl or $SO_2$-aryl (e.g., phenyl or naphthyl, where phenyl is preferred), where each aryl group is optionally substituted with 1 to 5 groups that are independently halogen, hydroxyl, alkyl, alkoxy, haloalkyl, haloalkoxy, CN or $NO_2$;

$R_{13}$ is H, aryl or $C_1$-$C_6$ alkyl optionally substituted with aryl (such as phenyl or naphthyl, more preferably, phenyl), hydroxyl or halogen, where each aryl group is optionally substituted with 1 to 5 groups that are independently halogen, hydroxyl, alkyl, alkoxy, haloalkyl, haloalkoxy, CN or $NO_2$.

In an embodiment of this aspect, $R_{10}$ is $C_1$-$C_4$ alkyl and $R_{11}$ is independently hydrogen or $C_1$-$C_4$ alkyl.

In still another embodiment of this aspect, $R_{11}$ is H.

In still another embodiment of this aspect, one of $R_{10}$ and $R_{11}$ is $CH_3$.

In another embodiment of this aspect, $R_{11}$ and $R_{11}$ together with the nitrogen to which they are attached may form a 3-8 membered ring, which optionally includes an additional heteroatom that is NH, $NR_{12}$, $NR_{13}$, O or S.

In still another embodiment of this aspect, $R_{10}$ and $R_{11}$ at each occurrence are independently phenyl optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$, and additionally $R_{11}$ may be H.

In another embodiment of this aspect, $R_{10}$ and $R_{11}$ at each occurrence are independently pyrazolyl, isoxazolyl, isothiazolyl, imidazolyl or thiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$, and additionally $R_{11}$ may be H.

In another embodiment of this aspect, $R_{10}$ and $R_{11}$ at each occurrence are independently thiadiazolyl, triazolyl or oxadiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$, and additionally $R_{11}$ may be H.

In yet still another embodiment of this aspect, $R_{13}$ is H, $C_1$-$C_4$ alkyl or benzyl, where then phenyl portion is optionally substituted with halogen, hydroxyl, $C_1$-$C_4$ alkyl, $C_1$-$C_4$ alkoxy, $CF_3$ or $OCF_3$. In another embodiment, $R_{13}$ is $C_1$-$C_4$ alkyl or benzyl.

In another aspect, provided herein are compounds of Formula 2a, 2b, 2c, 2d, 2e or 2f, wherein $R_{50}$ is —C(O)OR$_{11}$, —CONR$_{11}$R$_{11}$, —OC(O)NR$_{11}$R$_{11}$, —NR$_{11}$C(O)OR$_{10}$, —NR$_{11}$S(O)$_2$R$_{10}$, —OS(O)$_2$R$_{10}$, —S(O)$_2$R$_{10}$ or —NR$_{11}$C(O)R$_{10}$; wherein R$_{10}$ and R$_{11}$ at each occurrence are independently $C_1$-$C_6$ alkyl, heteroaryl that is selected from pyrazolyl, thiadiazolyl, triazolyl, isoxazolyl, isothiazolyl, imidazolyl, thiazolyl, oxadiazolyl, and pyridyl or aryl that is selected from phenyl and naphthyl, where the heteroaryl and aryl groups are optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or NO$_2$; and additionally R$_{11}$ may be H; or if two R$_{11}$ groups are on a nitrogen, then the two R$_{11}$ groups together with the nitrogen to which they are attached, may form a 3-8 membered ring optionally including an additional heteroatom such as NH, NR$_{12}$, NR$_{13}$, O or S;

$R_{12}$ is H, $C_1$-$C_6$ alkyl, aryl or SO$_2$-aryl (e.g., phenyl or naphthyl, where phenyl is preferred), where each aryl group is optionally substituted with 1 to 5 groups that are independently halogen, hydroxyl, alkyl, alkoxy, haloalkyl, haloalkoxy, CN or NO$_2$;

$R_{13}$ is H, aryl or $C_1$-$C_6$ alkyl optionally substituted with aryl (such as phenyl or naphthyl, more preferably, phenyl), hydroxyl or halogen, where each aryl group is optionally substituted with 1 to 5 groups that are independently halogen, hydroxyl, alkyl, alkoxy, haloalkyl, haloalkoxy, CN or NO$_2$.

In an embodiment of this aspect, $R_{10}$ is $C_1$-$C_4$ alkyl and $R_{11}$ is independently hydrogen or $C_1$-$C_4$ alkyl.

In still another embodiment of this aspect, $R_{11}$ is H.

In still another embodiment of this aspect, one of $R_{10}$ and $R_{11}$ is CH$_3$.

In another embodiment of this aspect, $R_{11}$ and $R_{11}$ together with the nitrogen to which they are attached form a 3-8 membered ring, which optionally includes an additional heteroatom that is NH, NR$_{12}$, NR$_{13}$, O or S.

In another embodiment of this aspect, $R_{10}$ and $R_{11}$ at each occurrence are independently phenyl optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or NO$_2$, and additionally R$_{11}$ may be H.

In another embodiment of this aspect, $R_{10}$ and $R_{11}$ at each occurrence are independently pyrazolyl, isoxazolyl, isothiazolyl, imidazolyl or thiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or NO$_2$, and additionally R$_{11}$ may be H.

In another embodiment of this aspect, $R_{10}$ and $R_{11}$ at each occurrence are independently thiadiazolyl, triazolyl or oxadiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or NO$_2$, and additionally R$_{11}$ may be H.

In yet still another embodiment of this aspect, $R_{13}$ is H, $C_1$-$C_4$ alkyl or benzyl, where then phenyl portion is optionally substituted with halogen, hydroxyl, $C_1$-$C_4$ alkyl, $C_1$-$C_4$ alkoxy, CF$_3$ or OCF$_3$. In another embodiment, $R_{13}$ is $C_1$-$C_4$ alkyl or benzyl.

In another aspect, provided herein are compounds of Formula 2a, 2b, 2c, 2d, 2e or 2f, wherein $R_{50}$ is heteroaryl that is selected from pyrazolyl, thiadiazolyl (e.g., 1,2,4-thiadiazolyl or 1,3,4-thiadiazolyl), triazolyl (e.g., 1,2,3-triazolyl or 1,2,4-triazolyl), isoxazolyl, isothiazolyl, imidazolyl, thiazolyl, oxadiazolyl (e.g., 1,2,4-oxadiazolyl or 1,3,4-oxadiazolyl), oxazolyl, tetrazolyl, and pyridyl, heterocycloalkyl that is selected from tetrahydrofuranyl, pyrrolidinyl, piperidinyl, morpholinyl, and imidazolidinyl, heterocycloalkyl that is selected from tetrahydrofuranyl, pyrrolidinyl, piperidinyl, morpholinyl, and imidazolidinyl, each of which is optionally substituted with 1 or more groups that are independently halogen, $C_1$-$C_6$ alkyl, $C_1$-$C_6$ alkoxy, hydroxy, $C_1$-$C_6$ hydroxyalkyl, $C_1$-$C_6$ haloalkoxy or $C_1$-$C_6$ haloalkyl.

In an embodiment of this aspect, $R_{50}$ is pyrazolyl or imidazolyl, each of which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., OCF$_3$) or $C_1$-$C_4$ haloalkyl (e.g., CF$_3$).

In an embodiment of this aspect, $R_{50}$ is thiazolyl or oxadiazolyl each of which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., OCF$_3$) or $C_1$-$C_4$ haloalkyl (e.g., CF$_3$).

In an embodiment of this aspect, $R_{50}$ is pyridyl, which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., OCF$_3$) or $C_1$-$C_4$ haloalkyl (e.g., CF$_3$).

In an embodiment of this aspect, $R_{50}$ is thiadiazolyl, which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., OCF$_3$) or $C_1$-$C_4$ haloalkyl (e.g., CF$_3$).

In an embodiment of this aspect, $R_{50}$ is triazolyl, which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., OCF$_3$) or $C_1$-$C_4$ haloalkyl (e.g., CF$_3$).

In an embodiment of this aspect, $R_{50}$ is isoxazolyl, which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., OCF$_3$) or $C_1$-$C_4$ haloalkyl (e.g., CF$_3$).

In an embodiment of this aspect, $R_{50}$ is isothiazolyl, which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., OCF$_3$) or $C_1$-$C_4$ haloalkyl (e.g., CF$_3$).

In an embodiment of this aspect, $R_{50}$ is selected from tetrahydrofuranyl, pyrrolidinyl, and imidazolidinyl, each of which is optionally substituted with 1 or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., OCF$_3$) or $C_1$-$C_4$ haloalkyl (e.g., CF$_3$).

In an embodiment of this aspect, $R_{50}$ is piperidinyl or morpholinyl, each of which is optionally substituted with 1 or more groups that are independently halogen, $C_1$-$C_4$ alkyl, $C_4$ alkoxy, hydroxy, $C_1$-$C_4$ hydroxyalkyl, $C_1$-$C_4$ haloalkoxy (e.g., OCF$_3$) or $C_1$-$C_4$ haloalkyl (e.g., CF$_3$).

In a further embodiment of this aspect, $R_{50}$ is unsubstituted.

In a still further embodiment of this aspect, $R_{50}$ is substituted with one group that is halogen, $C_1$-$C_2$ alkyl, $C_1$-$C_2$ alkoxy, hydroxy, $C_1$-$C_2$ hydroxyalkyl, $C_1$-$C_2$ haloalkoxy (e.g., OCF$_3$) or $C_1$-$C_2$ haloalkyl (e.g., CF$_3$).

In another aspect, provided herein are compounds of Formula 2a, 2b, 2c, 2d, 2e or 2f, wherein $R_{50}$ is $C_3$-$C_6$ cycloalkyl, which is optionally substituted with 1 or more groups that are independently halogen, $C_1$-$C_6$ alkyl, $C_1$-$C_6$ alkoxy, hydroxy, $C_1$-$C_6$ hydroxyalkyl, $C_1$-$C_6$ haloalkoxy or $C_1$-$C_6$ haloalkyl.

In an embodiment of this aspect, $R_{50}$ is unsubstituted $C_3$-$C_6$ cycloalkyl.

In another embodiment of this aspect, $R_{50}$ is $C_3$-$C_6$ cycloalkyl substituted with one or two groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., $OCF_3$) or $C_1$-$C_4$ haloalkyl (e.g., $CF_3$).

In still another embodiment, $R_{50}$ is cyclopropyl, cyclopentyl or cyclohexyl, each of which is optionally substituted with halogen, $C_1$-$C_2$ alkyl, $C_1$-$C_2$ alkoxy (e.g., methoxy), hydroxy, $C_1$-$C_2$ hydroxyalkyl, $C_1$-$C_2$ haloalkoxy (e.g., $OCF_3$) or $C_1$-$C_2$ haloalkyl (e.g., $CF_3$).

In still another embodiment, $R_{50}$ is cyclopropyl, substituted with one group that is halogen, $C_1$-$C_2$ alkyl, $C_1$-$C_2$ alkoxy (e.g., methoxy), hydroxy or $C_1$-$C_2$ hydroxyalkyl.

In another aspect, provided herein are compounds of Formula 2a, 2b, 2c, 2d, 2e or 2f, wherein $R_{50}$ is aryl that is selected from phenyl, benzo[d][1,3]dioxolyl, and naphthyl, each of which is optionally substituted with one or more groups that are independently halogen, $C_1$-$C_6$ alkyl, $C_1$-$C_6$ alkoxy, hydroxy, $C_1$-$C_6$ hydroxyalkyl, $C_1$-$C_6$ haloalkoxy or $C_1$-$C_6$ haloalkyl.

In an embodiment of this aspect, $R_{50}$ is phenyl, which is optionally substituted with one or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., $OCF_3$) or $C_1$-$C_4$ haloalkyl (e.g., $CF_3$).

In another embodiment of this aspect, $R_{50}$ is phenyl, which is unsubstituted.

In still yet another embodiment of this aspect, $R_{50}$ is phenyl, which is substituted with at least one group that is halogen, $C_1$-$C_2$ alkyl, $C_1$-$C_2$ alkoxy, hydroxy, $C_1$-$C_2$ hydroxyalkyl, $C_1$-$C_2$ haloalkoxy (e.g., $OCF_3$), $C_1$-$C_2$ haloalkyl (e.g., $CF_3$) or —CN.

In still yet another embodiment of this aspect, $R_{50}$ is phenyl, which is substituted with one group that is halogen, $C_1$-$C_2$ alkyl, $C_1$-$C_2$ alkoxy, hydroxy, $C_1$-$C_2$ hydroxyalkyl, $C_1$-$C_2$ haloalkoxy (e.g., $OCF_3$) or $C_1$-$C_2$ haloalkyl (e.g., $CF_3$).

In an embodiment of this aspect, $R_{50}$ is benzo[d][1,3]dioxolyl, which is optionally substituted with one or more groups that are independently halogen, $C_1$-$C_4$ alkyl, $C_1$-$C_4$ alkoxy, hydroxy, $C_1$-$C_4$ hydroxyalkyl, $C_1$-$C_4$ haloalkoxy (e.g., $OCF_3$) or $C_1$-$C_4$ haloalkyl (e.g., $CF_3$). In a further embodiment, the methylene group of the benzo[d][1,3]dioxolyl group is substituted with one or two $C_1$-$C_4$ alkyl groups (such as, e.g., one or two methyl groups).

In another embodiment of this aspect, $R_{so}$ is benzo[d][1,3]dioxolyl, which is unsubstituted.

In still yet another embodiment of this aspect, $R_{50}$ is benzo[d][1,3]dioxolyl, which is substituted with at least one group that is halogen, $C_1$-$C_2$ alkyl, $C_1$-$C_2$ alkoxy, hydroxy, $C_1$-$C_2$ hydroxyalkyl, $C_1$-$C_2$ haloalkoxy (e.g., $OCF_3$), $C_1$-$C_2$ haloalkyl (e.g., $CF_3$) or —CN.

In still yet another embodiment of this aspect, $R_{50}$ is benzo[d][1,3]dioxolyl, which is substituted with one group that is halogen, $C_1$-$C_2$ alkyl, $C_1$-$C_2$ alkoxy, hydroxy, $C_1$-$C_2$ hydroxyalkyl, $OCF_3$ or $CF_3$.

In one aspect, the compounds of Formula 2 are the compounds of Formula 2a.

In one aspect, the compounds of Formula 2 are the compounds of Formula 2b.

In one aspect, the compounds of Formula 2 are the compounds of Formula 2c.

In one aspect, the compounds of Formula 2 are the compounds of Formula 2d.

In one aspect, the compounds of Formula 2 are the compounds of Formula 2e.

In one aspect, the compounds of Formula 2 are the compounds of Formula 2f.

In one aspect, provided herein are compounds of Formulas 3a, 3b or 3c, i.e., compounds of Formula 3 having the formulas:

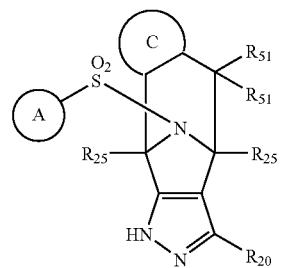

Formula 3a

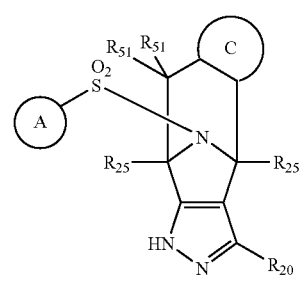

Formula 3b

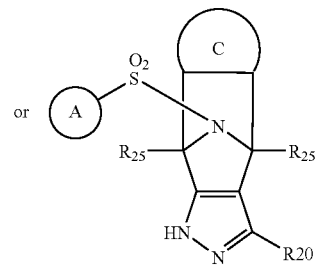

Formula 3c

In one aspect, provided herein are compounds of Formulas 3d, 3e or 3f, i.e., compounds of Formula 3 that have the following formulas:

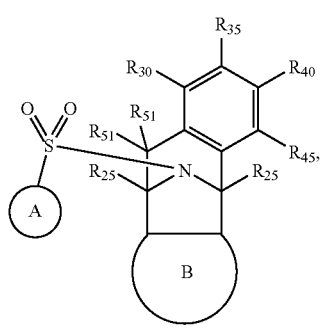

Formula 3d

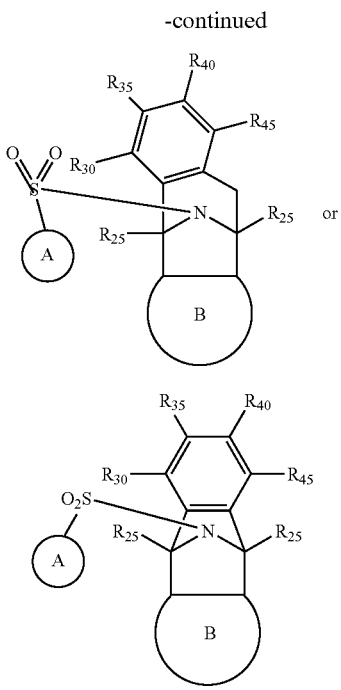

Formula 3e

Formula 3f including enantiomers and/or pharmaceutically acceptable salts thereof, wherein, the A-ring is as defined below;

B-ring is pyrazolyl, dihydropyrazolyl, pyrazolonyl or pyrazolidinonyl, each of which is optionally substituted with —$NR_{11}$—$C_2$-$C_6$ alkanoyl, $C_1$-$C_6$ alkyl, $C_3$-$C_6$ cycloalkyl, $C_2$-$C_4$ alkenyl, $C_2$-$C_4$ alkynyl, $C_1$-$C_4$ alkoxy, amino, $C_1$-$C_4$ alkylamino, $C_1$-$C_4$ dialkylamino, hydroxy, hydroxyalkyl, halo, $C_1$-$C_4$ haloalkyl, $C_1$-$C_4$ haloalkoxy, —$NR_{11}C(O)R_{10}$, —$NR_{11}SO_2R_{10}$ or CN, where $R_{10}$ and $R_{11}$ at each occurrence are independently $C_1$-$C_6$ alkyl, heteroaryl that is selected from pyrazolyl, thiadiazolyl, triazolyl, isoxazolyl, isothiazolyl, imidazolyl, thiazolyl, oxadiazolyl, and pyridyl or aryl that is selected from phenyl and naphthyl, where the heteroaryl and aryl groups are optionally substituted with 1 to 3 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN or $NO_2$; and additionally $R_{11}$ may be H; or if two $R_{11}$ groups are on a nitrogen, then the two $R_{11}$ groups together with the nitrogen to which they are attached, may form a 3-8 membered ring optionally including an additional heteroatom such as NH, $NR_{12}$, $NR_{13}$, O or S;

$R_{30}$, $R_{35}$, $R_{40}$, and $R_{45}$ are independently H, halogen, $C_1$-$C_6$ alkyl, $C_2$-$C_6$ alkenyl, $C_2$-$C_6$ alkynyl, $C_2$-$C_8$ haloalkenyl, $C_2$-$C_8$ haloalkynyl, —$C(O)OR_{11}$, —$SO_2NR_{11}R_{11}$, aryl $C_1$-$C_6$ alkyl, $C_3$-$C_6$ cycloalkyl, $C_1$-$C_6$ haloalkyl, $C_1$-$C_6$ haloalkoxy, CN, $NO_2$, hydroxyl, $C_1$-$C_6$ alkoxy, —$C_1$-$C_6$ alkyl-OH, —$C_1$-$C_6$ alkyl-$C_1$-$C_6$ alkoxy, phenyloxy, —$S(O_2)R_{10}$, —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, heteroaryl $C_1$-$C_6$ alkyl, heteroaryl, where the heteroaryl groups are oxazolyl, oxadiazolyl pyrazolyl, thiazolyl, pyridyl, pyrimidinyl, imidazolyl, indolyl, furanyl or thienyl, and wherein each heteroaryl group is optionally substituted with a $C_1$-$C_6$ alkyl group; heterocycloalkylalkyl, heterocycloalkyl, wherein the heterocycloalkyl groups are pyrrolidinyl, imidazolidinyl, piperidinyl or morpholinyl, wherein each heterocycloalkyl group is optionally substituted with one or two groups that are independently $C_1$-$C_6$ alkyl, $C_1$-$C_6$ alkoxy or halogen, phenyl, naphthyl, phenyloxy, naphthyloxy or phenyl $C_1$-$C_6$ alkyl, where the phenyl portions of the above are optionally substituted with one to five groups that are independently $C_1$-$C_6$ alkyl, $C_1$-$C_6$ alkoxy, hydroxyl, $C_1$-$C_4$ haloalkyl (e.g., $CF_3$) or halogen; and wherein two adjacent carbons of the C-ring optionally form a heterocycloalkyl or a heteroaryl ring, each of which is optionally substituted with 1, 2, 3 or 4 groups that are independently $C_1$-$C_4$ alkyl, $C_1$-$C_4$ alkoxy, halogen or $C_2$-$C_4$ alkanoyl wherein the alkanoyl group is optionally substituted with up to 3 halogen atoms; or two adjacent carbons of the fused aryl ring form a benzo ring which is optionally substituted with 1 to 4 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN or $NO_2$; and $R_{51}$ is as previously defined. In a further embodiment of this aspect, $R_{10}$ and $R_{11}$ at each occurrence are independently $C_1$-$C_6$ alkyl, heteroaryl that is selected from pyrazolyl, thiadiazolyl, triazolyl, isoxazolyl, isothiazolyl, imidazolyl, thiazolyl, oxadiazolyl, and pyridyl or aryl that is selected from phenyl and naphthyl, where the heteroaryl and aryl groups are optionally substituted with 1 to 3 groups that are independently halogen, hydroxyl, $C_1$-$C_6$ alkyl, $C_1$-$C_6$ alkoxy, halo $C_1$-$C_4$alkyl, halo $C_1$-$C_4$ alkoxy, CN or $NO_2$; and additionally $R_{11}$ may be H; or if two $R_{11}$ groups are on a nitrogen, then the two $R_{11}$ groups together with the nitrogen to which they are attached, may form a 3-8 membered ring optionally including an additional heteroatom such as NH, $NR_{12}$, $NR_{13}$, O or S;

$R_{12}$ is H, $C_1$-$C_6$ alkyl, aryl or —$SO_2$-aryl (e.g., phenyl or naphthyl, where phenyl is preferred), where each aryl group is optionally substituted with 1 to 5 groups that are independently halogen, hydroxyl, alkyl, alkoxy, haloalkyl, haloalkoxy, CN or $NO_2$;

$R_{13}$ is H, aryl or $C_1$-$C_6$ alkyl optionally substituted with aryl (such as phenyl or naphthyl, more preferably, phenyl), hydroxyl or halogen, where each aryl group is optionally substituted with 1 to 5 groups that are independently halogen, hydroxyl, alkyl, alkoxy, haloalkyl, haloalkoxy, CN or $NO_2$.

In an embodiment of this aspect, $R_{10}$ is $C_1$-$C_4$ alkyl and $R_{11}$ is independently hydrogen or $C_1$-$C_4$ alkyl.

In still another embodiment of this aspect, $R_{11}$ is H.

In still another embodiment of this aspect, one of $R_{10}$ and $R_{11}$ is $CH_3$.

In another embodiment of this aspect, $R_{11}$ and $R_{11}$ together with the nitrogen to which they are attached may form a 3-8 membered ring, which optionally includes an additional heteroatom that is NH, $NR_{12}$, $NR_{13}$, O or S.

In still another embodiment of this aspect, $R_{10}$ and $R_{11}$ at each occurrence are independently phenyl optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$; and additionally $R_{11}$ may be H.

In another embodiment of this aspect, $R_{10}$ and $R_{11}$ at each occurrence are independently pyrazolyl, isoxazolyl, isothiazolyl, imidazolyl or thiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$; and additionally $R_{11}$ may be H.

In another embodiment of this aspect, $R_{10}$ and $R_{11}$ at each occurrence are independently thiadiazolyl, triazolyl or oxadiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$; and additionally $R_{11}$ may be H.

In yet still another embodiment of this aspect, $R_{13}$ is H, $C_1$-$C_4$ alkyl or benzyl, where then phenyl portion is optionally substituted with halogen, hydroxyl, $C_1$-$C_4$ alkyl, $C_1$-$C_4$ alkoxy, $CF_3$ or $OCF_3$. In another embodiment, $R_{13}$ is $C_1$-$C_4$ alkyl or benzyl.

In another aspect, provided herein are compounds of Formulas 3a, 3b, and 3c (when the C-ring is benzo substituted with $R_{30}$, $R_{35}$, $R_{40}$, and $R_{45}$) 3d, 3e and/or 3f, wherein $R_{30}$, $R_{35}$, $R_{40}$, and $R_{45}$ are independently H, halogen, $C_1$-$C_6$ alkyl, $C_2$-$C_6$ alkenyl, $C_2$-$C_6$ alkynyl, $C_2$-$C_8$ haloalkenyl, $C_2$-$C_8$ haloalkynyl, —C(O)$OR_{11}$, —$SO_2NR_{11}R_{11}$, arylalkyl, cycloalkyl, $C_1$-$C_6$ haloalkyl, $C_1$-$C_6$ haloalkoxy, CN, $NO_2$, hydroxyl, $C_1$-$C_6$ alkoxy, —$C_1$-$C_3$ alkyl-OH, —$C_1$-$C_3$ alkyl-$C_1$-$C_4$ alkoxy, phenyloxy, —S($O_2$)$R_{10}$, —$NR_{11}R_{11}$, —C(O)$NR_{11}R_{11}$, —$NR_{11}$C(O)$R_{10}$, —$NR_{11}SO_2R_{10}$, —O—C(O)$NR_{11}R_{11}$, $C_2$-$C_6$ alkanoyl, oxazolyl, oxadiazolyl pyrazolyl, thiazolyl, pyridyl, pyrimidinyl, imidazolyl, indolyl, furanyl or thienyl, wherein each heteroaryl group is optionally substituted with a $C_1$-$C_6$ alkyl group, phenyl or phenyl $C_1$-$C_4$ alkyl, where the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen.

In one embodiment of this aspect, $R_{30}$, $R_{35}$, $R_{40}$, and $R_{45}$ are independently H, halogen, $C_1$-$C_6$ alkyl, hydroxyl, $C_1$-$C_6$ alkoxy, —$C_1$-$C_3$ alkyl-OH or —$C_1$-$C_3$ alkyl-alkoxy.

In one embodiment of this aspect, $R_{30}$, $R_{35}$, $R_{40}$, and $R_{45}$ are independently H, halogen, $C_1$-$C_4$ alkyl, hydroxyl, $C_1$-$C_4$ alkoxy, —$C_1$-$C_2$ alkyl-OH or —$C_1$-$C_2$ alkyl- $C_1$-$C_4$ alkoxy.

In one embodiment of this aspect, $R_{30}$, $R_{35}$, $R_{40}$, and $R_{45}$ are independently H, $C_2$-$C_6$ alkenyl, $C_2$-$C_6$ alkynyl, $C_2$-$C_6$ haloalkenyl or $C_2$-$C_6$ haloalkynyl. In one embodiment, the halo portion of the haloalkenyl or haloalkynyl group is F, Cl or Br.

In one embodiment of this aspect, $R_{30}$, $R_{35}$, $R_{40}$, and $R_{45}$ are independently H, —C(O)$OR_{11}$, —S($O_2$)$R_{10}$, —$NR_{11}R_{11}$, —$SO_2NR_{11}R_{11}$, —C(O)$NR_{11}R_{11}$, —$NR_{11}$C(O)$R_{10}$, —$NR_{11}SO_2R_{10}$, —O—C(O)$NR_{11}R_{11}$ or $C_2$-$C_6$ alkanoyl.

In one embodiment of this aspect, $R_{30}$ and $R_{35}$ or $R_{35}$ and $R_{40}$ or $R_{40}$ and $R_{45}$ are —$OCH_2O$— or —$OCH_2CH_2O$— wherein each methylene of —$OCH_2O$— or —$OCH_2CH_2O$— is optionally substituted with one or two $C_1$-$C_4$ alkyl groups.

In still another embodiment of this aspect, $R_{11}$ is H.

In still another embodiment of this aspect, one of $R_{10}$ and $R_{11}$ is $CH_3$.

In another embodiment of this aspect, $R_{11}$ and $R_{11}$ together with the nitrogen to which they are attached form a 3-8 membered ring, which optionally includes an additional heteroatom that is NH, $NR_{12}$, $NR_{13}$, O or S.

In still another embodiment of this aspect, $R_{10}$ and $R_{11}$ at each occurrence are independently phenyl optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$; and additionally $R_{11}$ may be H.

In another embodiment of this aspect, $R_{10}$ and $R_{11}$ at each occurrence are independently pyrazolyl, isoxazolyl, isothiazolyl, imidazolyl or thiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$; and additionally $R_{11}$ may be H.

In another embodiment of this aspect, $R_{10}$ and $R_{11}$ at each occurrence are independently thiadiazolyl, triazolyl or oxadiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$ and additionally $R_{11}$ may be H.

In another aspect, provided herein are compounds of Formulas 3a, 3b, and 3c (when the C-ring is benzo substituted with $R_{30}$, $R_{35}$, $R_{40}$, and $R_{45}$), 3d, 3e and/or 3f, wherein $R_{30}$, $R_{35}$, $R_{40}$, and $R_{45}$ are independently H, halogen, $C_1$-$C_4$ alkyl, —C(O)$OR_{11}$, —S($O_2$)$R_{10}$, —$SO_2NR_{11}R_{11}$, —$NR_{11}R_{11}$, —$NR_{11}$C(O)$R_{10}$, —$NR_{11}SO_2R_{10}$ or —O—C(O)$NR_{11}R_{11}$.

In an embodiment of this aspect, at least two of $R_{30}$, $R_{35}$, $R_{40}$, and $R_{45}$ are H, while another is H, halogen or C1-C4 alkyl, and the other is —C(O)$OR_{11}$, —S($O_2$)$R_{10}$, —$SO_2NR_{11}R_{11}$, —$NR_{11}R_{11}$, —C(O)$NR_{11}R_{11}$, —$NR_{11}$C(O)$R_{10}$, —$NR_{11}SO_2R_{10}$ or —O—C(O)$NR_{11}R_{11}$.

In an embodiment of this aspect, three of $R_{30}$, $R_{35}$, $R_{40}$, and $R_{45}$ are H, while the other is —C(O)$OR_{11}$, —S($O_2$)$R_{10}$, —$SO_2NR_{11}R_{11}$, —$NR_{11}R_{11}$, —C(O)$NR_{11}R_{11}$, —$NR_{11}$C(O)$R_{10}$, —$NR_{11}SO_2R_{10}$ or —O—C(O)$NR_{11}R_{11}$.

In yet another embodiment of this aspect, three of $R_{30}$, $R_{35}$, $R_{40}$, and $R_{45}$ are H, while the other is —$NR_{11}R_{11}$.

In yet another embodiment of this aspect, three of $R_{30}$, $R_{35}$, $R_{40}$, and $R_{45}$ are H, while the other is —C(O)$OR_{11}$.

In an embodiment of this aspect, three of $R_{30}$, $R_{35}$, $R_{40}$, and $R_{45}$ are H, while the other is —C(O)$NR_{11}R_{11}$ or —$NR_{11}$C(O)$R_{10}$.

In still another embodiment of this aspect, three of $R_{30}$, $R_{35}$, $R_{40}$, and $R_{45}$ are H, while the other is —O—C(O)$NR_{11}R_{11}$.

In still another embodiment of this aspect, two of $R_{30}$, $R_{35}$, $R_{40}$, and $R_{45}$ are H, while one is methyl and the other is —$NR_{11}R_{11}$, or —C(O)$NR_{11}R_{11}$.

In still another embodiment of this aspect, at least two of $R_{30}$, $R_{35}$, $R_{40}$, and $R_{45}$ are one of $R_{30}$, $R_{35}$, $R_{40}$, and $R_{45}$ is H or methyl and the other is —$NR_{11}R_{11}$, —$SO_2NR_{11}R_{11}$ or —$NR_{11}SO_2R_{10}$.

In an embodiment of this aspect, three of $R_{30}$, $R_{35}$, $R_{40}$, and $R_{45}$ are H, while the other is —C(O)$NR_{11}R_{11}$ or —$NR_{11}$C(O)$R_{10}$.

In still another embodiment of this aspect, three of $R_{30}$, $R_{35}$, $R_{40}$, and $R_{45}$ are H, while the other is —O—C(O)$NR_{11}R_{11}$.

In still another embodiment of this aspect, two of $R_{30}$, $R_{35}$, $R_{40}$, and $R_{45}$ are H, while one is methyl and the other is —$NR_{11}R_{11}$, —C(O)$NR_{11}R_{11}$ or —$NR_{11}$C(O)$R_{10}$.

In an embodiment of this aspect, three of $R_{30}$, $R_{35}$, $R_{40}$, and $R_{45}$ are H, while the other is —C(O)$OR_{11}$. In a further embodiment, $R_{11}$ is H or $C_1$-$C_4$ alkyl.

In another aspect, provided herein are compounds of Formulas 3a, 3b, and 3c (when the C-ring is benzo substituted with $R_{30}$, $R_{35}$, $R_{40}$, and $R_{45}$), 3d, 3e and/or 3f, wherein $R_{30}$, $R_{35}$, $R_{40}$, and $R_{45}$ are independently H, halogen, $C_1$-$C_4$ alkyl, $C_1$-$C_4$ alkoxy, phenyloxy, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, where the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen.

In another aspect, at least two of $R_{30}$, $R_{35}$, $R_{40}$, and $R_{45}$ are H.

In still another embodiment of this aspect, three of $R_{30}$, $R_{35}$, $R_{40}$, and $R_{45}$ are H.

In a still another embodiment of this aspect, $R_{30}$, $R_{35}$, $R_{40}$, and $R_{45}$ are H.

In another embodiment of this aspect, at least one of $R_{30}$, $R_{35}$, $R_{40}$, and $R_{45}$ is a halogen (e.g., F, Cl or Br). In a still another embodiment, at least two of $R_{30}$, $R_{35}$, $R_{40}$, and $R_{45}$ is a halogen (e.g., F, Cl or Br), where the halogens may be the same or different.

In yet still another embodiment of this aspect, $R_{30}$ and $R_{45}$ are H; and $R_{35}$ and $R_{40}$ are independently halogen, $C_1$-$C_4$ alkyl, $C_1$-$C_4$ alkoxy or $C_2$-$C_6$ alkanoyl.

In still another embodiment of this aspect, $R_{30}$ and $R_{45}$ are H; and $R_{35}$ and $R_{40}$ are independently halogen, $C_1$-$C_4$ alkyl, $C_1$-$C_4$ alkoxy, $C_2$-$C_6$ alkanoyl, phenyloxy, phenyl or phenyl $C_1$-$C_4$ alkyl, where the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen.

In still another embodiment of this aspect, $R_{30}$ and $R_{45}$ are H; and $R_{35}$ and $R_{40}$ are independently halogen, $C_1$-$C_4$ alkyl, $C_1$-$C_4$ alkoxy, $C_2$-$C_6$ alkanoyl, oxazolyl, pyrazolyl, thiazolyl, pyridyl, pyrimidinyl, imidazolyl, indolyl, furanyl or thienyl.

In yet still another embodiment of this aspect, $R_{35}$ and $R_{40}$ are H; and $R_{30}$ and $R_{45}$ are independently halogen, $C_1$-$C_4$ alkyl, $C_1$-$C_4$ alkoxy or $C_2$-$C_6$ alkanoyl.

In still another embodiment of this aspect, $R_{35}$ and $R_{40}$ are H; and $R_{30}$ and $R_{45}$ are independently halogen, $C_1$-$C_4$ alkyl, $C_1$-$C_4$ alkoxy, $C_2$-$C_6$alkanoyl, phenyloxy, phenyl or phenyl $C_1$-$C_4$ alkyl, where the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen.

In still another embodiment of this aspect, $R_{35}$ and $R_{40}$ are H; and $R_{30}$ and $R_{45}$ are independently halogen, $C_1$-$C_4$ alkyl, $C_1$-$C_4$ alkoxy, $C_2$-$C_6$ alkanoyl, oxazolyl, pyrazolyl, thiazolyl, pyridyl, pyrimidinyl, imidazolyl, indolyl, furanyl or thienyl.

In another aspect, provided herein are compounds of Formulas 3a, 3b, and 3c (when the C-ring is benzo substituted with $R_{30}$, $R_{35}$, $R_{40}$, and $R_{45}$), 3d, 3e and/or 3f, wherein $R_{30}$, $R_{35}$, $R_{40}$, and $R_{45}$ are independently H, halogen, $C_1$-$C_4$ alkyl, $C_1$-$C_4$ alkoxy, $C_2$-$C_6$alkanoyl; provided that two adjacent carbons of the fused aryl ring (the ring to which the $R_{30}$, $R_{35}$, $R_{40}$ and $R_{45}$ groups are attached) optionally form a heterocycloalkyl or a heteroaryl ring, each of which is optionally substituted with 1, 2, 3 or 4 groups that are independently $C_1$-$C_4$ alkyl, $C_1$-$C_4$ alkoxy, halogen or $C_1$-$C_4$ alkanoyl wherein the alkanoyl group is optionally substituted with up to 3 halogen atoms.

In one embodiment of this aspect, the heterocycloalkyl ring is piperidinyl, pyrrolidinyl or morpholinyl, and the heteroaryl ring is pyrazolyl, imidazolyl or pyridinyl, wherein each heterocycloalkyl or heteroaryl group is optionally substituted with 1, 2, 3 or 4 groups that are independently $C_1$-$C_4$ alkyl, $C_1$-$C_4$ alkoxy, halogen or $C_1$-$C_4$ alkanoyl wherein the alkanoyl group is optionally substituted with up to 3 halogen atoms.

In one embodiment of this aspect, the heterocycloalkyl ring is piperidinyl or pyrrolidinyl, each of which is optionally substituted with 1 or 2 groups that are independently $C_1$-$C_4$ alkyl, $C_1$-$C_4$ alkoxy, halogen or $C_2$-$C_4$ alkanoyl wherein the alkanoyl group is optionally substituted with up to 3 halogen atoms.

In one embodiment of this aspect, the heteroaryl ring is pyrazolyl, imidazolyl or pyridinyl, each of which is optionally substituted with 1 or 2 groups that are independently $C_1$-$C_4$ alkyl, $C_1$-$C_4$ alkoxy, halogen or $C_2$-$C_4$ alkanoyl wherein the alkanoyl group is optionally substituted with up to 3 halogen atoms.

In another aspect, provided herein are compounds of Formulas 3a, 3b, and 3c (when the C-ring is benzo substituted with $R_{30}$, $R_{35}$, $R_{40}$, and $R_{45}$), 3d, 3e and/or 3f, wherein $R_{30}$, $R_{35}$, $R_{40}$, and $R_{45}$ are independently H, halogen, $C_1$-$C_4$ alkyl, $C_1$-$C_4$ alkoxy, $C_2$-$C_6$ alkanoyl, $C_2$-$C_8$ alkenyl, $C_2$-$C_8$ alkynyl, $C_2$-$C_8$ haloalkenyl or $C_2$-$C_8$ haloalkynyl; provided that two adjacent carbons of the fused aryl ring form a benzo ring, which is optionally substituted with 1 to 4 groups that are independently halogen, hydroxyl, $C_1$-$C_4$ alkoxy, $C_1$-$C_4$ haloalkyl, $C_1$-$C_4$ haloalkoxy, CN or $NO_2$. In a further aspect, the benzo ring is unsubstituted.

In one embodiment of this aspect, $R_{30}$ and $R_{45}$ are independently H, halogen, hydroxyl, $C_1$-$C_4$ alkyl, $C_1$-$C_4$ alkoxy, and $R_{35}$, $R_{40}$, and the carbons to which they are attached form a benzo ring, which is optionally substituted with 1 to 4 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN or $NO_2$. In a further embodiment, the benzo ring is unsubstituted.

In one embodiment of this aspect, $R_{30}$ and $R_{35}$ are independently H, halogen, hydroxyl, $C_1$-$C_4$ alkyl, $C_1$-$C_4$ alkoxy, and $R_{40}$, $R_{45}$, and the carbons to which they are attached form a benzo ring, which is optionally substituted with 1 to 4 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN or $NO_2$. In a further embodiment, the benzo ring is unsubstituted.

In one embodiment of this aspect, $R_{40}$ and $R_{45}$ are independently H, halogen, hydroxyl, $C_1$-$C_4$ alkyl, $C_1$-$C_4$ alkoxy, and $R_{30}$, $R_{35}$, and the carbons to which they are attached form a benzo ring, which is optionally substituted with 1 to 4 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN or $NO_2$. In a further embodiment, the benzo ring is unsubstituted.

In one aspect, provided herein are compounds of Formulas 3a, 3b, and/or 3c, wherein the C-ring is heteroaryl or heterocycloalkyl ring that is optionally substituted with one or more groups that are independently halogen, $C_1$-$C_6$ alkyl, $C_1$-$C_6$ haloalkyl, $C_1$-$C_6$ haloalkoxy, $C_2$-$C_8$ alkenyl, $C_2$-$C_8$ alkynyl, $C_2$-$C_8$ haloalkenyl, $C_2$-$C_8$ haloalkynyl, —C(O)O$R_{11}$, CN, hydroxyl, $C_1$-$C_6$ alkoxy, —$C_1$-$C_6$ alkyl-OH, —$C_1$-$C_6$ alkyl-$C_1$-$C_6$alkoxy, aryloxy (e.g., phenyloxy), —S($O_2$)$R_{10}$, —$NR_{11}R_{11}$, —C(O)$NR_{11}R_{11}$, —$SO_2NR_{11}R_{11}$, —$NR_{11}$C(O)$R_{10}$, —$NR_{11}SO_2R_{10}$, —O—C(O)$NR_{11}R_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, wherein the phenyl portions of the above are optionally substituted e.g., with one or more groups that are independently $C_1$-$C_6$ alkyl, $C_1$-$C_6$ alkoxy, $C_1$-$C_4$ haloalkyl (e.g. $CF_3$), $C_1$-$C_4$ haloalkoxy (e.g. $OCF_3$), hydroxyl, CN, $NO_2$ or halogen; wherein each $R_{11}$ is independently $C_1$-$C_6$ alkyl, heteroaryl that is selected from pyrazolyl, thiadiazolyl, triazolyl, isoxazolyl, isothiazolyl, imidazolyl, thiazolyl, oxadiazolyl, and pyridyl or aryl that is selected from phenyl and naphthyl, where the heteroaryl and aryl groups are optionally substituted with 1 to 3 groups that are independently halogen, hydroxyl, alkyl, alkoxy, haloalkyl, haloalkoxy, CN or $NO_2$; or if two $R_{11}$ groups are on a nitrogen, then the two $R_{11}$ groups together with the nitrogen to which they are attached, may form a 3-8 membered ring optionally including an additional heteroatom such as NH, $NR_{12}$, $NR_{13}$, O or S; and additionally $R_{11}$ may be H.

In one embodiment of this aspect, the C-ring is heteroaryl or heterocycloalkyl ring that is optionally substituted with one or more groups that are independently $C_1$-$C_4$ alkyl, $C_1$-$C_4$ alkoxy, halogen, $C_1$-$C_4$ haloalkyl (e.g. $CF_3$) or $C_1$-$C_4$ haloalkoxy (e.g., $OCF_3$); $R_{51}$ is as previously defined, and n is 0 or 1.

In one embodiment of this aspect, the C-ring is heteroaryl or heterocycloalkyl ring that is optionally substituted with one or more groups that are independently $C_1$-$C_4$ alkyl, $C_1$-$C_4$ alkoxy, halogen, —S($O_2$)$R_{10}$, —$NR_{11}R_{11}$, —C(O)$NR_{11}R_{11}$, —$SO_2NR_{11}R_{11}$, —$NR_{11}$C(O)$R_{10}$, —$NR_{11}SO_2R_{10}$, —O—C(O)$NR_{11}R_{11}$ or —C(O)O$R_{11}$.

In one embodiment of this aspect, the C-ring is heteroaryl or heterocycloalkyl ring that is optionally substituted with one or more groups that are independently $C_1$-$C_4$ alkyl, halogen, $C_2$-$C_8$ alkenyl, $C_2$-$C_8$ alkynyl, $C_2$-$C_8$ haloalkenyl, $C_2$-$C_8$ haloalkynyl or —C(O)O$R_{11}$.

In an embodiment of this aspect, the C-ring is a pyridyl ring optionally substituted with one or more groups that are independently $C_1$-$C_4$ alkyl, $C_1$-$C_4$ alkoxy, halogen, $C_1$-$C_4$ haloalkyl (e.g. $CF_3$) or $C_1$-$C_4$ haloalkoxy (e.g., $OCF_3$). In a further embodiment, the C-ring is an unsubstituted pyridyl ring.

In an embodiment of this aspect, the C-ring is a pyridyl ring substituted with one or two groups that are independently $C_1$-$C_4$ alkyl, halogen, $C_2$-$C_8$ alkenyl, $C_2$-$C_8$ alkynyl, $C_2$-$C_8$ haloalkenyl, $C_2$-$C_8$ haloalkynyl or —C(O)O$R_{11}$, where $R_{11}$ is H or $C_1$-$C_6$ alkyl.

In an embodiment of this aspect, the C-ring is a thiazolyl ring optionally substituted with one or more groups that are independently $C_1$-$C_4$ alkyl, $C_1$-$C_4$ alkoxy, halogen, $C_1$-$C_4$ haloalkyl (e.g. $CF_3$) or $C_1$-$C_4$ haloalkoxy (e.g., $OCF_3$). In a further embodiment, the C-ring is an unsubstituted thiazolyl ring.

In an embodiment of this aspect, the C-ring is a thiazolyl ring substituted with one group that is $C_1$-$C_4$ alkyl, halogen, $C_2$-$C_8$ alkenyl, $C_2$-$C_8$ alkynyl, $C_2$-$C_8$ haloalkenyl, $C_2$-$C_8$ haloalkynyl or —C(O)O$R_{11}$, where $R_{11}$ is H or $C_1$-$C_6$ alkyl.

In an embodiment of this aspect, the C-ring is a pyrazolyl ring optionally substituted with one or more groups that are independently $C_1$-$C_4$ alkyl, $C_1$-$C_4$ alkoxy, halogen, $C_1$-$C_4$ haloalkyl (e.g. $CF_3$) or $C_1$-$C_4$ haloalkoxy (e.g., $OCF_3$). In a further embodiment, the C-ring is an unsubstituted pyrazolyl ring.

In an embodiment of this aspect, the C-ring is a pyrazolyl ring substituted with one group that is $C_1$-$C_4$ alkyl, halogen, $C_2$-$C_8$ alkenyl, $C_2$-$C_8$ alkynyl, $C_2$-$C_8$ haloalkenyl, $C_2$-$C_8$ haloalkynyl or —C(O)O$R_{11}$, where $R_{11}$ is H or $C_1$-$C_6$ alkyl.

In an embodiment of this aspect, the C-ring is a thienyl ring optionally substituted with one or more groups that are independently $C_1$-$C_4$ alkyl, $C_1$-$C_4$ alkoxy, halogen, $C_1$-$C_4$ haloalkyl (e.g. $CF_3$) or $C_1$-$C_4$ haloalkoxy (e.g., $OCF_3$). In a further embodiment, the C-ring is an unsubstituted thienyl ring.

In an embodiment of this aspect, the C-ring is a thienyl ring substituted with one group that is $C_1$-$C_4$ alkyl, halogen, $C_2$-$C_8$ alkenyl, $C_2$-$C_8$ alkynyl, $C_2$-$C_8$ haloalkenyl, $C_2$-$C_8$ haloalkynyl or —C(O)O$R_{11}$, where $R_{11}$ is H or $C_1$-$C_6$ alkyl.

In one aspect, the compounds of Formula 3 are the compounds of Formula 3a. In a further embodiment, the compounds of Formula 3a are of the formula:

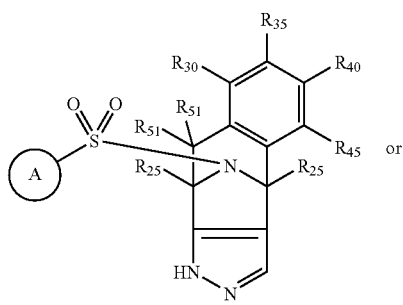

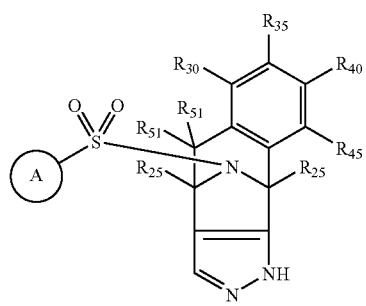

where $R_{25}$, $R_{30}$, $R_{35}$, $R_{40}$, $R_{45}$, $R_{51}$ are as described above and the A-ring is as described herein.

In one aspect, the compounds of Formula 3 are the compounds of Formula 3b. In a further embodiment, the compounds of Formula 3a are of the formula:

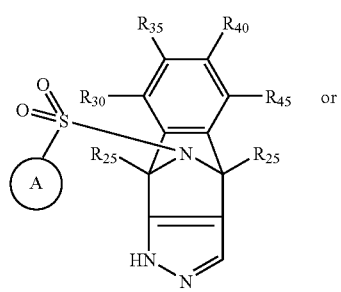

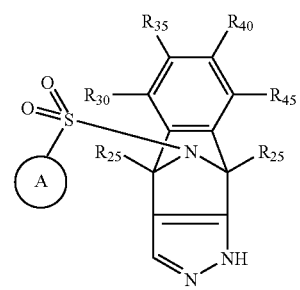

where $R_{25}$, $R_{30}$, $R_{35}$, $R_{40}$, $R_{45}$, $R_{51}$ are as described above and the A-ring is as described herein.

In one aspect, the compounds of Formula 3 are the compounds of Formula 3a.

In one aspect, the compounds of Formula 3 are the compounds of Formula 3b.

In one aspect, the compounds of Formula 3 are the compounds of Formula 3c.

In one aspect, the compounds of Formula 3 are the compounds of Formula 3d.

In one aspect, the compounds of Formula 3 are the compounds of Formula 3e.

In one aspect, the compounds of Formula 3 are the compounds of Formula 3f.

In one aspect, provided herein are compounds of Formulas 4a and/or 4b, i.e., compounds of Formula 4 having the formulas:

Formula 4a

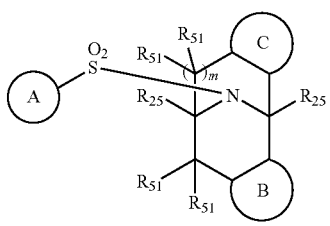

Formula 4b

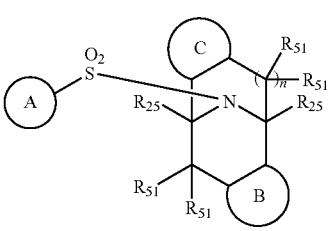

Wherein the A-ring, B-ring, C-ring, $R_{25}$, $R_{51}$, m and n are as defined above for Formula 4.

In another aspect, provided herein are compounds of Formulas 4c and/or 4d, i.e., compounds of Formula 4 having the formulas:

Formula 4c

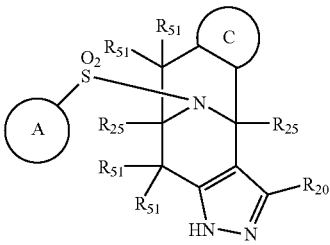

Formula 4d

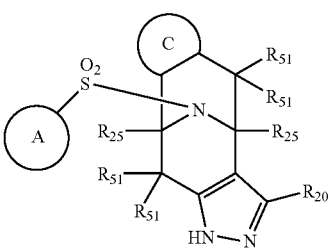

Wherein the A-ring, C-ring, $R_{20}$, $R_{25}$, and $R_{51}$ are as defined above.

In one aspect, provided herein are compounds of Formulas 4e, i.e., compounds of Formula 4 that have the following formula:

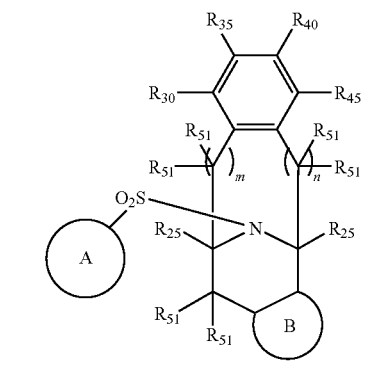

Wherein the A-ring, B-ring, $R_{20}$, $R_{25}$, $R_{30}$, $R_{35}$, $R_{40}$, $R_{45}$, $R_{51}$, m and n are as defined above.

In one aspect, provided herein are compounds of Formulas 4f and/or 4g, i.e., compounds of Formula 4 that have the following formula:

Formula 4f

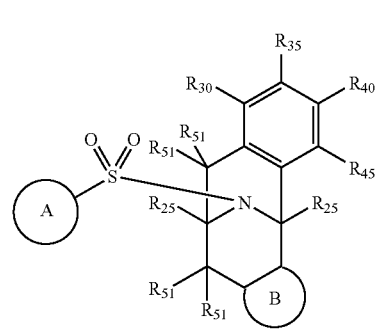

Formula 4g

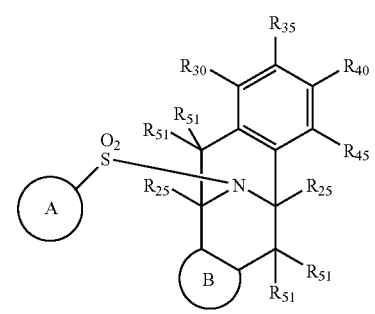

including enantiomers and/or pharmaceutically acceptable salts thereof, wherein, B-ring is pyrazolyl, dihydropyrazolyl, pyrazolonyl or pyrazolidinonyl, each of which is optionally substituted with $NR_{11}$—$C_2$-$C_6$ alkanoyl, $C_1$-$C_6$ alkyl, $C_3$-$C_6$ cycloalkyl, $C_2$-$C_4$ alkenyl, $C_2$-$C_4$ alkynyl, $C_1$-$C_4$ alkoxy, amino, $C_1$-$C_4$ alkylamino, $C_1$-$C_4$ dialkylamino, hydroxy, hydroxyalkyl, halo, $C_1$-$C_4$ haloalkyl, $C_1$-$C_4$ haloalkoxy, —$NR_{11}C(O)R_{10}$, —$NR_{11}SO_2R_{10}$ or CN;

$R_{30}$, $R_{35}$, $R_{40}$, and $R_{45}$ are independently H, halogen, $C_1$-$C_6$ alkyl, $C_2$-$C_6$ alkenyl, $C_2$-$C_6$ alkynyl, $C_2$-$C_8$ haloalkenyl, $C_2$-$C_8$ haloalkynyl, —$C(O)OR_{11}$, —$SO_2NR_{11}R_{11}$, aryl $C_1$-$C_6$ alkyl, $C_3$-$C_6$ cycloalkyl, $C_1$-$C_6$ haloalkyl, $C_1$-$C_6$ haloalkoxy, CN, $NO_2$, hydroxyl, $C_1$-$C_6$ alkoxy, —$C_1$-$C_6$ alkyl-OH, —$C_1$-$C_6$ alkyl-$C_1$-$C_6$ alkoxy, phenyloxy, —$S(O_2)$ $R_{10}$, —$NR_{11}R_{11}$, —$C(O)NR_{11}R_{11}$, —$NR_{11}C(O)R_{10}$, —$NR_{11}SO_2R_{10}$, —O—$C(O)NR_1,R_{11}$, $C_2$-$C_6$ alkanoyl, heteroaryl $C_1$-$C_6$ alkyl, heteroaryl, where the heteroaryl groups are oxazolyl, oxadiazolyl pyrazolyl, thiazolyl, pyridyl, pyrimidinyl, imidazolyl, indolyl, furanyl or thienyl, and wherein each heteroaryl group is optionally substituted with a $C_1$-$C_6$ alkyl group; heterocycloalkylalkyl, heterocycloalkyl, wherein the heterocycloalkyl groups are pyrrolidinyl, imidazolidinyl, piperidinyl or morpholinyl, wherein each heterocycloalkyl group is optionally substituted with one or two groups that are independently $C_1$-$C_6$ alkyl, $C_1$-$C_6$ alkoxy or halogen, phenyl, naphthyl, phenyloxy, naphthyloxy or phenyl $C_1$-$C_6$ alkyl, where the phenyl portions of the above are optionally substituted with one to five groups that are independently $C_1$-$C_6$ alkyl, $C_1$-$C_6$ alkoxy, hydroxyl, $C_1$-$C_4$ haloalky (e.g., $CF_3$) or halogen; and wherein two adjacent carbons of the fused aryl ring optionally form a heterocycloalkyl (e.g., —$OCH_2O$— or $OCH_2CH_2O$—) or a heteroaryl ring, each of which is optionally substituted with 1, 2, 3 or 4 groups that are independently $C_1$-$C_4$ alkyl, $C_1$-$C_4$ alkoxy, halogen or $C_2$-$C_4$ alkanoyl wherein the alkanoyl group is optionally substituted with up to 3 halogen atoms; or two adjacent carbons of the fused aryl ring form a benzo ring which is optionally substituted with 1 to 4 groups that are independently halogen, hydroxyl, $C_1$-$C_4$alkyl, $C_1$-$C_4$ alkoxy, $C_1$-$C_4$ haloalkyl, $C_1$-$C_4$ haloalkoxy, CN or $NO_2$;

each $R_{51}$ is independently absent, H, $C_1$-$C_4$ alkyl, halogen (e.g., F, Cl or Br), CN, amino, mono alkylamino, dialkylamino, OH, $C_1$-$C_4$ haloalkoxy (e.g., $OCF_3$) or $C_1$-$C_4$ haloalkyl (e.g., $CF_3$); or when there are two $R_{51}$ groups on a carbon atom, the two $R_{51}$ groups and the carbon to which they are attached may form a 3- to 6-membered cycloalkyl or heterocycloalkyl ring; or when there are two $R_{51}$ groups on a carbon, the two $R_{51}$ groups may form an oxo group; or when there are two $R_{51}$ groups on a carbon, the two $R_{51}$ groups may form an alkene group; or when there are two $R_{51}$ groups on a carbon, the two $R_{51}$ groups may form an oxime or a $C_1$-$C_4$ alkylated oxime (e.g., O-methyl oxime);

a non-bridgehead carbon (and any substituent or substituents thereon) in the [3.3.1], [3.2.1] or [2.2.1] ring systems may be replaced with an $NR_{15}$ group;

$R_{10}$ and $R_{11}$ at each occurrence are independently $C_1$-$C_6$ alkyl, heteroaryl that is selected from pyrazolyl, thiadiazolyl, triazolyl, isoxazolyl, isothiazolyl, imidazolyl, thiazolyl, oxadiazolyl, and pyridyl or aryl that is selected from phenyl and naphthyl, where the heteroaryl and aryl groups are optionally substituted with 1 to 3 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN or $NO_2$; and additionally $R_{11}$ may be H; or if two $R_{11}$ groups are on a nitrogen, then the two $R_{11}$ groups together with the nitrogen to which they are attached, may, form a 3-8 membered ring optionally including an additional heteroatom such as NH, $NR_{12}$, $NR_{13}$, O or S. In one embodiment of this aspect, the B-ring is pyrazolyl, which is optionally substituted with $C_1$-$C_4$ $NR_{11}$—$C_2$-$C_6$ alkanoyl (e.g., —$NR_{11}$—$C_2$alkanoyl, where $R_{11}$ is H or $C_1$-$C_4$ alkyl), alkyl, $C_3$-$C_6$ cycloalkyl, $C_2$-$C_4$ alkenyl, $C_2$-$C_4$ alkynyl, $C_1$-$C_4$ alkoxy, amino, $C_1$-$C_4$ alkylamino, $C_1$-$C_4$ dialkylamino, hydroxy $C_1$-$C_4$ alkyl, halo, $CF_3$, $OCF_3$ or CN;

$R_{12}$ is H, $C_1$-$C_6$ alkyl, aryl or —$SO_2$-aryl (e.g., phenyl or naphthyl, where phenyl is preferred), where each aryl group is optionally substituted with 1 to 5 groups that are independently halogen, hydroxyl, alkyl, alkoxy, haloalkyl, haloalkoxy, CN or $NO_2$; and $R_{13}$ is H, aryl or $C_1$-$C_6$ alkyl optionally substituted with aryl (such as phenyl or naphthyl, more preferably, phenyl), hydroxyl or halogen, where each aryl group is optionally substituted with 1 to 5 groups that are independently halogen, hydroxyl, alkyl, alkoxy, haloalkyl, haloalkoxy, CN or $NO_2$.

In another aspect, provided herein are compounds of Formulas 4a, 4b, 4c, 4d (when the C-ring is benzo substituted with $R_{30}$, $R_{35}$, $R_{40}$, and $R_{45}$), 4e, 4f and/or 4g, wherein $R_{30}$, $R_{35}$, $R_{40}$, and $R_{45}$ are independently H, halogen, $C_1$-$C_6$ alkyl, $C_1$-$C_6$ haloalkyl, $C_1$-$C_6$ haloalkoxy, CN, hydroxyl, $C_1$-$C_6$ alkoxy, $C_3$-$C_6$ cycloalkyl, —$C_1$-$C_3$ alkyl-OH, —$C_1$-$C_3$ alkyl-alkoxy, phenyloxy, —C(O)$OR_{11}$, —S($O_2$)$R_{10}$, —$NR_{11}R_{11}$, —C(O)$NR_{11}R_{11}$, —$SO_2NR_{11}R_{11}$, —$NR_{11}$C(O)$R_{10}$, —$NR_{11}SO_2R_{10}$, —O—C(O)$NR_{11}R_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, where the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen. In an embodiment of this aspect, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In one embodiment of this aspect, $R_{30}$, $R_{35}$, $R_{40}$, and $R_{45}$ are independently H, halogen (e.g., F), $C_1$-$C_6$ alkyl, hydroxyl, $C_1$-$C_4$ haloalkyl (e.g., $CF_3$), $C_1$-$C_4$ haloalkoxy (e.g., $OCF_3$), $C_1$-$C_6$ alkoxy, —$C_1$-$C_3$ alkyl-OH, CN or —$C_1$-$C_3$ alkyl-alkoxy.

In one embodiment of this aspect, $R_{30}$, $R_{35}$, $R_{40}$, and $R_{45}$ are independently H, halogen, $C_1$-$C_4$ alkyl, $CF_3$, $OCF_3$, hydroxyl, $C_1$-$C_4$ alkoxy, —$C_1$-$C_2$ alkyl-OH, CN or —$C_1$-$C_2$ alkyl- $C_1$-$C_4$ alkoxy.

In one embodiment of this aspect, $R_{30}$, $R_{35}$, $R_{40}$, and $R_{45}$ are independently H, halogen, methyl, ethyl, hydroxyl, $CF_3$, $OCF_3$. In a further embodiment, at least two of $R_{30}$, $R_{35}$, $R_{40}$, and $R_{45}$ are hydrogen. In a further embodiment, $R_{40}$ is $CF_3$. In a still further embodiment, $R_{35}$ is $CF_3$. In a further embodiment, $R_{40}$ is CN. In a still further embodiment, $R_{35}$ is CN. In a further embodiment, $R_{35}$ or $R_{40}$ is hydroxyl.

In one embodiment of this aspect, $R_{30}$, $R_{35}$, $R_{40}$, and $R_{45}$ are independently H, —C(O)$OR_{11}$, —S($O_2$)$R_{10}$, —$NR_{11}R_{11}$, —C(O)$NR_{11}R_{11}$, —$SO_2NR_{11}R_{11}$, —$NR_{11}$C(O)$R_{10}$, —$NR_{11}SO_2R_{10}$, —O—C(O)$NR_{11}R_{11}$ or $C_2$-$C_6$ alkanoyl.

In one embodiment of this aspect, $R_{30}$ and $R_{35}$ or $R_{35}$ and $R_{40}$ or $R_{40}$ and $R_{45}$ are —$OCH_2O$— or —$OCH_2CH_2O$— wherein each methylene of —$OCH_2O$— or —$OCH_2CH_2O$— is optionally substituted with one or two $C_1$-$C_4$ alkyl groups.

In still another embodiment of this aspect, $R_{11}$ is H.

In still another embodiment of this aspect, one of $R_{10}$ and $R_{11}$ is $CH_3$.

In another embodiment of this aspect, $R_{11}$ and $R_{11}$ together with the nitrogen to which they are attached form a 3-8 membered ring, which optionally includes an additional heteroatom that is NH, $NR_{12}$, $NR_{13}$, O or S.

In still another embodiment of this aspect, $R_{10}$ and $R_{11}$ at each occurrence are independently phenyl optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$; and additionally $R_{11}$ may be H.

In another embodiment of this aspect, $R_{10}$ and $R_{11}$ at each occurrence are independently pyrazolyl, isoxazolyl, isothiazolyl, imidazolyl or thiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$; and additionally $R_{11}$ may be H.

In another embodiment of this aspect, $R_{10}$ and $R_{11}$ at each occurrence are independently thiadiazolyl, triazolyl or oxadiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$ and additionally $R_{11}$ may be H.

In another aspect, provided herein are compounds of Formulas 4a, 4b, 4c, 4d (when the C-ring is benzo substituted with $R_{30}$, $R_{35}$, $R_{40}$, and $R_{45}$), 4e, 4f and/or 4g, wherein $R_{30}$, $R_{35}$, $R_{40}$, and $R_{45}$ are independently H, halogen (e.g., F), $C_1$-$C_4$ alkyl, —C(O)O$R_{11}$, —S($O_2$)$R_{10}$, —$SO_2NR_{11}R_{11}$, —$NR_{11}R_{11}$, —C(O)$NR_{11}R_{11}$, —$NR_{11}$C(O)$R_{10}$, —$NR_{11}SO_2R_{10}$ or —O—C(O)$NR_{11}R_{11}$.

In an embodiment of this aspect, at least two of $R_{30}$, $R_{35}$, $R_{40}$, and $R_{45}$ are H, while another is H, halogen or C1-C4 alkyl, and the other is —C(O)O$R_{11}$, —S($O_2$)$R_{10}$, —$SO_2NR_{11}R_{11}$, —$NR_{11}R_{11}$, —C(O)$NR_{11}R_{11}$, —$NR_{11}$C(O)$R_{10}$, —$NR_{11}SO_2R_{10}$ or —O—C(O)$NR_{11}R_{11}$. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In an embodiment of this aspect, three of $R_{30}$, $R_{35}$, $R_{40}$, and $R_{45}$ are H, while the other is —C(O)O$R_{11}$, —S($O_2$)$R_{10}$, —$SO_2NR_{11}R_{11}$, —$NR_{11}R_{11}$, —C(O)$NR_{11}R_{11}$, —$NR_{11}$C(O)$R_{10}$, —$NR_{11}SO_2R_{10}$ or —O—C(O)$NR_{11}R_{11}$. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In yet another embodiment of this aspect, three of $R_{30}$, $R_{35}$, $R_{40}$, and $R_{45}$ are H, while the other is —$NR_{11}R_{11}$. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_5$ groups that are alpha to the B-ring form form an oxime or a $C_1$-$C_4$ alkylated oxime (e.g., O-methyl oxime).

In yet another embodiment of this aspect, three of $R_{30}$, $R_{35}$, $R_{40}$, and $R_{45}$ are H, while the other is —$SO_2NR_{11}R_{11}$ or —$NR_{11}SO_2R_{10}$. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_5$ groups that are alpha to the B-ring form form an oxime or a $C_1$-$C_4$ alkylated oxime (e.g., O-methyl oxime).

In an embodiment of this aspect, three of $R_{30}$, $R_{35}$, $R_{40}$, and $R_{45}$ are H, while the other is —C(O)$NR_{11}R_{11}$ or —$NR_{11}$C(O)$R_{10}$. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_5$ groups that are alpha to the B-ring form form an oxime or a $C_1$-$C_4$ alkylated oxime (e.g., O-methyl oxime).

In still another embodiment of this aspect, three of $R_{30}$, $R_{35}$, $R_{40}$, and $R_{45}$ are H, while the other is —O—C(O)$NR_{11}R_{11}$. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_5$ groups that are alpha to the B-ring form form an oxime or a $C_1$-$C_4$ alkylated oxime (e.g., O-methyl oxime).

In still another embodiment of this aspect, two of $R_{30}$, $R_{35}$, $R_{40}$, and $R_{45}$ are H, while one is methyl and the other is —$NR_{11}R_{11}$, —C(O)$NR_{11}R_{11}$ or —$NR_{11}$C(O)$R_{10}$. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In an embodiment of this aspect, three of $R_{30}$, $R_{35}$, $R_{40}$, and $R_{45}$ are H, while the other is —C(O)O$R_{11}$. In a further embodiment, $R_{11}$ is H or $C_1$-$C_4$ alkyl. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In another aspect, provided herein are compounds of Formulas 4a, 4b, 4c, 4d (when the C-ring is benzo substituted with $R_{30}$, $R_{35}$, $R_{40}$, and $R_{45}$), 4e, 4f and/or 4g, wherein $R_{30}$, $R_{35}$, $R_{40}$, and $R_{45}$ are independently H, halogen, $C_1$-$C_4$ alkyl, $C_1$-$C_4$ alkoxy, $C_3$-$C_6$ cycloalkyl, phenyloxy, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl where the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen.

In another embodiment of this aspect, at least two of $R_{30}$, $R_{35}$, $R_{40}$, and $R_{45}$ are H.

In still another embodiment of this aspect, three of $R_{30}$, $R_{35}$, $R_{40}$, and $R_{45}$ are H.

In still another embodiment of this aspect, $R_{30}$, $R_{35}$, $R_{40}$, and $R_{45}$ are H.

In another embodiment of this aspect, at least one of $R_{30}$, $R_{35}$, $R_{40}$, and $R_{45}$ is a halogen (e.g., F, Cl or Br). In a still another embodiment, at least two of $R_{30}$, $R_{35}$, $R_{40}$, and $R_{45}$ is a halogen (e.g., F, Cl or Br), where the halogens may be the same or different.

In still another embodiment of this aspect, $R_{30}$, $R_{35}$, $R_{40}$, and $R_{45}$ are H; and the B-ring is unsubstituted pyrazolyl.

In yet still another embodiment of this aspect, $R_{30}$ and $R_{45}$ are H; and $R_{35}$ and $R_{40}$ are independently halogen (e.g., F, Cl or Br), $C_1$-$C_4$ alkyl, $C_1$-$C_4$ alkoxy or $C_2$-$C_6$ alkanoyl.

In yet still another embodiment of this aspect, $R_{30}$ and $R_{45}$ are H; and $R_{35}$ and $R_{40}$ and the carbons to which they are attached form a heterocycloalkyl ring. In a further embodiment, the heterocycloalkyl ring is —$OCH_2O$—, —$OCH_2CH_2O$— or —$OC(O)O$—. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In yet still another embodiment of this aspect, $R_{30}$ and $R_{45}$ are H; and $R_{35}$ and $R_{40}$ are independently halogen (e.g., F, Cl or Br), $C_1$-$C_4$ alkyl, $C_1$-$C_4$ alkoxy or $C_2$-$C_6$ alkanoyl. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen (e.g., F). In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In yet still another embodiment of this aspect, $R_{30}$ and $R_{45}$ are H; and $R_{35}$ and $R_{40}$ are independently halogen (e.g., F, Cl or Br), and the geminal $R_{51}$ groups that are alpha to the B-ring are both halogens.

In still another embodiment of this aspect, $R_{30}$ and $R_{45}$ are H; and $R_{35}$ and $R_{40}$ are independently halogen (e.g., F, Cl or Br), hydroxyl, $C_1$-$C_4$ alkyl, $C_1$-$C_4$ alkoxy, $C_2$-$C_6$ alkanoyl, phenyloxy, phenyl or phenyl $C_1$-$C_4$ alkyl, where the phenyl portions are optionally substituted with one or more groups that are independently $C_1$-$C_6$ alkyl, $C_1$-$C_6$ alkoxy, $C_1$-$C_4$ haloalky (e.g. $CF_3$) or halogen.

In still another embodiment of this aspect, $R_{30}$ and $R_{45}$ are H; and $R_{35}$ and $R_{40}$ are independently halogen (e.g., F, Cl or Br), $C_1$-$C_4$ alkyl, $C_1$-$C_4$ alkoxy, $C_2$-$C_6$ alkanoyl, oxazolyl, pyrazolyl, thiazolyl, pyridyl, pyrimidinyl, imidazolyl, indolyl, furanyl or thienyl.

In yet still another embodiment of this aspect, $R_{35}$ and $R_{40}$ are H; and $R_{30}$ and $R_{45}$ are independently halogen (e.g., F, Cl or Br), hydroxyl, $C_1$-$C_4$ alkyl, $C_1$-$C_4$ alkoxy or $C_2$-$C_6$ alkanoyl.

In yet still another embodiment of this aspect, $R_{35}$ and $R_{40}$ are H; and $R_{30}$ and $R_{45}$ are independently halogen (e.g., F, Cl or Br), hydroxyl, $C_1$-$C_4$ alkyl, $C_1$-$C_4$ alkoxy, cyclopropyl or $C_2$-$C_6$ alkanoyl; and the geminal $R_{51}$ groups that are alpha to the B-ring form an oxo group, an $C_2$-$C_4$ alkenyl group, an oxime, a $C_1$-$C_4$ alkylated oxime (e.g., O-methyl oxime), are both H or are both halogens (e.g., F). In a further embodiment, one of $R_{30}$ or $R_{45}$ is H, while the other is F or Cl.

In yet still another embodiment of this aspect, $R_{35}$ and $R_{40}$ are H; and $R_{30}$ and $R_{45}$ are independently H, halogen (e.g., F, Cl or Br), $C_1$-$C_4$ alkyl, $C_1$-$C_4$ alkoxy, cyclopropyl or $C_2$-$C_6$ alkanoyl; and the geminal $R_{51}$ groups that are alpha to the B-ring are both halogens, provided that at least one of $R_{30}$ and $R_{45}$ is not H. In another embodiment, both $R_{51}$ groups that are alpha to the B-ring are F. In a further embodiment, $R_{30}$ is halogen while $R_{45}$ is H. In another further embodiment, $R_{30}$ is H while $R_{45}$ is halogen. In another further embodiment, $R_{30}$ is cyclopropyl, while $R_{45}$ is H. In another further embodiment, $R_{30}$ is H while $R_{45}$ is cyclopropyl. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In yet still another embodiment of this aspect, $R_{35}$ and $R_{40}$ are H; and $R_{30}$ and $R_{45}$ are independently halogen (e.g., F, Cl or Br), methyl or methoxy. In a further embodiment, $R_{30}$ is halogen. In another further embodiment, $R_{45}$ is halogen. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen (e.g., F). In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In still another embodiment of this aspect, $R_{35}$ and $R_{40}$ are H; and $R_{30}$ and $R_{45}$ are independently halogen (e.g., F, Cl or Br), hydroxyl, $C_1$-$C_4$ alkyl, $C_1$-$C_4$ alkoxy, $C_2$-$C_6$ alkanoyl, phenyloxy, phenyl or phenyl $C_1$-$C_4$ alkyl. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen (e.g., F). In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In still another embodiment of this aspect, $R_{35}$ and $R_{40}$ are H; and $R_{30}$ and $R_{45}$ are independently halogen (e.g., F, Cl or Br), hydroxyl, $C_1$-$C_4$ alkyl, $C_1$-$C_4$ alkoxy, $C_2$-$C_6$ alkanoyl, oxazolyl, pyrazolyl, thiazolyl, pyridyl, pyrimidinyl, imidazolyl, indolyl, furanyl or thienyl. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen (e.g., F). In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In still another embodiment of this aspect, $R_{30}$, $R_{35}$, $R_{40}$, and $R_{45}$ are independently H, halogen (e.g., F, Cl or Br), $C_1$-$C_4$ alkyl or $C_1$-$C_4$ alkoxy; and one $R_{51}$ group is halogen or OH, while the other $R_{51}$ group is H. In a still further embodiment, the B-ring is unsubstituted. In a further embodiment, at least two of $R_{30}$, $R_{35}$, $R_{40}$, and $R_{45}$ are H. In a still further embodiment, $R_{30}$, $R_{35}$, $R_{40}$, and $R_{45}$ are H.

In still another embodiment of this aspect, $R_{30}$, $R_{35}$, $R_{40}$, and $R_{45}$ are independently H, halogen (e.g., F, Cl or Br), $C_1$-$C_4$ alkyl or $C_1$-$C_4$ alkoxy; and one $R_{51}$ group is halogen or OH, while the other $R_{51}$ group is H. In a still further embodiment, the B-ring is unsubstituted. In a further embodiment, at least one of $R_{30}$, $R_{35}$, $R_{40}$, and $R_{45}$ is halogen (e.g., F, Cl or Br), $C_1$-$C_4$ alkyl or $C_1$-$C_4$ alkoxy. In a still further embodiment, two of $R_{30}$, $R_{35}$, $R_{40}$, and $R_{45}$ are H.

In another aspect, provided herein are compounds of Formulas 4a, 4b, 4c, 4d (when the C-ring is benzo substituted with $R_{30}$, $R_{35}$, $R_{40}$, and $R_{45}$), 4e, 4f and/or 4g, wherein $R_{30}$, $R_{35}$, $R_{40}$, and $R_{45}$ are independently H, halogen, $C_1$-$C_4$ alkyl, $C_1$-$C_4$ alkoxy, $C_2$-$C_6$ alkanoyl, $C_2$-$C_8$ alkenyl, $C_2$-$C_8$ alkynyl, $C_2$-$C_8$ haloalkenyl or $C_2$-$C_8$ haloalkynyl; provided that two adjacent carbons of the fused aryl ring (the ring to which the $R_{30}$, $R_{35}$, $R_{40}$ and $R_{45}$ groups are attached) optionally form a heterocycloalkyl or a heteroaryl ring, each of which is optionally substituted with 1, 2, 3 or 4 groups that are independently $C_1$-$C_4$ alkyl, $C_1$-$C_4$ alkoxy, halogen or $C_1$-$C_4$ alkanoyl wherein the alkanoyl group is optionally substituted with up to 3 halogen atoms. In a further embodiment, the heterocycloalkyl ring is piperidinyl, pyrrolidinyl or morpholinyl, and the heteroaryl ring is pyrazolyl, imidazolyl or pyridinyl, wherein each heterocycloalkyl or heteroaryl group is optionally substituted with 1, 2, 3 or 4 groups that are independently $C_1$-$C_4$ alkyl, $C_1$-$C_4$ alkoxy, halogen or $C_1$-$C_4$ alkanoyl wherein the alkanoyl group is optionally substituted with up to 3 halogen atoms. In a further embodiment, the heterocycloalkyl ring is piperidinyl or pyrrolidinyl, each of which is optionally substituted with 1 or 2 groups that are independently $C_1$-$C_4$ alkyl, $C_1$-$C_4$ alkoxy, halogen or $C_2$-$C_4$ alkanoyl wherein the alkanoyl group is optionally substituted with up to 3 halogen atoms. In a further embodiment, the heteroaryl ring is pyrazolyl, imidazolyl or pyridinyl, each of which is optionally substituted with 1 or 2 groups that are independently $C_1$-$C_4$ alkyl, $C_1$-$C_4$alkoxy, halogen or $C_2$-$C_4$ alkanoyl wherein the alkanoyl group is optionally substituted with up to 3 halogen atoms.

In another aspect, provided herein are compounds of Formulas 4a, 4b, 4c, 4d (when the C-ring is benzo substituted with $R_{30}$, $R_{35}$, $R_{40}$, and $R_{45}$), 4e, 4f and/or 4g, wherein $R_{30}$, $R_{35}$, $R_{40}$, and $R_{45}$ are independently H, halogen, $C_1$-$C_4$ alkyl, $C_1$-$C_4$ alkoxy, $C_2$-$C_6$ alkanoyl; provided that two adjacent carbons of the fused aryl ring form a benzo ring, which is optionally substituted with 1 to 4 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN or $NO_2$.

In one embodiment of this aspect, $R_{30}$ and $R_{45}$ are independently H, halogen, hydroxyl, $C_1$-$C_4$ alkyl, $C_1$-$C_4$ alkoxy, and $R_{35}$, $R_{40}$, and the carbons to which they are attached form a benzo ring, which is optionally substituted with 1 to 4 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN or $NO_2$. In a further embodiment, the benzo ring is unsubstituted.

In one embodiment of this aspect, $R_{30}$ and $R_{35}$ are independently H, halogen, hydroxyl, $C_1$-$C_4$ alkyl, $C_1$-$C_4$ alkoxy, and $R_{40}$, $R_{45}$, and the carbons to which they are attached form a benzo ring, which is optionally substituted with 1 to 4 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN or $NO_2$. In a further embodiment, the benzo ring is unsubstituted.

In one embodiment of this aspect, $R_{40}$ and $R_{45}$ are independently H, halogen, hydroxyl, $C_1$-$C_4$ alkyl, $C_1$-$C_4$ alkoxy, and $R_{30}$, $R_{35}$, and the carbons to which they are attached form a benzo ring, which is optionally substituted with 1 to 4 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN or $NO_2$. In a further embodiment, the benzo ring is unsubstituted.

In one aspect, the compounds of Formula 4 are the compounds of Formula 4a.

In one aspect, the compounds of Formula 4 are the compounds of Formula 4b.

In one aspect, the compounds of Formula 4 are the compounds of Formula 4c.

In one aspect, the compounds of Formula 4 are the compounds of Formula 4d.

In one aspect, the compounds of Formula 4 are the compounds of Formula 4e.

In one aspect, the compounds of Formula 4 are the compounds of Formula 4f.

In one aspect, the compounds of Formula 4 are the compounds of Formula 4g.

In one aspect, the compounds of Formula 4 have the Formulas 4f1 and 4g1:

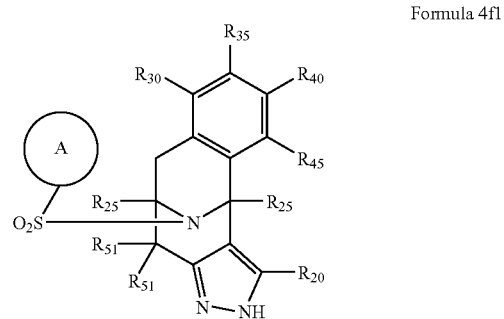

Formula 4f1

-continued

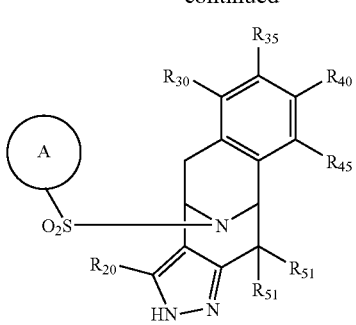

Formula 4g1 including stereoisomers, tautomers and mixtures of stereoisomers and/or tautomers, and/or pharmaceutical salts thereof, wherein $R_{30}$, $R_{35}$, $R_{40}$, $R_{45}$, and the A-ring are as previously defined; $R_{20}$ is H, $C_1$-$C_6$ alkyl, $C_1$-$C_6$ alkoxy, amino, $C_1$-$C_6$ alkylamino, $C_1$-$C_6$ dialkylamino, halo, $CF_3$ or $NHC(O)CH_3$; and $R_{51}$ is H, $C_1$-$C_4$ alkyl, F, Cl, Br, CN, amino, mono alkylamino, dialkylamino, OH, oxo, $=CH_2$, $=NOH$, $=NOCH_3$, $=NOCH_2CH_3$, or $CF_3$. In one embodiment, $R_{20}$ is H. In another embodiment, $R_{20}$ is methyl. In another embodiment, $R_{51}$ is H. In another embodiment, $R_{51}$ is F. In another embodiment, $R_{51}$ is OH. In another embodiment, $R_{51}$ is $CF_3$. In still another embodiment, $R_{51}$ is H and $R_{51}$ is F or Cl. In another embodiment, $R_{51}$ is OH. In another embodiment, $R_{51}$ is H. In another embodiment, $R_{20}$ is H and $R_{51}$ is F. In another embodiment, $R_{20}$ is H and $R_{51}$ is OH. In another embodiment, $R_{20}$ is H and the geminal $R_{51}$ groups form an oxo group. In another embodiment, $R_{20}$ is methyl and the geminal $R_{51}$ groups form an oxo group. In another embodiment, $R_{20}$ is H and the geminal $R_{51}$ groups form an $=CH_2$, group. In another embodiment, $R_{20}$ is methyl and the geminal $R_{51}$ groups form an $=CH_2$, group. In another embodiment, $R_{20}$ is H and the geminal $R_{51}$ groups form $=NOH$, $=NOCH_3$, or $=NOCH_2CH_3$. In another embodiment, $R_{20}$ is methyl and the geminal $R_{51}$ groups form an $=NOH$, $=NOCH_3$, or $=NOCH_2CH_3$.

In one aspect, the compounds of Formula 4 are the compounds of Formula 4f1.

In another aspect, the compounds of Formula 4 are the compounds of Formula 4g1.

In one aspect, provided herein are compounds of Formula 4h, i.e., compounds of Formula 4 having the formula

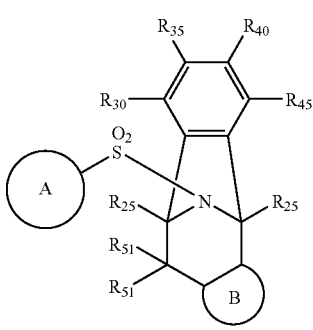

including enantiomers and/or pharmaceutically acceptable salts thereof, wherein, B-ring is pyrazolyl, dihydropyrazolyl, pyrazolonyl or pyrazolidinonyl, each of which is optionally substituted with $NR_{11}$—$C_2$-$C_6$ alkanoyl, $C_1$-$C_6$ alkyl, $C_3$-$C_6$ cycloalkyl, $C_2$-$C_4$ alkenyl, $C_2$-$C_4$ alkynyl, $C_1$-$C_4$ alkoxy, amino, $C_1$-$C_4$ alkylamino, $C_1$-$C_4$ dialkylamino, hydroxy, hydroxyalkyl, halo, $C_1$-$C_4$ haloalkyl, $C_1$-$C_4$ haloalkoxy, —$NR_{11}C(O)R_{10}$, —$NR_{11}SO_2R_{10}$ or CN;

$R_{30}$, $R_{35}$, $R_{40}$, and $R_{45}$ are independently H, halogen, $C_1$-$C_6$ alkyl, $C_2$-$C_8$ alkenyl, $C_2$-$C_8$ alkynyl, $C_2$-$C_8$ haloalkenyl, $C_2$-$C_8$ haloalkynyl, —$C(O)OR_{11}$, —$SO_2NR_{11}R_{11}$, aryl $C_1$-$C_6$ alkyl, $C_3$-$C_6$ cycloalkyl, $C_1$-$C_6$ haloalkyl, $C_1$-$C_6$ haloalkoxy, CN, $NO_2$, hydroxyl, $C_1$-$C_6$ alkoxy, —$C_1$-$C_6$ alkyl-OH, —$C_1$-$C_6$ alkyl-$C_1$-$C_6$ alkoxy, phenyloxy, —$S(O_2)$ $R_{10}$, —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, heteroaryl $C_1$-$C_6$ alkyl, heteroaryl, where the heteroaryl groups are oxazolyl, oxadiazolyl pyrazolyl, thiazolyl, pyridyl, pyrimidinyl, imidazolyl, indolyl, furanyl or thienyl, and wherein each heteroaryl group is optionally substituted with a $C_1$-$C_6$ alkyl group; heterocycloalkylalkyl, heterocycloalkyl, wherein the heterocycloalkyl groups are pyrrolidinyl, imidazolidinyl, piperidinyl or morpholinyl, wherein each heterocycloalkyl group is optionally substituted with one or two groups that are independently $C_1$-$C_6$ alkyl, $C_1$-$C_6$ alkoxy or halogen, phenyl, naphthyl, phenyloxy, naphthyloxy or phenyl $C_1$-$C_6$ alkyl, where the phenyl portions of the above are optionally substituted with one to five groups that are independently $C_1$-$C_6$ alkyl, $C_1$-$C_6$ alkoxy, hydroxyl, $C_1$-$C_4$ haloalky (e.g., $CF_3$) or halogen; and wherein two adjacent carbons and of the fused aryl ring optionally form a heterocycloalkyl (e.g., —$OCH_2O$— or —$OCH_2CH_2O$—) or a heteroaryl ring, each of which is optionally substituted with 1, 2, 3 or 4 groups that are independently $C_1$-$C_4$ alkyl, $C_1$-$C_4$ alkoxy, halogen or $C_2$-$C_4$ alkanoyl wherein the alkanoyl group is optionally substituted with up to 3 halogen atoms; or two adjacent carbons of the fused aryl ring form a benzo ring which is optionally substituted with 1 to 4 groups that are independently halogen, hydroxyl, alkyl, alkoxy, haloalkyl, haloalkoxy, CN or $NO_2$;

each $R_{51}$ is independently absent, H, $C_1$-$C_4$ alkyl, halogen (e.g., F, Cl or Br), CN, amino, mono alkylamino, dialkylamino, OH, $C_1$-$C_4$ haloalkoxy (e.g., $OCF_3$), $C_1$-$C_4$ haloalkyl (e.g., $CF_3$) or —CN; or when there are two $R_{51}$ groups on a carbon atom, the two $R_{51}$ groups and the carbon to which they are attached may form a 3- to 6-membered cycloalkyl or heterocycloalkyl ring; or when there are two $R_5$, groups on a carbon, the two $R_{51}$ groups may form an oxo group; or when there are two $R_{51}$ groups on a carbon, the two $R_{51}$ groups may form an alkene group; or when there are two $R_{51}$ groups on a carbon, the two $R_{51}$ groups may form an oxime or a $C_1$-$C_4$ alkylated oxime (e.g., O-methyl oxime);

a non-bridgehead carbon (and any substituent or substituents thereon) in the [3.3.1], [3.2.1] or [2.2.1] ring systems may be replaced with an $NR_{15}$ group. In a further embodiment, $R_{10}$ and $R_{11}$ at each occurrence are independently $C_1$-$C_6$ alkyl, heteroaryl that is selected from pyrazolyl, thiadiazolyl, triazolyl, isoxazolyl, isothiazolyl, imidazolyl, thiazolyl, oxadiazolyl, and pyridyl or aryl that is selected from phenyl and naphthyl, where the heteroaryl and aryl groups are optionally substituted with 1 to 3 groups that are independently halogen, hydroxyl, alkyl, alkoxy, haloalkyl, haloalkoxy, CN or $NO_2$; and additionally $R_{11}$ may be H;

or if two $R_{11}$ groups are on a nitrogen, then the two $R_{11}$ groups together with the nitrogen to which they are attached, may form a 3-8 membered ring optionally including an additional heteroatom such as NH, $NR_{12}$, $NR_{13}$, O or S;

$R_{12}$ is H, $C_1$-$C_6$ alkyl, aryl or —$SO_2$-aryl (e.g., phenyl or naphthyl, where phenyl is preferred), where each aryl group is optionally substituted with 1 to 5 groups that are independently halogen, hydroxyl, alkyl, alkoxy, haloalkyl, haloalkoxy, CN or $NO_2$;

$R_{13}$ is H, aryl or $C_1$-$C_6$ alkyl optionally substituted with aryl (such as phenyl or naphthyl, more preferably, phenyl), hydroxyl or halogen, where each aryl group is optionally substituted with 1 to 5 groups that are independently halogen, hydroxyl, alkyl, alkoxy, haloalkyl, haloalkoxy, CN or $NO_2$. In a further embodiment the B-ring is pyrazolyl, which is optionally substituted with $NR_{11}$—$C_2$-$C_6$ alkanoyl, $C_1$-$C_4$ alkyl, $C_3$-$C_6$ cycloalkyl, $C_2$-$C_4$ alkenyl, $C_2$-$C_4$ alkynyl, $C_1$-$C_4$ alkoxy, amino, $C_1$-$C_4$ alkylamino, $C_1$-$C_4$ dialkylamino, hydroxy $C_1$-$C_4$ alkyl, halo, $CF_3$, $OCF_3$ or CN.

In another aspect, provided herein are compounds of Formula 4h, wherein $R_{30}$, $R_{35}$, $R_{40}$, and $R_{45}$ are independently H, halogen, $C_1$-$C_6$ alkyl, $C_1$-$C_6$ haloalkyl, $C_1$-$C_6$ haloalkoxy, $C_2$-$C_8$ alkenyl, $C_2$-$C_8$ alkynyl, $C_2$-$C_8$ haloalkenyl, $C_2$-$C_8$ haloalkynyl, CN, hydroxyl, $C_1$-$C_6$ alkoxy, —$C_1$-$C_3$ alkyl-OH, —$C_1$-$C_3$ alkyl-alkoxy, phenyloxy, —$C(O)OR_{11}$, —$S(O_2)R_{10}$, —$NR_{11}R_{11}$, —$C(O)NR_{11}R_{11}$, —$SO_2NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, where the phenyl portions of the above are optionally substituted with one or more groups that are independently $C_1$-$C_6$ alkyl, $C_1$-$C_6$ alkoxy or halogen. In an embodiment of this aspect, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In one embodiment of this aspect, $R_{30}$, $R_{35}$, $R_{40}$, and $R_{45}$ are independently H, halogen (e.g., F), $C_1$-$C_6$ alkyl, hydroxyl, $C_1$-$C_4$ haloalkyl (e.g., $CF_3$), $C_1$-$C_4$ haloalkoxy (e.g., $OCF_3$), $C_2$-$C_6$ alkenyl, $C_2$-$C_6$ alkynyl, $C_2$-$C_6$ haloalkenyl, $C_2$-$C_6$ haloalkynyl, $C_1$-$C_6$ alkoxy, —$C_1$-$C_3$ alkyl-OH, CN or —$C_1$-$C_3$ alkyl-alkoxy.

In one embodiment of this aspect, $R_{30}$, $R_{35}$, $R_{40}$, and $R_{45}$ are independently H, halogen, $C_1$-$C_4$ alkyl, $CF_3$, $OCF_3$, hydroxyl, $C_1$-$C_4$ alkoxy, —$C_1$-$C_2$ alkyl-OH, CN or —$C_1$-$C_2$ alkyl- $C_1$-$C_4$ alkoxy.

In one embodiment of this aspect, $R_{30}$, $R_{35}$, $R_{40}$, and $R_{45}$ are independently H, halogen, $C_1$-$C_4$ alkyl, $C_2$-$C_6$ alkenyl, $C_2$-$C_6$ alkynyl, $C_2$-$C_6$ haloalkenyl, $C_2$-$C_6$ haloalkynyl or —$C(O)OR_{11}$. In a further embodiment, the halo portion of the haloalkenyl and haloalkynyl groups is F, Cl or Br.

In one embodiment of this aspect, two of $R_{30}$, $R_{35}$, $R_{40}$, and $R_{45}$ are H, while at least one of the other groups is halogen, $C_1$-$C_4$ alkyl, $C_2$-$C_6$ alkenyl, $C_2$-$C_6$ alkynyl, $C_2$-$C_6$ haloalkenyl, $C_2$-$C_6$ haloalkynyl or —$C(O)OR_{11}$. In a further embodiment, the halo portion of the haloalkenyl and haloalkynyl groups is F, Cl or Br.

In one embodiment of this aspect, $R_{30}$, $R_{35}$, $R_{40}$, and $R_{45}$ are independently H, halogen, methyl, ethyl, hydroxyl, $CF_3$ or $OCF_3$. In a further embodiment, at least two of $R_{30}$, $R_{35}$, $R_{40}$, and $R_{45}$ are hydrogen. In a further embodiment, $R_{40}$ is $CF_3$. In a still further embodiment, $R_{35}$ is $CF_3$. In a further embodiment, $R_{40}$ is CN. In a still further embodiment, $R_{35}$ is CN. In a further embodiment, $R_{35}$ or $R_{40}$ is hydroxyl.

In one embodiment of this aspect, $R_{30}$, $R_{35}$, $R_{40}$, and $R_{45}$ are independently H, —$C(O)OR_{11}$, —$S(O_2)R_{10}$, —$NR_{11}R_{11}$, —$C(O)NR_{11}R_{11}$, —$SO_2NR_{11}R_{11}$, —$NR_{11}C(O)R_{10}$, —$NR_{11}SO_2R_{10}$, —O—$C(O)NR_{11}R_{11}$ or $C_2$-$C_6$ alkanoyl.

In one embodiment of this aspect, $R_{30}$ and $R_{35}$ or $R_{35}$ and $R_{40}$ or $R_{40}$ and $R_{45}$ are —$OCH_2O$— or —$OCH_2CH_2O$— wherein each methylene of —$OCH_2O$— or —$OCH_2CH_2O$— is optionally substituted with one or two $C_1$-$C_4$ alkyl groups.

In still another embodiment of this aspect, $R_{11}$ is H.

In still another embodiment of this aspect, one of $R_{10}$ and $R_{11}$ is $CH_3$.

In another embodiment of this aspect, $R_{11}$ and $R_{11}$ together with the nitrogen to which they are attached may form a 3-8 membered ring, which optionally includes an additional heteroatom that is NH, $NR_{12}$, $NR_{13}$, O or S.

In still another embodiment of this aspect, $R_{10}$ and $R_{11}$ at each occurrence are independently phenyl optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$; and additionally $R_{11}$ may be H.

In another embodiment of this aspect, $R_{10}$ and $R_{11}$ at each occurrence are independently pyrazolyl, isoxazolyl, isothiazolyl, imidazolyl or thiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$; and additionally $R_{11}$ may be H.

In another embodiment of this aspect, $R_{10}$ and $R_{11}$ at each occurrence are independently thiadiazolyl, triazolyl or oxadiazolyl, each of which is optionally substituted with 1 to 3 groups that are independently halogen, hydroxyl, $C_1$-$C_6$ alkyl, $C_1$-$C_6$ alkoxy, halo $C_1$-$C_4$ alkyl, halo $C_1$-$C_4$ alkoxy, CN or $NO_2$ and additionally $R_{11}$ may be H.

In another aspect, provided herein are compounds of Formula 4h, wherein $R_{30}$, $R_{35}$, $R_{40}$, and $R_{45}$ are independently H, halogen (e.g., F), $C_1$-$C_4$ alkyl, —$C(O)OR_{11}$, —$S(O_2)R_{10}$, —$NR_{11}R_{11}$, —$C(O)NR_{11}R_{11}$, —$SO_2NR_{11}R_{11}$, —$NR_{11}C(O)R_{10}$, —$NR_{11}SO_2R_{10}$ or —O—$C(O)NR_{11}R_{11}$.

In an embodiment of this aspect, at least two of $R_{30}$, $R_{35}$, $R_{40}$, and $R_{45}$ are H, while another is H, halogen or $C_1$-$C_4$ alkyl, and the other is —$C(O)OR_{11}$, —$S(O_2)R_{10}$, —$SO_2NR_{11}R_{11}$, —$NR_{11}R_{11}$, —$C(O)NR_{11}R_{11}$, —$NR_{11}C(O)R_{10}$, —$NR_{11}SO_2R_{10}$ or —O—$C(O)NR_{11}R_{11}$. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In an embodiment of this aspect, three of $R_{30}$, $R_{35}$, $R_{40}$, and $R_{45}$ are H, while the other is —$C(O)OR_{11}$, —$S(O_2)R_{10}$, —$NR_{11}R_{11}$, —$C(O)NR_{11}R_{11}$, —$SO_2NR_{11}R_{11}$, —$NR_{11}C(O)R_{10}$, —$NR_{11}SO_2R_{10}$ or —O—$C(O)NR_{11}R_{11}$. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In yet another embodiment of this aspect, three of $R_{30}$, $R_{35}$, $R_{40}$, and $R_{45}$ are H, while the other is —$NR_{11}R_{11}$. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In yet another embodiment of this aspect, three of $R_{30}$, $R_{35}$, $R_{40}$, and $R_{45}$ are H, while the other is —$SO_2NR_{11}R_{11}$ or —$NR_{11}SO_2R_{10}$. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In an embodiment of this aspect, three of $R_{30}$, $R_{35}$, $R_{40}$, and $R_{45}$ are H, while the other is —$C(O)NR_{11}R_{11}$ or —$NR_{11}C(O)R_{10}$. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In still another embodiment of this aspect, three of $R_{30}$, $R_{35}$, $R_{40}$, and $R_{45}$ are H, while the other is —O—C(O)$NR_{11}R_{11}$. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In still another embodiment of this aspect, two of $R_{30}$, $R_{35}$, $R_{40}$, and $R_{45}$ are H, while one is methyl and the other is —$NR_{11}R_{11}$, —$C(O)NR_{11}R_{11}$ or —$NR_{11}C(O)R_{10}$. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In an embodiment of this aspect, three of $R_{30}$, $R_{35}$, $R_{40}$, and $R_{45}$ are H, while the other is —$C(O)OR_{11}$. In a further embodiment, $R_{11}$ is H or $C_1$-$C_4$ alkyl. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In another aspect, provided herein are compounds of Formula 4h, wherein $R_{30}$, $R_{35}$, $R_{40}$, and $R_{45}$ are independently H, halogen, $C_1$-$C_4$ alkyl, $C_1$-$C_4$ alkoxy, phenyloxy, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl where the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen.

In another embodiment of this aspect, at least two of $R_{30}$, $R_{35}$, $R_{40}$, and $R_{45}$ are H.

In still another embodiment of this aspect, three of $R_{30}$, $R_{35}$, $R_{40}$, and $R_{45}$ are H.

In still another embodiment of this aspect, $R_{30}$, $R_{35}$, $R_{40}$, and $R_{45}$ are H.

In still another embodiment of this aspect, $R_{30}$, $R_{35}$, $R_{40}$, and $R_{45}$ are H; and the B-ring is unsubstituted pyrazolyl.

In still another embodiment of this aspect, $R_{30}$, $R_{35}$, $R_{40}$, and $R_{45}$ are H; the B-ring is unsubstituted pyrazolyl; and the geminal $R_{51}$ groups that are alpha to the B-ring form an oxo group.

In still another embodiment of this aspect, $R_{30}$, $R_{35}$, $R_{40}$, and $R_{45}$ are H; the B-ring is unsubstituted pyrazolyl; and geminal $R_{51}$ groups that are alpha to the B-ring form an $C_2$-$C_4$ alkenyl group.

In still another embodiment of this aspect, $R_{30}$, $R_{35}$, $R_{40}$, and $R_{45}$ are H; the B-ring is unsubstituted pyrazolyl; and the geminal $R_{51}$ groups that are alpha to the B-ring form an oxime or a $C_1$-$C_4$ alkylated oxime (e.g., O-methyl oxime).

In still another embodiment of this aspect, $R_{30}$, $R_{35}$, $R_{40}$, and $R_{45}$ are H; the B-ring is unsubstituted pyrazolyl; and the geminal $R_{51}$ groups that are alpha to the B-ring are both H or one is H and the other is F or OH.

In yet still another embodiment of this aspect, $R_{30}$ and $R_{45}$ are H; and $R_{35}$ and $R_{40}$ are independently halogen (e.g., F, Cl or Br), $C_1$-$C_4$ alkyl, $C_1$-$C_4$ alkoxy or $C_2$-$C_6$ alkanoyl.

In yet still another embodiment of this aspect, $R_{30}$ and $R_{45}$ are H; and $R_{35}$ and $R_{40}$ and the carbons to which they are attached form a heterocycloalkyl ring. In a further embodiment, the heterocycloalkyl ring is $OCH_2O$—, $OCH_2CH_2O$— or —$OC(O)O$—. In a still further embodiment, the geminal $R_{51}$ groups that are alpha to the B-ring are both H.

In yet still another embodiment of this aspect, $R_{30}$ and $R_{45}$ are H; and $R_{35}$ and $R_{40}$ are independently halogen (e.g., F, Cl or Br), $C_1$-$C_4$ alkyl, $C_1$-$C_4$ alkoxy or $C_2$-$C_6$ alkanoyl; and the geminal $R_{51}$ groups that are alpha to the B-ring form an oxo group. In yet still another embodiment of this aspect, $R_{30}$ and $R_{45}$ are H; and $R_{35}$ and $R_{40}$ are independently halogen (e.g., F, Cl or Br), $C_1$-$C_4$ alkyl, $C_1$-$C_4$ alkoxy or $C_2$-$C_6$ alkanoyl; and the geminal $R_{51}$ groups that are alpha to the B-ring are both H.

In yet still another embodiment of this aspect, $R_{30}$ and $R_{45}$ are H; and $R_{35}$ and $R_{40}$ are independently halogen (e.g., F, Cl or Br), $C_1$-$C_4$ alkyl, $C_1$-$C_4$ alkoxy or $C_2$-$C_6$ alkanoyl; and the geminal $R_{51}$ groups that are alpha to the B-ring are both halogens. In another embodiment, both $R_{51}$ groups that are alpha to the B-ring are F.

In yet still another embodiment of this aspect, $R_{30}$ and $R_{45}$ are H; and $R_{35}$ and $R_{40}$ are independently halogen (e.g., F, Cl or Br), and the geminal $R_{51}$ groups that are alpha to the B-ring are both halogens.

In yet still another embodiment of this aspect, $R_{30}$ and $R_{45}$ are H; and $R_{35}$ and $R_{40}$ are independently halogen (e.g., F, Cl or Br), and the geminal $R_{51}$ groups that are alpha to the B-ring form an $C_2$-$C_4$ alkenyl group.

In yet still another embodiment of this aspect, $R_{30}$ and $R_{45}$ are H; and $R_{35}$ and $R_{40}$ are independently halogen (e.g., F, Cl or Br), and the geminal $R_{51}$ groups that are alpha to the B-ring form an oxime or a $C_1$-$C_4$ alkylated oxime (e.g., O-methyl oxime).

In still another embodiment of this aspect, $R_{30}$ and $R_{45}$ are H; and $R_{35}$ and $R_{40}$ are independently halogen (e.g., F, Cl or Br), hydroxyl, $C_1$-$C_4$ alkyl, $C_1$-$C_4$ alkoxy, $C_2$-$C_6$ alkanoyl, phenyloxy, phenyl or phenyl $C_1$-$C_4$ alkyl, where the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen.

In still another embodiment of this aspect, $R_{30}$ and $R_{45}$ are H; and $R_{35}$ and $R_{40}$ are independently halogen (e.g., F, Cl or Br), $C_1$-$C_4$ alkyl, $C_1$-$C_4$ alkoxy, $C_2$-$C_6$ alkanoyl, oxazolyl, pyrazolyl, thiazolyl, pyridyl, pyrimidinyl, imidazolyl, indolyl, furanyl or thienyl.

In yet still another embodiment of this aspect, $R_{35}$ and $R_{40}$ are H; and $R_{30}$ and $R_{45}$ are independently halogen (e.g., F, Cl or Br), hydroxyl, $C_1$-$C_4$ alkyl, $C_1$-$C_4$ alkoxy or $C_2$-$C_6$ alkanoyl.

In yet still another embodiment of this aspect, $R_{35}$ and $R_{40}$ are H; and $R_{30}$ and $R_{45}$ are independently halogen (e.g., F, Cl or Br), hydroxyl, $C_1$-$C_4$ alkyl, $C_1$-$C_4$ alkoxy or $C_2$-$C_6$ alkanoyl; and the geminal $R_{51}$ groups that are alpha to the B-ring form an oxo group. In a further embodiment, one of $R_{30}$ or $R_{45}$ is H, while the other is F or Cl.

In yet still another embodiment of this aspect, $R_{35}$ and $R_{40}$ are H; and $R_{30}$ and $R_{45}$ are independently halogen (e.g., F, Cl or Br), hydroxyl, $C_1$-$C_4$ alkyl, $C_1$-$C_4$ alkoxy or $C_2$-$C_6$ alkanoyl; and the geminal $R_{51}$ groups that are alpha to the B-ring are both hydrogen. In a further embodiment, one of $R_{30}$ or $R_{45}$ is H, while the other is F or Cl.

In yet still another embodiment of this aspect, $R_{35}$ and $R_{40}$ are H; and $R_{30}$ and $R_{45}$ are independently halogen (e.g., F, Cl or Br), hydroxyl, $C_1$-$C_4$ alkyl, $C_1$-$C_4$ alkoxy or $C_2$-$C_6$ alkanoyl; and the geminal $R_{51}$ groups that are alpha to the B-ring form an $C_2$-$C_4$ alkenyl group.

In yet still another embodiment of this aspect, $R_{35}$ and $R_{40}$ are H; and $R_{30}$ and $R_{45}$ are independently halogen (e.g., F, Cl or Br), hydroxyl, $C_1$-$C_4$ alkyl, $C_1$-$C_4$ alkoxy or $C_2$-$C_6$ alkanoyl; and the geminal $R_{51}$ groups that are alpha to the B-ring form an oxime or a $C_1$-$C_4$ alkylated oxime (e.g., O-methyl oxime).

In yet still another embodiment of this aspect, $R_{35}$ and $R_{40}$ are H; and $R_{30}$ and $R_{45}$ are independently H, halogen (e.g., F, Cl or Br), $C_1$-$C_4$ alkyl, $C_1$-$C_4$ alkoxy or $C_2$-$C_6$ alkanoyl; provided that at least one of $R_{30}$ and $R_{45}$ is not H. In another embodiment, both $R_{51}$ groups that are alpha to the B-ring are F. In a further embodiment, $R_{30}$ is halogen while $R_{45}$ is H. In another further embodiment, $R_{30}$ is H while $R_{45}$ is halogen. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In yet still another embodiment of this aspect, $R_{35}$ and $R_{40}$ are H; and $R_{30}$ and $R_{45}$ are independently halogen (e.g., F, Cl or Br), methyl or methoxy. In another embodiment, both $R_{51}$ groups that are alpha to the B-ring are F. In a further embodiment, $R_{30}$ is halogen. In another further embodiment, $R_{45}$ is halogen. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In still another embodiment of this aspect, $R_{35}$ and $R_{40}$ are H; and $R_{30}$ and $R_{45}$ are independently halogen (e.g., F, Cl or Br), hydroxyl, $C_1$-$C_4$ alkyl, $C_1$-$C_4$ alkoxy, $C_2$-$C_6$ alkanoyl, phenyloxy, phenyl or phenyl $C_1$-$C_4$ alkyl. In a further embodiment, the geminal $R_{51}$ groups that are alpha to the B-ring are both hydrogen. In another further embodiment, at least one of the geminal $R_{51}$ groups that are alpha to the B-ring is halogen. In another further embodiment, the geminal $R_{51}$ groups that are alpha to the B-ring are both halogen. In still another further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In still another embodiment of this aspect, $R_{35}$ and $R_{40}$ are H; and $R_{30}$ and $R_{45}$ are independently halogen (e.g., F, Cl or Br), hydroxyl, $C_1$-$C_4$ alkyl, $C_1$-$C_4$ alkoxy, $C_2$-$C_6$ alkanoyl, oxazolyl, pyrazolyl, thiazolyl, pyridyl, pyrimidinyl, imidazolyl, indolyl, furanyl or thienyl.

In still another embodiment of this aspect, $R_{30}$, $R_{35}$, $R_{40}$, and $R_{45}$ are independently H, halogen (e.g., F, Cl or Br), $C_1$-$C_4$ alkyl or $C_1$-$C_4$ alkoxy; and one $R_{51}$ group is halogen or OH, while the other $R_{51}$ group is H. In a still further embodiment, the B-ring is unsubstituted. In a further embodiment, at least two of $R_{30}$, $R_{35}$, $R_{40}$, and $R_{45}$ are H. In a still further embodiment, $R_{30}$, $R_{35}$, $R_{40}$, and $R_{45}$ are H.

In still another embodiment of this aspect, $R_{30}$, $R_{35}$, $R_{40}$, and $R_{45}$ are independently H, halogen (e.g., F, Cl or Br), $C_1$-$C_4$ alkyl or $C_1$-$C_4$ alkoxy; and one $R_{51}$ group is halogen or OH, while the other $R_{51}$ group is H. In a still further embodiment, the B-ring is unsubstituted. In a further embodiment, at least one of $R_{30}$, $R_{35}$, $R_{40}$, and $R_{45}$ is halogen (e.g., F, Cl or Br), $C_1$-$C_4$ alkyl or $C_1$-$C_4$ alkoxy. In a still further embodiment, two of $R_{30}$, $R_{35}$, $R_{40}$, and $R_{45}$ are H.

In another aspect, provided herein are compounds of Formula 4h, wherein $R_{30}$, $R_{35}$, $R_{40}$, and $R_{45}$ are independently H, halogen, $C_1$-$C_4$ alkyl, $C_1$-$C_4$ alkoxy, $C_2$-$C_6$ alkanoyl; provided that two adjacent carbons of the fused aryl ring (the ring to which the $R_{30}$, $R_{35}$, $R_{40}$ and $R_{45}$ groups are attached) optionally form a heterocycloalkyl or a heteroaryl ring, which is optionally substituted with 1, 2, 3 or 4 groups that are independently $C_1$-$C_4$ alkyl, $C_1$-$C_4$ alkoxy, halogen or $C_1$-$C_4$ alkanoyl wherein the alkanoyl group is optionally substituted with up to 3 halogen atoms. In a further embodiment, the heterocycloalkyl ring is piperidinyl, pyrrolidinyl or morpholinyl, and the heteroaryl ring is pyrazolyl, imidazolyl or pyridinyl, wherein each heterocycloalkyl or heteroaryl group is optionally substituted with 1, 2, 3 or 4 groups that are independently $C_1$-$C_4$ alkyl, $C_1$-$C_4$ alkoxy, halogen or $C_2$-$C_4$ alkanoyl wherein the alkanoyl group is optionally substituted with up to 3 halogen atoms. In a further embodiment, the heterocycloalkyl ring is piperidinyl or pyrrolidinyl, each of which is optionally substituted with 1 or 2 groups that are independently $C_1$-$C_4$ alkyl, $C_1$-$C_4$ alkoxy, halogen or $C_2$-$C_4$ alkanoyl wherein the alkanoyl group is optionally substituted with up to 3 halogen atoms. In a further embodiment, the heteroaryl ring is pyrazolyl, imidazolyl or pyridinyl, each of which is optionally substituted with 1 or 2 groups that are independently $C_1$-$C_4$ alkyl, $C_1$-$C_4$ alkoxy, halogen or $C_2$-$C_4$ alkanoyl wherein the alkanoyl group is optionally substituted with up to 3 halogen atoms.

In another aspect, provided herein are compounds of Formula 4h, wherein $R_{30}$, $R_{35}$, $R_{40}$, and $R_{45}$ are independently H, halogen, $C_1$-$C_4$ alkyl, $C_1$-$C_4$ alkoxy, $C_2$-$C_6$ alkanoyl; provided that two adjacent carbons of the fused aryl ring form a benzo ring, which is optionally substituted with 1 to 4 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN or $NO_2$.

In one embodiment of this aspect, $R_{30}$ and $R_{45}$ are independently H, halogen, hydroxyl, $C_1$-$C_4$ alkyl, $C_1$-$C_4$ alkoxy, and $R_{35}$, $R_{40}$, and the carbons to which they are attached form a benzo ring, which is optionally substituted with 1 to 4 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN or $NO_2$. In a further embodiment, the benzo ring is unsubstituted.

In one embodiment of this aspect, $R_{30}$ and $R_{35}$ are independently H, halogen, hydroxyl, $C_1$-$C_4$ alkyl, $C_1$-$C_4$ alkoxy, and $R_{40}$, $R_{45}$, and the carbons to which they are attached form a benzo ring, which is optionally substituted with 1 to 4 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN or $NO_2$. In a further embodiment, the benzo ring is unsubstituted.

In one embodiment of this aspect, $R_{40}$ and $R_{45}$ are independently H, halogen, hydroxyl, $C_1$-$C_4$ alkyl, $C_1$-$C_4$ alkoxy, and $R_{30}$, $R_{35}$, and the carbons to which they are attached form a benzo ring, which is optionally substituted with 1 to 4 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN or $NO_2$. In a further embodiment, the benzo ring is unsubstituted.

In another aspect, provided herein are compounds or salts of Formula 4i, i.e., compounds and/or salts of Formula 4h having the formula:

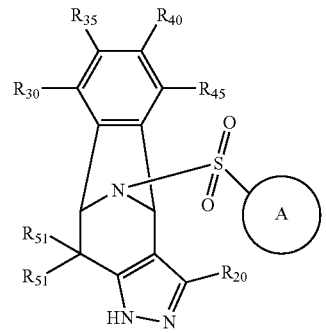

or pharmaceutically acceptable solvates, salts or mixtures thereof, wherein the A-ring is as defined below and $R_{30}$, $R_{35}$, $R_{40}$, $R_{45}$ and $R_{51}$ are as previously defined, and $R_{20}$ is H, $C_1$-$C_4$ alkyl, $C_1$-$C_4$ alkoxy, $-NR_{11}C(O)CH_3$, amino, $C_1$-$C_4$ alkylamino, $C_1$-$C_4$ dialkylamino, halo, $CF_3$, CN or NHC(O)$CH_3$; where $R_{11}$ is H or $C_1$-$C_6$ alkyl. In a further embodiment, $R_{30}$, $R_{35}$, $R_{40}$, and $R_{45}$ are independently H, halogen, $C_1$-$C_6$ alkyl, $C_1$-$C_6$ haloalkyl, $C_1$-$C_6$ haloalkoxy, CN, hydroxyl, $C_1$-$C_6$ alkoxy, $-C_1$-$C_3$ alkyl-OH, $-C_1$-$C_3$ alkyl-alkoxy, phenyloxy, $-S(O_2)R_{10}$, $-SO_2NR_{11}R_{11}$, $-NR_{11}R_{11}$, $-C(O)NR_{11}R_{11}$, $-NR_{11}C(O)R_{10}$, $-NR_{11}SO_2R_{10}$, $-O-C(O)NR_{11}R_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, where the phenyl portions of the above are optionally substituted with one or more groups that are independently $C_1$-$C_6$ alkyl, $C_1$-$C_6$ alkoxy or halogen.

In another aspect, the compounds of Formula 4i are compounds or salts of Formula 4i1:

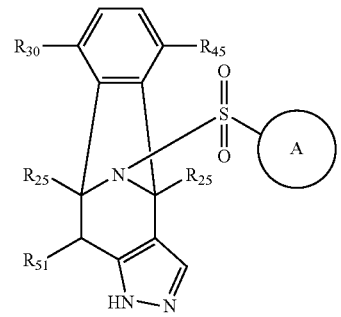

including stereoisomers, tautomers and mixtures of stereoisomers and/or tautomers, and/or pharmaceutical salts thereof, wherein $R_{30}$ and $R_{45}$ are independently H, halogen, $C_1$-$C_6$ alkyl, $C_1$-$C_6$ haloalkyl, $C_1$-$C_6$ haloalkoxy, CN, hydroxyl, $C_1$-$C_6$ alkoxy, $-C_1$-$C_3$ alkyl-OH, $-C_1$-$C_3$ alkyl-alkoxy, phenyloxy, $C_2$-$C_6$ alkenyl, $C_2$-$C_6$ alkynyl, $C_2$-$C_6$ haloalkenyl, $C_2$-$C_6$ haloalkynyl, $-C(O)OR_{11}$, $-S(O_2)R_{10}$, $-NR_{11}R_{11}$, $-C(O)NR_{11}R_{11}$, $-SO_2NR_{11}R_{11}$, $-NR_{11}C(O)R_{10}$, $-NR_{11}SO_2R_{10}$, $-O-C(O)NR_{11}R_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, where the phenyl portions of the above are optionally substituted with one or more groups that are independently $C_1$-$C_6$ alkyl, $C_1$-$C_6$ alkoxy, $C_1$-$C_4$ haloalky (e.g., $CF_3$) or halogen; and $R_{51}$ is H, $C_1$-$C_4$ alkyl, F, Cl, Br, CN, amino, mono alkylamino, dialkylamino, OH or $CF_3$.

In one embodiment of this aspect, $R_{30}$ and $R_{45}$ are independently H, halogen, $C_1$-$C_6$ alkyl, hydroxyl, $C_1$-$C_6$ alkoxy, —$C_1$-$C_3$ alkyl-OH or —$C_1$-$C_3$ alkyl-alkoxy; and $R_{51}$ is H, methyl, ethyl, F, Cl, Br or $CF_3$.

In one embodiment of this aspect, $R_{30}$ and $R_{45}$ are independently H, halogen, $C_1$-$C_6$ alkyl, hydroxyl, $C_1$-$C_6$ alkoxy, —$C_1$-$C_3$ alkyl-OH or —$C_1$-$C_3$ alkyl-alkoxy; and $R_{51}$ is CN, amino, mono alkylamino, dialkylamino.

In one embodiment of this aspect, at least one of $R_{30}$ and $R_{45}$ is $C_2$-$C_6$ alkenyl, $C_2$-$C_6$ alkynyl, $C_2$-$C_6$ haloalkenyl, $C_2$-$C_6$ haloalkynyl or —C(O)OR$_{11}$; and $R_{51}$ is H, methyl, ethyl, F, Cl, Br or $CF_3$. In a further embodiment, $R_{11}$ is H or $C_1$-$C_4$ alkyl.

In one embodiment of this aspect, $R_{30}$ and $R_{45}$ are independently H, halogen, $C_1$-$C_4$ alkyl, hydroxyl, $C_1$-$C_4$ alkoxy, —$C_1$-$C_2$ alkyl-OH or —$C_1$-$C_2$ alkyl- $C_1$-$C_4$ alkoxy; and $R_{51}$ is H, methyl, ethyl, F, Cl or $CF_3$.

In one embodiment of this aspect, $R_{30}$ and $R_{45}$ are independently H, F or Cl; and $R_{51}$ is H, F, Cl or Br.

In still another embodiment of this aspect, at least one of $R_{30}$ and $R_{45}$ is F; and $R_{51}$ is H, F or OH.

In yet another embodiment of this aspect, only one of $R_{30}$ and $R_{45}$ is F, while the other is H; and $R_{51}$ is H, F or OH.

In another embodiment of this aspect, $R_{30}$ and $R_{45}$ are both H; and $R_{51}$ is H or F.

In yet another embodiment of this aspect, $R_{30}$ and $R_{45}$ are both H; and $R_{51}$ is F.

In yet another embodiment of this aspect, $R_{30}$ and $R_{45}$ are both H; and $R_{51}$ is OH.

In yet another embodiment of this aspect, one of $R_{30}$ and $R_{45}$ is H, while the other is F, and $R_{51}$ is OH.

In another embodiment of this aspect, $R_{30}$, $R_{45}$, and $R_{51}$ are H.

In still another embodiment of this aspect, only one of $R_{30}$, $R_{45}$, and $R_{51}$ is F.

In still another embodiment of this aspect, $R_{30}$, $R_{45}$, and $R_{51}$ are F.

In one embodiment of this aspect, $R_{30}$ and $R_{45}$ are independently H, —C(O)OR$_{11}$, —S(O$_2$)R$_{10}$, —NR$_{11}$R$_{11}$, —C(O)NR$_{11}$R$_{11}$, —SO$_2$NR$_{11}$R$_{11}$, —NR$_{11}$C(O)R$_{10}$, —NR$_{11}$SO$_2$R$_{10}$, —O—C(O)NR$_{11}$R$_{11}$ or $C_2$-$C_6$ alkanoyl; where each $R_{11}$ is independently H or $C_1$-$C_4$ alkyl.

In another aspect, the compounds of Formula 4i are compounds of Formulas 4i2:

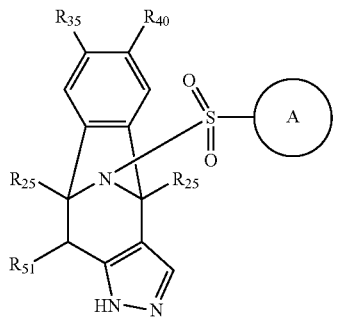

including stereoisomers, tautomers and mixtures of stereoisomers and/or tautomers, and/or pharmaceutical salts thereof, wherein $R_{35}$ and $R_{40}$ are independently H, halogen, $C_1$-$C_6$ alkyl, $C_1$-$C_6$ haloalkyl, $C_1$-$C_6$ haloalkoxy, CN, hydroxyl, $C_1$-$C_6$ alkoxy, —$C_1$-$C_3$ alkyl-OH, —$C_1$-$C_3$ alkyl-alkoxy, phenyloxy, $C_2$-$C_6$ alkenyl, $C_2$-$C_6$ alkynyl, $C_2$-$C_6$ haloalkenyl, $C_2$-$C_6$ haloalkynyl, —C(O)OR$_{11}$, —S(O$_2$)R$_{10}$, —NR$_{11}$R$_{11}$, —C(O)NR$_{11}$R$_{11}$, —SO$_2$NR$_{11}$R$_{11}$, —NR$_{11}$C(O)R$_{10}$, —NR$_{11}$SO$_2$R$_{10}$, —O—C(O)NR$_{11}$R$_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, wherein the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen; and $R_{51}$ is H, $C_1$-$C_4$ alkyl, F, Cl, Br, CN, amino, mono alkylamino, dialkylamino, OH or $CF_3$ In one embodiment of this aspect, $R_{35}$ and $R_{40}$ are independently H, halogen, $C_1$-$C_6$ alkyl, hydroxyl, $C_1$-$C_6$ alkoxy, —$C_1$-$C_3$ alkyl-OH or —$C_1$-$C_3$ alkyl-alkoxy; and $R_{51}$ is H, methyl, ethyl, F, $C_1$ or $CF_3$.

In one embodiment of this aspect, $R_{35}$ and $R_{40}$ are independently H, halogen, $C_1$-$C_6$ alkyl, hydroxyl, $C_1$-$C_6$ alkoxy, —$C_1$-$C_3$ alkyl-OH or —$C_1$-$C_3$ alkyl-alkoxy; and $R_{51}$ is CN, amino, mono alkylamino, dialkylamino.

In one embodiment of this aspect, at least one of $R_{35}$ and $R_{40}$ is $C_2$-$C_6$ alkenyl, $C_2$-$C_6$ alkynyl, $C_2$-$C_6$ haloalkenyl, $C_2$-$C_6$ haloalkynyl or —C(O)OR$_{11}$; and $R_{51}$ is H, methyl, ethyl, F, Cl, Br or $CF_3$. In a further embodiment, $R_{11}$ is H or $C_1$-$C_4$ alkyl.

In one embodiment of this aspect, $R_{35}$ and $R_{10}$ are independently H, halogen, $C_1$-$C_4$ alkyl, hydroxyl, $C_1$-$C_4$ alkoxy, —$C_1$-$C_2$ alkyl-OH or —$C_1$-$C_2$ alkyl-$C_1$-$C_4$ alkoxy; and $R_{51}$ is H, methyl, ethyl, F, $C_1$ or $CF_3$.

In one embodiment of this aspect, $R_{35}$ and $R_{40}$ are independently H, F or Cl; and $R_{51}$ is H, F or Cl.

In still another embodiment of this aspect, at least one of $R_{35}$ and $R_{40}$ is F; and $R_{51}$ is H, F or OH.

In yet another embodiment of this aspect, only one of $R_{35}$ and $R_{40}$ is F, while the other is H; and $R_{51}$ is H, F or OH.

In another embodiment of this aspect, $R_{35}$ and $R_{40}$ are both H; and $R_{51}$ is H, F, Cl or Br.

In another embodiment of this aspect, $R_{35}$ and $R_{40}$ are both H; and $R_{51}$ is CN, amino, mono alkylamino or dialkylamino.

In yet another embodiment of this aspect, $R_{35}$ and $R_{40}$ are both H; and $R_{51}$ is F.

In yet another embodiment of this aspect, $R_{35}$ and $R_{40}$ are both H; and $R_{51}$ is OH.

In yet another embodiment of this aspect, one of $R_{35}$ and $R_{40}$ is H, while the other is F, and $R_{51}$ is OH.

In another embodiment of this aspect, $R_{35}$, $R_{40}$, and $R_{51}$ are H.

In still another embodiment of this aspect, only one of $R_{35}$, $R_{40}$, and $R_{51}$ is F.

In still another embodiment of this aspect, $R_{35}$, $R_{40}$, and $R_{51}$ are F.

In one embodiment of this aspect, $R_{35}$ and $R_{40}$ are independently H, —C(O)OR$_{11}$, —S(O$_2$)R$_{10}$, —NR$_{11}$R$_{11}$, —C(O)NR$_{11}$R$_{11}$, —SO$_2$NR$_{11}$R$_{11}$, —NR$_{11}$C(O)R$_{10}$, —NR$_{11}$SO$_2$R$_{10}$, —O—C(O)NR$_{11}$R$_{11}$ or $C_2$-$C_6$ alkanoyl; where each $R_{11}$ is independently H or $C_1$-$C_4$ alkyl.

In another aspect, provided herein are compounds wherein the C-ring is phenyl substituted with $R_{30}$, $R_{35}$, $R_{40}$, and $R_{45}$; or heteroaryl, wherein the heteroaryl group is optionally substituted with H, halogen, $C_1$-$C_6$ alkyl, $C_1$-$C_6$ haloalkyl, $C_1$-$C_6$ haloalkoxy, CN, hydroxyl, $C_1$-$C_6$ alkoxy, —$C_1$-$C_3$ alkyl-OH, —$C_1$-$C_3$ alkyl-alkoxy, phenyloxy, —S(O$_2$)R$_{10}$, —SO$_2$NR$_{11}$R$_{11}$, —NR$_{11}$R$_{11}$, —C(O)NR$_{11}$R$_{11}$, —NR$_{11}$C(O)R$_{10}$, —NR$_{11}$SO$_2$R$_{10}$, —O—C(O)NR$_{11}$R$_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, wherein the phenyl portions of the above are optionally substituted with one or more groups that are independently $C_1$-$C_6$ alkyl, $C_1$-$C_6$ alkoxy, $C_1$-$C_4$ haloalky or halogen;

$R_{30}$, $R_{35}$, $R_{40}$, and $R_{45}$ are independently H, halogen, $C_1$-$C_6$ alkyl, $C_2$-$C_6$ alkenyl, $C_2$-$C_6$ alkynyl, $C_2$-$C_8$ haloalkenyl, $C_2$-$C_8$ haloalkynyl, —$SO_2NR_{11}R_{11}$, arylalkyl, cycloalkyl, $C_1$-$C_6$ haloalkyl, $C_1$-$C_6$ haloalkoxy, CN, $NO_2$, hydroxyl, $C_1$-$C_6$ alkoxy, —$C_1$-$C_6$ alkyl-OH, —$C_1$-$C_6$ alkyl-$C_1$-$C_6$ alkoxy, aryloxy, —$S(O_2)R_{10}$, —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, heteroarylalkyl, heteroaryl, wherein each heteroaryl group is optionally substituted with a $C_1$-$C_6$ alkyl group, heterocycloalkylalkyl, heterocycloalkyl, wherein each heterocycloalkyl group is optionally substituted e.g., with one or two groups that are independently $C_1$-$C_6$ alkyl, $C_1$-$C_6$ alkoxy or halogen, aryl, aryloxy or arylalkyl, where the aryl portions of the above are optionally substituted e.g., with one or more groups that are independently $C_1$-$C_6$ alkyl, $C_1$-$C_6$ alkoxy, hydroxyl, $C_1$-$C_4$ haloalky or halogen; and wherein when the C-ring is aryl or heteroaryl, two adjacent carbons of the C-ring optionally form a heterocycloalkyl or a heteroaryl ring, each of which is optionally substituted with one or more groups that are independently alkyl, alkoxy, halogen or $C_2$-$C_4$ alkanoyl wherein the alkanoyl group is optionally further substituted with up to 3 halogen atoms; or two adjacent carbons of the C-ring optionally form a benzo ring which is optionally substituted e.g., with 1 to 4 groups that are independently halogen, hydroxyl, alkyl, alkoxy, haloalkyl, haloalkoxy, CN or $NO_2$.

In another aspect, provided herein are compounds of Formulas 4j, i.e., compounds of Formulas 4, 4a, 4b, 4c, and/or 4d, wherein the C-ring is a heteroaryl or heterocycloalkyl ring that is optionally substituted with one or more groups that are independently halogen, $C_1$-$C_6$ alkyl, $C_1$-$C_6$ haloalkyl, $C_1$-$C_6$ haloalkoxy, $C_2$-$C_8$ alkenyl, $C_2$-$C_8$ alkynyl, $C_2$-$C_8$ haloalkenyl, $C_2$-$C_8$ haloalkynyl, —$C(O)OR_{11}$, CN, hydroxyl, $C_1$-$C_6$ alkoxy, —$C_1$-$C_3$ alkyl-OH, —$C_1$-$C_3$ alkyl-alkoxy, phenyloxy, —$S(O_2)R_{10}$, —$C(O)NR_{11}R_{11}$, —$SO_2NR_{11}R_{11}$, —$NR_{11}C(O)R_{10}$, $NR_{11}SO_2R_{10}$, —O—$C(O)NR_{11}R_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, wherein the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen. In a further embodiment, the C-ring is optionally substituted with $C_1$-$C_4$ alkyl, $C_1$-$C_4$ alkoxy, halogen, $C_1$-$C_4$ haloalkyl (e.g. $CF_3$) or $C_1$-$C_4$ haloalkoxy (e.g., $OCF_3$). In a still further embodiment, the C-ring is unsubstituted. In one embodiment, each $R_{10}$ and $R_{11}$ is independently $C_1$-$C_6$ alkyl or phenyl; and additionally $R_{11}$ may be H.

In a further embodiment of this aspect, the C-ring is a heteroaryl substituted with at least one group that is halogen, $C_1$-$C_6$ alkyl, $C_1$-$C_6$ haloalkyl, $C_1$-$C_6$ haloalkoxy, $C_2$-$C_8$ alkenyl, $C_2$-$C_8$ alkynyl, $C_2$-$C_8$ haloalkenyl, $C_2$-$C_8$ haloalkynyl.

In a further embodiment of this aspect, the C-ring is a heteroaryl substituted with at least one group that is —$C(O)OR_{11}$, CN, hydroxyl, $C_1$-$C_6$ alkoxy, —$C_1$-$C_3$ alkyl-OH, —$C_1$-$C_3$ alkyl-alkoxy, phenyloxy, —$S(O_2)R_{10}$, —$NR_{11}R_{11}$, —$C(O)NR_{11}R_{11}$, —$SO_2NR_{11}R_{11}$, —$NR_{11}C(O)R_{10}$, —$NR_{11}SO_2R_{10}$, —O—$C(O)NR_{11}R_{11}$ or $C_2$-$C_6$ alkanoyl. In a further embodiment of this aspect, the C-ring is a heteroaryl substituted with at least one group that is oxazolyl, pyrazolyl, thiazolyl, pyridyl, pyrimidinyl, imidazolyl, indolyl, furanyl, thienyl, phenyl or phenyl $C_1$-$C_4$ alkyl, wherein the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen.

In a further embodiment of this aspect, the C-ring is a heterocycloalkyl substituted with at least one group that is halogen, $C_1$-$C_6$ alkyl, $C_1$-$C_6$ haloalkyl, $C_1$-$C_6$ haloalkoxy, $C_2$-$C_8$ alkenyl, $C_2$-$C_8$ alkynyl, $C_2$-$C_8$ haloalkenyl or $C_2$-$C_8$ haloalkynyl.

In a further embodiment of this aspect, the C-ring is a heterocycloalkyl substituted with at least one group that is —$C(O)OR_{11}$, CN, hydroxyl, $C_1$-$C_6$ alkoxy, —$C_1$-$C_3$ alkyl-OH, —$C_1$-$C_3$ alkyl-alkoxy, phenyloxy, —$S(O_2)R_{10}$, —$NR_{11}R_{11}$, —$C(O)NR_{11}R_{11}$, —$SO_2NR_{11}R_{11}$, —$NR_{11}C(O)R_{10}$, —$NR_{11}SO_2R_{10}$, —O—$C(O)NR_{11}R_{11}$ or $C_2$-$C_6$ alkanoyl.

In a further embodiment of this aspect, the C-ring is a heterocycloalkyl substituted with at least one group that is oxazolyl, pyrazolyl, thiazolyl, pyridyl, pyrimidinyl, imidazolyl, indolyl, furanyl, thienyl, phenyl or phenyl $C_1$-$C_4$ alkyl, wherein the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen.

In an embodiment of this aspect, the C-ring is an optionally substituted (as described above) pyridyl ring. In a further embodiment, the C-ring is an unsubstituted pyridyl ring. In a still further embodiment, the geminal $R_{51}$ groups that are alpha to the B-ring are both H. In a yet further embodiment, the geminal $R_{51}$ groups that are alpha to the B-ring are both halogens. In another embodiment, both $R_{51}$ groups that are alpha to the B-ring are F. In a still further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In another embodiment of this aspect, the compounds of Formula 4j have the Formulas:

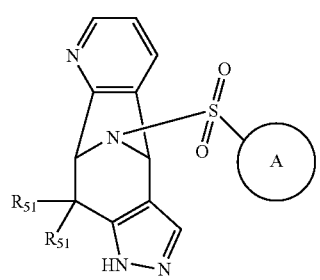

Formula 4k1

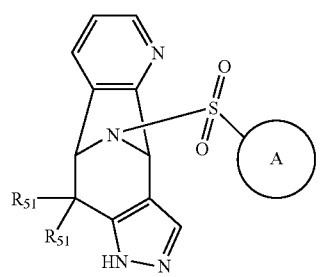

Formula 4k2

-continued

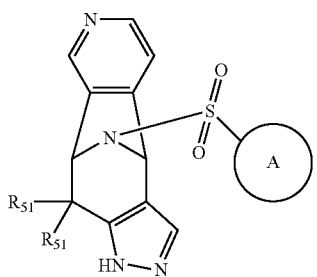

Formula 4k3

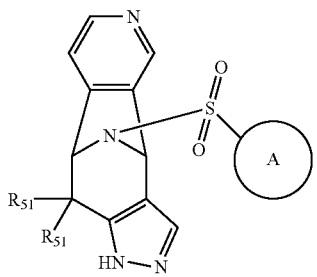

Formula 4k4 wherein each $R_{51}$ is H, $C_1$-$C_4$ alkyl, F, Cl, Br, CN, amino, mono alkylamino or dialkylamino, OH, $CF_3$ or both $R_{51}$ groups form an oxo group. In one embodiment, at least one $R_{51}$ is H. In another embodiment, one $R_{51}$ is H while the other is $R_{51}$ is F or Cl. In another embodiment, one $R_{51}$ is H, while the other $R_{51}$ is OH. In still another embodiment, both $R_{51}$ groups are halogen (e.g., F). In still another embodiment, both $R_{51}$ groups form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In an embodiment of this aspect, the C-ring is an optionally substituted (as described above) thiazolyl ring. In a still further embodiment, the geminal $R_{51}$ groups that are alpha to the B-ring are both H. In a yet further embodiment, the geminal $R_{51}$ groups that are alpha to the B-ring are both halogens. In another embodiment, both $R_{51}$ groups that are alpha to the B-ring are F. In a still further embodiment, the geminal $R_{51}$ groups that are alpha to the B-ring form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In another embodiment of this aspect, the compounds of Formula 4j have the formulas:

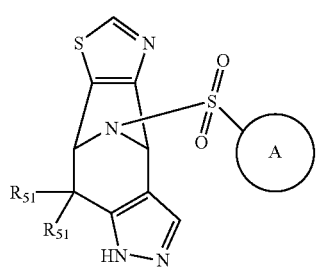

Formula 4l1

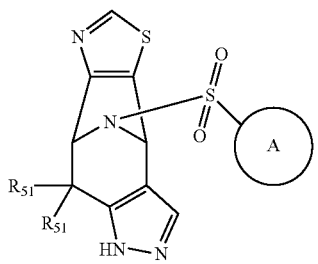

Formula 4l2 wherein each $R_{51}$ is H, $C_1$-$C_4$ alkyl, F, Cl, Br, CN, amino, mono alkylamino or dialkylamino, OH, $CF_3$ or both $R_{51}$ groups form an oxo group. In one embodiment, at least one $R_{51}$ is H. In another embodiment, one $R_{51}$ is H while the other is $R_{51}$ is F or Cl. In another embodiment, one $R_{51}$ is H, while the other $R_{51}$ is OH. In still another embodiment, both $R_{51}$ groups are halogen (e.g., F). In still another embodiment, both $R_{51}$ groups form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In an embodiment of this aspect, the C-ring is an optionally substituted (as described above) pyrazolyl ring. In a further embodiment, the C-ring is an unsubstituted pyrazolyl ring. In a still further embodiment, the geminal $R_{51}$ groups that are alpha to the B-ring are both H. In a yet further embodiment, the geminal $R_{51}$ groups that are alpha to the B-ring are both halogens. In another embodiment, both $R_{51}$ groups that are alpha to the B-ring are F. In a still further embodiment, the geminal $R_5$, groups that are alpha to the B-ring form an oxo group. In a still further embodiment, the C-ring is substituted with $C_1$-$C_4$ alkyl. In another embodiment of this aspect, one of the $R_{51}$ groups is H, while the other is halogen or OH.

In another embodiment of this aspect, the compounds of Formula 4j have the formula:

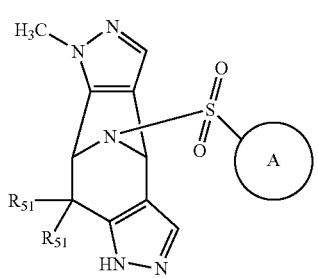

Formula 4m wherein each $R_{51}$ is H, $C_1$-$C_4$ alkyl, F, Cl, Br, CN, amino, mono alkylamino or dialkylamino, OH, $CF_3$ or both $R_{51}$ groups form an oxo group. In one embodiment, at least one $R_{51}$ is H. In another embodiment, one $R_{51}$ is H while the other is $R_{51}$ is F or Cl. In another embodiment, one $R_{51}$ is H, while the other $R_{51}$ is OH. In still another embodiment, both $R_{51}$ groups are halogen (e.g., F). In still another embodiment, both $R_{51}$ groups form an oxo group. In a still further embodiment, the geminal $R_{51}$ groups that are alpha to the B-ring form an $C_2$-$C_4$ alkenyl group. In a still further embodiment, the geminal $R_{51}$ groups that are alpha to the B-ring form form an oxime or a $C_1$-$C_4$ alkylated oxime (e.g., O-methyl oxime).

In an embodiment of this aspect, the C-ring is an optionally substituted (as described above) thienyl ring. In a further embodiment, the C-ring is an unsubstituted thienyl ring. In a still further embodiment, the geminal $R_{51}$ groups that are alpha to the B-ring are both H. In a yet further embodiment, the geminal $R_{51}$ groups that are alpha to the B-ring are both halogens. In another embodiment, both $R_{51}$ groups that are alpha to the B-ring are F. In a still further embodiment, the geminal $R_{51}$ groups that are alpha to the B-ring form an oxo group. In a still further embodiment, the C-ring is substituted with $C_1$-$C_4$ alkyl. In another embodiment of this aspect, one of the $R_{51}$ groups is H, while the other is halogen or OH.

In another aspect, provided herein are compounds of Formulas 1 (and aspects and embodiments thereof), 2 (and aspects and embodiments thereof), 3 (and aspects and embodiments thereof), and 4 (and aspects and embodiments thereof), (provided that the B-ring is not otherwise defined) wherein the B-ring is

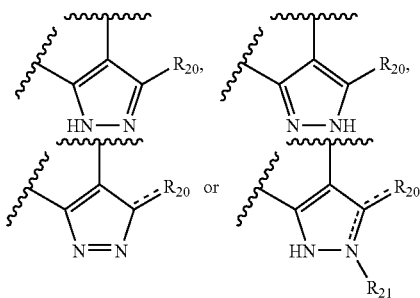

wherein the dashed bond represents an optional second bond;

$R_{20}$ is H, oxo (only when there is a double bond to $R_{20}$) $C_1$-$C_6$ alkyl, $C_1$-$C_6$ alkoxy, amino, $C_1$-$C_6$ alkylamino, $C_1$-$C_6$ dialkylamino, —$NR_{11}C(O)R_{10}$, halo, $CF_3$ or —NHC(O)CH$_3$;

$R_{21}$ is absent or hydrogen; provided that when there are two dashed bonds in the ring formula only one may form a double bond; still further, $R_{21}$ is absent when the dashed bond to the nitrogen is a bond, and thereby forms a double bond.

In another embodiment of this aspect, the B-ring has the formula:

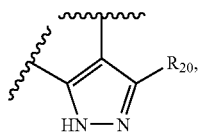

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, —$NR_{11}C(O)R_{10}$, halo or $CF_3$. In a further embodiment, $R_{20}$ is H, $C_1$-$C_4$ alkyl, $C_1$-$C_4$ alkoxy, amino, $C_1$-$C_4$ alkylamino, $C_1$-$C_4$ dialkylamino, halo or $CF_3$. In a further embodiment, $R_{20}$ is H.

In another embodiment of this aspect, the B-ring has the formula:

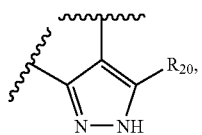

wherein $R_{20}$ is H, $C_1$-$C_4$ alkyl, $C_1$-$C_4$ alkoxy, amino, $C_1$-$C_4$ alkylamino, $C_1$-$C_4$ dialkylamino, —$NR_{11}C(O)R_{10}$, halo or $CF_3$. In a further embodiment, $R_{20}$ is H.

In another embodiment of this aspect, the B-ring has the formula:

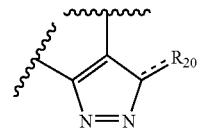

wherein $R_{20}$ is H, oxo (only if there is a double bond to the $R_{20}$ group), $C_1$-$C_4$ alkyl, $C_1$-$C_4$ alkoxy, amino, $C_1$-$C_4$ alkylamino, $C_1$-$C_4$ dialkylamino, —$NR_{11}C(O)R_{10}$, halo or $CF_3$; where the dashed bond represents an optional second bond. In a further embodiment, $R_{20}$ is oxo and the dashed line is a bond. In another embodiment, $R_{20}$ is H.

In another embodiment of this aspect, the B-ring has the formula:

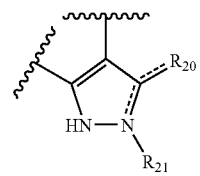

$R_{20}$ is H, oxo (only if there is a double bond to the $R_{20}$ group), $C_1$-$C_4$ alkyl, $C_1$-$C_4$ alkoxy, amino, $C_1$-$C_4$ alkylamino, $C_1$-$C_4$ dialkylamino, —$NR_{11}C(O)R_{10}$, halo or $CF_3$; and $R_{21}$ is absent or hydrogen; and where the dashed bond represents an optional second bond; provided that only one of the two dashed bonds may be a second bond, and thereby form a double bond; still further, $R_{21}$ is absent when the dashed bond to the nitrogen is a bond, and thereby forms a double bond to the nitrogen.

In another aspect, in the compounds of Formulas 1 (and aspects and embodiments thereof), 2 (and aspects and embodiments thereof), 3 (and aspects and embodiments thereof), and 4 (and aspects and embodiments thereof), the A-ring is phenyl or naphthyl (preferably phenyl), which is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, phenyloxy, —$S(O)_{0-2}$—($C_1$-$C_6$ alkyl), —$NR_{11}R_{11}$, —C(O)$NR_{11}R_{11}$, —$NR_{11}C(O)R_{10}$, —$NR_{11}SO_2R_{10}$, —O—C(O)$NR_{11}R_{11}$, $C_2$-$C_6$ alkanoyl, $C_0$-$C_3$alkylCO$_2R_{10}$, pyridyl, thienyl, furanyl, pyrrolyl, pyrrolidinyl, piperidinyl, piperazinyl, phenyl, phenyl $C_1$-$C_4$ alkyl, —OCH$_2$O—, —OCH$_2$CH$_2$O— or —SO$_2NR_{11}R_{11}$, wherein each methylene of —OCH$_2$O— or —OCH$_2$CH$_2$O— is optionally substituted with one or two $C_1$-$C_4$ alkyl groups.

In an embodiment of this aspect, the A-ring is phenyl, and has the following formula:

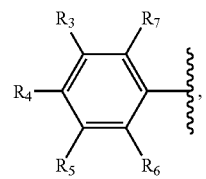

wherein, $R_3$, $R_4$, $R_5$, $R_6$, $R_7$ are independently of each other H, halogen, $C_1$-$C_6$ alkyl, $C_1$-$C_6$ haloalkyl, $C_1$-$C_6$ haloalkoxy, CN, hydroxyl, $C_1$-$C_6$ alkoxy, —$C_1$-$C_3$ alkyl-OH, —$C_1$-$C_3$ alkyl-alkoxy, phenyloxy, —$S(O_2)R_{10}$, —$NR_{11}R_{11}$, —$C(O)NR_{11}R_{11}$, —$SO_2NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, where the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen; or $R_4$ and $R_5$ or $R_5$ and $R_6$ and the carbons to which they are attached form a heterocycloalkyl or a heteroaryl ring which is optionally substituted with 1, 2, 3 or 4 groups that are independently $C_1$-$C_4$ alkyl, $C_1$-$C_4$ alkoxy, halogen or $C_1$-$C_4$ alkanoyl wherein the alkanoyl group is optionally substituted with up to 3 halogen atoms; or $R_4$ and $R_5$ or $R_5$ and $R_6$ and the carbons to which they are attached form a benzo ring which is optionally substituted with optionally substituted with 1 to 5 groups that are independently halogen, hydroxyl, alkyl, alkoxy, haloalkyl, haloalkoxy, CN or $NO_2$.

In an embodiment of this aspect, $R_3$ is H, halogen, $C_1$-$C_6$ alkyl, $C_1$-$C_6$ alkoxy, haloalkyl or CN; $R_4$ is H, halogen; $C_1$-$C_6$ alkyl; $C_1$-$C_6$ alkoxy; $C_1$-$C_6$ haloalkyl; haloalkoxy, CN, phenyloxy, —$SO_2$—($C_1$-$C_6$ alkyl), —$NR_{11}R_{11}$, —$C(O)NR_{11}R_{11}$, —$SO_2NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, oxazolyl, pyrazolyl, thiazolyl, pyridyl, furanyl, thienyl or phenyl; and $R_5$ is H, $C_1$-$C_6$ alkyl, —$SO_2$—$NR_{11}R_{11}$ or halogen.

In an embodiment of this aspect, $R_3$, $R_4$, $R_5$, $R_6$, $R_7$ are independently of each other H, halogen, $C_1$-$C_4$ alkyl, $C_1$-$C_4$ haloalkyl (e.g., $CF_3$), $C_1$-$C_4$ haloalkoxy (e.g., $OCF_3$), CN, hydroxyl, $C_1$-$C_4$ alkoxy, —$C_1$-$C_3$ alkyl-OH, —$C_1$-$C_3$ alkyl-$C_1$-$C_4$ alkoxy, phenyloxy, —$S(O_2)R_{10}$, —$NR_{11}R_{11}$, —$C(O)NR_{11}R_{11}$, —$SO_2NR_{11}R_{11}$, —$NR_{11}C(O)R_{10}$, —$NR_{11}SO_2R_{10}$, —O—$C(O)NR_{11}R_{11}$ or $C_2$-$C_4$ alkanoyl. In a further embodiment, each $R_{10}$ and $R_{11}$ is independently $C_1$-$C_6$ alkyl or phenyl; and additionally $R_{11}$ may be H.

In an embodiment of this aspect, $R_3$, $R_4$, $R_5$, $R_6$, $R_7$ are independently of each other H, halogen, $C_1$-$C_4$ alkyl, oxazolyl, pyrazolyl, thiazolyl, pyridyl, pyrimidinyl, imidazolyl, indolyl, furanyl, thienyl, phenyl or phenyl $C_1$-$C_4$ alkyl, where the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen.

In an embodiment of this aspect, $R_6$ and $R_7$ are independently H or methyl.

In an embodiment of this aspect, $R_3$ and $R_5$ are independently H, halo, $CF_3$, $CHF_2$ or methyl.

In an embodiment of this aspect, $R_4$, $R_6$ and $R_7$ are independently H, halo, $CF_3$, $CHF_2$ or methyl.

In an embodiment of this aspect, $R_4$ is H, halogen (in one aspect, I, Br, F or Cl), $C_1$-$C_6$ alkyl optionally substituted with halogen or hydroxyl, $C_1$-$C_6$ alkoxy, $OCF_3$ or CN.

In an embodiment of this aspect, $R_4$ is phenyloxy, —$SO_2$—($C_1$-$C_6$ alkyl), —$NR_{11}R_{11}$, —$C(O)NR_{11}R_{11}$, —$SO_2NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, oxazolyl, pyrazolyl, thiazolyl, pyridyl, furanyl, thienyl or phenyl.

In an embodiment of this aspect, $R_4$ is —$NR_{11}R_{11}$, —$C(O)NR_{11}R_{11}$ or —O—$C(O)NR_{11}R_{11}$.

In an embodiment of this aspect, $R_4$ is —$SO_2NR_{11}R_{11}$, —$NR_{11}C(O)R_{10}$ or —$NR_{11}SO_2R_{10}$.

In an embodiment of this aspect, $R_4$ is —$SO_2NR_{11}R_{11}$, —$NR_{11}C(O)R_{10}$ or —$NR_{11}SO_2R_{10}$ and $R_3$, $R_5$, $R_6$, and $R_7$ are H.

In an embodiment of this aspect, $R_4$ is —$C(O)NR_{11}R_{11}$.

In an embodiment of this aspect, $R_4$ is —$C(O)NR_{11}R_{11}$, and $R_3$, $R_5$, $R_6$, and $R_7$ are H.

In an embodiment of this aspect, $R_4$ is —O—$C(O)NR_{11}R_{11}$.

In an embodiment of this aspect, $R_4$ is —O—$C(O)NR_{11}R_{11}$, and $R_3$, $R_5$, $R_6$, and $R_7$ are H.

In an embodiment of this aspect, $R_4$ is —$NR_{11}R_{11}$.

In an embodiment of this aspect, $R_4$ is —$NR_{11}R_{11}$, and $R_3$, $R_5$, $R_6$, and $R_7$ are H.

In an embodiment of this aspect, $R_3$, $R_4$, $R_5$, $R_6$, and $R_7$ are H, halo, $CF_3$, $CHF_2$ or methyl.

In an embodiment of this aspect, $R_3$, $R_5$, $R_6$, and $R_7$ are H.

In an embodiment of this aspect, $R_4$ is chloro.

In an embodiment of this aspect, $R_4$ is chloro, and $R_3$, $R_5$, $R_6$, and $R_7$ are H.

In an embodiment of this aspect, $R_4$ is trihalomethyl, and $R_3$, $R_5$, $R_6$, and $R_7$ are H. In one embodiment, $R_4$ is $CCl_3$ or $CF_3$. In another embodiment, $R_4$ is $CF_3$.

In an embodiment of this aspect, at least one of $R_3$, $R_4$ or $R_5$ is chloro, and $R_6$ and $R_7$ are H.

In an embodiment of this aspect, $R_3$ is hydrogen, halogen, $C_1$-$C_4$ alkyl, $C_1$-$C_4$ alkoxy, $CF_3$ or CN; $R_4$ is hydrogen, halogen, $C_1$-$C_4$ alkyl, $C_1$-$C_4$ alkoxy, $CF_3$, $OCF_3$, CN, phenyloxy, —$SO_2$—($C_1$-$C_4$ alkyl), —$NR_{11}R_{11}$, —$C(O)NR_{11}R_{11}$, —$SO_2NR_{11}R_{11}$, —$NR_{11}C(O)R_{10}$, —$NR_{11}SO_2R_{10}$, —O—$C(O)NR_{11}R_{11}$ or $C_1$-$C_4$ alkanoyl, and $R_5$ is hydrogen, $C_1$-$C_4$ alkyl, —$SO_2NR_{11}R_{11}$ or halogen. In one embodiment, $R_6$ and $R_7$ are H.

In an embodiment of this aspect, $R_4$ is halogen (in one aspect, F or Cl), $C_1$-$C_4$ alkyl, $C_1$-$C_4$ alkoxy, $CF_3$, $OCF_3$ or CN. In a further embodiment, $R_3$, $R_5$, $R_6$, and $R_7$ are hydrogen.

In an embodiment of this aspect, $R_4$, $R_5$, $R_6$, and $R_7$ are hydrogen.

In an embodiment of this aspect, $R_3$ is hydrogen, halogen, $C_1$-$C_4$ alkyl, $C_1$-$C_4$ alkoxy, $CF_3$ or CN; $R_4$ is oxazolyl, pyrazolyl, thiazolyl, pyridyl, furanyl, thienyl or phenyl; and $R_5$ is hydrogen, $C_1$-$C_4$ alkyl, —$SO_2NR_{11}R_{11}$ or halogen. In one embodiment of this aspect, $R_6$ and $R_7$ are H.

In an embodiment of this aspect, $R_3$ is —$C(O)NR_{11}R_{11}$, —$SO_2NR_{11}R_{11}$, —$NR_{11}C(O)R_{10}$, —$NR_{11}SO_2R_{10}$ or —O—$C(O)NR_{11}R_{11}$, $R_4$ is H, $C_1$-$C_4$ alkyl or halogen, and $R_5$, $R_6$, and $R_7$ are H.

In an embodiment of this aspect, $R_4$ is halogen (in one aspect, F or Cl), $CH_3$, $OCH_3$, $CF_3$ or $OCF_3$.

In an embodiment of this aspect, $R_3$ is hydrogen, halogen, $C_1$-$C_2$ alkyl, $C_1$-$C_2$ alkoxy, $CF_3$ or CN; $R_4$ is hydrogen, halogen, $C_1$-$C_2$ alkyl, $C_1$-$C_2$ alkoxy, $C_1$-$C_2$ haloalkyl, $C_1$-$C_2$ haloalkoxy, CN, —$NR_{11}R_{11}$, $C_2$-$C_3$ alkanoyl, oxazolyl, pyrazolyl, thiazolyl, pyridyl, furanyl or thienyl; $R_5$ is hydrogen, $CH_3$ or F; and $R_6$ and $R_7$ are independently hydrogen or halogen.

In an embodiment of this aspect, $R_4$ is $CF_3$ or $OCF_3$. In one embodiment, $R_6$ and $R_7$ are H. In a further embodiment, $R_3$ and $R_5$ are also H.

In an embodiment of this aspect, $R_4$ and $R_5$ or $R_5$ and $R_6$ and the carbons to which they are attached form a benzo ring which is optionally substituted with optionally substituted with 1 or 2 groups that are independently halogen, hydroxyl, $C_1$-$C_4$ alkyl, $C_1$-$C_4$ alkoxy, $C_1$-$C_3$ haloalkyl, $C_1$-$C_3$ haloalkoxy, CN or $NO_2$.

In an embodiment of this aspect, $R_4$ and $R_5$ or $R_5$ and $R_6$ and the carbons to which they are attached form a pyridyl, pyrrolyl, thienyl, furanyl, pyrrolidinyl, piperidinyl ring, each of which is optionally substituted with 1, 2 or 3 groups that are independently $C_1$-$C_4$ alkyl, $C_1$-$C_4$ alkoxy, halogen or $C_1$-$C_4$ alkanoyl wherein the alkanoyl group is optionally substituted with up to 3 halogen atoms (e.g., F).

In an embodiment of this aspect, $R_6$ and $R_7$ are independently hydrogen or methyl.

In an embodiment of this aspect, $R_3$ and $R_5$ are independently hydrogen, halo or methyl.

In an embodiment of this aspect, $R_3$ and $R_4$ or $R_5$ and $R_6$ are —$OCH_2O$—, —$OCH_2CH_2O$—, wherein each methylene of —$OCH_2O$— or —$OCH_2CH_2O$— is optionally substituted with one or two $C_1$-$C_4$ alkyl groups. In one embodiment, each methylene is unsubstituted. In another embodiment, at least one methylene is substituted with at least one $C_1$-$C_4$ alkyl group.

In an embodiment of this aspect, $R_{11}$ at each occurrence is independently H or $C_1$-$C_5$ alkyl. In a further embodiment, $R_{10}$ is $C_1$-$C_4$ alkyl or phenyl.

In another aspect, in the compounds of Formulas 1 (and aspects and embodiments thereof), 2 (and aspects and embodiments thereof), 3 (and aspects and embodiments thereof), and 4 (and aspects and embodiments thereof), the A-ring is $C_3$-$C_8$ cycloalkyl, which is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, phenyloxy, —$S(O)_{0-2}$—($C_1$-$C_6$ alkyl), —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, $C_0$-$C_3$alkyl$CO_2R_{10}$, pyridyl, thienyl, furanyl, pyrrolyl, pyrrolidinyl, piperidinyl, piperazinyl, phenyl, phenyl $C_1$-$C_4$ alkyl or —$SO_2NR_{11}R_{11}$, where the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen.

In an embodiment of this aspect, the $C_3$-$C_8$ cycloalkyl is optionally substituted at a substitutable position with halogen, $C_1$-$C_4$ alkyl, $C_1$-$C_4$ alkoxy, $C_1$-$C_4$ haloalkyl, $C_1$-$C_4$ haloalkoxy, hydroxyl or $C_1$-$C_4$hydroxyalkyl. In one embodiment, the $C_3$-$C_8$ cycloalkyl group is substituted with one group. In one embodiment, the $C_3$-$C_8$ cycloalkyl group is substituted with one group that is —$NR_{11}R_{11}$, —$C(O)NR_{11}R_{11}$, —$SO_2NR_{11}R_{11}$, —$NR_{11}C(O)R_{10}$, —$NR_{11}SO_2R_{10}$ or —O—$C(O)NR_{11}R_{11}$, where $R_{10}$ and $R_{11}$ are independently $C_1$-$C_4$ alkyl or phenyl; and additionally $R_{11}$ may be H.

In yet still another embodiment of this aspect, the $C_3$-$C_8$ cycloalkyl is substituted with one or two groups that are independently methoxy, ethoxy, methyl, ethyl or halogen.

In an embodiment of this aspect, the A-ring is unsubstituted cyclopropyl.

In an embodiment of this aspect, the A-ring is unsubstituted cyclobutyl.

In an embodiment of this aspect, the A-ring is unsubstituted cyclopentyl.

In an embodiment of this aspect, the A-ring is unsubstituted cyclohexyl.

In an embodiment of this aspect, the A-ring is unsubstituted cycloheptyl.

In an embodiment of this aspect, the A-ring is unsubstituted cyclooctyl.

In another aspect, in the compounds of Formulas 1 (and aspects and embodiments thereof), 2 (and aspects and embodiments thereof), 3 (and aspects and embodiments thereof), and 4 (and aspects and embodiments thereof), the A-ring is heteroaryl, for instance, pyridyl, pyrimidyl, pyridazinyl, pyrazinyl, thienyl, furanyl, pyrrolyl, pyrazolyl or imidazolyl, each of which is optionally substituted at one or more substitutable positions with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, phenyloxy, —$S(O)_{0-2}$—($C_1$-$C_6$ alkyl), —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, $C_0$-$C_3$alkyl$CO_2R_{10}$, pyridyl, thienyl, furanyl, pyrrolyl, pyrrolidinyl, piperidinyl, piperazinyl, phenyl, phenyl $C_1$-$C_4$ alkyl or —$SO_2NR_{11}R_{11}$, where the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen.

In an embodiment of this aspect, the heteroaryl group is pyridyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H. In some embodiments the pyridyl group is substituted with one halogen, e.g. chloro. In an embodiment of this aspect, the pyridyl group is substituted with one $C_1$-$C_4$ haloalkyl group (e.g., $CF_3$). In a further embodiment of this aspect, the pyridyl group is 5-(trifluoromethyl)pyridin-2-yl or 6-(trifluoromethyl)pyridin-3-yl. In a still further embodiment of this aspect, the pyridyl group is 6-(trifluoromethyl)pyridin-3-yl. In another embodiment, the pyridyl group is substituted with one or two groups that are independently halogen, $C_1$-$C_4$ alkyl or $C_1$-$C_4$ alkoxy. In still another embodiment, the pyridyl group is substituted with one group that is —$NR_{11}R_{11}$, —$C(O)NR_{11}R_{11}$, —$NR_{11}C(O)R_{10}$ or —O—$C(O)NR_{11}R_{11}$. In yet another embodiment, the pyridyl group is substituted with one group that is —$SO_2$—($C_1$-$C_6$ alkyl) or —$SO_2NR_{11}R_{11}$. In still another embodiment, the pyridyl group is substituted with one or two groups that are independently $C_1$-$C_4$ alkyl, $C_1$-$C_4$ alkoxy or hydroxyl. In a further embodiment, the pyridyl group is unsubstituted.

In an embodiment of this aspect, the heteroaryl group is pyrimidyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H. In some embodiments the pyrimidyl group is substituted with one halogen, e.g. chloro. In another embodiment, the pyrimidyl group is substituted with one or two groups that are independently halogen, $C_1$-$C_4$ alkyl or $C_1$-$C_4$ alkoxy. In still another embodiment, the pyrimidyl group is substituted with one group that is —$NR_{11}R_{11}$, —$C(O)NR_{11}R_{11}$, —$NR_{11}C(O)R_{10}$, or —O—$C(O)NR_{11}R_{11}$. In yet another embodiment, the pyrimidyl group is substituted with one group that is —$SO_2$—($C_1$-$C_6$ alkyl) or —$SO_2NR_{11}R_{11}$. In still another embodiment, the pyrimidyl group is substituted with one or two groups that are independently $C_1$-$C_4$ alkyl, $C_1$-$C_4$ alkoxy or hydroxyl. In a further embodiment, the pyrimidyl group is unsubstituted.

In an embodiment of this aspect, the heteroaryl group is pyridazinyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H. In some embodiments the pyridazinyl group is substituted with one halogen, e.g. chloro. In another embodiment, the pyridazinyl group is substituted with one or two groups that are independently halogen, $C_1$-$C_4$ alkyl or $C_1$-$C_4$ alkoxy. In still another embodiment, the pyridazinyl group is substituted with one group that is —$NR_{11}R_{11}$, —$C(O)NR_{11}R_{11}$, —$NR_{11}C(O)R_{10}$ or —O—$C(O)NR_{11}R_{11}$. In yet another embodiment, the pyridazinyl group is substituted with one group that is —$SO_2$—($C_1$-$C_6$ alkyl) or —$SO_2NR_{11}R_{11}$. In still another embodiment, the pyridazinyl group is substituted with one or two groups that are independently $C_1$-$C_4$ alkyl, $C_1$-$C_4$ alkoxy or hydroxyl. In a further embodiment, the pyridazinyl group is unsubstituted.

In an embodiment of this aspect, the heteroaryl group is pyrazinyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H. In some embodiments the pyrazinyl group is substituted with one halogen, e.g. chloro. In another embodiment, the pyrazinyl group is substituted with one or two groups that are independently halogen, $C_1$-$C_4$ alkyl or $C_1$-$C_4$ alkoxy. In still another embodiment, the pyrazinyl group is substituted with one group that is —$NR_{11}R_{11}$, —$C(O)NR_{11}R_{11}$, —$NR_{11}C(O)R_{10}$, or —O—$C(O)NR_{11}R_{11}$. In yet another embodiment, the pyrazinyl group is substituted with one group that is —$SO_2$—($C_1$-$C_6$ alkyl) or —$SO_2NR_{11}R_{11}$. In still another embodiment, the pyrazinyl group is substituted with one or two groups that are independently $C_1$-$C_4$ alkyl, $C_1$-$C_4$ alkoxy or hydroxyl. In a further embodiment, the pyrazinyl group is unsubstituted.

In an embodiment of this aspect, the heteroaryl group is thienyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H. In some embodiments the thienyl group is substituted with one halogen, e.g. chloro. In one embodiment, the thienyl group is substituted at the 5-position with a Cl. In another embodiment, the heteroaryl group is 5-chlorothiophen-2-yl. In another embodiment, the thienyl group is substituted with one or two groups that are independently halogen, $C_1$-$C_4$ alkyl or $C_1$-$C_4$ alkoxy. In still another embodiment, the thienyl group is substituted with one group that is —$NR_{11}R_{11}$, —$C(O)NR_{11}R_{11}$, —$NR_{11}C(O)R_{10}$ or —O—$C(O)NR_{11}R_{11}$. In yet another embodiment, the thienyl group is substituted with one group that is —$SO_2$—($C_1$-$C_6$ alkyl) or —$SO_2NR_{11}R_{11}$. In still another embodiment, the thienyl group is substituted with one or two groups that are independently $C_1$-$C_4$ alkyl, $C_1$-$C_4$ alkoxy or hydroxyl. In a further embodiment, the thienyl group is unsubstituted.

In an embodiment of this aspect, the heteroaryl group is furanyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H. In some embodiments the furanyl group is substituted with one halogen, e.g. chloro. In another embodiment, the furanyl group is substituted with one or two groups that are independently halogen, $C_1$-$C_4$ alkyl or $C_1$-$C_4$ alkoxy. In still another embodiment, the furanyl group is substituted with one group that is —$NR_{11}R_{11}$, —$C(O)NR_{11}R_{11}$, —$NR_{11}C(O)R_{10}$, or —O—$C(O)NR_{11}R_{11}$. In yet another embodiment, the furanyl group is substituted with one group that is —$SO_2$—($C_1$-$C_6$ alkyl) or —$SO_2NR_{11}R_{11}$. In still another embodiment, the furanyl group is substituted with one or two groups that are independently $C_1$-$C_4$ alkyl, $C_1$-$C_4$ alkoxy or hydroxyl. In a further embodiment, the furanyl group is unsubstituted.

In an embodiment of this aspect, the heteroaryl group is pyrrolyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H. In some embodiments the pyrrolyl group is substituted with one halogen, e.g. chloro. In another embodiment, the pyrrolyl group is substituted with one or two groups that are independently halogen, $C_1$-$C_4$ alkyl or $C_1$-$C_4$ alkoxy. In still another embodiment, the pyrrolyl group is substituted with one group that is —$NR_{11}R_{11}$, —$C(O)NR_{11}R_{11}$, —$NR_{11}C(O)R_{10}$, or —O—$C(O)NR_{11}R_{11}$. In yet another embodiment, the pyrrolyl group is substituted with one group that is —$SO_2$—($C_1$-$C_6$ alkyl) or —$SO_2NR_{11}R_{11}$. In still another embodiment, the pyrrolyl group is substituted with one or two groups that are independently $C_1$-$C_4$ alkyl, $C_1$-$C_4$ alkoxy or hydroxyl. In a further embodiment, the pyrrolyl group is unsubstituted.

In another aspect, in the compounds of Formulas 1 (and aspects and embodiments thereof), 2 (and aspects and embodiments thereof), 3 (and aspects and embodiments thereof), and 4 (and aspects and embodiments thereof), the A-ring is:

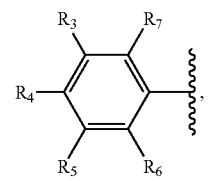

wherein, $R_3$, $R_4$, $R_5$, $R_6$, $R_7$ are independently of each other H, halogen, $C_1$-$C_4$ alkyl, $C_1$-$C_4$ haloalkyl, $C_1$-$C_4$ haloalkoxy, CN, hydroxyl, $C_1$-$C_4$ alkoxy, —$C_1$-$C_3$-$C_1$-$C_3$ alkyl-$C_1$-$C_4$ alkoxy, phenyloxy, —$S(O_2)R_{10}$, —$SO_2NR_{11}R_{11}$, —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$ or $C_2$-$C_4$ alkanoyl; or the A-ring is pyridyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H.

In a further embodiment of this aspect, the A-ring is phenyl or pyridyl, each of which is optionally substituted with halogen or $C_1$-$C_4$ haloalkyl (e.g., $CF_3$ or $CHF_2$).

In a further embodiment of this aspect, the A-ring is phenyl substituted with $R_3$, $R_4$, $R_5$, $R_6$ and $R_7$, wherein $R_4$ is halogen, $C_1$-$C_4$ alkyl, $C_1$-$C_4$ alkoxy, $CF_3$, $OCF_3$ or CN; and $R_3$, $R_5$, $R_6$, and $R_7$ are hydrogen.

In a further embodiment of this aspect, the A-ring is pyridyl, optionally substituted with one halogen or $CF_3$.

In another aspect, in the compounds of Formulas 1 (and aspects and embodiments thereof), 2 (and aspects and embodiments thereof), 3 (and aspects and embodiments thereof), and 4 (and aspects and embodiments thereof), the A-ring is heterocycloalkyl that is pyrrolidinyl, piperidinyl, piperazinyl, morpholinyl, thiomorpholinyl or thiomorpholinyl-S,S-dioxide, where each of the above rings is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, phenyloxy, —S(O)$_{0\text{-}2}$—($C_1$-$C_6$ alkyl), —$NR_{11}R_{11}$, —C(O)$NR_{11}R_{11}$, —$NR_{11}$C(O)$R_{10}$, —$NR_{11}SO_2R_{10}$, —O—C(O)$NR_{11}R_{11}$, $C_2$-$C_6$ alkanoyl, $C_0$-$C_3$alkyl$CO_2R_{10}$, pyridyl, thienyl, furanyl, pyrrolyl, pyrrolidinyl, piperidinyl, piperazinyl, phenyl, phenyl $C_1$-$C_4$ alkyl or —$SO_2NR_{11}R_{11}$, where the phenyl portions of the above are optionally substituted with one or more groups that are independently $C_1$-$C_6$ alkyl, $C_1$-$C_6$ alkoxy, $C_1$-$C_4$ haloalky (e.g. $CF_3$) or halogen.

In an embodiment of this aspect, the heterocycloalkyl group is pyrrolidinyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —C(O)$NR_{11}R_{11}$, —$NR_{11}$C(O)$R_{10}$, —$NR_{11}SO_2R_{10}$, —O—C(O)$NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H. In some embodiments the pyrrolidinyl group is substituted with one halogen, e.g. chloro. In another embodiment, the pyrrolidinyl group is substituted with one or two groups that are independently halogen, $C_1$-$C_4$ alkyl or $C_1$-$C_4$ alkoxy. In still another embodiment, the pyrrolidinyl group is substituted with one group that is —$NR_{11}R_{11}$, —C(O)$NR_{11}R_{11}$, —$NR_{11}$C(O)$R_{10}$, or —O—C(O)$NR_{11}R_{11}$. In yet another embodiment, the pyrrolidinyl group is substituted with one group that is —$SO_2$—($C_1$-$C_6$ alkyl), or —$SO_2NR_{11}R_{11}$. In still another embodiment, the pyrrolidinyl group is substituted with one or two groups that are independently $C_1$-$C_4$ alkyl, $C_1$-$C_4$ alkoxy or hydroxyl. In a further embodiment, the pyrrolidinyl group is unsubstituted.

In an embodiment of this aspect, the heterocycloalkyl group is piperidinyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —C(O)$NR_{11}R_{11}$, —$NR_{11}$C(O)$R_{10}$, —$NR_{11}SO_2R_{10}$, —O—C(O)$NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H. In some embodiments the pyrrolidinyl group is substituted with one halogen, e.g. chloro. In another embodiment, the pyrrolidinyl group is substituted with one or two groups that are independently halogen, $C_1$-$C_4$ alkyl or $C_1$-$C_4$ alkoxy. In still another embodiment, the pyrrolidinyl group is substituted with one group that is —$NR_{11}R_{11}$, —C(O)$NR_{11}R_{11}$, —$NR_{11}$C(O)$R_{10}$, —$NR_{11}SO_2R_{10}$, or —O—C(O)$NR_{11}R_{11}$. In yet another embodiment, the pyrrolidinyl group is substituted with one group that is —$SO_2$—($C_1$-$C_6$ alkyl) or —$SO_2NR_{11}R_{11}$. In still another embodiment, the pyrrolidinyl group is substituted with one or two groups that are independently $C_1$-$C_4$ alkyl, $C_1$-$C_4$ alkoxy or hydroxyl. In a further embodiment, the pyrrolidinyl group is unsubstituted.

In an embodiment of this aspect, the heterocycloalkyl group is piperazinyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —C(O)$NR_{11}R_{11}$, —$NR_{11}$C(O)$R_{10}$, —$NR_{11}SO_2R_{10}$, —O—C(O)$NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H. In some embodiments the pyrrolidinyl group is substituted with one halogen, e.g. chloro. In another embodiment, the pyrrolidinyl group is substituted with one or two groups that are independently halogen, $C_1$-$C_4$ alkyl or $C_1$-$C_4$ alkoxy. In still another embodiment, the pyrrolidinyl group is substituted with one group that is —$NR_{11}R_{11}$, —C(O)$NR_{11}R_{11}$, —$NR_{11}$C(O)$R_{10}$, or —O—C(O)$NR_{11}R_{11}$. In yet another embodiment, the pyrrolidinyl group is substituted with one group that is —$SO_2$—($C_1$-$C_6$ alkyl), —$NR_{11}SO_2R_{10}$ or —$SO_2NR_{11}R_{11}$. In still another embodiment, the pyrrolidinyl group is substituted with one or two groups that are independently $C_1$-$C_4$ alkyl, $C_1$-$C_4$ alkoxy or hydroxyl. In a further embodiment, the pyrrolidinyl group is unsubstituted.

In an embodiment of this aspect, the heterocycloalkyl group is morpholinyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —C(O)$NR_{11}R_{11}$, —$NR_{11}$C(O)$R_{10}$, —$NR_{11}SO_2R_{10}$, —O—C(O)$NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H. In some embodiments the pyrrolidinyl group is substituted with one halogen, e.g. chloro. In another embodiment, the pyrrolidinyl group is substituted with one or two groups that are independently halogen, $C_1$-$C_4$ alkyl or $C_1$-$C_4$ alkoxy. In still another embodiment, the pyrrolidinyl group is substituted with one group that is —$NR_{11}R_{11}$, —C(O)$NR_{11}R_{11}$—$NR_{11}$C(O)$R_{10}$, —$NR_{11}SO_2R_{10}$, or —O—C(O)$NR_{11}R_{11}$. In yet another embodiment, the pyrrolidinyl group is substituted with one group that is —$SO_2$—($C_1$-$C_6$ alkyl) or —$SO_2NR_{11}R_{11}$. In still another embodiment, the pyrrolidinyl group is substituted with one or two groups that are independently $C_1$-$C_4$ alkyl, $C_1$-$C_4$ alkoxy or hydroxyl. In a further embodiment, the pyrrolidinyl group is unsubstituted.

In an embodiment of this aspect, the heterocycloalkyl group is thiomorpholinyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —C(O)$NR_{11}R_{11}$, —$NR_{11}$C(O)$R_{10}$, —$NR_{11}SO_2R_{10}$, —O—C(O)$NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H. In some embodiments the pyrrolidinyl group is substituted with one halogen, e.g. chloro. In another embodiment, the pyrrolidinyl group is substituted with one or two groups that are independently halogen, $C_1$-$C_4$ alkyl or $C_1$-$C_4$ alkoxy. In still another embodiment, the pyrrolidinyl group is substituted with one group that is —$NR_{11}R_{11}$, —C(O)$NR_{11}R_{11}$, —$NR_{11}$C(O)$R_{10}$, —$NR_{11}SO_2R_{10}$, or —O—C(O)$NR_{11}R_{11}$. In yet another embodiment, the pyrrolidinyl group is substituted with one group that is —$SO_2$—($C_1$-$C_6$ alkyl) or —$SO_2NR_{11}R_{11}$. In still another embodiment, the pyrrolidinyl group is substituted with one or two groups that are independently $C_1$-$C_4$ alkyl, $C_1$-$C_4$ alkoxy or hydroxyl. In a further embodiment, the pyrrolidinyl group is unsubstituted.

In an embodiment of this aspect, the heterocycloalkyl group is thiomorpholinyl-S,S-dioxide, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H. In some embodiments the pyrrolidinyl group is substituted with one halogen, e.g. chloro. In another embodiment, the pyrrolidinyl group is substituted with one or two groups that are independently halogen, $C_1$-$C_4$ alkyl or $C_1$-$C_4$ alkoxy. In still another embodiment, the pyrrolidinyl group is substituted with one group that is —$NR_{11}R_{11}$, —$C(O)NR_{11}R_{11}$, —$NR_{11}C(O)R_{10}$, —$NR_{11}SO_2R_{10}$, or —O—$C(O)NR_{11}R_{11}$. In yet another embodiment, the pyrrolidinyl group is substituted with one group that is —$SO_2$—($C_1$-$C_6$ alkyl) or —$SO_2NR_{11}R_{11}$. In still another embodiment, the pyrrolidinyl group is substituted with one or two groups that are independently $C_1$-$C_4$ alkyl, $C_1$-$C_4$ alkoxy or hydroxyl. In a further embodiment, the pyrrolidinyl group is unsubstituted.

In another aspect, provided herein are compounds of Formulas 1, 2, 3, and 4, as well as all aspects and embodiments thereof, wherein each $R_{25}$ is independently H, $C_1$-$C_6$ alkyl, $C_1$-$C_6$ haloalkyl, —$C(O)OR_{11}$, —$C(O)NR_{11}R_{11}$, —($C_1$-$C_6$ alkyl)-$C(O)OR_{11}$, $C_1$-$C_6$ alkoxy $C_1$-$C_6$ alkyl, —$CONR_{11}R_{11}$, CN, $C_1$-$C_6$ alkyl-CN or hydroxy $C_1$-$C_6$ alkyl. In an embodiment, the two $R_{25}$ groups are the same. In another embodiment, the two $R_{25}$ groups are different.

In an embodiment of this aspect, each $R_{25}$ is independently H, $C_1$-$C_4$ alkyl, $C_1$-$C_4$ haloalkyl, hydroxy $C_1$-$C_4$ alkyl or $C_1$-$C_4$ alkoxyalkyl. In a further embodiment, $R_{25}$ is H or unsubstituted $C_1$-$C_4$ alkyl (e.g., $CH_3$). In a further embodiment, $R_{25}$ is H or hydroxy $C_1$-$C_4$ alkyl (e.g., hydroxymethyl). In a further embodiment, $R_{25}$ is H or $C_1$-$C_4$ alkoxy $C_1$-$C_4$ alkyl. In a further embodiment, $R_{25}$ is H or $C_1$-$C_4$ haloalkyl (e.g., $CF_3$, $CHF_2$, $CH_2F$, $CH_2Cl$). In a further embodiment, $R_{25}$ is $C_1$-$C_4$ alkyl or $C_1$-$C_4$ haloalkyl (e.g., $CF_3$, $CHF_2$, $CH_2F$, $CH_2Cl$). In a further embodiment, $R_{25}$ is $C_1$-$C_4$ alkyl or hydroxy $C_1$-$C_4$ alkyl (e.g., hydroxymethyl). In a further embodiment, $R_{25}$ is $C_1$-$C_4$ alkyl or $C_1$-$C_4$ alkoxy $C_1$-$C_4$ alkyl.

In an embodiment of this aspect, each $R_{25}$ is independently H, —$C(O)OR_{11}$, —($C_1$-$C_6$ alkyl)-$C(O)OR_{11}$. In a further embodiment, $R_{25}$ is H or —$C(O)OR_{11}$, —($C_1$-$C_6$ alkyl)-$C(O)OR_{11}$. In a further embodiment, $R_{13}$ is H or unsubstituted $C_1$-$C_4$ alkyl. In a further embodiment, $R_{13}$ is H. In a still further embodiment, $R_{13}$ is $C_1$-$C_4$ alkyl substituted with at least one group that is phenyl, naphthyl, hydroxyl, $C_1$-$C_6$ alkoxy or halogen, where the phenyl and naphthyl groups are unsubstituted. In a further embodiment, $R_{13}$ is $C_1$-$C_4$ alkyl substituted with phenyl, wherein the phenyl is substituted with 1 to 5 groups that are independently halogen, hydroxyl, $C_1$-$C_4$ alkyl, $C_1$-$C_4$ alkoxy, $C_1$-$C_4$ haloalkyl (e.g., $CF_3$), $C_1$-$C_4$ haloalkoxy (e.g., $OCF_3$), CN or $NO_2$.

In an embodiment of this aspect, each $R_{25}$ is independently H, $C_1$-$C_6$ alkyl-CN or CN.

In a further embodiment of this aspect, $R_{25}$ is H, —$C(O)OR_{11}$ or —$CONR_{11}R_{11}$. In a still further embodiment, each $R_{11}$ is independently H, $C_3$-$C_6$ cycloalkyl, heteroaryl that is pyrazolyl, thiadiazolyl (e.g., 1,2,4-thiadiazolyl or 1,3,4-thiadiazolyl), triazolyl (e.g., 1,2,3-triazolyl or 1,2,4-triazolyl), isoxazolyl, isothiazolyl, imidazolyl, thiazolyl, oxadiazolyl (e.g., 1,2,4-oxadiazolyl or 1,3,4-oxadiazolyl), oxazolyl, tetrazolyl or pyridyl, heterocycloalkyl that is selected from tetrahydrofuranyl, pyrrolidinyl, piperidinyl, morpholinyl, and imidazolidinyl, phenyl, $C_2$-$C_6$ alkanoyl or $C_1$-$C_6$ alkyl optionally substituted e.g., with —$C(O)OR_{11}$ or alkoxy, where the alkoxy group is optionally further substituted with —$C(O)OR_{11}$, and where the heteroaryl and aryl groups are optionally substituted e.g., with 1 to 3 groups that are independently halogen, hydroxyl, $C_1$-$C_4$ alkyl, $C_1$-$C_4$ alkoxy, $C_1$-$C_4$ haloalkyl, $C_1$-$C_4$ haloalkoxy, CN or $NO_2$; or the two $R_{11}$ groups together with the nitrogen to which they are attached, form a 3-8 membered ring that optionally contains an additional heteroatom such as e.g., NH, $NR_{12}$, $NR_{13}$, O or S, and $R_{13}$ is H or $C_1$-$C_6$ alkyl.

In another embodiment of this aspect, each $R_{25}$ is independently H, $C_1$-$C_4$ alkyl, $C_1$-$C_4$ haloalkyl, hydroxy $C_1$-$C_4$ alkyl, $C_1$-$C_4$ alkoxyalkyl, —$C(O)OR_{11}$ or —$C(O)NR_{11}R_{11}$.

In another embodiment of this aspect, each $R_{11}$ is independently H or $C_1$-$C_4$ alkyl optionally substituted with —$C(O)OR_{11}$ or alkoxy, where $R_{11}$ is H or $C_1$-$C_4$ alkyl.

In another embodiment of this aspect, each $R_{25}$ is independently H, hydroxymethyl, methyl or —$CO_2CH_3$.

In another embodiment of this aspect, each $R_{25}$ is H.

The compounds of Formulas 1, 2, 3, and 4 encompass the sulfonamido derivatives of the invention as disclosed, and/or the pharmaceutically acceptable salts, solvates or polymorphs of such compounds. In addition, the compounds of this invention include the individual stereochemical and geometrical isomers, tautomers, and mixtures thereof, arising from the selection of substituent groups. Certain compounds of this invention may exist in isomeric forms. The invention contemplates all such stereoisomers both in pure form and in admixture, as well as racemic mixtures.

DEFINITIONS

The definitions and explanations below are for the terms as used throughout this entire document including both the specification and the claims. Throughout the specification and the appended claims, a given formula or name shall encompass all isomers thereof, such as stereoisomers, geometrical isomers, optical isomers, tautomers, and mixtures thereof where such isomers exist, as well as pharmaceutically acceptable salts and solvates thereof, such as for instance hydrates.

It should be noted that, as used in this specification and the appended claims, the singular forms "a," "an," and "the" include plural referents unless the content clearly dictates otherwise. Thus, e.g., reference to a composition containing "a compound" includes a mixture of two or more compounds. It should also be noted that the term "or" is generally employed in its sense including "and/or" unless the content clearly dictates otherwise.

Where multiple substituents are indicated as being attached to a structure, it is to be understood that the substituents can be the same or different. Thus e.g. "$R_m$ optionally substituted with 1, 2, 3 or 4 $R_q$ groups" indicates that $R_m$ is substituted with 1, 2, 3 or 4 $R_q$ groups, where the $R_q$ groups can be the same or different. It will be understood by those skilled in the art with respect to any group containing one or more substituents that such groups are not intended to introduce any substitution or substitution patterns that are sterically impractical and for synthetically non-feasable.

APP, amyloid precursor protein, is defined as any APP polypeptide, including APP variants, mutations, and <isoforms, e.g., as disclosed in U.S. Pat. No. 5,766,846.

A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42 or 43.

Pharmaceutically acceptable refers to those properties and/or substances that are acceptable to the patient from a toxicological and/or safety point of view.

A therapeutically effective amount is defined as an amount effective to reduce or lessen at least one symptom of the disease being treated or to reduce or delay onset of one or more clinical markers or symptoms of the disease.

By "alkanoyl" is meant an acyl radical Alk-C(O)—, wherein Alk is an alkyl radical as defined herein. Examples of alkanoyl include acetyl, propionyl, butyryl, isobutyryl, valeryl, isovaleryl, 2-methyl-butyryl, 2,2-dimethylpropionyl, valeryl, hexanoyl, heptanoyl, octanoyl and the like.

The term "alkyl," by itself or as part of another substituent, means, unless otherwise stated, a straight or branched chain hydrocarbon radical, which can include di- and multivalent radicals, having the number of carbon atoms designated (e.g., $C_1$-$C_{10}$ means one to ten carbon atoms). Typically, an alkyl group will have from 1 to 10 carbon atoms, with those groups having from 1 to 8 carbon atoms, from 1 to 6 carbon atoms or from 1 to 4 carbon atoms being preferred. A "lower alkyl" group is an alkyl group having from 1 to 4 carbon atoms. The term "alkyl" includes "alkylene" wherever appropriate, e.g., when the formula indicates that the alkyl group is divalent or when substituents are joined to form a ring. Examples of alkyl radicals include, but are not limited to methyl, ethyl, n-propyl, iso-propyl, n-butyl, tert-butyl, iso-butyl and sec-butyl, as well as homologs and isomers of, e.g., n-pentyl, n-hexyl, n-heptyl and n-octyl.

The term "alkylene" by itself or as part of another substituent means a divalent (diradical) alkyl group, wherein alkyl is defined herein. "Alkylene" is exemplified, but not limited, by —$CH_2CH_2CH_2CH_2$—. Typically, an "alkylene" group will have from 1 to 24 carbon atoms, with those groups having 10 or fewer carbon atoms (e.g., 1 to 8 or 1 to 6 carbon atoms) being preferred in the present invention. A "lower alkylene" is an alkylene group having from 1 to 4 carbon atoms.

By "aryl" is meant an aromatic carbocyclic group having a single ring or multiple condensed rings in which at least one is an aromatic hydrocarbon, (e.g., 1,2,3,4-tetrahydronaphthyl, naphthyl). When the "aryl" group includes a non-aromatic ring (such as in 1,2,3,4-tetrahydronaphthyl) or heteroaryl group then the "aryl" group is linked to the core/remainder of the molecule via the aromatic, hydrocarbon ring. Non-limiting examples of aryl groups include phenyl, 1-naphthyl, 2-naphthyl, qinoline, indanyl, indenyl, dihydronaphthyl, fluorenyl, tetralinyl, benzo[d][1,3]dioxolyl or 6,7,8,9-tetrahydro-5H-benzo[a]cycloheptenyl. Preferred "aryl" groups include phenyl, benzo[d][1,3]dioxolyl and naphthyl. Particularly preferred is phenyl.

By "aryloxy" is meant the group —O-aryl, where aryl is as defined herein. More preferably the aryl portion of the aryloxy group is phenyl or naphthyl, still more preferably, phenyl.

By "arylalkyl" is meant the group -alkyl-aryl, wherein alkyl and aryl are defined herein.

By the term "halogen" in the present invention is meant fluorine, bromine, chlorine, and/or iodine.

The term "alkenyl" by itself or as part of another substituent refers to a straight or branched chain hydrocarbon radical having from 2 to 12 carbon atoms and at least one carbon-carbon double bond. A typical alkenyl group has from 2 to 10 carbon atoms and at least one double bond. Preferred alkenyl groups have from 2 to 8 carbon atoms or from 2 to 6 carbon atoms and from 1 to 3 double bonds. Exemplary "alkenyl" groups include vinyl, 2-propenyl, 1-but-3-enyl, crotyl, 2-(butadienyl), 2,4-pentadienyl, 3-(1,4-pentadienyl), 2-isopentenyl, 1-pent-3-enyl, 1-hex-5-enyl and the like.

The term "alkynyl" by itself or as part of another substituent refers to a straight or branched chain, unsaturated or polyunsaturated hydrocarbon radical having from 2 to 12 carbon atoms and at least one triple bond. A typical "alkynyl" group has from 2 to 10 carbon atoms and at least one triple bond. Preferred "alkynyl" groups have from 2 to 6 carbon atoms and at least one triple bond. Exemplary "alkynyl" groups include prop-1-ynyl, prop-2-ynyl (i.e., propargyl), ethynyl and 3-butynyl.

The term "cycloalkyl" by itself or in combination with other terms, represents a saturated carbocyclic radical having from 3 to 8 carbon atoms, with those groups having from 3 to 6 carbon atoms (e.g., $C_3$-$C_6$cycloalkyl) being preferred. Examples of cycloalkyl include, but are not limited to, cyclopropyl, cyclobutyl, cyclopentyl, cyclohexyl, cycloheptyl, cycloheptyl and the like. The term "cycloalkyl" also includes bridged, polycyclic (e.g., bicyclic) structures, such as norbornyl, adamantyl and bicyclo[2.2.1]heptyl. The "cycloalkyl" group can be fused to at least one (e.g., 1 to 3) other rings selected from aromatic (e.g., phenyl), heteroaromatic (e.g., pyridyl) or non-aromatic (e.g., heterocyclic) rings. When the "cycloalkyl" group is fused to an aryl, heteroaryl or heterocyclic ring, then the "cycloalkyl" portion of the fused ring system is attached to the core/remainder of the molecule.

By "oxo" is meant the group =O.

By "halogen" in the present invention is meant fluorine, bromine, chlorine, and/or iodine.

By "haloalkyl" is meant an alkyl radical having the meaning as defined above wherein one or more hydrogens are replaced by a halogen. Examples of such haloalkyls include chloromethyl, 1-bromoethyl, fluoromethyl, difluoromethyl, trifluoromethyl, 1,1,1-trifluoroethyl and the like.

The term "heteroaryl" or "heteroaromatic" refers to a polyunsaturated, 5-, 6- or 7-membered aromatic moiety containing at least one heteroatom (e.g., 1 to 5 heteroatoms, and preferably 1-3 heteroatoms) selected from N, O, S, Si and B (preferably N, O and S), wherein the nitrogen and sulfur atoms are optionally oxidized, and the nitrogen atom(s) are optionally quaternized. The "heteroaryl" group can be a single ring or be fused to other aryl, heteroaryl, cycloalkyl or heterocycloalkyl rings (e.g., from 1 to 3 other rings). When the "heteroaryl" group includes a fused aryl, cycloalkyl or heterocycloalkyl ring, then the "heteroaryl" group is attached to the core/remainder of the molecule via the heteroaryl ring. A heteroaryl group can be attached to the remainder of the molecule through a carbon- or heteroatom. Non-limiting examples of heteroaryl groups include pyridyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridyl, benzotetrahydrofuranyl, benzotetrahydrothienyl, purinyl, benzodioxolyl, triazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include imidazolyl, pyrazolyl, thiadiazolyl, triazolyl, isoxazolyl, isothiazolyl, imidazolyl, thiazolyl, oxadiazolyl, and pyridyl. Other exemplary heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, pyridin-4-yl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

The term "heterocycloalkyl", "heterocyclic", "heterocycle" or "heterocyclyl", by itself or in combination with other terms, represents is a carbocyclic, non-aromatic ring (e.g., 3- to 8-membered ring and preferably 4-, 5-, 6- or 7-membered ring) containing at least one and up to 5 heteroatoms (e.g., from 1 to 4 heteroatoms selected from nitrogen, oxygen and sulfur) or a fused ring system of 4- to 8-membered rings, containing at least one and up to 10 heteroatoms (e.g., from 1 to 5 heteroatoms selected from nitrogen, oxygen and sulfur) in stable combinations known to those of skill in the art. The "heterocyclic" group may be fused to one or more aryl, heteroaryl or cycloalkyl rings. In such fused ring systems, the "heterocyclic" group is attached to the core/remainder of the molecule via the saturated, heterocyclic ring. A heteroatom can occupy the position at which the heterocycle is attached to the core/remainder of the molecule. Exemplary heterocycloalkyl or heterocyclic groups of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, imidazolidinyl, tetrahydropyranyl, piperidinyl, tetrahydrofuranyl, tetrahydrothienyl, piperidinyl, homopiperidinyl, homomorpholinyl, homothiomorpholinyl, dioxanyl, dioxolanyl, dioxolan-2-onyl, dihydrodioxinyl, dioxol-2-onyl, dioxolyl, homothiomorpholinyl S,S-dioxide, oxazolidinonyl, dihydropyrazolyl, dihydropyrrolyl, dihydropyrazolyl, dihydropyridyl, dihydropyrimidinyl, dihydrofuryl, dihydropyranyl, tetrahydrothienyl S-oxide, tetrahydrothienyl S,S-dioxide, homothiomorpholinyl S-oxide, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "hydrogen" or "H" is understood to also encompass the isotopes deuterium and tritium. Hydrogen (rather than deuterium or tritium) is preferred.

The term "neurodegenerative diseases" includes any disease or condition characterized by problems with movements, such as ataxia, and conditions affecting cognitive abilities (e.g., memory) as well as conditions generally related to all types of dementia. "Neurodegenerative diseases" may be associated with impairment or loss of cognitive abilities, potential loss of cognitive abilities and/or impairment or loss of brain cells. Exemplary "neurodegenerative diseases" include Alzheimer's disease, Parkinson's disease, amyotrophic lateral sclerosis (ALS), Down syndrome, dementia, multi-infarct dementia, mild cognitive impairment (MCI), epilepsy, seizures, Huntington's disease, neurodegeneration induced by viral infection (e.g. AIDS, encephalopathies), traumatic brain injuries, as well as ischemia and stroke.

Most compounds were named using Autonom 2000 4.01.305, which is available from Beilstein Information Systems, Inc, Englewood, Colo., ChemDraw v.10.0, (available from Cambridgesoft at 100 Cambridge Park Drive, Cambridge, Mass. 02140) or ACD Name pro (e.g., version 12), which is available from Advanced Chemistry Development, Inc., at 110 Yonge Street, 14$^{th}$ floor, Toronto, Ontario, Canada M5c 1T4. Alternatively, the names were generated based on the IUPAC rules or were derived from names originally generated using the aforementioned nomenclature programs.

The compounds of this invention may contain one or more asymmetric carbon atoms, so that the compounds can exist in different stereoisomeric forms. These compounds can be, e.g., racemates, chiral non-racemic or diastereomers. In these situations, the single enantiomers, i.e., optically active forms can be obtained by asymmetric synthesis or by resolution of the racemates. Resolution of the racemates can be accomplished, e.g., by conventional methods such as crystallization in the presence of a resolving agent; chromatography, using, e.g. a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The invention also encompasses prodrugs of the compounds of Formulas 1, 2, 3 and 4.

Provided herein are also the acylated prodrugs of the compounds of Formulas 1, 2, 3 and 4. Those skilled in the art will recognize various synthetic methodologies, which may be employed to prepare non-toxic pharmaceutically acceptable addition salts and acylated prodrugs of the compounds encompassed by Formulas 1, 2, 3 and 4.

The term "acid prodrug group" denotes a moiety that is converted in vivo into an active carboxylic acid compound of Formulas 1, 2, 3 and 4. Such prodrug groups are generally known in the art and include ester forming groups, to form an ester prodrug; such as benzyloxy, di($C_1$-$C_6$)alkylaminoethyloxy, acetoxymethyl, pivaloyloxymethyl, phthalidoyl, ethoxycarbonyloxyethyl, 5-methyl-2-oxo-1,3-dioxol-4-yl methyl, and ($C_1$-$C_6$)alkoxy optionally substituted by N-morpholino and amide-forming groups such as di($C_1$-$C_6$)alkylamino. Preferred prodrug groups include $C_1$-$C_6$ alkoxy forming an ester, and O.M$_+$ where M$_+$ represents a cation to form a salt of the acid. Preferred cations include sodium, potassium, and ammonium. Other cations include magnesium and calcium. Further preferred prodrug groups include O⁻M⁺⁺ where M⁺⁺ is a divalent cation such as magnesium or calcium.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

The invention also encompasses the prodrugs of the compounds of Formulas 1, 2, 3 and 4. Those skilled in the art will recognize various synthetic methodologies that may be employed to prepare non-toxic pharmaceutically acceptable prodrugs of the compounds encompassed by Formulas 1, 2, 3, and 4. Those skilled in the art will recognize a wide variety of non-toxic pharmaceutically acceptable solvates, such as water, ethanol, mineral oil, vegetable oil, and dimethylsulfoxide.

Pharmaceutical Compositions

In one embodiment, the invention provides a pharmaceutical composition comprising at least one compound of the invention (e.g., those of Formula 1, Formula 2, Formula 3, Formula 4 or any aspects and embodiments thereof) and at least one pharmaceutically acceptable carrier. The term "pharmaceutically acceptable carrier" includes all pharmaceutically acceptable ingredients known to those of skill in the art and includes solvents, solid or liquid diluents, vehicles, adjuvants, excipients, glidants, binders, granulating agents, dispersing agents, suspending agents, wetting agents, lubricating agents, disintegrants, solubilizers, stabilizers, emulsifiers, fillers, preservatives (e.g., anti-oxidants), flavoring agents, sweetening agents, thickening agents, buffering agents, coloring agents and the like, as well as any mixtures thereof. Exemplary carriers (i.e., excipients) are described in, e.g., *Handbook of Pharmaceutical Manufacturing Formulations*, Volumes 1-6, Niazi, Sarfaraz K., Taylor & Francis Group 2005, which is incorporated herein by reference in its entirety.

In one embodiment, the invention provides a pharmaceutical composition comprising at least one compound Formulas 1-5, and aspects and embodiments of each of the above, and at least one pharmaceutically acceptable solvent, adjuvant, excipient, carrier, glidant, binder and/or disintegrant.

The compounds or compositions of the invention may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular or intrathecal injection or infusion techniques and the like. In addition, there is provided a pharmaceutical formulation comprising a compound of general Formulas 1, 2, 3, and 4 and a pharmaceutically acceptable carrier. One or more compounds of general Formulas 1, 2, 3, and 4 may be present in association with one or more non-toxic pharmaceutically acceptable carriers and/or diluents and/or adjuvants, and if desired other active ingredients. The pharmaceutical compositions containing compounds of Formulas 1, 2, 3 and 4 may be in a form suitable for oral use, e.g., as tablets, troches, lozenges, aqueous or oily suspensions, dispersible powders or granules, emulsion, hard or soft capsules or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be e.g., inert diluents, such as calcium carbonate, sodium carbonate, lactose, calcium phosphate or sodium phosphate; granulating and disintegrating agents, e.g., corn starch or alginic acid; binding agents, e.g. starch, gelatin or acacia, and lubricating agents, e.g. magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. E.g., a time delay material such as glyceryl monosterate or glyceryl distearate may be employed.

Formulations for oral use may also be presented as hard gelatin capsules, wherein the active ingredient is mixed with an inert solid diluent, e.g., calcium carbonate, calcium phosphate or kaolin or as soft gelatin capsules wherein the active ingredient is mixed with water or an oil medium, e.g. peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, e.g. sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, e.g., lecithin or condensation products of an alkylene oxide with fatty acids, e.g. polyoxyethylene stearate or condensation products of ethylene oxide with long chain aliphatic alcohols, e.g. heptadecaethyleneoxycetanol or condensation products of ethylene oxide with partial esters derived from fatty acids and a hexitol such as polyoxyethylene sorbitol monooleate or condensation products of ethylene oxide with partial esters derived from fatty acids and hexitol anhydrides, e.g. polyethylene sorbitan monooleate. The aqueous suspensions may also contain one or more preservatives, e.g. ethyl or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, e.g. arachis oil, olive oil, sesame oil or coconut oil or in a mineral oil such as liquid paraffin. The oily suspensions may contain a thickening agent, e.g. beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, e.g. sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, e.g. gum acacia or gum tragacanth, naturally-occurring phosphatides, e.g. soy bean, lecithin, and esters or partial esters derived from fatty acids and hexitol, anhydrides, e.g. sorbitan monooleate, and condensation products of the said partial esters with ethylene oxide, e.g. polyoxyethylene sorbitan monooleate. The emulsions may also contain sweetening and flavoring agents.

Syrups and elixirs may be formulated with sweetening agents, e.g. glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, e.g. as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formulas 1, 2, 3, and 4 may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formulas 1, 2, 3, and 4 may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream or as a suppository, containing the active ingredients in a total amount of, e.g., 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, e.g. at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily, dispersed phase of the cream formulations. Emulsifiers and emulsion stabilizers suitable for use in the formulation of the invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The anti-inflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

Formulations suitable for inhalation or insufflation include solutions and suspensions in pharmaceutically acceptable aqueous or organic solvents or mixtures thereof, and powders. The liquid or solid compositions may contain suitable pharmaceutically acceptable excipients as describe above. The compositions may be administered by oral or nasal respiratory route for local or systemic effect. Compositions may be nebulized by use of inert gases or vaporized, and breathed directly from the nebulizing/vaporizing device or the nebulizing device may be attached to a facemask tent or intermittent positive pressure-breathing machine.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

The disclosures in this document of all articles and references, including patents, are incorporated herein by reference in their entirety.

General Synthetic Procedures

The starting materials and various intermediates may be obtained from commercial sources, prepared from commercially available compounds, and/or prepared using known synthetic methods.

The compounds of the invention can be prepared using methods known in the art of organic synthesis. E.g., the compounds of the invention, as well as all intermediates, can be synthesized by known processes using either solution or solid phase techniques, as shown below. Representative procedures for preparing compounds of the invention are outlined in the following schemes.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. E.g., numerous protecting groups are described in T. W. Greene and G. M. Wuts, Protecting Groups in Organic Synthesis, Second Edition, Wiley, New York, 1991, and references cited therein.

Scheme 1

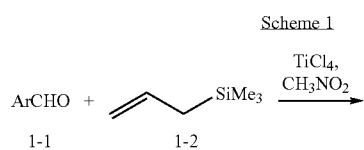

In the above scheme, the A-ring is defined as described above, R is an amino protecting group, and Ar is an aryl group.

One method for obtaining compounds of Formula 1 may be to couple aldehyde 1-1 with allylsilane 1-2 in the presence of titanium tetrachloride to afford the double allylation product, 1-3. Ring-closing metathesis of 1-3 may afford cyclopentene 1-4 (see: Durand, A-C; et al. *Synth. Commun.* 2005, 35(13), 1825). Treatment of 1-4 with OsO$_4$/NMO may afford diol 1-5. Oxidative cleavage of the diol may afford dialdehyde 1-6. Mannich condensation of 1-6 with acetone-1,3-dicarboxylic acid (1-7) and an amine may afford bicyclic ketone 1-8 (see: Mach, R. H.; et al. *J. Med. Chem.* 1993, 36(23), 3707). Conversion of 1-8 to 1-9 may be effected by using conditions familiar to one of ordinary skill in the art and the conditions may vary depending, on the nature of R. Sulfonylation of 1-9 with a sulfonylchloride of formula A-SO$_2$Cl, wherein A is as defined above, in the presence of a base may give compound 1-10. Treatment of 1-10 with an acylating agent such as DMF-DMA followed by cyclization with hydrazine may give compounds of formula 1-11.

Scheme 2

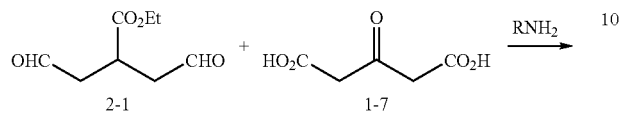

2-1   1-7

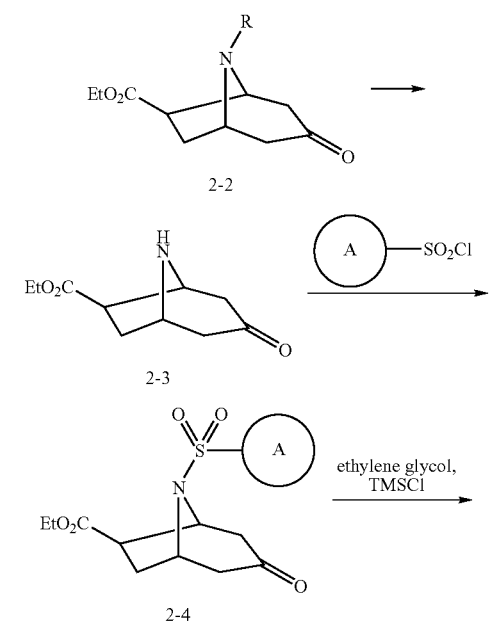

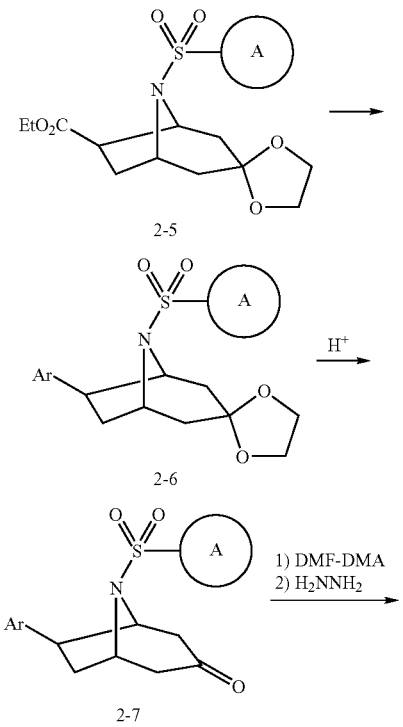

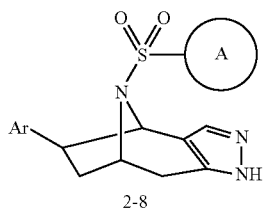

2-8

In the above scheme, the A-ring is defined as described above and R is a protecting group, and Ar is an aryl group.

Another method for obtaining compounds of Formula 1 is to prepare an azabicylo[3.2.1]nonane containing an alkoxycarbonyl group that may be elaborated to a heteroaromatic group as shown in the scheme above. Mannich condensation of dialdehyde 2-1 with acetonedicarboxylic acid (1-7) and an amine may afford bicyclic ketone 2-2. Conversion of 2-2 to 2-3 may be effected by using conditions familiar to one of ordinary skill in the art and the conditions may vary depending on the nature of R. Sulfonylation of 2-3 with a sulfonylchloride of formula A-SO$_2$Cl, wherein A is as defined above, in the presence of a base may give compound 2-4. Protection of the ketone may be accomplished using ethylene glycol in the presence of a Lewis acid to give 2-5. Conversion of the alkoxycarbonyl group to a heteroaryl ring may be accomplished by numerous methods familiar to one skilled in the art (see: Gupta, R. R.; Kumar, M.; Gupta, V. *Heterocyclic Chemistry* Vol. I-Vol. III, Springer-Verlag: Berlin, 1999) to give compound 2-6. Deprotection of the ketone followed by treatment with an acylating agent such as DMF-DMA and cyclization with hydrazine may give compounds of formula 2-8.

Scheme 3

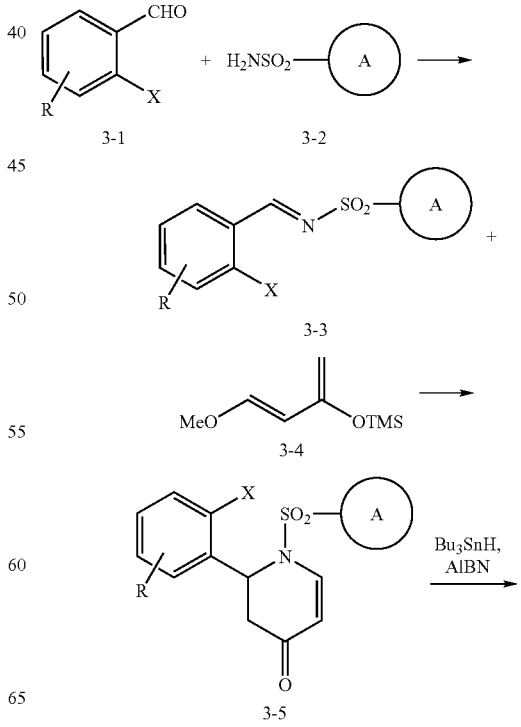

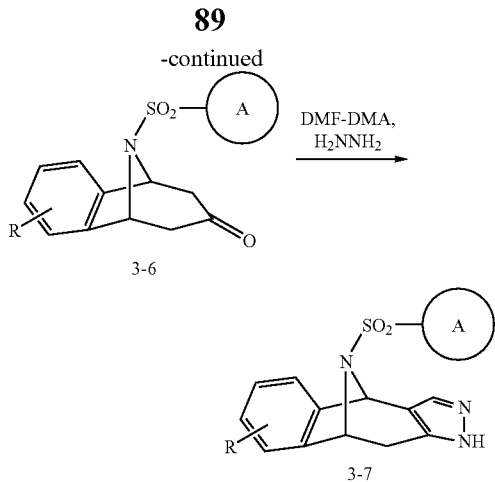

In the above scheme, the A-ring is defined as described above and R equivalent to $R_{30}$, $R_{35}$, $R_{40}$ and/or $R_{45}$, and X is a halogen.

One method for obtaining compounds of the invention is to couple a 2-halobenzaldehyde such as 3-1 with sulfonamide 3-2 to afford sulfonimine 3-3 (see e.g.: Castellano, S.; et al. *J. Am. Chem. Soc.* 2007, 129(18), 5843). Cycloaddition of 3-3 with a diene such as 3-4 may form dihydropyridinone 3-5. Radical cyclization of 3-5 with a reagent such as $Bu_3SnH$/AIBN may give nortropanone 3-6. Treatment of 3-6 with an acylating agent such as DMF-DMA followed by cyclization with hydrazine may give compounds of formula 3-7.

Certain compounds of this invention are prepared from other compounds of this invention via known reactions and functional group transformations. Examples of such transformations are ester hydrolysis, amide formation, and reductive alkylation; with examples of these are described in the preparations below. Starting materials are obtained from commercial sources or prepared by known methods as described in the examples below.

Methods

Method of Treatment

In one embodiment, provided herein is a method of treating a neurodegenerative disease comprising administering to a mammalian subject (e.g., a human subject) in need thereof a pharmaceutically effective amount of a compound or salt of Formulas 1, 2, 3 or 4 (or any embodiment thereof) or a pharmaceutical composition comprising at least one compound of Formulas 1, 2, 3 or 4 (or any embodiment thereof). In one example, the neurodegenerative disease is a member selected from Alzheimer's Disease, diffuse Lewy body type of Alzheimer's disease, Parkinson's disease, Down syndrome, dementia, mild cognitive impairment (MCI), amyotrophic lateral sclerosis (ALS), traumatic brain injuries, cerebral ischemic brain damage, ischemic or hemorrhaging stroke, hereditary cerebral hemorrhage with amyloidosis of the dutch-type and cerebral amyloid angiopathy. In a particular example, the neurodegenerative disease is Alzheimer's disease or diffuse Lewy body type of Alzheimer's disease. Thus, in one example, the invention provides a method of treating Alzheimer's disease or diffuse Lewy body type of Alzheimer's disease comprising administering a therapeutically effective amount of a compound or salt of Formulas 1, 2, 3 or 4 to a patient in need of such treatment.

In another embodiment, the invention provides a method of treating a disease selected from epilepsy, seizures, Hunington's disease, multiple sclerosis, cancer, age-related macular degeneration, diabetic retinopathy and retinal neurodegeneration related to glaucoma or ocular trauma, the method comprising administering to a mammalian subject (e.g., a human subject) in need thereof a pharmaceutically effective amount of a compound or salt of Formulas 1, 2, 3 or 4 (or any embodiment thereof) or a pharmaceutical composition comprising at least one compound of Formulas 1, 2, 3 or 4 (or any embodiment thereof). In a particular example, the invention provides a method of treating cancer selected from medulloblastoma (e.g., with high levels of the Notch2 gene), colorectal cancers (treated with compounds of the invention alone or in conjunction with taxanes), lung cancers, acute lymphoblastic leukemia and other hematologic cancers, Kaposi's sarcoma, breast cancer and melanoma, the method comprising administering to a mammalian subject (e.g., a human subject) in need thereof a pharmaceutically effective amount of a compound or salt of Formulas 1, 2, 3 or 4 (or any embodiment thereof) or a pharmaceutical composition comprising at least one compound of Formulas 1, 2, 3 or 4 (or any embodiment thereof).

The invention further provides a method of treating a disease state in a cell, a group of cells (e.g. mammalian tissue) or an organism (e.g., human), comprising: administering a compound and/or salts of Formulas 1, 2, 3, and/or 4, to the cell, group of cells or organism, wherein the disease is selected from the group consisting of cancer, intraocular disorders (e.g. age related macular degeneration), protein deposition-related diseases, Down's syndrome, Hereditary Cerebral Hemorrhage with Amyloidosis of the Dutch-Type, cerebral amyloid angiopathy, Parkinson's disease, progressive supranuclear palsy, dementia associated with cortical basal degeneration, and diffuse Lewy body type of Alzheimer's disease.

Still further, the invention provides a method of inhibiting angiogenesis in a mammalian tissue or an organism (e.g., human), comprising administering a pharmaceutically effective amount of a compound of the invention or a pharmaceutically acceptable salt thereof, to the tissue or the organism.

Further still, provided herein is a method of inhibiting angiogenesis in a mammalian tissue or organism, comprising administering a pharmaceutically effective amount of a compound of Formulas 1, 2, 3, and/or 4 or pharmaceutically acceptable salt(s) thereof, to the tissue or the organism, wherein the compound (or pharmaceutical composition) is administered to prevent, treat or cure a condition treatable by inhibiting angiogenesis.

In Vitro Methods

In one embodiment, the compounds and compositions of the invention can be used in an in vitro assay measuring gamma-secretase activity. In one example, the gamma-secretase activity is measured by detecting cleavage of a gamma-secretase substrate (e.g., APP or Notch). In another example, the compounds and compositions of the invention can be used in an in vitro assay for identifying candidate compounds that are capable of inhibiting gamma-secretase activity.

The invention also provides a method for screening for a substance which initiates or increases angiogenesis, comprising: measuring an activity of a gamma-secretase pathway in the presence of a candidate compound in a suitable model; measuring an activity of a gamma-secretase pathway in the absence of a candidate compound; and comparing said activity in the presence of a candidate compound with said activity in the absence of the candidate compound, wherein a change in activity indicates that said candidate initiates or increases angiogenesis.

EXAMPLES

General

Reagents and solvents obtained from commercial suppliers were used without further purification unless otherwise stated. Thin layer chromatography was performed on percolated 0.25 mm silica gel plates (E. Merck, silica gel 60, F254). Visualization was achieved using UV illumination or staining with phosphomolybdic acid, ninhydrin or other common staining reagents. Flash chromatography was performed using either a Biotage Flash 40 system and prepacked silica gel columns or hand packed columns (E. Merck silica gel 60, 230-400 mesh). Preparatory HPLC was performed on a Varian Prepstar high performance liquid chromatograph. $^1$H NMR spectra were recorded on either a Varian Gemini 300 MHz spectrometer or a Bruker Avance 300 MHz spectrometer. Chemical shifts are reported in ppm (δ) and were calibrated using the undeuterated solvent resonance as internal standard. Mass spectra were recorded on an Agilent series 1100 mass spectrometer connected to an Agilent series 1100 HPLC.

Example 1

Synthesis of 9-benzyl-7-oxo-9-aza-bicyclo[3.3.1]nonane-3-carboxylic acid ethyl ester (3)

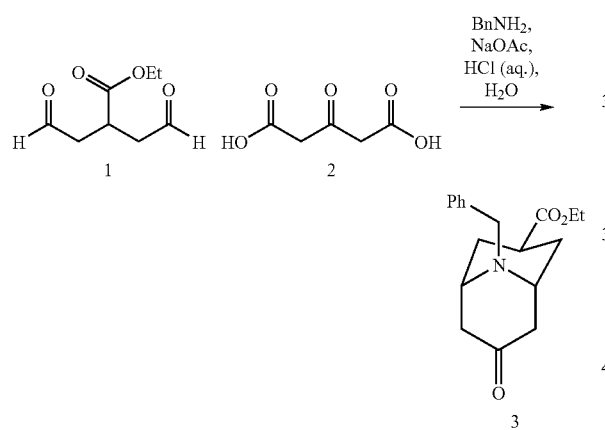

Acetone-1,3-dicarboxylic acid (2) (8.81 g, 60.36 mmol) and sodium acetate (5.04 g, 61.5 mmol) were added to a solution of 4-oxo-2-(2-oxo-ethyl)-butyric acid ethyl ester (1) (European Patent EP 0330788A1) (10.3 g, 60.36 mmol) in H$_2$O (75 mL). Benzylamine (6.59 mL, 60.36 mmol) was dissolved in aqueous HCl (3 N, 41 mL) and was subsequently added to the stirring solution of the dialdehyde and the dicarboxylic acid over a 15 minute period. The reaction mixture was stirred for 3 days at room temperature after which the pH was adjusted to 8 by the addition of potassium carbonate. The resulting solution was extracted with CH$_2$Cl$_2$ (4×50 mL), the organic extracts dried (Na$_2$SO$_4$), filtered and concentrated under vacuum. The resulting residue was purified by silica gel chromatography, (eluant hexane/EtOAc 9/1 to 1/1, v/v) to give 7.43 g (40%) of 9-benzyl-7-oxo-9-aza-bicyclo[3.3.1]nonane-3-carboxylic acid ethyl ester (3) as a brown oil. Retention time (min)=0.963, method [1], MS (ESI) 302.2 (M+H); $^1$H NMR (300 MHz, CDCl$_3$) δ 7.43-7.10 (m, 5H), 4.10 (q, J=7.1 Hz, 2H), 3.91 (s, 2H), 3.41-3.38 (m, 2H), 2.74 (dd, J=16.5, 6.6 Hz, 2H), 2.61-2.48 (m, 1H), 2.30 (d, J=16.5 Hz, 2H), 2.08 (dt, J=3.8 Hz, J=13.2 Hz, 2H), 1.81-1.72 (m, 2H), 1.22 (t, J=7.1 Hz, 3H).

Example 2

Synthesis of 7-oxo-9-aza-bicyclo[3.3.1]nonane-3-carboxylic acid ethyl ester (4)

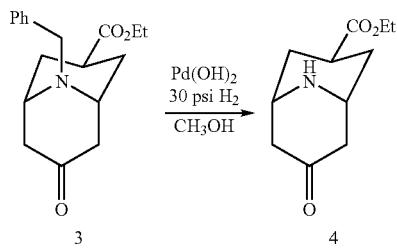

9-Benzyl-7-oxo-9-aza-bicyclo[3.3.1]nonane-3-carboxylic acid ethyl ester (3) (11.1 g, 36.8 mmol) was dissolved in MeOH (30 mL) and added to a suspension of palladium hydroxide (1 g) in MeOH (10 mL) in a Parr bottle. The Parr bottle was filled with hydrogen (30 psi) and evacuated three times. The Parr bottle was refilled with hydrogen (30 psi) and shook for 12 h. The suspension was filtered through Celite and concentrated under vacuum to give 7.81 g (quantitative yield) of 7-oxo-9-aza-bicyclo[3.3.1]nonane-3-carboxylic acid ethyl ester as a yellow oil. Retention time (min)=0.369, method [1], MS (ESI) 212.1 (M+H).

Example 3

Synthesis of 9-(4-chloro-benzenesulfonyl)-7-oxo-9-aza-bicyclo[3.3.1]nonane-3-carboxylic acid ethyl ester (6)

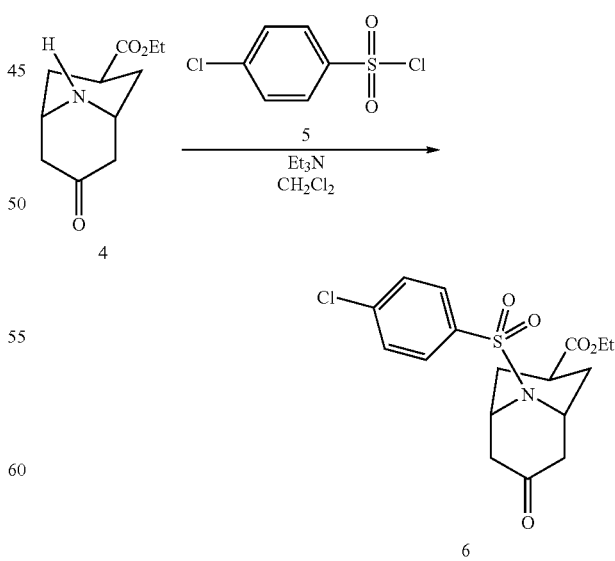

7-Oxo-9-aza-bicyclo[3.3.1]nonane-3-carboxylic acid ethyl ester (4) (5.91 g, 27.9 mmol) was dissolved in CH$_2$Cl$_2$ (60 mL). Et₃N (7.76 mL, 55.9 mmol) and 4-chlorobenzenesulfonyl chloride (5) (7.08 g, 33.6 mmol) were added and the reaction mixture was stirred at room temperature for 2 h. The reaction mixture was diluted with CH₂Cl₂ (50 mL) and washed with saturated NaHCO₃ (50 mL). The aqueous phase was separated and extracted once with CH₂Cl₂ (50 mL). The combined organic phases were then dried (Na₂SO₄), filtered, concentrated under vacuum and the residue was purified on a silica gel column (eluant hexane/EtOAc, 9/1 to 1/1) to give 9.52 g (88%) of 9-(4-chloro-benzenesulfonyl)-7-oxo-9-aza-bicyclo[3.3.1]nonane-3-carboxylic acid ethyl ester (6). Retention time (min)=2.100, method [1], MS (ESI) 408.1 (M+Na); $^1$H NMR (CDCl₃) δ 7.81 (d, J=8.2 Hz, 2H), 7.51 (d, J=8.2 Hz, 2H), 4.61-4.57 (m, 2H), 4.09 (q, J=7.1 Hz, 2H), 2.80 (dd, J=17.0, 7.1 Hz, 2H), 2.67-2.51 (m, 1H), 2.41 (d, J=16.4 Hz, 2H), 1.99-1.90 (m, 2H), 1.80 (dt, J=13.2, 4.4 Hz, 2H), 1.20 (t, J=7.1 Hz, 3H).

Example 4

Synthesis of 9-(4-chloro-benzenesulfonyl)-6-hydroxymethylene-7-oxo-9-aza-bicyclo[3.3.1]nonane-3-carboxylic acid ethyl ester (7)

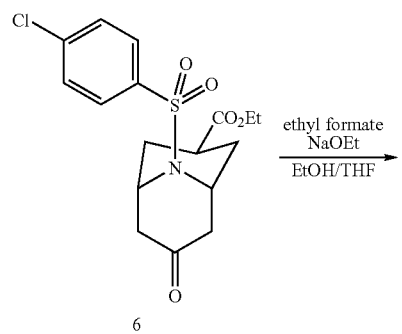

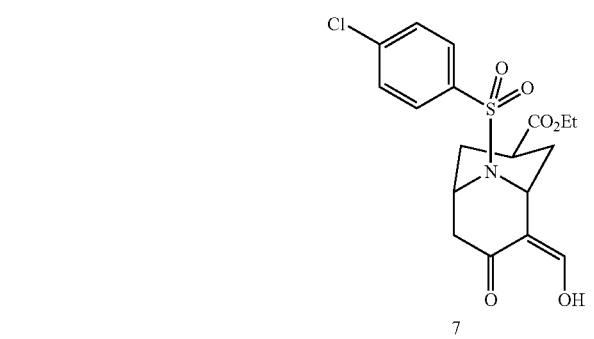

9-(4-Chloro-benzenesulfonyl)-7-oxo-9-aza-bicyclo[3.3.1]nonane-3-carboxylic acid ethyl ester (6) (2.49 g, 6.45 mmol) was dissolved in THF/ethanol (14 mL, 1/1, v/v). Ethyl formate (5.19 mL, 64.53 mmol) was added followed by sodium ethoxide (6.2 mL of 21% solution in ethanol). The resulting mixture was heated to 60° C. for 30 minutes after which the solution was cooled to room temperature and quenched by the addition of saturated aqueous NH₄Cl (10 mL). The resulting mixture was extracted with EtOAc (2×20 mL) and the combined organic phases were dried (Na₂SO₄); filtered and concentrated under vacuum to yield 2.51 g (94%) of 9-(4-chloro-benzenesulfonyl)-6-hydroxymethylene-7-oxo-9-aza-bicyclo [3.3.1]nonane-3-carboxylic acid ethyl ester (7) as a yellow oil. Retention time (min)=2.017, method [1], MS (ESI) 414.0 (M+H).

Example 5

Synthesis of 12-(4-chloro-benzenesulfonyl)-4,5,12-triaza-tricyclo[6.3.1.0₂,₆]dodeca-2(6),3-diene-10-carboxylic acid ethyl ester (8)

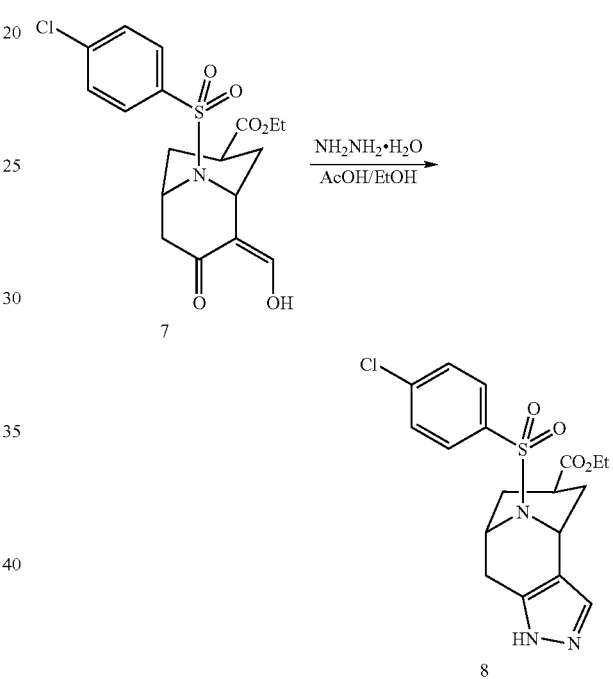

To a solution of 9-(4-chloro-benzenesulfonyl)-6-hydroxymethylene-7-oxo-9-aza-bicyclo[3.3.1]nonane-3-carboxylic acid ethyl ester (7) (2.48 g, 5.99 mmol) in ethanol (10 mL) was added glacial acetic acid (0.2 mL) followed by hydrazine monohydrate (2.9 mL, 59.9 mmol). The reaction mixture was stirred at room temperature for 1 h after which saturated NaHCO₃ (10 mL) was added. The resulting solution was extracted with EtOAc (3×20 mL); the organic extracts were combined, dried (Na₂SO₄), filtered, concentrated and purified by silica gel column chromatography (eluant hexane/EtOAc, 9/1 to 1/1) and preparative HPLC to give 12-(4-chloro-benzenesulfonyl)-4,5,12-triaza-tricyclo[6.3.1.0₂,₆] dodeca-2(6),3-diene-10-carboxylic acid ethyl ester (8) as a white solid. Retention time (min)=1.739, method [1], MS (ESI) 410.1 (M+H); $^1$H NMR (CDCl₃) δ 7.66 (d, J=8.2 Hz, 2H), 7.51 (s, 1H), 7.38 (d, J=8.2 Hz, 2H), 5.37 (bs, 1H), 4.61-4.55 (m, 1H), 4.09 (q, J=7.1 Hz, 2H), 3.04 (dd, J=17.6, 7.1 Hz, 1H), 2.67 (d, J=17.6 Hz, 1H), 2.48-2.31 (m, 1H), 2.11-1.91 (m, 4H), 1.20 (t, J=7.1 Hz, 3H).

Example 6

Synthesis of 12-(4-Chloro-benzenesulfonyl)-4,5,12-triaza-tricyclo[6.3.1.0$_{2,6}$]dodeca-2(6),3-diene-10-carboxylic acid (9)

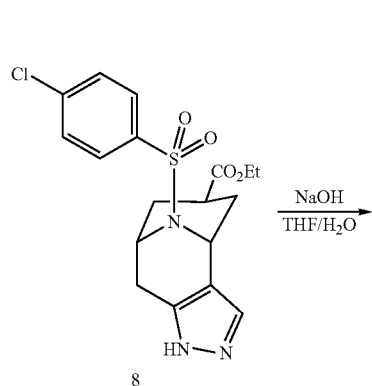

Example 7

[12-(4-Chloro-benzenesulfonyl)-4,5,12-triaza-tricyclo[6.3.1.0$_{2,6}$]dodeca-2,5-dien-10-yl]-methanol (10)

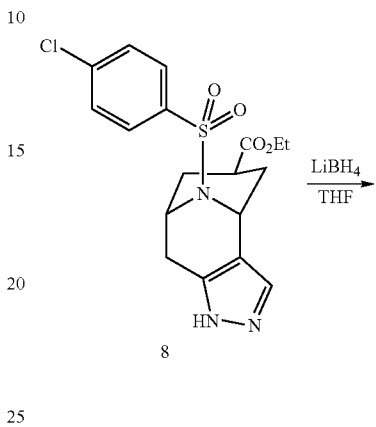

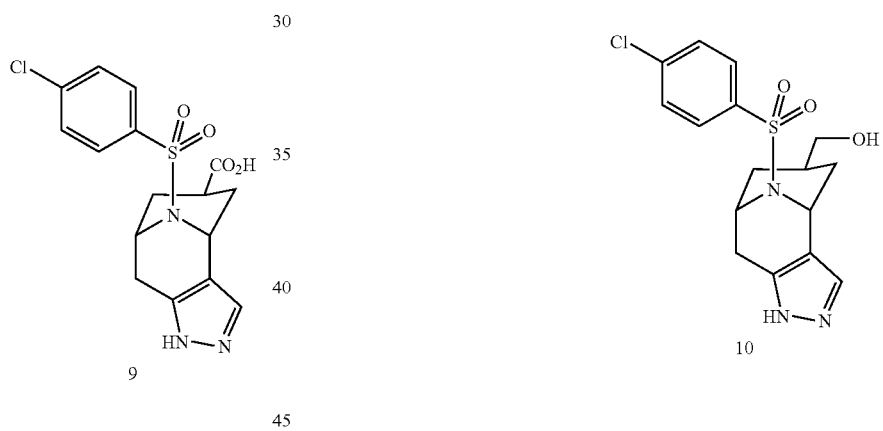

Sodium hydroxide (0.5 mL, 3 N solution) was added to a solution 12-(4-chloro-benzenesulfonyl)-4,5,12-triaza-tricyclo[6.3.1.0$_{2,6}$]dodeca-2(6),3-diene-10-carboxylic acid ethyl ester (8) (321 mg, 0.783 mmol) in THF (2 mL). The resulting mixture was stirred at room temperature for 4 h. The reaction mixture was extracted with EtOAc (2×5 mL) and the combined organic phases were dried (Na$_2$SO$_4$), filtered, concentrated and purified by preparative HPLC to give 12-(4-chloro-benzenesulfonyl)-4,5,12-triaza-tricyclo[6.3.1.0$_{2,6}$]dodeca-2(6),3-diene-10-carboxylic acid (9) as a white solid. Retention time (min)=1.316, method [1], MS (ESI) 382.0 (M+H); $^1$H NMR (CDCl$_3$) δ 7.56 (d, J=8.7 Hz, 2H), 7.30-7.22 (m, 3H), 5.30-5.25 (m, 1H), 4.54-4.45 (m, 1H), 2.80 (dd, J=17.0, J=7.7 Hz, 1H), 2.50 (d, J=17.0 Hz, 1H), 2.42-2.30 (m, 1H), 2.24-1.85 (m, 4H).

Lithium borohydride (17 mg, 0.80 mmol) was added to a solution of 12-(4-chloro-benzenesulfonyl)-4,5,12-triaza-tricyclo[6.3.1.0$_{2,6}$]dodeca-2(6),3-diene-10-carboxylic acid ethyl ester (8) (328 mg, 0.80 mmol) in THF (3 mL). The resulting solution was stirred at room temperature for 18 h then heated to 60° C. for 2 h. The reaction was quenched by the addition of water (5 mL) and the resulting mixture was extracted with EtOAc (3×5 mL). The combined organic phases were dried (Na$_2$SO$_4$), filtered, concentrated and purified by silica gel column chromatography (eluant hexane/EtOAc, 9/1 to 1/1) and preparative HPLC to give [12-(4-chloro-benzenesulfonyl)-4,5,12-triaza-tricyclo[6.3.1.0$_{2,6}$]dodeca-2,5-dien-10-yl]-methanol (10) as a white solid. Retention time (min)=1.242, method [1], MS (ESI) 368.0 (M+H); $^1$H NMR (CDCl$_3$) δ 7.73 (d, J=8.2 Hz, 2H), 7.58 (s, 1H), 7.38 (d, J=8.2 Hz, 2H), 5.33 (s, 1H), 4.48 (d, J=7.1 Hz, 1H), 3.41 (d, J=2.7 Hz, 2H), 3.08 (dd, J=17.6, 7.7 Hz, 1H), 2.62 (d, J=17.6 Hz, 1H), 1.81-1.54 (m, 5H).

Example 8

Synthesis of (11-{[4-(trifluoromethyl)phenyl]sulfonyl}-1,4,9,10-tetrahydro-4,9-epiminobenzo[4,5]cyclohepta[1,2-c]pyrazole) (18)

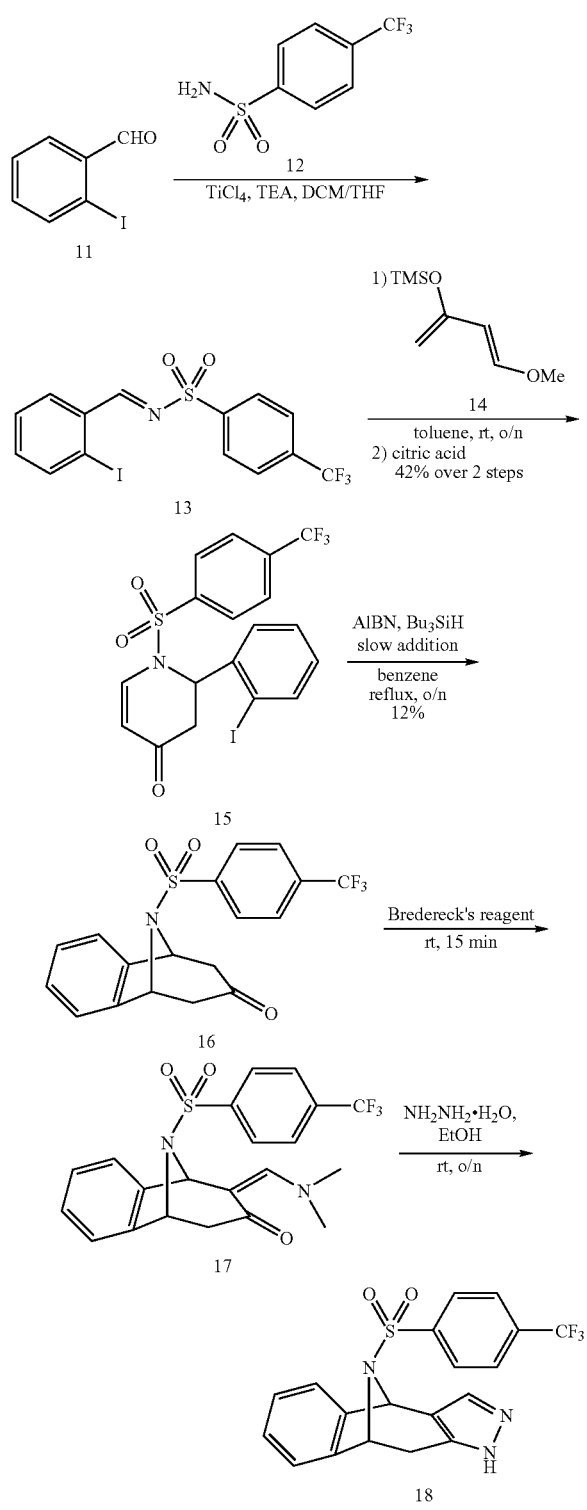

8.1. (E)-N-(2-Iodobenzylidene)-4-(trifluoromethyl) benzene-sulfonamide (13)

To the mixture of 2-iodobenzaldehyde (11) (12.3 g, 53 mmol) and 4-trifluoromethylbenzenesulfonamide (12) (12.15 g, 54 mmol) in CH$_2$Cl$_2$ (110 mL) and THF (27 mL) was added triethylamine (22.5 mL) and titanium(IV) chloride (3 mL) at 0° C. After stirring at 0° C. for 2 h, the solid was separated via Celite filtration. The filtrate was concentrated under reduced pressure to dryness, triturated with toluene to give 27 g of a yellow solid as the crude product (3) which was used without further purification.

8.2. 2-(2-Iodophenyl)-1-(4-(trifluoromethyl)phenylsulfonyl)-2,3-dihydropyridin-4(1H)-one (15)

To the suspension of 27 g of (3) from step 1 in toluene (250 mL) was added Danishefsky's diene (14) (10 g) at room temperature. The suspension was stirred at room temperature (became clear in a few minutes) for 2 hours. 2 N citric acid (40 mL) was added and the mixture was stirred at room temperature overnight. The organic layer was separated and the aqueous layer was extracted with EtOAc (2×50 mL). The organic layers were combined and concentrated under reduced pressure to give a reddish oil. After flash chromatography on silica gel, a sticky yellow gel was isolated as the product (15) (11g, 42% in two steps). $^1$H NMR (CDCl$_3$) δ 7.98 (d, J=8.1 Hz, 1H), 7.77-7.71 (m, 3H), 7.56 (d, J=8.7 Hz, 2H), 6.84-6.77 (m, 3H), 5.81 (d, J=8.1 Hz, 1H), 5.47 (d, J=8.1 Hz, 1H), 3.04 (dd, J=8.1, 16.5 Hz, 1H), 2.61 (d, J=16.5 Hz, 1H).

8.3. (10-{[4-(Trifluoromethyl)phenyl]sulfonyl}-5,6,8,9-tetrahydro-7H-5,9-epiminobenzo[7]annulen-7-one) (16)

To a solution of compound 15 (1.65 g, 3.25 mmol) in benzene (300 mL) at 80° C. was added a solution of AIBN (105 mg, 20% mol) and tri(n-butyl)tin hydride (0.86 mL, 3.25 mmol) in benzene (20 mL) over a 2 hour period. The mixture was heated at reflux for 48 h. After evaporation of the solvent, the residue was purified via flash chromatography on silica gel to give a white solid as the product (16) (150 mg, 12%). $^1$H NMR (CDCl$_3$) δ 7.66 (d, J=8.4 Hz, 2H), 7.41 (d, J=8.4 Hz, 2H), 7.0-6.9 (m, 4H), 5.25 (dd, J=3.3 Hz, 2H), 3.14 (dd, J=4.5, 16.8 Hz, 2H), 2.58 (d, J=16 Hz, 2H).

8.4. (6-[(Dimethylamino)methylidene]-10-{[4-(trifluoromethyl)phenyl]sulfonyl}-5,6,8,9-tetrahydro-7H-5,9-epiminobenzo[7]annulen-7-one) (17)

Compound 16 (15 mg, 0.04 mmol) was mixed with 0.3 mL of Bredereck's reagent and the mixture was stirred at room temperature for 30 min. The reaction was quenched with water (1 mL) and extracted with EtOAc. After evaporation of the solvent, the crude product was obtained as a yellow oil and used without further purification.

8.5. (11-{[4-(Trifluoromethyl)phenyl]sulfonyl}-1,4,9,10-tetrahydro-4,9-epiminobenzo[4,5]cyclohepta[1,2-c]pyrazole) (18)

Compound 17 was dissolved in EtOH (0.5 mL) and hydrazine monohydrate (6 □L) was then added. The mixture was stirred at room temperature overnight. Solvent was removed under reduced pressure and the crude product was purified by HPLC to give a white solid as the pure product (18) (8 mg, 50% in two steps). $^1$H NMR (CDCl$_3$) δ 7.71 (d, J=8.7 Hz, 2H), 7.45

(d, J=8.7 Hz, 2H), 7.07-7.04 (m, 1H), 6.99-6.93 (m, 3H), 5.83 (s, 1H), 5.38 (d, J=5.1 Hz, 1H), 3.53 (dd, J=5.1, 16.2 Hz, 1H), 2.85 (d, J=16.2 Hz, 1H).

Example 9

Synthesis of (11-{[6-(trifluoromethyl)pyridin-3-yl]sulfonyl}-1,4,9,10-tetrahydro-4,9-epiminobenzo[4,5]cyclohepta[1,2-c]pyrazole) (21)

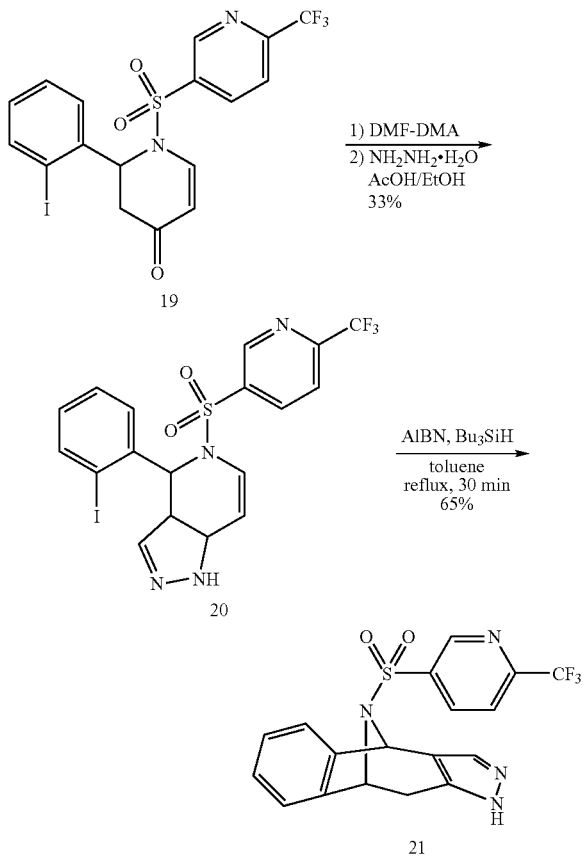

9.1. (4-(2-Iodophenyl)-5-{[6-(trifluoromethyl)pyridin-3-yl]sulfonyl}-4,5-dihydro-1H-pyrazolo[4,3-c]pyridine) (20)

Compound 19 (200 mg, 0.39 mmol), similarly prepared as described for compound 15 in Example 8 using compound 23 in place of compound 12, was mixed with DMF-DMA complex (1.7 mL) and the mixture was heated at 75° C. for 30 min. After evaporation of the excess DMF-DMA, the residue was dissolved in AcOH/EtOH (2 mL, 1:1) and hydrazine monohydrate (0.11 mL) was added. The mixture was stirred at room temperature for 2 hours and concentrated under reduced pressure to dryness. The crude product was purified by flash chromatography on silica gel to give a white solid as the pure product (20) (69 mg, 33%). $^1$H NMR (CDCl$_3$) δ 8.95 (d, J=2.4 Hz, 1H), 8.06 (dd, J=2.1, 8.1 Hz, 1H), 7.72 (d, J=8.1 Hz, 1H), 7.60 (d, J=8.1 Hz, 1H), 7.50 (s, 1H), 7.20 (dd, J=1.8, 7.8 Hz, 1H), 7.12 (d, J=8.4 Hz, 1H), 6.96 (t, J=7.8 Hz, 1H), 6.84-6.79 (m, 2H), 6.09 (d, J=8.1 Hz, 1H).

9.2. (11-{[6-(Trifluoromethyl)pyridin-3-yl]sulfonyl}-1,4,9,10-tetrahydro-4,9-epiminobenzo[4,5]cyclohepta[1,2-c]pyrazole) (21)

Compound 20 (62 mg, 0.12 mmol) was dissolved in toluene (10 mL) and treated with AIBN (8 mg) and Bu$_3$SnH (55 μL) sequentially at 120° C. The mixture was stirred at 120° C. for 30 minutes. After evaporation of the solvent, the residue was purified by flash chromatography on silica gel to give a white solid as the pure product (21) (31 mg, 65%). $^1$H NMR (CDCl$_3$) δ 8.86 (d, J=1.5 Hz, 1H), 8.01 (dd, J=1.5, 7.5 Hz, 1H-1), 7.44 (d, J=8.1 Hz, 1H), 7.35 (s, 1H), 7.09-7.07 (m, 1H), 6.97-6.85 (m, 3H), 5.86 (s, 1H), 5.38 (d, J=5.4 Hz, 1H), 3.45 (dd, J=5.4, 16.5 Hz, 1H), 2.84 (d, J=16.5 Hz, 1H).

Example 10

Synthesis of 6-(trifluoromethyl)pyridine-3-sulfonamide (23)

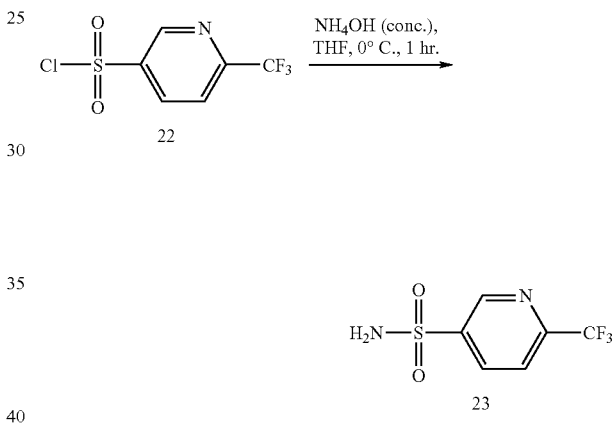

A two neck, 2 L round bottom flask, containing a magnetic stirbar and fitted with an addition funnel was charged with concentrated aqueous ammonium hydroxide (600 mL). The solution was cooled to 0° C. The sulfonyl chloride, 22, (54.4 g, 221 mmol) was dissolved in THF (300 mL) and placed in the addition funnel. The sulfonyl chloride solution was added to the cold ammonium hydroxide solution at 0° C. over 15-20 minutes. The reaction was stirred at 0° C. for 1 hr. The reaction solution was partially concentrated under vacuum with a cold water bath to provide temperature regulation of the evaporation flask during 3 hours. (Attention—the excess ammonia is evaporated under vacuum and on large scale the vapor should be trapped by bubbling the rotary evaporator exhaust through an aqueous acid solution.) Once the reaction solution volume was reduced to approximately half the starting volume, a white solid formed in the aqueous solution. The slurry was extracted with EtOAc (500 mL) and the organic solution was washed with bicarbonate solution (NaHCO$_3$ aq., 300 mL) and brine (300 mL). The organic solution was dried over MgSO$_4$, filtered through a small pad of basic alumina (200 mL), and concentrated under vacuum. The white solid was dried under vacuum over night to yield 43.9 g of compound 23 (194 mmol, 87.8% yield, m.p. 192-193° C.). $^1$H NMR (DMSO-d$_6$) δ 9.16 (d, J=1.6 Hz, 1H), 8.48 (dd, J=8.3, 1.6 Hz, 1H), 8.18 (d, J=8.3 Hz, 1H), 7.88 (s, 2H).

Example 11

Synthesis of 12-{[4-(trifluoromethyl)phenyl]sulfonyl}-4,5,10,11-tetrahydro-2H-4,10-epiminobenzo[5,6]cycloocta[1,2-c]pyrazole (31) and 12-{[4-(trifluoromethyl)phenyl]sulfonyl}-4,5,6,11-tetrahydro-2H-5,11-epiminobenzo[4,5]cycloocta[1,2-c]pyrazole (32)

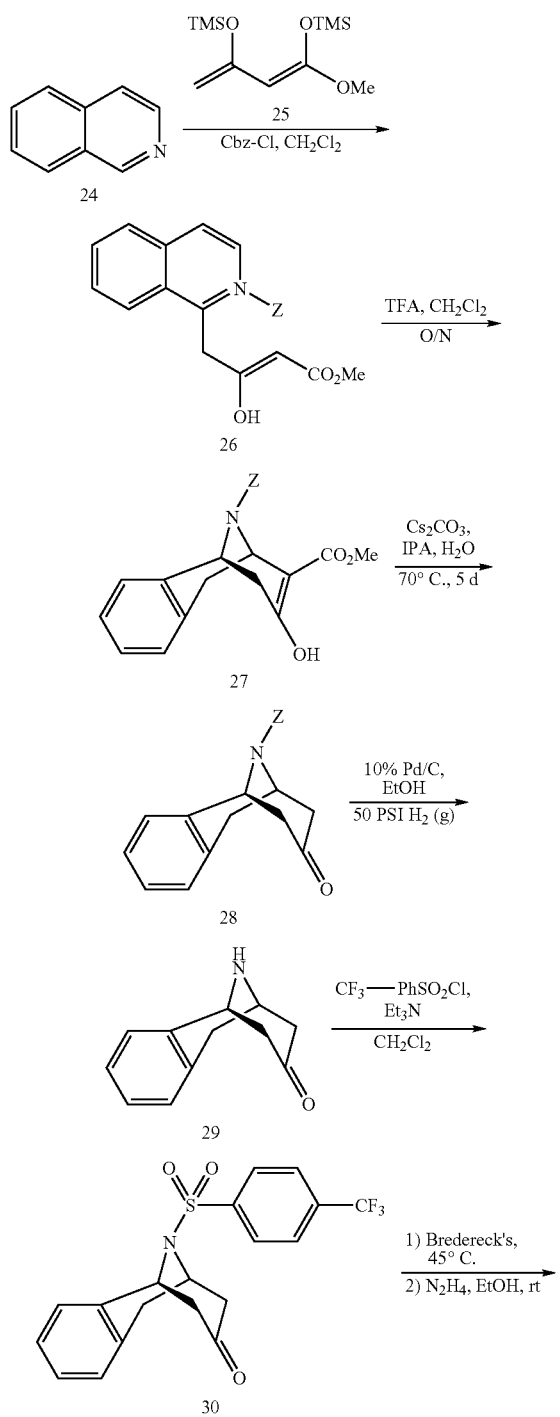

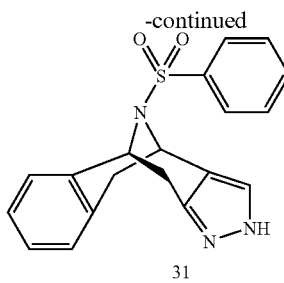

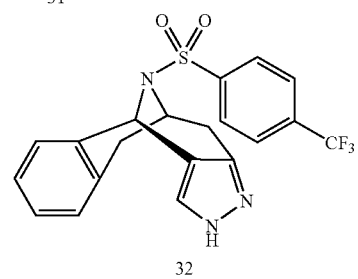

11.1. Benzyl 1-(4-methoxy-2,4-dioxobutyl)isoquinoline-2(1H)-carboxylate (26)

To the mixture of isoquinoline (24) (2.05 g, 15.9 mmol) in 150 mL of CH$_2$Cl$_2$ at 0° C. was added (Z)-4-methoxy-2,2,8,8-tetramethyl-6-methylene-3,7-dioxa-2,8-disilanon-4-ene (25) (8.29 g, 31.8 mmol), followed by benzyl chloroformate (2.7 mL, 19.1 mmol). After stirring at room temperature overnight, 100 mL of NH$_4$Cl (aq) was added to the mixture. The organic layer was separated and the aqueous layer was extracted with CH$_2$Cl$_2$ (3×100 mL). The combined organic extracts were dried over Na$_2$SO$_4$. After the desiccant was filtered off, the organic extracts were concentrated under reduced pressure to provide (26) as a yellow oil (6.73 g). $^1$H NMR indicated about a 1:2 ratio of keto:enol tautomers. This crude oil was used in the next reaction without further purification.

11.2. 11-Benzyl 8-methyl-7-hydroxy-5,6,9,10-tetrahydro-5,9-epiminobenzo[8]annulene-8,11-dicarboxylate (27)

To a mixture of ester (26) (6.73 g, 17.7 mmol) in 60 mL of CH$_2$Cl$_2$ at room temperature was added trifluoroacetic acid (2.6 mL, 35.5 mmol). This mixture was stirred at room temperature overnight. Additional trifluoroacetic acid (2.6 mL, 35.5 mmol) was added and the mixture for stirred overnight at room temperature. To this mixture were carefully added 40 mL of sat. NaHCO$_3$ (aq). After the effervescence had subsided, the layers were separated; and the aqueous layer was extracted with CH$_2$Cl$_2$ (3×30 mL). The combined organic extracts were dried over Na$_2$SO$_4$. After the desiccant was filtered off, the organic extracts were concentrated under reduced pressure to provide (27) as a yellow liquid (2.79 g). This crude liquid was used in the next reaction without further purification.

11.3. Benzyl-7-oxo-5,6,7,8,9,10-hexahydro-5,9-epiminobenzo[9]annulene-11-carboxylate (28)

To a mixture of ester (27) (2.79 mg, 7.35 mmol) in 60 mL of isopropanol and 20 mL of water was added Cs$_2$CO$_3$ (47.9 g, 147 mmol) The slurry was heated at 90° C. for 20 h. Additional Cs$_2$CO$_3$ (47.9 g, 147 mmol) was added and the mixture was stirred at 90° C. for 20 h. Additional Cs$_2$CO$_3$ (47.9 g, 147 mmol) was added and the mixture was stirred at 90° C. for another two days. The mixture was carefully quenched with 100 mL of 6 N HCl. The aqueous solution was extracted with EtOAc (3×100 mL). The combined organic extracts were washed with 10% NaCl (aq) (250 mL) and dried over Na$_2$SO$_4$. After the desiccant was filtered off, the organic extracts were concentrated under reduced pressure to provide a crude oil. After flash chromatography on silica gel, a thick light yellow oil (28) (1.13 g) was obtained.

11.4. 5,8,9,10-Tetrahydro-5,9-epiminobenzo[8]annulen-7(6H)-one (29)

To a mixture of carbamate (28) (1.13 g) in 100 mL of MeOH in a Parr bottle was added 500 mg of 10% Pd/C. This slurry was shaken under 50 psi of H$_2$ (g) at room temperature overnight. The mixture was filtered through a pad of Celite and rinsed with CH$_2$Cl$_2$ (2×100 mL). The solution was concentrated to a crude yellow oil (29) (130 mg) and used in the next reaction without further purification.

11.5. 11-{[4-(Trifluoromethyl)phenyl]sulfonyl}-5,8,9,10-tetrahydro-5,9-epiminobenzo[8]annulen-7(6H)-one (30)

To a mixture of amine (130 mg, 0.69 mmol) (29) in 7 mL of CH$_2$Cl$_2$ at room temperature was added triethylamine (0.2 mL), followed by 4-trifluoromethylbenzenesulfonyl chloride (204 mg, 0.83 mmol). This mixture was stirred at room temperature overnight. The mixture was concentrated under reduced pressure to a crude oil. After flash chromatography on silica gel, a white solid (30) (290 mg) was obtained.

11.6. 12-{[4-(Trifluoromethyl)phenyl]sulfonyl}-4,5,10,11-tetrahydro-2H-4,10-epiminobenzo[5,6]cycloocta[1,2-c]pyrazole (31) and 12-{[4-(trifluoromethyl)phenyl]sulfonyl}-4,5,6,11-tetrahydro-2H-5,11-epiminobenzo[4,5]cycloocta[1,2-c]pyrazole (32)

To ketone 30 (290 mg, 0.73 mmol) was added tert-butoxybis(dimethylamino)methane (2.56 g, 14.67 mmol). This mixture was heated at 45° C. for 1 h. The mixture was diluted with 50 mL of H$_2$O and extracted with EtOAc (3×50 mL). The combined organic extracts were dried over Na$_2$SO$_4$. After the desiccant was filtered off, the organic extracts were concentrated under reduced pressure to provide a crude oil. This crude oil was suspended in 7 mL of EtOH. To this solution was added hydrazine hydrate (73.4 mg, 1.47 mmol). This mixture was stirred at room temperature overnight. The mixture was diluted with water (50 mL) and extracted with EtOAc (3×50 mL). The combined organic extracts were washed with 10% NaCl (aq) (100 mL) and dried over Na$_2$SO$_4$. After the desiccant was filtered off, the organic extracts were concentrated under reduced pressure to provide a crude oil. After flash chromatography on silica gel, a yellow solid (31) (32.1 mg) $^1$H NMR (CDCl$_3$) δ 7.90 (d, J=8.1 Hz, 2H), 7.64 (d, J=8.2 Hz, 2H), 7.40 (s, 1H), 7.19-7.09 (m, 3H), 6.93 (d, J=7.7 Hz, 1H), 5.53 (d, J=5.3 Hz, 1H), 5.49 (d, J=5.2 Hz, 1H), 3.32 (dd, J=16.5, 6.1 Hz, 1H), 3.16 (dd, J=15.9, 5.7 Hz, 1H), 2.85 (d, J=16.3 Hz, 1H), 2.73 (d, J=16.4 Hz, 114); and a yellow solid (32) (35.8 mg) $^1$H NMR (CDCl$_3$) δ 7.62 (d, J=8.2 Hz, 2H), 7.41 (d, J=8.3 Hz, 2H), 7.33 (s, 1H), 7.15 (d, J=7.4 Hz, 1H), 7.06 (d, J=7.4 Hz, 1H), 6.95 (dt, J=1.5, 7.5 Hz, 1H), 6.59 (d, J=7.6 Hz, 1H), 6.01 (s, 1H), 4.88-4.84 (m, 1H), 3.24 (dd, J=16.1, 6.1 Hz, 1H), 3.08 (d, J=17.9, 9.6 Hz, 1H), 2.75 (dd, J=17.3, 1.1 Hz, 1H); 2.46 (d, J=17.9 Hz, 1H) were obtained.

Example 12

Synthesis of 6-(4-fluorophenyl)-12-{[4-(trifluoromethyl)phenyl]sulfonyl}-4,5,10,11-tetrahydro-2H-4,10-epiminobenzo[5,6]cycloocta[1,2-c]pyrazole (37) and 7-(4-fluorophenyl)-12-{[4-(trifluoromethyl)phenyl]sulfonyl}-4,5,6,11-tetrahydro-2H-5,11-epiminobenzo[4,5]cycloocta[1,2-c]pyrazole (38)

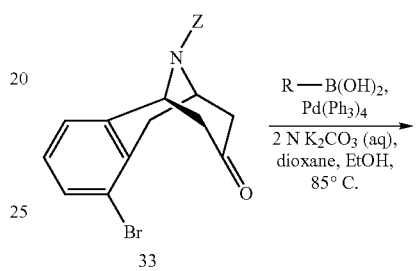

33

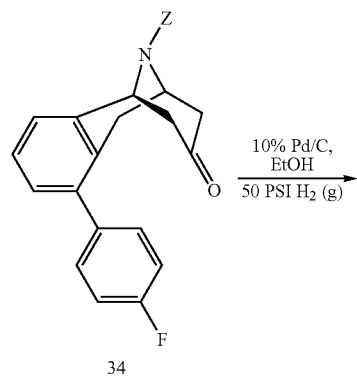

34

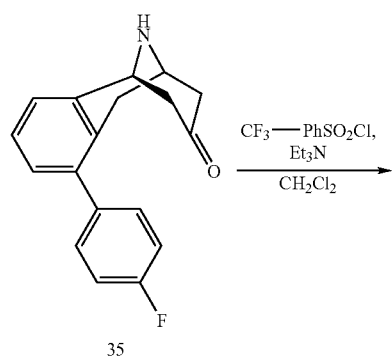

35

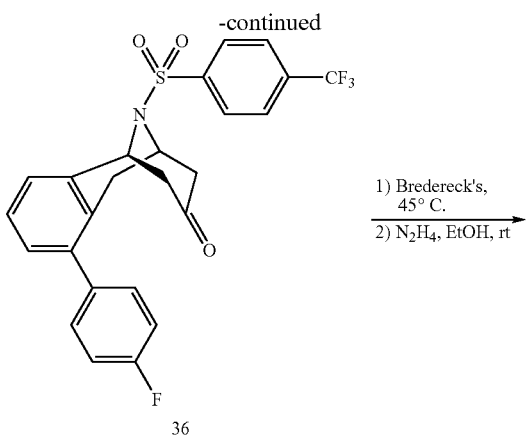

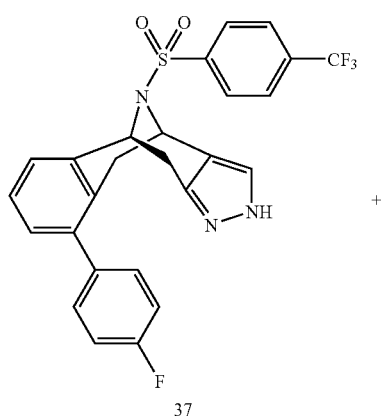

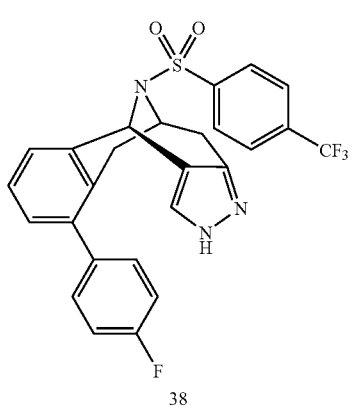

12.1 Benzyl-1-(4-fluorophenyl)-7-oxo-5,6,7,8,9,10-hexahydro-5,9-epiminobenzo[8]annulene-11-carboxylate (34)

To a mixture of ketone 33 (243 mg, 0.61 mmol), prepared as described for compound 28 in Example 11 using 5-bromoisoquinoline, in 2M $K_2CO_3$ (aq) (6 mL), dioxane (6 mL), and EtOH (1.2 mL) was added 4-fluorophenyl boronic acid (102 mg, 0.73 mmol), followed by palladium tetrakis(triphenylphosphine) (35 mg, 0.03 mmol). This mixture was stirred at 85.° C. overnight. The mixture was filtered through a pad of Celite and rinsed with EtOAc (20 mL). The solution was diluted with 30 mL of $H_2O$, and the layers were separated. The aqueous layer was extracted with EtOAc (3×50 mL). The combined organic extracts were washed with 10% NaCl (aq) (150 mL) and dried over $Na_2SO_4$. After the desiccant was filtered off, the organic extracts were concentrated under reduced pressure to provide a crude oil. After flash chromatography on silica gel, a yellow foam (34) (148 mg) was obtained. 12.2. 1-(4-Fluorophenyl)-5,8,9,10-tetrahydro-5,9-epiminobenzo[8]annulen-7(6H)-one (35)

To a mixture of carbamate (34) (144 mg) in 100 mL of MeOH in a Parr bottle was added 35 mg of 10% Pd/C. This slurry was shaken under 50 psi of $H_2$ (gas) at room temperature overnight. The mixture was filtered through a pad of Celite and rinsed with $CH_2Cl_2$ (2×100 mL). The solution was concentrated to a crude yellow oil (35) (110 mg) and used in the next reaction without further purification.

12.3. (5S)-1-(4-Fluorophenyl)-11-{[4-(trifluoromethyl)phenyl]sulfonyl}-5,8,9,10-tetrahydro-5,9-epiminobenzo[8]annulen-7(6H)-one (36)

To a mixture of crude amine (110 mg) (35) in 4 mL of $CH_2Cl_2$ at room temperature was added triethylamine (0.1 mL) followed by 4-trifluoromethylbenzenesulfonyl chloride (101 mg, 0.42 mmol). This mixture was stirred at room temperature overnight. The mixture was concentrated under reduced pressure to a crude oil. After flash chromatography on silica gel, a white waxy solid (36) (119 mg) was obtained.

12.4. 6-(4-Fluorophenyl)-12-{[4-(trifluoromethyl)phenyl]sulfonyl}-4,5,10,11-tetrahydro-2H-4,10-epiminobenzo[5,6]cycloocta[1,2-c]pyrazole (37) and 7-(4-fluorophenyl)-12-{[4-(trifluoromethyl)phenyl]sulfonyl}-4,5,6,11-tetrahydro-2H-5,11-epiminobenzo[4,5]cycloocta[1,2-c]pyrazole (38)

To ketone (119 mg, 0.24 mmol) (36) was added tert-butoxybis(dimethylamino)methane (1 mL, 4.86 mmol). This mixture was heated at 45° C. for 1 h. The mixture was diluted with 50 mL of $H_2O$ and extracted with EtOAc (3×50 mL). The combined organic extracts were dried over $Na_2SO_4$. After the desiccant was filtered off, the organic extracts were concentrated under reduced pressure to provide a crude oil. This crude oil was suspended in 2 mL of EtOH. To this solution was added hydrazine hydrate (24.3 mg, 0.49 mmol). This mixture was stirred at room temperature overnight. The mixture was diluted with water (30 mL) and extracted with EtOAc (3×30 mL). The combined organic extracts were washed with 10% NaCl (aq) (100 mL) and dried over $Na_2SO_4$. After the desiccant was filtered off, the organic extracts were concentrated under reduced pressure to provide a crude oil. After flash chromatography on silica gel, a yellow solid (37) (19.8 mg) $^1$H NMR (CDCl$_3$) δ 7.90 (d, J=8.2 Hz, 2H), 7.65 (d, J=8.2 Hz, 2H), 7.30 (s, 1H), 7.25-7.18 (m, 2H), 7.08-6.93 (m, 5H), 5.59 (d, J=5.3 Hz, 1H), 5.44 (d, J=5.5 Hz, 1H), 3.20 (dd, J=5.7, 16.0 Hz, 1H), 3.04 (dd, J=5.4, 16.3 Hz, 1H), 2.92 (d, J=16.8 Hz, 1H), 2.42 (d, J=15.7 Hz, 1H); and a yellow solid (38) (16.4 mg) $^1$H NMR (CDCl$_3$) δ 7.61 (d, J=7.9 Hz, 2H), 7.46 (d, J=8.3 Hz, 2H), 7.41 (s, 1H), 7.25 (dd, J=1.2, 7.6 Hz, 1H), 7.17 (t, J=7.4 Hz, 1H), 7.02 (t, J=8.7 Hz, 2H), 6.89 (dd, J=1.4, 7.5 Hz, 1H), 6.83-6.79 (m, 2H), 6.12 (s, 1H), 4.77-4.72 (m, 1H), 3.26 (dd, J=5.6, 15.9 Hz, 1H), 2.87-2.81 (m, 1H), 2.75 (d, J=16.9 Hz, 1H), 2.28 (d, J=18.6 Hz, 1H) were obtained.

Example 13

Synthesis of 6-cyclopropyl-12-{[6-(trifluoromethyl)pyridin-3-yl]sulfonyl}-4,5,10,11-tetrahydro-2H-4,10-epiminobenzo[5,6]cycloocta[1,2-c]pyrazole (42) and 7-cyclopropyl-12-{[6-(trifluoromethyl)pyridin-3-yl]sulfonyl}-4,5,6,11-tetrahydro-2H-5,11-epiminobenzo[4,5]cycloocta[1,2-c]pyrazole (43)

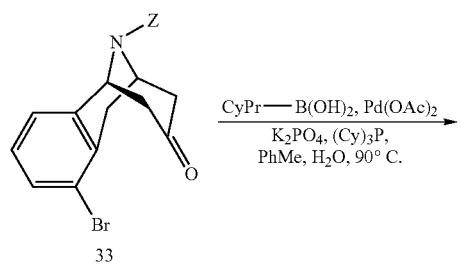

33

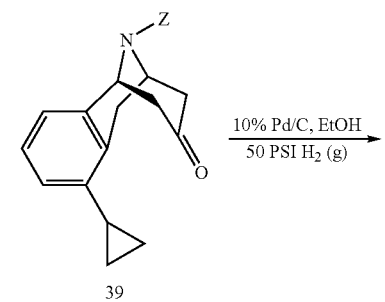

39

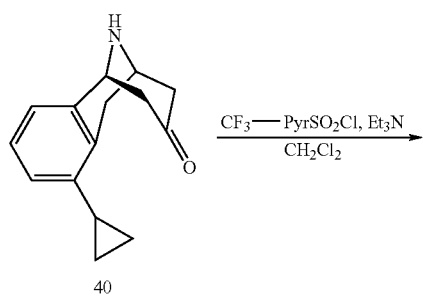

40

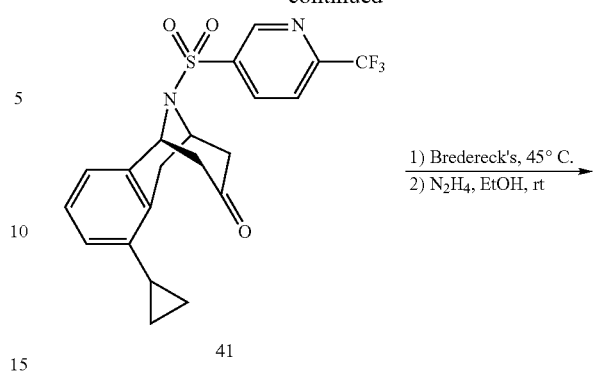

41

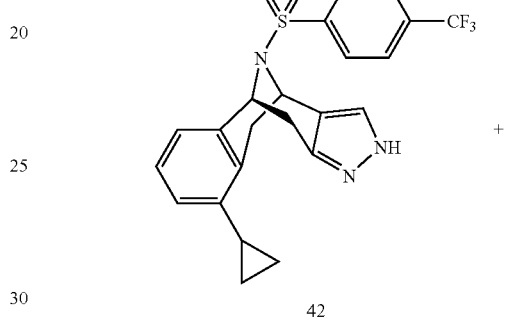

42    +

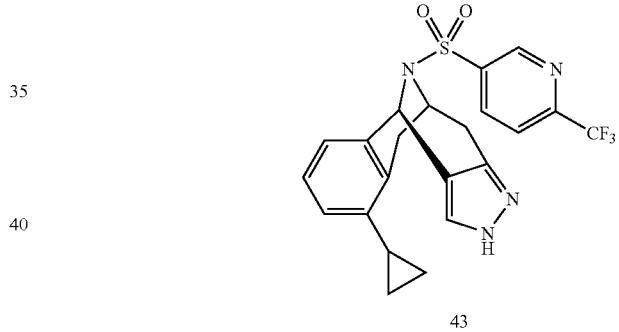

43

13.1. Benzyl 1-cyclopropyl-7-oxo-5,6,7,8,9,10-hexahydro-5,9-epiminobenzo[8]annulene-11-carboxylate (39)

To a mixture of ketone (33) (400 mg, 1 mmol) in toluene (4.5 mL), and H₂O (0.2 mL) was added cyclopropylboronic acid (112 mg, 1.3 mmol), potassium phosphate (743 mg, 3.5 mmol), tricyclohexylphosphine (28 mg, 0.1 mmol), and palladium acetate (11 mg, 0.05 mmol). This mixture was stirred at 90° C. overnight. The mixture was filtered through a pad of Celite and rinsed with EtOAc (20 mL). The solution was diluted with 30 mL of H₂O, and the layers were separated. The aqueous layer was extracted with EtOAc (3×50 mL). The combined organic extracts were washed with 10% NaCl (aq) (150 mL) and dried over Na₂SO₄. After the desiccant was filtered off, the organic extracts were concentrated under reduced pressure to provide a crude oil. After flash chromatography on silica gel, a yellow oil (39) (330 mg) was obtained.

13.2. 1-Cyclopropyl-5,8,9,10-tetrahydro-5,9-epiminobenzo[8]annulen-7(6H)-one (40)

To a mixture of carbamate (39) (330 mg) in 100 mL of MeOH in a Parr bottle was added 50 mg of 10% Pd/C. This slurry was shaken under 50 psi of $H_2$ (gas) at room temperature overnight. The mixture was filtered through a pad of Celite and rinsed with $CH_2Cl_2$ (2×100 mL). The solution was concentrated to a crude tan solid (40) (192 mg) and used in the next reaction without further purification.

13.3. 1-Cyclopropyl-11-{[6-(trifluoromethyl)pyridin-3-yl]sulfonyl}-5,8,9,10-tetrahydro-5,9-epiminobenzo[8]annulen-7(6H)-one (41)

To a mixture of crude amine (192 mg) (40) in 8 mL of $CH_2Cl_2$ at room temperature was added triethylamine (0.23 mL), followed by 6-(trifluoromethyl)pyridine-3-sulfonyl chloride (244 mg, 0.99 mmol). This mixture was stirred at room temperature overnight. The mixture was concentrated under reduced pressure. After flash chromatography on silica gel, a white solid (41) (281 mg) was obtained.

13.4. 6-Cyclopropyl-12-{[6-(trifluoromethyl)pyridin-3-yl]sulfonyl}-4,5,10,11-tetrahydro-2H-4,10-epiminobenzo[5,6]cycloocta[1,2-c]pyrazole (42) and 7-Cyclopropyl-12-{[6-(trifluoromethyl)pyridin-3-yl]sulfonyl}-4,5,6,11-tetrahydro-2H-5,11-epiminobenzo[4,5]cycloocta[1,2-c]pyrazole (43)

To ketone (278 mg, 0.64 mmol) (41) was added tert-butoxybis(dimethylamino)methane (2.22 g, 12.74 mmol). This mixture was heated at 45° C. for 1.5 h. The mixture was diluted with 50 mL of $H_2O$ and extracted with EtOAc (3×50 mL). The combined organic extracts were dried over $Na_2SO_4$. After the dessicant was filtered off, the organic extracts were concentrated under reduced pressure to provide a crude oil. This crude oil was resuspended in 6 mL of EtOH. To this solution was added hydrazine-hydrate (61 mg, 1.22 mmol). This mixture was stirred at room temperature overnight. The mixture was diluted with water (30 mL) and extracted with EtOAc (3×30 mL). The combined organic extracts were washed with 10% NaCl (aq) (100 mL) and dried over $Na_2SO_4$. After the desiccant was filtered off, the organic extracts were concentrated under reduced pressure to provide a crude oil. After HPLC, a white solid (42) (17.9 mg) $^1$H NMR (CDCl$_3$) δ 9.07 (d, J=2.0 Hz, 1H), 8.20 (dd, J=1.9, 8.2 Hz, 1H), 7.65 (d, J=8.0 Hz, 1H), 7.54 (s, 1H), 7.15 (t, J=7.6 Hz, 1H), 7.02 (d, J=7.5 Hz, 1H), 6.88 (d, J=7.6 Hz, 1H), 5.64 (d, J=5.7 Hz, 1H), 5.53 (d, J=5.1 Hz, 1H), 3.35 (dd, J=6.3, 16.5 Hz, 1H), 3.16 (dd, J=5.8, 17 Hz, 1H), 3.00 (d, J=11.1 Hz, 1H), 2.94 (d, J=11.4 Hz, 1H); 1.58-1.49 (m, 1H); 0.91-0.77 (m, 2H); 0.51-0.35 (m, 2H); and a white solid (43) (23.8 mg) $^1$H NMR (CDCl$_3$) δ 8.88 (d, J=1.9 Hz, 1H), 7.87 (dd, J=1.9, 8.2 Hz, 1H), 7.50 (s, 1H), 7.38 (d, J=8.2 Hz, 1H), 7.06 (t, J=4.4 Hz, 1H), 6.76-6.71 (m, 1H), 6.06 (s, 1H), 5.05-5.00 (m, 1H), 3.42 (dd, J=5.6, 16.5 Hz, 1H), 3.30 (dd, J=9.9, 18.5 Hz, 1H), 2.95 (d, J=16.5 Hz, 1H), 2.38 (d, J=18.6 Hz, 1H); 1.32-1.23 (m, 1H); 0.84-0.72 (m, 2H), 0.46-0.37 (m, 1H); 0.30-0.24 (m, 1H) were obtained.

Example 14

Synthesis of 4-bromo-11-{[6-(trifluoromethyl)pyridin-3-yl]sulfonyl}-5,8,9,10-tetrahydro-5,9-epiminobenzo[8]annulen-7(6H)-one (45)

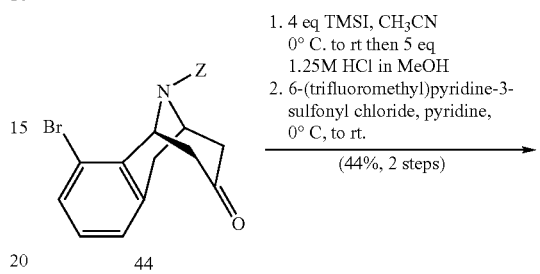

1. 4 eq TMSI, CH$_3$CN
   0° C. to rt then 5 eq
   1.25M HCl in MeOH
2. 6-(trifluoromethyl)pyridine-3-sulfonyl chloride, pyridine, 0° C, to rt.

(44%, 2 steps)

To an ice chilled solution of ketone 44 (706 mg, 1.76 mmol), prepared as described for compound 28 in Example 11 using 8-bromoisoquinoline, in acetonitrile (17 mL) was added TMSI (960 μL, 7.05 mmol). The reaction mixture was allowed to warm to room temperature over two hours at which time LC/MC analysis determined no starting material remained. The reaction mixture was chilled to 0° C. and treated with 1.25 M HCl in MeOH (7 ml, 8.80 mmol) and allowed to warm to room temperature over 1.5 hours. Concentration yielded 530 mg of a thick brown residue which was dissolved in pyridine (9 mL), chilled to 0° C., and treated with 6-(trifluoromethyl)pyridine-3-sulfonyl chloride (1.07 g, 4.37 mmol). After stirring over night at room temperature, LC/MS analysis revealed the presence of starting material so the reaction mixture was treated with 6-(trifluoromethyl)pyridine-3-sulfonyl chloride (644 mg, 2.65 mmol) and stirred at room temperature for five days. The reaction mixture was then diluted with EtOAc and water (20 mL each). The organic portion was washed with 0.2 N citric acid (6×35 mL), water (1×20 mL), sat. aq. NaHCO$_3$ (3×25 mL), brine (1×20 mL), dried (MgSO$_4$), filtered and concentrated. The crude product was purified by silica gel chromatography to yield 366 mg (44%) of compound 45. $^1$H NMR (CDCl$_3$) δ 9.05 (d, J=2.1 Hz, 1H), 8.16 (dd, J=8.0, 1.0 Hz, 1H), 7.60 (d, J=8.4 Hz, 1H), 7.39 (d, J=8.4 Hz), 6.97 (t, J=7.8 Hz, 1H), 6.77 (d, J=7.2 Hz, 1H), 5.79-5.75 (m, 1H), 4.98 (t, J=7.8 Hz, 1H), 3.07-2.93 (m, 3H), 2.78-2.64 (m, 2H), 2.46 (d, J=15.0 Hz, 1H).

Example 15

Synthesis of 10-fluoro-11-{[4-(trifluoromethyl)phenyl]sulfonyl}-1,4,9,10-tetrahydro-4,9-epiminobenzo[4,5]cyclohepta[1,2-c]pyrazole (49)

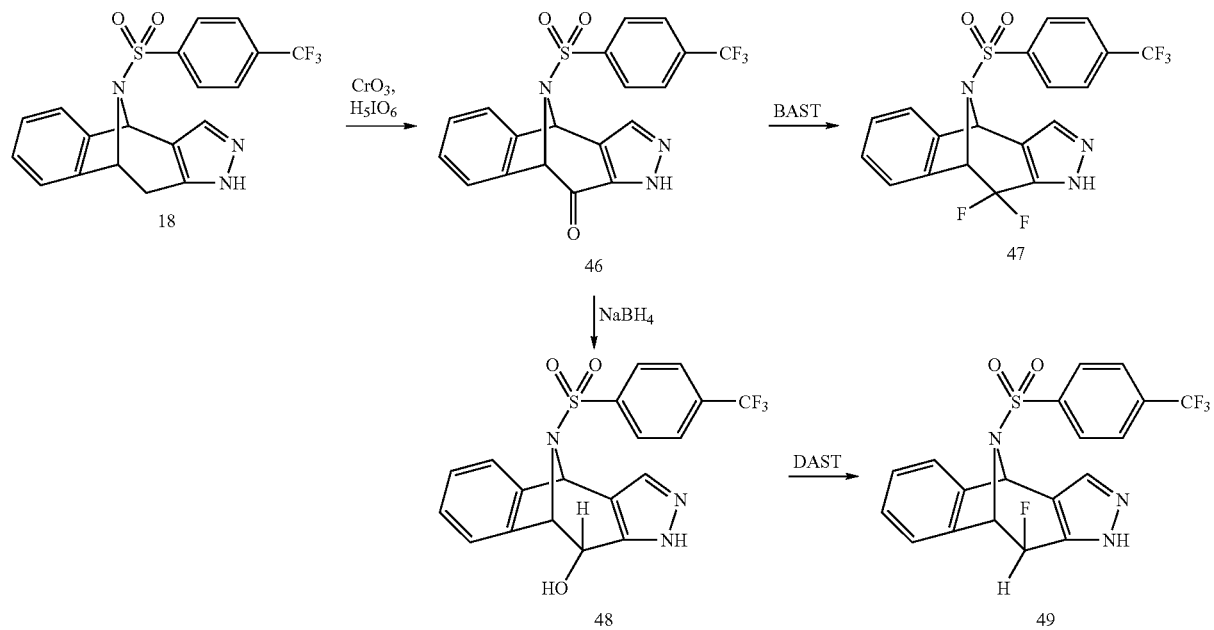

15.1. 11-{[4-(trifluoromethyl)phenyl]sulfonyl}-4,9-dihydro-4,9-epiminobenzo[4,5]cyclohepta[1,2-c]pyrazol-10(1H)-one (46)

To a solution of periodic acid (532 mg, 2.33 mmol) in acetonitrile (6 mL) was added chromium (VI) oxide (9 mg, 0.09 mmol). After stirring for 5 minutes, compound 18 (200 mg, 0.49 mmol) in acetonitrile (6 mL) was added. The resulting solution was stirred at room temperature overnight. TLC analysis (1:1 EtOAc:hexanes) and LC/MS indicated completion of reaction. The reaction was then quenched with water (20 mL) and extracted with $CH_2Cl_2$ (30 mL×3). The combined organic layers were dried over $Na_2SO_4$, filtered, and concentrated under reduced pressure to give the crude product. Purification by flash chromatography over silica gel, eluting with 0 to 60% EtOAc in hexanes, gave the title compound (162 mg, 78% yield). $^1$H NMR (CDCl$_3$) δ 7.77 (d, J=8.3 Hz, 2H), 7.62 (s, 1H), 7.53 (d, J=8.3 Hz, 2H), 7.25-7.28 (m, 1H), 7.11-7.02 (m, 3H), 6.18 (s, 1H), 5.44 (s, 1H).

15.2. 10,10-difluoro-11-{[4-(trifluoromethyl)phenyl]sulfonyl}-1,4,9,10-tetrahydro-4,9-epiminobenzo[4,5]cyclohepta[1,2-c]pyrazole (47)

Compound 46 (36 mg, 0.09 mmol) was dissolved in bis(2-methoxyethyl)aminosulfur trifluoride (BAST) (0.5 mL) and heated at 80° C. for 30 minutes. LC/MS showed no starting material. The reaction mixture was cooled to room temperature and added dropwise to a cold saturated aqueous sodium bicarbonate solution. After stirring for 10 minutes, the mixture was extracted with $CH_2Cl_2$ (3×), dried over $Na_2SO_4$, filtered, and concentrated under reduced pressure to give the crude product. Purification by preparative HPLC gave the title compound (12 mg, 25% yield) as a TFA salt. $^1$H NMR (CDCl$_3$) δ 7.79 (d, 2H, J=8.2 Hz), 7.52 (d, 2H, J=8.3 Hz), 7.45 (s, 1H), 7.25-7.29 (m, 1H), 6.94-7.06 (m, 3H), 6.00 (s, 1H), 5.47 (d, 1H, J=10.6 Hz).

15.3. 11-{[4-(trifluoromethyl)phenyl]sulfonyl}-1,4,9,10-tetrahydro-4,9-epiminobenzo[4,5]cyclohepta[1,2-c]pyrazol-10-ol (48)

To a suspension of compound 46 (158 mg, 0.38 mmol) in MeOH (7 mL) was added sodium borohydride (29 mg, 0.75 mmol). The mixture was stirred at room temperature for 30 minutes. TLC analysis (1:1 EtOAc:hexanes) indicated completion of reaction. The reaction was then quenched with water (20 mL) and extracted with $CH_2Cl_2$ (30 mL×3). The combined organic layers were dried over $Na_2SO_4$, filtered, and concentrated under reduced pressure to give the crude product. Purification by flash chromatography over silica gel, eluting with 0 to 80% EtOAc in hexanes, gave the title compound (137 mg, 86% yield). $^1$H NMR (CDCl$_3$) δ 7.82 (d, J=8.3 Hz, 2H), 7.53 (d, J=8.3 Hz, 2H), 7.48 (s, 1H), 7.10-7.07 (m, 1H), 6.93-6.86 (m, 3H), 5.91 (s, 1H), 5.30-5.23 (m, 2H).

15.4. 10-fluoro-11-{[4-(trifluoromethyl)phenyl]sulfonyl}-1,4,9,10-tetrahydro-4,9-epiminobenzo[4,5]cyclohepta[1,2-c]pyrazole (49)

To a solution of (diethylamino)sulfur trifluoride (DAST) (14 mg, 0.09 mmol) in $CH_2Cl_2$ (4 mL) at −78° C. was added a solution of compound 48 (21 mg, 0.05 mmol) in $CH_2Cl_2$ (2 mL). The reaction mixture was stirred at this temperature for 6 h, at 4h more DAST (14 mg, 0.09 mmol) was added. The reaction was quenched with saturated aqueous sodium bicarbonate (10 mL) and extracted with CH₂Cl₂ (20 mL×3). The combined organic layers were dried over Na₂SO₄, filtered, and concentrated under reduced pressure to give the crude product. Purification by flash chromatography over silica gel, eluting with 0 to 70% EtOAc in hexanes, gave the title compound (8.5 mg, 40% yield). ¹H NMR (CDCl₃) δ 7.80 (d, J=8.3 Hz, 2H), 7.49 (d, J=8.3 Hz, 2H), 7.40 (s, 1H), 7.19-7.16 (m, 1H), 7.03-6.94 (m, 3H), 6.01 (s, 1H), 5.61-5.44 (m, 2H).

Example 16

Synthesis of 10-[(4-chlorophenyl)sulfonyl]-6-(3-methyl-1,2,4-oxadiazol-5-yl)-4,5,6,7,8,9-hexahydro-1H-4,8-epiminocycloocta[c]pyrazole (54)

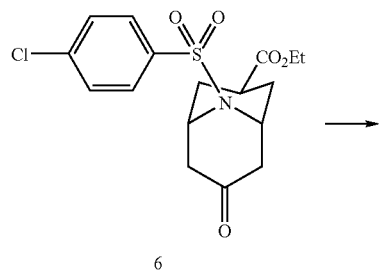
6

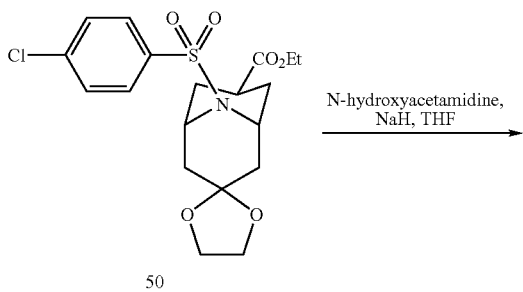
50

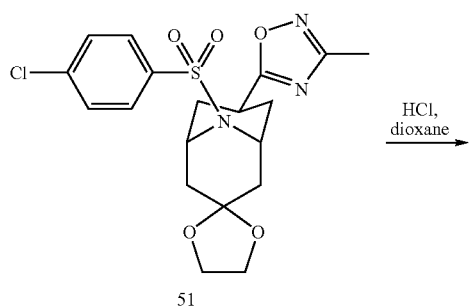
51

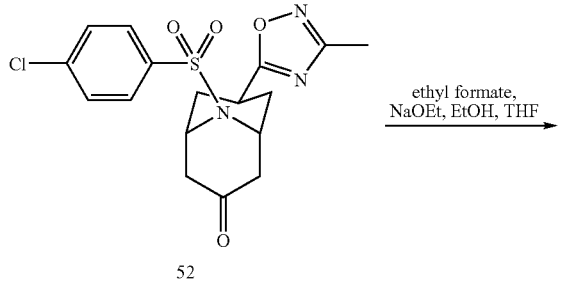
52

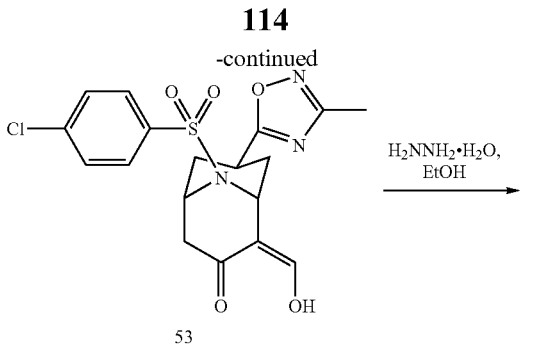
53

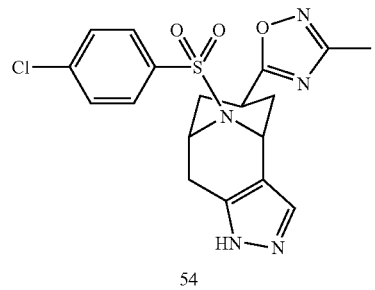
54

16.1. Ethyl 9-[(4-chlorophenyl)sulfonyl]spiro[9-azabicyclo[3.3.1]nonane-3,2'-[1,3]dioxolane]-7-carboxylate (50)

To a solution of 9-(4-chloro-benzenesulfonyl)-7-oxo-9-azabicyclo[3.3.1]nonane-3-carboxylic acid ethyl ester (6) (1.62 g, 4.19 mmol) in CH₂Cl₂ (14 mL) was added ethylene glycol (0.94 mL, 16.7 mmol) and TMSCl (1.06 mL, 8.39 mmol). The resulting solution was heated to reflux for 48 h and was subsequently washed with saturated aqueous NaHCO₃ (10 mL). The organic phase was dried (Na₂SO₄), filtered and concentrated under vacuum to yield 1.62 g (90%) of compound 50. MS (ESI) 430.1 (M+H).

16.2. 9-[(4-Chlorophenyl)sulfonyl]-7-(3-methyl-1,2,4-oxadiazol-5-yl)spiro[9-azabicyclo[3.3.1]nonane-3,2'-[1,3]-dioxolane] (51)

Sodium hydride (60% dispersion, 43 mg, 1.09 mmol) was added to a solution of N-hydroxy acetamidine (81 mg, 1.09 mmol) in THF (2 mL) and the resulting mixture was stirred at 50° C. for 15 minutes. Ethyl 9-[(4-chlorophenyl)sulfonyl] spiro[9-azabicyclo[3.3.1]nonane-3,2'-[1,3]dioxolane]-7-carboxylate (50) (0.394 g, 0.916 mmol) in THF (2 mL) was added to the reaction mixture and the resulting solution was stirred at room temperature for 1 hour. The mixture was diluted with EtOAc and washed with H₂O. The organic phase was dried (Na₂SO₄), filtered and concentrated under vacuum to yield 0.40 g (quant.) of compound 51. MS (ESI) 440.1 (M+H).

16.3. 9-[(4-Chlorophenyl)sulfonyl]-7-(3-methyl-1,2,4-oxadiazol-5-yl)-9-azabicyclo[3.3.1]nonan-3-one (52)

9-[(4-Chlorophenyl)sulfonyl]-7-(3-methyl-1,2,4-oxadiazol-5-yl)spiro[9-azabicyclo[3.3.1]nonane-3,2'-[1,3]dioxolane] (51) (0.40 g, 0.916 mmol) was covered with HCl in dioxane (4 N, 2 mL). The reaction mixture was stirred at room temperature for 2 h after which it was diluted with EtOAc and washed with aqueous sodium hydroxide (1 N). The organic phase was dried (Na₂SO₄), filtered and concentrated under vacuum to yield 0.36 g (quant.) of 9-[(4-chlorophenyl)sulfonyl]-7-(3-methyl-1,2,4-oxadiazol-5-yl)-9-azabicyclo[3.3.1]nonan-3-one (52). MS (ESI) 396.1 (M+H).

16.4. 9-[(4-Chlorophenyl)sulfonyl]-2-(hydroxymethylidene)-7-(3-methyl-1,2,4-oxadiazol-5-yl)-9-azabicyclo[3.3.1]nonan-3-one (53)

9-[(4-Chlorophenyl)sulfonyl]-7-(3-methyl-1,2,4-oxadiazol-5-yl)-9-azabicyclo[3.3.1]nonan-3-one (52) (0.357 g, 0.902 mmol) was dissolved in THF/EtOH (2 mL, 1/1, v/v). Ethyl formate (0.725 mL, 9.02 mmol) was added followed by sodium ethoxide (1.01 mL of 21% solution in EtOH). The resulting mixture was stirred at 50° C. for 1 hour after which the solution was cooled back to room temperature and quenched by the addition of saturated aqueous NH$_4$Cl. The resulting mixture was extracted with EtOAc and the combined organic phases were dried (Na$_2$SO$_4$), filtered and concentrated under vacuum to give 9-[(4-chlorophenyl)sulfonyl]-2-(hydroxymethylidene)-7-(3-methyl-1,2,4-oxadiazol-5-yl)-9-azabicyclo[3.3.1]nonan-3-one (53). MS (ESI) 424.0 (M+H).

16.5. 10-[(4-Chlorophenyl)sulfonyl]-6-(3-methyl-1,2,4-oxadiazol-5-yl)-4,5,6,7,8,9-hexahydro-1H-4,8-epiminocycloocta[c]pyrazole (54)

To a solution of 9-[(4-chlorophenyl)sulfonyl]-2-(hydroxymethylidene)-7-(3-methyl-1,2,4-oxadiazol-5-yl)-9-azabicyclo[3.3.1]nonan-3-one (53) (0.38 g, 0.902 mmol) in EtOH (5 mL) was added glacial acetic acid (0.1 mL) followed by hydrazine monohydrate (0.44 mL, 9.02 mmol). The reaction mixture was stirred at room temperature for 2 h and then at 50° C. for a further 2 h. The resulting solution was diluted with EtOAc and washed with H$_2$O. The organic phase was dried (Na$_2$SO$_4$), filtered, concentrated and purified by silica gel column chromatography (eluant hexane/EtOAc, 9/1 to 2/8) and preparative HPLC to give 10-[(4-chlorophenyl)sulfonyl]-6-(3-methyl-1,2,4-oxadiazol-5-yl)-4,5,6,7,8,9-hexahydro-1H-4,8-epiminocycloocta[c]pyrazole (54). MS (ESI) 420.1 (M+H). $^1$H NMR (300 MHz, CDCl$_3$) δ 7.67 (d, J=8.8 Hz, 2H), 7.52 (s, 1H), 7.39 (d, J=8.8 Hz, 2H), 5.43 (bs, 1H), 4.66 (bs, 1H), 3.06 (m, 1H), 2.72 (d, J=17.6 Hz, 1H), 2.34 (s, 3H), 2.32-2.09 (m, 4H).

Example 17

Synthesis of 9-[(4-Chlorophenyl)sulfonyl]-7-(1-methoxycyclopropyl)spiro[9-azabicyclo[3.3.1]nonane-3,2'-[1,3]-dioxolane] (56)

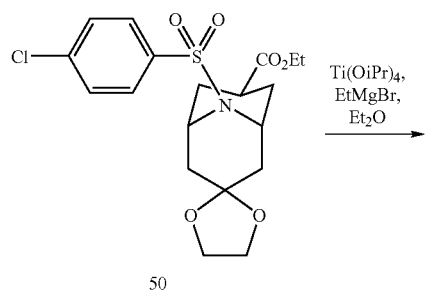

50

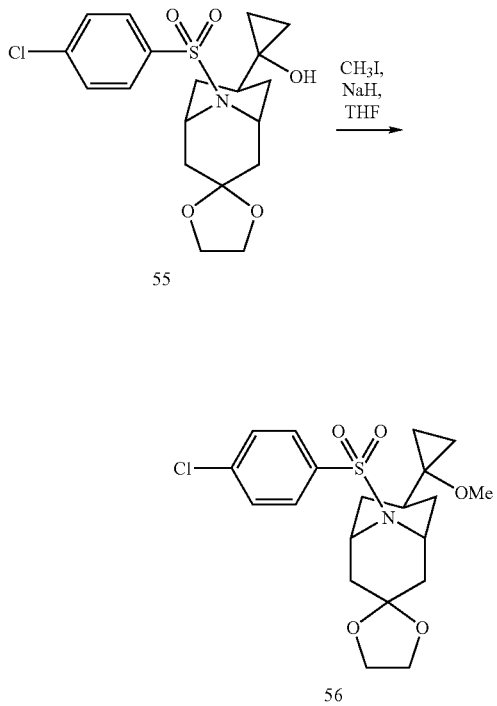

17.1. 1-{9-[(4-Chlorophenyl)sulfonyl]spiro[9-azabicyclo[3.3.1]nonane-3,2'-[1,3]dioxolan]-7-yl}cyclopropanol (55)

Ethyl 9-[(4-chlorophenyl)sulfonyl]spiro[9-azabicyclo[3.3.1]nonane-3,2'-[1,3]dioxolane]-7-carboxylate (50) (395 mg, 0.918 mmol) was dissolved in Et$_2$O (2 mL) and the resulting solution was cooled to −78° C. Ti(O-i-Pr)$_4$ was added followed by EtMgBr dropwise over 10 minutes. The reaction mixture was warmed to room temperature and stirred for 18 h. The resulting solution was diluted with EtOAc and washed with saturated aqueous NH$_4$Cl. The organic phase was dried (Na$_2$SO$_4$), filtered, and concentrated to give 1-{9-[(4-chlorophenyl)sulfonyl]spiro[9-azabicyclo[3.3.1]nonane-3,2'-[1,3]dioxolan]-7-yl}cyclopropanol (55). MS (ESI) 414.1 (M+H).

17.2. 9-[(4-Chlorophenyl)sulfonyl]-7-(1-methoxycyclopropyl)spiro[9-azabicyclo[3.3.1]nonane-3,2'-[1,3]dioxolane] (56)

Sodium hydride (60% dispersion in mineral oil, 46 mg, 1.16 mol) was added to a solution of 1-{9-[(4-chlorophenyl)sulfonyl]spiro[9-azabicyclo[3.3.1]nonane-3,2'-[1,3]dioxolan]-7-yl}cyclopropanol (55) (321 mg, 0.775 mmol) in THF (2 mL). The resulting solution was stirred for 10 minutes, after which iodomethane (72 μL, 1.16 mmol) was added. The reaction mixture was stirred at room temperature for 18 h and was subsequently diluted with EtOAc and washed with brine. The organic phase was dried (Na$_2$SO$_4$), filtered, and concentrated to give 9-[(4-chlorophenyl)sulfonyl]-7-(1-methoxycyclopropyl)spiro[9-azabicyclo[3.3.1]nonane-3,2'-[1,3]dioxolane] (56). MS (ESI) 428.1 (M+H).

Example 18

Synthesis of 10-[(4-chlorophenyl)sulfonyl]-4,5,6,7,8,9-hexahydro-1H-4,8-epiminocycloocta[c]pyrazole-6-carbonitrile (62)

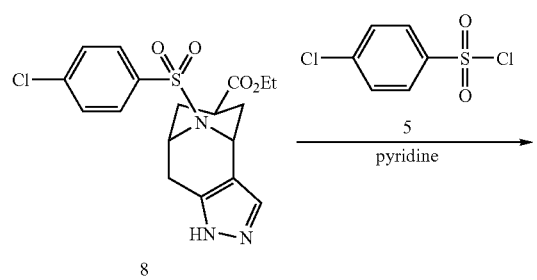

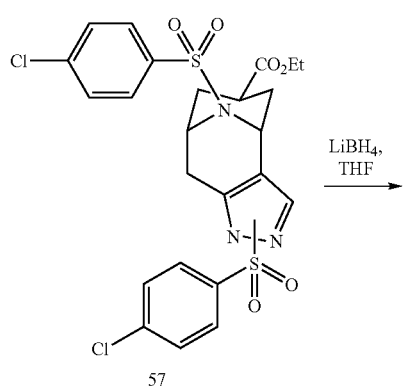

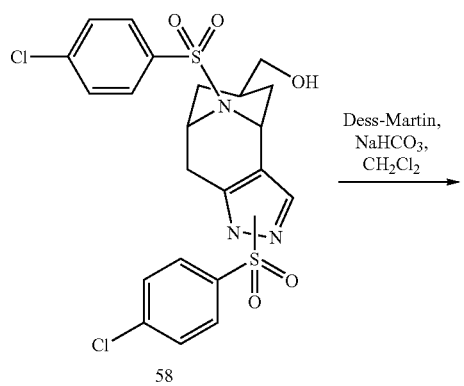

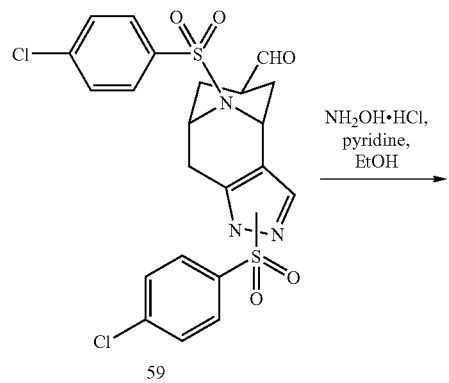

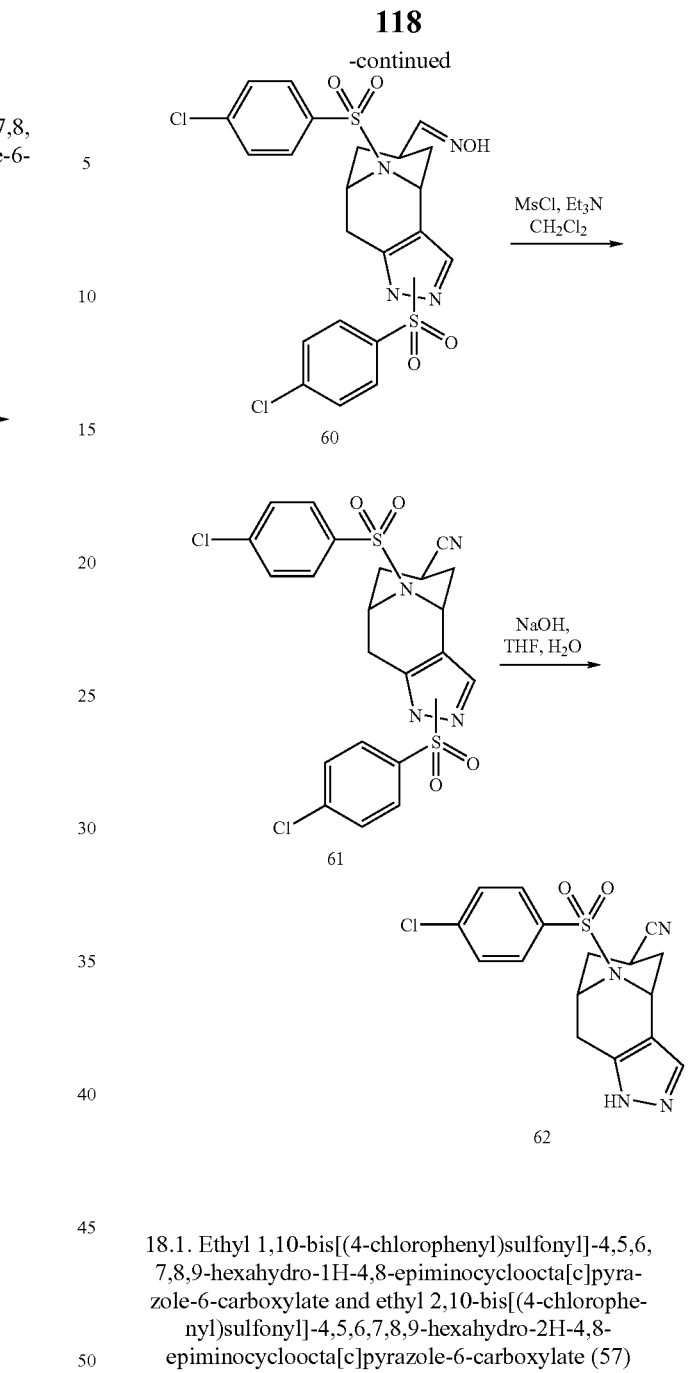

18.1. Ethyl 1,10-bis[(4-chlorophenyl)sulfonyl]-4,5,6,7,8,9-hexahydro-1H-4,8-epiminocycloocta[c]pyrazole-6-carboxylate and ethyl 2,10-bis[(4-chlorophenyl)sulfonyl]-4,5,6,7,8,9-hexahydro-2H-4,8-epiminocycloocta[c]pyrazole-6-carboxylate (57)

4-Chlorobenzenesulfonyl chloride (0.315 g, 1.49 mmol) was added to a solution of ethyl 10-(4-chlorophenyl)sulfonyl-4,5,6,7,8,9-hexahydro-1H-4,8-epiminocycloocta[c]pyrazole-6-carboxylate (8) (0.51 g, 1.24 mmol) in pyridine (5 mL) and the resulting mixture was stirred at room temperature for 1 h. The resulting solution was diluted with $CH_2Cl_2$ and washed with aqueous 1N Ha then saturated aqueous $NaHCO_3$. The organic phase was dried ($Na_2SO_4$), filtered, concentrated and purified by silica gel column chromatography (eluant hexane/EtOAc, 20/1 to 1/1) to give ethyl 1,10-bis[(4-chlorophenyl)sulfonyl]-4,5,6,7,8,9-hexahydro-1H-4,8-epiminocycloocta[c]pyrazole-6-carboxylate and ethyl 2,10-bis[(4-chlorophenyl)sulfonyl]-4,5,6,7,8,9-hexahydro-2H-4,8-epiminocycloocta[c]pyrazole-6-carboxylate (57) (0.721 mmol, 1.23 mmol, quant). MS (ESI) 584.0 (M+H).

18.2. {1,10-Bis[(4-chlorophenyl)sulfonyl]-4,5,6,7,8,9-hexahydro-1H-4,8-epiminocycloocta[c]pyrazol-6-yl}methanol and {2,10-bis[(4-chlorophenyl)sulfonyl]-4,5,6,7,8,9-hexahydro-2H-4,8-epiminocycloocta[c]pyrazol-6-yl}methanol (58)

Lithium borohydride (10 mg, 0.516 mmol) was added to a solution of ethyl 1,10-bis[(4-chlorophenyl)sulfonyl]-4,5,6,7,8,9-hexahydro-1H-4,8-epiminocycloocta[c]pyrazole-6-carboxylate and ethyl 2,10-bis[(4-chlorophenyl)sulfonyl]-4,5,6,7,8,9-hexahydro-2H-4,8-epiminocycloocta[c]pyrazole-6-carboxylate (57) (0.151 mg, 0.258 mmol) in THF (1 mL) and the resulting solution was stirred at room temperature for 2 h. The reaction mixture was diluted with EtOAc and washed with water. The organic phase was dried ($Na_2SO_4$), filtered and concentrated to give {1,10-bis[(4-chlorophenyl)sulfonyl]-4,5,6,7,8,9-hexahydro-1H-4,8-epiminocycloocta[c]pyrazol-6-yl}methanol and {2,10-Bis[(4-chlorophenyl)sulfonyl]-4,5,6,7,8,9-hexahydro-2H-4,8-epiminocycloocta[c]pyrazol-6-yl}methanol (58). MS (ESI) 542.0 (M+H).

18.3. 1,10-Bis[(4-chlorophenyl)sulfonyl]-4,5,6,7,8,9-hexahydro-1H-4,8-epiminocycloocta[c]pyrazole-6-carbaldehyde and 2,10-bis[(4-chlorophenyl)sulfonyl]-4,5,6,7,8,9-hexahydro-2H-4,8-epiminocycloocta[c]pyrazole-6-carbaldehyde (59)

Dess-Martin periodinane (128 mg, 0.304 mmol) was added to a solution of {1,10-bis[(4-chlorophenyl)sulfonyl]-4,5,6,7,8,9-hexahydro-1H-4,8-epiminocycloocta[c]pyrazol-6-yl}methanol and {2,10-Bis[(4-chlorophenyl)sulfonyl]-4,5,6,7,8,9-hexahydro-2H-4,8-epiminocycloocta[c]pyrazol-6-yl}methanol (58) (110 mg, 0.202 mmol) containing sodium bicarbonate (76 mg, 0.912 mmol). The resulting suspension was stirred at room temperature for 2 h after which a mixture of saturated aqueous $NaHCO_3$ and saturated aqueous $Na_2SO_4$ (1/1, v/v) was added. The organic phase was dried ($Na_2SO_4$), filtered, concentrated and purified by silica gel column chromatography (eluant hexane/EtOAc, 4/1 to 1/1) to give 1,10-bis[(4-chlorophenyl)sulfonyl]-4,5,6,7,8,9-hexahydro-1H-4,8-epiminocycloocta[c]pyrazole-6-carbaldehyde and 2,10-bis[(4-chlorophenyl)sulfonyl]-4,5,6,7,8,9-hexahydro-2H-4,8-epiminocycloocta[c]pyrazole-6-carbaldehyde (59) (95 mg, 0.175 mmol, 87%). MS (ESI) 540.0 (M+H).

18.4. 1-{1,10-Bis[(4-chlorophenyl)sulfonyl]-4,5,6,7,8,9-hexahydro-1H-4,8-epiminocycloocta[c]pyrazol-6-yl}-N-hydroxymethanimine and 1-{2,10-Bis[(4-chlorophenyl)sulfonyl]-4,5,6,7,8,9-hexahydro-1H-4,8-epiminocycloocta[c]pyrazol-6-yl}-N-hydroxymethanimine (60)

Hydroxylamine hydrochloride (18 mg, 0.252 mmol) was added to a solution of 1,10-bis[(4-chlorophenyl)sulfonyl]-4,5,6,7,8,9-hexahydro-1H-4,8-epiminocycloocta[c]pyrazole-6-carbaldehyde and 2,10-bis[(4-chlorophenyl)sulfonyl]-4,5,6,7,8,9-hexahydro-2H-4,8-epiminocycloocta[c]pyrazole-6-carbaldehyde (59) (91 mg, 0.168 mmol) in EtOH/pyridine (2 ml, 1/1, v/v) and the resulting solution was stirred at room temperature for 2 h. The reaction mixture was diluted with $CH_2Cl_2$ and washed with saturated aqueous $NaHCO_3$. The organic phase was dried ($Na_2SO_4$), filtered and concentrated to give 1-{1,10-bis[(4-chlorophenyl)sulfonyl]-4,5,6,7,8,9-hexahydro-1H-4,8-epiminocycloocta[c]pyrazol-6-yl}-N-hydroxymethanimine and 1-{2,10-bis[(4-chlorophenyl)sulfo-nyl]-4,5,6,7,8,9-hexahydro-1H-4,8-epiminocycloocta[c]pyrazol-6-yl}-N-hydroxymethanimine (60). MS (ESI) 555.0 (M+H).

18.5. 1,10-Bis[(4-chlorophenyl)sulfonyl]-4,5,6,7,8,9-hexahydro-1H-4,8-epiminocycloocta[c]pyrazole-6-carbonitrile and 2,10-Bis[(4-chlorophenyl)sulfonyl]-4,5,6,7,8,9-hexahydro-2H-4,8-epiminocycloocta[c]pyrazole-6-carbonitrile (61)

Methanesulfonyl chloride (30 µL, 0.390 mmol) and triethylamine (162 µL, 1.17 mmol) were added to a solution of 1-{1,10-bis[(4-chlorophenyl)sulfonyl]-4,5,6,7,8,9-hexahydro-1H-4,8-epiminocycloocta[c]pyrazol-6-yl}-N-hydroxymethanimine and 1-{2,10-bis[(4-chlorophenyl)sulfonyl]-4,5,6,7,8,9-hexahydro-1H-4,8-epiminocycloocta[c]pyrazol-6-yl}-N-hydroxymethanimine (60) (73 mg, 0.130 mmol) in $CH_2Cl_2$ (1 mL) and the resulting solution was stirred at room temperature for 0.5 h. The reaction mixture was diluted with $CH_2Cl_2$ and washed with saturated aqueous $NaHCO_3$. The organic phase was dried ($Na_2SO_4$), filtered, and concentrated to give 1,10-bis[(4-chlorophenyl)sulfonyl]-4,5,6,7,8,9-hexahydro-1H-4,8-epiminocycloocta[c]pyrazole-6-carbonitrile and 2,10-bis[(4-chlorophenyl)sulfonyl]-4,5,6,7,8,9-hexahydro-2H-4,8-epiminocycloocta[c]pyrazole-6-carbonitrile (61). MS (ESI) 537.0 (M+H).

18.6. 10-[(4-Chlorophenyl)sulfonyl]-4,5,6,7,8,9-hexahydro-1H-4,8-epiminocycloocta[c]pyrazole-6-carbonitrile (62)

Sodium hydroxide (130 µL of a 3N aqueous solution) was added to a solution of 1,10-bis[(4-chlorophenyl)sulfonyl]-4,5,6,7,8,9-hexahydro-1H-4,8-epiminocycloocta[c]pyrazole-6-carbonitrile and 2,10-bis[(4-chlorophenyl)sulfonyl]-4,5,6,7,8,9-hexahydro-2H-4,8-epiminocycloocta[c]pyrazole-6-carbonitrile (61) (69 mg, 0.13 mmol) in THF (0.5 mL) and the resulting solution was stirred at room temperature for 5 h. The reaction mixture was diluted with EtOAc and washed with brine. The organic phase was dried ($Na_2SO_4$), filtered, concentrated and purified by preparative HPLC to give 10-[(4-chlorophenyl)sulfonyl]-4,5,6,7,8,9-hexahydro-1H-4,8-epiminocycloocta[c]pyrazole-6-carbonitrile (62). MS (ESI) 363.1 (M+H). $^1$H NMR (300 MHz, $CDCl_3$) δ 7.62 (d, J=8.8 Hz, 2H), 7.43 (s, 1H), 7.35 (d, J=8.8 Hz, 2H), 5.38 (bs, 1H), 4.61-4.52 (m, 1H), 2.93 (dd, J=17.0, 6.6 Hz, 1H), 2.71-2.52 (m, 2H), 2.32-1.98 (m, 4H).

Example 19

Synthesis of 6-(4-fluorophenyl)-11-{[6-(trifluoromethyl)pyridin-3-yl]sulfonyl}-1,4,9,10-tetrahydro-4,9-epiminobenzo[4,5]cyclohepta[1,2-c]pyrazole (66)

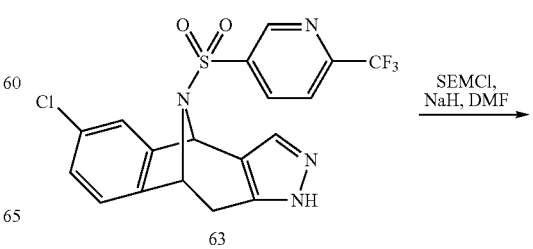

63

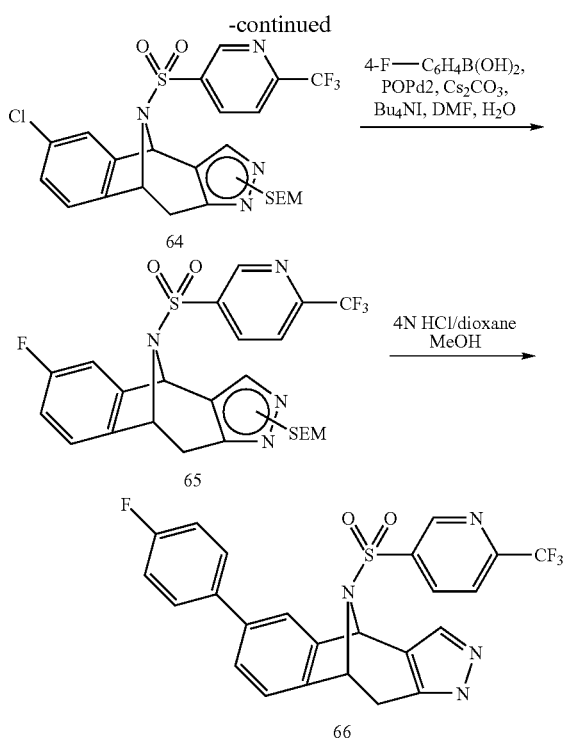

19.1. 6-Chloro-11-{[6-(trifluoromethyl)pyridin-3-yl]sulfonyl}-1-{[2-(trimethylsilyl)ethoxy]methyl}-1,4,9,10-tetrahydro-4,9-epiminobenzo[4,5]cyclohepta[1,2-c]pyrazole and 6-Chloro-11-{[6-(trifluoromethyl)pyridin-3-yl]sulfonyl}-2-[2-(trimethylsilyl)ethoxy]-2,4,9,10-tetrahydro-4,9-epiminobenzo[4,5]cyclohepta[1,2-c]pyrazole (64)

To a suspension of NaH (4.21 mmol, 0.17 g) in DMF (10 mL) at 0° C. was added compound 63 (1.40 mmol, 0.62 g). The reaction mixture was stirred for 10 minutes prior to the addition of 2-(trimethylsilyl)ethoxymethyl chloride (4.21 mmol, 0.70 g). The reaction mixture was stirred for 2 h at 0° C., and then quenched with saturated aqueous NH₄Cl (10 mL). The reaction mixture was diluted with EtOAc (25 mL). The two layers were separated. The organic layer was dried with MgSO₄, filtered and concentrated. The resulting residue was purified by flash chromatography (30% EtOAc in hexanes) to afford compound 64 (0.57 g, 72%) as a regioisomeric mixture of alkylated pyrazoles.

19.2. 6-(4-Fluorophenyl)-11-{[6-(trifluoromethyl)pyridin-3-yl]sulfonyl}-1,4,9,10-tetrahydro-4,9-epiminobenzo[4,5]cyclohepta[1,2-c]pyrazole (66)

To a solution of 64 (0.26 mmol, 0.15 g) and 4-fluorophenylboronic acid (1.31 mmol, 0.18 g) in THF (3 mL) was added dihydrogen di-ε-chlorodichlorobis(di-tert-butylphosphinito-kP)dipalladate(2-) (0.008 mmol, 0.005 g), and Cs₂CO₃ (1.31 mmol, 0.43 g). The reaction mixture was irradiated in the microwave for 60 minutes at 145° C. (300 W). The reaction mixture was diluted with MeOH (5 mL) and filtered through a pad of Celite. The filtrate was concentrated, and the resulting residue was dissolved in MeOH (2 mL). The temperature was decreased to 0° C. and 4N HCl in dioxane (5 mL) was added. The reaction mixture was warmed to room temperature and then plunged into a preheated 60° C. oil bath and stirred for 18 h. The reaction mixture was cooled to room temperature and concentrated. The resulting residue was dissolved in CH₂Cl₂ (5 mL) and the temperature was decreased to 0° C. The reaction mixture was diluted with saturated aqueous NaHCO₃ (5 mL) and stirred for 5 minutes. The two layers were then separated, and the organic layer was dried with MgSO₄, filtered and concentrated. The resulting residue was purified by flash chromatography (70% EtOAc in hexanes) to afford compound 66 (0.07 g, 54%).

Example 20

Synthesis of (10.5)-5-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol and (4R,10R)-8-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol (70a and 70b)

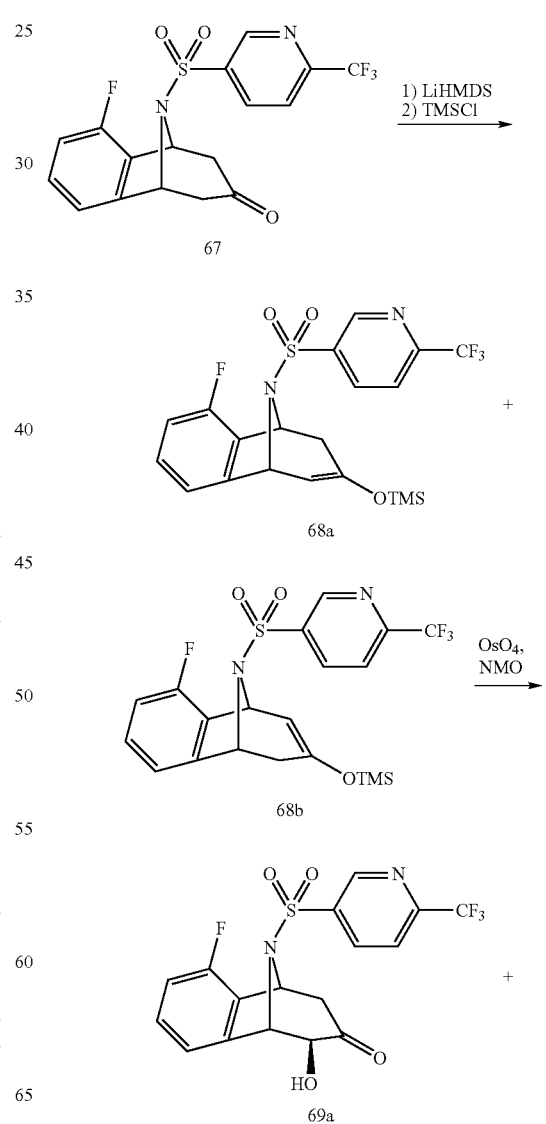

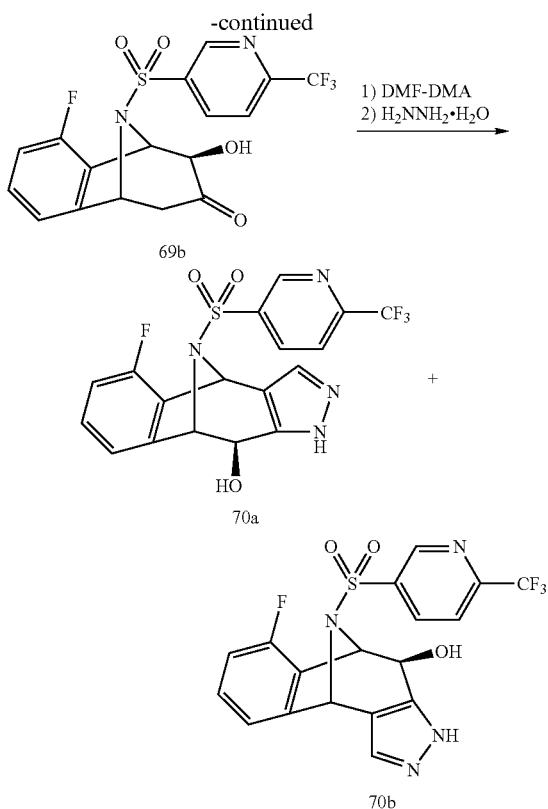

To a solution of 67 (525 mg, 1.31 mmol) in THF (10 mL) at −78° C. was added LiHMDS (1.0M in THF, 1.97 mL, 1.97 mmol) over 5 minutes. After the mixture was stirred at −78° C. for 30 min, chlorotrimethylsilane (500 µL, 3.94 mmol) was added dropwise and stirred at this temperature for 60 minutes. The reaction was quenched with sat. aq. NaHCO₃ (10 mL) and extracted with CH₂Cl₂ (3×50 mL). The organic layers were combined, dried over Na₂SO₄, filtered, and concentrated under reduced pressure to give a mixture of regioisomers (577 mg) consisting of racemates 68a and 68b.

20.2. (6S)-1-Fluoro-6-hydroxy-10-{[6-(trifluoromethyl)pyridin-3-yl]sulfonyl}-5,6,8,9-tetrahydro-7H-5,9-epiminobenzo[7]annulen-7-one and (8R)-1-Fluoro-8-hydroxy-10-{[6-(trifluoromethyl)pyridin-3-yl]sulfonyl}-5,6,8,9-tetrahydro-7H-5,9-epiminobenzo[7]annulen-7-one (69a and 69b)

To a solution of 68a and 68b (1.31 mmol) in THF (9 mL) was added 4-methylmorpholine N-oxide (198 mg, 1.31 mmol), water (4 mL), and osmium tetroxide (4 wt. % in water, 253 µL, 0.04 mmol). The mixture was stirred at room temperature overnight, quenched with a 10% aqueous solution of Na₂S₂O₃ (15 mL), and extracted with CH₂Cl₂ (3×50 mL). The combined organic layers were concentrated under reduced pressure and the material was purified by flash chromatography (eluting with 0 to 50% EtOAc in hexane) to give a mixture of regioisomers consisting of racemates 69a and 69b (57 mg, 10% yield).

20.3. (10S)-5-Fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol and (4R,10R)-8-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol (70a and 70b)

The above mixture (69a and 69b) (0.14 mmol) was heated with neat DMF-DMA (2 mL) at 100° C. for 60 min. The reaction mixture was concentrated under reduced pressure, dried on high vacuum and dissolved in acetic acid (3 mL). The solution was cooled in an ice bath and treated with hydrazine hydrate (15 µL, 0.31 mmol). The mixture was stirred at room temperature overnight. The solvent was removed under reduced pressure. The residue was purified by flash chromatography (solid load, 0 to 100% EtOAc in hexane) to give a mixture of regioisomers consisting of racemates 70a and 70b. Individual stereoisomers were isolated by chiral HPLC.

Example 21

Synthesis of (+/−)-9-methyl-11-{[4-(trifluoromethyl)phenyl]sulfonyl}-4,9-dihydro-4,9-epiminobenzo[4,5]cyclohepta[1,2-c]pyrazol-10(1H)-one (82)

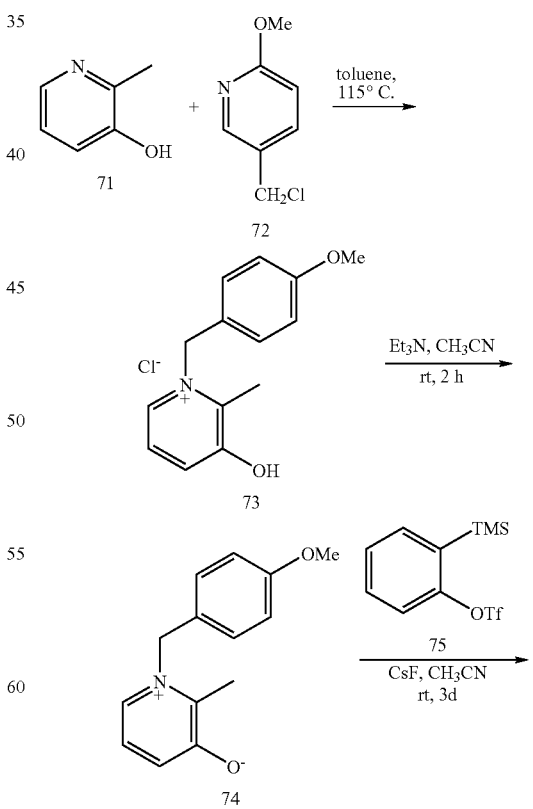

-continued

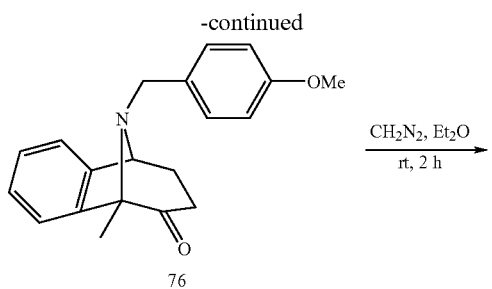

76

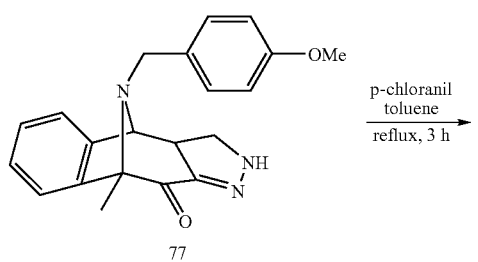

77

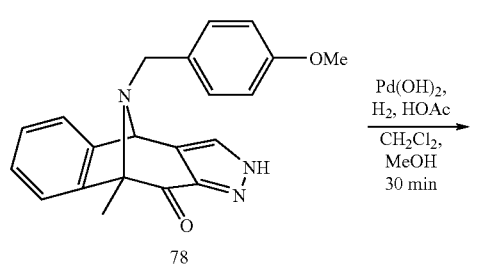

78

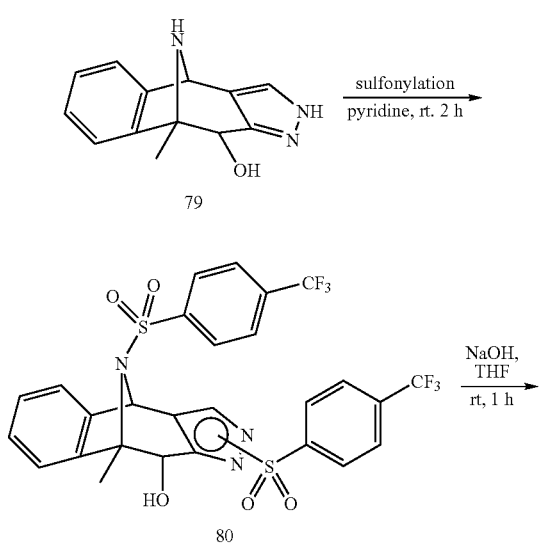

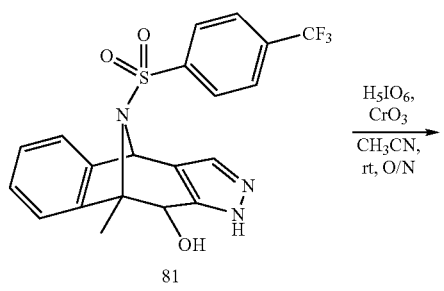

81

-continued

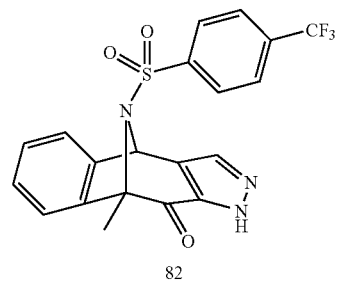

82

21.1. 3-Hydroxy-1-(4-methoxybenzyl)-2-methylpyridinium chloride (73)

To a suspension of 2-methyl-3-hydroxypyridine (71) (10 g, 91.6 mmol) in toluene (45 mL) was added 4-methyoxybenzyl chloride (72) (12.4 mL, 1 eq). The mixture was refluxed overnight. The solvent was concentrated to about ⅓ of the volume. After cooling, the solid was isolated via filtration and washed with a small amount of toluene to give the desired product, which was used without further purification. $^1$H NMR (d$_6$-DMSO) δ 8.61 (d, 1H, J=6 Hz), 8.16 (d, 1H, J=8.4 Hz), 7.85 (t, 1H, J=6.9 Hz), 7.28 (d, 2H, J=8.1 Hz), 7.02 (d, 2H, J=8.4 Hz), 5.82 (s, 2H), 3.79 (s 3H), 2.59 (s, 3H).

21.2. 1-(4-Methoxybenzyl)-2-methylpyridinium-3-olate (74)

To a suspension of compound 73 (23g) in CH$_3$CN (200 mL) was added triethylamine (15 mL) and the mixture was stirred at room temperature for 1.5 hours. The solvent was concentrated to about ¼ of the volume. The solid was isolated via filtration and washed with a small amount of CH$_3$CN to give the desired product, which was used without further purification. $^1$H NMR (d$_6$-DMSO) δ 8.57 (d, 1H, J=6 Hz), 8.08 (d, 1H, J=8.1 Hz), 7.82 (t, 1H, J=7.5 Hz), 7.25 (d, 2H, J=8.7 Hz), 6.99 (d, 2H, J=8.4 Hz), 5.78 (s, 2H), 3.74 (s 3H), 2.51 (s, 3H).

21.3. (+/−)-10-(4-Methoxybenzyl)-5-methyl-5,9-dihydro-6H-5,9-epiminobenzo[7]annulen-6-one (76)

To a suspension of compound 73 (11.97 g) in CH$_3$CN (125 mL) was added 2-(trimethylsilyl)phenyl trifluoromethanesulfonate (75) (30 g) and CsF (20 g). The mixture was stirred at room temperature for 3 days. Water was added to quench the reaction and most of the CH$_3$CN was removed via rotavaporator. The residue was extracted with EtOAc, washed with water and brine, and dried over MgSO$_4$. After concentration of the solvent, the crude product was purified by silica gel chromatography, eluting with a gradient of 100% hexane to 80% EtOAc/hexane over 30 min. The pure product was isolated as a brown oil. $^1$H NMR (CDCl$_3$) δ 7.30-7.24 (m 3H), 7.21-7.15 (m, 3H), 7.01 (dd, 1H, J=5.1, 9.6 Hz), 6.87 (d, 2H, J=8.7 Hz), 5.62 (d, 2H, J=9.6 Hz), 4.31 (d, 1H, J=5.1 Hz), 3.81 (s 3H), 1.65 (s, 3H).

21.4. (+/−)-11-(4-Methoxybenzyl)-9-methyl-3,3a,4,9-tetrahydro-4,9-epiminobenzo[4,5]cyclohepta[1,2-c]pyrazol-10(2H)-one (77)

Diazomethane in ether (75 mL) (prepared from 2.5 g NMMG) was added with caution to compound 75 (2.6 g) and the solution was stirred at room temperature for 2 hours. The excess diazomethane was quenched by adding HOAc. The solvent was removed to afford the desired product as a yellow solid consisting of a mixture of the two regioisomers. The product was used without further purification.

21.5. (+/−)-11-(4-Methoxybenzyl)-9-methyl-4,9-dihydro-4,9-epiminobenzo[4,5]cyclohepta[1,2-c]pyrazol-10(2H)-one (78)

To a solution of compound 77 (3.6 g) in toluene (300 mL) was added p-chloranil (7.66 g) and the mixture was refluxed for 3 hours. The solvent was removed and the residue was purified by silica gel chromatography, eluted with 100% hexane to 50% EtOAc/hexane over 30 min.

21.6. (+/−)-9-Methyl-2,4,9,10-tetrahydro-4,9-epiminobenzo[4,5]cyclohepta[1,2-c]pyrazol-10-ol (79)

To a solution of compound 78 (104 mg) in MeOH/CH$_2$Cl$_2$ (2:1, 10 mL) were added a few drops of 3N HCl and Pd/C (10%, 40 mg). Hydrogenation was carried out on a Parr shaker at 50 psi of H$_2$ for 30 minutes. The catalyst was filtered off and the solvent was removed. The crude material was purified by preparative HPLC to afford the product as a white solid. $^1$H NMR (CD$_3$OD) δ 7.73 (s 1H), 7.48-7.37 (m, 4H), 5.94 (s, 1H), 5.17 (s 1H), 2.00 (s, 3H).

21.7. (+/−)-9-Methyl-1,11-bis{[4-(trifluoromethyl)phenyl]sulfonyl}-1,4,9,10-tetrahydro-4,9-epiminobenzo[4,5]cyclohepta[1,2-c]pyrazol-10-ol and (+/−)-9-Methyl-2,11-bis{[4-(trifluoromethyl)phenyl]sulfonyl}-2,4,9,10-tetrahydro-4,9-epiminobenzo[4,5]cyclohepta[1,2-c]pyrazol-10-ol (80)

To a solution of compound 79 (34.2 mg) in pyridine (0.6 mL) was added 4-trifluoromethylbenzenesulfonyl chloride (147.3 mg). The mixture was stirred at room temperature for 2 hours. The reaction was quenched with water and extracted with EtOAc. The organic layers were combined and washed with water, sat. aq. NaHCO$_3$, HCl, brine and dried over MgSO$_4$. After removal of the solvent, the bis-sulfonylated mixture of regioisomers was isolated as a yellow oil.

21.8. (+/−)-9-methyl-11-{[4-(trifluoromethyl)phenyl]sulfonyl}-1,4,9,10-tetrahydro-4,9-epiminobenzo[4,5]cyclohepta[1,2-c]pyrazol-10-ol (81)

To a solution of compound 80 (61 mg) in THF (3 mL) was added 0.5 N NaOH (3 mL). The resulting mixture was stirred at room temperature for 1 hour and concentrated in vacuo. The aqueous mixture was then extracted with EtOAc. The organic layers were combined, dried over MgSO$_4$, filtered and the solvent was removed to afford the product as an off-white solid.

21.9. (+/−)-9-methyl-11-{[4-(trifluoromethyl)phenyl]sulfonyl}-4,9-dihydro-4,9-epiminobenzo[4,5]cyclohepta[1,2-c]pyrazol-10(1H)-one (82)

H$_5$IO$_6$ (153 mg) was suspended in CH$_3$CN (3.1 mL) and CrO$_3$ (6.1 mg) was added to the mixture. The resulting mixture was stirred at room temperature for 15 min at which point the mixture became a homogeneous solution. To this solution was added a solution of the compound 8b (34 mg) in CH$_3$CN (5 mL) and a yellow precipitate formed. The mixture was stirred at room temperature overnight. Water and sat. aq. NaHCO$_3$ were added to quench the reaction and the solvent was concentrated to remove most of the CH$_3$CN. EtOAc was added and the organic layer was washed with water, brine and dried over MgSO$_4$. After evaporation of the solvent, an off-white solid was afforded as the pure product. $^1$H NMR (CDCl$_3$) δ 7.83 (d, 2H, J=8.4 Hz), 7.67 (s, 1H), 7.63 (d, 2H, J=8.4 Hz), 7.29-7.17 (m, 4H), 6.28 (s, 1H), 1.92 (s, 3H).

Example 22

Synthesis of 3,6-Dibromopicolinaldehyde (85)

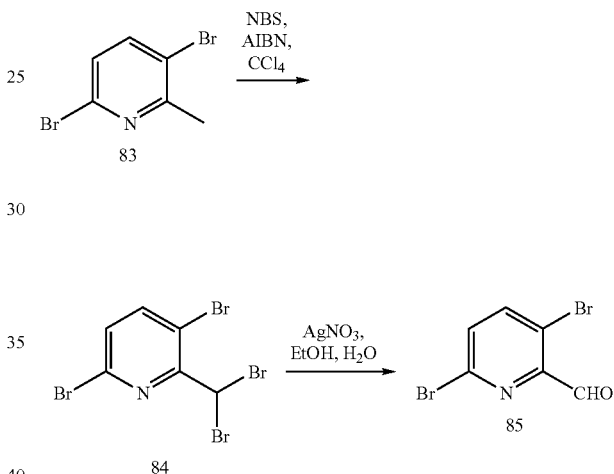

22.1. 3,6-Dibromo-2-(dibromomethyl)pyridine (84)

To a solution of 3,6-dibromo-2-methylpyridine (5.34 g, 21 mmol) in CCl$_4$ (50 mL) was added N-bromosuccinimide (7.57 g, 42 mmol) and 2,2'-azobis(2-methylpropionitrile) (0.70 g, 4.3 mmol). The mixture was heated at 70° C. overnight and cooled to room temperature. The solid was removed by filtration and the filtrate was concentrated under reduced pressure. The product was obtained after flash chromatography eluting with 0-10% EtOAc in hexane (8.17 g).

22.2. 3,6-Dibromopicolinaldehyde (85)

A solution of silver nitrate (8.5 g, 50 mmol) in water (26 mL) was added dropwise to a solution of compound 84 (8.17 g, 20 mmol) in refluxing EtOH (100 mL). The mixture was stirred at 80° C. for 5 hours. After the mixture was cooled to room temperature, it was diluted with water (100 mL), extracted with EtOAc (3×), dried over Na$_2$SO$_4$, filtered and concentrated under reduced pressure. The product was obtained after silica gel chromatography eluting with 0-40% EtOAc in hexane (2.85 g, 51% over two steps).

Example 23

Synthesis of 6-[3-(1H-Imidazol-1-yl)phenyl]-10-{[4-(trifluoromethyl)-phenyl]sulfonyl}-4,5,6,7,8,9-hexahydro-1H-4,8-epiminocycloocta[c]pyrazole (94)

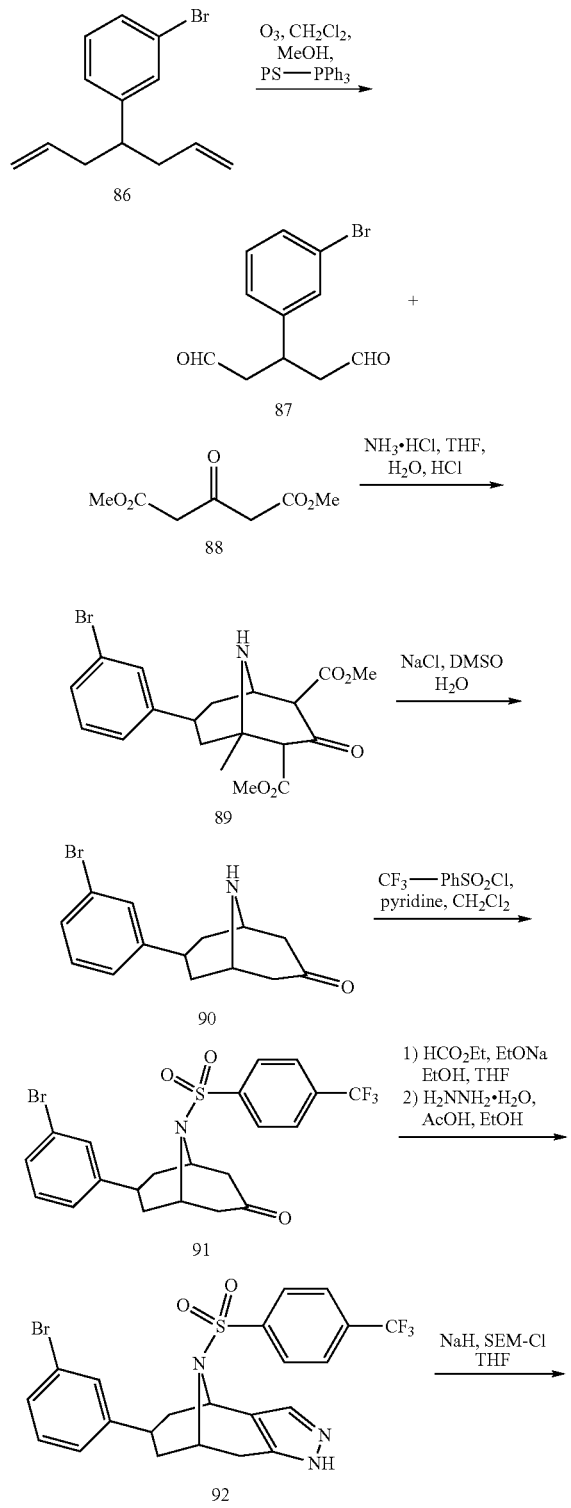

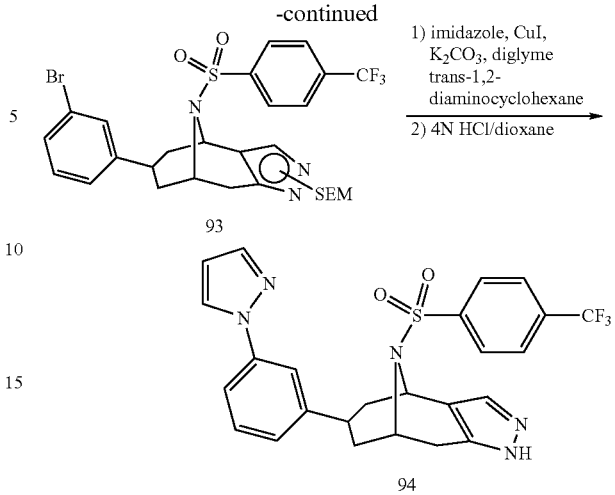

23.1. 3-(3-Bromophenyl)pentanedial (87)

Ozone was bubbled through a solution of 1-bromo-3-(hepta-1,6-dien-4-yl)benzene (6.14 g, 24.4 mmol) in $CH_3OH$ (10 ml) and $CH_2Cl_2$ (90 ml) at −78° C. for 30 min at which time the solution was pale blue. Nitrogen was then bubbled through the solution for 5 min and the solution became clear. Polymer support triphenylphosphine (20 g, 60.0 mmol) was added and the solution stirred at −78° C. for 30 min. The dry ice/acetone bath was removed and the heterogeneous mixture was stirred for 1 h. The heterogeneous mixture was filtered through Celite and the filtrate was concentrated to afford compound 87.

23.2. Dimethyl 7-(3-bromophenyl)-3-oxo-9-azabicyclo[3.3.1]nonane-2,4-dicarboxylate (89)

3-(3-Bromophenyl)pentanedial (87), dimethyl 3-oxopentanedioate (88) (5.78 g, 33.2 mmol), ammonium chloride (14.42 g, 270 mmol) in THF (100 ml), 10% aqueous HCl (100 ml), and water (100 ml) was stirred for 18 h. Sodium acetate was then added until the pH was 4-5. After stirring for 6 h, the solution was extracted with EtOAc. The combined organic extracts were washed with saturated aqueous $Na_2CO_3$, dried over $MgSO_4$, filtered and concentrated to afford compound 89.

23.3. 7-(3-Bromophenyl)-9-azabicyclo[3.3.1]nonan-3-one (90)

Dimethyl 7-(3-bromophenyl)-3-oxo-9-azabicyclo[3.3.1]nonane-2,4-dicarboxylate (89) and NaCl (61.22 g, 1.05 mol) in DMSO (200 ml) and water (10 ml) was placed into a preheated oil bath at 160° C. After stirring for 14 h, the solution was cooled to ambient temperature and exhaustively extracted with EtOAc. The combined organic extracts were dried over $MgSO_4$, filtered, and concentrated to afford compound 90.

23.4. 7-(3-Bromophenyl)-9-{[4-(trifluoromethyl)phenyl]sulfonyl}-9-azabicyclo[3.3.1]nonan-3-one (91)

7-(3-Bromophenyl)-9-azabicyclo[3.3.1]nonan-3-one (90) and 4-(trifluoromethyl)benzene-1-sulfonyl chloride (12.25 g, 50.1 mmol) in pyridine (100 ml) and CH₂Cl₂ (100 ml) was stirred for 24 h. The solution was concentrated and flash chromatographed with CH₂Cl₂ as the eluant to yield 2.29 g (19% yield over 4 steps) of compound 91 as a pink solid.

23.5. 6-(3-Bromophenyl)-10-{[4-(trifluoromethyl)phenyl]sulfonyl}-4,5,6,7,8,9-hexahydro-1H-4,8-epiminocycloocta[c]pyrazole (92)

21% NaOEt (6 ml, 16.1 mmol) was added to a solution of 7-(3-Bromophenyl)-9-(4-(trifluoromethyl)phenylsulfonyl)-9-azabicyclo[3.3.1]nonan-3-one (90) (2.28 g, 4.54 mmol) and ethyl formate (6 ml, 74.5 mmol) in THF (20 ml). The solution was placed into a preheated oil bath at 60° C. After stirring for 30 min, the solution was cooled to ambient temperature, diluted with saturated aqueous NH₄Cl, and extracted with EtOAc. The combined organic extracts were dried over MgSO₄, filtered, and concentrated to afford 7-(3-bromophenyl)-2-(hydroxymethylene)-9-(4-(trifluoromethyl)phenylsulfonyl)-9-azabicyclo[3.3.1]nonan-3-one. Hydrazine monohydrate (3 ml) was added to a solution of 7-(3-bromophenyl)-2-(hydroxymethylene)-9-(4-(trifluoromethyl)phenylsulfonyl)-9-azabicyclo[3.3.1]nonan-3-one and glacial acetic acid (1 ml) in EtOH (20 ml). After stirring for 18 h, the solution was concentrated to afford compound 92.

23.6. 6-(3-Bromophenyl)-10{[4-(trifluoromethyl)phenyl]sulfonyl}-1-{[2-(trimethylsilyl)ethoxy]methyl}-4,5,6,7,8,9-hexahydro-1H-4,8-epiminocyclocta-[c]pyrazole and 6-(3-Bromophenyl)-10{[4-(trifluoromethyl)phenyl]sulfonyl}-2-{[2-(trimethylsilyl)ethoxy]methyl}-4,5,6,7,8,9-hexahydro-2H-4,8-epiminocycloocta[c]-pyrazole (93)

60% Sodium hydride (0.41 g, 10.3 mmol) was added to a solution of compound 92 in THF (50 mL). After stirring for 1 h, SEM-Cl (3.0 ml, 17.0 mmol) was added. After stirring for 1 h, the solution was diluted with saturated aqueous NH₄Cl, and extracted with CH₂Cl₂. The combined organic extracts were dried over MgSO₄, filtered, and concentrated. The residue was flash chromatographed with 9:1, 4:1, 7:3, 3:2, 1:1, and 2:3 hexanes:EtOAc as the eluant to yield 2.06 g (69% yield over 3 steps) of the product as a orange oil.

23.7. 6-[3-(1H-Imidazol-1-yl)phenyl]-10-{[4-(trifluoromethyl)phenyl]sulfonyl}-4,5,6,7,8,9-hexahydro-1H-4,8-epiminocycloocta[c]pyrazole (94)

To a solution of compound 93 (0.07 mmol, 0.05 g) and pyrazole (1.52 mmol, 0.10 g) in dimethoxyethane (1 mL) was added copper iodide (0.02 mmol, 0.004 g), trans-1,2-diaminocyclohexane (0.02 mmol, 0.002 g), and potassium carbonate (0.76 mmol, 0.11 g). The reaction mixture was irradiated in a microwave for 35 minutes at 220° C. (300 W). The reaction mixture was diluted with MeOH (5 mL) and filtered through a pad of Celite. The filtrate was concentrated, and the resulting residue was dissolved in MeOH (2 mL). The temperature was decreased to 0° C. and 4N HCl in dioxane (3 mL) was added. The reaction mixture was warmed to room temperature and then plunged into a preheated 60° C. oil bath and stirred for 18 h. The reaction mixture was cooled to room temperature and concentrated. The resulting residue was dissolved in CH₂Cl₂ (5 mL) and the temperature was decreased to 0° C. The reaction mixture was diluted with saturated aqueous NaHCO₃ (5 mL) and stirred for 5 minutes. The two layers were then separated, and the organic layer was dried with MgSO₄, filtered and concentrated. The resulting residue was purified by silica gel chromatography (5% MeOH in CH₂Cl₂) to afford compound 94 (0.04 g, 56%).

Example 24

Synthesis of 3-(benzo[d][1,3]dioxol-5-yl)pentanedial (100)

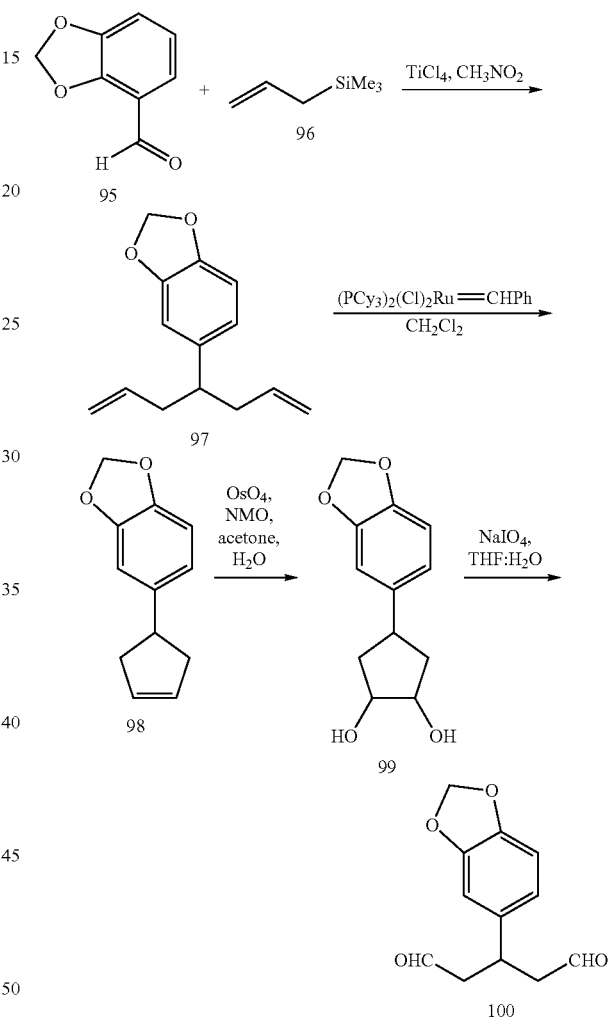

24.1. 5-(Hepta-1,6-dien-4-yl)benzo[d][1,3]dioxole (97)

To a solution of nitromethane (133.2 mmol, 7.15 g) and CH₂Cl₂ (100 mL) at −78° C. was added TiCl₄ (56.61 mmol, 10.73 g) and aldehyde 95 (33.10 mmol, 5.00 g). The reaction mixture was stirred for 20 minutes prior to the dropwise addition of allyltrimethylsilane (96) (66.61 mmol, 7.61 g). The reaction mixture was stirred at −78° C. for 18 h. The reaction mixture was poured directly into a solution of saturated aqueous NaCl and warmed to room temperature. The two layers were separated and the organic layer was dried with MgSO₄, filtered and concentrated. The resulting residue was purified by silica gel chromatography (10% EtOAc in hexanes) to afford compound 97 (1.49 g, 21%).

24.2. 5-(Cyclopent-3-enyl)benzo[d][1,3]dioxole (98)

To a solution of Grubbs I (0.345 mmol, 0.284 g) in $CH_2Cl_2$ was added diene 97 (6.91 mmol, 1.49 g). The reaction mixture was stirred at room temperature for 48 h. The reaction mixture was purified by flash chromatography (hexanes) to afford compound 98 (0.42 g, 32%).

24.3. 4-(Benzo[d][1,3]dioxol-5-yl)cyclopentane-1,2-diol (99)

To a solution of 4-methylmorpholine N-oxide (2.89 mmol, 0.339 g) and $OsO_4$ (0.013 mmol, 0.081 mL) in acetone (5 mL) and $H_2O$ (1.5 mL) at 0° C. was added cyclopentene 98 (2.22 mmol, 0.42 g). The reaction mixture was stirred for 18 h at room temperature. The temperature was then decreased to 0° C. and the reaction mixture was quenched with saturated aqueous $Na_2SO_3$. The reaction mixture was stirred for 3 h while warming to room temperature. The acetone was removed by rotary evaporation and the temperature was again decreased to 0° C. The pH was adjusted to pH 2 through the addition of concentrated $H_2SO_4$. The reaction mixture was washed with EtOAc (3×, 25 mL). The combined organic layers were dried with $MgSO_4$, filtered and concentrated. The resulting residue was purified by flash chromatography (EtOAc) to afford compound 99 (0.42 g, 86%).

24.4. 3-(Benzo[d][1,3]dioxol-5-yl)pentanedial (100)

To a solution of sodium periodate (1.91 mmol, 0.41 g) in THF (3 mL) and $H_2O$ (2 mL) at 0° C. was added diol 99 (1.91 mmol, 0.42 g). The reaction mixture was stirred at room temperature for 3 h. The reaction mixture was filtered, and the resulting dialdehyde 100 was used as is, as an aqueous solution.

Example 25

Synthesis of 5,5-dimethyl-9-{[4-(trifluoromethyl) phenyl]sulfonyl}-5,6,7,8-tetrahydro-2H-4,7-epiminopyrazolo[4,3-b]azepine and 6,6-dimethyl-9-{[4-(trifluoromethyl)phenyl]sulfonyl}-2,5,6,8-tetrahydro-4H-4,7-epiminopyrazolo[3,4-c]azepine (109a and 109b)

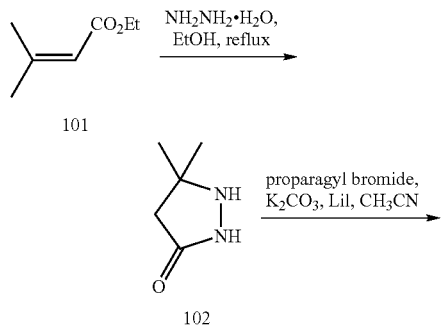

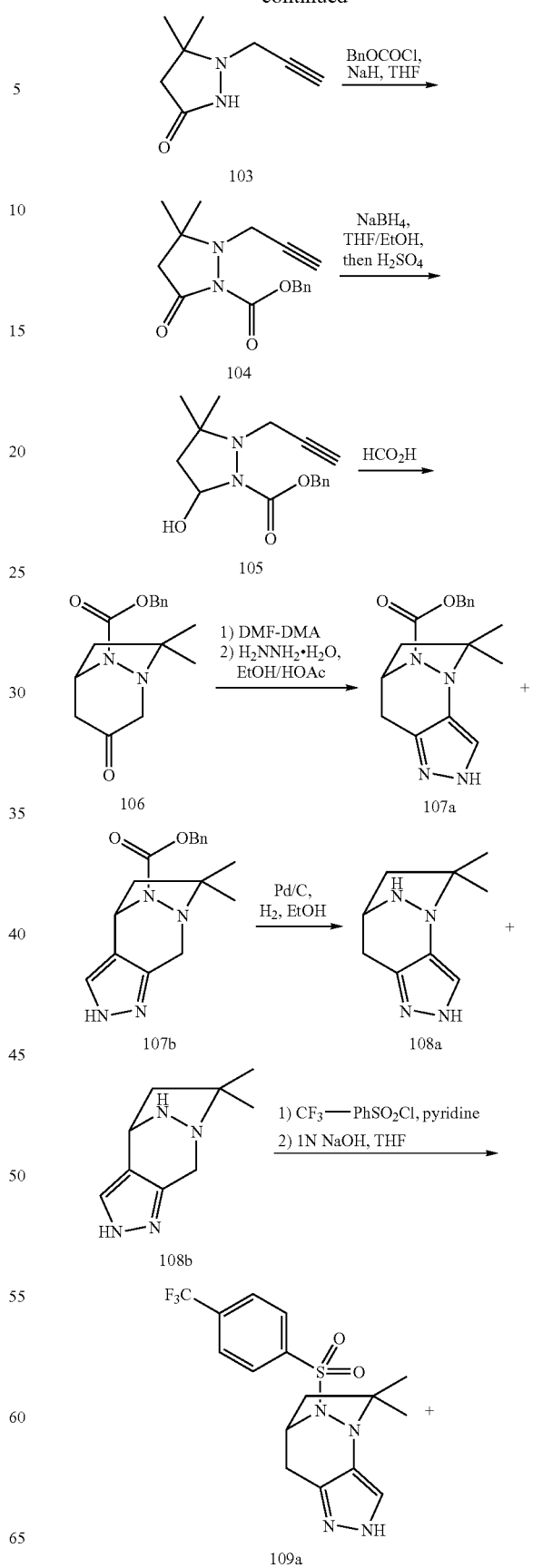

-continued

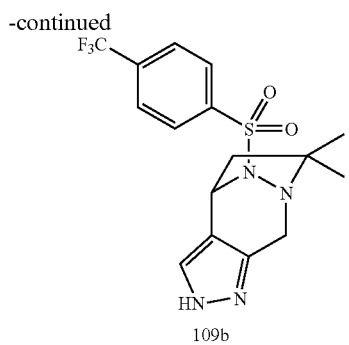
109b

25.1. 5,5-Dimethylpyrazolidin-3-one (102)

To a solution of hydrazine hydrate (4.4 g, 88 mmol) in EtOH (50 ml) was added ethyl 3,3-dimethylacrylate (101) (10.0 g, 78 mmol) in EtOH (40 mL) dropwise at room temperature over 1 h. The resulting reaction mixture was stirred at room temperature for 1 h and then heated to reflux for 4 hrs. Progress of the reaction was monitored through TLC. Upon complete consumption of starting material, solvent was evaporated and the crude material was purified through column chromatography eluting with MeOH/CH$_2$Cl$_2$ (1:25) to provide 2 (7.0 g) in 78% yield as colorless liquid, which slowly converted to solid upon long standing. $^1$H NMR (CDCl$_3$) δ 6.95 (bs, 1H), 4.09 (bs, 1H), 2.33 (s, 2H), 1.31 (s, 6H).

25.2. 5,5-Dimethyl-1-(prop-2-ynyl)pyrazolidin-3-one (103)

To a solution of 102 (10.0 g, 87.7 mmol) in acetonitrile (100 mL) was added K$_2$CO$_3$ (12.7 g, 92 mmol), LiI (0.59 g, 4.4 mmol) and propargyl bromide (11.0 g, 92 mmol). The resulting reaction mixture was refluxed for 24 h. Progress of the reaction was monitored using TLC. Upon completion of the starting material, the crude reaction mixture was filtered in a small pad of Celite and the solvent was evaporated under vacuum at room temperature. The crude material was passed through column eluting with EtOAc/hexane (3:7) to afford 103 (5.9 g) in 45% yield as a crystalline, pale yellow solid. $^1$H NMR (CDCl$_3$) δ 7.45 (bs, 1H), 3.53 (d, J=2.2 Hz, 2H), 2.46 (s, 2H), 2.29 (t, J=2.6 Hz, 1H), 1.35 (s, 6H).

25.3. Benzyl 3,3-dimethyl-5-oxo-2-(prop-2-ynyl)pyrazolidine-1-carboxylate (104)

To a suspension of NaH (1.7 g, 71 mmol) in THF was added 103 (9.0 g, 59.2 mmol) dropwise at 0° C. The resulting slurry was stirred for additional 1 h at 0° C. followed by introduction of benzyl chloroformate (30.4 g, 177.7 mmol) at the same temperature. The resulting reaction mixture was slowly warmed up to room temperature and stirred for another 2 h. Upon complete consumption of starting material, monitored through TLC, the reaction mixture was quenched with saturated NH$_4$Cl. The reaction mixture was extracted with EtOAc (50×2 mL), washed with water (30 mL), brine and dried over Na$_2$SO$_4$. Solvent was evaporated under vacuum at room temperature and the crude residue was purified by column chromatography eluting with EtOAc/hexanes (1:10) to afford 104 (8.8 g) in 52% yield as a colorless oil. $^1$H NMR (CDCl$_3$) δ 7.48-7.27 (m, 5H), 5.35 (s, 2H), 3.85 (s, 2H), 2.79 (bs, 2H), 2.29 (s, 1H), 1.38 (s, 6H).

25.4. Benzyl 5-hydroxy-3,3-dimethyl-2-(prop-2-ynyl)pyrazolidine-1-carboxylate (105)

To a stirred solution of 104 (3.0 g, 10.48 mmol) in THF (75 mL) and EtOH (50 mL), sodium borohydride (2.6 g, 68.1 mmol) was added at −20° C. followed by few drops of conc. H$_2$SO$_4$ and stirred for 3 h at −20° C. The reaction mixture was quenched with sat. NaHCO$_3$ solution at −20° C. and allowed to reach room temperature. The reaction mixture was concentrated under reduced pressure and the residue was dissolved in EtOAc. The organic layer was washed with water, dried over Na$_2$SO$_4$ and concentrated under reduced pressure to get crude compound which was purified through silica gel column chromatography, eluted with 15% EtOAc/hexanes to get 105 (2.3 g, 76%). $^1$H NMR (CDCl$_3$) δ 7.26-7.37 (m, 5H), 5.76 (m, 1H), 5.25 (s, 2H), 3.80-3.60 (m, 3H), 2.48-2.38 (m, 1H), 2.22 (m, 2H), 1.38 (s, 3H), 1.18 (s, 3H).

25.5. Benzyl 7,7-dimethyl-3-oxo-1,8-diazabicyclo [3.2.1]octane-8-carboxylate (106)

A stirred solution of 105 (2.5 g, 8.6 mmol) in formic acid (10 mL) was heated at 100° C. for 5 h. After complete consumption of 105 (as monitored by TLC), formic acid was evaporated under reduced pressure. The residue was dissolved in EtOAc (100 mL) and washed with saturated with NaHCO$_3$ solution (2×50 mL), water (50 mL) and brine solution (50 mL). The organic layer was dried over anhydrous Na$_2$SO$_4$ and concentrated under reduced pressure to give the crude compound which was purified through preparative HPLC to afford 106 (0.52 g, 18%). $^1$H NMR (CDCl$_3$) δ 7.30-7.40 (m, 5H), 5.25 (s, 2H), 3.62 (m, 1H), 2.76 (m, 1H), 2.42 (m, 1H), 2.20 (m, 1H), 2.09 (s, 1H), 1.65 (m, 1H), 1.22 (s, 3H), 1.13 (s, 3H).

25.6. Benzyl 5,5-dimethyl-5,6,7,8-tetrahydro-2H-4, 7-epiminopyrazolo[4,3-b]azepine-9-carboxylate and Benzyl 6,6-dimethyl-2,5,6,8-tetrahydro-4H-4,7-epiminopyrazolo[3,4-c]azepine-9-carboxylate (107a and 107b)

A DMF-DMA solution (700 μL) of 106 (53 mg, 0.18 mmol) was heated at 100° C. for 2 hours at which time LC/MS analysis determined no starting material remained. The reaction mixture was cooled and diluted with water and EtOAc. The separated organic phase was washed with water (2×20 mL), brine (1×20 mL), dried (MgSO$_4$) and filtered. Concentration yielded 62 mg (0.18 mmol) of an oil which was dissolved in 25:1 EtOH/glacial HOAc (1 mL) and treated with hydrazine hydrate (43 μL, 0.90 mmol). After a few hours additional hydrazine hydrate was added (84 μL, 1.8 mmol) and the reaction mixture was allowed to stir overnight at room temperature. The reaction was then concentrated and the residue was dissolved in EtOAc and washed with sat NaHCO$_3$ (2×20 mL), brine (1×20 mL), dried (MgSO$_4$), filtered and concentrated to give 34 mg of a golden oil which was purified by preparative HPLC to give 107a and 107b as approximately a 4:1 mixture of pyrazole regioisomers as determined by HPLC analysis.

25.7. 5,5-Dimethyl-5,6,7,8-tetrahydro-2H-4,7-epiminopyrazolo[4,3-b]azepine and 6,6-Dimethyl-2,5,6,8-tetrahydro-4H-4,7-epiminopyrazolo[3,4-c]azepine (108a and 108b)

A Parr bottle was charged with 107 (132 mg, 0.42 mmol) 10 wt % Pd/C (13 mg), and absolute EtOH (5 mL) and placed under 35 psi H$_2$. After shaking overnight, the reaction mixture was filtered through a pad of Celite and concentrated to give 81 mg (100%) of 108a and 108b as an oil which was used without purification.

25.8. 5,5-dimethyl-9-{[4-(trifluoromethyl)phenyl]sulfonyl}-5,6,7,8-tetrahydro-2H-4,7-epiminopyrazolo[4,3-b]azepine and 6,6-dimethyl-9-{[4-(trifluoromethyl)phenyl]sulfonyl}-2,5,6,8-tetrahydro-4H-4,7-epiminopyrazolo[3,4-c]azepine (109a and 109b)

The regioisomeric mixture of pyrazoles 108a and 108b (81 mg, 0.45 mmol) was dissolved in pyridine (4.5 mL) and chilled to 0° C. in an ice bath to which was added 4-(trifluoromethyl)benzenesulfonyl chloride (1.1 g, 4.54 mmol). The reaction was warmed to room temperature and stirred overnight. Additional 4-(trifluoromethyl)benzenesulfonyl chloride (444 mg, 1.82 mmol) was added to the reaction and stirring was continued for 48 hours. The reaction mixture was then diluted with EtOAc and water. The organic portion was washed with water (1×20 mL), 0.5 N HCL (3×15 mL), water (1×10 mL), sat NaHCO$_3$ (3×20 mL) brine (1×20 mL), dried (MgSO$_4$), filtered and concentrated to a thick yellow oil. The crude product was purified by preparative thin later chromatography eluting with 3:1 hexanes/EtOAc to give the bis-sulfonylated pyrazoles as a thick clear oil: (MH$^+$)$^+$=595.1. The purified product was dissolved in THF (3 mL) to which was added 1N NaOH (1 mL). The two phase solution was rigorously stirred overnight at which time LC/MS analysis determined no starting material remained. The reaction mixture was concentrated and the residue was dissolved in EtOAc and washed with water (3×15), brine (1×10), dried (MgSO$_4$) filtered and concentrated to give 82 mg (85%) of 109a and 109b as a 5:1 mixture of pyrazoles. $^1$H-NMR (Major pyrazole regioisomer) (CDCl$_3$) δ 7.92 (d, J=8.4 Hz, 2H), 7.60 (d, J=8.4 Hz, 2H), 7.28 (s, 1H), 4.87 (m, 1H), 3.09 (dd, J=16.5, 4.8 Hz, 1H), 2.51 (d, J=16.2 Hz, 1H), 2.40 (m, 1H), 1.55 (d, J=12.0 Hz, 1H), 1.28 (s, 3H), 1.02 (s, 3H).

Example 26

Synthesis of 5-cyclopropyl-9-{[4-(trifluoromethyl)phenyl]sulfonyl}-2,4,5,6,7,8-hexahydro-4,7-epiminocyclohepta[c]pyrazole (119)

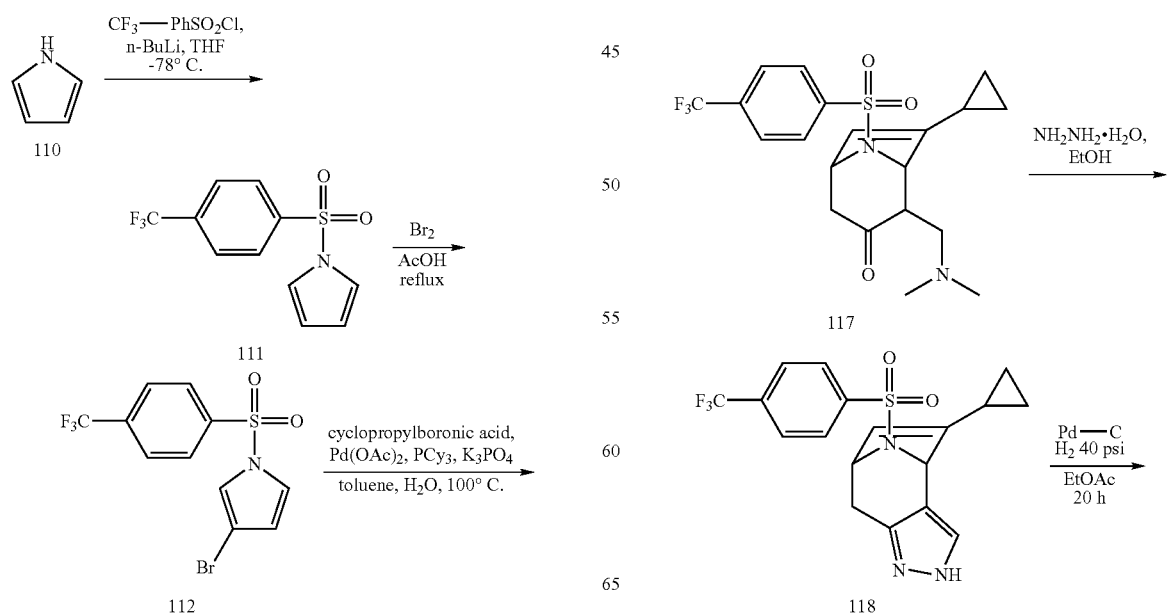

-continued

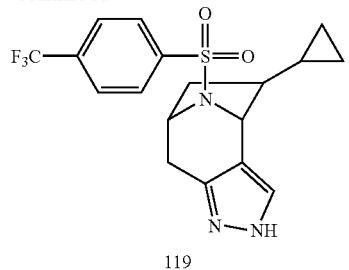

119

26.1. 1-(4-(Trifluoromethyl)phenylsulfonyl)-1H-pyrrole (111)

n-BuLi (56 mL, 89.7 mmol) was added to a solution of 1H-pyrrole (6.02 g, 89.7 mmol) in THF (179 mL) at −78° C. over 10 minutes. 4-(trifluoromethyl)benzene-1-sulfonyl chloride (26.3 g, 107.6 mmol) was dissolved in THF (20 mL) and added to the reaction mixture over 30 minutes. The reaction was stirred for 30 minutes then allowed to warm to room temperature and stirred for a further 18 h. The solution was diluted with EtOAc washed with brine and the organic phase was separated, dried (Na$_2$SO$_4$), filtered and concentrated under vacuum and purified on a silica gel column (eluant hexane/EtOAc 99/1 to 4/1, v/v) to give compound 111 (21.4 g, 77.7 mmol, 87%). MS (ESI) 276.1 (M+H).

26.2. 3-Bromo-1-(4-(trifluoromethyl)phenylsulfonyl)-1H-pyrrole (112)

Bromine (4.12 mL, 80.1 mmol) was added to a solution of 1-(4-(trifluoromethyl)phenylsulfonyl)-1H-pyrrole (111) (21 g, 76.2 mmol) in acetic acid (254 mL) and the resulting solution was heated to 100° C. for 1 h. The mixture was diluted with CH$_2$Cl$_2$ and poured slowly into ice cold aqueous sodium hydroxide (3 N). The solution was adjusted to pH 7 with aqueous sodium hydroxide (3 N), extracted with CH$_2$Cl$_2$. The organic phase was separated, dried (Na$_2$SO$_4$), filtered and concentrated under vacuum and purified on a silica gel column (eluant hexane/EtOAc, 4/1, v/v) to give compound 112 (20.4 g, 57.6 mmol, 75%). MS (ESI) 354.0 (M+H).

26.3. 3-Cyclopropyl-1-(4-(trifluoromethyl)phenyl-sulfonyl)-1H-pyrrole (113)

Cyclopropyl boronic acid (1.6 g, 18.7 mmol), palladium (II) acetate (323 mg, 1.44 mmol), tricyclohexylphosphine (808 mg, 2.88 mmol) and potassium phosphate (10.7 g, 50.5 mmol) were added to a solution of 3-bromo-1-(4-(trifluoromethyl)phenylsulfonyl)-1H-pyrrole (5.11 g, 14.4 mmol) in toluene/H$_2$O (75 mL, 19/1). The resulting suspension was evacuated and purged with nitrogen three times and then placed in an oil bath pre-heated to 100° C. The reaction was stirred for 6 h and was subsequently concentrated under vacuum. The residue was purified on a silica gel column (eluant hexane/EtOAc, 9/1, v/v) to give compound 113 (3.21 g, 10.1 mmol, 71%). MS (ESI) 316.1 (M+H).

26.4. 2,4-Dibromo-6-cyclopropyl-8-(4-(trifluoromethyl)phenylsulfonyl)-8-azabicyclo[3.2.1]oct-6-en-3-one (115)

Diethyl zinc (18.1 mL, 18.1 mmol of a 1M solution in hexane) was added to a solution of 3-cyclopropyl-1-(4-(trifluoromethyl)phenylsulfonyl)-1H-pyrrole (3.18 g, 10.1 mmol) and tetrabromoacetone (7.53 g, 20.1 mmol) in toluene at −10° C. The reaction mixture was stirred at room temperature for 17 h and was subsequently diluted with EtOAc and washed with saturated aqueous Na$_2$CO$_3$. The organic phase was separated, dried (Na$_2$SO$_4$), filtered, concentrated under vacuum and purified on a silica gel column (eluant hexane/EtOAc, 9/1 to 7/3, v/v) to give compound 115 (3.31 g, 6.25 mmol, 62%). MS (ESI) 530.0 (M+H).

26.5. 6-cyclopropyl-8-{[4-(trifluoromethyl)phenyl]sulfonyl}-8-aza bicyclo[3.2.1]oct-6-en-3-one (116)

Zinc-copper couple (3.21 g, 24.8 mmol) was added to a solution of 2,4-dibromo-6-cyclopropyl-8-(4-(trifluoromethyl)phenylsulfonyl)-8-azabicyclo[3.2.1]oct-6-en-3-one (3.29 g, 6.21 mmol) in a saturated methanolic solution of NH$_4$Cl (24 mL). The reaction mixture was stirred at room temperature for 4 h and was subsequently filtered though Celite. The filtrate was concentrated under vacuum, re-dissolved in CH$_2$Cl$_2$ and washed with saturated aqueous Na$_2$CO$_3$. The organic phase was separated, dried (Na$_2$SO$_4$), filtered, concentrated under vacuum and purified on a silica gel column (eluant hexane/EtOAc, 9/1 to 1/1, v/v) to give compound 116 (1.68 g, 4.52 mmol, 73%). MS (ESI) 372.1 (M+H).

26.6. 7-cyclopropyl-2-[(dimethylamino)methylidene]-8-{[4-(trifluoromethyl)phenyl]sulfonyl}-8-azabicyclo[3.2.1]oct-6-en-3-one (117)

6-Cyclopropyl-8-(4-(trifluoromethyl)phenylsulfonyl)-8-azabicyclo[3.2.1]oct-6-en-3-one (1.02 g, 2.74 mmol), was dissolved in DMF-DMA (6 mL) and heated to 100° C. for 4 h. The reaction mixture was concentrated under vacuum to give compound 117. MS (ESI) 427.1 (M+H)

26.7. 5-cyclopropyl-9-{[4-(trifluoromethyl)phenyl]sulfonyl}-2,4,7,8-tetrahydro-4,7-epiminocyclohepta[c]pyrazole (118)

7-Cyclopropyl-2-((dimethylamino)methylene)-8-(4-(trifluoromethyl)phenylsulfonyl)-8-azabicyclo[3.2.1]oct-6-en-3-one (1.16 g, 2.74 mmol) was dissolved in ethanol (13 mL) and hydrazine monohydrate (1.3 mL, 27.4 mmol) was added. The resulting solution was stirred at room temperature for 1 h after which EtOAc was added. The solution was washed with brine, dried (Na$_2$SO$_4$), filtered, concentrated under vacuum and purified on a silica gel column (eluant hexane/EtOAc, 3/1 to 1/1) to give compound 118 as a mixture of regioisomers. MS (ESI) 395.1 (M+H).

26.8. 5-cyclopropyl-9-{[4-(trifluoromethyl)phenyl]sulfonyl}-2,4,5,6,7,8-hexahydro-4,7-epiminocyclohepta[c]pyrazole (119)

A suspension of 7-cyclopropyl-2-((dimethylamino)methylene)-8-(4-(trifluoromethyl)phenylsulfonyl)-8-azabicyclo[3.2.1]oct-6-en-3-one (107 mg, 0.27 mmol) and Pd/C (20 mg) in EtOAc (2 mL) was stirred under an atmosphere of hydrogen (30 psi) for 18 h. The resulting suspension was filtered through Celite and concentrated under vacuum. The residue was purified by preparative HPLC to give compound 119. MS (ESI) 398.1 (M+H).

Example 27

Synthesis of 1-[4-(10-{[4-(trifluoromethyl)phenyl]sulfonyl}-4,5,6,7,8,9-hexahydro-1H-4,8-epiminocycloocta[c]pyrazol-6-yl)phenyl]ethanone (122)

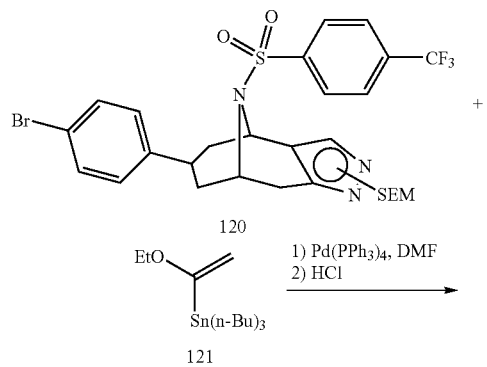

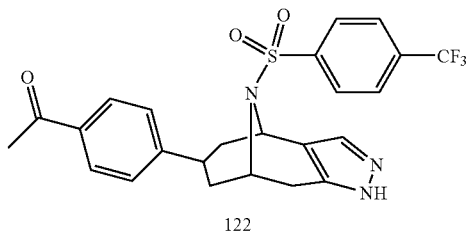

122

Tetrakis(triphenylphosphine)palladium (200 mg, 173 umol) was added to a solution of compound 120 (170 mg, 324 umol) and tributyl-(1-ethoxy-vinyl)-stannane (121) (610 mg, 1.69 mmol) in DMF (5 ml) and placed into a preheated oil bath at 90° C. After stirring for 18 h, the solution was cooled to ambient temperature and 10% aqueous HCl was added. After stirring for another 18 h, the solution was filtered and the crude product was purified by HPLC to afford the title compound 122.

The compounds in Table 1 were prepared essentially according to the methods and procedures described above.

| Ex. No. | Structure/Compound Name/Mass Spec (M + H)/ $^1$H-NMR (300 MHz)/Experimental Procedures | γAPP IC$_{50}$ (nM) |
|---|---|---|
| 28 | ethyl 10-[(4-chlorophenyl)sulfonyl]-1,4,5,7,8,9-hexahydro-6H-4,8-epiminopyrazolo[4,3-d]azocine-6-carboxylate; MS 411.0. Prepared by treatment of 10-[(4-chlorophenyl)sulfonyl]-4,5,6,7,8,9-hexahydro-1H-4,8-epiminopyrazolo[4,3-d]azocine (WO2007/022502) with ethyl chloroformate followed by hydrolysis of the N-ethylcarbamoylpyrazole with NaOH. | C |
| 29 | 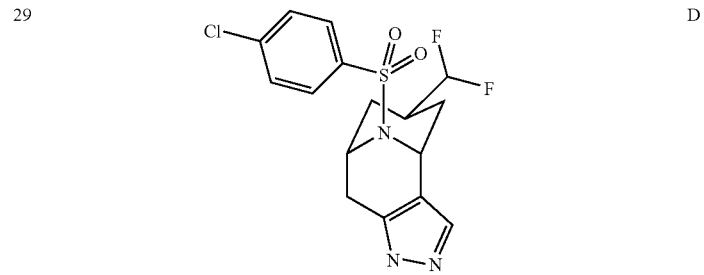<br>10-[(4-chlorophenyl)sulfonyl]-6-(difluoromethyl)-4,5,6,7,8,9-hexahydro-1H-4,8-epiminocycloocta[c]pyrazole; MS 388.0. Prepared by sulfonylation of ethyl 10-[(4-chlorophenyl)sulfonyl]-4,5,6,7,8,9-hexahydro-1H-4,8-epiminocycloocta[c]pyrazole-6-carboxylate (WO2007/022502) with 4-chlorobenzenesulfonyl chloride followed by reduction of the ester with LiBH$_4$, oxidation with Dess-Martin periodinane, and treatment DAST. The N-sulfonylpyrazole was then hydrolyzed with NaOH. | D |
| 30 | 1-{10-[(4-chlorophenyl)sulfonyl]-1,4,5,7,8,9-hexahydro-6H-4,8-epiminopyrazolo[4,3-d]azocin-6-yl}propan-1-one; MS 395.0. Prepared from 10-[(4-chlorophenyl)sulfonyl]-4,5,6,7,8,9-hexahydro-1H-4,8-epiminopyrazolo[4,3-d]azocine (WO2007/022502) and propionic anhydride, and hydrolysis of the N-propionoylpyrazole with NaOH. | B |

-continued

| Ex. No. | Structure/Compound Name/Mass Spec (M + H)/ ¹H-NMR (300 MHz)/Experimental Procedures | γAPP IC$_{50}$ (nM) |
|---|---|---|
| 31 | 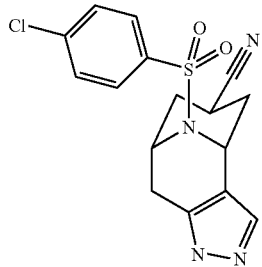<br>(±)-10-[(4-chlorophenyl)sulfonyl]-4,5,6,7,8,9-hexahydro-1H-4,8-epiminocycloocta[c]pyrazole-6-carbonitrile; MS 363.1. ¹H NMR (CDCl$_3$) δ 7.62 (d, J = 8.8 Hz, 2H), 7.43 (s, 1H), 7.35 (d, J = 8.8 Hz, 2H), 5.38 (bs, 1H), 4.61-4.52 (m, 1H), 2.93 (dd, J = 17.0, 6.6 Hz, 1H), 2.71-2.52 (m, 2H), 2.32-1.98 (m, 4H). Prepared as described in Example 18. | D |
| 32 | 2-methoxyethyl 10-[(4-chlorophenyl)sulfonyl]-1,4,5,7,8,9-hexahydro-6H-4,8-epiminopyrazolo[4,3-d]azocine-6-carboxylate; MS 441.0. Prepared by treatment of 10-[(4-chlorophenyl)sulfonyl]-4,5,6,7,8,9-hexahydro-1H-4,8-epiminopyrazolo[4,3-d]azocine (WO2007/022502) with 2-methoxyethyl chloroformate followed by hydrolysis of the N-methoxyethylcarbamoyl-pyrazole with NaOH. | B |
| 33 | 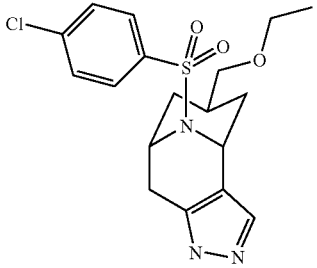<br>10-[(4-chlorophenyl)sulfonyl]-6-(ethoxymethyl)-4,5,6,7,8,9-hexahydro-1H-4,8-epiminocycloocta[c]pyrazole; MS 396.1. Prepared by protection of ethyl 10-[(4-chlorophenyl)sulfonyl]-4,5,6,7,8,9-hexahydro-1H-4,8-epiminocycloocta[c]pyrazole-6-carboxylate (WO2007/022502) with SEM-Cl followed by reduction of the ester with LiBH4, and alkylation with ethyl iodide and treatment with 4N HCl in dioxane. | D |
| 34 | 10-[(4-chlorophenyl)sulfonyl]-6-(methoxymethyl)-4,5,6,7,8,9-hexahydro-1H-4,8-epiminocycloocta[c]pyrazole; MS 382.1. Prepared by protection of ethyl 10-[(4-chlorophenyl)sulfonyl]-4,5,6,7,8,9-hexahydro-1H-4,8-epiminocycloocta[c]pyrazole-6-carboxylate (WO2007/022502) with SEM-Cl followed by reduction of the ester with LiBH4, and alkylation with methyl iodide and treatment with 4N HCl in dioxane. | D |
| 35 | propan-2-yl 10-[(4-chlorophenyl)sulfonyl]-1,4,5,7,8,9-hexahydro-6H-4,8-epiminopyrazolo[4,3-d]azocine-6-carboxylate; MS 425.0. Prepared by treatment of 10-[(4-chlorophenyl)sulfonyl]-4,5,6,7,8,9-hexahydro-1H-4,8-epiminopyrazolo[4,3-d]azocine (WO2007/022502) with isopropyl chloroformate followed by hydrolysis of the N-isopropylcarbamoylpyrazole with NaOH. | A |
| 36 | 10-[(4-chlorophenyl)sulfonyl]-6-(methylsulfonyl)-4,5,6,7,8,9-hexahydro-1H-4,8-epiminopyrazolo[4,3-d]azocine; MS 417.0. Prepared by treatment of 10-[(4-chlorophenyl)sulfonyl]-4,5,6,7,8,9-hexahydro-1H-4,8-epiminopyrazolo-[4,3-d]azocine (WO2007/022502) with methanesulfonyl-chloride followed by hydrolysis of the resulting N-sulfonylpyrazole with NaOH. | A |
| 37 | (±)-10-[(4-chlorophenyl)sulfonyl]-6-(3-methyl-1,2,4-oxadiazol-5-yl)-4,5,6,7,8,9-hexahydro-1H-4,8-epiminocycloocta[c]pyrazole; MS 420.1. ¹H NMR (CDCl$_3$) δ 7.67 (d, J = 8.8 Hz, 2H), 7.52 (s, 1H), 7.39 (d, J = 8.8 Hz, 2H), 5.43 (bs, 1H), 4.66 (bs, 1H), 3.06 (m, 1H), 2.72 (d, J = 17.6 Hz, 1H), 2.34 (s, 3H), 2.32-2.09 (m, 4H). Prepared as described in Example 16. | D |
| 38 | 10-[(4-chlorophenyl)sulfonyl]-6-(cyclopropylsulfonyl)-4,5,6,7,8,9-hexahydro-1H-4,8-epiminopyrazolo[4,3-d]azocine; MS 453.0. Prepared by treatment of 10-[(4-chlorophenyl)sulfonyl]-4,5,6,7,8,9-hexahydro-1H-4,8-epimino-pyrazolo[4,3-d]azocine (WO2007/022502) with cyclopropanesulfonylchloride followed by hydrolysis of the resulting N-sulfonylpyrazole with NaOH. | A |

-continued

| Ex. No. | Structure/Compound Name/Mass Spec (M + H)/ ¹H-NMR (300 MHz)/Experimental Procedures | γAPP IC$_{50}$ (nM) |
|---|---|---|
| 39 | 10-[(4-chlorophenyl)sulfonyl]-N,N-dimethyl-1,4,5,7,8,9-hexahydro-6H-4,8-epiminopyrazolo[4,3-d]azocine-6-carboxamide; MS 410.1. ¹H NMR (CDCl3) δ 7.63 (d, J = 8.8 Hz, 2H), 7.36 (s, 1H), 7.34 (d, J = 8.8 Hz, 2H), 5.18 (s, 1H), 4.34 (s, 1H), 2.82 (d, J = 13.2 Hz, 1H), 3.46-3.33 (m, 2H), 3.21 (dd, J = 13, 3.2 Hz, 1H), 2.93-2.78 (m, 2H), 2.51 (s, 6H). Prepared by treatment of 10-[(4-chlorophenyl)sulfonyl]-4,5,6,7,8,9-hexahydro-1H-4,8-epiminopyrazolo[4,3-d]azocine (WO2007/022502) with N,N-dimethylcarbamoylchloride followed by hydrolysis of the resulting N,N-dimethylcarbamoylpyrazole with NaOH. | C |
| 40 | 10-[(4-chlorophenyl)sulfonyl]-6-(ethylsulfonyl)-4,5,6,7,8,9-hexahydro-1H-4,8-epiminopyrazolo[4,3-d]azocine; MS 431.0. Prepared by treatment of 10-[(4-chlorophenyl)sulfonyl]-4,5,6,7,8,9-hexahydro-1H-4,8-epiminopyrazolo-[4,3-d]azocine (WO2007/022502) with ethanesulfonylchloride followed by hydrolysis of the resulting N-sulfonylpyrazole with NaOH. | A |
| 41 | (−)-10-[(4-chlorophenyl)sulfonyl]-4,5,6,7,8,9-hexahydro-1H-4,8-epiminocycloocta[c]pyrazole-6-carbonitrile; MS 363.1. ¹H NMR (CDCl$_3$) δ 7.62 (d, J = 8.8 Hz, 2H), 7.43 (s, 1H), 7.35 (d, J = 8.8 Hz, 2H), 5.38 (bs, 1H), 4.61-4.52 (m, 1H), 2.93 (dd, J = 17.0, 6.6 Hz, 1H), 2.71-2.52 (m, 2H), 2.32-1.98 (m, 4H). Prepared as described in Example 18 followed by chiral chromatographic separation of stereoisomers. | A |
| 42 | (+)-10-[(4-chlorophenyl)sulfonyl]-4,5,6,7,8,9-hexahydro-1H-4,8-epiminocycloocta[c]pyrazole-6-carbonitrile; MS 363.1. ¹H NMR (CDCl$_3$) δ 7.62 (d, J = 8.8 Hz, 2H), 7.43 (s, 1H), 7.35 (d, J = 8.8 Hz, 2H), 5.38 (bs, 1H), 4.61-4.52 (m, 1H), 2.93 (dd, J = 17.0, 6.6 Hz, 1H), 2.71-2.52 (m, 2H), 2.32-1.98 (m, 4H). Prepared as described in Example 18 followed by chiral chromatographic separation of stereoisomers. | D |
| 43 | (±)-10-[(4-chlorophenyl)sulfonyl]-6-(1-methoxycyclopropyl)-4,5,6,7,8,9-hexahydro-1H-4,8-epiminocycloocta[c]pyrazole; MS 408.1. ¹H NMR (CDCl$_3$) δ 7.62 (d, J = 8.6 Hz, 2H), 7.34 (s, 1H), 7.32 (d, J = 8.8 Hz, 2H), 5.35 (bs, 1H), 4.57 (d, J = 7.9 Hz, 1H)), 3.05 (s, 3H), 2.86 (dd, J = 17.1, 6.6 Hz, 1H), 2.51 (d J = 17.1, 1H), 1.75-1.61 (m, 5H), 0.66-0.63 (m, 2H), 0.33-0.29 (m, 2H). Prepared as described in Example 16 using compound 56 of Example 17. | C |

| Ex. No. | Structure/Compound Name/Mass Spec (M + H)/ ¹H-NMR (300 MHz)/Experimental Procedures | γAPP IC₅₀ (nM) |
|---|---|---|
| 44 | 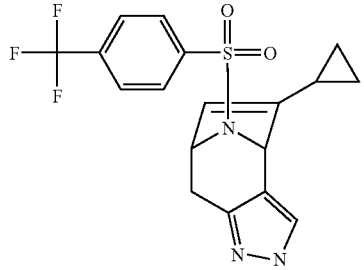<br>5-cyclopropyl-9-{[4-(trifluoromethyl)phenyl]sulfonyl}-1,4,7,8-tetrahydro-4,7-epiminocyclohepta[c]pyrazole; MS 396.1. Major isomer: ¹H NMR (CDCl₃) δ 8.01 (d, J = 8.7 Hz, 2H), 7.75 (d, J = 8.7 Hz, 2H), 7.49 (s, 1H), 5.36-5.31 (m, 1H), 5.05 (s, 1H), 4.94-4.92 (m, 1H), 3.24-3.21 (m, 1H), 2.65 (d, J = 16.5 Hz, 1H), 1.16-1.11 (m, 1H), 0.66-0.59 (m, 2H), 0.17-0.65 (m, 2H). Minor isomer: ¹H NMR (CDCl₃) δ 8.01 (d, J = 8.7 Hz, 2H), 7.75 (d, J = 8.7 Hz, 2H), 7.42 (s, 1H), 5.53-5.52 (m, 1H), 5.07-5.05 (m, 1H), 4.70 (d, J = 5.4 Hz, 1H), 3.30-3.28 (m, 1H), 2.86 (d, J = 16.5 Hz, 1H), 1.16-1.11 (m, 1H), 0.66-0.59 (m, 2H), 0.17-0.65 (m, 2H). Prepared as described in Example 26. | D |
| 45 | 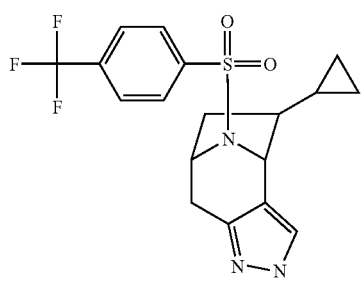<br>5-cyclopropyl-9-{[4-(trifluoromethyl)phenyl]sulfonyl}-1,4,5,6,7,8-hexahydro-4,7-epiminocyclohepta[c]pyrazole; MS 398.1. Major isomer: ¹H NMR (CDCl₃) δ 7.91 (d, J = 8.0 Hz, 2H), 7.68 (d, J = 8.0 Hz, 2H), 7.56 (s, 1H), 4.95 (d, J = 5.5 Hz, 1H), 4.56-4.53 (m, 1H), 3.09 (dd, J = 16.7, 4.4 Hz, 1H), 2.65 (d, J = 16.7 Hz, 1H), 1.82-1.77 (m, 2H), 1.64-1.62 (m, 1H), 0.58-0.42 (m, 2H), 0.27-0.35 (m, 3H). Minor isomer: ¹H NMR (CDCl₃) δ 7.91 (d, J = 8.0 Hz, 2H), 7.68 (d, J = 8.0 Hz, 2H), 7.42 (s, 1H), 5.13 (d, J = 6.4 Hz, 1H), 4.65-4.58 (m, 1H), 3.23 (d, J = 16.7, 1H), 2.52-2.46 (m, 1H), 1.82-1.77 (m, 2H), 1.64-1.62 (m, 1H), 0.58-0.42 (m, 2H), 0.27-0.35 (m, 3H). Prepared as described in Example 26. | D |
| 46 | 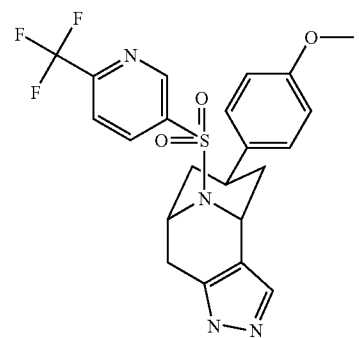<br>(±)-6-(4-methoxyphenyl)-10-{[6-(trifluoromethyl)pyridin-3-yl]sulfonyl}-4,5,6,7,8,9-hexahydro-1H-4,8-epiminocycloocta[c]pyrazole; MS 479.1<br>¹H NMR (CDCl₃) δ 8.95 (s, 1H), 8.15 (d, J = 7.6 Hz, 1H), 7.64 (d, J = 8.1 Hz, 1H), 7.26 (d, J = 13.2 Hz, 1H), 7.01 (d, J = 8.2 Hz, 2H), 6.81 (d, J = 8.0 Hz, 2H), 5.41 (s, 1H), 4.68 (s, 1H), 3.76 (s, 3H), 2.76 (m, 3H), 2.12 (m, 2H), 1.87 (m, 2H). Prepared as described in Example 5 using 3-(4-methoxyphenyl)-pentanedial and 6-(trifluoromethyl)pyridine-3-sulfonyl chloride. | D |

| Ex. No. | Structure/Compound Name/Mass Spec (M + H)/ ¹H-NMR (300 MHz)/Experimental Procedures | γAPP IC₅₀ (nM) |
|---|---|---|
| 47 | 5,5-dimethyl-9-{[4-(trifluoromethyl)phenyl]sulfonyl}-5,6,7,8-tetrahydro-1H-4,7-epiminopyrazolo[4,3-b]azepine; and 6,6-dimethyl-9-{[4-(trifluoromethyl)phenyl]sulfonyl}-4,5,6,8-tetrahydro-1H-4,7-epiminopyrazolo[3,4-c]azepine; MS 387.1. ¹H-NMR (CDCl₃) δ 7.92 (d, J = 8.4 Hz, 2H), 7.60 (d, J = 8.4 Hz, 2H), 7.28 (s, 1H), 4.87 (m, 1H), 3.09 (dd, J = 16.5, 4.8 Hz, 1H), 2.51 (d, J = 16.2 Hz, 1H), 2.40 (m, 1H), 1.55 (d, J = 12.0 Hz, 1H), 1.28 (s, 3H), 1.02 (s, 3H). Prepared as described in Example 25. | B |
| 48 | (±)-6-phenyl-10-{[6-(trifluoromethyl)pyridin-3-yl]sulfonyl}-4,5,6,7,8,9-hexahydro-1H-4,8-epiminocycloocta[c]pyrazole; MS 449.1. ¹H NMR (CDCl₃) δ 8.96 (d, J = 1.7 Hz, 1H), 8.16 (dd, J = 8.1, 1.7 Hz, 1H), 7.64, (d, J = 8.1 Hz, 1H), 7.23 (m, 4H), 7.08 (d, J = 6.9 Hz, 2H), 5.43 (s, 1H), 4.69 (s, 1H), 2.78 (m, 3H), 2.68 (d, J = 17.3 Hz, 1H), 2.21 (ddd, J = 12.8, 11.2, 3.8 Hz, 2H), 1.89 (m, 2H). Prepared as described in Example 5 using 3-phenylglutar-aldehyde and 6-(trifluoromethyl)pyridine-3-sulfonyl chloride. | D |
| 49 | (±)-6-phenyl-10-{[4-(trifluoromethyl)phenyl]sulfonyl}-4,5,6,7,8,9-hexahydro-1H-4,8-epiminocycloocta[c]pyrazole; MS 448.1. ¹H NMR (CDCl₃) δ 7.86 (d, J = 8.2 Hz, 2H), 7.62 (d, J = 8.3, 2H), 7.22, (m, 4H), 7.04 (m, 2H), 5.41 (s, 1H), 4.67 (s, 1H), 2.85 (dd, J = 17.1, 7.7 Hz, 1H), 2.76 (m, 1H), 2.65 (d, J = 17.1 Hz, 1H), 2.13 (m, 2H), 1.86 (m, 2H). Prepared as described in Example 5 using 3-phenylglutaraldehyde and 4-(trifluoromethyl)benzene-1-sulfonyl chloride. | D |
| 50 | (±)-10-[(5-chlorothiophen-2-yl)sulfonyl]-6-phenyl-4,5,6,7,8,9-hexahydro-1H-4,8-epiminocycloocta[c]pyrazole; MS 420.0. ¹H NMR (CDCl₃) δ 7.34 (s, 1H), 7.24 (m, 4H), 7.22, (m, 4H), 7.06 (m, 2H), 6.76 (d, J = 4.0, 1H), 5.38 (s, 1H), 4.67 (t, J = 5.5 Hz, 1H), 3.11 (dd, J = 17.0, 7.7 Hz 1H), 2.77 (m, 1H), 2.72 (d, J = 17.0 Hz, 2H), 2.15 (m, 2H), 1.86 (m, 2H). Prepared as described Example 5 using 3-phenylglutaraldehyde and 5-chlorothiophene-2-sulfonyl chloride. | D |
| 51 | 6-(1-methyl-1H-pyrazol-3-yl)-10-{[4-(trifluoromethyl)phenyl]sulfonyl}-4,5,6,7,8,9-hexahydro-1H-4,8-epiminocycloocta[c]pyrazole and 6-(1-methyl-1H-pyrazol-5-yl)-10-{[4-(trifluoromethyl)phenyl]sulfonyl}-4,5,6,7,8,9-hexahydro-1H-4,8-epiminocycloocta[c]pyrazole; MS 452.1. ¹H NMR (CDCl₃) δ 7.83 (m, 2H), 7.58 (m, 2H), 7.35 (d, J = 1.8 Hz, 1H), 7.30 (s, 1H), 7.21 (s, 1H), 5.96 (d, J = 1.9 Hz, 1H), 5.94 (d, J = 2.1 Hz, 1H), 5.40 (s, 1H), 5.36 (s, 1H), 4.62 (m, 1H), 3.76 (s, 3H), 3.54 (s, 3H), 2.88 (m, 6H), 2.59 (dd, J = 17.1, 12.6 Hz, 2H), 2.02 (m, 8H). | C |
| 52 | (±)-11-{[4-(trifluoromethyl)phenyl]sulfonyl}-1,4,9,10-tetrahydro-4,9-epiminobenzo[4,5]cyclohepta[1,2-c]pyrazole; MS 452.1. ¹H NMR (CDCl₃) δ 7.71 (d, J = 9 Hz, 2H), 7.46-7.44 (m, 3H), 7.06-6.99 (m, 1H), 6.98-6.93 (m, 3H), 5.83 (s, 1H), 5.38 (d, J = 5.1 Hz, 1H), 4.57 (bs, 1H), 3.53 (dd, J = 5.1, 16.2 Hz, 1H), 2.85 (d, J = 16.5 Hz, 1H). Prepared as described in Example 8. | D |
| 53 | (±)-exo-6-(4-fluorophenyl)-10-{[6-(trifluoromethyl)pyridin-3-yl]sulfonyl}-4,5,6,7,8,9-hexahydro-1H-4,8-epiminocycloocta[c]pyrazole; MS 467.1. ¹H NMR (CDCl₃) δ 8.94 (s, 1H), 8.16 (dd, J = 8.1, 1.5 Hz, 1H), 7.64 (d, J = 8.2 Hz, 1H), 7.30 (s, 1H), 7.00 (m, 4H), 5.42 (s, 1H), 4.67 (s, 1H), 2.75 (m, 3H), 2.11 (m, 2H), 1.87 (m, 2H). Prepared as described in Example 5 using 3-(4-fluorophenyl)pentanedial and 6-(trifluoromethyl)pyridine-3-sulfonyl chloride. | D |
| 54 | (±)-10-{[6-(trifluoromethyl)pyridin-3-yl]sulfonyl}-6-[4-(trifluoromethyl)-1,3-thiazol-2-yl]-4,5,6,7,8,9-hexahydro-1H-4,8-epiminocycloocta[c]pyrazole; MS 524.1. ¹H NMR (CDCl₃) δ 8.96 (s, 1H), 8.15 (d, 1H, J = 8.2 Hz), 7.66 (s, 1H), 7.64 (d, 1H, J = 8.2 Hz), 7.32 (s, 1H), 5.46 (s, 1H), 4.72 (br s, 1H), 3.31 (br s, 1H), 2.76 (m, 2H), 2.26 (m, 4H). | D |
| 55 | 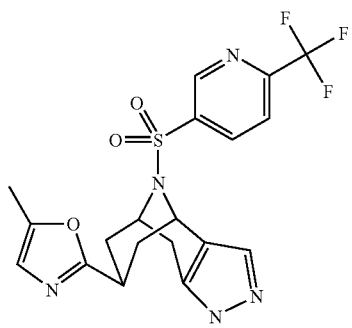(±)-6-(5-methyl-1,3-oxazol-2-yl)-10-{[6-(trifluoromethyl)pyridin-3-yl]sulfonyl}-4,5,6,7,8,9-hexahydro-1H-4,8-epiminocycloocta[c]pyrazole; MS 454.1. ¹H NMR (CDCl₃) δ 8.9 (d, J = 1.6 Hz, 1H), 8.13 (dd, J = 8.2, 1.9 Hz, 1H), 7.62 (d, J = 8.2 Hz, 1H), 7.22 (s, 1H), 6.52 (s, 1H), 5.39 (s, | D |

-continued

| Ex. No. | Structure/Compound Name/Mass Spec (M + H)/ ¹H-NMR (300 MHz)/Experimental Procedures | γAPP IC$_{50}$ (nM) |
|---|---|---|
| | 1H), 4.64 (s, 1H), 2.95 (m, 1H), 2.78 (dd, J = 17.3, 7.6 Hz, 1H), 2.62 (d, J = 17.3 Hz, 1H), 2.14 (m, 8H). Prepared as described in Example using 3-(5-methyl-oxazol-2-yl)pentanedial and 6-(trifluoromethyl)pyridine-3-sulfonyl chloride. | |
| 56 | (±)-endo-6-(4-fluorophenyl)-10-{[6-(trifluoromethyl)pyridin-3-yl]sulfonyl}-4,5,6,7,8,9-hexahydro-1H-4,8-epiminocycloocta[c]pyrazole; MS 467.1 ¹H NMR (CDCl$_3$) δ 9.0 (d, J = 1.9 Hz, 1H), 8.24 (dd, J =8.2, 2.0 Hz, 1H), 7.73 (d, J = 8.2 Hz, 1H), 7.39 (s, 1H), 6.96 (m, 4H), 5.32 (d, J = 9.3 Hz, 1H), 4.73 (m, 1H), 2.89 (m, 1H), 2.68 (m, 2H), 2.58 (d, J = 15.9 Hz, 1H), 2.27 (m, 1H), 1.54 (m, 2H). Prepared as described in Example 5 using 3-(4-fluorophenyl)pentanedial and 6-(trifluoromethyl)pyridine-3-sulfonyl chloride. | D |
| 57 | (±)-6-(5-methyl-1,3-thiazol-2-yl)-10-{[6-(trifluoromethyl)pyridin-3-yl]sulfonyl}-4,5,6,7,8,9-hexahydro-1H-4,8-epiminocycloocta[c]pyrazole; MS 470.1. ¹H NMR (CDCl$_3$) δ 8.99 (s, 1H), 8.18 (d, 1H, J = 8.0 Hz), 7.70 (d, 1H, J = 8.0 Hz), 7.46 (s, 1H), 7.40 (s, 1H), 5.46 (br s, 1H), 4.72 (br s, 1H), 3.38 (br s, 1H), 2.87 (m, 2H), 2.48 (s, 3H), 2.21 (m, 4H). | C |
| 58 | (±)-6-(1H-benzimidazol-2-yl)-10-[(4-chlorophenyl)sulfonyl]-4,5,6,7,8,9-hexahydro-1H-4,8-epiminocycloocta[c]pyrazole; MS 454.1. ¹H-NMR (CD$_3$OD) δ 7.76-7.71 (m, 4H), 7.61-7.60 (m, 2H), 7.49 (s, 1H), 7.44-7.40 (m, 3H), 5.61-5.56 (m, 1H), 4.58-4.54 (m, 1H), 3.48-3.50 (m, 1H), 2.86 (dd, J = 17.6, 7.7 Hz, 1H), 2.70 (d, J = 18.1 Hz, 1H), 2.50-2.41 (m, 4H). Prepared by alkylation of methyl 10-[(4-chlorophenyl)sulfonyl]-4,5,6,7,8,9-hexahydro-1H-4,8-epiminocycloocta[c]pyrazole-6-carboxylate (WO 2007022502) with trimethylsilylethoxymethyl chloride followed by hydrolysis with KOH and amide formation using 1,2-benzenediamine, HBTU, and i-Pr$_2$EtN in DMF. The amide was then treated with TFA in EtOH at 120° C. in a microwave reactor to afford the benzamidazole, which was dealkylated using 4N HCl/dioxane. | C |
| 59 | (±)-5-(4-fluorophenyl)-9-{[4-(trifluoromethyl)phenyl]sulfonyl}-1,4,7,8-tetrahydro-4,7-epiminocyclohepta[c]pyrazole; MS 450.0. ¹H NMR (CDCl$_3$) δ 7.86 (d, 2H, J = 8.2 Hz), 7.70 (d, 2H, J = 8.3 Hz), 7.41 (s, 1H), 7.05-7.10 (m, 2H), 6.92-6.98 (m, 2H), 5.76 (s, 1H), 5.64 (d, 1H, J = 2.6 Hz), 5.04-5.06 (m, 1H), 3.34 (dd, 1H, J = 16.4, 5.6 Hz), 2.73 (d, 1H, J = 16.3 Hz). | C |
| 60 | 6-(4-fluorophenyl)-9-{[4-(trifluoromethyl)phenyl]sulfonyl}-1,4,7,8-tetrahydro-4,7-epiminocyclohepta[c]pyrazole; MS 449.9. ¹H NMR (CDCl$_3$) δ 7.87 (d, 2H, J = 8.1 Hz), 7.60 (d, 2H, J = 8.3 Hz), 7.42 (s, 1H), 7.08-7.13 (m, 2H), 6.95-7.01 (m, 2H), 6.24 (d, 1H, J = 2.4 Hz), 5.50 (d, 1H, J = 2.4 Hz), 5.34 (d, 1H, J = 5.5 Hz), 3.39 (dd, 1H, J = 16.6, 5.7 Hz), 2.89 (d, 1H, J = 16.7 Hz). | C |
| 61 | 5-(4-fluorophenyl)-9-{[4-(trifluoromethyl)phenyl]sulfonyl}-1,4,5,6,7,8-hexahydro-4,7-epiminocyclohepta[c]pyrazole; MS 452.1. ¹H NMR (CDCl$_3$) δ 7.95 (d, 2H, J = 8.2 Hz), 7.71 (d, 2H, J = 8.3 Hz), 6.80-6.95 (m, 3H), 6.77-6.82 (m, 2H), 5.12 (d, 1H, J = 5.5 Hz), 4.76-4.81 (m, 1H), 3.80-3.87 (m, 1H), 3.15 (dd, 1H, J = 16.5 Hz, J = 4.4 Hz), 2.73-2.82 (m, 2H), 1.77 (dd, 1H, J = 12.3 Hz, J = 8.5 Hz). | D |
| 62 | ![structure] (±)-6,7-difluoro-11-{[4-(trifluoromethyl)phenyl]sulfonyl}-1,4,9,10-tetrahydro-4,9-epiminobenzo[4,5]cyclohepta[1,2-c]pyrazole; MS 442.1. ¹H NMR (CDCl$_3$) δ 7.78 (d, 2H, J = 8.3 Hz), 7.61 (d, 2H, J = 8.3 Hz), 7.50 (s, 1H), 6.94-7.01 (dd, 1H, J = 8.9, 6.9 Hz), 6.77-6.83 (dd, 1H, J = 8.8, 6.9 Hz), 5.84 (s, 1H), 5.39 (d, 1H, J = 5.3 Hz), 3.52 (dd, 1H, J = 16.6, 5.6 Hz), 2.86 (d, 1H, J = 16.6 Hz). Prepared as described in Example 8 using 2-bromo-4,5-difluorobenzaldehyde. | D |
| 63 | 6-(4-fluorophenyl)-9-{[4-(trifluoromethyl)phenyl]sulfonyl}-1,4,5,6,7,8-hexahydro-4,7-epiminocyclohepta[c]pyrazole; MS 452.0. ¹H NMR (CDCl$_3$) δ 7.94 (d, 2H, J = 8.2 Hz), 7.71 (d, 2H, J = 8.3 Hz), 7.59 (s, 1H), 6.92-6.99 (m, 2H), 6.76-6.82 (m, 2H), 5.27 (d, 1H, J = 6.5 Hz), 4.68-4073 (m, 1H), 3.95-4.03 (m, 1H), 2.75-2.89 (m, 2H), 2.13-2.26 (m, 2H). | B |

| Ex. No. | Structure/Compound Name/Mass Spec (M + H)/ ¹H-NMR (300 MHz)/Experimental Procedures | γAPP IC$_{50}$ (nM) |
|---|---|---|
| 64 | 6-[(E)-2-chloroethenyl]-10-[(4-chlorophenyl)sulfonyl]-4,5,6,7,8,9-hexahydro-1H-4,8-epiminocycloocta[c]pyrazole; MS 398.0. ¹H NMR (CDCl$_3$) δ 11.30 (broad s, 1H), 7.66 (d, J = 8.4 Hz, 2H), 7.50 (broad s, 1H), 7.38 (d, J = 8.4 Hz, 2H), 5.91 (d, J = 13.2 Hz, 1H), 5.70 (dd, J = 13.2 and 7.2 Hz, 1H), 5.34 (broad s, 1H), 4.57 (broad s, 1H), 2.95 (broad s, 1H), 2.63 (broad m, 1H), 2.22 (broad m, 1H), 1.78 (broad m, 4H). Prepared by protection of ethyl 10-[(4-chlorophenyl)sulfonyl]-4,5,6,7,8,9-hexahydro-1H-4,8-epiminocycloocta-[c]pyrazole-6-carboxylate (WO2007/022502) with SEM-Cl followed by reduction of the ester with LiBH4, oxidation with Dess-Martin periodinane, and treatment with (chloromethylene)triphenyl-phosphorane followed by treatment with 4N HCl in dioxane and chromatographic separation of isomers. | D |
| 65 | 10-[(4-chlorophenyl)sulfonyl]-6-[(1E)-3,3,3-trifluoroprop-1-en-1-yl]-4,5,6,7,8,9-hexahydro-1H-4,8-epiminocycloocta[c]pyrazole; MS 432.0 ¹H NMR (CDCl$_3$) δ 8.40 (broad s, 1H), 7.65 (d, J = 8.4 Hz, 2H), 7.50 (broad s, 1H), 7.37 (d, J = 8.4 Hz, 2H), 6.19 (m, 1H), 5.54 (m, 1H), 5.39 (broad s, 1H), 4.60 (broad s, 1H), 2.95 (broad s, 1H), 2.63 (broad s, 1H), 2.31 (broad s, 1H), 1.83 (broad m, 4H). Prepared by protection of ethyl 10-[(4-chlorophenyl)-sulfonyl]-4,5,6,7,8,9-hexahydro-1H-4,8-epiminocycloocta[c]-pyrazole-6-carboxylate (WO2007/022502) with SEM-Cl followed by reduction of the ester with LiBH4, oxidation with Dess-Martin periodinane, and treatment with diphenyl(2,2,2-trifluoroethyl)phosphine oxide and TBAF in THF, followed by treatment with 4N HCl in dioxane and chromatographic separation of isomers. | D |
| 66 | 10-[(4-chlorophenyl)sulfonyl]-6-[(1Z)-3,3,3-trifluoroprop-1-en-1-yl]-4,5,6,7,8,9-hexahydro-1H-4,8-epiminocycloocta[c]pyrazole; MS 432.0 ¹H NMR (CDCl$_3$) δ 7.62 (d, J = 8.1 Hz, 2H), 7.32 (d, J = 8.1 Hz, 3H), 5.75 (m, 1H), 5.59 (m, 1H), 5.34 (broad s, 1H), 4.59 (broad s, 1H), 4.34 (broad s, 1H), 2.80 (broad m, 2H), 2.58 (broad s, 1H), 1.78 (broad m, 4H). Prepared by protection of ethyl 10-[(4-chlorophenyl)sulfonyl]-4,5,6,7,8,9-hexahydro-1H-4,8-epiminocycloocta[c]-pyrazole-6-carboxylate (WO2007/022502) with SEM-Cl followed by reduction of the ester with LiBH4, oxidation with Dess-Martin periodinane, and treatment with diphenyl (2,2,2-trifluoroethyl)-phosphine oxide and TBAF in THF, followed by treatment with 4N HCl in dioxane and chromatographic separation of isomers. | D |
| 67 | 6-[(Z)-2-chloroethenyl]-10-[(4-chlorophenyl)sulfonyl]-4,5,6,7,8,9-hexahydro-1H-4,8-epiminocycloocta[c]pyrazole; MS 398.0. ¹H NMR (CDCl$_3$) δ 10.13 (broad s, 1H), 7.65 (d, J = 8.1 Hz, 2H), 7.38 (broad s, 1H), 7.32 (d, J = 8.1 Hz, 2H), 5.99 (d, J = 7.2 Hz, 1H), 5.52 (t, J = 7.2 Hz, 1H), 5.35 (broad s, 1H), 4.59 (broad s, 1H), 2.92 (broad s, 1H), 2.70 (broad m, 2H), 1.80 (broad m, 4H). Prepared by protection of ethyl 10-[(4-chlorophenyl)sulfonyl]-4,5,6,7,8,9-hexahydro-1H-4,8-epiminocycloocta[c]-pyrazole-6-carboxylate (WO2007/022502) with SEM-Cl followed by reduction of the ester with LiBH4, oxidation with Dess-Martin periodinane, and treatment with (chloromethylene)triphenylphosphorane followed by treatment with 4N HCl in dioxane and chromatographic separation of isomers. | D |

| Ex. No. | Structure/Compound Name/Mass Spec (M + H)/ $^1$H-NMR (300 MHz)/Experimental Procedures | γAPP IC$_{50}$ (nM) |
|---|---|---|
| 68 | 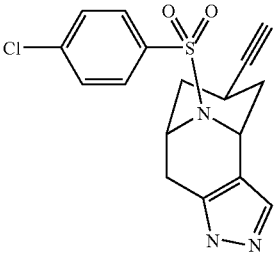<br>10-[(4-chlorophenyl)sulfonyl]-6-ethynyl-4,5,6,7,8,9-hexahydro-1H-4,8-epiminocycloocta[c]pyrazole; MS 362.1. $^1$H NMR (CDCl$_3$) δ 7.66 (d, J = 8.0 Hz, 2H), 7.41 (bs, 1H), 7.38 (d, J = 8.0 Hz, 2H), 5.33 (s, 1H), 4.54 (s, 1H), 2.94-2.92 (m, 1H), 2.63-2.58 (m, 1H), 2.42-2.40 (m, 1H), 2.11-1.91 (m, 5H). Prepared by protection of ethyl 10-[(4-chlorophenyl)sulfonyl]-4,5,6,7,8,9-hexahydro-1H-4,8-epiminocycloocta[c]pyrazole-6-carboxylate (WO2007/022502) with SEM-Cl followed by reduction of the ester with LiBH4, and oxidation with Dess-Martin periodinane to give 10-[(4-chlorophenyl)sulfonyl]-1-{[2-(trimethylsilyl)ethoxy]methyl}-4,5,6,7,8,9-hexahydro-1H-4,8-epiminocycloocta[c]pyrazole-6-carbaldehyde. The aldehyde was then treated with dimethyl (1-diazo-2-oxopropyl)phosphonate and K2CO3 in CH3CN to give 10-[(4-chlorophenyl)sulfonyl]-6-ethynyl-1-{[2-(trimethylsilyl)ethoxy]-methyl}-4,5,6,7,8,9-hexahydro-1H-4,8-epiminocycloocta[c]pyrazole which was deprotected with 4N HCl in dioxane. | D |
| 69 | 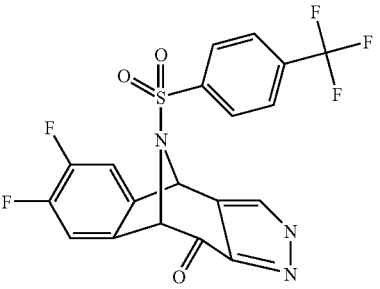<br>(±)-6,7-difluoro-11-{[4-(trifluoromethyl)phenyl]sulfonyl}-4,9-dihydro-4,9-epiminobenzo[4,5]cyclohepta[1,2-c]pyrazol-10(1H)-one; MS 456.1. $^1$H NMR (CD$_3$OD) δ 7.89 (d, 2H, J = 8.2 Hz), 7.71 (s, 1H), 7.67 (d, 2H, J = 8.6 Hz), 7.22-7.28 (m, 1H), 7.09-7.15 (m, 1H), 6.30 (s, 1H), 5.53 (s, 1H). Prepared by oxidation of 6,7-difluoro-11-{[4-(trifluoromethyl)phenyl]-sulfonyl}-1,4,9,10-tetrahydro-4,9-epiminobenzo[4,5]cyclohepta[1,2-c]pyrazole using the methods described in Example 15. | D |
| 70 | (±)-6-(3-fluorophenyl)-10-{[6-(trifluoromethyl)pyridin-3-yl]sulfonyl}-4,5,6,7,8,9-hexahydro-1H-4,8-epiminocycloocta[c]pyrazole; MS 467.1 $^1$H NMR (CDCl$_3$) δ 8.94 (d, J = 1.9 Hz, 1H), 8.16 (dd, J = 8.2, 1.8 Hz, 1H), 7.64 (d, J = 8.0 Hz, 1H), 7.31 (s, 1H), 7.20 (m, 1H), 6.81 (m, 3H), 5.43 (s, 1H), 4.69 (s, 1H), 2.74 (m, 2H), 2.67 (d, J = 17.3 Hz, 1H), 2.14 (m, 2H), 1.88 (m, 2H). Prepared as described in Example 5 using 3-(3-fluorophenyl)pentanedial and 6-(trifluoromethyl)pyridine-3-sulfonyl chloride. | D |
| 71 | 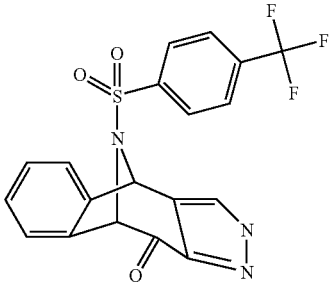<br>(±)-11-{[4-(trifluoromethyl)phenyl]sulfonyl}-4,9-dihydro-4,9-epiminobenzo[4,5]cyclohepta[1,2-c]pyrazol-10(1H)-one; MS 420.0 | D |

| Ex. No. | Structure/Compound Name/Mass Spec (M + H)/ $^1$H-NMR (300 MHz)/Experimental Procedures | γAPP IC$_{50}$ (nM) |
|---|---|---|
| | $^1$H NMR (CDCl$_3$) δ 7.74 (d, 2H, J = 8.2 Hz), 7.65 (s, 1H), 7.48 (d, 2H, J = 8.3 Hz), 7.25-7.30 (m, 1H), 7.04-7.14 (m, 3H), 6.15 (s, 1H), 5.42 (s, 1H). Prepared as described in Example 15. | |
| 72 | (−)-11-{[4-(trifluoromethyl)phenyl]sulfonyl}-1,4,9,10-tetrahydro-4,9-epiminobenzo[4,5]cyclohepta[1,2-c]pyrazole; MS 406.1. $^1$H NMR (CDCl$_3$) δ 7.72 (d, 2H, J = 8.3 Hz), 7.46 (d, 2H, J = 8.3 Hz), 7.37 (s, 1H), 7.04-7.08 (m, 1H), 6.84-6.98 (m, 3H), 5.83 (s, 1H), 5.39 (d, 1H, J = 5.4 Hz), 3.50 (dd, 1H, J = 16.2, 5.5 Hz), 2.85 (d, 1H, J = 16.2 Hz). Prepared as described in Example 8 followed by chiral chromatographic separation of enantiomers. | A |
| 73 | (±)-11-{[4-(trifluoromethyl)phenyl]sulfonyl}-1,4,9,10-tetrahydro-4,9-epiminobenzo[4,5]cyclohepta[1,2-c]pyrazole; MS 406.1. $^1$H NMR (CDCl$_3$) δ 7.72 (d, 2H, J = 8.3 Hz), 7.46 (d, 2H, J = 8.3 Hz), 7.37 (s, 1H), 7.04-7.08 (m, 1H), 6.84-6.98 (m, 3H), 5.83 (s, 1H), 5.39 (d, 1H, J = 5.4 Hz), 3.50 (dd, 1H, J = 16.2, 5.5 Hz), 2.85 (d, 1H, J = 16.2 Hz). Prepared as described in Example 8 followed by chiral chromatographic separation of enantiomers. | D |
| 74 | (±)-10,10-difluoro-11-{[4-(trifluoromethyl)phenyl]sulfonyl}-1,4,9,10-tetrahydro-4,9-epiminobenzo[4,5]cyclohepta[1,2-c]pyrazole; MS 442.1 $^1$H NMR (CDCl$_3$) δ 7.79 (d, 2H, J = 8.2 Hz), 7.52 (d, 2H, J = 8.3 Hz), 7.45 (s, 1H), 7.25-7.29 (m, 1H), 6.94-7.06 (m, 3H), 6.00 (s, 1H), 5.47 (d, 1H, J = 10.6 Hz). Prepared as described in Example 15. | D |
| 75 | (±)-7-phenyl-10-{[4-(trifluoromethyl)phenyl]sulfonyl}-4,5,6,7,8,9-hexahydro-1H-4,8-epiminocycloocta[c]pyrazole; MS 448.1. $^1$H-NMR (CDCl$_3$) δ 7.81 (d, 2H, J = 8.0 Hz), 7.56 (d, 2H, J = 8.0 Hz), 7.34 (m, 1H), 7.32 (d, 2H, J = 7.2 Hz), 7.26 (s, 1H), 7.18 (d, 2H, J = 7.2 Hz), 5.36 (m, 1H), 4.53 (m, 1H), 3.30 (m, 1H), 2.43-2.15 (m, 2H), 1.76 (m, 2H), 1.38-1.16 (m, 2H). Prepared as described in Example 5 using 3-phenyltetrahydro-2H-pyran-2,6-diol and 4-trifluoromethylbenzenesulfonyl chloride. | D |
| 76 | (±)-10-[(4-chlorophenyl)sulfonyl]-6-(3-methylisoxazol-5-yl)-4,5,6,7,8,9-hexahydro-1H-4,8-epiminocycloocta[c]pyrazole; MS 419.0. $^1$H NMR (CDCl$_3$) δ 7.68 (d, J = 8.2 Hz, 2H), 7.56 (s, 1H), 7.41 (d, J = 8.2 Hz, 2H), 5.79 (s, 1H), 5.43 (s, 1H), 4.67-4.64 (m, 1H), 3.09 (dd, J = 18.3, 7.26 Hz, 1H), 2.93-2.91 (m, 1H), 2.76 (d J = 18, 1H), 2.26 (s, 3H), 2.20-2.03 (m, 4H). Prepared by alkylation of 10-[(4-chlorophenyl)sulfonyl]-6-ethynyl-4,5,6,7,8,9-hexahydro-1H-4,8-epiminocycloocta[c]pyrazole with trimethylsilylethoxymethyl chloride followed by treatment with acetaldehyde oxime, NCS, and Et$_3$N in CH$_2$Cl$_2$ and deprotection with 4N HCl/dioxane. | D |
| 77 | (±)-6,7,10,10-tetrafluoro-11-{[4-(trifluoromethyl)phenyl]sulfonyl}-1,4,9,10-tetrahydro-4,9-epiminobenzo[4,5]cyclohepta[1,2-c]pyrazole; MS 478.0 $^1$H NMR (CDCl$_3$) δ 7.85 (d, 2H, J = 8.0 Hz), 7.64 (d, 2H, J = 8.2 Hz), 7.43 (s, 1H), 7.13-7.20 (m, 1H), 6.85-6.93 (m, 1H), 5.95 (s, 1H), 5.44 (d, 1H, J = 10.2 Hz). Prepared by fluorination of 6,7-difluoro-11-{[4-(trifluoromethyl)-phenyl]sulfonyl}-4,9-dihydro-4,9-epiminobenzo[4,5]cyclohepta[1,2-c]pyrazol-10(1H)-one using the methods described in Example 15. | D |

| Ex. No. | Structure/Compound Name/Mass Spec (M + H)/ ¹H-NMR (300 MHz)/Experimental Procedures | γAPP IC₅₀ (nM) |
|---|---|---|
| 78 | (+)-6-(3-fluorophenyl)-10-{[6-(trifluoromethyl)pyridin-3-yl]sulfonyl}-4,5,6,7,8,9-hexahydro-1H-4,8-epiminocycloocta[c]pyrazole; MS 467.1 ¹H NMR (CDCl₃) δ 8.94 (d, J = 1.9 Hz, 1H), 8.16 (dd, J = 8.2, 1.8 Hz, 1H), 7.64 (d, J = 8.0 Hz, 1H), 7.31 (s, 1H), 7.20 (m, 1H), 6.81 (m, 3H), 5.43 (s, 1H), 4.69 (s, 1H), 2.74 (m, 2H), 2.67 (d, J = 17.3 Hz, 1H), 2.14 (m, 2H), 1.88 (m, 2H). Prepared as described in Example 5 using 3-(3-fluorophenyl)-pentanedial and 6-(trifluoromethyl)pyridine-3-sulfonyl chloride followed by chiral chromatographic separation of stereoisomers. | D |
| 79 | (−)-6-(3-fluorophenyl)-10-{[6-(trifluoromethyl)pyridin-3-yl]sulfonyl}-4,5,6,7,8,9-hexahydro-1H-4,8-epiminocycloocta[c]pyrazole; MS 467.1 ¹H NMR (CDCl₃) δ 8.94 (d, J = 1.9 Hz, 1H), 8.16 (dd, J = 8.2, 1.8 Hz, 1H), 7.64 (d, J = 8.0 Hz, 1H), 7.31 (s, 1H), 7.20 (m, 1H), 6.81 (m, 3H), 5.43 (s, 1H), 4.69 (s, 1H), 2.74 (m, 2H), 2.67 (d, J = 17.3 Hz, 1H), 2.14 (m, 2H), 1.88 (m, 2H). Prepared as described above for the stereoisomer. | A |
| 80 | (±)-6-(1,3-dimethyl-1H-1,2,4-triazol-5-yl)-10-{[4-(trifluoromethyl)phenyl]sulfonyl}-4,5,6,7,8,9-hexahydro-1H-4,8-epiminocycloocta[c]pyrazole; MS 467.1. ¹H NMR (CDCl₃) δ 7.86 (d, J = 8.3 Hz, 2H), 7.63 (d, J = 8.3 Hz, 2H), 7.33 (s, 1H), 5.40 (s, 1H), 4.63 (t, J = 5.3 Hz, 1H), 3.52 (s, 3H), 2.92 (m, 2H), 2.65 (d, J = 15.9 Hz, 1H), 2.32 (m, 5H), 1.86 (m, 2H). | B |
| 81 | (±)-9-{[4-(trifluoromethyl)phenyl]sulfonyl}-1,4,7,8-tetrahydro-4,7-epiminocyclohepta[c]pyrazole; MS 322.1. ¹H NMR (CDCl₃) δ 7.75 (d, J = 8.6 Hz, 2H), 7.52 (d, J = 8.6 Hz, 2H), 7.41 (s, 1H), 6.10 (m, 1H), 5.58 (dd, J = 5.9, 2.3 Hz, 1H), 5.41 (d, J = 2.3 Hz, 1H), 4.66 (s, 1H), 3.09 (dd, J = 16.5, 5.8 Hz, 1H), 2.58 (d, J = 16.5 Hz, 1H). | C |
| 82 | (±)-6-(1H-1,2,4-triazol-3-yl)-10-{[4-(trifluoromethyl)phenyl]sulfonyl}-4,5,6,7,8,9-hexahydro-1H-4,8-epiminocycloocta[c]pyrazole; MS 439.1. ¹H NMR (CDCl₃) δ 8.16 (s, 1H), 7.86 (d, 2H, J = 8.2 Hz, 2H), 7.64 (d, J = 8.3 Hz, 2H), 7.36 (s, 1H), 5.42 (m, 1H), 4.64 (m, 1H), 3.04-3.13 (m, 1H), 2.89-2.97 (m, 1H), 2.66-2.72 (m, 1H), 2.02-2.38 (m, 4H). | B |
| 83 | (−)-7-phenyl-10-{[4-(trifluoromethyl)phenyl]sulfonyl}-4,5,6,7,8,9-hexahydro-1H-4,8-epiminocycloocta[c]pyrazole; MS 448.1. ¹H-NMR (CDCl₃) δ 7.82 (d, J = 8.2 Hz, 1H), 7.57 (d, J = 8.2 Hz, 1H), 7.37 (m, 1H), 7.33 (d, J = 7.3 Hz, 2H), 7.29 (s, 1H), 7.20 (d, J = 7.3 Hz, 2H), 5.37 (m, 1H), 4.54 (dd, J = 4.6, 7.6 Hz, 1H), 3.31 (m, 1H), 2.44-2.14 (m, 3H), 1.86- | A |

| Ex. No. | Structure/Compound Name/Mass Spec (M + H)/ $^1$H-NMR (300 MHz)/Experimental Procedures | γAPP IC$_{50}$ (nM) |
|---|---|---|
| | 1.70 (m, 3H). Prepared as described in Example 5 using 3-phenyl-tetrahydro-2H-pyran-2,6-diol and 4-trifluoromethylbenzenesulfonyl chloride, followed by chiral chromatographic separation of stereoisomers. | |
| 84 | (±)-7-phenyl-10-{[4-(trifluoromethyl)phenyl]sulfonyl}-4,5,6,7,8,9-hexahydro-1H-4,8-epiminocycloocta[c]pyrazole; MS 448.0 $^1$H-NMR (CDCl$_3$) δ 7.82 (d, J = 8.2 Hz, 1H), 7.57 (d, J = 8.2 Hz, 1H), 7.37 (m, 1H), 7.33 (d, J = 7.3 Hz, 2H), 7.29 (s, 1H), 7.20 (d, J = 7.3 Hz, 2H), 5.37 (m, 1H), 4.54 (dd, J = 4.6, 7.6 Hz, 1H), 3.31 (m, 1H), 2.44-2.14 (m, 3H), 1.86-1.70 (m, 3H). Prepared as described above for the stereoisomer. | D |
| 85 | (±)-6-(5-methyl-1H-1,2,4-triazol-3-yl)-10-{[4-(trifluoromethyl)-phenyl]sulfonyl}-4,5,6,7,8,9-hexahydro-1H-4,8-epiminocycloocta[c]pyrazole; MS 453.1. $^1$H NMR (CDCl$_3$) δ 7.93 (d, J = 8.2 Hz, 2H), 7.69 (d, J = 8.3 Hz, 2H), 7.41 (s, 1H), 5.49 (s, 1H), 4.72 (m, 1H), 2.83 (dd, J = 17.4, 7.6 Hz, 1H), 2.63 (d, J = 17.4 Hz, 1H), 2.51 (s, 3H), 2.16 (m, 4H). | A |
| 86 | 10-[(4-chlorophenyl)sulfonyl]-6-(prop-1-yn-1-yl)-4,5,6,7,8,9-hexahydro-1H-4,8-epiminocycloocta[c]pyrazole; MS 376.0. $^1$H NMR (CDCl$_3$) δ 7.68 (d, J = 8.4 Hz, 2H), 7.47 (s, 1H), 7.37 (d, J = 8.4 Hz, 2H), 5.29 (bs, 1H), 4.53-4.51 (m, 1H), 2.96 (dd, J = 17.6, 6.7 Hz, 1H), 2.61 (d, J = 17.6, 1H), 2.35 (bs, 1H), 2.03-1.74 (m, 4H), 1.73 (d, J = 2.1 Hz, 3H). Prepared by alkylation of 10-[(4-chlorophenyl)sulfonyl]-6-ethynyl-1-{[2-(trimethylsilyl)ethoxy]-methyl}-4,5,6,7,8,9-hexahydro-1H-4,8-epiminocycloocta[c]pyrazole with methyl-iodide and LHMDS in THF followed by deprotection with 4N HCl in dioxane. | D |
| 87 | 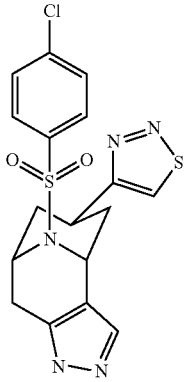<br>(±)-6-(1,2,3-thiadiazol-4-yl)-10-{[4-(trifluoromethyl)phenyl]sulfonyl}-4,5,6,7,8,9-hexahydro-1H-4,8-epiminocycloocta[c]pyrazole; MS 422.0 $^1$H-NMR (CDCl$_3$) δ 8.15 (s, 1H), 7.70 (d, J = 8.8 Hz, 2H), 7.54 (s, 1H), 7.40 (d, J = 8.8 Hz, 2H), 5.50-5.44 (m, 1H), 4.80-4.65 (m, 1H), 3.50-3.38 (m, 1H), 3.08 (dd, J = 17.6 Hz, 7.7 Hz, 1H), 2.78 (d, J = 17.6 Hz, 1H), 2.40-2.17 (m, 4H). Prepared by alkylation of methyl 10-[(4-chlorophenyl)sulfonyl]-4,5,6,7,8,9-hexahydro-1H-4,8-epiminocycloocta[c]pyrazole-6-carboxylate (WO 2007022502) with trimethylsilylethoxymethyl chloride followed by treatment with methoxymethylamine hydrochloride and HATU in THF and Et$_3$N to afford the amide which was converted to the ketone with methylmagnesium bromide. The ketone was sequentially treated with tosylhydrazine/HOAc, thionyl chloride, and finally 4N HCl/dioxane. | D |
| 88 | 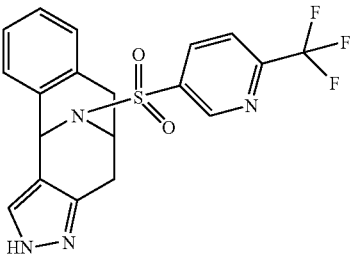<br>(±)-12-{[6-(trifluoromethyl)pyridin-3-yl]sulfonyl}-4,5,10,11-tetrahydro-1H-4,10-epiminobenzo[5,6]cycloocta[1,2-c]pyrazole; MS 421.0. 1H NMR (CD$_3$OD) δ 8.82 (s, 1H), 8.11 (d, J = 8.3 Hz, 1H), 7.58 (d, J = 8.7 Hz, 1H), 7.47 (br, 1H), 7.26 (d, J = 6.4 Hz, 1H), 7.06 (t, J = 7.3 Hz, 1H), 6.91 (t, | D |

| Ex. No. | Structure/Compound Name/Mass Spec (M + H)/ ¹H-NMR (300 MHz)/Experimental Procedures | γAPP IC₅₀ (nM) |
|---|---|---|
|  | J = 7.5 Hz, 1H), 6.60 (d, J = 6.7 Hz, 1H), 6.07 (br, 1H), 5.04-4.98 (br, 1H), 3.20-3.10 (m, 2H), 2.77 (d, J = 19 Hz, 1H), 2.46 (d, J = 18 Hz, 1H). Prepared as described in Example 11 using 6-(trifluoromethyl)pyridine-3-sulfonyl chloride. |  |
| 89 | 5-phenyl-10-{[4-(trifluoromethyl)phenyl]sulfonyl}-4,5,6,7,8,9-hexahydro-1H-4,8-epiminocycloocta[c]pyrazole; MS 448.1. ¹H-NMR (CDCl₃) (Mixture of isomers) δ 7.68 (d, J = 8.2 Hz, 1H), 7.59-7.39 (m, 12H), 7.37-7.24 (m, 6H), 5.60 (s, 1H), 5.35 (m, 1H), 4.77 (d, J = 7.6 Hz, 1H), 5.37 (m, 1H), 4.48 (t, J = 6.2 Hz, 1H), 3.10-2.89 (m, 4H), 2.72 (d, J = 17.2 Hz, 1H), 2.60 (d, J = 17.2 Hz, 1H), 2.27 (m, 2H), 2.02-1.80 (m, 4H), 1.59 (m, 2H). | D |
| 90 | 6-(pyridin-3-yl)-10-{[4-(trifluoromethyl)phenyl]sulfonyl}-4,5,6,7,8,9-hexahydro-1H-4,8-epiminocycloocta[c]pyrazole; MS 449.0. ¹H-NMR (CDCl₃) δ 8.44 (m, 1H), 8.35 (s, 1H), 7.92 (d, J = 6.0 Hz, 2H, major diast.), 7.86 (d, J = 9.0 Hz, 2H, minor diast.), 7.70 (d, J = 6.0 Hz, 2H, major diast.), 7.63 (d, J = 9 Hz, 2H, minor diast.), 7.41-7.30 (m, 1H), 2.71-7.16 (m, 2H), 5.46 (s, 1H minor diast.), 5.37 (d, J = 9 Hz, 1H, major diast.), 4.78-4.71 (m, 1H), 2.96-2.82 (m, 1H), 2.78-2.71 (m, 2H), 2.69-2.46 (m, 1H), 2.37-2.27 (m, 1H), 2.07-2.05 (m, 1H), 1.67-1.60 (m, 1H), 1.08-0.87 (m, 1H). | C |
| 91 | (±)-12-{[4-(trifluoromethyl)phenyl]sulfonyl}-1,4,10,11-tetrahydro-4,10-epimino[1,3]benzodioxolo[5',6':4,5]cyclohepta[1,2-c]pyrazole; MS 449.9 ¹H NMR (CDCl₃) δ 7.78 (d, J = 8.3 Hz, 2H), 7.58 (d, J = 8.4 Hz, 2H), 7.54 (s, 1H), 6.54 (s, 1H), 6.39 (s, 1H), 5.86 (s, 1H), 5.82 (s, 1H), 5.73 (s, 1H), 5.31 (d, J = 5.2 Hz, 1H), 3.54 (dd, J = 16.9, 5.5 Hz, 1H), 2.88 (d, J = 16.7 Hz, 1H). Prepared as described in Example 8 using 6-bromo-3,4-(methylenedioxy)-benzaldehyde. | D |
| 92 | (±)-10-[(4-chlorophenyl)sulfonyl]-6-(5-methyl-1,3,4-thiadiazol-2-yl)-4,5,6,7,8,9-hexahydro-1H-4,8-epiminocycloocta[c]pyrazole; MS 436.1 ¹H-NMR (CDCl₃) δ 7.66 (d, J = 7.7 Hz, 2H), 7.39 (d, J = 8.2 Hz, 2H), 7.26 (s, 1H), 5.60-5.40 (m, 1H), 4.70-4.60 (m, 1H), 3.97-3.86 (m, 1H), 3.40-3.25 (m, 2H), 2.75 (s, 3H), 2.36-2.13 (m, 4H). Prepared by alkylation of methyl 10-[(4-chlorophenyl)sulfonyl]-4,5,6,7,8,9-hexahydro-1H-4,8-epiminocycloocta[c]pyrazole-6-carboxylate (WO 2007022502) with trimethylsilylethoxymethyl chloride followed by hydrolysis with LiOH•H₂O and acylhydrazide formation using acetylhydrazine and HATU. The acylhydrazide was then treated with Lawesson's reagent and NaHCO₃ in toluene followed by dealkylation with 4N HCl/dioxane. | B |
| 93 | (±)-10-[(4-chlorophenyl)sulfonyl]-6-(1H-1,2,3-triazol-4-yl)-4,5,6,7,8,9-hexahydro-1H-4,8-epiminocycloocta[c]pyrazole; MS 405.0. ¹H NMR (CDCl₃) δ 7.68 (d, J = 7.7 Hz, 2H), 7.46 (m, 2H), 7.37 (d, J = 7.7 Hz, 2H), 5.42-5.44 (m, 1H), 4.65-4.67 (m, 1H), 2.99 (dd, J = 17.7, 8.2, 1H), 2.81 (d, J = 17.7 Hz, 1H), 2.01-2.21 (m, 5H). Prepared by alkylation of 10-[(4-chlorophenyl)sulfonyl]-6-ethynyl-4,5,6,7,8,9-hexahydro-1H-4,8-epiminocycloocta[c]pyrazole with trimethylsilylethoxymethyl chloride followed by treatment with sodium azide and CuSO₄ in DMF/H₂O followed by deprotection with 4N HCl/dioxane. | D |

| Ex. No. | Structure/Compound Name/Mass Spec (M + H)/ $^1$H-NMR (300 MHz)/Experimental Procedures | γAPP IC$_{50}$ (nM) |
|---|---|---|
| 94 | 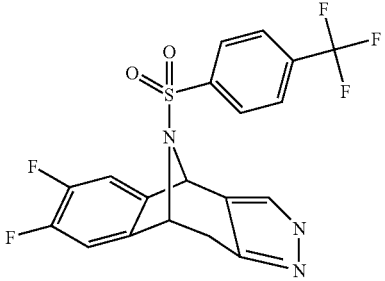<br>(−)-6,7-difluoro-11-{[4-(trifluoromethyl)phenyl]sulfonyl}-1,4,9,10-tetrahydro-4,9-epiminobenzo[4,5]cyclohepta[1,2-c]pyrazole; MS 442.1. $^1$H NMR (CDCl$_3$) δ 7.78 (d, J = 8.3 Hz, 2H), 7.58 (d, J = 8.1 Hz, 2H), 7.38 (s, 1H), 6.92-6.97 (m, 1H), 6.73-6.78 (m, 1H), 5.82 (s, 1H), 5.37 (d, J = 5.6 Hz, 1H), 3.47 (dd, J = 16.3, 5.7 Hz, 1H), 2.82 (d, J = 16.4 Hz, 1H). Prepared as described in Example 8 using 2-bromo-4,5-difluorobenzaldehyde followed by chiral chromatographic separation of enantiomers. | A |
| 95 | (+)-6,7-difluoro-11-{[4-(trifluoromethyl)phenyl]sulfonyl}-1,4,9,10-tetrahydro-4,9-epiminobenzo[4,5]cyclohepta[1,2-c]pyrazole; MS 442.1 $^1$H NMR (CDCl$_3$) δ 7.78 (d, J = 8.3 Hz, 2H), 7.58 (d, J = 8.1 Hz, 2H), 7.38 (s, 1H), 6.92-6.97 (m, 1H), 6.73-6.78 (m, 1H), 5.82 (s, 1H), 5.37 (d, J = 5.6 Hz, 1H), 3.47 (dd, J = 16.3, 5.7 Hz, 1H), 2.82 (d, J = 16.4 Hz, 1H). Prepared as described above for the (−)-enantiomer. | D |
| 96 | 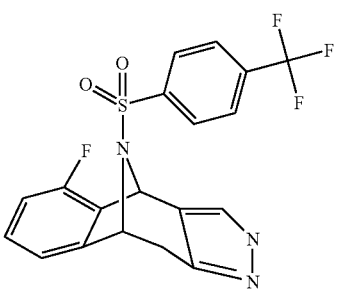<br>(±)-5-fluoro-11-{[4-(trifluoromethyl)phenyl]sulfonyl}-1,4,9,10-tetrahydro-4,9-epiminobenzo[4,5]cyclohepta[1,2-c]pyrazole; MS 424.0 $^1$H NMR (CDCl$_3$) δ 7.76 (d, J = 7.7 Hz, 2H), 7.50 (d, J = 7.3 Hz, 2H), 7.43 (s, 1H), 6.90-6.97 (m, 1H), 6.84 (d, J = 7.2 Hz, 1H), 6.60 (t, J = 8.6 Hz, 1H), 6.03 (s, 1H), 5.41 (d, 1H, J = 5.6 Hz), 3.56 (dd, J = 16.3, 5.7 Hz, 1H), 2.87 (d, J = 16.2 Hz, 1H). Prepared as described in Example 8 using 6-fluoro-2-iodobenzaldehyde followed by chromatographic separation of regioisomers. | D |
| 97 | (±)-8-fluoro-11-{[4-(trifluoromethyl)phenyl]sulfonyl}-1,4,9,10-tetrahydro-4,9-epiminobenzo[4,5]cyclohepta[1,2-c]pyrazole; MS 424.0. $^1$H NMR (CDCl$_3$) δ 7.75 (d, J = 7.9 Hz, 2H), 7.50 (d, J = 8.0 Hz, 2H), 7.38 (s, 1H), 6.87-6.97 (m, 1H), 6.55-6.70 (m, 2H), 5.85 (s, 1H), 5.57 (d, 1H, J = 4.5 Hz), 3.53 (dd, J = 16.3, 5.4 Hz, 1H), 2.92 (d, J = 16.5 Hz, 1H). Prepared as described in Example 8 using 6-fluoro-2-iodobenzaldehyde followed by chromatographic separation of regioisomers. | D |
| 98 | 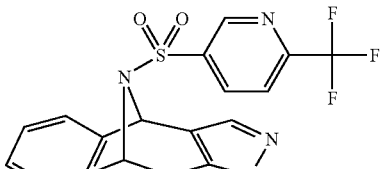<br>(±)-11-{[6-(trifluoromethyl)pyridin-3-yl]sulfonyl}-1,4,9,10-tetrahydro-4,9-epiminobenzo[4,5]cyclohepta[1,2-c]pyrazole; MS 407.0. $^1$H NMR (CDCl$_3$) δ 8.86 (d, J = 1.8 Hz, 1H), 8.00 (dd, J = 1.8, 7.8 Hz, 1H), 7.48 (d, J = 8.4 Hz, 1H), 7.35 (s, 1H), 7.09-7.07 (m, 2H), 6.97-6.89 (m, 3H), 5.86 (s, 1H), 5.38 (d, 1H, J = 5.1 Hz), 3.45 (dd, J = 16.8, 5.7 Hz, 1H), 2.83 (d, J = 16.8 Hz, 1H). Prepared as described in Example 9. | D |

| Ex. No. | Structure/Compound Name/Mass Spec (M + H)/ $^1$H-NMR (300 MHz)/Experimental Procedures | γAPP IC$_{50}$ (nM) |
|---|---|---|
| 99 | (−)-11-{[4-(trifluoromethyl)phenyl]sulfonyl}-1,4,9,10-tetrahydro-4,9-epiminopyrazolo[4',3':4,5]cyclohepta[1,2-b]pyridine; MS 407.0 $^1$H-NMR (CDCl$_3$) δ 8.03 (d, 1H, J = 5.0 Hz), 7.75 (d, J = 8.2 Hz, 1H), 7.50 (d, J = 8.2 Hz, 1H), 7.47 (s, 1H), 7.33 (d, J = 7.6 Hz, 1H), 6.83 (dd, J = 5.0, 7.6 Hz, 1H), 5.84 (s, 1H), 5.39 (d, J = 5.6 Hz, 1H), 3.55 (dd, J = 5.6, 16.4 Hz, 2H). Prepared as described in Example 8 using 2-bromo-3-pyridine-carbox-aldehyde followed by chromatographic separation of regio and stereoisomers. | A |
| 100 | (+)-11-{[4-(trifluoromethyl)phenyl]sulfonyl}-1,4,9,10-tetrahydro-4,9-epiminopyrazolo[4',3':4,5]cyclohepta[1,2-b]pyridine; MS 407.0. $^1$H-NMR (CDCl$_3$) δ 8.03 (d, J = 5.0 Hz, 1H), 7.75 (d, J = 8.2 Hz, 1H), 7.50 (d, J = 8.2 Hz, 1H), 7.47 (s, 1H), 7.33 (d, J = 7.6 Hz, 1H), 6.83 (dd, J = 5.0, 7.6 Hz, 1H), 5.84 (s, 1H), 5.39 (d, J = 5.6 Hz, 1H), 3.55 (dd, J = 5.6, 16.4 Hz, 2H). Prepared as described in Example 8 using 2-bromo-3-pyridine-carboxaldehyde followed by chromatographic separation of regio and stereoisomers. | D |
| 101 | (+)-11-{[4-(trifluoromethyl)phenyl]sulfonyl}-1,4,9,10-tetrahydro-4,9-epiminopyrazolo[3',4':5,6]cyclohepta[1,2-b]pyridine; MS 407.0. $^1$H-NMR (CDCl$_3$) δ 8.15 (d, J = 5.0 Hz, 1H), 7.76 (d, J = 8.2 Hz, 1H), 7.52 (d, J = 8.2 Hz, 1H), 7.40 (s, 1H), 7.13 (d, J = 7.6 Hz, 1H), 6.81 (dd, J = 5.0, 7.6 Hz, 1H), 5.88 (s, 1H), 5.40 (d, J = 5.6 Hz, 1H), 3.53 (dd, J = 5.6, 16.4 Hz, 2H). Prepared as described in Example 8 using 2-bromo-3-pyridine-carboxaldehyde followed by chromatographic separation of regio and stereoisomers. | D |
| 102 | (−)-11-{[4-(trifluoromethyl)phenyl]sulfonyl}-1,4,9,10-tetrahydro-4,9-epiminopyrazolo[3',4':5,6]cyclohepta[1,2-b]pyridine; MS 407.0. $^1$H-NMR (CDCl$_3$) δ 8.15 (d, J = 5.0 Hz, 1H), 7.76 (d, J = 8.2 Hz, 1H), 7.52 (d, J = 8.2 Hz, 1H), 7.40 (s, 1H), 7.13 (d, J = 7.6 Hz, 1H), 6.81 (dd, J = 5.0, 7.6 Hz, 1H), 5.88 (s, 1H), 5.40 (d, J = 5.6 Hz, 1H), 3.53 (dd, J = 5.6, 16.4 Hz, 2H). Prepared as described in Example 8 using 2-bromo-3-pyridine-carboxaldehyde followed by chromatographic separation of regio and stereoisomers. | B |
| 103 | (±)-5-fluoro-11-{[4-(trifluoromethyl)phenyl]sulfonyl}-4,9-dihydro-4,9-epiminobenzo[4,5]cyclohepta[1,2-c]pyrazol-10(1H)-one; MS 438.1 $^1$H NMR (CDCl$_3$) δ 7.78 (d, J = 8.1 Hz, 2H), 7.72 (s, 1H), 7.52 (d, J = 8.3 Hz, 2H), 7.00-7.10 (m, 2H), 6.74 (t, J = 8.1 Hz, 1H), 6.35 (s, 1H), 5.47 (s, 1H). Prepared by oxidation of 5-fluoro-11-{[4-(trifluoromethyl)phenyl]sulfonyl}-1,4,9,10-tetrahydro-4,9-epiminobenzo[4,5]cyclohepta[1,2-c]pyrazole using the methods described in Example 15. | D |

| Ex. No. | Structure/Compound Name/Mass Spec (M + H)/ ¹H-NMR (300 MHz)/Experimental Procedures | γAPP IC₅₀ (nM) |
|---|---|---|
| 104 | 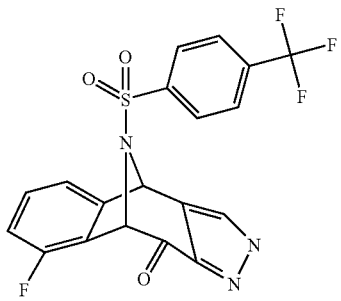<br>(±)-8-fluoro-11-{[4-(trifluoromethyl)phenyl]sulfonyl}-4,9-dihydro-4,9-epiminobenzo[4,5]cyclohepta[1,2-c]pyrazol-10(1H)-one; MS 438.0<br>¹H NMR (CDCl₃) δ 7.78 (d, J = 8.2 Hz, 2H), 7.72 (s, 1H), 7.52 (d, J = 8.3 Hz, 2H), 7.03-7.10 (m, 1H), 6.93 (d, J = 7.3 Hz, 1H), 6.73 (t, J = 8.3 Hz, 1H), 6.17 (s, 1H), 5.63 (s, 1H). Prepared by oxidation of 8-fluoro-11-{[4-(trifluoromethyl)phenyl]-sulfonyl}-1,4,9,10-tetrahydro-4,9-epiminobenzo-[4,5]cyclohepta[1,2-c]pyrazole using the methods described in Example 15. | D |
| 105 | (±)-6,7-difluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 443.1<br>¹H NMR (CDCl₃) δ 8.94 (s, 1H), 8.13 (dd, J = 8.3, 2.1 Hz, 1H), 7.63 (d, J = 8.3 Hz, 1H), 7.41 (s, 1H), 7.02 (dd, J = 8.8, 6.9 Hz, 1H), 6.84 (dd, J = 8.7, 6.8 Hz, 1H), 5.87 (s, 1H), 5.41 (d, J = 5.4 Hz, 1H), 3.41 (dd, J = 16.5, 5.6 Hz, 1H), 2.83 (d, J = 16.5 Hz, 1H). Prepared as described in Example 9 using 5-(2-bromo-4,5-difluorophenyl)-4-(6-(trifluoromethyl)pyridin-3-ylsulfonyl)cyclohex-2-enone, which was prepared as described in Example 8 using 2-bromo-4,5-difluorobenzaldehyde and sulfonamide 23. | D |
| 106 | 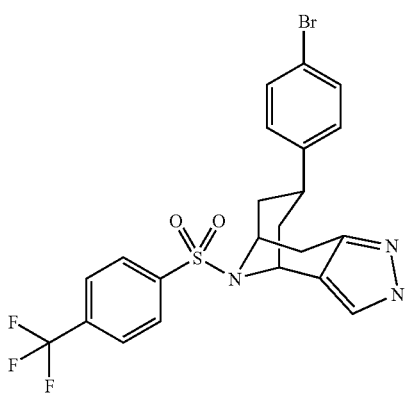<br>(±)-6-(4-bromophenyl)-10-{[4-(trifluoromethyl)phenyl]sulfonyl}-4,5,6,7,8,9-hexahydro-1H-4,8-epiminocycloocta[c]pyrazole; MS 528.0<br>¹H NMR (CDCl₃) δ 7.88 (d, J = 8.4 Hz, 2H), 7.66 (d, J = 8.4 Hz, 2H), 7.40 (d, J = 8.4 Hz, 2H), 7.37 (s, 1H), 6.96 (d, J = 8.4 Hz, 2H), 5.44 (s, 1H), 4.69 (s, 1H), 2.96 (dd, J = 17.4 and 7.5 Hz, 1H), 2.69 (m, 2H), 2.13 (m, 2H), 1.86 (m, 2H). Prepared as described in Example 23 using 1-bromo-4-(hepta-1,6-dien-4-yl)benzene. | D |

| Ex. No. | Structure/Compound Name/Mass Spec (M + H)/ $^1$H-NMR (300 MHz)/Experimental Procedures | γAPP IC$_{50}$ (nM) |
|---|---|---|
| 107 | 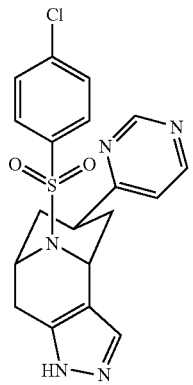<br><br>(±)-10-[(4-chlorophenyl)sulfonyl]-6-(pyridin-4-yl)-4,5,6,7,8,9-hexahydro-1H-4,8-epiminocycloocta[c]pyrazole; MS 416.1. $^1$H-NMR (CDCl$_3$) δ 9.11 (s, 1H), 8.66 (d, J = 5.5 Hz, 1H), 7.68 (d, J = 8.8 Hz, 2H), 7.49 (s, 1H), 7.39 (d, J = 8.24 Hz, 2H), 7.15 (d, J = 5.5 Hz, 1H), 5.52-5.43 (m, 1H), 4.75-4.64 (m, 1H), 3.04 (dd, J = 17.6, 7.7 Hz, 1H), 2.95-2.82 (m, 1H), 2.72 (d, J = 18.2 Hz, 1H), 2.33-2.19 (m, 2H), 2.03-1.95 (m, 2H). Prepared by alkylation of methyl 10-[(4-chlorophenyl)sulfonyl]-4,5,6,7,8,9-hexahydro-1H-4,8-epiminocycloocta[c]pyrazole-6-carboxylate (WO 2007022502) with trimethylsilylethoxymethyl chloride followed by treatment with methoxymethylamine hydrochloride and HATU in THF and Et$_3$N to afford the amide, which was converted to the ketone with methylmagnesium bromide. The ketone was then treated with ethyl formate and NaOEt in THF, formamidine hydrochloride and NaOEt in EtOH, and 4N HCl/dioxane. | D |
| 108 | 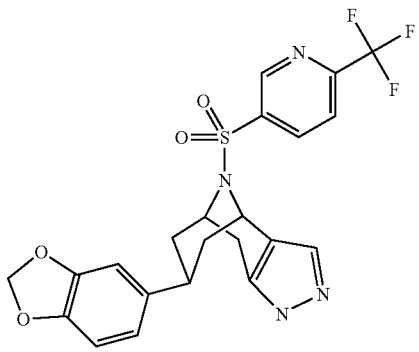<br><br>(±)-6-(1,3-benzodioxol-5-yl)-10-{[6-(trifluoromethyl)pyridin-3-yl]sulfonyl}-4,5,6,7,8,9-hexahydro-1H-4,8-epiminocycloocta[c]pyrazole; MS 493.1 $^1$H NMR (CDCl$_3$) δ 8.94 (d, J = 1.9 Hz, 1H), 8.15 (dd, J = 8.2, 1.9 Hz, 1H), 7.64 (d, J = 8.1 Hz, 1H), 7.30 (s, 1H), 6.70 (d, J = 7.9 Hz, 1H), 6.58 (d, J = 1.6 Hz, 1H), 6.52 (dd, J = 8.0, 1.6 Hz, 1H), 5.90 (s, 2H), 5.41 (s, 1H), 4.67 (s, 1H), 2.71 (m, 3H), 2.10 (m, 2H), 1.86 (m, 2H). Prepared as described in Example 5 using dialdehyde 100. | D |
| 109 | (±)-12-{[4-(trifluoromethyl)phenyl]sulfonyl}-1,4,10,11-tetrahydro-4,10-epimino[1,3]benzodioxolo[5',6':4,5]cyclohepta[1,2-c]pyrazol-7-one; MS 464.0. $^1$H NMR (CDCl$_3$) δ 7.78 (d, J = 8.2 Hz, 2H), 7.54 (d, 2H, J = 8.2 Hz), 7.35 (s, 1H), 7.06 (s, 1H), 6.87 (s, 1H), 5.88 (s, 1H), 5.42 (d, J = 5.4 Hz, 1H), 3.38 (dd, J = 16.2, 5.6 Hz, 1H), 2.78 (d, J = 16.4 Hz, 1H). | >100 |

| Ex. No. | Structure/Compound Name/Mass Spec (M + H)/ ¹H-NMR (300 MHz)/Experimental Procedures | γAPP IC$_{50}$ (nM) |
|---|---|---|
| 110 | (−)-6,7-difluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 443.0 <br> ¹H NMR (CDCl$_3$) δ 8.94 (s, 1H), 8.13 (dd, J = 8.3, 2.1 Hz, 1H), 7.63 (d, J = 8.3 Hz, 1H), 7.41 (s, 1H), 7.02 (dd, J = 8.8, 6.9 Hz, 1H), 6.84 (dd, J = 8.7, 6.8 Hz, 1H), 5.87 (s, 1H), 5.41 (d, J = 5.4 Hz, 1H), 3.41 (dd, J = 16.5, 5.6 Hz, 1H), 2.83 (d, J = 16.5 Hz, 1H). Prepared as described in Example 9 using 5-(2-bromo-4,5-difluorophenyl)-4-(6-(trifluoromethyl)pyridin-3-ylsulfonyl)-cyclohex-2-enone, followed by chiral chromatographic separation of stereoisomers. | A |
| 111 | (+)-6,7-difluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 443.0 <br> ¹H NMR (CDCl$_3$) δ 8.94 (s, 1H), 8.13 (dd, J = 8.3, 2.1 Hz, 1H), 7.63 (d, J = 8.3 Hz, 1H), 7.41 (s, 1H), 7.02 (dd, J = 8.8, 6.9 Hz, 1H), 6.84 (dd, J = 8.7, 6.8 Hz, 1H), 5.87 (s, 1H), 5.41 (d, J = 5.4 Hz, 1H), 3.41 (dd, J = 16.5, 5.6 Hz, 1H), 2.83 (d, J = 16.5 Hz, 1H). Prepared as described above for the enantiomer. | D |
| 112 | (±)-3-[4-(10-{[4-(trifluoromethyl)phenyl]sulfonyl}-4,5,6,7,8,9-hexahydro-1H-4,8-epiminocycloocta[c]pyrazol-6-yl)phenyl]-1,3-oxazolidin-2-one; MS 533.0. ¹H NMR (CDCl$_3$) δ 7.88 (d, J = 8.4 Hz, 2H), 7.66 (d, J = 8.4 Hz, 2H), 7.46 (d, J = 8.7 Hz, 2H), 7.42 (s, 1H), 7.02 (d, J = 8.7 Hz, 2H), 5.45 (s, 1H), 4.69 (s, 1H), 4.50 (m, 2H), 4.05 (m, 2H), 2.96 (dd, J = 17.7 and 7.2 Hz, 1H), 2.69 (m, 2H), 2.00 (broad m, 4H). Prepared as described in Example 23 using 1-bromo-4-(hepta-1,6-dien-4-yl)benzene and oxazolidin-2-one. | D |
| 113 | (±)-6-[4-(1H-imidazol-1-yl)phenyl]-10-{[4-(trifluoromethyl)phenyl]sulfonyl}-4,5,6,7,8,9-hexahydro-1H-4,8-epiminocycloocta[c]pyrazole; MS 514.0. ¹H NMR (CDCl$_3$) δ 8.71 (s, 1H), 7.88 (d, J = 8.4 Hz, 2H), 7.64 (d, J = 8.4 Hz, 2H), 7.48 (s, 1H), 7.39 (broad m, 6H), 5.48 (s, 1H), 4.73 (s, 1H), 2.90 (dd, J = 17.1 and 7.8 Hz, 1H), 2.70 (m, 2H), 2.24 (m, 2H), 1.98 (m, 2H). Prepared as described in Example 23 using 1-bromo-4-(hepta-1,6-dien-4-yl)benzene and imidazole. | D |

| Ex. No. | Structure/Compound Name/Mass Spec (M + H)/ ¹H-NMR (300 MHz)/Experimental Procedures | γAPP IC₅₀ (nM) |
|---|---|---|
| 114 | 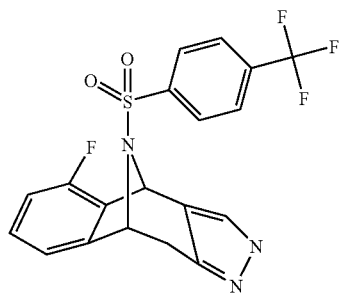<br><br>(−)-5-fluoro-11-{[4-(trifluoromethyl)phenyl]sulfonyl}-1,4,9,10-tetrahydro-4,9-epiminobenzo[4,5]cyclohepta[1,2-c]pyrazole; MS 424.1. ¹H NMR (CDCl₃) δ 7.76 (d, J = 7.7 Hz, 2H), 7.50 (d, J = 7.3 Hz, 2H), 7.43 (s, 1H), 6.90-6.97 (m, 1H), 6.84 (d, J = 7.2 Hz, 1H), 6.60 (t, J = 8.6 Hz, 1H), 6.03 (s, 1H), 5.41 (d, 1H, J = 5.6 Hz), 3.56 (dd, J = 16.3, 5.7 Hz, 1H), 2.87 (d, J = 16.2 Hz, 1H). Prepared as described in Example 8 using 6-fluoro-2-iodobenzaldehyde followed by chromatographic separation of regio- and stereoisomers. | B |
| 115 | (+)-5-fluoro-11-{[4-(trifluoromethyl)phenyl]sulfonyl}-1,4,9,10-tetrahydro-4,9-epiminobenzo[4,5]cyclohepta[1,2-c]pyrazole; MS 424.1. ¹H NMR (CDCl₃) δ 7.76 (d, J = 7.7 Hz, 2H), 7.50 (d, J = 7.3 Hz, 2H), 7.43 (s, 1H), 6.90-6.97 (m, 1H), 6.84 (d, J = 7.2 Hz, 1H), 6.60 (t, J = 8.6 Hz, 1H), 6.03 (s, 1H), 5.41 (d, 1H, J = 5.6 Hz), 3.56 (dd, J = 16.3, 5.7 Hz, 1H), 2.87 (d, J = 16.2 Hz, 1H). Prepared as described above for the enantiomer. | D |
| 116 | 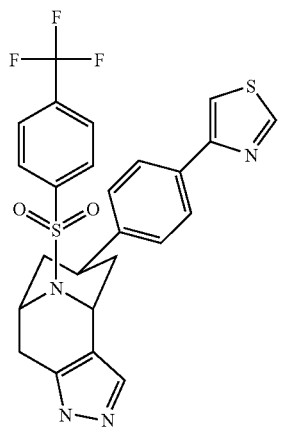<br><br>(±)-6-[4-(1,3-thiazol-4-yl)phenyl]-10-{[4-(trifluoromethyl)phenyl]sulfonyl}-4,5,6,7,8,9-hexahydro-1H-4,8-epiminocycloocta[c]pyrazole; MS 531.1 ¹H NMR (CDCl₃) δ 8.99 (d, J = 2.2 Hz, 1H), 7.91 (d, J = 8.24 Hz, 2H), 7.80 (d, J = 8.24 Hz, 2H), 7.65 (d, J = 8.8 Hz, 2H), 7.55-7.50 (m, 2H), 7.13 (d, J = 8.24 Hz, 2H), 5.47 (m, 1H), 4.80-4.70 (m, 1H), 3.07 (dd, J = 17.6, 7.7 Hz, 1H), 2.82-2.64 (m, 2H), 2.25-2.08 (m, 2H), 2.0-1.91 (m, 2H). | D |

| Ex. No. | Structure/Compound Name/Mass Spec (M + H)/ ¹H-NMR (300 MHz)/Experimental Procedures | γAPP IC₅₀ (nM) |
|---|---|---|
| 117 | 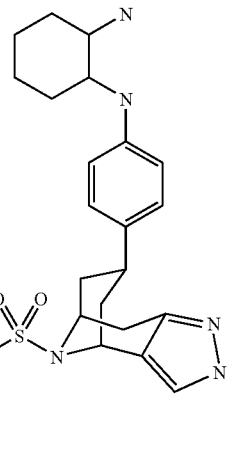<br>N-[4-(10-{[4-(trifluoromethyl)phenyl]sulfonyl}-4,5,6,7,8,9-hexahydro-1H-4,8-epiminocycloocta[c]pyrazol-6-yl)phenyl]cyclohexane-1,2-diamine; MS 560.0. ¹H NMR (DMSO-d₆) δ 7.95 (d, J = 8.4 Hz, 2H), 7.81 (d, J = 8.4 Hz, 4H), 7.33 (s, 1H), 6.74 (d, J = 8.4 Hz, 2H), 6.51 (d, J = 8.4 Hz, 2H), 5.28 (s, 1H), 4.53 (s, 1H), 1.70 (broad m, 8H), 1.21 (m, 4H). Prepared as described in Example 23 using 1-bromo-4-(hepta-1,6-dien-4-yl)benzene and cyclohexane-1,2-diamine. | A |
| 118 | 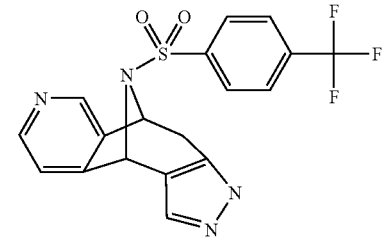<br>(+)-11-{[4-(trifluoromethyl)phenyl]sulfonyl}-1,4,9,10-tetrahydro-4,9-epiminopyrazolo[4',3':4,5]cyclohepta[1,2-c]pyridine; MS 407.0. ¹H NMR (CDCl₃) δ 8.40 (s, 1H), 8.20 (d, J = 5.0 Hz, 1H), 7.76 (d, J = 8.2 Hz, 2H), 7.52 (d, J = 8.2 Hz, 2H), 7.36 (s, 1H), 6.85 (d, J = 5.0 Hz, 1H), 5.87 (s, 1H), 5.52 (d, J = 5.6 Hz, 1H), 3.51 (dd, J = 5.6, 16.2 Hz, 1H), 2.83 (d, J = 16.2 Hz, 1H). Prepared as described in Example 8 using 3-bromo-4-pyridine-carboxaldehyde followed by chromatographic separation of regio- and stereoisomers. | D |
| 119 | (+)-11-{[4-(trifluoromethyl)phenyl]sulfonyl}-1,4,9,10-tetrahydro-4,9-epiminopyrazolo[3',4':5,6]cyclohepta[1,2-c]pyridine; MS 407.0. ¹H NMR (CDCl₃) δ 8.26 (d, J = 5.0 Hz, 1H), 8.23 (s, 1H), 7.76 (d, J = 8.2 Hz, 2H), 7.52 (d, J = 8.2 Hz, 2H), 7.37 (s, 1H), 7.06 (d, J = 5.0 Hz, 1H), 6.00 (s, 1H), 5.38 (d, J = 5.6 Hz, 1H), 3.49 (dd, J = 5.6, 16.2 Hz, 1H), 2.81 (d, J = 16.2 Hz, 1H). Prepared as described in Example 8 using 3-bromo-4-pyridinecarbox-aldehyde followed by chromatographic separation of regio- and stereoisomers. | D |
| 120 | (−)-11-{[4-(trifluoromethyl)phenyl]sulfonyl}-1,4,9,10-tetrahydro-4,9-epiminopyrazolo[3',4':5,6]cyclohepta[1,2-c]pyridine; MS 407.0<br>¹H NMR (CDCl₃) δ 8.26 (d, J = 5.0 Hz, 1H), 8.23 (s, 1H), 7.76 (d, J = 8.2 Hz, 2H), 7.52 (d, J = 8.2 Hz, 2H), 7.37 (s, 1H), 7.06 (d, J = 5.0 Hz, 1H), 6.00 (s, 1H), 5.38 (d, J = 5.6 Hz, 1H), 3.49 (dd, J = 5.6, 16.2 Hz, 1H), 2.81 (d, J = 16.2 Hz, 1H). Prepared as described above for the enantiomer. | A |

| Ex. No. | Structure/Compound Name/Mass Spec (M + H)/ ¹H-NMR (300 MHz)/Experimental Procedures | γAPP IC₅₀ (nM) |
|---|---|---|
| 121 | 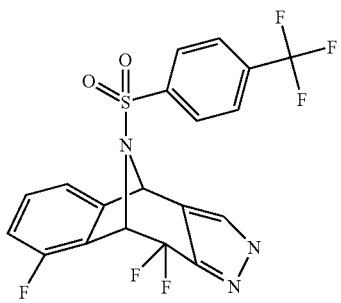<br>(±)-8,10,10-trifluoro-11-{[4-(trifluoromethyl)phenyl]sulfonyl}-1,4,9,10-tetrahydro-4,9-epiminobenzo[4,5]cyclohepta[1,2-c]pyrazole; MS 460.1<br>¹H NMR (CDCl₃) δ 7.81 (d, J = 6.8 Hz, 2H), 7.56 (d, J = 7.7 Hz, 2H), 7.49 (s, 1H), 6.99-7.06 (m, 1H), 6.68-6.79 (m, 2H), 5.99 (s, 1H), 5.66 (d, J = 10.2 Hz, 1H). Prepared as described in Example 15 using (±)-8-fluoro-11-{[4-(trifluoromethyl)phenyl]sulfonyl}-4,9-dihydro-4,9-epiminobenzo[4,5]-cyclohepta[1,2-c]pyrazol-10(1H)-one. | D |
| 122 | 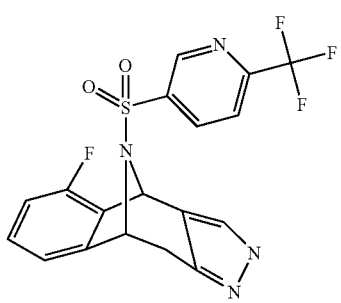<br>(±)-5-fluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 425.0<br>¹H NMR (CDCl₃) δ 8.90 (s, 1H), 8.10 (d, J = 8.3 Hz, 1H), 7.55 (d, J = 8.2 Hz, 1H), 7.44 (s, 1H), 6.96-7.03 (m, 1H), 6.91 (d, J = 7.3 Hz, 1H), 6.66 (t, 1H, J = 8.4 Hz), 6.08 (s, 1H), 5.44 (d, J = 5.3 Hz, 1H), 3.50 (dd, J = 16.4, 5.7 Hz, 1H), 2.88 (d, J = 16.4 Hz, 1H). Prepared as described in Example 9 using 5-(2-bromo-6-fluorophenyl)-4-(6-(trifluoromethyl)pyridin-3-ylsulfonyl)cyclohex-2-enone which was prepared as described in Example 8 using 6-fluoro-2-iodobenzaldehyde and sulfonamide 23. | D |
| 123 | 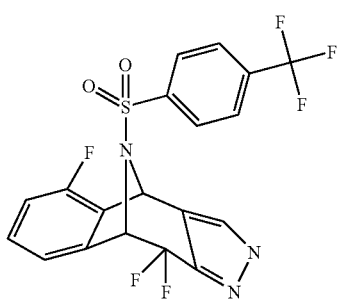<br>(±)-5,10,10-trifluoro-11-{[4-(trifluoromethyl)phenyl]sulfonyl}-1,4,9,10-tetrahydro-4,9-epiminobenzo[4,5]cyclohepta[1,2-c]pyrazole; MS 460.0<br>¹H NMR (CDCl₃) δ 7.82 (d, J = 8.2 Hz, 2H), 7.56 (d, J = 8.2 Hz, 2H), 7.49 (s, 1H), 6.98-7.10 (m, 2H), 6.68 (t, J = 8.0 Hz, 1H), 6.18 (s, 1H), 5.49 (d, J = 10.6 Hz, 1H). Prepared by fluorination of 5-fluoro-11-{[4-(trifluoromethyl)-phenyl]sulfonyl}-4,9-dihydro-4,9-epiminobenzo[4,5]-cyclohepta[1,2-c]pyrazol-10(1H)-one using the methods described in Example 15. | D |

| Ex. No. | Structure/Compound Name/Mass Spec (M + H)/ $^1$H-NMR (300 MHz)/Experimental Procedures | γAPP IC$_{50}$ (nM) |
|---|---|---|
| 124 | 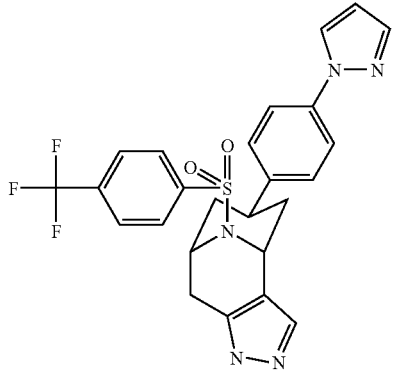<br>(±)-6-[4-(1H-pyrazol-1-yl)phenyl]-10-{[4-(trifluoromethyl)phenyl]sulfonyl}-4,5,6,7,8,9-hexahydro-1H-4,8-epiminocycloocta[c]pyrazole; MS 514.1 $^1$H NMR (CDCl$_3$) δ 7.91-7.89 (m, 3H), 7.74-7.67 (m, 3H), 7.60 (d, J = 8.3 Hz, 2H), 7.46 (s, 1H), 7.15 (d, J = 8.6 Hz, 2H), 6.47 (dd, J = 2.0, 1.9 Hz, 1H), 5.46 (s, 1H), 4.72 (bs, 1H), 2.99 (dd, J = 17.8, 7.7 Hz, 1H), 2.77-2.69 (m, 2H), 2.22 (dd, J = 12.8, 4.5 Hz, 1H), 2.14 (dd, J = 12.8, 3.9 Hz, 1H), 1.96-1.87 (m, 2H). Prepared as described in Example 23 using 1-bromo-4-(hepta-1,6-dien-4-yl)benzene. | D |
| 125 | 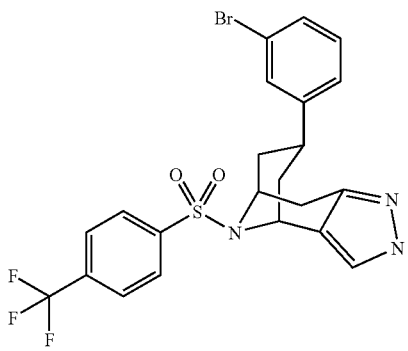<br>(±)-6-(3-bromophenyl)-10-{[4-(trifluoromethyl)phenyl]sulfonyl}-4,5,6,7,8,9-hexahydro-1H-4,8-epiminocycloocta[c]pyrazole; MS 526.0. $^1$H NMR (CDCl$_3$) δ 7.89 (d, J = 8.4 Hz, 2H), 7.69 (d, J = 8.4 Hz, 2H), 7.50 (s, 1H), 7.35 (d, J = 7.8 Hz, 1H), 7.21 (s, 1H), 1.16 (t, J = 7.8 Hz, 1H), 7.00 (d, J = 7.8 Hz, 1H), 5.46 (s, 1H), 4.71 (s, 1H), 2.96 (dd, J = 17.4 and 7.8 Hz, 1H), 2.70 (m, 2H), 2.17 (m, 2H), 1.90 (m, 2H). Prepared as described in Example 23. | D |
| 126 | (±)-6-(1H-tetrazol-5-yl)-10-{[4-(trifluoromethyl)phenyl]sulfonyl}-4,5,6,7,8,9-hexahydro-1H-4,8-epiminocycloocta[c]pyrazole; MS 440.1. $^1$H NMR (MeOD) δ 7.93 (d, J = 8.2 Hz, 2H), 7.70 (d, J = 8.3 Hz, 2H), 7.48 (s, 1H), 5.50 (s, 1H), 4.74 (m, 1H), 3.23 (m, 1H), 2.86 (dd, J = 17.5, 7.6 Hz, 1H), 2.68 (d, J = 17.5 Hz, 1H), 2.18 (m, 1H). | A |
| 127 | 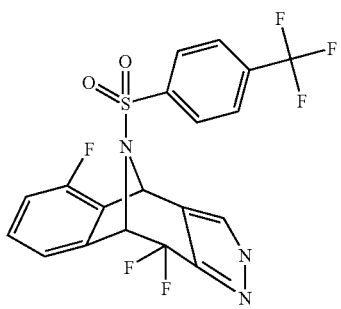<br>(−)-5,10,10-trifluoro-11-{[4-(trifluoromethyl)phenyl]sulfonyl}-1,4,9,10-tetrahydro-4,9-epiminobenzo[4,5]cyclohepta[1,2-c]pyrazole; MS 460.1 $^1$H NMR (CDCl$_3$) δ 7.82 (d, J = 8.2 Hz, 2H), 7.56 (d, J = 8.2 Hz, 2H), 7.49 | D |

| Ex. No. | Structure/Compound Name/Mass Spec (M + H)/ ¹H-NMR (300 MHz)/Experimental Procedures | γAPP IC$_{50}$ (nM) |
|---|---|---|
|  | (s, 1H), 6.98-7.10 (m, 2H), 6.68 (t, J = 8.0 Hz, 1H), 6.18 (s, 1H), 5.49 (d, J = 10.6 Hz, 1H). Prepared by fluorination of 5-fluoro-11-{[4-(trifluoromethyl)-phenyl]sulfonyl}-4,9-dihydro-4,9-epiminobenzo[4,5]cyclohepta[1,2-c]pyrazol-10(1H)-one using the methods described in Example 15 followed by chiral chromatographic separation of stereoisomers. |  |
| 128 | (+)-5,10,10-trifluoro-11-{[4-(trifluoromethyl)phenyl]sulfonyl}-1,4,9,10-tetrahydro-4,9-epiminobenzo[4,5]cyclohepta[1,2-c]pyrazole; MS 460.1 ¹H NMR (CDCl$_3$) δ 7.82 (d, J = 8.2 Hz, 2H), 7.56 (d, J = 8.2 Hz, 2H), 7.49 (s, 1H), 6.98-7.10 (m, 2H), 6.68 (t, J = 8.0 Hz, 1H), 6.18 (s, 1H), 5.49 (d, J = 10.6 Hz, 1H). Prepared as described above for the enantiomer. | D |
| 129 | (−)-5-fluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 425.1 ¹H NMR (CDCl$_3$) δ 8.90 (s, 1H), 8.10 (dd, J = 8.2, 1.7 Hz, 1H), 7.55 (dd, J = 8.2, 0.6 Hz, 1H), 7.46 (s, 1H), 6.96-7.03 (m, 1H), 6.91 (d, 1H, J = 7.3 Hz), 6.66 (t, 1H, J = 8.43 Hz), 6.08 (s, 1H), 5.44 (d, 1H, J = 5.6 Hz), 3.50 (dd, J = 16.4, 5.7 Hz, 1H), 2.88 (d, J = 16.4 Hz, 1H). Prepared as described in Example 9 using 5-(2-bromo-6-fluorophenyl)-4-(6-(trifluoromethyl)pyridin-3-ylsulfonyl)cyclohex-2-enone which was prepared as described in Example 8 using 6-fluoro-2-iodobenzaldehyde and sulfonamide 23 followed by chiral chromatographic separation of stereoisomers. | >10 |
| 130 | (+)-5-fluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 425.1 ¹H NMR (CDCl$_3$) δ 8.90 (s, 1H), 8.10 (dd, J = 8.2, 1.7 Hz, 1H), 7.55 (dd, J = 8.2, 0.6 Hz, 1H), 7.46 (s, 1H), 6.96-7.03 (m, 1H), 6.91 (d, 1H, J = 7.3 Hz), 6.66 (t, 1H, J = 8.43 Hz), 6.08 (s, 1H), 5.44 (d, 1H, J = 5.6 Hz), 3.50 (dd, J = 16.4, 5.7 Hz, 1H), 2.88 (d, J = 16.4 Hz, 1H). Prepared as described above for the enantiomer. | D |
| 131 | (±)-5,8-difluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 443.0 ¹H NMR (CDCl$_3$) δ 8.93 (d, J = 1.7 Hz, 1H), 8.16 (dd, J = 8.3, 2.2 Hz, 1H), 7.63 (d, J = 8.2 Hz, 1H), 7.48 (s, 1H), 6.67 (t, J = 5.4 Hz, 2H), 6.08 (s, 1H), 5.61 (d, J = 5.6 Hz, 1H), 3.51 (dd, J = 16.6, 5.7 Hz, 1H), 2.95 (d, J = 16.6 Hz, 1H). Prepared as described in Example 9 using 5-(2-bromo-3,6-difluorophenyl)-4-(6-(trifluoromethyl)pyridin-3-ylsulfonyl)cyclohex-2-enone which was prepared as described in Example 8 using 2-bromo-3,6-difluorobenzaldehyde and sulfonamide 23. | D |

-continued

| Ex. No. | Structure/Compound Name/Mass Spec (M + H)/ $^1$H-NMR (300 MHz)/Experimental Procedures | γAPP IC$_{50}$ (nM) |
|---|---|---|
| 132 | 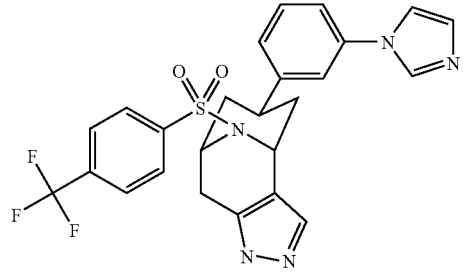<br>(±)-6-[3-(1H-imidazol-1-yl)phenyl]-10-{[4-(trifluoromethyl)phenyl]-sulfonyl}-4,5,6,7,8-hexahydro-1H-4,8-epiminocycloocta[c]pyrazole; MS 514.1. $^1$H NMR (CDCl$_3$) δ 7.84 (d, J = 8.3 Hz, 2H), 7.60 (d, J = 8.3 Hz, 2H), 7.37 (m, 2H), 7.22 (m, 3H), 7.10 (m, 2H), 5.43 (s, 1H), 4.68 (m, 1H), 2.85 (2H), 2.65 (d, J = 17.1 Hz, 1H), 2.19 (m, 2H), 1.88 (m, 2H). Prepared as described in Example 23 using imidazole. | D |
| 133 | 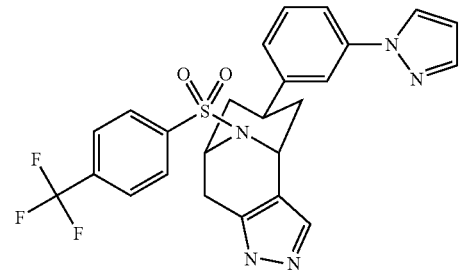<br>(±)-6-[3-(1H-pyrazol-1-yl)phenyl]-10-{[4-(trifluoromethyl)phenyl]sulfonyl}-4,5,6,7,8,9-hexahydro-1H-4,8-epiminocycloocta[c]pyrazole; MS 514.1 $^1$H NMR (CDCl$_3$) δ 7.87 (m, 3H), 7.64 (m, 10H), 7.45 (m, 2H), 7.32 (m, 3H), 7.99 (m, 1H), 6.44 (m, 1H), 5.42 (s, 1H), 4.64 (m, 1H), 3.77 (m, 1H), 3.60 (m, 2H), 2.85 (m, 2H), 2.65 (d, J = 17.0 Hz, 1H), 2.16 (m, 2H), 1.88 (m, 2H). Prepared as described in Example 23. | D |
| 134 | 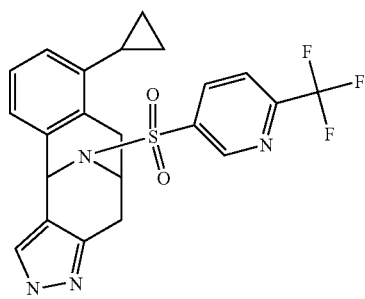<br>(±)-7-cyclopropyl-12-{[6-(trifluoromethyl)pyridin-3-yl]sulfonyl}-4,5,6,11-tetrahydro-3H-5,11-epiminobenzo[4,5]cycloocta[1,2-c]pyrazole; MS 461.0 $^1$H NMR (CDCl$_3$) δ 8.88 (d, J = 1.9 Hz, 1H), 7.87 (dd, J = 1.9, 8.2 Hz, 1H), 7.50 (s, 1H), 7.38 (d, J = 8.2 Hz, 1H), 7.06 (t, J = 4.4 Hz, 1H), 6.76-6.71 (m, 1H), 6.06 (s, 1H), 5.05-5.00 (m, 1H), 3.42 (dd, J = 5.6, 16.5 Hz, 1H), 3.30 (dd, J = 9.9, 18.5 Hz, 1H), 2.95 (d, J = 16.5 Hz, 1H), 2.38 (d, J = 18.6 Hz, 1H); 1.32-1.23 (m, 1H); 0.84-0.72 (m, 2H), 0.46-0.37 (m, 1H), 0.30-0.24 (m, 1H). Prepared as described in Example 13. | D |

| Ex. No. | Structure/Compound Name/Mass Spec (M + H)/ ¹H-NMR (300 MHz)/Experimental Procedures | γAPP IC₅₀ (nM) |
|---|---|---|
| 135 | 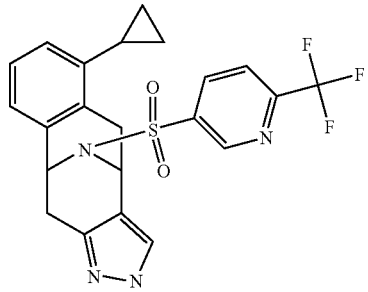<br><br>(±)-6-cyclopropyl-12-{[6-(trifluoromethyl)pyridin-3-yl]sulfonyl}-4,5,10,11-tetrahydro-1H-4,10-epiminobenzo[5,6]cycloocta[1,2-c]pyrazole; MS 461.0 ¹H NMR (CDCl₃) δ 9.07 (d, J = 2.0 Hz, 1H), 8.20 (dd, J = 1.9, 8.2 Hz, 1H), 7.65 (d, J = 8.0 Hz, 1H), 7.54 (s, 1H), 7.15 (t, J = 7.6 Hz, 1H), 7.02 (d, J = 7.5 Hz, 1H), 6.88 (d, J = 7.6 Hz, 1H), 5.64 (d, J = 5.7 Hz, 1H), 5.53 (d, J = 5.1 Hz, 1H), 3.35 (dd, J = 6.3, 16.5 Hz, 1H), 3.16 (dd, J = 5.8, 17 Hz, 1H), 3.00 (d, J = 11.1 Hz, 1H), 2.94 (d, J = 11.4 Hz, 1H); 1.58-1.49 (m, 1H); 0.91-0.77 (m, 2H); 0.51-0.35 (m, 2H). Prepared as described in Example 13. | D |
| 136 | (±)-10-[(4-chlorophenyl)sulfonyl]-6-(1-methyl-1H-1,2,3-triazol-5-yl)-4,5,6,7,8,9-hexahydro-1H-4,8-epiminocycloocta[c]pyrazole; MS 419.1 ¹H NMR (CDCl₃) δ 7.68 (d, J = 8.2 Hz, 2H), 7.44 (s, 1H), 7.37 (d, J = 8.2 Hz, 2H), 7.30 (s, 1H), 5.42-5.43 (m, 1H), 4.63-4.65 (m, 1H), 4.11 (s, 3H), 2.91-2.96 (m, 2H), 2.69 (d, J = 17.6 Hz, 1H), 1.96-2.16 (m, 4H). | D |
| 137 | 10-[(4-chlorophenyl)sulfonyl]-6-(1-methyl-1H-1,2,3-triazol-4-yl)-4,5,6,7,8,9-hexahydro-1H-4,8-epiminocycloocta[c]pyrazole (enantiomer A); MS 419.1<br>¹H NMR (CDCl₃) δ 7.68 (d, J = 8.0 Hz, 2H), 7.51 (s, 1H), 7.46 (s, 1H), 7.38 (d, J = 8.0 Hz, 2H), 5.45-5.47 (m, 1H), 4.66-4.69 (m, 1H), 3.96 (s, 3H), 2.98-3.07 (m, 2H), 2.67 (d, J = 17.6 Hz, 1H), 1.92-2.16 (m, 4H). Prepared from the racemic mixture by chiral separation. | A |
| 138 | 10-[(4-chlorophenyl)sulfonyl]-6-(1-methyl-1H-1,2,3-triazol-4-yl)-4,5,6,7,8,9-hexahydro-1H-4,8-epiminocycloocta[c]pyrazole (enantiomer B); MS 419.1 ¹H NMR (CDCl₃) δ 7.67 (d, J = 8.3 Hz, 2H), 7.45 (s, 1H), 7.37 (s, 1H), 7.36 (d, J = 8.3 Hz, 2H), 5.45-5.47 (m, 1H), 4.65-4.68 (m, 1H), 3.85 (s, 3H), 2.87-2.97 (m, 2H), 2.62 (d, J = 17.1 Hz, 1H), 1.88-2.18 (m, 4H). Prepared from the racemic mixture by chiral separation | B |
| 139 | (−)-10-[(4-chlorophenyl)sulfonyl]-6-(2-methyl-2H-1,2,3-triazol-4-yl)-4,5,6,7,8,9-hexahydro-1H-4,8-epiminocycloocta[c]pyrazole; MS 419.1 ¹H NMR (CDCl₃) δ 7.64 (d, J = 8.9 Hz, 2H), 7.28-7.33 (m, 3H), 7.22 (s, 1H) 5.40-5.43 (m, 1H), 4.61-4.63 (m, 1H), 4.07 (s, 3H), 3.05-3.08 (m, 1H), 2.85 (dd, J = 17.2, 7.8 Hz, 1H), 2.62 (d, J = 17.2 Hz, 1H), 2.00-2.18 (m, 4H). | >300 |
| 140 | (+)-10-[(4-chlorophenyl)sulfonyl]-6-(2-methyl-2H-1,2,3-triazol-4-yl)-4,5,6,7,8,9-hexahydro-1H-4,8-epiminocycloocta[c]pyrazole; MS 419.1 ¹H NMR (CDCl₃) δ 7.70 (d, J = 8.2 Hz, 2H), 7.55 (s, 1H), 7.41 (d, J = 8.2 Hz, 2H), 7.30 (s, 1H) 5.41-5.43 (m, 1H), 4.63-4.65 (m, 1H), 4.08 (s, 3H), 3.01-3.08 (m, 2H), 2.80 (d, J = 17 8 Hz, 1H), 2.03-2.15 (m, 4H). | C |
| 141 | 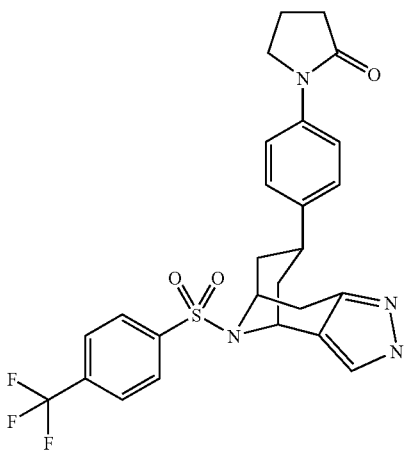 | D |

| Ex. No. | Structure/Compound Name/Mass Spec (M + H)/ ¹H-NMR (300 MHz)/Experimental Procedures | γAPP IC₅₀ (nM) |
|---|---|---|
| | (±)-1-[4-(10-{[4-(trifluoromethyl)phenyl]sulfonyl}-4,5,6,7,8,9-hexahydro-1H-4,8-epiminocycloocta[c]pyrazol-6-yl)phenyl]pyrrolidin-2-one; MS 531.0 ¹H NMR (CDCl₃) δ 7.89 (d, J = 8.4 Hz, 2H), 7.68 (d, J = 8.4 Hz, 2H), 7.50 (d, J = 8.4 Hz, 2H), 7.46 (s, 1H), 7.06 (d, J = 8.4 Hz, 2H), 5.44 (s, 1H), 4.69 (s, 1H), 3.85 (t, J = 7.2 Hz, 2H), 3.00 (dd, J = 17.4 and 7.5 Hz, 1H), 2.68 (m, 4H), 2.18 (m, 4H), 1.87 (m, 2H). Prepared as described in Example 23 using 1-bromo-4-(hepta-1,6-dien-4-yl)benzene and pyrrolidin-2-one. | |
| 142 | [chemical structure] (±)-methyl 4-{[4-(10-{[4-(trifluoromethyl)phenyl]sulfonyl}-4,5,6,7,8,9-hexahydro-1H-4,8-epiminocycloocta[c]pyrazol-6-yl)phenyl]amino}butanoate; MS 563.0. ¹H NMR (CDCl₃) δ 7.89 (d, J = 8.4 Hz, 2H), 7.66 (d, J = 8.4 Hz, 2H), 7.43 (s, 1H), 6.98 (d, J = 7.8 Hz, 2H), 6.87 (d, J = 7.8 Hz, 2H), 5.43 (s, 1H), 4.67 (s, 1H), 3.69 (s, 3H), 3.26 (m, 2H), 2.96 (dd, J = 16.5 and 7.2 Hz, 1H), 2.66 (m, 2H), 2.45 (m, 2H), 2.04 (m, 4H), 1.94 (m, 2H). Prepared as described in Example 23 using 1-bromo-4-(hepta-1,6-dien-4-yl)benzene and methyl 4-aminobutanoate. | D |
| 143 | (±)-4-[4-(10-{[4-(trifluoromethyl)phenyl]sulfonyl}-4,5,6,7,8,9-hexahydro-1H-4,8-epiminocycloocta[c]pyrazol-6-yl)phenyl]morpholin-3-one; MS 547.0 ¹H NMR (CDCl₃) δ 7.89 (d, J = 8.4 Hz, 2H), 7.68 (d, J = 8.4 Hz, 2H), 7.40 (s, 1H), 7.23 (d, J = 8.4 Hz, 2H), 7.10 (d, J = 8.4 Hz, 2H), 5.45 (s, 1H), 4.69 (s, 1H), 4.35 (s, 2H), 4.04 (m, 2H), 3.74 (m, 2H), 2.96 (m, 1H), 2.73 (m, 2H), 2.13 (m, 2H), 1.86 (m, 2H). Prepared as described in Example 23 using 1-bromo-4-(hepta-1,6-dien-4-yl)benzene and morpholin-3-one. | B |
| 144 | (±)-methyl (2-{[4-(10-{[4-(trifluoromethyl)phenyl]sulfonyl}-4,5,6,7,8,9-hexahydro-1H-4,8-epiminocycloocta[c]pyrazol-6-yl)phenyl]amino}-ethoxy)acetate; MS 579.0. ¹H NMR (CDCl₃) δ 7.89 (d, J = 8.1 Hz, 2H), 7.68 (d, J = 8.1 Hz, 2H), 7.47 (s, 1H), 7.00 (m, 4H), 5.44 (s, 1H), 4.68 (s, 1H), 4.19 (s, 2H), 3.87 (t, J = 4.8 Hz, 2H), 3.80 (s, 3H), 3.45 (t, J = 4.5 Hz, 2H), 3.00 (dd, J = 17.7 and 7.8 Hz, 1H), 2.65 (m, 2H), 2.12 (m, 2H), 1.86 (m, 2H). Prepared as described in Example 23 using 1-bromo-4-(hepta-1,6-dien-4-yl)benzene and methyl 2-(2-aminoethoxy)acetate. | A |
| 145 | (±)-(2-{[4-(10-{[4-(trifluoromethyl)phenyl]sulfonyl}-4,5,6,7,8,9-hexahydro-1H-4,8-epiminocycloocta[c]pyrazol-6-yl)phenyl]amino}ethoxy)acetic acid; MS 565.0. ¹H NMR (DMSO-d₆) δ 8.68 (s, 1H), 7.93 (d, J = 8.1 Hz, 2H), 7.68 (d, J = 8.1 Hz, 2H), 7.34 (s, 1H), 6.80 (d, J = 8.1 Hz, 2H), 6.60 (d, J = 8.1 Hz, 2H), 5.39 (s, 1H), 4.68 (s, 1H), 2.70 (m, 2H), 1.77 (m, 4H). Prepared as described in Example 23 using 1-bromo-4-(hepta-1,6-dien-4-yl)benzene and 2-(2-aminoethoxy)acetic acid. | D |
| 146 | (±)-methyl N-[4-(10-{[4-(trifluoromethyl)phenyl]sulfonyl}-4,5,6,7,8,9-hexahydro-1H-4,8-epiminocycloocta[c]pyrazol-6-yl)phenyl]-b-alaninate; MS 549.0. ¹H NMR (CDCl₃) δ 7.89 (d, J = 8.4 Hz, 2H), 7.68 (d, J = 8.4 Hz, 2H), 7.33 (s, 1H), 6.95 (d, J = 8.4 Hz, 2H), 6.84 (d, J = 8.4 Hz, 2H), 5.44 (s, 1H), 4.69 (s, 1H), 3.72 (s, 3H), 3.52 (t, J = 6.3 Hz, 2H), 3.00 (dd, J = 17.7 and 7.8 Hz, 1H), 2.70 (m, 4H), 2.12 (m, 2H), 1.86 (m, 2H). Prepared as described in Example 23 using 1-bromo-4-(hepta-1,6-dien-4-yl)benzene and methyl 3-aminopropanoate. | D |
| 147 | (±)-6-[4-(1H-1,2,4-triazol-1-yl)phenyl]-10-{[4-(trifluoromethyl)phenyl]-sulfonyl}-4,5,6,7,8,9-hexahydro-1H-4,8-epiminocycloocta[c]pyrazole; MS 515.0. ¹H NMR (CDCl₃) δ 8.63 (s, 1H), 8.16 (s, 1H), 7.89 (d, J = 8.1 Hz, 2H), 7.70 (d, J = 8.1 Hz, 2H), 7.61 (d, J = 8.7 Hz, 2H), 7.51 (s, 1H), 7.23 (d, J = 8.7 Hz, 2H), 5.49 (s, 1H), 4.74 (s, 1H), 3.00 (dd, J = 17.4 and 7.5 Hz, 1H), 2.80 (m, 2H), 2.19 (m, 2H), 1.94 (m, 2H). Prepared as described in Example 23 using 1-bromo-4-(hepta-1,6-dien-4-yl)benzene and 4H-1,2,4-triazole. | C |

| Ex. No. | Structure/Compound Name/Mass Spec (M + H)/ ¹H-NMR (300 MHz)/Experimental Procedures | γAPP IC$_{50}$ (nM) |
|---|---|---|
| 148 | 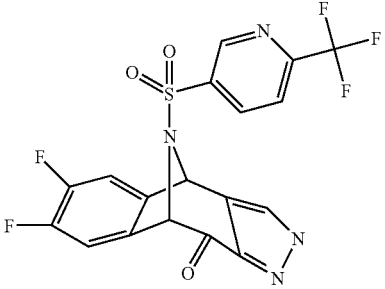<br>(±)-6,7-difluoro-11-{[6-(trifluoromethyl)pyridin-3-yl]sulfonyl}-4,9-dihydro-4,9-epiminobenzo[4,5]cyclohepta[1,2-c]pyrazol-10(1H)-one; MS 457.0 ¹H NMR (CDCl$_3$) δ 8.93 (d, J = 1.5 Hz, 1H), 8.15 (dd, J = 8.2, 1.7 Hz, 1H), 7.71 (s, 1H), 7.63 (d, J = 8.3 Hz, 1H), 7.21-7.28 (m, 1H), 7.09 (dd, J = 8.4, 6.9 Hz, 1H), 6.21 (s, 1H), 5.43 (s, 1H). Prepared by oxidation of 6,7-difluoro-11-{[6-(trifluoromethyl)pyridin-3-yl]sulfonyl}-1,4,9,10-tetrahydro-4,9-epimino-benzo-[4,5]cyclohepta[1,2-c]pyrazole using the methods described in Example 15. | D |
| 149 | 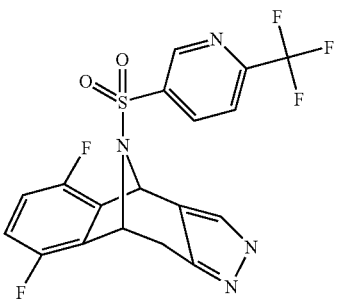<br>(−)-5,8-difluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 443.1 ¹H NMR (CDCl$_3$) δ 8.93 (d, J = 1.7 Hz, 1H), 8.16 (dd, J = 8.3, 2.2 Hz, 1H), 7.63 (d, J = 8.2 Hz, 1H), 7.48 (s, 1H), 6.67 (t, J = 5.4 Hz, 2H), 6.08 (s, 1H), 5.61 (d, J = 5.6 Hz, 1H), 3.51 (dd, J = 16.6, 5.7 Hz, 1H), 2.95 (d, J = 16.6 Hz, 1H). Prepared as described in Example 9 using 5-(2-bromo-3,6-difluorophenyl)-4-(6-(trifluoromethyl)pyridin-3-ylsulfonyl)cyclohex-2-enone, followed by chiral chromatographic separation of stereoisomers. | C |
| 150 | (+)-5,8-difluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 443.1 ¹H NMR (CDCl$_3$) δ 8.93 (d, J = 1.7 Hz, 1H), 8.16 (dd, J = 8.3, 2.2 Hz, 1H), 7.63 (d, J = 8.2 Hz, 1H), 7.48 (s, 1H), 6.67 (t, J = 5.4 Hz, 2H), 6.08 (s, 1H), 5.61 (d, J = 5.6 Hz, 1H), 3.51 (dd, J = 16.6, 5.7 Hz, 1H), 2.95 (d, J = 16.6 Hz, 1H). Prepared as described above for the enantiomer. | D |
| 151 | (±)-7-fluoro-5-methyl-11-{[6-(trifluoromethyl)pyridin-3-yl]sulfonyl}-1,4,9,10-tetrahydro-4,9-epiminobenzo[4,5]cyclohepta[1,2-c]pyrazole; MS 439.1. ¹H NMR (CDCl$_3$) δ 8.90 (s, 1H), 8.07 (d, J = 8.2 Hz, 1H), 7.55 (d, J = 8.3 Hz, 1H), 7.40 (s, 1H), 6.91 (d, J = 6.5 Hz, 1H), 6.62 (d, J = 8.5 Hz, 1H), 5.83 (s, 1H), 5.33 (d, J = 5.4 Hz, 1H), 3.44 (dd, J = 16.4, 5.6 Hz, 1H), 2.83 (d, J = 16.4 Hz, 1H). Prepared as described in Example 9 using 5-(2-bromo-4-fluoro-6-methylphenyl)-4-(6-(trifluoromethyl)pyridin-3-ylsulfonyl)cyclohex-2-enone, which was prepared as described in Example 8 using 2-bromo-4-fluoro-6-methylbenzaldehyde and sulfonamide 23. | D |
| 152 | (±)-N-[4-(10-{[4-(trifluoromethyl)phenyl]sulfonyl}-4,5,6,7,8,9-hexahydro-1H-4,8-epiminocyloocta[c]pyrazol-6-yl)phenyl]acetamide; MS 505.0 ¹H NMR (CDCl$_3$) δ 7.89 (d, J = 8.7 Hz, 2H), 7.70 (d, J =8.7 Hz, 2H), 7.46 (s, 1H), 7.40 (d, J = 9.0 Hz, 2H), 7.18 (s, 1H), 7.01 (d, J = 9.0 Hz, 2H), 5.44 (s, 1H), 4.69 (s, 1H), 3.00 (dd, J = 17.1, 7.2 Hz, 1H), 2.66 (m, 2H), 2.18 (s, 3H), 2.20 (m, 2H), 1.87 (m, 2H). Prepared as described in Example 23 using 1-bromo-4-(hepta-1,6-dien-4-yl)benzene and acetamide. | D |
| 153 | (±)-1-[4-(10-{[4-(trifluoromethyl)phenyl]sulfonyl}-4,5,6,7,8,9-hexahydro-1H-4,8-epiminocyloocta[c]pyrazol-6-yl)phenyl]azetidin-2-one; MS 517.0 ¹H NMR (CD$_3$OD) δ 7.94 (d, J = 8.4 Hz, 2H), 7.70 (d, J = 8.4 Hz, 2H), 7.38 (s, 1H), 7.28 (d, J = 8.4 Hz, 2H), 7.10 (d, J = 8.4 Hz, 2H), 5.45 (s, 1H), 4.70 (s, 1H), 3.66 (t, J = 4.5 Hz, 2H), 3.10 (t, J = 4.5 Hz, 2H), 2.85 (m, 3H), 2.10 (m, 2H), 1.87 (m, 2H). Prepared as described in Example 23 using 1-bromo-4-(hepta-1,6-dien-4-yl)benzene and azetidin-2-one. | D |

| Ex. No. | Structure/Compound Name/Mass Spec (M + H)/ ¹H-NMR (300 MHz)/Experimental Procedures | γAPP IC$_{50}$ (nM) |
|---|---|---|
| 154 | (±)-1-[4-(10-{[4-(trifluoromethyl)phenyl]sulfonyl}-4,5,6,7,8,9-hexahydro-1H-4,8-epiminocycloocta[c]pyrazol-6-yl)phenyl]ethanone; MS 490.0. ¹H NMR (CDCl$_3$) δ 7.87 (m, 4H), 7.64 (d, J = 8.7 Hz, 2H), 7.38 (s, 1H), 7.17 (d, J = 8.7 Hz, 2H), 5.46 (s, 1H), 4.71 (s, 1H), 2.87 (m, 2H), 2.66 (m, 1H), 2.60 (s, 3H), 2.20 (m, 2H), 1.90 (m, 2H). Prepared as described in Example 27. | C |
| 155 | (±)-6-(trifluoromethyl)-11-{[4-(trifluoromethyl)phenyl]sulfonyl}-1,4,9,10-tetrahydro-4,9-epiminobenzo[4,5]cyclohepta[1,2-c]pyrazole; MS 474.0 ¹H NMR (CDCl$_3$) δ 7.72 (d, J = 8.1 Hz, 2H), 7.50-7.47 (m, 3H), 7.34 (s, 1H), 7.24 (d, J = 7.2 Hz, 1H), 7.01 (d, J = 7.2 Hz, 1H), 5.90 (s, 1H), 5.45 (d, J = 6.0 Hz, 1H), 3.58 (dd, J = 6.0, 16.5 Hz, 1H), 2.90 (d, J = 16.5 Hz, 1H). Prepared as described in Example 8 using 2-bromo-5-(trifluoromethyl)benzaldehyde, followed by chromatographic separation of regioisomers. | D |
| 156 | (±)-7-(trifluoromethyl)-11-{[4-(trifluoromethyl)phenyl]sulfonyl}-1,4,9,10-tetrahydro-4,9-epiminobenzo[4,5]cyclohepta[1,2-c]pyrazole; MS 474.1 ¹H NMR (CDCl$_3$) δ 7.72 (d, J = 8.1 Hz, 2H), 7.50-7.47 (m, 3H), 7.28-7.26 (m, 1H), 7.20 (d, J = 7.8 Hz, 1H), 7.15 (s, 1H), 5.91 (s, 1H), 5.45 (d, J = 5.7 Hz, 1H), 3.58 (dd, J = 5.4, 16.5 Hz, 1H), 2.89 (d, J = 16.5 Hz, 1H). Prepared as described in Example 8 using 2-Bromo-5-(trifluoromethyl)benzaldehyde followed by chromatographic separation regioisomers. | D |
| 157 | (±)-6,7,10,10-tetrafluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 479.0. ¹H NMR (CDCl$_3$): δ 9.01 (s, 1H), 8.22 (d, J = 8.3 Hz, 1H), 7.72 (d, J = 8.3 Hz, 1H), 7.52 (s, 1H), 7.30-7.20 (m, 1H), 7.02-6.96 (m, 1H), 6.05 (s, 1H), 5.52 (d, J = 10.1 Hz, 1H). Prepared by fluorination of 6,7-difluoro-11-{[6-(trifluoromethyl)pyridin-3-yl]sulfonyl}-4,9-dihydro-4,9-epimino-benzo-[4,5]cyclohepta[1,2-c]pyrazol-10(1H)-one using the methods described in Example 15. | D |
| 158 | <br>(−)-7-fluoro-5-methyl-11-{[6-(trifluoromethyl)pyridin-3-yl]sulfonyl}-1,4,9,10-tetrahydro-4,9-epiminobenzo[4,5]cyclohepta[1,2-c]pyrazole; MS 439.1. ¹H NMR (CDCl$_3$): δ 8.90 (s, 1H), 8.07 (d, J = 8.2 Hz, 1H), 7.55 (d, J = 8.23 Hz, 1H), 7.40 (s, 1H), 6.91 (d, J = 6.5 Hz, 1H), 6.62 (d, J = 8.5 Hz, 1H), 5.83 (s, 1H), 5.33 (d, J = 5.4 Hz, 1H), 3.44 (dd, J = 16.4, 5.6 Hz, 1H), 2.83 (d, J = 16.4 Hz, 1H). Prepared as described in Example 9 using 5-(2-bromo-4-fluoro-6-methylphenyl)-4-(6-(trifluoromethyl)pyridin-3-ylsulfonyl)cyclo-hex-2-enone, followed by chiral chromatographic separation of stereoisomers. | >10 |
| 159 | (+)-7-fluoro-5-methyl-11-{[6-(trifluoromethyl)pyridin-3-yl]sulfonyl}-1,4,9,10-tetrahydro-4,9-epiminobenzo[4,5]cyclohepta[1,2-c]pyrazole; MS 439.1. ¹H NMR (CDCl$_3$): δ 8.90 (s, 1H), 8.07 (d, J = 8.2 Hz, 1H), 7.55 (d, J = 8.23 Hz, 1H), 7.40 (s, 1H), 6.91 (d, J = 6.5 Hz, 1H), 6.62 (d, J = 8.5 Hz, 1H), 5.83 (s, 1H), 5.33 (d, J = 5.4 Hz, 1H), 3.44 (dd, J = 16.4, 5.6 Hz, 1H), 2.83 (d, J = 16.4 Hz, 1H). Prepared as described above for the enantiomer. | D |
| 160 | | D |

| Ex. No. | Structure/Compound Name/Mass Spec (M + H)/ ¹H-NMR (300 MHz)/Experimental Procedures | γAPP IC$_{50}$ (nM) |
|---|---|---|
| | 13-{[4-(trifluoromethyl)phenyl]sulfonyl}-7,10,11,12-tetrahydro-7,12-epiminonaphtho[2',1':4,5]cyclohepta[1,2-c]pyrazole; MS 456.1. ¹H NMR (CDCl$_3$) (Diastereomers) δ 7.71-7.60 (m, 2H), 7.67 (m, 2H), 7.62 (d, J = 8.2 Hz, 4H), 7.51 (t, J = 7.2 Hz, 2H), 7.45-7.37 (m, 2H), 7.46 (d, J = 8.6 Hz, 1H), 7.43 (s, 1H), 7.41 (m, 1H), 7.39 (s, 1H), 7.17 (d, J = 8.6 Hz, 1H), 7.15 (d, J = 8.2 Hz, 4H), 7.02 (d, J = 8.6 Hz, 1H), 6.27 (s, 1H), 5.93 (s, 1H), 5.85 (d, J = 5.5 Hz, 1H), 5.52 (d, J = 5.5 Hz, 1H), 3.60 (dd, J = 5.5, 16.0 Hz, 1H), 3.58 (dd, J = 5.5, 16.0 Hz, 1H), 2.98 (d, J = 16.0 Hz, 1H) 2.90 (d, J = 16.0 Hz, 1H). Prepared as described in Example 8 using 1-bromo-2-naphthalene-carboxaldehyde. | |
| 161 | (−)-5-fluoro-11-{[6-(trifluoromethyl)pyridin-3-yl]sulfonyl}-4,9-dihydro-4,9-epiminobenzo[4,5]cyclohepta[1,2-c]pyrazol-10(1H)-one; MS 439.0. ¹H NMR (CDCl$_3$): δ 8.96 (d, J = 1.8 Hz, 1H), 8.21 (dd, J = 8.2, 2.1 Hz, 1H), 7.77 (s, 1H), 7.64 (d, J = 8.3 Hz, 1H), 7.13-7.02 (m, 2H), 6.74 (t, J = 8.2 Hz, 1H), 6.51 (s, 1H), 5.57 (s, 1H). Prepared by oxidation of 5-fluoro-11-{[6-(trifluoromethyl)pyridin-3-yl]sulfonyl}-1,4,9,10-tetrahydro-4,9-epiminobenzo[4,5]cyclohepta[1,2-c]pyrazole using the methods described in Example 15. | D |
| 162 | (±)-7-(4-fluorophenyl)-12-{[4-(trifluoromethyl)phenyl]sulfonyl}-4,5,6,11-tetrahydro-3H-5,11-epiminobenzo[4,5]cycloocta[1,2-c]pyrazole; MS 514.1. ¹H NMR (CDCl$_3$) δ 7.61 (d, J = 7.9 Hz, 2H), 7.46 (d, J = 8.3 Hz, 2H), 7.41 (s, 1H), 7.25 (dd, J = 1.2, 7.6 Hz, 1H), 7.17 (t, J = 7.4 Hz, 1H), 7.02 (t, J = 8.7 Hz, 2H), 6.89 (dd, J = 1.4, 7.5 Hz, 1H), 6.83-6.79 (m, 2H), 6.12 (s, 1H), 4.77-4.72 (m, 1H), 3.26 (dd, J = 5.6, 15.9 Hz, 1H), 2.87-2.81 (m, 1H), 2.75 (d, J = 16.9 Hz, 1H), 2.28 (d, J = 18.6 Hz, 1H). Prepared as described in Example 12. | D |
| 163 | (±)-12-{[4-(trifluoromethyl)phenyl]sulfonyl}-4,5,10,11-tetrahydro-1H-4,10-epiminobenzo[5,6]cycloocta[1,2-c]pyrazole; MS 419.9. ¹H NMR (CDCl$_3$) δ 7.90 (d, J = 8.1 Hz, 2H), 7.64 (d, J = 8.2 Hz, 2H), 7.40 (s, 1H), 7.19-7.09 (m, 3H), 6.93 (d, J = 7.7 Hz, 1H), 5.53 (d, J = 5.3 Hz, 1H), 5.49 (d, J = 5.2 Hz, 1H), 3.32 (dd, J = 6.1, 16.5 Hz, 1H), 3.16 (dd, J = 5.7, 15.9 Hz, 1H), 2.85 (d, J = 16.3 Hz, 1H), 2.73 (d, J = 16.4 Hz, 1H). Prepared as described in Example 11. | D |
| 164 | (±)-12-{[4-(trifluoromethyl)phenyl]sulfonyl}-4,5,6,11-tetrahydro-3H-5,11-epiminobenzo[4,5]cycloocta[1,2-c]pyrazole; MS 419.9. ¹H NMR (CDCl$_3$) δ 7.62 (d, J = 8.2 Hz, 2H), 7.41 (d, J = 8.3 Hz, 2H), 7.33 (s, 1H), 7.15 (d, J = 7.4 Hz, 1H), 7.06 (d, J = 7.4 Hz, 1H), 6.95 (dt, J = 1.5, 7.5 Hz, 1H), 6.59 (d, J = 7.6 Hz, 1H), 6.01 (s, 1H), 4.88-4.84 (m, 1H), 3.24 (dd, J = 6.1, 16.1 Hz, 1H), 3.08 (d, J = 9.6, 17.9 Hz, 1H), 2.75 (dd, J = 1.1, 17.3 Hz, 1H); 2.46 (d, J = 17.9 Hz, 1H). Prepared as described in Example 11. | D |
| 165 | (±)-6-(4-fluorophenyl)-12-{[4-(trifluoromethyl)phenyl]sulfonyl}-4,5,10,11-tetrahydro-1H-4,10-epiminobenzo[5,6]cycloocta[1,2-c]pyrazole; MS 514.1 ¹H NMR (CDCl$_3$) δ 7.90 (d, J = 8.2 Hz, 2H), 7.65 (d, J = 8.2 Hz, 2H), 7.30 (s, 1H), 7.25-7.18 (m, 2H), 7.08-6.93 (m, 5H), 5.59 (d, J = 5.3 Hz, 1H), 5.44 (d, J = 5.5 Hz, 1H), 3.20 (dd, J = 5.7, 16.0 Hz, 1H), 3.04 (dd, J = 5.4, 16.3 Hz, 1H), 2.92 (d, J = 16.8 Hz, 1H), 2.42 (d, J = 15.7 Hz, 1H). Prepared as described in Example 12. | D |
| 166 | 5,10,10-trifluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 461.0. ¹H NMR (CDCl$_3$): δ 8.96 (s, 1H), 8.18 (d, J = 8.3 Hz, 1H), 7.65 (d, J = 8.2 Hz, 1H), 7.57 (s, 1H), 7.18-7.07 (m, 2H), 6.82-6.76 (m, 1H), 6.23 (s, 1H), 5.54 (d, J = 10.4 Hz, 1H). Prepared by fluorination of 5-fluoro-11-{[6-(trifluoromethyl)pyridin-3-yl]sulfonyl}-4,9-dihydro-4,9-epiminobenzo-[4,5]cyclohepta[1,2-c]pyrazol-10(1H)-one using the methods described in Example 15. | D |
| 167 | (±)-11-{[6-(trifluoromethyl)pyridin-3-yl]sulfonyl}-1,4,9,10-tetrahydro-4,9-epiminobenzo[4,5]cyclohepta[1,2-c]pyrazole-7-carbonitrile; MS 432.0 ¹H NMR (CDCl$_3$): δ 8.92 (d, J = 2.0 Hz, 1H), 8.13 (dd, J = 8.2, 2.1 Hz, 1H), 7.61 (d, J = 8.2 Hz, 1H), 7.49 (s, 1H), 7.41 (s, 1H), 7.38 (dd, J = 7.8, 1.4 Hz, 1H), 7.14 (d, J = 7.8 Hz, 1H), 6.00 (s, 1H), 5.49 (d, J = 5.3 Hz, 1H), | D |

| Ex. No. | Structure/Compound Name/Mass Spec (M + H)/ ¹H-NMR (300 MHz)/Experimental Procedures | γAPP IC₅₀ (nM) |
|---|---|---|
| | 3.42 (dd, J = 16.6, 5.7 Hz, 1H), 2.83 (d, J = 16.6 Hz, 1H). Prepared as described in Example 9 using 3-bromo-4-(5-oxo-2-(6-(trifluoromethyl)pyridin-3-ylsulfonyl)cyclohex-3-enyl)benzonitrile, which was prepared as described in Example 8 using 2-bromo-4-cyanobenzaldehyde and sulfonamide 23. | |
| 168 | (+)-13-{[4-(trifluoromethyl)phenyl]sulfonyl}-7,10,11,12-tetrahydro-7,12-epiminonaphtho[2',1':4,5]cyclohepta[1,2-c]pyrazole; MS 456.1. ¹H-NMR (CDCl₃) δ 7.67 (m, 2H), 7.62 (d, J = 8.2 Hz, 2H), 7.51 (t, J = 7.2 Hz, 1H), 7.45-7.37 (m, 2H), 7.39 (s, 1H), 7.15 (d, J = 8.2 Hz, 2H), 7.02 (d, J = 8.6 Hz, 1H), 5.93 (s, 1H), 5.85 (d, J = 5.5 Hz, 1H), 3.60 (dd, J = 5.5, 16.0 Hz, 1H), 2.98 (d, J = 16.0 Hz, 1H). Prepared as described in Example 8 using 1-bromo-2-naphthalenecarboxaldehyde, followed by chromatographic separation of regio- and stereoisomers. | D |
| 169 | (−)-13-{[4-(trifluoromethyl)phenyl]sulfonyl}-7,10,11,12-tetrahydro-7,12-epiminonaphtho[2',1':4,5]cyclohepta[1,2-c]pyrazole; MS 456.1. ¹H-NMR (CDCl₃) δ 7.67 (m, 2H), 7.62 (d, J = 8.2 Hz, 2H), 7.51 (t, J = 7.2 Hz, 1H), 7.45-7.37 (m, 2H), 7.39 (s, 1H), 7.15 (d, J = 8.2 Hz, 2H), 7.02 (d, J = 8.6 Hz, 1H), 5.93 (s, 1H), 5.85 (d, J = 5.5 Hz, 1H), 3.60 (dd, J = 5.5, 16.0 Hz, 1H), 2.98 (d, J = 16.0 Hz, 1H). Prepared as described above for the enantiomer. | C |
| 170 | (+)-13-{[4-(trifluoromethyl)phenyl]sulfonyl}-7,8,9,12-tetrahydro-7,12-epiminonaphtho[1',2':4,5]cyclohepta[1,2-c]pyrazole; MS 456.1. ¹H-NMR (CDCl₃) δ 7.71-7.60 (m, 2H), 7.62 (d, J = 8.2 Hz, 2H), 7.51 (t, J = 7.2 Hz, 1H), 7.46 (d, J = 8.6 Hz, 1H), 7.43 (s, 1H), 7.41 (m, 1H), 7.17 (d, J = 8.6 Hz, 1H), 7.15 (d, J = 8.2 Hz, 2H), 6.27 (s, 1H), 5.52 (d, J = 5.5 Hz, 1H), 3.58 (dd, J = 5.5, 16.0 Hz, 1H), 2.90 (d, J = 16.0 Hz, 1H). Prepared as described in Example 8 using 1-bromo-2-naphthalenecarboxaldehyde, followed by chromatographic separation of regio- and stereoisomers. | D |
| 171 | (−)-13-{[4-(trifluoromethyl)phenyl]sulfonyl}-7,8,9,12-tetrahydro-7,12-epiminonaphtho[1',2':4,5]cyclohepta[1,2-c]pyrazole; MS 456.1. ¹H-NMR (CDCl₃) δ 7.71-7.60 (m, 2H), 7.62 (d, J = 8.2 Hz, 2H), 7.51 (t, J = 7.2 Hz, 1H), 7.46 (d, J = 8.6 Hz, 1H), 7.43 (s, 1H), 7.41 (m, 1H), 7.17 (d, J = 8.6 Hz, 1H), 7.15 (d, J = 8.2 Hz, 2H), 6.27 (s, 1H), 5.52 (d, J = 5.5 Hz, 1H), 3.58 (dd, J = 5.5, 16.0 Hz, 1H), 2.90 (d, J = 16.0 Hz, 1H). Prepared as described above for the enantiomer. | C |
| 172 | (−)-11-{[6-(trifluoromethyl)pyridin-3-yl]sulfonyl}-1,4,9,10-tetrahydro-4,9-epiminobenzo[4,5]cyclohepta[1,2-c]pyrazole-7-carbonitrile; MS 432.0 ¹H NMR (CDCl₃): δ 8.92 (d, J = 2.0 Hz, 1H), 8.13 (dd, J = 8.2, 2.1 Hz, 1H), 7.61 (d; J = 8.2 Hz, 1H), 7.49 (s, 1H), 7.41 (s, 1H), 7.38 (dd, J = 7.8, 1.4 Hz, 1H), 7.14 (d, J = 7.8 Hz, 1H), 6.00 (s, 1H), 5.49 (d, J = 5.3 Hz, 1H), 3.42 (dd, J = 16.6, 5.7 Hz, 1H), 2.83 (d, J = 16.6 Hz, 1H). Prepared as described in Example 9 using 3-bromo-4-(5-oxo-2-(6-(trifluoromethyl)pyridin-3-ylsulfonyl)cyclohex-3-enyl)benzonitrile, followed by chiral chromatographic separation of stereoisomers. | A |
| 173 | (−)-11-{[4-(trifluoromethyl)phenyl]sulfonyl}-4,9-dihydro-4,9-epiminobenzo[4,5]cyclohepta[1,2-c]pyrazol-10(1H)-one; MS 420.1. ¹H NMR (CDCl₃): δ 7.77 (d, J = 8.3 Hz, 2H), 7.62 (s, 1H), 7.53 (d, J = 8.3 Hz, 2H), 7.25-7.28 (m, 1H), 7.11-7.02 (m, 3H), 6.18 (s, 1H), 5.44 (s, 1H). Prepared as described in Example 15 followed by chiral chromatographic separation of stereoisomers. | D |

-continued

| Ex. No. | Structure/Compound Name/Mass Spec (M + H)/ ¹H-NMR (300 MHz)/Experimental Procedures | γAPP IC₅₀ (nM) |
|---|---|---|
| 174 | (+)-11-{[6-(trifluoromethyl)pyridin-3-yl]sulfonyl}-1,4,9,10-tetrahydro-4,9-epiminobenzo[4,5]cyclohepta[1,2-c]pyrazole-7-carbonitrile; MS 432.0. ¹H NMR (CDCl₃): δ 8.92 (d, J = 2.0 Hz, 1H), 8.13 (dd, J = 8.2, 2.1 Hz, 1H), 7.61 (d, J = 8.2 Hz, 1H), 7.49 (s, 1H), 7.41 (s, 1H), 7.38 (dd, J = 7.8, 1.4 Hz, 1H), 7.14 (d, J = 7.8 Hz, 1H), 6.00 (s, 1H), 5.49 (d, J = 5.3 Hz, 1H), 3.42 (dd, J = 16.6, 5.7 Hz, 1H), 2.83 (d, J = 16.6 Hz, 1H). Prepared as described in Example 9 using 3-bromo-4-(5-oxo-2-(6-(trifluoromethyl)pyridin-3-ylsulfonyl)cyclohex-3-enyl)benzonitrile which was prepared as described in Example 8 using 2-bromo-4-cyanobenzaldehdye and sulfonamide 23 followed by chiral chromatographic separation of stereoisomers. | D |
| 175 | (+)-endo-11-{[4-(trifluoromethyl)phenyl]sulfonyl}-1,4,9,10-epiminobenzo[4,5]cyclohepta[1,2-c]pyrazol-10-ol; MS 422.1. ¹H NMR (CDCl₃): δ 7.82 (d, J = 8.3 Hz, 2H), 7.53 (d, J = 8.3 Hz, 2H), 7.48 (s, 1H), 7.10-7.07 (m, 1H), 6.93-6.86 (m, 3H), 5.91 (s, 1H), 5.30-5.23 (m, 2H). Prepared as described in Example 15. | D |
| 176 | (±)-6-fluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 425.1. ¹H-NMR (CDCl₃) δ 8.96 (s, 1H), 8.08 (d, J = 8.2 Hz, 1H), 7.55 (d, J = 8.6 Hz, 1H) 7.36 (s, 1H), 7.08 (m, 1H), 6.67 (m, 2H), 6.86 (s, 1H), 5.38 (d, J = 5.5 Hz, 1H), 3.40 (dd, J = 5.5, 16.0 Hz, 1H), 2.77 (d, J = 16.0 Hz, 1H). Prepared as described in Example 9 using 5-(2-bromo-5-fluorophenyl)-4-(6-(trifluoro-methyl)pyridin-3-ylsulfonyl)cyclohex-2-enone which was prepared as described in Example 8 using 2-bromo-5-fluorobenzaldehyde and sulfonamide 23. | D |
| 177 | (±)-6-[3-(trifluoromethyl)phenyl]-12-{[4-(trifluoromethyl)phenyl]sulfonyl}-4,5,10,11-tetrahydro-1H-4,10-epiminobenzo[5,6]cycloocta[1,2-c]pyrazole; MS 564.1. ¹H NMR (CDCl₃) δ 7.91 (d, J = 8.2 Hz, 2H), 7.65 (d, J = 8.2 Hz, 2H), 7.63-7.57 (m, 1H), 7.49 (d, J = 7.7 Hz, 1H), 7.30 (s, 1H), 7.26-7.20 (m, 3H), 7.03 (dd, J = 1.6, 7.1 Hz, 1H), 5.60 (d, J = 5.3 Hz, 1H), 5.47 (d, J = 5.5 Hz, 1H), 3.25 (dd, J = 5.6, 16.0 Hz, 1H), 3.08 (dd, J = 5.8, 16.5 Hz, 1H), 2.93 (d, J = 15.4 Hz, 1H), 2.38 (d, J = 17.8 Hz, 1H). Prepared as described in Example 12 using 3-trifluoromethylphenylboronic acid | D |
| 178 | (±)-7-[3-(trifluoromethyl)phenyl]-12-{[4-(trifluoromethyl)phenyl]sulfonyl}-4,5,6,11-tetrahydro-3H-5,11-epiminobenzo[4,5]cycloocta[1,2-c]pyrazole; MS 564.1. ¹H NMR (CDCl₃) δ 7.62 (d, J = 8.3 Hz, 2H), 7.57 (d, J = 7.9 Hz, 1H), 7.46 (d, J = 8.7 Hz, 2H), 7.44-7.41 (m, 1H), 7.40 (s, 1H), 7.17 (t, J = 7.5 Hz, 2H), 7.09 (s, 1H), 7.02 (d, J = 7.1 Hz, 1H), 6.87 (dd, J = 1.4, 7.6 Hz, 1H), 6.12 (s, 1H), 4.77-4.74 (m, 1H), 3.24 (dd, J = 5.6, 16.0 Hz, 1H), 2.83 (dd, J = 9.5, 18 Hz, 1H), 2.73 (d, J = 16.4 Hz, 1H), 2.23 (d, J = 17.8 Hz, 1H). Prepared as described in Example 12 using 3-trifluoromethylphenylboronic acid | D |
| 179 | | B |

| Ex. No. | Structure/Compound Name/Mass Spec (M + H)/ ¹H-NMR (300 MHz)/Experimental Procedures | γAPP IC$_{50}$ (nM) |
|---|---|---|
|  | (−)-6-fluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 425.1 ¹H-NMR (CDCl$_3$) δ 8.96 (s, 1H), 8.08 (d, J = 8.2 Hz, 1H), 7.55 (d, J = 8.6 Hz, 1H) 7.36 (s, 1H), 7.08 (m, 1H), 6.67 (m, 2H), 6.86 (s, 1H), 5.38 (d, J = 5.5 Hz, 1H), 3.40 (dd, J = 5.5, 16.0 Hz, 1H), 2.77 (d, J = 16.0 Hz, 1H). Prepared as described in Example 9 using 5-(2-bromo-5-fluorophenyl)-4-(6-(trifluoromethyl)pyridin-3-ylsulfonyl)cyclohex-2-enone, followed by chiral chromatographic separation of stereoisomers. |  |
| 180 | (+)-6-fluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 425.1 ¹H-NMR (CDCl$_3$) δ 8.96 (s, 1H), 8.08 (d, J = 8.2 Hz, 1H), 7.55 (d, J = 8.6 Hz, 1H) 7.36 (s, 1H), 7.08 (m, 1H), 6.67 (m, 2H), 6.86 (s, 1H), 5.38 (d, J = 5.5 Hz, 1H), 3.40 (dd, J = 5.5, 16.0 Hz, 1H), 2.77 (d, J = 16.0 Hz, 1H). Prepared as described above for the enantiomer. | D |
| 181 | (±)-9-fluoro-12-{[4-(trifluoromethyl)phenyl]sulfonyl}-4,5,10,11-tetrahydro-1H-4,10-epiminobenzo[5,6]cycloocta[1,2-c]pyrazole; MS 438.0 ¹H NMR (CDCl$_3$) δ 7.92 (d, J = 8.2 Hz, 2H), 7.65 (d, J = 8.3 Hz, 2H), 7.41 (s, 1H), 7.11 (dt, J = 5.9, 8.0 Hz, 1H), 6.89 (t, J = 9.2 Hz, 1H), 6.75 (d, J = 7.7 Hz, 1H), 5.70 (d, J = 5.7 Hz, 1H), 5.56 (d, J = 5.6 Hz, 1H), 3.32 (dd, J = 5.8, 16.6 Hz, 1H), 3.07 (dd, J = 5.6, 16.3 Hz, 1H), 2.89 (d, J = 16.3 Hz, 1H), 2.76 (d, J = 16.2 Hz, 1H). Prepared as described in Example 11 using 8-fluoroisoquinoline. | D |
| 182 | (±)-10-fluoro-12-{[4-(trifluoromethyl)phenyl]sulfonyl}-4,5,6,11-tetrahydro-3H-5,11-epiminobenzo[4,5]cycloocta[1,2-c]pyrazole; MS 438.0 ¹H NMR (CDCl$_3$) δ 7.73 (d, J = 8.2 Hz, 2H), 7.47 (d, J = 8.3 Hz, 2H), 7.39 (s, 1H), 6.93 (dt, J = 5.9, 8.0 Hz, 1H), 6.77 (t, J = 8.5 Hz, 1H), 6.50 (d, J = 7.6 Hz, 1H), 6.37 (s, 1H), 4.95-4.90 (m, 1H), 3.28-3.17 (m, 2H), 2.71 (d, J = 16.3 Hz, 1H), 2.76 (d, J = 17.9 Hz, 1H). Prepared as described in Example 11 using 8-fluoroisoquinoline. | D |
| 183 | [Structure image] (±)-8-fluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 424.9 ¹H NMR (CDCl$_3$): δ 8.90 (s, 1H), 8.10 (d, J = 8.2 Hz, 1H), 7.55 (d, J = 8.2 Hz, 1H), 7.42 (s, 1H), 7.02-6.94 (m, 1H), 6.75-6.64 (m, 2H), 5.90 (s, 1H), 5.60 (d, J = 5.4 Hz, 1H), 3.49 (dd, J = 16.5, 5.6 Hz, 1H), 2.94 (d, J = 16.5 Hz, 1H). Prepared as described in Example 9 using 5-(2-bromo-3-fluorophenyl)-4-(6-(trifluoromethyl)-pyridin-3-ylsulfonyl)cyclohex-2-enone, which was prepared as described in Example 8 using 2-bromo-3-fluorobenzaldehyde and sulfonamide 23. | D |
| 184 | (−)-8-fluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 425.1 ¹H NMR (CDCl$_3$): δ 8.90 (s, 1H), 8.10 (d, J = 8.2 Hz, 1H), 7.55 (d, J = 8.2 Hz, 1H), 7.42 (s, 1H), 7.02-6.94 (m, 1H), 6.75-6.64 (m, 2H), 5.90 (s, 1H), 5.60 (d, J = 5.4 Hz, 1H), 3.49 (dd, J = 16.5, 5.6 Hz, 1H), 2.94 (d, J = 16.5 Hz, 1H). Prepared as described above for the racemic mixture, followed by chiral chromatographic separation of stereoisomers. | B |
| 185 | (+)-8-fluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 425.1 ¹H NMR (CDCl$_3$): δ 8.90 (s, 1H), 8.10 (d, J = 8.2 Hz, 1H), 7.55 (d, J = 8.2 Hz, 1H), 7.42 (s, 1H), 7.02-6.94 (m, 1H), 6.75-6.64 (m, 2H), 5.90 (s, 1H), 5.60 (d, J = 5.4 Hz, 1H), 3.49 (dd, J = 16.5, 5.6 Hz, 1H), 2.94 (d, J = 16.5 Hz, 1H). Prepared as described above for the racemic mixture, followed by chiral chromatographic separation of stereoisomers. | D |
| 186 | (+)-exo-10-fluoro-11-{[4-(trifluoromethyl)phenyl]sulfonyl}-1,4,9,10-tetrahydro-4,9-epiminobenzo[4,5]cyclohepta[1,2-c]pyrazole; MS 424.0 ¹H NMR (CDCl$_3$): δ 7.80 (d, J = 8.3 Hz, 2H), 7.49 (d, J = 8.3 Hz, 2H), 7.40 (s, 1H), 7.19-7.16 (m, 1H), 7.03-6.94 (m, 3H), 6.01 (s, 1H), 5.61-5.44 (m, 2H). Prepared as described in Example 15. | D |

| Ex. No. | Structure/Compound Name/Mass Spec (M + H)/ ¹H-NMR (300 MHz)/Experimental Procedures | γAPP IC₅₀ (nM) |
|---|---|---|
| 187 | 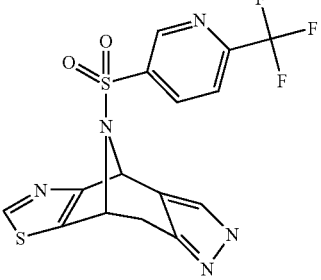<br>(±)-10-{[6-(trifluoromethyl)pyridin-3-yl]sulfonyl}-1,4,8,9-tetrahydro-4,8-epiminopyrazolo[3',4':5,6]cyclohepta[1,2-d][1,3]thiazole; MS 414.0<br>¹H NMR (CDCl₃): δ 8.97 (d, J = 2.2 Hz, 1H), 8.45 (s, 1H), 8.16 (dd, J = 8.2, 2.2 Hz, 1H), 7.67 (d, J = 8.2 Hz, 1H), 7.57 (s, 1H), 5.97 (s, 1H), 5.60 (d, J = 5.2 Hz, 1H), 3.53 (dd, J = 16.6, 5.5 Hz, 1H), 2.90 (d, J = 16.6 Hz, 1H). Prepared as described in Example 9 using 2-(5-bromothiazol-4-yl)-1-(6-(trifluoromethyl)pyridin-3-ylsulfonyl)-2,3-dihydropyridin-4(1H)-one which was prepared as described in Example 8 using 5-bromothiazole-4-carbaldehyde and sulfonamide 23. | C |
| 188 | (−)-10-{[6-(trifluoromethyl)pyridin-3-yl]sulfonyl}-1,4,8,9-tetrahydro-4,8-epiminopyrazolo[3',4':5,6]cyclohepta[1,2-d][1,3]thiazole; MS 414.0<br>¹H NMR (CDCl₃ with a drop of CD₃OD): δ 8.93 (s, 1H), 8.41 (s, 1H), 8.14 (dd, J = 8.2, 2.0 Hz, 1H), 7.63 (d, J = 8.2 Hz, 1H), 7.44 (s, 1H), 5.92 (s, 1H), 5.56 (d, J = 5.3 Hz, 1H), 3.41 (dd, J = 16.4, 5.5 Hz, 1H), 2.81 (d, J = 16.4 Hz, 1H). Prepared as described above for the racemic mixture, followed by chiral chromatographic separation of stereoisomers. | A |
| 189 | (+)-10-{[6-(trifluoromethyl)pyridin-3-yl]sulfonyl}-1,4,8,9-tetrahydro-4,8-epiminopyrazolo[3',4':5,6]cyclohepta[1,2-d][1,3]thiazole; MS 414.0<br>¹H NMR (CDCl₃ with a drop of CD₃OD): δ 8.93 (s, 1H), 8.41 (s, 1H), 8.14 (dd, J = 8.2, 2.0 Hz, 1H), 7.63 (d, J = 8.2 Hz, 1H), 7.44 (s, 1H), 5.92 (s, 1H), 5.56 (d, J = 5.3 Hz, 1H), 3.41 (dd, J = 16.4, 5.5 Hz, 1H), 2.81 (d, J = 16.4 Hz, 1H). Prepared as described above for the racemic mixture, followed by chiral chromatographic separation of stereoisomers. | C |
| 190 | 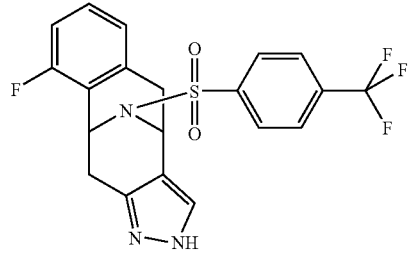<br>(−)-9-fluoro-12-{[4-(trifluoromethyl)phenyl]sulfonyl}-4,5,10,11-tetrahydro-1H-4,10-epiminobenzo[5,6]cycloocta[1,2-c]pyrazole; MS 438.1<br>¹H NMR (CDCl₃) δ 7.92 (d, J = 8.2 Hz, 2H), 7.65 (d, J = 8.3 Hz, 2H), 7.41 (s, 1H), 7.11 (dt, J = 5.9, 8.0 Hz, 1H), 6.89 (t, J = 9.2 Hz, 1H), 6.75 (d, J = 7.7 Hz, 1H), 5.70 (d, J = 5.7 Hz, 1H), 5.56 (d, J = 5.6 Hz, 1H), 3.32 (dd, J = 5.8, 16.6 Hz, 1H), 3.07 (dd, J = 5.6, 16.3 Hz, 1H), 2.89 (d, J = 16.3 Hz, 1H), 2.76 (d, J = 16.2 Hz, 1H). Prepared as described in Example 11 using 8-fluoroisoquinoline followed by chiral chromatographic separation of stereoisomers (ChiralPak AD 20 × 250 nm column). | D |
| 191 | (+)-9-fluoro-12-{[4-(trifluoromethyl)phenyl]sulfonyl}-4,5,10,11-tetrahydro-1H-4,10-epiminobenzo[5,6]cycloocta[1,2-c]pyrazole; MS 438.1<br>¹H NMR (CDCl₃) δ 7.92 (d, J = 8.2 Hz, 2H), 7.65 (d, J = 8.3 Hz, 2H), 7.41 (s, 1H), 7.11 (dt, J = 5.9, 8.0 Hz, 1H), 6.89 (t, J = 9.2 Hz, 1H), 6.75 (d, J = 7.7 Hz, 1H), 5.70 (d, J = 5.7 Hz, 1H), 5.56 (d, J = 5.6 Hz, 1H), 3.32 (dd, J = 5.8, 16.6 Hz, 1H), 3.07 (dd, J = 5.6, 16.3 Hz, 1H), 2.89 (d, J = 16.3 Hz, 1H), 2.76 (d, J = 16.2 Hz, 1H). Prepared as described above for the enantiomer. | D |
| 192 | (−)-8-fluoro-11-{[6-(trifluoromethyl)pyridin-3-yl]sulfonyl}-4,9-dihydro-4,9-epiminobenzo[4,5]cyclohepta[1,2-c]pyrazol-10(1H)-one; MS 439.0<br>¹H NMR (CDCl₃ with a drop of CD₃OD): δ 8.84 (s, 1H), 8.13 (d, J = 8.3 Hz, 1H), 7.64 (d, J = 8.3 Hz, 1H), 7.56 (s, 1H), 7.15-7.08 (m, 1H), 6.97 (d, J = 7.5 Hz, 1H), 6.81-6.74 (m, 1H), 6.18 (s, 1H), 5.62 (s, 1H). Prepared by oxidation of 8-fluoro-11-{[6-(trifluoromethyl)pyridin-3-yl]sulfonyl}- | D |

| Ex. No. | Structure/Compound Name/Mass Spec (M + H)/ ¹H-NMR (300 MHz)/Experimental Procedures | γAPP IC₅₀ (nM) |
|---|---|---|
| | 1,4,9,10-tetrahydro-4,9-epiminobenzo[4,5]cyclohepta[1,2-c]pyrazole using the methods described in Example 15, followed by chiral chromatographic separation of stereoisomers. | |
| 193 | (+)-8-fluoro-11-{[6-(trifluoromethyl)pyridin-3-yl]sulfonyl}-4,9-dihydro-4,9-epiminobenzo[4,5]cyclohepta[1,2-c]pyrazol-10(1H)-one; MS 439.0 ¹H NMR (CDCl₃): δ 8.93 (s, 1H), 8.17 (d, J = 7.7 Hz, 1H), 7.72 (s, 1H), 7.64 (d, J = 8.2 Hz, 1H), 7.15-7.05 (m, 1H), 7.00-6.94 (m, 1H), 6.80-6.72 (m, 1H), 6.27 (s, 1H), 5.69 (s, 1H). Prepared as described above for the enantiomer. | B |
| 194 | (±)-methyl 11-{[6-(trifluoromethyl)pyridin-3-yl]sulfonyl}-1,4,9,10-tetrahydro-4,9-epiminobenzo[4,5]cyclohepta[1,2-c]pyrazole-6-carboxylate; MS 465.1. ¹H-NMR (CDCl₃) δ 8.88 (s, 1H), 8.05 (d, J = 8.4 Hz, 1H), 7.74 (d, J = 7.8 Hz, 1H) 7.58 (s, 1H), 7.50 (d, J = 8.4 Hz, 1H), 7.40 (s, 1H), 7.23 (d, J = 7.8 Hz, 1H), 5.90 (s, 1H), 5.47 (d, J = 5.5 Hz, 1H), 3.86 (s, 3H), 3.48 (dd, J = 5.5, 16.4 Hz, 1H), 2.86 (d, J = 16.4 Hz, 1H). Prepared as described in Example 9 using methyl 4-bromo-3-(5-oxo-2-(6-(trifluoromethyl)pyridin-3-ylsulfonyl)cyclohex-3-enyl)benzoate which was prepared as described in Example 8 using methyl 4-bromo-3-formylbenzoate and sulfonamide 23. | A |
| 195 | (±)-exo-11-{[4-(trifluoromethyl)phenyl]sulfonyl}-1,4,9,10-tetrahydro-4,9-epiminobenzo[4,5]cyclohepta[1,2-c]pyrazol-10-ol; MS 422.1. ¹H NMR (CDCl₃): δ 7.74 (d, J = 8.2 Hz, 2H), 7.46 (d, J = 8.1 Hz, 2H), 7.38 (s, 1H), 7.10-7.05 (m, 1H), 6.95-6.85 (m, 3H), 5.88 (s, 1H), 5.26 (s, 1H), 4.81 (s, 1H). Prepared as described in Example 20 using compound 16. | C |
| 196 | 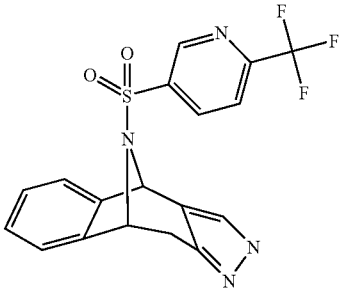(−)-11-{[6-(trifluoromethyl)pyridin-3-yl]sulfonyl}-1,4,9,10-tetrahydro-4,9-epiminobenzo[4,5]cyclohepta[1,2-c]pyrazole; MS 407.1. ¹H NMR (CDCl₃ with a drop of CD₃OD): δ 8.88 (s, 1H), 8.03 (d, J = 7.7 Hz, 1H), 7.48 (d, J = 8.0 Hz, 1H), 7.39 (s, 1H), 7.14-7.07 (m, 1H), 7.03-6.90 (m, 3H), 5.87 (s, 1H), 5.40 (d, J = 3.9 Hz, 1H), 3.48 (dd, J = 16.2, 4.7 Hz, 1H), 2.87 (d, J = 16.3 Hz, 1H). Prepared as described in Example 9 followed by chiral chromatographic separation of stereoisomers. | >30 |
| 197 | (+)-11-{[6-(trifluoromethyl)pyridin-3-yl]sulfonyl}-1,4,9,10-tetrahydro-4,9-epiminobenzo[4,5]cyclohepta[1,2-c]pyrazole; MS 407.1. ¹H NMR (CDCl₃ with a drop of CD₃OD): δ 8.88 (s, 1H), 8.03 (d, J = 7.7 Hz, 1H), 7.48 (d, J = 8.0 Hz, 1H), 7.39 (s, 1H), 7.14-7.07 (m, 1H), 7.03-6.90 (m, 3H), 5.87 (s, 1H), 5.40 (d, J = 3.9 Hz, 1H), 3.48 (dd, J = 16.2, 4.7 Hz, 1H), 2.87 (d, J = 16.3 Hz, 1H). Prepared as described in Example 9 followed by chiral chromatographic separation of stereoisomers. | D |
| 198 | (±)-exo-10-fluoro-11-{[4-(trifluoromethyl)phenyl]sulfonyl}-1,4,9,10-tetrahydro-4,9-epiminobenzo[4,5]cyclohepta[1,2-c]pyrazole; MS 424.0 ¹H NMR (CDCl₃ with a drop of CD₃OD): δ 7.76 (d, J = 7.6 Hz, 2H), 7.46 (d, J = 7.6 Hz, 2H), 7.36 (s, 1H), 7.18-7.13 (m, 1H), 6.98-6.88 (m, 3H), 5.96 (s, 1H), 5.60-5.39 (m, 2H). Prepared as described in Example 15. | D |
| 199 | endo-5-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol; MS 441.0 ¹H NMR (CD₃OD): δ 8.96 (s, 1H), 8.31 (dd, J = 8.3, 2.2 Hz, 1H), 7.71 (d, J = 8.3 Hz, 1H), 7.58 (s, 1H), 7.01-6.93 (m, 2H), 6.69-6.60 (m, 1H), 6.17 (s, 1H), 5.40-5.30 (m, 2H). Prepared by reduction of 5-fluoro-11-{[6-(trifluoromethyl)pyridin-3-yl]sulfonyl}-4,9-dihydro-4,9-epiminobenzo[4,5]cyclohepta[1,2-c]pyrazol-10(1H)-one using the methods described in Example 15. | D |

| Ex. No. | Structure/Compound Name/Mass Spec (M + H)/ ¹H-NMR (300 MHz)/Experimental Procedures | γAPP IC$_{50}$ (nM) |
|---|---|---|
| 200 | (−)-11-{[6-(trifluoromethyl)pyridin-3-yl]sulfonyl}-4,9-dihydro-4,9-epiminobenzo[4,5]cyclohepta[1,2-c]pyrazol-10(1H)-one; MS 421.0 ¹H NMR (CDCl$_3$): δ 8.95 (s, 1H), 8.14 (d, J = 8.3 Hz, 1H), 7.69 (s, 1H), 7.58 (d, J = 8.3 Hz, 1H), 7.32-7.27 (m, 1H), 7.15-7.02 (m, 3H), 6.31 (s, 1H), 5.52 (s, 1H). Prepared by oxidation of 11-{[6-(trifluoromethyl)pyridin-3-yl]sulfonyl}-1,4,9,10-tetrahydro-4,9-epiminobenzo[4,5]cyclohepta[1,2-c]pyrazole using the methods described in Example 15 followed by chiral chromatographic separation of stereoisomers. | D |
| 201 | (+)-6-(3-methyl-1,2,4-oxadiazol-5-yl)-11-{[6-(trifluoromethyl)pyridin-3-yl]sulfonyl}-1,4,9,10-tetrahydro-4,9-epiminobenzo[4,5]cyclohepta[1,2-c]pyrazole; MS 489.1. ¹H-NMR (CDCl$_3$) δ 8.90 (s, 1H), 8.10 (d, J = 8.6 Hz, 1H), 7.82 (d, J = 7.8 Hz, 1H) 7.70 (s, 1H), 7.53 (d, J = 8.2 Hz, 1H), 7.40 (s, 1H), 7.33 (d, J = 7.8 Hz, 1H), 5.97 (s, 1H), 5.50 (d, J = 5.5 Hz, 1H), 3.46 (dd, J = 5.5, 16.4 Hz, 1H), 2.86 (d, J = 16.4 Hz, 1H), 2.44 (s, 3H). Prepared by treatment of (±)-methyl 11-{[6-(trifluoromethyl)-pyridin-3-yl]sulfonyl}-1,4,9,10-tetrahydro-4,9-epiminobenzo[4,5]cyclohepta[1,2-c]pyrazole-6-carboxylate with N-hydroxyacetamidine as described for compound 51 in Example 16 followed by chiral chromatographic separation of stereoisomers. | A |
| 202 | (−)-6-(3-methyl-1,2,4-oxadiazol-5-yl)-11-{[6-(trifluoromethyl)pyridin-3-yl]sulfonyl}-1,4,9,10-tetrahydro-4,9-epiminobenzo[4,5]cyclohepta[1,2-c]pyrazole; MS 489.1. ¹H-NMR (CDCl$_3$) δ 8.90 (s, 1H), 8.10 (d, J = 8.6 Hz, 1H), 7.82 (d, J = 7.8 Hz, 1H) 7.70 (s, 1H), 7.53 (d, J = 8.2 Hz, 1H), 7.40 (s, 1H), 7.33 (d, J = 7.8 Hz, 1H), 5.97 (s, 1H), 5.50 (d, J = 5.5 Hz, 1H), 3.46 (dd, J = 5.5, 16.4 Hz, 1H), 2.86 (d, J = 16.4 Hz, 1H), 2.44 (s, 3H). Prepared as described above for the (+)-enantiomer. | A |
| 203 | (−)-methyl 11-{[6-(trifluoromethyl)pyridin-3-yl]sulfonyl}-1,4,9,10-tetrahydro-4,9-epiminobenzo[4,5]cyclohepta[1,2-c]pyrazole-6-carboxylate; MS 465.1 ¹H-NMR (CDCl$_3$) δ 8.88 (s, 1H), 8.05 (d, J = 8.4 Hz, 1H), 7.74 (d, J = 7.8 Hz, 1H) 7.58 (s, 1H), 7.50 (d, J = 8.4 Hz, 1H), 7.40 (s, 1H), 7.23 (d, J = 7.8 Hz, 1H), 5.90 (s, 1H), 5.47 (d, J = 5.5 Hz, 1H), 3.86 (s, 3H), 3.48 (dd, J = 5.5, 16.4 Hz, 1H), 2.86 (d, J = 16.4 Hz, 1H). Prepared as described in Example 9 using methyl 4-bromo-3-(5-oxo-2-(6-(trifluoromethyl)pyridin-3-ylsulfonyl)cyclohex-3-enyl)benzoate, followed by chiral chromatographic separation of stereoisomers. | A |
| 204 | (±)-7-methyl-10-{[6-(trifluoromethyl)pyridin-3-yl]sulfonyl}-4,7,8,9-tetrahydro-1H-4,8-epiminocyclohepta[1,2-c:5,4-c']dipyrazole; MS 411.0 ¹H-NMR (CDCl$_3$) δ 8.89 (s, 1H), 8.03 (d, J = 8.4 Hz, 1H), 7.53 (s, 1H), 7.50 (d, J = 8.4 Hz, 1H), 7.34 (s, 1H), 5.96 (s, 1H), 5.52 (d, J = 5.5 Hz, 1H), 3.63 (s, 3H), 3.41 (dd, J = 5.5, 16.4 Hz, 1H), 2.90 (d, J = 16.4 Hz, 1H). | D |
| 205 | (+)-methyl 11-{[6-(trifluoromethyl)pyridin-3-yl]sulfonyl}-1,4,9,10-tetrahydro-4,9-epiminobenzo[4,5]cyclohepta[1,2-c]pyrazole-6-carboxylate; MS 465.1. ¹H-NMR (CDCl$_3$) δ 8.88 (s, 1H), 8.05 (d, J = 8.4 Hz, 1H), 7.74 (d, J = 7.8 Hz, 1H) 7.58 (s, 1H), 7.50 (d, J = 8.4 Hz, 1H), 7.40 (s, 1H), 7.23 (d, J = 7.8 Hz, 1H), 5.90 (s, 1H), 5.47 (d, J = 5.5 Hz, 1H), 3.86 (s, 3H), 3.48 (dd, J = 5.5, 16.4 Hz, 1H), 2.86 (d, J = 16.4 Hz, 1H). Prepared as described in Example 9 using methyl 4-bromo-3-(5-oxo-2-(6-(trifluoromethyl)pyridin-3-ylsulfonyl)cyclohex-3-enyl)benzoate, followed by chiral chromatographic separation of stereoisomers. | C |

| Ex. No. | Structure/Compound Name/Mass Spec (M + H)/ ¹H-NMR (300 MHz)/Experimental Procedures | γAPP IC$_{50}$ (nM) |
|---|---|---|
| 206 | exo-10-fluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 425.1 ¹H NMR (CD$_3$OD): δ 8.94 (d, J = 1.9 Hz, 1H), 8.26 (dd, J = 8.2, 1.9 Hz, 1H), 7.65 (d, J = 8.2 Hz, 1H), 7.60 (s, 1H), 7.30-7.27 (m, 1H), 7.02-6.91 (m, 3H), 6.13 (s, 1H), 5.70 (dd, J = 10.6, 1.6 Hz, 1H), 5.25 ((dd, J = 52.0, 1.9 Hz, 1H). Prepared by fluorination of 11-{[6-(trifluoromethyl)pyridin-3-yl]sulfonyl}-1,4,9,10-tetrahydro-4,9-epiminobenzo[4,5]cyclohepta[1,2-c]pyrazol-10-ol using the methods described in Example 15. | D |
| 207 | (+)-exo-5,10-difluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 443.1. ¹H NMR (CD$_3$OD): δ 8.98 (s, 1H), 8.33 (d, J = 8.2 Hz, 1H), 7.73 (d, J = 8.2 Hz, 1H), 7.66 (s, 1H), 7.15 (d, J = 7.4 Hz, 1H), 7.08-7.00 (m, 1H), 6.73-6.66 (m, 1H), 6.34 (s, 1H), 5.78 (d, J = 10.4 Hz, 1H), 5.55 ((dd, J = 51.7, 1.9 Hz, 1H). Prepared by fluorination of 5-fluoro-11-{[6-(trifluoromethyl)-pyridin-3-yl]sulfonyl}-1,4,9,10-tetrahydro-4,9-epiminobenzo[4,5]-cyclohepta[1,2-c]pyrazol-10-ol using the methods described in Example 15. | D |
| 208 | endo-11-{[6-(trifluoromethyl)pyridin-3-yl]sulfonyl}-1,4,9,10-tetrahydro-4,9-epiminobenzo[4,5]cyclohepta[1,2-c]pyrazol-10-ol; MS 423.1. ¹H NMR (CDCl$_3$ with a drop of CD$_3$OD): δ 8.84 (s, 1H), 7.99 (d, J = 8.2 Hz, 1H), 7.44 (d, J = 8.2 Hz, 1H), 7.33 (s, 1H), 7.17-7.10 (m, 1H), 6.95-6.85 (m, 3H), 5.78 (s, 1H), 5.35-5.23 (m, 2H). Prepared by reduction of 11-{[6-(trifluoro-methyl)pyridin-3-yl]sulfonyl}-4,9-dihydro-4,9-epiminobenzo[4,5]-cyclo-hepta[1,2-c]pyrazol-10(1H)-one using the methods described in Example 15. | D |
| 209 | (±)-11-{(4-chlorophenyl)sulfonyl]-5-fluoro-1,4,9,10-tetrahydro-4,9-epiminobenzo[4,5]cyclohepta[1,2-c]pyrazole; MS 390.4. ¹H NMR (CDCl$_3$) δ 7.54 (m, 3H), 7.22 (m, 2H), 7.01 (m, 1H), 6.86 (m, 1H), 6.66 (t, J = 8.4 Hz, 1H), 6.01 (s, 1H), 5.42 (d, J = 5.4 Hz, 1H), 3.58 (dd, J = 16.7, 5.4 Hz, 1H), 2.85 (d, J = 16.6 Hz, 1H). Prepared as described in Example 9 using 2-(2-bromo-6-fluorophenyl)-1-(4-chlorophenylsulfonyl)-2,3-dihydropyridin-4(1H)-one which was prepared as described in Example 8 using 2-bromo-6-fluorobenzaldehyde and 4-chlorobenzenesulfonamide. | D |
| 210 | (±)-5-fluoro-11-[(4-fluorophenyl)sulfonyl]-1,4,9,10-tetrahydro-4,9-epiminobenzo[4,5]cyclohepta[1,2-c]pyrazole; MS 374.0. ¹H NMR (CDCl$_3$) δ 7.62 (m, 3H), 6.96 (m, 4H), 6.67 (t, J = 8.4 Hz, 1H), 6.02 (s, 1H), 5.44 (d, J = 5.2 Hz, 1H), 3.57 (dd, J = 16.9, 5.6 Hz, 1H), 2.94 (d, J = 16.7 Hz, 1H). Prepared as described in Example 9 using 2-(2-bromo-6-fluorophenyl)-1-(4-fluorophenylsulfonyl)-2,3-dihydropyridin-4(1H)-one which was prepared as described in Example 8 using 2-bromo-6-fluorobenzaldehyde and 4-fluorobenzenesulfonamide. | D |
| 211 | (±)-5-fluoro-11-{[5-(trifluoromethyl)pyridin-2-yl]sulfonyl}-1,4,9,10-tetrahydro-4,9-epiminobenzo[4,5]cyclohepta[1,2-c]pyrazole; MS 425.1 ¹H NMR (CDCl$_3$) δ 8.56 (s, 1H), 7.90 (s, 2H), 7.35 (s, 1H), 6.91 (m, 2H), 6.59 (at, J = 8.0 Hz, 1H), 6.13 (s, 1H), 5.57 (d, J = 5.5 Hz, 1H), 3.57 (dd, | D |

| Ex. No. | Structure/Compound Name/Mass Spec (M + H)/ ¹H-NMR (300 MHz)/Experimental Procedures | γAPP IC₅₀ (nM) |
|---|---|---|
|  | J = 16.2, 5.7 Hz, 1H), 2.85 (d, J = 16.1 Hz, 1H). Prepared as described in Example 9 using 2-(2-bromo-6-fluorophenyl)-1-(4-fluorophenylsulfonyl)-2,3-dihydropyridin-4(1H)-one which was prepared as described in Example 8 using 2-bromo-6-fluorobenzaldehyde and 5-(trifluoromethyl)-2-pyridinesulfonamide. |  |
| 212 | 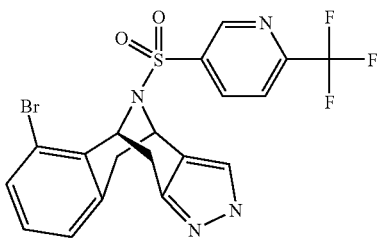

(+)-9-bromo-12-{[6-(trifluoromethyl)pyridin-3-yl]sulfonyl}-4,5,10,11-tetrahydro-1H-4,10-epiminobenzo[5,6]cycloocta[1,2-c]pyrazole; MS 499.0 ¹H-NMR (CDCl₃) δ 9.08 (d, J = 2.1 Hz, 1H), 8.24 (dd, J = 6.5, 2.1 Hz, 1H), 7.68 (d, J = 8.1 Hz, 1H), 7.45-7.42 (m, 2H), 7.02 (t, J = 7.8 Hz, 1H), 6.90 (d, J = 7.5 Hz, 1H), 5.69 (d, J = 4.8 Hz, 1H), 5.50 (d, J = 5.4 Hz, 1H), 3.36 (dd, J = 16, 5.7 Hz, 1H), 3.16-3.11 (m, 2H), 2.79 (d, J = 16 Hz, 1H). Prepared as described in Example 13 using compound 45 followed by chiral chromatographic separation of stereoisomers. | D |
| 213 | (−)-9-bromo-12-{[6-(trifluoromethyl)pyridin-3-yl]sulfonyl}-4,5,10,11-tetrahydro-1H-4,10-epiminobenzo[5,6]cycloocta[1,2-c]pyrazole; MS 499.0 ¹H NMR (CDCl₃) δ 9.08 (d, J = 2.1 Hz, 1H), 8.24 (dd, J = 6.5, 2.1 Hz, 1H), 7.68 (d, J = 8.1 Hz, 1H), 7.45-7.42 (m, 2H), 7.02 (t, J = 7.8 Hz, 1H), 6.90 (d, J = 7.5 Hz, 1H), 5.69 (d, J = 4.8 Hz, 1H), 5.50 (d, J = 5.4 Hz, 1H), 3.36 (dd, J = 16, 5.7 Hz, 1H), 3.16-3.11 (m, 2H), 2.79 (d, J = 16 Hz, 1H). Prepared as described in Example 13 using compound 45 followed by chiral chromatographic separation of stereoisomers. | C |
| 214 | exo-8,10-difluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 443.1 ¹H NMR (CDCl₃ with a drop of CD₃OD): δ 8.96 (d, J = 1.9 Hz, 1H), 8.18 (dd, J = 8.2, 1.9 Hz, 1H), 7.60 (d, J = 8.2 Hz, 1H), 7.42 (s, 1H), 7.06-6.99 (m, 1H), 6.83 (d, J = 7.4 Hz, 1H), 6.71 (t, J = 8.4 Hz, 1H), 6.09 (s, 1H), 5.77 (dd, J = 10.0, 1.3 Hz, 1H), 5.55 (dd, J = 51.2, 1.7 Hz, 1H). Prepared by fluorination of 8-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol using the methods described in Example 15. | D |
| 215 | (+)-8,10,10-trifluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 461.1 ¹H NMR (CD₃OD): δ 9.02 (s, 1H), 8.37 (d, J = 6.4 Hz, 1H), 7.76-7.70 (m, 2H), 7.10-7.00 (m, 1H), 6.95-6.87 (m, 1H), 6.80-6.68 (m, 1H), 6.28 (s, 1H), 5.90 (d, J = 8.0 Hz, 1H). Prepared by fluorination of 8-fluoro-11-{[6-(trifluoromethyl)pyridin-3-yl]sulfonyl}-4,9-dihydro-4,9-epiminobenzo[4,5]-cyclohepta[1,2-c]pyrazol-10(1H)-one using the methods of Example 15. | D |
| 216 | 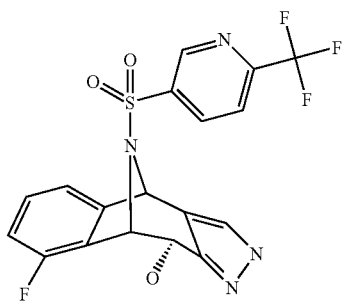

endo-8-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol; MS 441.1 ¹H NMR (CD₃OD): δ 8.94 (s, 1H), 8.30-8.25 (m, 1H), 7.71 (d, J = 8.2 Hz, 1H), 7.55 (s, 1H), 7.00-6.90 (m, 1H), 6.83-6.79 (m, 1H), 6.67-6.60 (m, 1H), 6.05 (s, 1H), 5.56-5.52 (m, 1H), 5.38-5.30 (m, 1H). Prepared by reduction of 8-fluoro-11-{[6-(trifluoromethyl)pyridin-3-yl]sulfonyl}-4,9-dihydro-4,9-epiminobenzo[4,5]-cyclohepta[1,2-c]pyrazol-10(1H)-one using the methods described in Example 15. | C |

| Ex. No. | Structure/Compound Name/Mass Spec (M + H)/ ¹H-NMR (300 MHz)/Experimental Procedures | γAPP IC$_{50}$ (nM) |
|---|---|---|
| 217 | 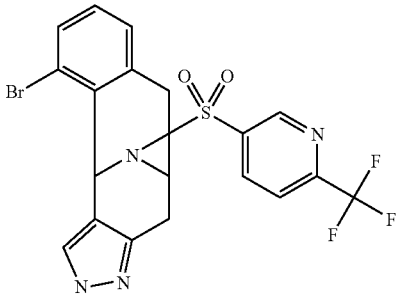<br>(−)-10-bromo-12-{[6-(trifluoromethyl)pyridin-3-yl]sulfonyl}-4,5,6,11-tetrahydro-3H-5,11-epiminobenzo[4,5]cycloocta[1,2-c]pyrazole; MS 499.0 ¹H NMR (CDCl₃) δ 8.89 (d J = 1.5 Hz, 1H), 7.98 (dd, J = 6.0, 2.1 Hz, 1H,) 7.64 (s, 1H), 7.46 (d, J = 8.1 Hz, 1H), 7.30 (d, J = 9.3 Hz, 1H), 6.83 (t, J = 8.4 Hz, 1H), 6.60 (d, J = 6.0 Hz, 1H), 6.49 (s, 1H), 4.98, (t, J = 7.2 Hz, 1H), 3.31 (dd, J = 16, 6.3 Hz, 1H), 3.18 (dd, J = 16, 9.9 Hz, 1H) 2.67 (d, J = 15 Hz, 1H), 2.51 (d, J = 18 Hz, 1H). Prepared as described in Example 11 using compound 45, followed by chiral chromatographic separation of stereoisomers. | D |
| 218 | (+)-10-bromo-12-{[6-(trifluoromethyl)pyridin-3-yl]sulfonyl}-4,5,6,11-tetrahydro-3H-5,11-epiminobenzo[4,5]cycloocta[1,2-c]pyrazole; MS 499.0 ¹H NMR (CDCl₃) δ 8.89 (d J = 1.5 Hz, 1H), 7.98 (dd, J = 6.0, 2.1 Hz, 1H,) 7.64 (s, 1H), 7.46 (d, J = 8.1 Hz, 1H), 7.30 (d, J = 9.3 Hz, 1H), 6.83 (t, J = 8.4 Hz, 1H), 6.60 (d, J = 6.0 Hz, 1H), 6.49 (s, 1H), 4.98, (t, J = 7.2 Hz, 1H), 3.31 (dd, J = 16, 6.3 Hz, 1H), 3.18 (dd, J = 16, 9.9 Hz, 1H) 2.67 (d, J = 15 Hz, 1H), 2.51 (d, J = 18 Hz, 1H). Prepared as described above for the enantiomer. | D |
| 219 | (±)-6-chloro-11-{[6-(trifluoromethyl)pyridin-3-yl]sulfonyl}-1,4,9,10-tetrahydro-4,9-epiminobenzo[4,5]cyclohepta[1,2-c]pyrazole; MS 441.1 ¹H NMR (CDCl₃) δ 8.90 (s, 1H), 8.06 (dd, J = 8.2, 2.0 Hz, 1H), 7.55 (d, J = 8.2 Hz, 1H), 7.35 (s, 1H), 6.97 (m, 3H), 5.83 (s, 1H), 5.39 (d, J = 5.3 Hz, 1H), 3.39 (dd, J = 16.4, 5.6 Hz, 1H), 2.79 (d, J = 16.3 Hz, 1H). Prepared as described in Example 9 using 5-(2-bromo-5-chlorophenyl)-4-(6-(trifluoromethyl)pyridin-3-ylsulfonyl)cyclohex-2-enone which was prepared as described in Example 8 using 2-bromo-5-chlorobenzaldehyde and sulfonamide 23. | D |
| 220 | (±)-methyl 11-{[6-(trifluoromethyl)pyridin-3-yl]sulfonyl}-1,4,9,10-tetrahydro-4,9-epiminobenzo[4,5]cyclohepta[1,2-c]pyrazole-8-carboxylate; MS 465.1. ¹H NMR (CDCl₃) δ 8.84 (s, 1H), 8.02 (d, J = 8.2 Hz, 1H), 7.61 (d, J = 7.6 Hz, 1H), 7.46 (d, J = 8.2 Hz, 1H) 7.40 (s, 1H), 7.10 (m, 2H), 6.02 (d, J = 5.4 Hz, 1H), 7.02 (d, J = 8.6 Hz, 1H), 5.91 (s, 1H), 3.95 (s, 3H), 3.49 (dd, J = 5.4, 16.8 Hz, 1H), 3.01 (d, J = 16.8 Hz, 1H). Prepared as described in Example 9 using methyl 2-bromo-3-(5-oxo-2-(6-(trifluoromethyl)pyridin-3-ylsulfonyl)cyclohex-3-enyl)benzoate (prepared as described in Example 8 from methyl 2-bromo-3-formylbenzoate and sulfonamide 23). | D |
| 221 | 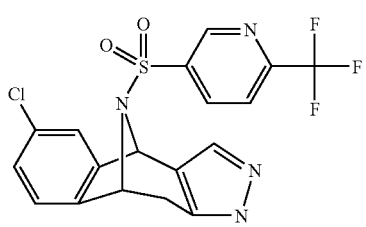<br>(−)-6-chloro-11-{[6-(trifluoromethyl)pyridin-3-yl]sulfonyl}-1,4,9,10-tetrahydro-4,9-epiminobenzo[4,5]cyclohepta[1,2-c]pyrazole; MS 441.1 ¹H NMR (CDCl₃) δ 8.90 (s, 1H), 8.06 (dd, J = 8.2, 2.0 Hz, 1H), 7.55 (d, J = 8.2 Hz, 1H), 7.35 (s, 1H), 6.97 (m, 3H), 5.83 (s, 1H), 5.39 (d, J = 5.3 Hz, 1H), 3.39 (dd, J = 16.4, 5.6 Hz, 1H), 2.79 (d, J = 16.3 Hz, 1H). Prepared as described in Example 9 using 5-(2-bromo-5-chlorophenyl)-4-(6-(trifluoromethyl)pyridin-3-ylsulfonyl)-cyclohex-2-enone, followed by chromatographic separation of stereoisomers. | C |
| 222 | (+)-6-chloro-11-{[6-(trifluoromethyl)pyridin-3-yl]sulfonyl}-1,4,9,10-tetrahydro-4,9-epiminobenzo[4,5]cyclohepta[1,2-c]pyrazole; MS 441.1 ¹H NMR (CDCl₃) δ 8.90 (s, 1H), 8.06 (dd, J = 8.2, 2.0 Hz, 1H), 7.55 (d, | D |

| Ex. No. | Structure/Compound Name/Mass Spec (M + H)/ ¹H-NMR (300 MHz)/Experimental Procedures | γAPP IC₅₀ (nM) |
|---|---|---|
| | J = 8.2 Hz, 1H), 7.35 (s, 1H), 6.97 (m, 3H), 5.83 (s, 1H), 5.39 (d, J = 5.3 Hz, 1H), 3.39 (dd, J = 16.4, 5.6 Hz, 1H), 2.79 (d, J = 16.3 Hz, 1H). Prepared as described above for the enantiomer. | |
| 223 | 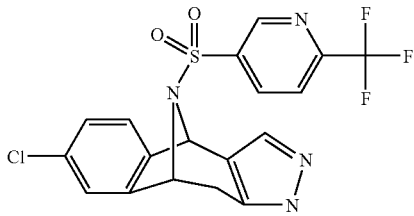<br>(−)-7-chloro-11-{[6-(trifluoromethyl)pyridin-3-yl]sulfonyl}-1,4,9,10-tetrahydro-4,9-epiminobenzo[4,5]cyclohepta[1,2-c]pyrazole; MS 441.1 ¹H NMR (CDCl₃) δ 8.89 (s, 1H), 8.08 (dd, J = 8.2, 2.0 Hz, 1H), 7.55 (d, J = 8.2 Hz, 1H), 7.24 (s, 1H), 6.95 (m, 3H), 5.88 (s, 1H), 5.38 (d, J = 5.3 Hz, 1H), 3.41 (dd, J = 16.4, 5.6 Hz, 1H), 2.82 (d, J = 16.3 Hz, 1H). Prepared as described in Example 8 using 2-bromo-5-chlorobenzaldehyde and sulfonamide 23 followed by chromatographic separation of region- and stereoisomers. | B |
| 224 | (+)-7-chloro-11-{[6-(trifluoromethyl)pyridin-3-yl]sulfonyl}-1,4,9,10-tetrahydro-4,9-epiminobenzo[4,5]cyclohepta[1,2-c]pyrazole; MS 441.1 ¹H NMR (CDCl₃) δ 8.89 (s, 1H), 8.08 (dd, J = 8.2, 2.0 Hz, 1H), 7.55 (d, J = 8.2 Hz, 1H), 7.24 (s, 1H), 6.95 (m, 3H), 5.88 (s, 1H), 5.38 (d, J = 5.3 Hz, 1H), 3.41 (dd, J = 16.4, 5.6 Hz, 1H), 2.82 (d, J = 16.3 Hz, 1H). Prepared as described in Example 8 using 2-bromo-5-chlorobenzaldehyde and sulfonamide 23 followed by chromatographic separation of region- and stereoisomers. | D |
| 225 | (±)-11-{[6-(trifluoromethyl)pyridin-3-yl]sulfonyl}-1,4,9,10-tetrahydro-4,9-epiminobenzo[4,5]cyclohepta[1,2-c]pyrazol-6-ol; MS 423.1. ¹H NMR (CD₃OD) δ 8.90 (s, 1H), 8.22 (dd, J = 8.2, 2.0 Hz, 1H), 7.66 (d, J = 8.2 Hz, 1H), 7.54 (s, 1H), 6.91 (d, J = 8.0 Hz, 3H), 6.32 (m, 2H), 5.88 (s, 1H), 5.43 (d, J = 5.0 Hz, 1H), 4.95 (s, 1H), 3.34 (dd, J = 16.4, 5.4 Hz, 1H), 2.80 (d, J = 16.3 Hz, 1H). Prepared as described in Example 9 using 5-(2-bromo-5-hydroxyphenyl)-4-(6-(trifluoromethyl)pyridin-3-ylsulfonyl)cyclohex-2-enone which was prepared as described in Example 8 using 2-bromo-5-hydroxybenzaldehyde and sulfonamide 23. | D |
| 226 | 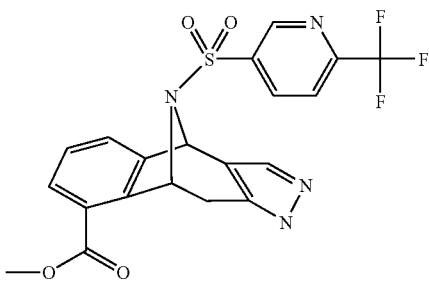<br>(+)-methyl 11-{[6-(trifluoromethyl)pyridin-3-yl]sulfonyl}-1,4,9,10-tetrahydro-4,9-epiminobenzo[4,5]cyclohepta[1,2-c]pyrazole-8-carboxylate; MS 465.1. ¹H NMR (CDCl₃) δ 8.84 (s, 1H), 8.02 (d, J = 8.2 Hz, 1H), 7.61 (d, J = 7.6 Hz, 1H), 7.46 (d, J = 8.2 Hz, 1H) 7.40 (s, 1H), 7.10 (m, 2H), 6.02 (d, J = 5.4 Hz, 1H), 7.02 (d, J = 8.6 Hz, 1H), 5.91 (s, 1H), 3.95 (s, 3H), 3.49 (dd, J = 5.4, 16.8 Hz, 1H), 3.01 (d, J = 16.8 Hz, 1H). Prepared as described in Example 9 using methyl 2-bromo-3-(5-oxo-2-(6-(trifluoromethyl)pyridin-3-ylsulfonyl)cyclohex-3-enyl)benzoate, followed by chiral chromatographic separation of enantiomers. | D |
| 227 | (−)-methyl 11-{[6-(trifluoromethyl)pyridin-3-yl]sulfonyl}-1,4,9,10-tetrahydro-4,9-epiminobenzo[4,5]cyclohepta[1,2-c]pyrazole-8-carboxylate; MS 465.1 ¹H NMR (CDCl₃) δ 8.84 (s, 1H), 8.02 (d, J = 8.2 Hz, 1H), 7.61 (d, J = 7.6 Hz, 1H), 7.46 (d, J = 8.2 Hz, 1H) 7.40 (s, 1H), 7.10 (m, 2H), 6.02 (d, J = 5.4 Hz, 1H), 7.02 (d, J = 8.6 Hz, 1H), 5.91 (s, 1H), 3.95 (s, 3H), 3.49 (dd, J = 5.4, 16.8 Hz, 1H), 3.01 (d, J = 16.8 Hz, 1H). Prepared as described in Example 9 using methyl 2-bromo-3-(5-oxo-2-(6-(trifluoromethyl)pyridin-3-ylsulfonyl)cyclohex-3-enyl)benzoate, followed by chiral chromatographic separation of enantiomers. | C |

| Ex. No. | Structure/Compound Name/Mass Spec (M + H)/ $^1$H-NMR (300 MHz)/Experimental Procedures | γAPP IC$_{50}$ (nM) |
|---|---|---|
| 228 | 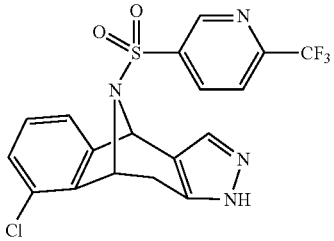<br>(+)-8-chloro-11-{[6-(trifluoromethyl)pyridin-3-yl]sulfonyl}-1,4,9,10-tetrahydro-4,9-epiminobenzo[4,5]cyclohepta[1,2-c]pyrazole; MS 441.0 $^1$H NMR (CD$_3$OD) δ 8.86 (s, 1H), 8.08, (d, J = 8.2 Hz, 1H), 7.54 (d, J = 8.2 Hz, 1H), 7.38 (s, 1H), 6.89 (m, 2H), 6.81 (m, 1H), 5.89 (s, 1H), 5.49 (d J = 5.5 Hz, 1H), 3.47 (dd J = 16.5, 5.6 Hz, 1H), 2.98 (d J = 16.4 Hz, 1H). Prepared as described in Example 9 using 6-(2-bromo-3-chlorophenyl)-5-(6-(trifluoromethyl)pyridin-3-ylsulfonyl)-4,5-dihydro-1H-pyrazolo[4,3-c]pyridine, followed by chromatographic separation of regio- and stereoisomers. | D |
| 229 | 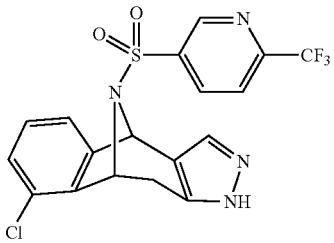<br>(−)-8-chloro-11-{[6-(trifluoromethyl)pyridin-3-yl]sulfonyl}-1,4,9,10-tetrahydro-4,9-epiminobenzo[4,5]cyclohepta[1,2-c]pyrazole; MS 441.0 $^1$H NMR (CD$_3$OD) δ 8.87 (d, J = 2.0 Hz, 1H), 8.08, (dd, J = 8.2, 1.7 Hz, 1H), 7.54 (dd, J = 8.2, 0.5 Hz, 1H), 7.46 (s, 1H), 6.89 (m, 2H), 6.91 (m, 3H), 5.96 (s, 1H), 5.45 (d J = 5.4 Hz, 1H), 3.52 (dd J = 16.4, 5.6 Hz, 1H), 2.87 (d J = 15.9 Hz, 1H). Prepared as described in Example 9 using 6-(2-bromo-3-chlorophenyl)-5-(6-(trifluoromethyl)pyridin-3-ylsulfonyl)-4,5-dihydro-1H-pyrazolo[4,3-c]pyridine, followed by chromatographic separation of regio- and stereoisomers. | C |
| 230 | 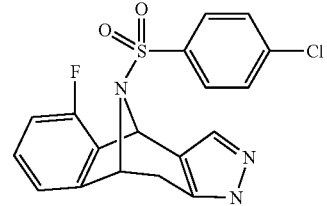<br>(−)-11-[(4-chlorophenyl)sulfonyl]-5-fluoro-1,4,9,10-tetrahydro-4,9-epiminobenzo[4,5]cyclohepta[1,2-c]pyrazole; MS 390.1. $^1$H NMR (CD$_3$OD) δ 7.54 (m, 3H), 7.20, (m, 2H), 7.01 (m, 1H), 6.88 (d, J = 7.32 Hz, 1H), 6.66 (t, J = 8.5 Hz, 1H), 6.01 (s, 1H), 5.42 (d J = 5.4 Hz, 1H), 3.58 (dd J = 16.4, 5.6 Hz, 1H), 2.91 (d J = 15.9 Hz, 1H). Prepared as described in Example 9 using 6-(2-bromo-6-fluorophenyl)-5-(6-(trifluoromethyl)pyridin-3-ylsulfonyl)-4,5-dihydro-1H-pyrazolo[4,3-c]pyridine, followed by chromatographic separation of regio- and stereoisomers. | A |
| 231 | (+)-11-[(4-chlorophenyl)sulfonyl]-5-fluoro-1,4,9,10-tetrahydro-4,9-epiminobenzo[4,5]cyclohepta[1,2-c]pyrazole; MS 390.1. $^1$H NMR (CD$_3$OD) δ 7.54 (m, 3H), 7.20, (m, 2H), 7.01 (m, 1H), 6.88 (d, J = 7.32 Hz, 1H), 6.66 (t, J = 8.5 Hz, 1H), 6.01 (s, 1H), 5.42 (d J = 5.4 Hz, 1H), 3.58 (dd J = 16.4, 5.6 Hz, 1H), 2.91 (d J = 15.9 Hz, 1H). Prepared as described above for the (−)-stereoisomer. | D |

-continued

| Ex. No. | Structure/Compound Name/Mass Spec (M + H)/ ¹H-NMR (300 MHz)/Experimental Procedures | γAPP IC₅₀ (nM) |
|---|---|---|
| 232 | 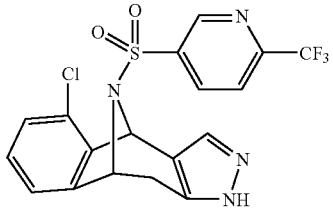<br>(−)-5-chloro-11-{[6-(trifluoromethyl)pyridin-3-yl]sulfonyl}-1,4,9,10-tetrahydro-4,9-epiminobenzo[4,5]cyclohepta[1,2-c]pyrazole; MS 441.0<br>¹H NMR (CD₃OD) δ 8.86 (s, 1H), 8.08, (d, J = 8.2 Hz, 1H), 7.54 (d, J = 8.2 Hz, 1H), 7.38 (s, 1H), 6.89 (m, 2H), 6.81 (m, 1H), 5.89 (s, 1H), 5.49 (d J = 5.5 Hz, 1H), 3.47 (dd J = 16.5, 5.6 Hz, 1H), 2.98 (d J = 16.4 Hz, 1H).<br>Prepared as described in Example 9 using 6-(2-bromo-6-chlorophenyl)-5-(6-(trifluoro-methyl)pyridin-3-ylsulfonyl)-4,5-dihydro-1H-pyrazolo[4,3-c]pyridine, followed by chromatographic separation of regio- and stereoisomers. | B |
| 233 | (+)-5-chloro-11-{[6-(trifluoromethyl)pyridin-3-yl]sulfonyl}-1,4,9,10-tetrahydro-4,9-epiminobenzo[4,5]cyclohepta[1,2-c]pyrazole; MS 441.0<br>¹H NMR (CD₃OD) δ 8.86 (s, 1H), 8.08, (d, J = 8.2 Hz, 1H), 7.54 (d, J = 8.2 Hz, 1H), 7.38 (s, 1H), 6.89 (m, 2H), 6.81 (m, 1H), 5.89 (s, 1H), 5.49 (d J = 5.5 Hz, 1H), 3.47 (dd J = 16.5, 5.6 Hz, 1H), 2.98 (d J = 16.4 Hz, 1H).<br>Prepared as described above for the (−)-stereoisomer. | D |
| 234 | 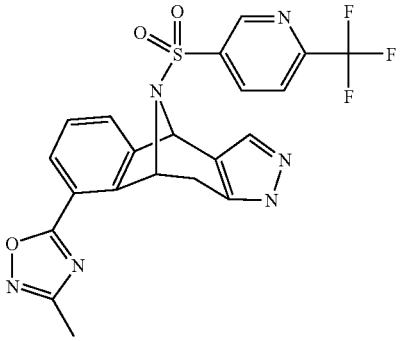<br>(+)-8-(3-methyl-1,2,4-oxadiazol-5-yl)-11-{[6-(trifluoromethyl)pyridin-3-yl]sulfonyl}-1,4,9,10-tetrahydro-4,9-epiminobenzo[4,5]cyclohepta[1,2-c]pyrazole; MS 489.1. ¹H NMR (CD₃OD) δ 8.85 (d, J = 1.9 Hz, 1H), 8.01, (dd, J = 8.1, 1.9 Hz, 1H), 7.71 (m, 1H), 7.45 (d, J = 8.1 Hz, 1H), 7.41 (s, 1H), 7.15 (m, 2H), 6.16 (d, J = 5.7 Hz, 1H), 5.95 (s, 1H), 3.51 (dd J = 16.8, 5.9 Hz, 1H), 3.06 (d, J = 16.6 Hz, 1H), 2.53 (s, 3H). Prepared by condensation of a mixture of methyl 11-{[6-(trifluoromethyl)pyridin-3-yl]sulfonyl}-1-{[2-(trimethylsilyl)ethoxy]methyl}-1,4,9,10-tetrahydro-4,9-epiminobenzo[4,5]-cyclohepta[1,2-c]pyrazole-8-carboxylate and methyl 11-{[6-(trifluoromethyl)-pyridin-3-yl]sulfonyl}-2-{[2-(trimethyl-silyl)ethoxy]methyl}-2,4,9,10-tetrahydro-4,9-epiminobenzo[4,5]cyclohepta[1,2-c]pyrazole-8-carboxylate, which was prepared by alkylation of methyl 11-{[6-(trifluoromethyl)pyridin-3-yl]sulfonyl}-1,4,9,10-tetrahydro-4,9-epiminobenzo[4,5]cyclohepta[1,2-c]pyrazole-8-carboxylate as described in Example 19, with N-hydroxyacetamidine as described in Example 16 followed by dealkylation with 4N HCl/dioxane and chromatographic separation of stereoisomers. | D |
| 235 | (−)-8-(3-methyl-1,2,4-oxadiazol-5-yl)-11-{[6-(trifluoromethyl)pyridin-3-yl]sulfonyl}-1,4,9,10-tetrahydro-4,9-epiminobenzo[4,5]cyclohepta[1,2-c]pyrazole; MS 489.1. ¹H NMR (CD₃OD) δ 8.85 (d, J = 1.9 Hz, 1H), 8.01, (dd, J = 8.1, 1.9 Hz, 1H), 7.71 (m, 1H), 7.45 (d, J = 8.1 Hz, 1H), 7.41 (s, 1H), 7.15 (m, 2H), 6.16 (d, J = 5.7 Hz, 1H), 5.95 (s, 1H), 3.51 (dd J = 16.8, 5.9 Hz, 1H), 3.06 (d, J = 16.6 Hz, 1H), 2.53 (s, 3H). Prepared as described above for the (+)-stereoisomer. | C |

| Ex. No. | Structure/Compound Name/Mass Spec (M + H)/ ¹H-NMR (300 MHz)/Experimental Procedures | γAPP IC$_{50}$ (nM) |
|---|---|---|
| 236 | 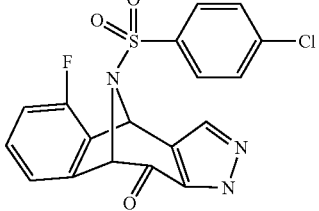<br>(±)-11-[(4-chlorophenyl)sulfonyl]-5-fluoro-4,9-dihydro-4,9-epiminobenzo[4,5]cyclohepta[1,2-c]pyrazol-10(1H)-one; MS 404.0<br>¹H NMR (CD$_3$OD) δ 7.64 (s, 1H), 7.57, (m, 2H), 7.24 (m, 2H), 7.05 (m, 2H), 6.74 (m, 1H), 6.34 (s, 1H), 5.43 (s, 1H). Prepared by oxidation of (±)-11-[(4-chlorophenyl)sulfonyl]-5-fluoro-1,4,9,10-tetrahydro-4,9-epiminobenzo[4,5]-cyclohepta[1,2-c]pyrazole using the methods described in Example 15. | D |
| 237 | 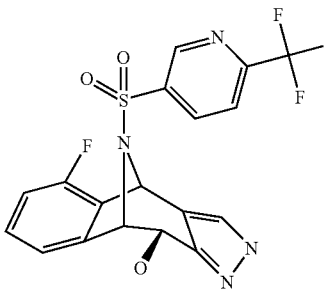<br>(−)-(10S)-5-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol; MS 441.1<br>¹H NMR (CDCl$_3$ with a drop of CD$_3$OD) δ 8.89 (s, 1H), 8.12 (d, J = 8.2 Hz, 1H), 7.54 (d, J = 8.2 Hz, 1H), 7.40 (s, 1H), 6.95-6.90 (m, 2H), 6.64-6.58 (m, 1H), 6.07 (s, 1H), 5.28 (s, 1H), 4.71 (s, 1H). Prepared as described in Example 20. | A |
| 238 | (+)-(10S)-5-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol; MS 441.0<br>¹H NMR (CDCl$_3$ with a drop of CD$_3$OD) δ 8.89 (s, 1H), 8.12 (d, J = 8.2 Hz, 1H), 7.54 (d, J = 8.2 Hz, 1H), 7.40 (s, 1H), 6.95-6.90 (m, 2H), 6.64-6.58 (m, 1H), 6.07 (s, 1H), 5.28 (s, 1H), 4.71 (s, 1H). Prepared as described in Example 20. | D |
| 239 | 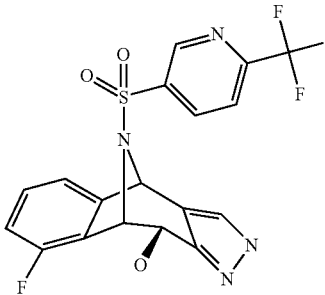<br>(−)-(10S)-8-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol; MS 441.1<br>¹H NMR (CDCl$_3$ with a drop of CD$_3$OD) δ 8.90 (s, 1H), 8.13 (d, J = 8.3 Hz, 1H), 7.55 (d, J = 8.3 Hz, 1H), 7.37 (s, 1H), 6.98-6.90 (m, 1H), 6.74 (d, J = 7.4 Hz, 1H), 6.63 (t, J = 8.4 Hz, 1H), 5.91 (s, 1H), 5.44 (s, 1H), 4.79 (s, 1H). Prepared as described in Example 20. | A |
| 240 | (+)-(10S)-8-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol; MS 441.1<br>¹H NMR (CDCl$_3$ with a drop of CD$_3$OD) δ 8.90 (s, 1H), 8.13 (d, J = 8.3 Hz, 1H), 7.55 (d, J = 8.3 Hz, 1H), 7.37 (s, 1H), 6.98-6.90 (m, 1H), 6.74 (d, J = 7.4 Hz, 1H), 6.63 (t, J = 8.4 Hz, 1H), 5.91 (s, 1H), 5.44 (s, 1H), 4.79 (s, 1H). Prepared as described in Example 20. | C |

| Ex. No. | Structure/Compound Name/Mass Spec (M + H)/ ¹H-NMR (300 MHz)/Experimental Procedures | γAPP IC$_{50}$ (nM) |
|---|---|---|
| 241 | 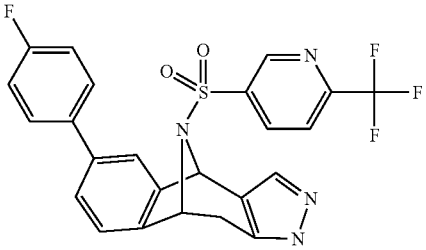<br>(±)-6-(4-fluorophenyl)-11-{[6-(trifluoromethyl)pyridin-3-yl]sulfonyl}-1,4,9,10-tetrahydro-4,9-epiminobenzo[4,5]cyclohepta[1,2-c]pyrazole; MS 501.1. ¹H NMR (CD$_3$OD) δ 8.94 (d, J = 1.8 Hz, 1H), 8.07 (dd, J = 8.1, 1.8 Hz, 1H), 7.45 (d, J = 8.2 Hz, 1H), 7.26 (m, 2H), 7.08 (m, 5H), 5.97 (s, 1H), 5.45 (d, J = 5.3 Hz, 1H), 3.47 (dd, J = 16.3, 5.6 Hz, 1H), 2.86 (d, J = 16.1 Hz, 1H). Prepared as described in Example 19. | D |
| 242 | (−)-11-[(4-chlorophenyl)sulfonyl]-5-fluoro-4,9-dihydro-4,9-epiminobenzo[4,5]cyclohepta[1,2-c]pyrazol-10(1H)-one; MS 404.0<br>¹H NMR (CD$_3$OD) δ 7.68 (s, 1H), 7.56, (m, 2H), 7.22 (m, 2H), 7.05 (m, 2H), 6.75 (m, 1H), 6.33 (s, 1H), 5.43 (s, 1H). Prepared by oxidation of (±)-11-[(4-chlorophenyl)sulfonyl]-5-fluoro-1,4,9,10-tetrahydro-4,9-epiminobenzo[4,5]-cyclohepta[1,2-c]pyrazole using the methods described in Example 15 followed by chiral chromatographic separation of stereoisomers. | D |
| 243 | (+)-11-[(4-chlorophenyl)sulfonyl]-5-fluoro-4,9-dihydro-4,9-epiminobenzo[4,5]cyclohepta[1,2-c]pyrazol-10(1H)-one; MS 404.0<br>¹H NMR (CD$_3$OD) δ 7.68 (s, 1H), 7.56, (m, 2H), 7.22 (m, 2H), 7.05 (m, 2H), 6.75 (m, 1H), 6.33 (s, 1H), 5.43 (s, 1H). Prepared as described above for the (−)-stereoisomer. | C |
| 244 | 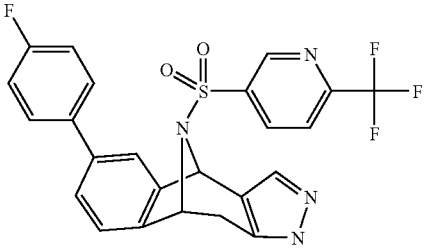<br>(−)-6-(4-fluorophenyl)-11-{[6-(trifluoromethyl)pyridin-3-yl]sulfonyl}-1,4,9,10-tetrahydro-4,9-epiminobenzo[4,5]cyclohepta[1,2-c]pyrazole; MS 501.0. ¹H NMR (CD$_3$OD) δ 8.91 (d, J = 2.0 Hz, 1H), 8.04 (dd, J = 8.1, 1.8 Hz, 1H), 7.45 (d, J = 8.2 Hz, 1H), 7.28 (m, 2H), 7.09 (m, 5H), 5.89 (s, 1H), 5.45 (d, J = 5.3 Hz, 1H), 3.48 (dd, J = 16.3, 5.6 Hz, 1H), 2.86 (d, J = 16.1 Hz, 1H). Prepared as described in Example 19 followed by chiral chromatographic separation of stereoisomers. | A |
| 245 | (+)-6-(4-fluorophenyl)-11-{[6-(trifluoromethyl)pyridin-3-yl]sulfonyl}-1,4,9,10-tetrahydro-4,9-epiminobenzo[4,5]cyclohepta[1,2-c]pyrazole; MS 501.0. ¹H NMR (CD$_3$OD) δ 8.91 (d, J = 2.0 Hz, 1H), 8.04 (dd, J = 8.1, 1.8 Hz, 1H), 7.45 (d, J = 8.2 Hz, 1H), 7.28 (m, 2H), 7.09 (m, 5H), 5.89 (s, 1H), 5.45 (d, J = 5.3 Hz, 1H), 3.48 (dd, J = 16.3, 5.6 Hz, 1H), 2.86 (d, J = 16.1 Hz, 1H). Prepared as described in Example 19 followed by chiral chromatographic separation of stereoisomers. | C |
| 246 | 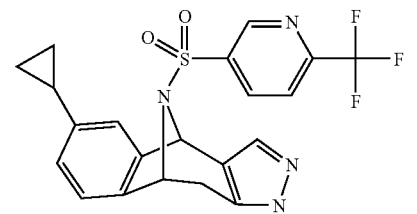<br>(−)-6-cyclopropyl-11-{[6-(trifluoromethyl)pyridin-3-yl]sulfonyl}-1,4,9,10-tetrahydro-4,9-epiminobenzo[4,5]cyclohepta[1,2-c]pyrazole; MS 447.0<br>¹H NMR (CD$_3$OD) δ 8.86 (d, J = 2.0 Hz, 1H), 7.99 (dd, J = 7.8, 1.7 Hz, 1H), 7.44 (d, J = 8.2 Hz, 1H), 7.36 (s, 1H), 6.92 (d, J = 7.7 Hz, 1H), 6.61 | A |

| Ex. No. | Structure/Compound Name/Mass Spec (M + H)/ ¹H-NMR (300 MHz)/Experimental Procedures | γAPP IC₅₀ (nM) |
|---|---|---|
| | (m, 2H), 5.76 (s, 1H), 5.34 (d, J = 5.3 Hz, 1H), 3.44 (dd, J = 16.3, 5.6 Hz, 1H), 2.80 (d, J = 16.1 Hz, 1H), 1.67 (m, 1H), 0.87 (m, 2H), 0.47 (m, 2H). Prepared as described in Example 19 using cyclopropylboronic acid followed by chromatographic separation of stereoisomers. | |
| 247 | (+)-6-cyclopropyl-11-{[6-(trifluoromethyl)pyridin-3-yl]sulfonyl}-1,4,9,10-tetrahydro-4,9-epiminobenzo[4,5]cyclohepta[1,2-c]pyrazole; MS 447.0 ¹H NMR (CD₃OD) δ 8.86 (d, J = 2.0 Hz, 1H), 7.99 (dd, J = 7.8, 1.7 Hz, 1H), 7.44 (d, J = 8.2 Hz, 1H), 7.36 (s, 1H), 6.92 (d, J = 7.7 Hz, 1H), 6.61 (m, 2H), 5.76 (s, 1H), 5.34 (d, J = 5.3 Hz, 1H), 3.44 (dd, J = 16.3, 5.6 Hz, 1H), 2.80 (d, J = 16.1 Hz, 1H), 1.67 (m, 1H), 0.87 (m, 2H), 0.47 (m, 2H). Prepared as described in Example 19 using cyclopropylboronic acid followed by chromatographic separation of stereoisomers. | D |
| 248 | (+)-6-bromo-11-{[6-(trifluoromethyl)pyridin-3-yl]sulfonyl}-1,4,9,10-tetrahydro-4,9-epiminopyrazolo[3',4':5,6]cyclohepta[1,2-b]pyridine; MS 488.0. ¹H NMR (CDCl₃) δ 8.93 (s, 1H), 8.15 (d, J = 8.2 Hz, 1H), 7.65 (d, J = 8.2 Hz, 1H), 7.54 (s, 1H), 7.35 (d, J = 7.9 Hz, 1H), 7.15 (d, J = 7.9 Hz, 1H), 5.84 (s, 1H), 5.46 (d, J = 5.0 Hz, 1H), 3.49 (dd, J = 16.6, 5.4 Hz, 1H), 2.84 (d, J = 16.6 Hz, 1H). Prepared as described in Example 9 using 2-(3,6-dibromopyridin-2-yl)-1-(6-(trifluoromethyl)pyridin-3-ylsulfonyl)-2,3-dihydropyridin-4(1H)-one which was prepared as described in Example 8 using sulfonamide 23 and 3,6-dibromopicolinaldehyde, which was prepared as described in Example 22, followed by chiral chromatographic separation of stereoisomers. | D |
| 249 | (−)-6-bromo-11-{[6-(trifluoromethyl)pyridin-3-yl]sulfonyl}-1,4,9,10-tetrahydro-4,9-epiminopyrazolo[3',4':5,6]cyclohepta[1,2-b]pyridine; MS 488.0. ¹H NMR (CDCl₃) δ 8.93 (s, 1H), 8.15 (d, J = 8.2 Hz, 1H), 7.65 (d, J = 8.2 Hz, 1H), 7.54 (s, 1H), 7.35 (d, J = 7.9 Hz, 1H), 7.15 (d, J = 7.9 Hz, 1H), 5.84 (s, 1H), 5.46 (d, J = 5.0 Hz, 1H), 3.49 (dd, J = 16.6, 5.4 Hz, 1H), 2.84 (d, J = 16.6 Hz, 1H). Prepared as described above for the (+)-stereoisomer. | A |
| 250 | (+)-6-bromo-11-{[6-(trifluoromethyl)pyridin-3-yl]sulfonyl}-1,4,9,10-tetrahydro-4,9-epiminobenzo[4,5]cyclohepta[1,2-c]pyrazole; MS 484.9 ¹H NMR (CDCl₃) δ 8.89 (d, J = 2.1 Hz, 1H), 8.05 (dd, J = 2.4, 8.4 Hz, 1H), 7.54 (d, J = 8.1 Hz, 1H), 7.38 (s, 1H), 7.14 (dd, J = 1.8, 8.1 Hz, 1H), 7.08 (s, 1H), 7.00 (d, J = 7.8 Hz, 1H), 5.83 (s, 1H), 5.37 (d, J = 5.4 Hz, 1H), 3.42 (dd, J = 5.4, 16.5 Hz, 1H), 2.80 (d, J = 16.5 Hz, 1H). Prepared as described in Example 9 using 2-(2,5-dibromophenyl)-1-(6-(trifluoromethyl)pyridin-3-ylsulfonyl)-2,3-dihydropyridin-4(1H)-one which was prepared as described in Example 8 using 2,5-dibromobenzaldehyde and sulfonamide 23 followed by chromatographic separation of stereoisomers. | D |
| 251 | (−)-6-bromo-11-{[6-(trifluoromethyl)pyridin-3-yl]sulfonyl}-1,4,9,10-tetrahydro-4,9-epiminobenzo[4,5]cyclohepta[1,2-c]pyrazole; MS 484.9 ¹H NMR (CDCl₃) δ 8.89 (d, J = 1.5 Hz, 1H), 8.05 (dd, J = 1.8, 8.1 Hz, 1H), 7.55 (d, J = 7.5 Hz, 1H), 7.38 (s, 1H), 7.14 (dd, J = 1.2, 7.8 Hz, 1H), 7.08 (s, 1H), 7.00 (d, J = 8.1 Hz, 1H), 5.83 (s, 1H), 5.37 (d, J = 4.8 Hz, 1H), 3.42 (dd, J = 5.4, 16.5 Hz, 1H), 2.80 (d, J = 16.5 Hz, 1H). Prepared as described above for the (+)-stereoisomer. | C |

| Ex. No. | Structure/Compound Name/Mass Spec (M + H)/ ¹H-NMR (300 MHz)/Experimental Procedures | γAPP IC$_{50}$ (nM) |
|---|---|---|
| 252 | (±)-(11-{[6-(trifluoromethyl)pyridin-3-yl]sulfonyl}-1,4,9,10-tetrahydro-4,9-epiminobenzo[4,5]cyclohepta[1,2-c]pyrazol-8-yl)methanol; MS 437.1 ¹H NMR (CD$_3$OD with a drop of DMSO-d$_6$) δ 8.92 (s, 1H), 8.22 (d, J = 8.2 Hz, 1H), 7.63 (d, J = 8.2 Hz, 1H), 7.53 (s, 1H), 6.92-6.88 (m, 3H), 6.00 (s, 1H), 5.73 (d, J = 5.4 Hz, 1H), 4.56 (s, 2H), 3.40 (dd, J = 16.5, 5.4 Hz, 1H), 3.03 (d, J = 16.5 Hz, 1H). Prepared by LiAlH$_4$ reduction of (±)-methyl 11-{[6-(trifluoromethyl)pyridin-3-yl]sulfonyl}-1,4,9,10-tetrahydro-4,9-epiminobenzo[4,5]cyclohepta[1,2-c]pyrazole-8-carboxylate. | D |
| 253 | methyl (±)-11-{[6-(trifluoromethyl)-1,2-dihydropyridin-3-yl]sulfonyl}-1,4,9,10-tetrahydro-4,9-epiminobenzo[4,5]cyclohepta[1,2-c]pyrazole-8-carboxylate; MS 467.1. ¹H NMR (CDCl$_3$) δ 7.83 (d, J = 7.8 Hz, 1H), 7.41-7.35 (m, 2H), 7.25 (d, J = 7.6 Hz, 1H), 6.95 (d, J = 5.5 Hz, 1H), 5.91 (d, J = 5.8 Hz, 1H), 5.83 (s, 1H), 5.78 (d, J = 4.8 Hz, 1H), 4.99 (s, 1H), 3.96 (s, 3H), 3.54 (dd, J = 16.6, 5.9 Hz, 1H), 3.06 (d, J = 16.6 Hz, 1H), 2.89 (s, 2H). | D |
| 254 | (+)-6-(4-fluorophenyl)-11-{[6-(trifluoromethyl)pyridin-3-yl]sulfonyl}-1,4,9,10-tetrahydro-4,9-epiminopyrazolo[3',4':5,6]cyclohepta[1,2-b]pyridine; MS 502.1. ¹H NMR (CDCl$_3$) δ 8.95 (d, J = 2.1 Hz, 1H), 8.13 (dd, J = 8.2, 1.8 Hz, 1H), 7.77-7.72 (m, 2H), 7.56 (s, 1H), 7.50 (t, J = 8.1 Hz, 2H), 7.25 (d, J = 7.9 Hz, 1H), 7.13 (t, J = 8.7 Hz, 2H), 5.91 (s, 1H), 5.50 (d, J = 5.4 Hz, 1H), 3.54 (dd, J = 16.4, 5.6 Hz, 1H), 2.90 (d, J = 16.4 Hz, 1H). Prepared by Pd-mediated coupling of (+)-6-bromo-11-{[6-(trifluoromethyl)pyridin-3-yl]sulfonyl}-1,4,9,10-tetrahydro-4,9-epiminopyrazolo-[3',4':5,6]cyclohepta-[1,2-b]pyridine with 4-fluorophenylboronic acid as described in Example 13. | C |
| 255 | (+)-6-cyclopropyl-11-{[6-(trifluoromethyl)pyridin-3-yl]sulfonyl}-1,4,9,10-tetrahydro-4,9-epiminopyrazolo[3',4':5,6]cyclohepta[1,2-b]pyridine; MS 448.1. ¹H NMR (CDCl$_3$) δ 8.88 (s, 1H), 8.08 (d, J = 7.6 Hz, 1H), 7.55 (d, J = 8.3 Hz, 1H), 7.51 (s, 1H), 7.24 (d, J = 7.8 Hz, 1H), 6.67 (d, J = 7.8 Hz, 1H), 5.73 (s, 1H), 5.40 (d, J = 5.2 Hz, 1H), 3.51 (dd, J = 16.4, 5.5 Hz, 1H), 2.83 (d, J = 16.4 Hz, 1H), 1.86-1.82 (m, 1H), 0.97-0.73 (m, 4H). Prepared by Pd-mediated coupling of (+)-6-bromo-11-{[6-(trifluoromethyl)pyridin-3-yl]sulfonyl}-1,4,9,10-tetrahydro-4,9-epiminopyrazolo[3',4':5,6]cyclohepta-[1,2-b]pyridine with cyclopropylboronic acid as described in Example 13, followed by chiral chromatographic separation of stereoisomers. | C |
| 256 | (−)-6-cyclopropyl-11-{[6-(trifluoromethyl)pyridin-3-yl]sulfonyl}-1,4,9,10-tetrahydro-4,9-epiminopyrazolo[3',4':5,6]cyclohepta[1,2-b]pyridine; MS 448.1. ¹H NMR (CDCl$_3$) δ 8.88 (s, 1H), 8.08 (d, J = 7.6 Hz, 1H), 7.55 (d, J = 8.3 Hz, 1H), 7.51 (s, 1H), 7.24 (d, J = 7.8 Hz, 1H), 6.67 (d, J = 7.8 Hz, 1H), 5.73 (s, 1H), 5.40 (d, J = 5.2 Hz, 1H), 3.51 (dd, J = 16.4, 5.5 Hz, 1H), 2.83 (d, J = 16.4 Hz, 1H), 1.86-1.82 (m, 1H), 0.97-0.73 (m, 4H). Prepared as described above for the (+)-stereoisomer. | A |
| 257 | (±)-8-(fluoromethyl)-11-{[6-(trifluoromethyl)pyridin-3-yl]sulfonyl}-1,4,9,10-tetrahydro-4,9-epiminobenzo[4,5]cyclohepta[1,2-c]pyrazole; MS 439.1 ¹H NMR (CDCl$_3$) δ 8.89 (s, 1H), 8.04 (d, J = 8.2 Hz, 1H), 7.47 (d, J = 8.2 | D |

| Ex. No. | Structure/Compound Name/Mass Spec (M + H)/ ¹H-NMR (300 MHz)/Experimental Procedures | γAPP IC₅₀ (nM) |
|---|---|---|
| | Hz, 1H), 7.42 (s, 1H), 7.00-6.85 (m, 3H), 5.89 (s, 1H), 5.63 (d, J = 5.5 Hz, 1H), 5.40 (d, J = 2.5 Hz, 1H), 5.25 (d, J = 2.5 Hz, 1H), 3.51 (dd, J = 16.5, 5.7 Hz, 1H), 2.95 (d, J = 16.5 Hz, 1H). Prepared by fluorination of (±)-(11-{[6-(trifluoromethyl)pyridin-3-yl]sulfonyl}-1,4,9,10-tetrahydro-4,9-epiminobenzo[4,5]cyclohepta[1,2-c]pyrazol-8-yl)methanol using DAST as described in Example 15. | |
| 258 | (±)-7-fluoro-11-{[6-(trifluoromethyl)pyridin-3-yl]sulfonyl}-1,4,9,10-tetrahydro-4,9-epiminopyrazolo[3',4':5,6]cyclohepta[1,2-b]pyridine; MS 426.1. ¹H NMR (CD₃OD) δ 8.97 (s, 1H), 8.31 (d, J = 8.3 Hz, 1H), 7.94 (s, 1H), 7.79 (d, J = 8.1 Hz, 1H), 7.61 (s, 1H), 7.49 (d, J = 8.1 Hz, 1H), 5.92 (s, 1H), 5.65 (d, J = 5.4 Hz, 1H), 3.40 (dd, J = 16.5, 5.3 Hz, 1H), 2.83 (d, J = 16.3 Hz, 1H). Prepared as described in Example 9 using 2-(3-bromo-5-fluoropyridin-2-yl)-1-(6-(trifluoromethyl)pyridin-3-ylsulfonyl)-2,3-dihydropyridin-4(1H)-one which was prepared as described in Example 8 using 3-bromo-5-fluoropicolinaldehyde and sulfonamide 23. | D |
| 259 | (−)-7-fluoro-11-{[6-(trifluoromethyl)pyridin-3-yl]sulfonyl}-2,4,9,10-tetrahydro-4,9-epiminopyrazolo[3',4':5,6]cyclohepta[1,2-b]pyridine; MS 426.1. ¹H NMR (CD₃OD) δ 8.97 (s, 1H), 8.31 (d, J = 8.3 Hz, 1H), 7.94 (s, 1H), 7.79 (d, J = 8.1 Hz, 1H), 7.61 (s, 1H), 7.49 (d, J = 8.1 Hz, 1H), 5.92 (s, 1H), 5.65 (d, J = 5.4 Hz, 1H), 3.40 (dd, J = 16.5, 5.3 Hz, 1H), 2.83 (d, J = 16.3 Hz, 1H). Prepared as described in Example 9 using 2-(3-bromo-5-fluoropyridin-2-yl)-1-(6-(trifluoromethyl)pyridin-3-ylsulfonyl)-2,3-dihydropyridin-4(1H)-one, which was prepared as described in Example 8 using 3-bromo-5-fluoropicolinaldehyde and sulfonamide 23, followed by chiral chromatographic separation of stereoisomers. | A |
| 260 | (+)-7-fluoro-11-{[6-(trifluoromethyl)pyridin-3-yl]sulfonyl}-2,4,9,10-tetrahydro-4,9-epiminopyrazolo[3',4':5,6]cyclohepta[1,2-b]pyridine; MS 426.0. ¹H NMR (CD₃OD) δ 8.97 (s, 1H), 8.31 (d, J = 8.3 Hz, 1H), 7.94 (s, 1H), 7.79 (d, J = 8.1 Hz, 1H), 7.61 (s, 1H), 7.49 (d, J = 8.1 Hz, 1H), 5.92 (s, 1H), 5.65 (d, J = 5.4 Hz, 1H), 3.40 (dd, J = 16.5, 5.3 Hz, 1H), 2.83 (d, J = 16.3 Hz, 1H). Prepared as described above for the (−)-stereoisomer. | D |
| 261 | 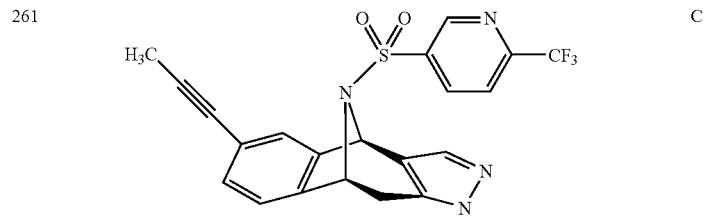<br>(4R,9S)-6-(prop-1-yn-1-yl)-11-{[6-(trifluoromethyl)pyridin-3-yl]sulfonyl}-1,4,9,10-tetrahydro-4,9-epiminobenzo[4,5]cyclohepta[1,2-c]pyrazole; MS 445.0. ¹H NMR (CDCl₃) δ 8.90 (d, J = 1.8 Hz, 1H), 8.00 (dd, J = 1.8, 8.1 Hz, 1H), 7.52 (d, J = 8.1 Hz, 1H), 7.44 (s, 1H), 7.02 (bs, 2H), 6.93 (s, 1H), 5.82 (s, 1H), 5.38 (d, J = 4.8 Hz, 1H), 3.48 (dd, J = 16.5, 5.1 Hz, 1H), 2.85 (d, J = 16.5 Hz, 1H), 1.98 (s, 3H). Prepared by alkylation of 6-bromo-11-{[6-(trifluoromethyl)pyridin-3-yl]sulfonyl}-1,4,9,10-tetrahydro-4,9-epiminobenzo[4,5]cyclohepta[1,2-c]pyrazole with SEM-Cl followed by Stille coupling with tributylpropynylstannane in toluene in the presence of Pd(PPh₃)₄. | C |
| 262 | 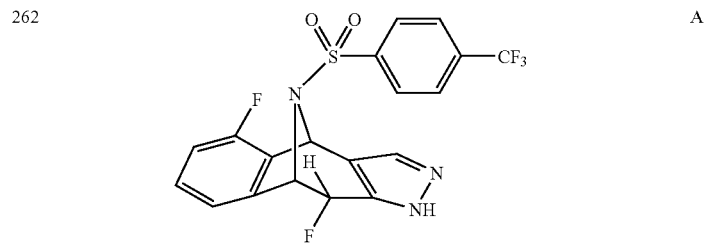<br>(−)-exo-5,10-difluoro-11-{[4-(trifluoromethyl)phenyl]sulfonyl}-1,4,9,10-tetrahydro-4,9-epiminobenzo[4,5]cyclohepta[1,2-c]pyrazole; MS 442.1 ¹H NMR (CDCl₃) δ 7.83 (d, J = 8.2 Hz, H), 7.53 (d, J = 8.2, 2H), 7.45 (s, 1H), 6.93 (m, 2H), 6.60 (m, 1H), 6.18 (s, 1H), 5.59 (m, 1H), 5.43 (d, J = 1.9 Hz, 1H). Prepared as described in Example 15 using (±)-5-fluoro-11-{[4-(trifluoromethyl)phenyl]sulfonyl}-4,9-dihydro-4,9-epiminobenzo[4,5]-cyclohepta[1,2-c]pyrazol-10(1H)-one followed by chiral chromatographic separation of stereoisomers. | A |

| Ex. No. | Structure/Compound Name/Mass Spec (M + H)/ ¹H-NMR (300 MHz)/Experimental Procedures | γAPP IC₅₀ (nM) |
|---|---|---|
| 263 | (+)-5,10-difluoro-11-{[4-(trifluoromethyl)phenyl]sulfonyl}-1,4,9,10-tetrahydro-4,9-epiminobenzo[4,5]cyclohepta[1,2-c]pyrazole; MS 442.1 ¹H NMR (CDCl₃) δ 7.82 (d, J = 8.2 Hz, 1H), 7.54 (d, J = 8.2, 2H), 7.46 (s, 1H), 6.97 (m, 2H), 6.64 (m, 1H), 6.14 (s, 1H), 5.58 (m, 1H), 5.42 (d, J = 1.9 Hz, 1H). Prepared as described above for the (−)-stereoisomer. | D |
| 264 | (±)-8-chloro-11-{[6-(trifluoromethyl)pyridin-3-yl]sulfonyl}-4,9-dihydro-4,9-epiminobenzo[4,5]cyclohepta[1,2-c]pyrazol-10(1H)-one; MS 455.1 ¹H NMR (CDCl₃) δ 8.86 (s, 1H), 8.20 (d, J = 8.2 Hz, 1H), 7.68 (d, J = 8.2, 1H), 7.62 (s, 1H), 7.04 (m, 3H), 6.29 (s, 1H), 5.58 (s, 1H). Prepared by oxidation of 8-chloro-11-{[6-(trifluoromethyl)pyridin-3-yl]sulfonyl}-1,4,9,10-tetrahydro-4,9-epiminobenzo[4,5]cyclohepta[1,2-c]pyrazole using the methods described in Example 15. | D |
| 265 | (±)-8-chloro-N-hydroxy-11-{[6-(trifluoromethyl)pyridin-3-yl]sulfonyl}-4,9-dihydro-4,9-epiminobenzo[4,5]cyclohepta[1,2-c]pyrazol-10(1H)-imine; MS 470.0. ¹H NMR (CDCl₃) δ 14.8 (s, 1H), 9.34 (s, 1H), 9.15 (s, 1H), 8.37 (dd, J = 8.2, 1.6 Hz, 1H), 7.71 (d, J = 8.2 Hz, 1H), 7.64 (s, 1H), 6.92 (m, 4H), 6.63 (s, 1H). Prepared by treatment of (±)-8-chloro-11-{[6-(trifluoromethyl)-pyridin-3-yl]sulfonyl}-4,9-dihydro-4,9-epiminobenzo[4,5]cyclohepta[1,2-c]pyrazol-10(1H)-one with hydroxylamine hydrochloride and NaHCO₃ in CH₃CN/H2O (3:1). | D |
| 266 | (±)-8-(4-fluorophenyl)-11-{[6-(trifluoromethyl)pyridin-3-yl]sulfonyl}-1,4,9,10-tetrahydro-4,9-epiminobenzo[4,5]cyclohepta[1,2-c]pyrazole; MS 501.1. ¹H NMR (CDCl₃) δ 8.79 (d, J = 2.0 Hz, 1H), 8.00 (dd, J = 8.2, 1.8 Hz, 1H), 7.51 (d, J = 8.1 Hz, 1H), 7.41 (s, 1H), 7.19 (m, 4H), 6.95 (m, 3H), 5.92 (s, 1H), 5.39 (d, J = 5.5 Hz, 1H), 3.38 (dd, J = 16.4, 5.7 Hz, 1H), 2.85 (d, J = 16.4 Hz, 1H). Prepared as described in Example 19 using 8-chloro-11-{[6-(trifluoromethyl)pyridin-3-yl]sulfonyl}-1,4,9,10-tetrahydro-4,9-epiminobenzo[4,5]cyclohepta[1,2-c]pyrazole. | D |
| 267 | (4S,9S,10R)-5,10-difluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 443.1. ¹H NMR (CDCl₃) δ 10.36 (s, 1H), 8.92 (d, J = 2.1 Hz, 1H), 8.11 (dd, J = 8.2, 2.2 Hz, 1H), 7.57 (d, J = 8.3 Hz, 1H), 7.49 (s, 1H), 6.97-7.04 (m, 2H), 6.65-6.71 (m, 1H), 6.14 (dd, J = 52.8, 6.3 Hz, 1H), 6.07 (s, 1H), 5.53 (d, J = 6.2 Hz, 1H). Prepared as the minor component of fluorination of 5-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol using the methods described in Example 15, followed by chiral chromatographic separation of stereoisomers. | D |
| 268 | (4R,9R,10R)-5,10-difluoro-11-{[6-(trifluoromethyl)pyridin-3-yl]sulfonyl}-1,4,9,10-tetrahydro-4,9-epiminobenzo[4,5]cyclohepta[1,2-c]pyrazole; MS 443.1. ¹H NMR (CDCl₃) δ 10.27 (s, 1H), 8.97 (d, J = 1.9 Hz, 1H), 8.20 (dd, J = 8.3, 1.8 Hz, 1H), 7.62 (d, J = 8.2 Hz, 1H), 7.51 (s, 1H), 7.05-7.11 (m, 2H), 6.74-6.81 (m, 1H), 6.23 (s, 1H), 5.65 (d, J = 10.4 Hz, 1H), 5.52 (dd, J = 52.1, 1.8 Hz, 1H). Prepared by fluorination of 5-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol using the methods described in Example 15 followed by chiral chromatographic separation of stereoisomers. | A |
| 269 | | D |

| Ex. No. | Structure/Compound Name/Mass Spec (M + H)/ $^1$H-NMR (300 MHz)/Experimental Procedures | γAPP IC$_{50}$ (nM) |
|---|---|---|
|  | (±)-8-chloro-N-methoxy-11-{[6-(trifluoromethyl)pyridin-3-yl]sulfonyl}-4,9-dihydro-4,9-epiminobenzo[4,5]cyclohepta[1,2-c]pyrazol-10(1H)-imine; MS 484.2. $^1$H NMR (CDCl$_3$) δ 8.89 (d, J = 2.1 Hz, 0.3H), 8.83 (d, J = 2.1 Hz, 1H), 8.04 (dd, J = 8.2, 1.8 Hz, 1H), 7.94 (dd, J = 8.2, 1.8 Hz, 0.3H), 7.56 (s, 1H), 7.52 (m, 1H), 7.49 (s, 1H), 7.05 (s, 1), 7.02 (s, 3H), 6.65 (s, 1H), 6.03 (m, 1.3H), 4.12 (s, 3H), 4.08 (s, 1H). Prepared by treatment of (±)-8-chloro-11-{[6-(trifluoromethyl)pyridin-3-yl]sulfonyl}-4,9-dihydro-4,9-epiminobenzo[4,5]cyclohepta[1,2-c]pyrazol-10(1H)-one with methoxylamine hydrochloride and NaHCO$_3$ in EtOH/THF (1:1). |  |
| 270 | (±)-8-cyclopropyl-11-{[6-(trifluoromethyl)pyridin-3-yl]sulfonyl}-1,4,9,10-tetrahydro-4,9-epiminobenzo[4,5]cyclohepta[1,2-c]pyrazole; MS 447.0 $^1$H NMR (CDCl$_3$) δ 8.87 (d, J = 1.9 Hz, 1H), 7.99 (dd, J = 8.2, 2.0 Hz, 1H), 7.44 (d, J = 8.2 Hz, 1H), 7.38 (s, 1H), 6.84 (t, J = 7.5 Hz, 1H), 6.72 (d, J = 7.3 Hz, 1H), 6.41 (d, J = 7.7 Hz, 1H), 5.85 (s, 1H), 5.56 (d, J = 5.5 Hz, 1H), 3.51 (dd, J = 16.2, 5.6 Hz, 1H), 2.99 (d, J = 15.7 Hz, 1H), 1.66 (m, 1H), 0.98 (m, 2H), 0.60 (m, 2H). Prepared as described in Example 19 using cyclopropylboronic acid and 8-chloro-11-{[6-(trifluoromethyl)pyridin-3-yl]sulfonyl}-1,4,9,10-tetrahydro-4,9-epiminobenzo[4,5]-cyclohepta[1,2-c]pyrazole. | D |
| 271 | exo-10-fluoro-11-{[6-(trifluoromethyl)pyridin-3-yl]sulfonyl}-2,4,9,10-tetrahydro-4,9-epiminobenzo[4,5]cyclohepta[1,2-c]pyrazole; MS 425.0 $^1$H NMR (CD$_3$OD) δ 8.94 (s, 1H), 8.25 (d, J = 8.2 Hz, 1H), 7.62 (m, 2H), 7.27 (d, J = 6.9 Hz, 1H), 6.94 (m, 3H), 6.15 (s, 1H), 5.71 (d, J = 10.6 Hz, 1H), 5.55 (d, J = 52.1 Hz, 1H). Prepared as described in Example 15 using (−)-11-{[6-(trifluoromethyl)pyridin-3-yl]sulfonyl}-1,4,9,10-tetrahydro-4,9-epiminobenzo[4,5]cyclohepta[1,2-c]pyrazole. | A |
| 272 | [Structure diagram]<br><br>(±)-8-chloro-10-methylidene-11-{[6-(trifluoromethyl)pyridin-3-yl]sulfonyl}-1,4,9,10-tetrahydro-4,9-epiminobenzo[4,5]cyclohepta[1,2-c]pyrazole; MS 453.1. $^1$H NMR (CDCl$_3$) δ 8.78 (d, J = 2.1 Hz, 1H), 8.11 (dd, J = 8.4, 1.8 Hz, 1H), 7.55 (d, J = 8.4 Hz, 1H), 7.38, (s, 1H), 7.05 (m, 3H), 6.06 (s, 1H), 5.74 (s, 1H), 5.60 (s, 1H), 5.49 (s, 1H). Prepared by alkylation of (±)-8-chloro-11-{[6-(trifluoromethyl)pyridin-3-yl]sulfonyl}-4,9-dihydro-4,9-epiminobenzo-[4,5]cyclohepta[1,2-c]pyrazol-10(1H)-one with trimethylsilylethoxymethyl chloride as described in Example 19 followed by alkene formation using Tebbe reagent and dealkylation using 4N HCl/dioxane. | D |
| 273 | (±)-5-(4-fluorophenyl)-11-{[6-(trifluoromethyl)pyridin-3-yl]sulfonyl}-1,4,9,10-tetrahydro-4,9-epiminobenzo[4,5]cyclohepta[1,2-c]pyrazole; MS 501.2. $^1$H NMR (CDCl$_3$) δ 8.65 (s, 1H), 7.93 (d, J = 6.5 Hz, 1H), 7.55 (s, 1H), 7.48 (d, J = 8.1 Hz, 1H), 7.10 (m, 6H), 6.87 (d, J = 7.4 Hz, 1H), 5.74 (s, 1H), 5.44 (d, J = 5.1 Hz, 1H), 3.60 (dd, J = 16.7, 4.7 Hz, 1H), 3.04 (d, J = 16.9 Hz, 1H). Prepared as described in Example 19 using 5-chloro-11-{[6-(trifluoromethyl)pyridin-3-yl]sulfonyl}-1,4,9,10-tetrahydro-4,9-epiminobenzo[4,5]cyclohepta[1,2-c]pyrazole. | >100 |
| 274 | (±)-5-cyclopropyl-11-{[6-(trifluoromethyl)pyridin-3-yl]sulfonyl}-1,4,9,10-tetrahydro-4,9-epiminobenzo[4,5]cyclohepta[1,2-c]pyrazole; MS 447.2 $^1$H NMR (CDCl$_3$) δ 8.90 (d, J = 1.7 Hz, 1H), 8.02 (dd, J = 8.1, 1.7 Hz, 1H), 7.46 (d, J = 8.2 Hz, 1H), 6.89 (m, 2H), 6.43 (m, 1H), 6.07 (s, 1H), 5.45 (d, J = 5.1 Hz, 1H), 3.60 (dd, J = 16.2, 5.6 Hz, 1H), 2.92 (d, J = 15.7 Hz, 1H), 1.67 (m, 1H), 0.98 (m, 2H), 0.51 (m, 2H). Prepared as described in Example 19 using 5-chloro-11-{[6-(trifluoromethyl)pyridin-3-yl]sulfonyl}-1,4,9,10-tetrahydro-4,9-epiminobenzo[4,5]cyclohepta[1,2-c]pyrazole and cyclopropylboronic acid. | D |

| Ex. No. | Structure/Compound Name/Mass Spec (M + H)/ ¹H-NMR (300 MHz)/Experimental Procedures | γAPP IC₅₀ (nM) |
|---|---|---|
| 275 | (−)-9-methyl-11-{[6-(trifluoromethyl)pyridin-3-yl]sulfonyl}-4,9-dihydro-4,9-epiminobenzo[4,5]cyclohepta[1,2-c]pyrazol-10(1H)-one; MS 435.1. ¹H NMR (CDCl₃) δ 8.92 (d, 1H, J = 2.4 Hz), 8.16 (dd, J = 2.4, 8.4 Hz, 1H), 7.70 (d, 1H, J = 8.4 Hz), 7.67 (s, 1H), 7.30-7.21 (m, 4H), 6.30 (s, 1H), 1.96 (s, 3H). Prepared as described in Example 21 using 6-(trifluoromethyl)pyridine-3-sulfonyl chloride followed by chiral chromatographic separation of the stereoisomers. | D |
| 276 | (+)-9-methyl-11-{[6-(trifluoromethyl)pyridin-3-yl]sulfonyl}-4,9-dihydro-4,9-epiminobenzo[4,5]cyclohepta[1,2-c]pyrazol-10(1H)-one; MS 435.1 ¹H NMR (CDCl₃) δ 8.94 (d, 1H, J = 2.1 Hz), 8.16 (dd, J = 2.4, 8.4 Hz, 1H), 7.70 (d, 1H, J = 8.4 Hz), 7.66 (s, 1H), 7.32-7.18 (m, 4H), 6.30 (s, 1H), 1.96 (s, 3H). Prepared as described above for the (−)-stereoisomer. | >30 |
| 277 | (−)-9-methyl-11-{[4-(trifluoromethyl)phenyl]sulfonyl}-4,9-dihydro-4,9-epiminobenzo[4,5]cyclohepta[1,2-c]pyrazol-10(1H)-one; MS 434.0 ¹H NMR (CDCl₃) δ 7.83 (d, 2H, J = 8.4 Hz), 7.67 (s, 1H), 7.63 (d, 2H, J = 8.4 Hz), 7.29-7.17 (m, 4H), 6.28 (s, 1H), 1.92 (s, 3H). Prepared as described in Example 21 followed by chiral chromatographic separation of stereoisomers. | D |
| 278 | (+)-9-methyl-11-{[4-(trifluoromethyl)phenyl]sulfonyl}-4,9-dihydro-4,9-epiminobenzo[4,5]cyclohepta[1,2-c]pyrazol-10(1H)-one; MS 434.0 ¹H NMR (CDCl₃) δ 7.83 (d, 2H, J = 8.4 Hz), 7.67 (s, 1H), 7.63 (d, 2H, J = 8.4 Hz), 7.29-7.17 (m, 4H), 6.28 (s, 1H), 1.92 (s, 3H). Prepared as described above for the (−)-stereoisomer. | >30 |

In the above table, "A" respresents IC₅₀ values of >1 μM; "B" represents IC₅₀ values of 500 nM to 999 nM; "C" respresent IC₅₀ values of 100 nM to 499 nM; and "D" respresent IC₅₀ values of <100 nM. IC₅₀ values were generated using the assay described in Example A.

Example A

Gamma-Secretase APP Assay

The gamma-secretase APP enzyme assay was designed to measure the specific proteolytic cleavage of an APP substrate (MBP-C125 Swe fusion protein) at the Aβ40 site. The assay used a partially purified extract of IMR-32 cell membranes as the gamma-secretase enzyme preparation and a recombinant fusion protein containing the C-terminal 125 amino acids of the Swedish variant of the APP (MBP-C125swe) as the substrate. This assay involved two steps beginning with the enzymatic reaction generating a cleavage product that was captured with an immobilized antibody specific for the neo-epitope Aβ40 site. The captured cleavage product was then detected in a sandwich ELISA assay with a biotinylated reporter antibody that is specific to Aβ(17-28). Streptavidin-linked alkaline phosphatase was then added that would generate a fluorescent signal proportional to the amount of cleavage product. This assay was used to discover small molecule inhibitors of gamma-secretase.

Materials and Methods

Briefly, a 149 mg/ml solution of BIGCHAP detergent was made with water at 42° C. and then rotated for 30 minutes at the same temperature. This warmed solution of BigCHAPS (N,N-Bis(3-D-gluconamidopropyl)cholamide) detergent was used to dissolve Brain Extract Type-V (lipid containing a minimum of 40% phosphatidylethanolamine) from Sigma (St. Louis, Mo.) to a concentration of 8 mg/ml. This solution containing BigCHAPS and lipid at 8 mg/ml is then diluted to 0.53 mg/ml lipid with a pre-warmed solution of Hepes and sodium chloride. This final solution containing Hepes buffer, sodium chloride, BigCHAPS detergent and lipid is used to create working solutions of both gamma-secretase (25 Units) and the MBP-C 125 substrate (0.05 mg/ml).

Gamma-secretase was then added to a 96-well micro-titre plate and then incubated with various concentrations of inhibitor for 30 minutes at 37° C. MBPC125 substrate was then added to initiate the reaction that would run for two hours at 37° C. The reaction was quenched with the addition of SDS to a final concentration of 0.1% and then 100 μl of the reaction mixture was transferred to a capture ELISA plate and incubated overnight at 4° C. Detection of the cleavage product was performed using a standard sandwich ELISA assay and quantified using a six point standard curve. Compounds of the invention have IC50 values of less than 10 μM.

Example B

Gamma-Notch In Vitro Assay

This assay employs the same enzyme preparation that was used in the gamma-APP in vitro enzyme assay (described in Example C, below), but at a two-fold higher concentration, and the same reaction buffers and materials for diluting the enzyme. The fusion protein APP substrate was replaced by an analogous Notch fusion protein substrate expressed in bacteria and purified by affinity chromatography prior to incubation with enzyme. The Gamma Notch assay was designed to measure the specific proteolytic cleavage of a Notch substrate (Notch ΔE) at the position corresponding to Val 1744 of full-length Notch, also known as the epsilon cleavage site, on the Notch substrate. The specific product was measured by a sandwich ELISA utilizing a neo-epitope specific capture antibody 9F3 specific for the N-terminus of the cleaved NICD product and a biotinylated reporter antibody anti-HA-biotin (Roche) directed against the HA-tag at the C-terminus of the substrate.

Bacterial Expression and Affinity Purification of Notch Fusion Protein Substrate A recombinant Notch fusion protein containing sequential HA and His-6 epitope tags at the C-terminus, was expressed in *E. coli*, and affinity purified from lysates using a Nickel-sepharose column and imidazole elution using standard procedures. This purified Notch fusion protein was employed as a substrate for in vitro cleavage by the gamma secretase enzyme (prepared from IMR32 cells). The Notch fusion protein was constructed so as to be analogous to the APP C99 fragment. Thus, the Notch fusion protein was comprised of 99 amino-acids flanking the trans-membrane domain of mouse Notch1, beginning with the 17 residues amino-terminal to the trans-membrane domain, also encompassing the 17 residue trans-membrane domain, and extending 66 residues into the cytoplasmic domain. The amino-terminus of the fusion protein begins at residue #1711 of mouse Notch, and extends C-terminally to residue #1809, followed by an in-frame epitope tag fusion of the HA tag, and six histidine residues. The epitope tags were incorporated to facilitate ELISA detection of the NICD cleavage product using an anti-HA antibody, and for easier purification of the fusion protein substrate from *E. coli* lysates using Nickel column affinity chromatography, respectively.

Following overnight expression of the fusion protein in *E. coli*, the substrate was purified on a nickel-sepharose column from lysates. Purity of the 16 kDa Notch fusion protein substrate eluted from the nickel-affinity column was confirmed by SDS-PAGE. Fractions containing the desired protein were then pooled, adjusted to 0.5-0.6 mg/ml final concentration in 3M Guanidine-HCl, 0.1% Triton X-100 with 20 mM DTT, and stored at −80° C. in aliquots until use in the enzyme reaction. This protein was not stable over long periods, and would aggregate even in the above storage buffer at −80° C. Therefore, a new preparation was necessary to prepare every three months to keep an active inventory to support in-house screening activities.

Bacterial Expression and Purification of Recombinant Notch Intracellular Domain (NICD) Standard for ELISA The NICD standard was produced as a fusion protein from a construct containing an initiating methionine and an enterokinase cleavage site before the gamma-secretase product NICD (Met-EK-NICD), with a carboxy-terminal calmodulin binding peptide fusion tag, and an HA epitope tag. The fusion protein was produced in *E. coli*, affinity purified using a calmodulin affinity resin, and assayed for protein concentration. The protein was then cleaved with enterokinase in order to produce the free N-terminus of the NICD product. The enterokinase cleaved protein was separated by SDS-PAGE on a 12% Tris-glycine gel. Enterokinase cleavage products were detected by Western blotting using an antibody against the HA-tag. Densitometry was used to measure the efficiency of the EK cleavage. The estimated concentration of EK cleaved NICD standard was calculated (% of NICD/total HA-reactive protein). The standard was stored at −40° C. On the day of each assay, an aliquot of the NICD standard was serially diluted 1:1 in Casein Diluent (Media Facility) to generate a standard curve with 0-200 ng/ml NICD.

In vitro Reaction of Notch Substrate with Enzyme

Purified substrate (above) was desalted immediately prior to use on a NAP-25 column, and its concentration was determined using the Biorad DC protein assay. Substrate was diluted 1:20 in the final reaction with a 1:20 dilution of gamma-secretase enzyme (0.4 mg/ml final in Type V phospholipid solubilized in BigCHAP, 50 mM MES pH6.0, 4 mM DTT, 0.02% TX-100) and incubated in the presence of protease inhibitors (1 mM 1,10-phenanthroline, 5 μg/ml E64, and 5 μg/ml leupeptin), plus or minus a range of gamma-secretase inhibitor concentrations. All reactions were incubated at 37° C. in 96-well plates for 3 hrs and then quenched with 0.1% SDS for 10 min at room temperature.

Quenched reactions were then diluted 1:1 Casein Diluent with 500 mM NaCl, 0.02% TritonX-100 and transferred to a 9F3-coated ELISA capture plate overnight at 4° C. NICD standards (section 4.2 above, serially diluted 2× over a concentration range from a starting concentration of 50 ng/ml) were used for establishing a standard curve. The NICD reaction product and concentration standards captured on the plate were quantified using an ELISA detection scheme. A biotinylated-HA antibody (1 μg/ml final conc., Roche Cat#. 1666851), followed by alkaline phosphatase conjugated streptavidin (diluted 1000× from stock, Roche Cat# 1089161) were incubated in the ELISA capture plate with washing steps (Tris buffered saline, 0.1% Tween20) in between each incubation step. The alkaline phosphatase reaction was developed by incubation with 100 μl/well Fluorescent Substrate A for 15 min at RT, and the extent of fluorescence, which was proportional to the amount of cleaved Notch, was quantified using a Cytofluor plate reader set @ 360 nm Excitation, 460 nm Emission.

Example C

Notch Signaling Assay

The Notch signaling assay is a luciferase reporter gene based readout from cellular lysates generated from the SNC dual cell assay. Following transfer of conditioned media (to measure for Aβ from SNC cells incubated overnight with inhibitors), the cells were rinsed in PBS, lysed, and assayed for Luciferase reporter gene activity using a protocol and reagents provided by the manufacturer (Promega). The samples were kept in the dark until read in a luminometer (Safire plate reader, Tecan).

Cell Culture and Inhibitor Treatment

CHO cells stably transfected with the SweAPP and Notch☐E constructs were plated on 96-well tissue culture plates at 15,000 cells per well in 130 μl media/well the day before the compound treatment. Cells were cultured in DMEM containing 2 mM glutamine, 10% FBS, 0.5 mg/ml G418, 1 mg/ml hygromycin, and 2.8 mg/ml puromycin. Compounds were diluted first 4-fold and then 10-fold for six successive dilutions in DMSO as 250× final concentration stocks. The compounds were then added to cells using media which had been pre-warmed to 37° C., at a final DMSO concentration of 0.4%. After 18 h, 100 µl of conditioned media was removed from each well and saved for the ELISA assay. The wells were washed with 200 µl/well of cold PBS with $MgCl_2$ and $CaCl_2$. The wash buffer was aspirated and the cells were lysed in 40 µl lysis reagent (20 mM Tris, pH 7.5, 0.2% TX 100, 100 mM NaCl, 2 mM EDTA, 2× complete protease inhibitors) per well for 30 minutes to complete the lysis. 100 µl of luciferase reagent was then added to all wells (Promega catalog number #E1501) and luminescence measured using a Safire II plate reader (Tecan). This assay was performed in a fully automated manner using the Stacatto platform (Caliper Life Sciences).

Aβ 40 and Aβ 42 Specific ELISA

The conditioned media (CM) from CHO cells stably transfected with the SweAPP and NotchΔE constructs was directly taken from the well undiluted for the Aβ(X-40) and Aβ (X-42) ELISA assays after overnight incubation with the test compound. The capture antibody for the Aβ(X-40) ELISA was 266 and the reporter antibody was biotinylated-2G3 (directed towards Aβ40). The capture antibody for the Aβ(X-42) ELISA assay was also 266 where the reporter antibody was biotinylated-21F12 (directed towards Aβ42). Aβ(1-40) and Aβ(1-42) synthetic peptide standard curves were used to calculate the CM Aβ concentrations. The $IC_{50}$ determinations of the compounds were calculated using the GraphPad Prism program choosing the sigmoidal dose response variable slope equation.

Example D

SNC Dual Cell Assay for Simultaneous Assay of A-Beta Reduction and Notch Signaling Following Gamma Secretase Inhibition in Cells Production of Stably Transfected CHO Cells Overexpressing APP(SWE), Notch-Δe, and a Notch Intracellular Domain Responsive Luciferase Reporter Gene and Development of SNC Dual Cell Assay.

In order to facilitate testing the potency of gamma-secretase inhibitors on two substrates (APP and Notch) simultaneously, a dual-assay using a CHO cell line stably expressing APPSwe, a Notch substrate lacking the ecto-domain, and a Notch responsive Luciferase reporter gene was developed. CHOswe cells stably over-express the Swedish FAD isoform of APP, and secrete large amounts of Aβ peptide into the conditioned media from endogenous β- and γ-secretase enzyme activity. A Notch intracellular domain (NICD) responsive reporter gene, and the constitutive gamma-secretase Notch substrate, NotchΔE, were stably introduced into CHOswe cells in a two step process. CHOswe cells were first stably transfected to express a NICD responsive luciferase reporter gene construct (pGL2-CBF-Luc). Numerous stable clones (SCH clones), were identified which displayed gamma-inhibitor-sensitive Notch signaling upon transient expression with Notch-ΔE. The best three clones SCH-32, SCH-33 and SCH-54 were selected as the host cells for subsequent stable expression of Notch-ΔE as the final step of dual-assay line generation. Stable cell lines expressing rat NotchΔE were then identified in the second step by including a gamma-secretase inhibitor in the selection process (to suppress Notch/NICD toxicity) following transfection of the rat Notch-ΔE construct.

The SCH-32, SCH-33 and SCH-54 clones were transfected with the Notch-SE expression vector (pIRES-ZEDN), respectively. This vector drives expression of a truncated rat Notch construct corresponding to the c-terminal product following ecto-domain shedding of full length rat Notch protein. The c-terminal product is a constitutive substrate for gamma-secretase cleavage, resulting in release of the cytoplasmic Notch intracellular domain (NICD) product, which translocates to the nucleus and relieves CBF repressed genes. Subsequently, pIRES-ZEDN transfected cells were re-plated at low density in the presence of test compound, and selected with three antibiotics (G418 (0.5 mg/ml)/Hygro (1 mg/ml)/Puro (2.5 mg/ml)). The antibiotic-resistant colonies (named SNC clones for the dual-assay components: APPSwe/NotchΔE/CBF) were isolated and expanded for characterization of Aβ secretion, and NICD responsive reporter gene activity (i.e. luciferase signal in the presence versus absence of test compound). Based on optimal Aβ secretion, and best signal/background of reporter gene activity, we selected the clone designated as SNC-204B8 as the dual-assay stable line for our subsequent profiling more gamma-secretase inhibitors.

A typical dual-assay experiment was performed as follows:
Day 1, the SNC cells were plated in 96-well assay plates in inhibitor-free media.

Day 2, the cells were fed with fresh media (inhibitor free) and treated with test compounds over a concentration range 0 nM to 40,000 nM (in 10× incremental dilutions) one hour after the media change. The cells were treated with compounds overnight at 37° C.

Day 3, Notch signaling and part I of Aβ-ELISA was performed: for the Aβ-production assay, conditioned media were collected and added to plates coated with antibody 266 for Aβ capture overnight. For the Notch signaling assay, the cells were lysed and luciferase activity from the lysate was measured using the Promega kit (see below).

Day 4, Aβ-ELISA part II was conducted using 3D6-biotin/AP-streptavidin antibodies.

Example E

Alternative Notch Signaling Assays

Assay systems described in the following references can also be used to measure modulation (e.g., inhibition) of Notch signaling by compounds of the invention. An exemplary reporter gene assay for Notch signaling was described in Hsieh, J. J., T. Henkel, P. Salmon, E. Robey, M. G. Peterson and S. D. Hayward (1996). "Truncated mammalian Notch1 activates CBF1/RBPJk-repressed genes by a mechanism resembling that of Epstein-Barr virus EBNA2 and by Lu, F. M. and S. E. Lux, *Mol. Cell. Biol.* 1996, 16(3): 952-9; "Constitutively active human Notch1 binds to the transcription factor CBF1 and stimulates transcription through a promoter containing a CBF 1-responsive element." *Proc Natl Acad Sci USA* 93(11): 5663-7. Another reporter gene based Notch signaling assay uses a constitutively active rat Notch1 construct (ZEDN1) as described in Shawber, C., D. Nofziger, J. J. Hsieh, C. Lindsell, O. Bogler, D. Hayward and G. Weinmaster (1996). "Notch signaling inhibits muscle cell differentiation through a CBF 1-independent pathway." *Development* 122(12): 3765-73 in combination with the CBF1 repressible Luciferase reporter gene 4xwtCBF1Luc as described in Hsieh, J. J., T. Henkel, P. Salmon, E. Robey, M. G. Peterson and S. D. Hayward (1996). "Truncated mammalian Notch1 activates CBF 1/RBPJk-repressed genes by a mechanism resembling that of Epstein-Barr virus EBNA2." *Mol Cell Biol* 16(3): 952-9). Each of the above references is incorporated herein by reference in their entirety.

When 4xwtCBF1 Luciferase is co-transfected with NotchδE (ZEDN1), gamma-secretase cleavage of NotchδE releases the Notch intracellular domain (NICD), which translocates to the nucleus and de-represses CBF1 mediated transcriptional repression, leading to transcription of the Luciferase reporter gene. Luciferase activity is easily assayed in cell extracts using commercially available kits. The activity of the reporter gene is directly correlated with gamma secretase cleavage of NotchδE, and as such, a reduction in Luciferase activity provides a convenient measure of inhibition of gamma secretase cleavage of NotchδE. A comparison of the $IC_{50}$ values of compounds for inhibition of Notch signaling versus inhibition of beta-amyloid production in 293sw cells is employed to guide in the selection of compounds that have the desired property of potent inhibition of beta-amyloid synthesis with minimal inhibition of Notch signaling.

Notch Selectivity Data

Evidence indicates that the gamma secretase complex, comprised of the presenilin subunits, mediates the intramembrane cleavage of amyloid precursor protein (APP) as well as the Notch family of proteins. Unexpectedly, the inventors have discovered that certain compounds of the invention potently inhibit gamma secretase-mediated cleavage of APP (inhibition of beta-amyloid synthesis, e.g., as described in Example A) but exhibit reduced proteolytic cleavage of a Notch substrate (e.g., NotchΔE, as described in Example B) or inhibition of Notch signaling (e.g., as described in Examples C and D). E.g., compounds disclosed herein exhibit greater selectivity for the inhibition of APP cleavage (i.e., gamma secretase-mediated beta-amyloid production) versus inhibition of Notch cleavage or inhibition of Notch signaling when compared to known gamma-secretase inhibitors. In the following, compounds, which can inhibit enzymatic cleavage of Notch (e.g., by inhibiting the corresponding gamma secretase activity) (e.g., as described in Example B) or Notch signaling (e.g., as described in Example C), are referred to as having "in vitro Notch activity" or "Notch activity". Assays, which can be used to determine Notch activities are known to those of skill in the art. Exemplary assays are described herein in Examples B, C, D and E.

Certain compounds disclosed herein are characterized by desirable, low Notch activity. In one example, the compounds of the invention are characterized by an in vitro Notch activity (e.g., as measured using the assay described in Example B) equivalent to an $IC_{50}$ value larger than about 20 nM, about 30, about 40 or about 50 nM. In another example, the compounds of the invention are characterized by an in vitro Notch activity equivalent to an $IC_{50}$ value larger than about 100 nM, larger than about 200 nM, larger than about 300 nM, larger than about 400 nM, larger than about 500 nM, larger than about 600 nM, larger than about 700 nM, larger than about 800 nM, larger than about 900 nM or larger than about 1 μM. In yet another example, the compounds of the invention are characterized by an in vitro Notch activity equivalent to an $IC_{50}$ value larger than about 2 μM, larger than about 3 μM, larger than about 4 μM, larger than about 5 μM, larger than about 6 μM, larger than about 7 μM, larger than about 8 μM, larger than about 9 μM or larger than about 10 μM.

In yet another example, the compounds of the invention are characterized by a ratio of Notch activity (i.e., Notch $IC_{50}$) to APP activity (i.e., Aβ $IC_{50}$) (e.g., as measured by a in vitro assays as described in Examples A and B, respectively; or a dual assay as described in Example D) (e.g., selectivity ratio Notch $IC_{50}$/Aβ $ED_{50}$) of larger than about 500, larger than about 400 or larger than about 300. In a further example, the Notch/APP selectivity ratio is larger than about 200, larger than about 150 or larger than about 100. In a further example, the Notch/APP selectivity ratio is larger than about 90, larger than about 80, larger than about 70, larger than about 60, larger than about 50, larger than about 40, larger than about 30, larger than about 20 or larger than about 10. In yet a further example, the Notch/APP selectivity ratio is larger than about 9, larger than about 8, larger than about 7, larger than about 6, larger than about 5, larger than about 4, larger than about 3, larger than about 2 or larger than about 1. In a particular embodiment, the compounds of the invention are characterized by a selectivity ratio (i.e., Notch $IC_{50}$/Aβ $ED_{50}$) of larger than about 50. Exemplary compounds and their Notch/APP selectivity ratios are summarized in Table 2, below.

TABLE 2

Compound selectivity for cleavage of the Aβ peptide over Notch

| Compound Name | Selectivity Ratio (Notch $IC_{50}$/Aβ $ED_{50}$) |
|---|---|
| (±)-10-[(4-chlorophenyl)sulfonyl]-6-(3-methylisoxazol-5-yl)-4,5,6,7,8,9-hexahydro-1H-4,8-epiminocycloocta[c]pyrazole | (++++) |
| (−)-5-fluoro-11-{[6-(trifluoromethyl)pyridin-3-yl]sulfonyl}-4,9-dihydro-4,9-epiminobenzo[4,5]cyclohepta[1,2-c]pyrazol-10(1H)-one | (++++) |
| (−)-8-fluoro-11-{[6-(trifluoromethyl)pyridin-3-yl]sulfonyl}-4,9-dihydro-4,9-epiminobenzo[4,5]cyclohepta[1,2-c]pyrazol-10(1H)-one | (++++) |
| (±)-10-[(4-chlorophenyl)sulfonyl]-6-(3-methyl-1,2,4-oxadiazol-5-yl)-4,5,6,7,8,9-hexahydro-1H-4,8-epiminocycloocta[c]pyrazole | (++++) |
| (±)-10-[(5-chlorothiophen-2-yl)sulfonyl]-6-phenyl-4,5,6,7,8,9-hexahydro-1H-4,8-epiminocycloocta[c]pyrazole | (++++) |
| (±)-exo-6-(4-fluorophenyl)-10-{[6-(trifluoromethyl)pyridin-3-yl]sulfonyl}-4,5,6,7,8,9-hexahydro-1H-4,8-epiminocycloocta[c]pyrazole | (+++) |
| (+)-endo-11-{[4-(trifloromethyl)phenyl]sulfonyl}-1,4,9,10-tetrahydro-4,9-epiminobenzo[4,5]cyclohepta[1,2-c]pyrazol-10-ol | (+++) |
| (±)-10-[(4-chlorophenyl)sulfonyl]-4,5,6,7,8,9-hexahydro-1H-4,8-epiminocycloocta[c]pyrazole-6-carbonitrile | (+++) |
| (±)-10-{[6-(trifluoromethyl)pyridin-3-yl]sulfonyl}-6-[4-(trifluoromethyl)-1,3-thiazol-2-yl]-4,5,6,7,8,9-hexahydro-1H-4,8-epiminocycloocta[c]pyrazole | (+++) |

TABLE 2-continued

Compound selectivity for cleavage of the Aβ peptide over Notch

| Compound Name | Selectivity Ratio (Notch IC$_{50}$/Aβ ED$_{50}$) |
|---|---|
| (+)-6-(3-fluorophenyl)-10-{[6-(trifluoromethyl)pyridin-3-yl]sulfonyl}-4,5,6,7,8,9-hexahydro-1H-4,8-epiminocycloocta[c]pyrazole | (+++) |
| (+)-5,10-difluoro-11-{[4-(trifluoromethyl)phenyl]sulfonyl}-1,4,9,10-tetrahydro-4,9-epiminobenzo[4,5]cyclohepta[1,2-c]pyrazole | (++) |
| (±)-6-(1,2,3-thiadiazol-4-yl)-10-{[4-(trifluoromethyl)phenyl]sulfonyl}-4,5,6,7,8,9-hexahydro-1H-4,8-epiminocycloocta[c]pyrazole | (++) |
| (±)-endo-6-(4-fluorophenyl)-10-{[6-(trifluoromethyl)pyridin-3-yl]sulfonyl}-4,5,6,7,8,9-hexahydro-1H-4,8-epiminocycloocta[c]pyrazole | (++) |
| 5-phenyl-10-{[4-(trifluoromethyl)phenyl]sulfonyl}-4,5,6,7,8,9-hexahydro-1H-4,8-epiminocycloocta[c]pyrazole | (++) |
| (±)-7-[3-(trifluoromethyl)phenyl]-12-{[4-(trifluoromethyl)phenyl]sulfonyl}-4,5,6,11-tetrahydro-3H-5,11-epiminobenzo[4,5]cycloocta[1,2-c]pyrazole | (++) |
| (±)-7-fluoro-11-{[6-(trifluoromethyl)pyridin-3-yl]sulfonyl}-1,4,9,10-tetrahydro-4,9-epiminopyrazolo[3',4': 5,6]cyclohepta[1,2-b]pyridine | (+) |
| (±)-6-[3-(1H-pyrazol-1-yl)phenyl]-10-{[4-(trifluoromethyl)phenyl]sulfonyl}-4,5,6,7,8,9-hexahydro-1H-4,8-epiminocycloocta[c]pyrazole | (+) |
| (±)-6-(3-bromophenyl)-10-{[4-(trifluoromethyl)phenyl]sulfonyl}-4,5,6,7,8,9-hexahydro-1H-4,8-epiminocycloocta[c]pyrazole | (+) |
| (±)-6-(1,3-benzodioxol-5-yl)-10-{[6-(trifluoromethyl)pyridin-3-yl]sulfonyl}-4,5,6,7,8,9-hexahydro-1H-4,8-epiminocycloocta[c]pyrazole | (+) |
| (−)-6-bromo-11-{[6-(trifluoromethyl)pyridin-3-yl]sulfonyl}-1,4,9,10-tetrahydro-4,9-epiminobenzo[4,5]cyclohepta[1,2-c]pyrazole | (+) |

In the above table, (++++) means a ratio of Notch IC$_{50}$/Aβ EC$_{50}$ (determined as described in Example D) of >200; (+++) means a ratio from about 150 to about 199; (++) means a ratio from about 100 to about 149; and (+) means a ratio from about 50 to about 99.

The invention and the manner and process of making and using it, are now described in such full, clear, concise and exact terms as to enable any person skilled in the art to which it pertains, to make and use the same. It is to be understood that the foregoing describes preferred aspects of the invention and that modifications may be made therein without departing from the spirit or scope of the invention as set forth in the claims. To particularly point out and distinctly claim the subject matter regarded as invention, the following claims conclude this specification.

What is claimed is:
1. A compound of the formula:

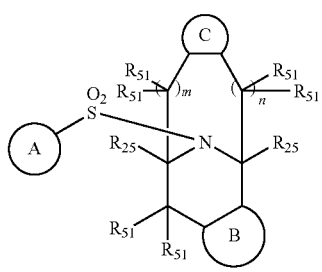

or a pharmaceutically acceptable salt thereof, wherein, m and n are independently 0 or 1, provided that m+n is 0 or 1;

the A-ring is aryl, cycloalkyl, heteroaryl or heterocycloalkyl, where each ring is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, aryloxy, —S(O)$_{0-2}$—($C_1$-$C_6$ alkyl), —NR$_{11}$R$_{11}$, —C(O)NR$_{11}$R$_{11}$, —NR$_{11}$C(O)R$_{10}$, —NR$_{11}$SO$_2$R$_{10}$, —O—C(O)NR$_{11}$R$_{11}$, NO$_2$, CN, $C_2$-$C_6$ alkanoyl, $C_0$-$C_3$alkylCO$_2$R$_{11}$, heteroaryl, heterocycloalkyl, aryl, arylalkyl, —OCH$_2$O—, —OCH$_2$CH$_2$O— or —SO$_2$NR$_{11}$R$_{11}$;

the B-ring is pyrazolyl, dihydropyrazolyl, pyrazolonyl or pyrazolidinonyl, each of which is optionally substituted with $C_1$-$C_6$ alkyl, $C_3$-$C_6$ cycloalkyl, $C_2$-$C_4$ alkenyl, $C_2$-$C_4$ alkynyl, $C_2$-$C_4$ alkoxy, amino, $C_1$-$C_4$ alkylamino, $C_1$-$C_4$ dialkylamino, hydroxy, hydroxyalkyl, halo, $C_1$-$C_4$ haloalkyl, $C_1$-$C_4$ haloalkoxy, —C(O)NR$_{11}$R$_{11}$, —NR$_{11}$C(O)R$_{10}$, —NR$_{11}$SO$_2$R$_{10}$ or CN;

wherein the C-ring is aryl substituted with R$_{30}$, R$_{35}$, R$_{40}$, and R$_{45}$ or heteroaryl, optionally substituted with halogen, $C_1$-$C_6$ alkyl, $C_1$-$C_6$ haloalkyl, $C_1$-$C_6$ haloalkoxy, CN, hydroxyl, $C_1$-$C_6$ alkoxy, —$C_1$-$C_3$ alkyl-OH, —$C_1$-$C_3$ alkyl-alkoxy, phenyloxy, —S(O$_2$)R$_{10}$, —SO$_2$NR$_{11}$R$_{11}$, —C(O)NR$_{11}$R$_{11}$, —NR$_{11}$C(O)R$_{10}$, —NR$_{11}$SO$_2$R$_{10}$, —O—C(O)NR$_{11}$R$_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, wherein the phenyl portions of the above are optionally substituted with one or more groups that are independently $C_1$-$C_6$ alkyl, $C_1$-$C_6$ alkoxy, $C_1$-$C_4$ haloalky or halogen;

R$_{30}$, R$_{35}$, R$_{40}$, and R$_{45}$ are independently H, halogen, $C_1$-$C_6$ alkyl, $C_2$-$C_6$ alkenyl, $C_2$-$C_6$ alkynyl, $C_2$-$C_8$ haloalkenyl, $C_2$-$C_8$ haloalkynyl, —$SO_2NR_{11}R_{11}$, arylalkyl, cycloalkyl, $C_1$-$C_6$ haloalkyl, $C_1$-$C_6$ haloalkoxy, CN, $NO_2$, hydroxyl, $C_1$-$C_6$ alkoxy, —$C_1$-$C_6$ alkyl-OH, —$C_1$-$C_6$ alkyl-$C_1$-$C_6$ alkoxy, aryloxy, —$S(O_2)R_{10}$, —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, heteroarylalkyl, heteroaryl, wherein each heteroaryl group is optionally substituted with a $C_1$-$C_6$ alkyl group, heterocycloalkylalkyl, heterocycloalkyl, wherein each heterocycloalkyl group is optionally substituted with one or two groups that are independently $C_1$-$C_6$ alkyl, $C_1$-$C_6$ alkoxy or halogen, aryl, aryloxy or arylalkyl, where the aryl portions of the above are optionally substituted with one or more groups that are independently $C_1$-$C_6$ alkyl, $C_1$-$C_6$ alkoxy, hydroxyl, $C_1$-$C_4$ haloalky or halogen; and wherein two adjacent substituents on the C-ring together with the carbons to which they are attached optionally form a heterocycloalkyl or a heteroaryl ring, each of which is optionally substituted with one or more groups that are independently alkyl, alkoxy, halogen or $C_2$-$C_4$ alkanoyl wherein the alkanoyl group is optionally further substituted with up to 3 halogen atoms; or two adjacent carbons of the C-ring optionally form a benzo ring which is optionally substituted with 1 to 4 groups that are independently halogen, hydroxyl, alkyl, alkoxy, haloalkyl, haloalkoxy, CN or $NO_2$;

each $R_{25}$ is independently H, $C_1$-$C_6$ alkyl, $C_1$-$C_6$ haloalkyl, —$C(O)OR_{11}$, —$(C_1$-$C_6$ alkyl)—$C(O)OR_{11}$, $C_1$-$C_6$ alkoxy $C_1$-$C_6$ alkyl, —$C(O)OR_{11}$, —$CONR_{11}R_{11}$, CN, $C_1$-$C_6$ alkyl-CN or hydroxy $C_1$-$C_6$ alkyl;

each $R_{51}$ is independently absent, H, $C_1$-$C_4$ alkyl, halogen, CN, amino, mono alkylamino or dialkylamino, OH or $C_1$-$C_4$ haloalkyl; further when there are two $R_{51}$ groups on a carbon atom, the two $R_{51}$ groups and the carbon to which they are attached may form a 3 to 6 membered cycloalkyl ring; or when there are two $R_{51}$ groups on a carbon, the two $R_{51}$ groups may form an oxo group;

$R_{10}$ and $R_{11}$ at each occurrence are independently $C_1$-$C_6$ alkyl, heteroaryl that is selected from pyrazolyl, thiadiazolyl, triazolyl, isoxazolyl, isothiazolyl, imidazolyl, thiazolyl, oxadiazolyl, and pyridyl or aryl that is selected from phenyl and naphthyl, where the heteroaryl and aryl groups are optionally substituted with 1 to 3 groups that are independently halogen, hydroxyl, alkyl, alkoxy, haloalkyl, haloalkoxy, CN or $NO_2$; and additionally $R_{11}$ may be H; or if two $R_{11}$ groups are on a nitrogen, then the two $R_{11}$ groups together with the nitrogen to which they are attached, may form a 3-8 membered ring optionally including an additional heteroatom such as NH, $NR_{12}$, $NR_{13}$, O or S;

$R_{12}$ is H, $C_1$-$C_6$ alkyl, aryl or —$SO_2$-aryl, where each aryl is optionally substituted with 1 to 5 groups that are independently halogen, hydroxyl, alkyl, alkoxy, haloalkyl, haloalkoxy, CN or $NO_2$; and $R_{13}$ is H, aryl or $C_1$-$C_6$ alkyl optionally substituted with aryl, hydroxyl or halogen, where each aryl is optionally substituted with 1 to 5 groups that are independently halogen, hydroxyl, alkyl, alkoxy, haloalkyl, haloalkoxy, CN or $NO_2$.

2. The compound according to claim 1, wherein the A-ring is phenyl, and has the following formula:

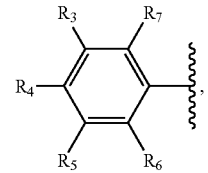

wherein, $R_3$, $R_4$, $R_5$, $R_6$, $R_7$ are independently of each other H, halogen, $C_1$-$C_6$ alkyl, $C_1$-$C_6$ haloalkyl, $C_1$-$C_6$ haloalkoxy, CN, hydroxyl, $C_1$-$C_6$ alkoxy, —$C_1$-$C_3$ alkyl-OH, —$C_1$-$C_3$ alkyl-alkoxy, phenyloxy, —$S(O_2)R_{10}$, —$NR_{11}R_{11}$, —$C(O)NR_{11}R_{11}$, —$SO_2NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, where the phenyl portions of the above are optionally substituted with one or more groups that are independently $C_1$-$C_6$ alkyl, $C_1$-$C_6$ alkoxy, $C_1$-$C_4$ haloalky or halogen; or $R_4$ and $R_5$ or $R_5$ and $R_6$ and the carbons to which they are attached form a heterocycloalkyl or a heteroaryl ring which is optionally substituted with 1, 2, 3 or 4 groups that are independently $C_1$-$C_4$ alkyl, $C_1$-$C_4$ alkoxy, halogen or $C_1$-$C_4$ alkanoyl wherein the alkanoyl group is optionally substituted with up to 3 halogen atoms; or $R_4$ and $R_5$ or $R_5$ and $R_6$ and the carbons to which they are attached form a benzo ring which is optionally substituted with 1 to 5 groups that are independently halogen, hydroxyl, alkyl, alkoxy, haloalkyl, haloalkoxy, CN or $NO_2$; or the A-ring is $C_3$-$C_8$ cycloalkyl, which is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, phenyloxy, —$S(O)_{0-2}$—$(C_1$-$C_6$ alkyl), —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, $C_0$-$C_3$alkyl$CO_2R_{10}$, pyridyl, thienyl, furanyl, pyrrolyl, pyrrolidinyl, piperidinyl, piperazinyl, phenyl, phenyl $C_1$-$C_4$ alkyl or —$SO_2NR_{11}R_{11}$, where the phenyl portions of the above are optionally substituted with one or more groups that are independently $C_1$-$C_6$ alkyl, $C_1$-$C_6$ alkoxy, $C_1$-$C_4$ haloalky or halogen; or the A-ring is heteroaryl that is pyridyl, pyrimidyl, pyridazinyl, pyrazinyl, thienyl, furanyl, pyrrolyl, pyrazolyl or imidazolyl, each of which is optionally substituted at one or more substitutable positions with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, phenyloxy, —$S(O)_{0-2}$—$(C_1$-$C_6$ alkyl), —$NR_{11}R_{11}$, —$C(O)NR_{11}R_{11}$, —$NR_{11}C(O)R_{10}$, —$NR_{11}SO_2R_{10}$, —O—$C(O)NR_{11}R_{11}$, $C_2$-$C_6$ alkanoyl, $C_0$-$C_3$alkyl$CO_2R_{10}$, pyridyl, thienyl, furanyl, pyrrolyl, pyrrolidinyl, piperidinyl, piperazinyl, phenyl, phenyl $C_1$-$C_4$ alkyl or —$SO_2NR_{11}R_{11}$, where the phenyl portions of the above are optionally substituted with one or more groups that are independently $C_1$-$C_6$ alkyl, $C_1$-$C_6$ alkoxy, $C_1$-$C_4$ haloalky or halogen;

the A-ring is heterocycloalkyl that is pyrrolidinyl, piperidinyl, piperazinyl, morpholinyl, thiomorpholinyl or thiomorpholinyl-S,S-dioxide, where each of the above rings is optionally substituted at a substitutable position with halogen, $C_1$-$C_6$ alkyl, $C_2$-$C_6$ alkenyl, $C_2$-$C_6$ alkynyl, $C_1$-$C_6$ alkoxy, haloalkyl, haloalkoxy, hydroxyl, hydroxyalkyl, CN, phenyloxy, —S(O)$_{0-2}$—($C_1$-$C_6$ alkyl), —NR$_{11}$R$_{11}$, —C(O)NR$_{11}$R$_{11}$, —NR$_{11}$C(O)R$_{10}$, —NR$_{11}$SO$_2$R$_{10}$, —O—C(O)NR$_{11}$R$_{11}$, $C_2$-$C_6$ alkanoyl, $C_0$-$C_3$alkylCO$_2$R$_{10}$, pyridyl, thienyl, furanyl, pyrrolyl, pyrrolidinyl, piperidinyl, piperazinyl, phenyl, phenyl $C_1$-$C_4$ alkyl or —SO$_2$NR$_{11}$R$_{11}$, where the phenyl portions of the above are optionally substituted with one or more groups that are independently $C_1$-$C_6$ alkyl, $C_1$-$C_6$ alkoxy, $C_1$-$C_4$ haloalky or halogen.

3. The compound according to claim 2, wherein the A-ring is phenyl or pyridyl, each of which is optionally substituted with halogen or $C_1$-$C_4$ haloalkyl.

4. The compound according to claim 2, wherein the C-ring is phenyl substituted with R$_{30}$, R$_{35}$, R$_{40}$, and R$_{45}$; or heteroaryl, wherein the heteroaryl group is optionally substituted with H, halogen, $C_1$-$C_6$ alkyl, $C_1$-$C_6$ haloalkyl, $C_1$-$C_6$ haloalkoxy, CN, hydroxyl, $C_1$-$C_6$ alkoxy, —$C_1$-$C_3$ alkyl-OH, —$C_1$-$C_3$ alkyl-alkoxy, phenyloxy, —S(O$_2$)R$_{10}$, —SO$_2$NR$_{11}$R$_{11}$, —NR$_{11}$R$_{11}$, —C(O)NR$_{11}$R$_{11}$, —NR$_{11}$C(O)R$_{10}$, —NR$_{11}$SO$_2$R$_{10}$, —O—C(O)NR$_{11}$R$_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, wherein the phenyl portions of the above are optionally substituted with one or more groups that are independently $C_1$-$C_6$ alkyl, $C_1$-$C_6$ alkoxy, $C_1$-$C_4$ haloalky or halogen;

R$_{30}$, R$_{35}$, R$_{40}$, and R$_{45}$ are independently H, halogen, $C_1$-$C_6$ alkyl, $C_2$-$C_6$ alkenyl, $C_2$-$C_6$ alkynyl, $C_2$-$C_8$ haloalkenyl, $C_2$-$C_8$ haloalkynyl, —SO$_2$NR$_{11}$R$_{11}$, arylalkyl, cycloalkyl, $C_1$-$C_6$ haloalkyl, $C_1$-$C_6$ haloalkoxy, CN, NO$_2$, hydroxyl, $C_1$-$C_6$ alkoxy, —$C_1$-$C_6$ alkyl-OH, —$C_1$-$C_6$-alkyl-$C_1$-$C_6$ alkoxy, aryloxy, —S(O$_2$)R$_{10}$, —NR$_{11}$R$_{11}$, —C(O)NR$_{11}$R$_{11}$, —NR$_{11}$C(O)R$_{10}$, —NR$_{11}$SO$_2$R$_{10}$, —O—C(O)NR$_{11}$R$_{11}$, $C_2$-$C_6$ alkanoyl, heteroarylalkyl, heteroaryl, wherein each heteroaryl group is optionally substituted with a $C_1$-$C_6$ alkyl group, heterocycloalkylalkyl, heterocycloalkyl, wherein each heterocycloalkyl group is optionally substituted with one or two groups that are independently $C_1$-$C_6$ alkyl, $C_1$-$C_6$ alkoxy or halogen, aryl, aryloxy or arylalkyl, where the aryl portions of the above are optionally substituted with one or more groups that are independently $C_1$-$C_6$ alkyl, $C_1$-$C_6$ alkoxy, hydroxyl, $C_1$-$C_4$ haloalky or halogen; and wherein when the C-ring is aryl or heteroaryl, two adjacent carbons of the C-ring optionally form a heterocycloalkyl or a heteroaryl ring, each of which is optionally substituted with one or more groups that are independently alkyl, alkoxy, halogen or $C_2$-$C_4$ alkanoyl wherein the alkanoyl group is optionally further substituted with up to 3 halogen atoms; or two adjacent carbons of the C-ring optionally form a benzo ring which is optionally substituted with 1 to 4 groups that are independently halogen, hydroxyl, alkyl, alkoxy, haloalkyl, haloalkoxy, CN or NO$_2$.

5. The compound according to claim 4, of the formula:

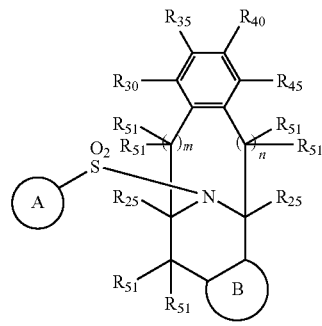

or pharmaceutically acceptable salt thereof, wherein each R$_{25}$ is independently H, $C_1$-$C_4$ alkyl, $C_1$-$C_4$ haloalkyl, hydroxy $C_1$-$C_4$ alkyl, $C_1$-$C_4$ alkoxyalkyl, —C(O)OR$_{11}$ or —C(O)NR$_{11}$R$_{11}$; and each R$_{51}$ is independently absent, H, $C_1$-$C_4$ alkyl, F, Cl, Br, CN, amino, mono alkylamino or dialkylamino, OH or CF$_3$; further, when there are two R$_{51}$ groups on a carbon atom, the two R$_{51}$ groups and the carbon to which they are attached may form a 3- to 6-membered cycloalkyl or heterocycloalkyl ring; or when there are two R$_{51}$ groups on a carbon, the two R$_{51}$ groups may form an oxo group.

6. The compound according to claim 5, wherein the B-ring is pyrazolyl, which is optionally substituted with —NR$_{11}$— $C_2$-$C_6$ alkanoyl, $C_1$-$C_4$ alkyl, $C_3$-$C_6$ cycloalkyl, $C_2$-$C_4$ alkenyl, $C_2$-$C_4$ alkynyl, $C_1$-$C_4$ alkoxy, amino, $C_1$-$C_4$ alkylamino, $C_1$-$C_4$ dialkylamino, hydroxy $C_1$-$C_4$ alkyl, halo, CF$_3$, OCF$_3$ or CN.

7. The compound according to claim 6, of the formula:

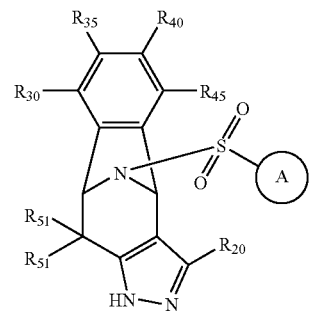

or pharmaceutically acceptable salt thereof, wherein

R$_{20}$ is H, $C_1$-$C_4$ alkyl, $C_1$-$C_4$ alkoxy, —NR$_{11}$C(O)CH$_3$, amino, $C_1$-$C_4$ alkylamino, $C_1$-$C_4$ dialkylamino, halo, CF$_3$ or CN; where R$_{11}$ is H or $C_1$-$C_6$ alkyl; and R$_{30}$, R$_{35}$, R$_{40}$, and R$_{45}$ are independently H, halogen, $C_1$-$C_6$ alkyl, $C_1$-$C_6$ haloalkyl, $C_1$-$C_6$ haloalkoxy, CN, hydroxyl, $C_1$-$C_6$ alkoxy, —$C_1$-$C_3$ alkyl-OH, —$C_1$-$C_3$ alkyl-alkoxy, phenyloxy, —S(O$_2$)R$_{10}$, —SO$_2$NR$_{11}$R$_{11}$, —NR$_{11}$R$_{11}$, —C(O)NR$_{11}$R$_{11}$, —NR$_{11}$C(O)R$_{10}$, —NR$_{11}$SO$_2$R$_{10}$, —O—C(O)NR$_{11}$R$_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, where the phenyl portions of the above are optionally substituted with one or more groups that are independently $C_1$-$C_6$ alkyl, $C_1$-$C_6$ alkoxy or halogen.

8. The compound according to claim 7, wherein the A-ring is:

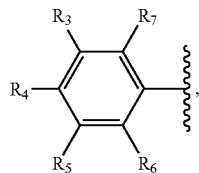

wherein, $R_3$, $R_4$, $R_5$, $R_6$, $R_7$ are independently of each other H, halogen, $C_1$-$C_4$ alkyl, $C_1$-$C_4$ haloalkyl, $C_1$-$C_4$ haloalkoxy, CN, hydroxyl, $C_1$-$C_4$ alkoxy, —$C_1$-$C_3$ alkyl-OH, —$C_1$-$C_3$ alkyl-$C_1$-$C_4$ alkoxy, phenyloxy, —S($O_2$)$R_{10}$, —$SO_2NR_{11}R_{11}$, —$NR_{11}R_{11}$, —C(O)$NR_{11}R_{11}$, —$NR_{11}$C(O)$R_{10}$, —$NR_{11}SO_2R_{10}$, —O—C(O)$NR_{11}R_{11}$ or $C_2$-$C_4$ alkanoyl; or the A-ring is pyridyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —C(O)$NR_{11}R_{11}$, —$NR_{11}$C(O)$R_{10}$, —$NR_{11}SO_2R_{10}$, —O—C(O)$NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H.

9. The compound according to claim 8, wherein the A-ring is phenyl, $R_4$ is halogen, $C_1$-$C_4$ alkyl, $C_1$-$C_4$ alkoxy, $CF_3$, $OCF_3$ or CN; and $R_3$, $R_5$, $R_6$, and $R_7$ are hydrogen.

10. The compound according to claim 8, wherein the A-ring is pyridyl, optionally substituted with one halogen or $CF_3$.

11. The compound according to claim 8, wherein at least one $R_{51}$ group is halogen.

12. The compound according to claim 8, wherein the two $R_{51}$ groups are both H, both halogen or form an oxo group.

13. The compound according to claim 8, of the formula:

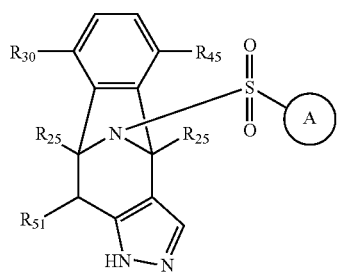

or a pharmaceutically acceptable salt thereof, wherein each $R_{25}$ is independently H or $CH_3$;

$R_{30}$ and $R_{45}$ are independently H, halogen, $C_1$-$C_6$ alkyl, $C_1$-$C_6$ haloalkyl, $C_1$-$C_6$ haloalkoxy, CN, hydroxyl, $C_1$-$C_6$ alkoxy, —$C_1$-$C_3$ alkyl-OH, —$C_1$-$C_3$ alkyl-alkoxy, phenyloxy, $C_2$-$C_6$ alkenyl, $C_2$-$C_6$ alkynyl, $C_2$-$C_6$ haloalkenyl, $C_2$-$C_6$ haloalkynyl, —C(O)$OR_{11}$, —S($O_2$)$R_{10}$, —$NR_{11}R_{11}$, —C(O)$NR_{11}R_{11}$, —$SO_2NR_{11}R_{11}$, —$NR_{11}$C(O)$R_{10}$, —$NR_{11}SO_2R_{10}$, —O—C(O)$NR_{11}R_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, where the phenyl portions of the above are optionally substituted with one or more groups that are independently $C_1$-$C_6$ alkyl, $C_1$-$C_6$ alkoxy, $C_1$-$C_4$ haloalky or halogen; and $R_{51}$ is H, $C_1$-$C_4$ alkyl, F, Cl, Br, CN, amino, mono alkylamino or dialkylamino, OH or $CF_3$.

14. The compound according to claim 13, wherein at least one of $R_{30}$ and $R_{45}$ is F; and $R_{51}$ is H, F or OH.

15. The compound according to claim 8, of the formula:

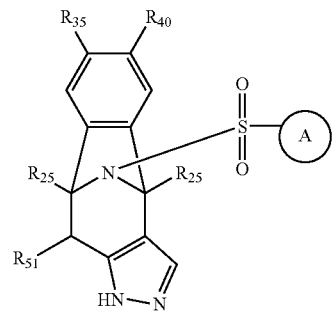

or a pharmaceutically acceptable salt thereof, wherein each $R_{25}$ is independently H or $CH_3$;

$R_{35}$ and $R_{40}$ are independently H, halogen, $C_1$-$C_6$ alkyl, $C_1$-$C_6$ haloalkyl, $C_1$-$C_6$ haloalkoxy, CN, hydroxyl, $C_1$-$C_6$ alkoxy, —$C_1$-$C_3$ alkyl-OH, —$C_1$-$C_3$ alkyl-alkoxy, phenyloxy, $C_2$-$C_6$ alkenyl, $C_2$-$C_6$ alkynyl, $C_2$-$C_6$ haloalkenyl, $C_2$-$C_6$ haloalkynyl, —C(O)$OR_{11}$, —S($O_2$)$R_{10}$, —$SO_2NR_{11}R_{11}$, —C(O)$NR_{11}R_{11}$, —$SO_2NR_{11}R_{11}$, —$NR_{11}$C(O)$R_{10}$, —$NR_{11}SO_2R_{10}$, —O—C(O)$NR_{11}R_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, wherein the phenyl portions of the above are optionally substituted with one or more groups that are independently $C_1$-$C_6$ alkyl, $C_1$-$C_6$ alkoxy, $C_1$-$C_4$ haloalky or halogen; and $R_{51}$ is H, $C_1$-$C_4$ alkyl, F, Cl, Br, CN, amino, mono alkylamino or dialkylamino, OH or $CF_3$.

16. The compound according to claim 15, wherein at least one of $R_{35}$ and $R_{40}$ is F; and $R_{51}$ is H, F or OH.

17. The compound according to claim 2, wherein the C-ring is a heteroaryl or heterocycloalkyl ring that is optionally substituted with one or more groups that are independently halogen, $C_1$-$C_6$ alkyl, $C_1$-$C_6$ haloalkyl, $C_1$-$C_6$ haloalkoxy, $C_2$-$C_8$ alkenyl, $C_2$-$C_8$ alkynyl, $C_2$-$C_8$ haloalkenyl, $C_2$-$C_8$ haloalkynyl, —C(O)$OR_{11}$, CN, hydroxyl, $C_1$-$C_6$ alkoxy, —$C_1$-$C_3$ alkyl-OH, —$C_1$-$C_3$ alkyl-alkoxy, phenyloxy, —S($O_2$)$R_{10}$, —$NR_{11}R_{11}$, —C(O)$NR_{11}R_{11}$, —$SO_2NR_{11}R_{11}$, —$NR_{11}$C(O)$R_{10}$, —$NR_{11}SO_2R_{10}$, —O—C(O)$NR_{11}R_{11}$, $C_2$-$C_6$ alkanoyl, oxazolyl, pyrazolyl, thiazolyl, pyridyl, pyrimidinyl, imidazolyl, indolyl, furanyl, thienyl, phenyl or phenyl $C_1$-$C_4$ alkyl, wherein the phenyl portions of the above are optionally substituted with one or more groups that are independently $C_1$-$C_6$ alkyl, $C_1$-$C_6$ alkoxy, $C_1$-$C_4$ haloalky or halogen; each $R_{10}$ and $R_{11}$ is independently $C_1$-$C_6$ alkyl or phenyl; and additionally $R_{11}$ may be H; and the B-ring is pyrazoyl, which is optionally substituted with $C_1$-$C_4$ alkyl, $C_3$-$C_6$ cycloalkyl, $C_2$-$C_4$ alkenyl, $C_2$-$C_4$ alkynyl, $C_1$-$C_4$ alkoxy, amino, $C_1$-$C_4$ alkylamino, $C_1$-$C_4$ dialkylamino, hydroxy $C_1$-$C_4$ alkyl, halo, $CF_3$, $OCF_3$ or CN.

18. The compound according to claim 17, wherein the A-ring is phenyl, and has the following formula:

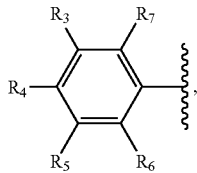

wherein, $R_3$, $R_4$, $R_5$, $R_6$, $R_7$ are independently of each other H, halogen, $C_1$-$C_4$ alkyl, $C_1$-$C_4$ haloalkyl, $C_1$-$C_4$ haloalkoxy, CN, hydroxyl, $C_1$-$C_4$ alkoxy, —$C_1$-$C_3$ alkyl-OH, —$C_1$-$C_3$ alkyl-$C_1$-$C_4$ alkoxy, phenyloxy, —$S(O_2)R_{10}$, —$SO_2NR_{11}R_{11}$, —$NR_{11}R_{11}$, —$C(O)NR_{11}R_{11}$, —$NR_{11}C(O)R_{10}$, —$NR_{11}SO_2R_{10}$, —O—C(O)$NR_{11}R_{11}$ or $C_2$-$C_4$ alkanoyl; or the A-ring is pyridyl, which is optionally substituted at one or more substitutable positions with groups that are independently halogen, $C_1$-$C_6$ alkyl, $C_1$-$C_6$ alkoxy, $CF_3$, $OCF_3$, hydroxyl, CN, phenyloxy, —$SO_2$—($C_1$-$C_6$ alkyl), —$NR_{11}R_{11}$, —$C(O)NR_{11}R_{11}$, —$NR_{11}C(O)R_{10}$, —$NR_{11}SO_2R_{10}$, —O—C(O)$NR_{11}R_{11}$, $C_2$-$C_6$ alkanoyl, pyridyl, phenyl or —$SO_2NR_{11}R_{11}$, where each $R_{10}$ and $R_{11}$ is independently $C_1$-$C_6$ alkyl or phenyl; and additionally $R_{11}$ may be H; and each $R_{25}$ is independently H or $CH_3$.

19. The compound according to claim 17, wherein the A-ring is phenyl or pyridyl, each of which is optionally substituted with halogen or $C_1$-$C_4$ haloalkyl.

20. A pharmaceutical composition comprising a compound of claim 1 and at least one pharmaceutically acceptable carrier.

21. A method of treating Alzheimer's Disease comprising administering a therapeutically effective amount of a compound or a pharmaceutically acceptable salt of claim 1 to a mammalian subject in need of such treatment.

22. The method of claim 21, wherein the mammalian subject is a human.

23. A method of treating Alzheimer's Disease, comprising administering a therapeutically effective amount of a pharmaceutical composition of claim 20 to a human in need of such treatment.

24. A compound that is (±)-11-{[4-(trifluoromethyl)phenyl]sulfonyl}-1,4,9,10-tetrahydro-4,9-epiminobenzo[4,5]cyclohepta[1,2-c]pyrazole;

(±)-6,7-difluoro-11-{[4-(trifluoromethyl)phenyl]sulfonyl}-1,4,9,10-tetrahydro-4,9-epiminobenzo[4,5]cyclohepta[1,2-c]pyrazole;

(±)-6,7-difluoro-11-{[4-(trifluoromethyl)phenyl]sulfonyl}-4,9-dihydro-4,9-epiminobenzo[4,5]cyclohepta[1,2-c]pyrazol-10(1H)-one;

(±)-11-{[4-(trifluoromethyl)phenyl]sulfonyl}-4,9-dihydro-4,9-epiminobenzo[4,5]cyclohepta[1,2-c]pyrazol-10(1H)-one;

(−)-11-{[4-(trifluoromethyl)phenyl]sulfonyl}-1,4,9,10-tetrahydro-4,9-epiminobenzo[4,5]cyclohepta[1,2-c]pyrazole;

(+)-11-{[4-(trifluoromethyl)phenyl]sulfonyl}-1,4,9,10-tetrahydro-4,9-epiminobenzo[4,5]cyclohepta[1,2-c]pyrazole;

(±)-10,10-difluoro-11-{[4-(trifluoromethyl)phenyl]sulfonyl}-1,4,9,10-tetrahydro-4,9-epiminobenzo[4,5]cyclohepta[1,2-c]pyrazole;

(±)-6,7,10,10-tetrafluoro-11-{[4-(trifluoromethyl)phenyl]sulfonyl}-1,4,9,10-tetrahydro-4,9-epiminobenzo[4,5]cyclohepta[1,2-c]pyrazole;

(±)-12-{[6-(trifluoromethyl)pyridin-3-yl]sulfonyl}-4,5,10,11-tetrahydro-1H-4,10-epiminobenzo[5,6]cycloocta[1,2-c]pyrazole;

(±)-12-{[4-(trifluoromethyl)phenyl]sulfonyl}-1,4,10,11-tetrahydro-4,10-epimino[1,3]benzodioxolo[5',6':4,5]cyclohepta[1,2-c]pyrazole;

(−)-6,7-difluoro-11-{[4-(trifluoromethyl)phenyl]sulfonyl}-1,4,9,10-tetrahydro-4,9-epiminobenzo[4,5]cyclohepta[1,2-c]pyrazole;

(+)-6,7-difluoro-11-{[4-(trifluoromethyl)phenyl]sulfonyl}-1,4,9,10-tetrahydro-4,9-epiminobenzo[4,5]cyclohepta[1,2-c]pyrazole;

(±)-5-fluoro-11-{[4-(trifluoromethyl)phenyl]sulfonyl}-1,4,9,10-tetrahydro-4,9-epiminobenzo[4,5]cyclohepta[1,2-c]pyrazole;

(±)-8-fluoro-11-{[4-(trifluoromethyl)phenyl]sulfonyl}-1,4,9,10-tetrahydro-4,9-epiminobenzo[4,5]cyclohepta[1,2-c]pyrazole;

(±)-11-{[6-(trifluoromethyl)pyridin-3-yl]sulfonyl}-1,4,9,10-tetrahydro-4,9-epiminobenzo[4,5]cyclohepta[1,2-c]pyrazole;

(−)-11-{[4-(trifluoromethyl)phenyl]sulfonyl}-1,4,9,10-tetrahydro-4,9-epiminopyrazolo[4',3':4,5]cyclohepta[1,2-b]pyridine;

(+)-11-{[4-(trifluoromethyl)phenyl]sulfonyl}-1,4,9,10-tetrahydro-4,9-epiminopyrazolo[4',3':4,5]cyclohepta[1,2-b]pyridine;

(+)-11-{[4-(trifluoromethyl)phenyl]sulfonyl}-1,4,9,10-tetrahydro-4,9-epiminopyrazolo[3',4':5,6]cyclohepta[1,2-b]pyridine;

(−)-11-{[4-(trifluoromethyl)phenyl]sulfonyl}-1,4,9,10-tetrahydro-4,9-epiminopyrazolo[3',4':5,6]cyclohepta[1,2-b]pyridine;

(±)-5-fluoro-11-{[4-(trifluoromethyl)phenyl]sulfonyl}-4,9-dihydro-4,9-epiminobenzo[4,5]cyclohepta[1,2-c]pyrazol-10(1H)-one;

(±)-8-fluoro-11-{[4-(trifluoromethyl)phenyl]sulfonyl}-4,9-dihydro-4,9-epiminobenzo[4,5]cyclohepta[1,2-c]pyrazol-10(1H)-one;

(±)-6,7-difluoro-11-{[6-(trifluoromethyl)pyridin-3-yl]sulfonyl}-1,4,9,10-tetrahydro-4,9-epiminobenzo[4,5]cyclohepta[1,2-c]pyrazole;

(±)-12-{[4-(trifluoromethyl)phenyl]sulfonyl}-1,4,10,11-tetrahydro-4,10-epimino[1,3]benzodioxolo[5',6':4,5]cyclohepta[1,2-c]pyrazol-7-one;

(−)-6,7-difluoro-11-{[6-(trifluoromethyl)pyridin-3-yl]sulfonyl}-1,4,9,10-tetrahydro-4,9-epiminobenzo[4,5]cyclohepta[1,2-c]pyrazole;

(+)-6,7-difluoro-11-{[6-(trifluoromethyl)pyridin-3-yl]sulfonyl}-1,4,9,10-tetrahydro-4,9-epiminobenzo[4,5]cyclohepta[1,2-c]pyrazole;

(−)-5-fluoro-11-{[4-(trifluoromethyl)phenyl]sulfonyl}-1,4,9,10-tetrahydro-4,9-epiminobenzo[4,5]cyclohepta[1,2-c]pyrazole;

(+)-5-fluoro-11-{[4-(trifluoromethyl)phenyl]sulfonyl}-1,4,9,10-tetrahydro-4,9-epiminobenzo[4,5]cyclohepta[1,2-c]pyrazole;

(+)-11-{[4-(trifluoromethyl)phenyl]sulfonyl}-1,4,9,10-tetrahydro-4,9-epiminopyrazolo[4',3':4,5]cyclohepta[1,2-c]pyridine;

(+)-11-{[4-(trifluoromethyl)phenyl]sulfonyl}-1,4,9,10-tetrahydro-4,9-epiminopyrazolo[3',4':5,6]cyclohepta[1,2-c]pyridine;

(−)-11-{[4-(trifluoromethyl)phenyl]sulfonyl}-1,4,9,10-tetrahydro-4,9-epiminopyrazolo[3',4':5,6]cyclohepta[1,2-c]pyridine;

(±)-8,10,10-trifluoro-11-{[4-(trifluoromethyl)phenyl]sulfonyl}-1,4,9,10-tetrahydro-4,9-epiminobenzo[4,5]cyclohepta[1,2-c]pyrazole;

(±)-5-fluoro-11-{[6-(trifluoromethyl)pyridin-3-yl]sulfonyl}-1,4,9,10-tetrahydro-4,9-epiminobenzo[4,5]cyclohepta[1,2-c]pyrazole;

(±)-5,10,10-trifluoro-11-{[4-(trifluoromethyl)phenyl]sulfonyl}-1,4,9,10-tetrahydro-4,9-epiminobenzo[4,5]cyclohepta[1,2-c]pyrazole;

(−)-5,10,10-trifluoro-11-{[4-(trifluoromethyl)phenyl]sulfonyl}-1,4,9,10-tetrahydro-4,9-epiminobenzo[4,5]cyclohepta[1,2-c]pyrazole;

(+)-5,10,10-trifluoro-11-{[4-(trifluoromethyl)phenyl]sulfonyl}-1,4,9,10-tetrahydro-4,9-epiminobenzo[4,5]cyclohepta[1,2-c]pyrazole;

(−)-5-fluoro-11-{[6-(trifluoromethyl)pyridin-3-yl]sulfonyl}-1,4,9,10-tetrahydro-4,9-epiminobenzo[4,5]cyclohepta[1,2-c]pyrazole;

(+)-5-fluoro-11-{[6-(trifluoromethyl)pyridin-3-yl]sulfonyl}-1,4,9,10-tetrahydro-4,9-epiminobenzo[4,5]cyclohepta[1,2-c]pyrazole;

(±)-5,8-difluoro-11-{[6-(trifluoromethyl)pyridin-3-yl]sulfonyl}-1,4,9,10-tetrahydro-4,9-epiminobenzo[4,5]cyclohepta[1,2-c]pyrazole;

(±)-7-cyclopropyl-12-{[6-(trifluoromethyl)pyridin-3-yl]sulfonyl}-4,5,6,11-tetrahydro-3H-5,11-epiminobenzo[4,5]cycloocta[1,2-c]pyrazole;

(±)-6-cyclopropyl-12-{[6-(trifluoromethyl)pyridin-3-yl]sulfonyl}-4,5,10,11-tetrahydro-1H-4,10-epiminobenzo[5,6]cycloocta[1,2-c]pyrazole;

(±)-6,7-difluoro-11-{[6-(trifluoromethyl)pyridin-3-yl]sulfonyl}-4,9-dihydro-4,9-epiminobenzo[4,5]cyclohepta[1,2-c]pyrazol-10(1H)-one;

(−)-5,8-difluoro-11-{[6-(trifluoromethyl)pyridin-3-yl]sulfonyl}-1,4,9,10-tetrahydro-4,9-epiminobenzo[4,5]cyclohepta[1,2-c]pyrazole;

(+)-5,8-difluoro-11-{[6-(trifluoromethyl)pyridin-3-yl]sulfonyl}-1,4,9,10-tetrahydro-4,9-epiminobenzo[4,5]cyclohepta[1,2-c]pyrazole;

(±)-7-fluoro-5-methyl-11-{[6-(trifluoromethyl)pyridin-3-yl]sulfonyl}-1,4,9,10-tetrahydro-4,9-epiminobenzo[4,5]cyclohepta[1,2-c]pyrazole;

(±)-6-(trifluoromethyl)-11-{[4-(trifluoromethyl)phenyl]sulfonyl}-1,4,9,10-tetrahydro-4,9-epiminobenzo[4,5]cyclohepta[1,2-c]pyrazole;

(±)-7-(trifluoromethyl)-11-{[4-(trifluoromethyl)phenyl]sulfonyl}-1,4,9,10-tetrahydro-4,9-epiminobenzo[4,5]cyclohepta[1,2-c]pyrazole;

(±)-6,7,10,10-tetrafluoro-11-{[6-(trifluoromethyl)pyridin-3-yl]sulfonyl}-1,4,9,10-tetrahydro-4,9-epiminobenzo[4,5]cyclohepta[1,2-c]pyrazole;

(−)-7-fluoro-5-methyl-11-{[6-(trifluoromethyl)pyridin-3-yl]sulfonyl}-1,4,9,10-tetrahydro-4,9-epiminobenzo[4,5]cyclohepta[1,2-c]pyrazole;

(+)-7-fluoro-5-methyl-11-{[6-(trifluoromethyl)pyridin-3-yl]sulfonyl}-1,4,9,10-tetrahydro-4,9-epiminobenzo[4,5]cyclohepta[1,2-c]pyrazole;

13-{[4-(trifluoromethyl)phenyl]sulfonyl}-7,10,11,12-tetrahydro-7,12-epiminonaphtho[2',1':4,5]cyclohepta[1,2-c]pyrazole;

(−)-5-fluoro-11-{[6-(trifluoromethyl)pyridin-3-yl]sulfonyl}-4,9-dihydro-4,9-epiminobenzo[4,5]cyclohepta[1,2-c]pyrazol-10(1H)-one;

(±)-7-(4-fluorophenyl)-12-{[4-(trifluoromethyl)phenyl]sulfonyl}-4,5,6,11-tetrahydro-3H-5,11-epiminobenzo[4,5]cycloocta[1,2-c]pyrazole;

(±)-12-{[4-(trifluoromethyl)phenyl]sulfonyl}-4,5,10,11-tetrahydro-1H-4,10-epiminobenzo[5,6]cycloocta[1,2-c]pyrazole;

(±)-12-{[4-(trifluoromethyl)phenyl]sulfonyl}-4,5,6,11-tetrahydro-3H-5,11-epiminobenzo[4,5]cycloocta[1,2-c]pyrazole;

(±)-6-(4-fluorophenyl)-12-{[4-(trifluoromethyl)phenyl]sulfonyl}-4,5,10,11-tetrahydro-1H-4,10-epiminobenzo[5,6]cycloocta[1,2-c]pyrazole;

5,10,10-trifluoro-11-{[6-(trifluoromethyl)pyridin-3-yl]sulfonyl}-1,4,9,10-tetrahydro-4,9-epiminobenzo[4,5]cyclohepta[1,2-c]pyrazole;

(±)-11-{[6-(trifluoromethyl)pyridin-3-yl]sulfonyl}-1,4,9,10-tetrahydro-4,9-epiminobenzo[4,5]cyclohepta[1,2-c]pyrazole-7-carbonitrile;

(+)-13-{[4-(trifluoromethyl)phenyl]sulfonyl}-7,10,11,12-tetrahydro-7,12-epiminonaphtho[2',1':4,5]cyclohepta[1,2-c]pyrazole;

(−)-13-{[4-(trifluoromethyl)phenyl]sulfonyl}-7,10,11,12-tetrahydro-7,12-epiminonaphtho[2',1':4,5]cyclohepta[1,2-c]pyrazole;

(+)-13-{[4-(trifluoromethyl)phenyl]sulfonyl}-7,8,9,12-tetrahydro-7,12-epiminonaphtho[1',2':4,5]cyclohepta[1,2-c]pyrazole;

(−)-13-{[4-(trifluoromethyl)phenyl]sulfonyl}-7,8,9,12-tetrahydro-7,12-epiminonaphtho[1',2':4,5]cyclohepta[1,2-c]pyrazole;

(−)-11-{[6-(trifluoromethyl)pyridin-3-yl]sulfonyl}-1,4,9,10-tetrahydro-4,9-epiminobenzo[4,5]cyclohepta[1,2-c]pyrazole-7-carbonitrile;

(−)-11-{[4-(trifluoromethyl)phenyl]sulfonyl}-4,9-dihydro-4,9-epiminobenzo[4,5]cyclohepta[1,2-c]pyrazol-10(1H)-one;

(+)-11-{[6-(trifluoromethyl)pyridin-3-yl]sulfonyl}-1,4,9,10-tetrahydro-4,9-epiminobenzo[4,5]cyclohepta[1,2-c]pyrazole-7-carbonitrile;

(+)-endo-11-{[4-(trifluoromethyl)phenyl]sulfonyl}-1,4,9,10-tetrahydro-4,9-epiminobenzo[4,5]cyclohepta[1,2-c]pyrazol-10-ol;

(±)-6-fluoro-11-{[6-(trifluoromethyl)pyridin-3-yl]sulfonyl}-1,4,9,10-tetrahydro-4,9-epiminobenzo[4,5]cyclohepta[1,2-c]pyrazole;

(±)-6-[3-(trifluoromethyl)phenyl]-12-{[4-(trifluoromethyl)phenyl]sulfonyl}-4,5,10,11-tetrahydro-1H-4,10-epiminobenzo[5,6]cycloocta[1,2-c]pyrazole;

(±)-7-[3-(trifluoromethyl)phenyl]-12-{[4-(trifluoromethyl)phenyl]sulfonyl}-4,5,6,11-tetrahydro-3H-5,11-epiminobenzo[4,5]cycloocta[1,2-c]pyrazole;

(−)-6-fluoro-11-{[6-(trifluoromethyl)pyridin-3-yl]sulfonyl}-1,4,9,10-tetrahydro-4,9-epiminobenzo[4,5]cyclohepta[1,2-c]pyrazole;

(+)-6-fluoro-11-{[6-(trifluoromethyl)pyridin-3-yl]sulfonyl}-1,4,9,10-tetrahydro-4,9-epiminobenzo[4,5]cyclohepta[1,2-c]pyrazole;

(±)-9-fluoro-12-{[4-(trifluoromethyl)phenyl]sulfonyl}-4,5,10,11-tetrahydro-1H-4,10-epiminobenzo[5,6]cyclohepta[1,2-c]pyrazole;

(±)-10-fluoro-12-{[4-(trifluoromethyl)phenyl]sulfonyl}-4,5,6,11-tetrahydro-3H-5,11-epiminobenzo[4,5]cycloocta[1,2-c]pyrazole;

- (±)-8-fluoro-11-{[6-(trifluoromethyl)pyridin-3-yl]sulfonyl}-1,4,9,10-tetrahydro-4,9-epiminobenzo[4,5]cyclohepta[1,2-c]pyrazole;
- (−)-8-fluoro-11-{[6-(trifluoromethyl)pyridin-3-yl]sulfonyl}-1,4,9,10-tetrahydro-4,9-epiminobenzo[4,5]cyclohepta[1,2-c]pyrazole;
- (+)-8-fluoro-11-{[6-(trifluoromethyl)pyridin-3-yl]sulfonyl}-1,4,9,10-tetrahydro-4,9-epiminobenzo[4,5]cyclohepta[1,2-c]pyrazole;
- (+)-exo-10-fluoro-11-{[4-(trifluoromethyl)phenyl]sulfonyl}-1,4,9,10-tetrahydro-4,9-epiminobenzo[4,5]cyclohepta[1,2-c]pyrazole;
- (±)-10-{[6-(trifluoromethyl)pyridin-3-yl]sulfonyl}-1,4,8,9-tetrahydro-4,8-epiminopyrazolo[3',4':5,6]cyclohepta[1,2-d][1,3]thiazole;
- (−)-10-{[6-(trifluoromethyl)pyridin-3-yl]sulfonyl}-1,4,8,9-tetrahydro-4,8-epiminopyrazolo[3',4':5,6]cyclohepta[1,2-d][1,3]thiazole;
- (+)-10-{[6-(trifluoromethyl)pyridin-3-yl]sulfonyl}-1,4,8,9-tetrahydro-4,8-epiminopyrazolo[3',4':5,6]cyclohepta[1,2-d][1,3]thiazole;
- (−)-9-fluoro-12-{[4-(trifluoromethyl)phenyl]sulfonyl}-4,5,10,11-tetrahydro-1H-4,10-epiminobenzo[5,6]cycloocta[1,2-c]pyrazole;
- (+)-9-fluoro-12-{[4-(trifluoromethyl)phenyl]sulfonyl}-4,5,10,11-tetrahydro-1H-4,10-epiminobenzo[5,6]cycloocta[1,2-c]pyrazole;
- (−)-8-fluoro-11-{[6-(trifluoromethyl)pyridin-3-yl]sulfonyl}-4,9-dihydro-4,9-epiminobenzo[4,5]cyclohepta[1,2-c]pyrazol-10(1H)-one;
- (+)-8-fluoro-11-{[6-(trifluoromethyl)pyridin-3-yl]sulfonyl}-4,9-dihydro-4,9-epiminobenzo[4,5]cyclohepta[1,2-c]pyrazol-10(1H)-one;
- (±)-methyl 11-{[6-(trifluoromethyl)pyridin-3-yl]sulfonyl}-1,4,9,10-tetrahydro-4,9-epiminobenzo[4,5]cyclohepta[1,2-c]pyrazole-6-carboxylate;
- (±)-exo-11-{[4-(trifluoromethyl)phenyl]sulfonyl}-1,4,9,10-tetrahydro-4,9-epiminobenzo[4,5]cyclohepta[1,2-c]pyrazol-10-ol;
- (−)-11-{[6-(trifluoromethyl)pyridin-3-yl]sulfonyl}-1,4,9,10-tetrahydro-4,9-epiminobenzo[4,5]cyclohepta[1,2-c]pyrazole;
- (+)-11-{[6-(trifluoromethyl)pyridin-3-yl]sulfonyl}-1,4,9,10-tetrahydro-4,9-epiminobenzo[4,5]cyclohepta[1,2-c]pyrazole;
- (±)-exo-10-fluoro-11-{[4-(trifluoromethyl)phenyl]sulfonyl}-1,4,9,10-tetrahydro-4,9-epiminobenzo[4,5]cyclohepta[1,2-c]pyrazole;
- endo-5-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol;
- (−)-11-{[6-(trifluoromethyl)pyridin-3-yl]sulfonyl}-4,9-dihydro-4,9-epiminobenzo[4,5]cyclohepta[1,2-c]pyrazol-10(1H)-one;
- (+)-6-(3-methyl-1,2,4-oxadiazol-5-yl)-11-{[6-(trifluoromethyl)pyridin-3-yl]sulfonyl}-1,4,9,10-tetrahydro-4,9-epiminobenzo[4,5]cyclohepta[1,2-c]pyrazole;
- (−)-6-(3-methyl-1,2,4-oxadiazol-5-yl)-11-{[6-(trifluoromethyl)pyridin-3-yl]sulfonyl}-1,4,9,10-tetrahydro-4,9-epiminobenzo[4,5]cyclohepta[1,2-c]pyrazole;
- (−)-methyl 11-{[6-(trifluoromethyl)pyridin-3-yl]sulfonyl}-1,4,9,10-tetrahydro-4,9-epiminobenzo[4,5]cyclohepta[1,2-c]pyrazole-6-carboxylate;
- (±)-7-methyl-10-{[6-(trifluoromethyl)pyridin-3-yl]sulfonyl}-4,7,8,9-tetrahydro-1H-4,8-epiminocyclohepta[1,2-c:5,4-c']dipyrazole;
- (+)-methyl 11-{[6-(trifluoromethyl)pyridin-3-yl]sulfonyl}-1,4,9,10-tetrahydro-4,9-epiminobenzo[4,5]cyclohepta[1,2-c]pyrazole-6-carboxylate;
- exo-10-fluoro-11-{[6-(trifluoromethyl)pyridin-3-yl]sulfonyl}-1,4,9,10-tetrahydro-4,9-epiminobenzo[4,5]cyclohepta[1,2-c]pyrazole;
- (+)-exo-5,10-difluoro-11-{[6-(trifluoromethyl)pyridin-3-yl]sulfonyl}-1,4,9,10-tetrahydro-4,9-epiminobenzo[4,5]cyclohepta[1,2-c]pyrazole;
- endo-11-{[6-(trifluoromethyl)pyridin-3-yl]sulfonyl}-1,4,9,10-tetrahydro-4,9-epiminobenzo[4,5]cyclohepta[1,2-c]pyrazol-10-ol;
- (±)-11-[(4-chlorophenyl)sulfonyl]-5-fluoro-1,4,9,10-tetrahydro-4,9-epiminobenzo[4,5]cyclohepta[1,2-c]pyrazole;
- (±)-5-fluoro-11-[(4-fluorophenyl)sulfonyl]-1,4,9,10-tetrahydro-4,9-epiminobenzo[4,5]cyclohepta[1,2-c]pyrazole;
- (±)-5-fluoro-11-{[5-(trifluoromethyl)pyridin-2-yl]sulfonyl}-1,4,9,10-tetrahydro-4,9-epiminobenzo[4,5]cyclohepta[1,2-c]pyrazole;
- (+)-9-bromo-12-{[6-(trifluoromethyl)pyridin-3-yl]sulfonyl}-4,5,10,11-tetrahydro-1H-4,10-epiminobenzo[5,6]cycloocta[1,2-c]pyrazole;
- (−)-9-bromo-12-{[6-(trifluoromethyl)pyridin-3-yl]sulfonyl}-4,5,10,11-tetrahydro-1H-4,10-epiminobenzo[5,6]cycloocta[1,2-c]pyrazole;
- exo-8,10-difluoro-11-{[6-(trifluoromethyl)pyridin-3-yl]sulfonyl}-1,4,9,10-tetrahydro-4,9-epiminobenzo[4,5]cyclohepta[1,2-c]pyrazole;
- (+)-8,10,10-trifluoro-11-{[6-(trifluoromethyl)pyridin-3-yl]sulfonyl}-1,4,9,10-tetrahydro-4,9-epiminobenzo[4,5]cyclohepta[1,2-c]pyrazole;
- endo-8-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol;
- (−)-10-bromo-12-{[6-(trifluoromethyl)pyridin-3-yl]sulfonyl}-4,5,6,11-tetrahydro-3H-5,11-epiminobenzo[4,5]cycloocta[1,2-c]pyrazole;
- (+)-10-bromo-12-{[6-(trifluoromethyl)pyridin-3-yl]sulfonyl}-4,5,6,11-tetrahydro-3H-5,11-epiminobenzo[4,5]cycloocta[1,2-c]pyrazole;
- (±)-6-chloro-11-{[6-(trifluoromethyl)pyridin-3-yl]sulfonyl}-1,4,9,10-tetrahydro-4,9-epiminobenzo[4,5]cyclohepta[1,2-c]pyrazole;
- (±)-methyl 11-{[6-(trifluoromethyl)pyridin-3-yl]sulfonyl}-1,4,9,10-tetrahydro-4,9-epiminobenzo[4,5]cyclohepta[1,2-c]pyrazole-8-carboxylate;
- (−)-6-chloro-11-{[6-(trifluoromethyl)pyridin-3-yl]sulfonyl}-1,4,9,10-tetrahydro-4,9-epiminobenzo[4,5]cyclohepta[1,2-c]pyrazole;
- (+)-6-chloro-11-{[6-(trifluoromethyl)pyridin-3-yl]sulfonyl}-1,4,9,10-tetrahydro-4,9-epiminobenzo[4,5]cyclohepta[1,2-c]pyrazole;
- (−)-7-chloro-11-{[6-(trifluoromethyl)pyridin-3-yl]sulfonyl}-1,4,9,10-tetrahydro-4,9-epiminobenzo[4,5]cyclohepta[1,2-c]pyrazole;
- (+)-7-chloro-11-{[6-(trifluoromethyl)pyridin-3-yl]sulfonyl}-1,4,9,10-tetrahydro-4,9-epiminobenzo[4,5]cyclohepta[1,2-c]pyrazole;
- (±)-11-{[6-(trifluoromethyl)pyridin-3-yl]sulfonyl}-1,4,9,10-tetrahydro-4,9-epiminobenzo[4,5]cyclohepta[1,2-c]pyrazol-6-ol;
- (+)-methyl 11-{[6-(trifluoromethyl)pyridin-3-yl]sulfonyl}-1,4,9,10-tetrahydro-4,9-epiminobenzo[4,5]cyclohepta[1,2-c]pyrazole-8-carboxylate;

(−)-methyl 11-{[6-(trifluoromethyl)pyridin-3-yl]sulfonyl}-1,4,9,10-tetrahydro-4,9-epiminobenzo[4,5]cyclohepta[1,2-c]pyrazole-8-carboxylate;
(+)-8-chloro-11-{[6-(trifluoromethyl)pyridin-3-yl]sulfonyl}-1,4,9,10-tetrahydro-4,9-epiminobenzo[4,5]cyclohepta[1,2-c]pyrazole;
(−)-8-chloro-11-{[6-(trifluoromethyl)pyridin-3-yl]sulfonyl}-1,4,9,10-tetrahydro-4,9-epiminobenzo[4,5]cyclohepta[1,2-c]pyrazole;
(−)-11-[(4-chlorophenyl)sulfonyl]-5-fluoro-1,4,9,10-tetrahydro-4,9-epiminobenzo[4,5]cyclohepta[1,2-c]pyrazole;
(+)-11-[(4-chlorophenyl)sulfonyl]-5-fluoro-1,4,9,10-tetrahydro-4,9-epiminobenzo[4,5]cyclohepta[1,2-c]pyrazole;
(−)-5-chloro-11-{[6-(trifluoromethyl)pyridin-3-yl]sulfonyl}-1,4,9,10-tetrahydro-4,9-epiminobenzo[4,5]cyclohepta[1,2-c]pyrazole;
(+)-5-chloro-11-{[6-(trifluoromethyl)pyridin-3-yl]sulfonyl}-1,4,9,10-tetrahydro-4,9-epiminobenzo[4,5]cyclohepta[1,2-c]pyrazole;
(+)-8-(3-methyl-1,2,4-oxadiazol-5-yl)-11-{[6-(trifluoromethyl)pyridin-3-yl]sulfonyl}-1,4,9,10-tetrahydro-4,9-epiminobenzo[4,5]cyclohepta[1,2-c]pyrazole;
(−)-8-(3-methyl-1,2,4-oxadiazol-5-yl)-11-{[6-(trifluoromethyl)pyridin-3-yl]sulfonyl}-1,4,9,10-tetrahydro-4,9-epiminobenzo[4,5]cyclohepta[1,2-c]pyrazole;
(±)-11-[(4-chlorophenyl)sulfonyl]-5-fluoro-4,9-dihydro-4,9-epiminobenzo[4,5]cyclohepta[1,2-c]pyrazol-10(1H)-one;
(−)-(10S)-5-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol;
(+)-(10S)-5-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol;
(−)-(10S)-8-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol;
(+)-(10S)-8-fluoro-11-{[6-(trifluoromethyl)pyridin-3-yl]sulfonyl}-1,4,9,10-tetrahydro-4,9-epiminobenzo[4,5]cyclohepta[1,2-c]pyrazol-10-ol;
(±)-6-(4-fluorophenyl)-11-{[6-(trifluoromethyl)pyridin-3-yl]sulfonyl}-1,4,9,10-tetrahydro-4,9-epiminobenzo[4,5]cyclohepta[1,2-c]pyrazole;
(−)-11-[(4-chlorophenyl)sulfonyl]-5-fluoro-4,9-dihydro-4,9-epiminobenzo[4,5]cyclohepta[1,2-c]pyrazol-10(1H)-one;
(+)-11-[(4-chlorophenyl)sulfonyl]-5-fluoro-4,9-dihydro-4,9-epiminobenzo[4,5]cyclohepta[1,2-c]pyrazol-10(1H)-one;
(−6-(4-fluorophenyl)-11-{[6-(trifluoromethyl)pyridin-3-yl]sulfonyl}-1,4,9,10-tetrahydro-4,9-epiminobenzo[4,5]cyclohepta[1,2-c]pyrazole;
(+)-6-(4-fluorophenyl)-11-{[6-(trifluoromethyl)pyridin-3-yl]sulfonyl}-1,4,9,10-tetrahydro-4,9-epiminobenzo[4,5]cyclohepta[1,2-c]pyrazole;
(−)-6-cyclopropyl-11-{[6-(trifluoromethyl)pyridin-3-yl]sulfonyl}-1,4,9,10-tetrahydro-4,9-epiminobenzo[4,5]cyclohepta[1,2-c]pyrazole;
(+)-6-cyclopropyl-11-{[6-(trifluoromethyl)pyridin-3-yl]sulfonyl}-1,4,9,10-tetrahydro-4,9-epiminobenzo[4,5]cyclohepta[1,2-c]pyrazole;
(+)-6-bromo-11-{[6-(trifluoromethyl)pyridin-3-yl]sulfonyl}-1,4,9,10-tetrahydro-4,9-epiminopyrazolo[3',4':5,6]cyclohepta[1,2-b]pyridine;
(+)-6-bromo-11-{[6-(trifluoromethyl)pyridin-3-yl]sulfonyl}-1,4,9,10-tetrahydro-4,9-epiminopyrazolo[3',4':5,6]cyclohepta[1,2-b]pyridine;
(+)-6-bromo-11-{[6-(trifluoromethyl)pyridin-3-yl]sulfonyl}-1,4,9,10-tetrahydro-4,9-epiminobenzo[4,5]cyclohepta[1,2-c]pyrazole;
(−)-6-bromo-11-{[6-(trifluoromethyl)pyridin-3-yl]sulfonyl}-1,4,9,10-tetrahydro-4,9-epiminobenzo[4,5]cyclohepta[1,2-c]pyrazole;
(±)-(11-{[6-(trifluoromethyl)pyridin-3-yl]sulfonyl}-1,4,9,10-tetrahydro-4,9-epiminobenzo[4,5]cyclohepta[1,2-c]pyrazol-8-yl)methanol;
methyl (±)-11-{[6-(trifluoromethyl)-1,2-dihydropyridin-3-yl]sulfonyl}-1,4,9,10-tetrahydro-4,9-epiminobenzo[4,5]cyclohepta[1,2-c]pyrazole-8-carboxylate;
(+)-6-(4-fluorophenyl)-11-{[6-(trifluoromethyl)pyridin-3-yl]sulfonyl}-1,4,9,10-tetrahydro-4,9-epiminopyrazolo[3',4':5,6]cyclohepta[1,2-b]pyridine;
(+)-6-cyclopropyl-11-{[6-(trifluoromethyl)pyridin-3-yl]sulfonyl}-1,4,9,10-tetrahydro-4,9-epiminopyrazolo[3',4':5,6]cyclohepta[1,2-b]pyridine;
(−)-6-cyclopropyl-11-{[6-(trifluoromethyl)pyridin-3-yl]sulfonyl}-1,4,9,10-tetrahydro-4,9-epiminopyrazolo[3',4':5,6]cyclohepta[1,2-b]pyridine;
(±)-8-(fluoromethyl)-11-{[6-(trifluoromethyl)pyridin-3-yl]sulfonyl}-1,4,9,10-tetrahydro-4,9-epiminobenzo[4,5]cyclohepta[1,2-c]pyrazole;
(±)-7-fluoro-11-{[6-(trifluoromethyl)pyridin-3-yl]sulfonyl}-1,4,9,10-tetrahydro-4,9-epiminopyrazolo[3',4':5,6]cyclohepta[1,2-b]pyridine;
(−)-7-fluoro-11-{[6-(trifluoromethyl)pyridin-3-yl]sulfonyl}-2,4,9,10-tetrahydro-4,9-epiminopyrazolo[3',4':5,6]cyclohepta[1,2-b]pyridine;
(+)-7-fluoro-11-{[6-(trifluoromethyl)pyridin-3-yl]sulfonyl}-2,4,9,10-tetrahydro-4,9-epiminopyrazolo[3',4':5,6]cyclohepta[1,2-b]pyridine;
(4R,9 S)-6-(prop-1-yn-1-yl)-11-{[6-(trifluoromethyl)pyridin-3-yl]sulfonyl}-1,4,9,10-tetrahydro-4,9-epiminobenzo[4,5]cyclohepta[1,2-c]pyrazole;
(−)-exo-5,10-difluoro-11-{[4-(trifluoromethyl)phenyl]sulfonyl}-1,4,9,10-tetrahydro-4,9-epiminobenzo[4,5]cyclohepta[1,2-c]pyrazole;
(+)-5,10-difluoro-11-{[4-(trifluoromethyl)phenyl]sulfonyl}-1,4,9,10-tetrahydro-4,9-epiminobenzo[4,5]cyclohepta[1,2-c]pyrazole;
(±)-8-chloro-11-{[6-(trifluoromethyl)pyridin-3-yl]sulfonyl}-4,9-dihydro-4,9-epiminobenzo[4,5]cyclohepta[1,2-c]pyrazol-10(1H)-one;
(±)-8-chloro-N-hydroxy-11-{[6-(trifluoromethyl)pyridin-3-yl]sulfonyl}-4,9-dihydro-4,9-epiminobenzo[4,5]cyclohepta[1,2-c]pyrazol-10(1H)-imine;
(±)-8-(4-fluorophenyl)-11-{[6-(trifluoromethyl)pyridin-3-yl]sulfonyl}-1,4,9,10-tetrahydro-4,9-epiminobenzo[4,5]cyclohepta[1,2-c]pyrazole;
(4S,9S,10R)-5,10-difluoro-11-{[6-(trifluoromethyl)pyridin-3-yl]sulfonyl}-1,4,9,10-tetrahydro-4,9-epiminobenzo[4,5]cyclohepta[1,2-c]pyrazole;
(4R,9R,10R)-5,10-difluoro-11-{[6-(trifluoromethyl)pyridin-3-yl]sulfonyl}-1,4,9,10-tetrahydro-4,9-epiminobenzo[4,5]cyclohepta[1,2-c]pyrazole;
(±)-8-chloro-N-methoxy-11-{[6-(trifluoromethyl)pyridin-3-yl]sulfonyl}-4,9-dihydro-4,9-epiminobenzo[4,5]cyclohepta[1,2-c]pyrazol-10(1H)-imine;
(±)-8-cyclopropyl-11-{[6-(trifluoromethyl)pyridin-3-yl]sulfonyl}-1,4,9,10-tetrahydro-4,9-epiminobenzo[4,5]cyclohepta[1,2-c]pyrazole;

exo-10-fluoro-11-{[6-(trifluoromethyl)pyridin-3-yl]sulfonyl}-2,4,9,10-tetrahydro-4,9-epiminobenzo[4,5]cyclohepta[1,2-c]pyrazole;

(±)-8-chloro-10-methylidene-11-{[6-(trifluoromethyl)pyridin-3-yl]sulfonyl}-1,4,9,10-tetrahydro-4,9-epiminobenzo[4,5]cyclohepta[1,2-c]pyrazole;

(±)-5-(4-fluorophenyl)-11-{[6-(trifluoromethyl)pyridin-3-yl]sulfonyl}-1,4,9,10-tetrahydro-4,9-epiminobenzo[4,5]cyclohepta[1,2-c]pyrazole;

(±)-5-cyclopropyl-11-{[6-(trifluoromethyl)pyridin-3-yl]sulfonyl}-1,4,9,10-tetrahydro-4,9-epiminobenzo[4,5]cyclohepta[1,2-c]pyrazole;

(−)-9-methyl-11-{[6-(trifluoromethyl)pyridin-3-yl]sulfonyl}-4,9-dihydro-4,9-epiminobenzo[4,5]cyclohepta[1,2-c]pyrazol-10(1H)-one;

(+)-9-methyl-11-{[6-(trifluoromethyl)pyridin-3-yl]sulfonyl}-4,9-dihydro-4,9-epiminobenzo[4,5]cyclohepta[1,2-c]pyrazol-10(1H)-one;

(−)-9-methyl-11-{[4-(trifluoromethyl)phenyl]sulfonyl}-4,9-dihydro-4,9-epiminobenzo[4,5]cyclohepta[1,2-c]pyrazol-10(1H)-one;

(+)-9-methyl-11-{[4-(trifluoromethyl)phenyl]sulfonyl}-4,9-dihydro-4,9-epiminobenzo[4,5]cyclohepta[1,2-c]pyrazol-10(1H)-one, or a pharmaceutically acceptable salt thereof.

\* \* \* \* \*